(12) United States Patent
Yu et al.

(10) Patent No.: US 10,815,225 B2
(45) Date of Patent: Oct. 27, 2020

(54) ANTIPROLIFERATION COMPOUNDS AND USES THEREOF

(71) Applicants: Merck Patent GmbH, Darmstadt (DE); Vertex Pharmaceuticals Incorporated, Boston, MA (US)

(72) Inventors: Henry Yu, Darmstadt (DE); Michael Clark, Boston, MA (US); Guy Bemis, Boston, MA (US); Michael Boyd, Boston, MA (US); Kishan Chandupatla, Boston, MA (US); Philip Collier, Boston, MA (US); Hongbo Deng, Southborough, MA (US); Huijun Dong, Arlington, MA (US); Warren Dorsch, Boston, MA (US); Russell R. Hoover, Harvard, MA (US); Mac Arthur Johnson, Jr., Derry, NH (US); Shashank Kukarni, Darmstadt (DE); Marina Penney, Acton, MA (US); Steven Ronkin, Boston, MA (US); Darin Takemoto, Belmont, MA (US); Qing Tang, Acton, MA (US); Nathan D. Waal, Cambridge, MA (US); Tiansheng Wang, Concord, MA (US); David J. Lauffer, Stow, MA (US); Pan Li, Lexington, MA (US)

(73) Assignees: MERCK PATENT GMBH, Darmstadt (DE); VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 16/391,419

(22) Filed: Apr. 23, 2019

(65) Prior Publication Data

US 2019/0322658 A1 Oct. 24, 2019

Related U.S. Application Data

(60) Provisional application No. 62/661,719, filed on Apr. 24, 2018.

(51) Int. Cl.
| | |
|---|---|
| *A61P 35/00* | (2006.01) |
| *A61K 31/506* | (2006.01) |
| *A61K 31/553* | (2006.01) |
| *C07D 401/14* | (2006.01) |
| *C07D 413/04* | (2006.01) |
| *C07D 413/14* | (2006.01) |
| *C07D 491/107* | (2006.01) |
| *C07D 417/14* | (2006.01) |
| *C07D 491/113* | (2006.01) |
| *C07D 403/04* | (2006.01) |

(52) U.S. Cl.
CPC ............ *C07D 413/14* (2013.01); *A61P 35/00* (2018.01); *C07D 401/14* (2013.01); *C07D 403/04* (2013.01); *C07D 413/04* (2013.01); *C07D 417/14* (2013.01); *C07D 491/107* (2013.01); *C07D 491/113* (2013.01)

(58) Field of Classification Search
CPC ..... A61P 35/00; A61K 31/506; A61K 31/553; C07D 401/14; C07D 413/04; C07D 413/14; C07D 491/107
See application file for complete search history.

(56) References Cited

U.S. PATENT DOCUMENTS

| 8,420,820 B2 | 4/2013 | Wucherer-Plietker et al. |
| 2011/0136787 A1 | 6/2011 | Schoenfeld |

FOREIGN PATENT DOCUMENTS

| WO | 2010/114179 | 10/2010 |

OTHER PUBLICATIONS

International Search Report and Written Opinion for PCT/US2019/028607 dated Jul. 9, 2019.

*Primary Examiner* — Brenda L Coleman
(74) *Attorney, Agent, or Firm* — Andrea L.C. Reid; Dechert LLP

(57) ABSTRACT

The present invention provides compounds of Formula I', or pharmaceutically acceptable salts thereof, pharmaceutical compositions thereof, and methods of use thereof for treating cellular proliferative disorders (e.g., cancer).

50 Claims, No Drawings

ANTIPROLIFERATION COMPOUNDS AND USES THEREOF

TECHNICAL FIELD OF THE INVENTION

The present invention relates to compounds and methods useful for treating cellular proliferative disorders (e.g., cancer). The invention also provides pharmaceutically acceptable compositions comprising compounds of the present invention and methods of using said compositions in the treatment of various proliferative disorders.

BACKGROUND OF THE INVENTION

Cellular proliferative disorders comprise malignant and non-malignant cell populations which differ from the surround tissue morphologically and/or genotypically. Examples of cellular proliferative disorders include, for example, solid tumors, cancer, diabetic retinopathy, intraocular neovascular syndromes, macular degeneration, rheumatoid arthritis, psoriasis, and endometriosis. Cancer is a group of diseases involving abnormal cell proliferation with the potential to invade or spread to other parts of the body. According to Centers for Disease Control and Prevention (CDC), Cancer is the second leading cause of death in the United States. Therefore, additional treatments for cellular proliferative disorders are desired to provide patients with more options.

SUMMARY OF THE INVENTION

It has now been found that compounds of the present invention, and pharmaceutically acceptable compositions thereof, are useful for treating proliferative disorders (e.g., cancer). In one aspect, the present invention provides a compound of Formula I:

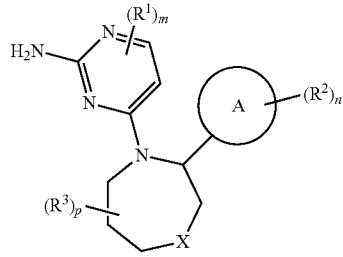

or a pharmaceutically acceptable salt thereof, wherein each variable is as defined and described herein.

Compounds of the present invention, and pharmaceutically acceptable compositions thereof, are useful for treating a variety of proliferative disorders (e.g., cancer) as described herein.

DETAILED DESCRIPTION OF CERTAIN EMBODIMENTS

1. General Description of Certain Embodiments of the Invention

It has been found that the compounds of the present invention, or salts thereof, exhibit pronounced efficacy in multiple cell-line-derived and patient-derived xenograft models. For example, the compounds of the invention, or salts thereof, are found to lead to complete and durable regression in models of non-small cell lung cancer (NSCLC), myeloma, hepatocellular carcinoma (HCC), breast cancer, and melanoma. It has also been found that the compounds of the invention result in enhanced inhibition of cell viability, particularly the cells where Wolframin (WFS1) is overexpressed. Without wishing to be bound by any specific theory, it is believed that the compounds of the invention cause calcium release from the endoplasmic reticulum (ER) via a putative $Ca^{2+}$ channel known as Wolframin (WFS1), which induces ER stress and the "unfolded protein response" (UPR) and leads to cell death.

In one aspect, the present invention provides a compound of formula I:

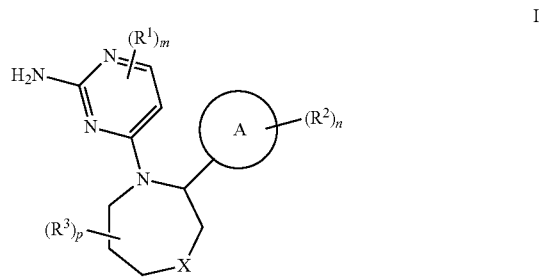

or a pharmaceutically acceptable salt thereof, wherein:

Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^1$ is independently hydrogen or $C_{1-3}$ aliphatic; or
two $R^1$ groups are optionally taken together with their intervening atoms to form a 5-8 membered partially unsaturated fused carbocyclic ring;

each of $R^2$ is independently hydrogen, halogen, —CN, —NO$_2$, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, or R; or
two $R^2$ groups are optionally taken together to form =O;

each $R^3$ is independently hydrogen or $C_{1-3}$ aliphatic; or:
two $R^3$ groups are optionally taken together to form =O;
two $R^3$ groups are optionally taken together to form =CH$_2$;
two $R^3$ groups are optionally taken together with their intervening atoms to form a 5-8 membered saturated spirocyclic ring having 0-2 heteroatoms independently selected from nitrogen, oxygen or sulfur; or
two $R^3$ groups are optionally taken together with their intervening atoms to form a 5-8 membered saturated bridged bicyclic ring having 0-2 heteroatoms independently selected from nitrogen, oxygen or sulfur;

each R is independently hydrogen or an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;
X is —O—, —N(R)—, —N(S(O)$_2$(R))—, —S—, —S(O)—, —S(O)$_2$—, —CH$_2$—, —CH(R$^3$)—, or —C(R$^3$)$_2$—;
m is 0, 1, or 2;
n is 0, 1, 2, 3, 4 or 5; and
p is 0, 1, or 2.

In one aspect, the present invention provides a compound of formula I':

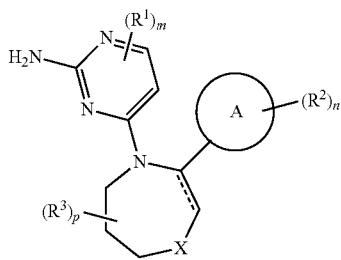

or a pharmaceutically acceptable salt thereof, wherein:
Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur; or an 8-10 membered bicyclic heteroaromatic ring having 1-5 heteroatoms independently selected from nitrogen, oxygen, or sulfur;
each R$^1$ is independently hydrogen, or C$_{1-3}$ aliphatic optionally substituted by 1-6 halogen; or
two R$^1$ groups are optionally taken together with their intervening atoms to form a 5-8 membered partially unsaturated fused carbocyclic ring;
each of R$^2$ is independently hydrogen, halogen, —CN, —NO$_2$, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, —S(O)$_2$NR$_2$, or R; or
two R$^2$ groups are optionally taken together to form =O; or
two R$^2$ groups are optionally taken together with their intervening atoms to form a 3-8 membered saturated spirocyclic ring having 0-2 heteroatoms independently selected from nitrogen, oxygen or sulfur;
each R$^3$ is independently hydrogen, —OH, or C$_{1-3}$ aliphatic; or
two R$^3$ groups are optionally taken together to form =O; or two R$^3$ groups are optionally taken together to form =CH$_2$; or
two R$^3$ groups are optionally taken together with their intervening atoms to form a 3-8 membered saturated spirocyclic ring having 0-2 heteroatoms independently selected from nitrogen, oxygen or sulfur; or
two R$^3$ groups are optionally taken together with their intervening atoms to form a 5-8 membered saturated bridged bicyclic ring having 0-2 heteroatoms independently selected from nitrogen, oxygen or sulfur;
each R is independently hydrogen or an optionally substituted group selected from C$_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;
===== is a single bond or a double bond;
X is —O—, —N(R)—, —N(S(O)$_2$(R))—, —S—, —S(O)—, —S(O)$_2$—, —CH$_2$—, —CH(R$^3$)—, or —C(R$^3$)$_2$—;
m is 0, 1, or 2;
n is 0, 1, 2, 3, 4 or 5; and
p is 0, 1, or 2.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

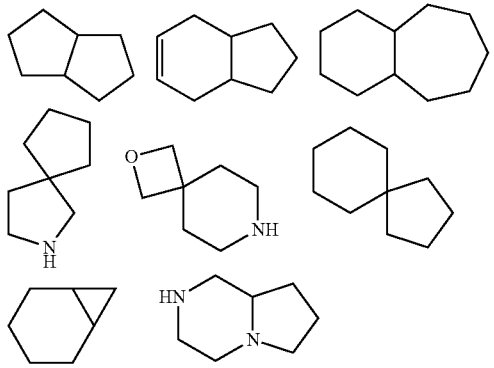

Exemplary bridged bicyclics include:

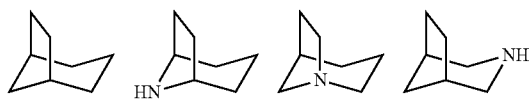

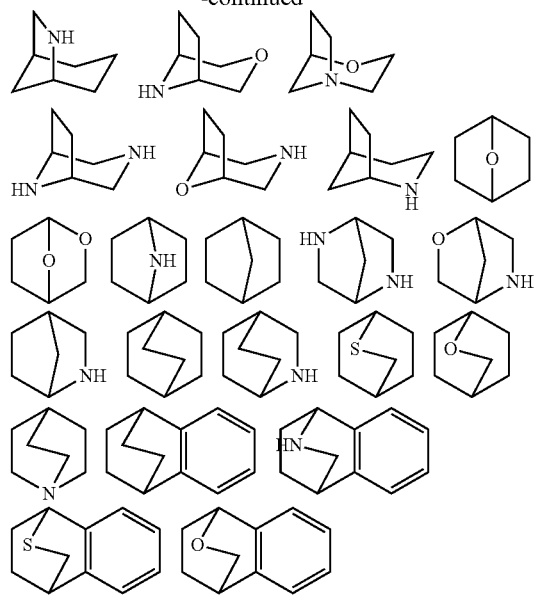

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR⁺ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure

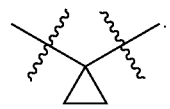 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$S(O)(NR°)R°$; —$S(O)_2N=C(NR°_2)_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$.

Each $R°$ is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from =O and =S; or each $R^\circ$ is optionally substituted with a monovalent substituent independently selected from halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0}CH(OR^\bullet)_2$; —$O(haloR^\bullet)$, —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet{}_2$, —$NO_2$, —$SiR^\bullet{}_3$, —$OSiR^\bullet{}_3$, —$C(O)SR^\bullet$, —$(C_{1-4}$ straight or branched alkylene)$C(O)OR^\bullet$, or —$SSR^\bullet$.

Each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, or a divalent substituent bound to vicinal substitutable carbons of an "optionally substituted" group is —$O(CR^*_2)_{2-3}O$—, wherein each independent occurrence of $R^*$ is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When $R^*$ is $C_{1-6}$ aliphatic, $R^*$ is optionally substituted with halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet{}_2$, or —$NO_2$, wherein each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently —$R^\dagger$, —$NR^\dagger{}_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger{}_2$, —$C(S)NR^\dagger{}_2$, —$C(NH)NR^\dagger{}_2$, or —$N(R^\dagger)S(O)_2R^\dagger$; wherein each $R^\dagger$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet{}_2$, or —$NO_2$, wherein each $R^\bullet$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

3. Description of Exemplary Embodiments

In one aspect, the present invention provides a compound of formula I:

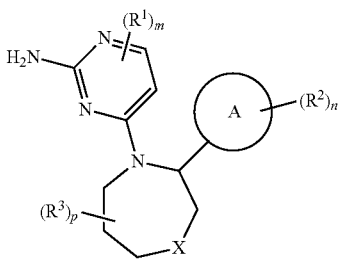

or a pharmaceutically acceptable salt thereof, wherein:
Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^1$ is independently hydrogen or $C_{1-3}$ aliphatic; or
two $R^1$ groups are optionally taken together with their intervening atoms to form a 5-8 membered partially unsaturated fused carbocyclic ring;

each of $R^2$ is independently hydrogen, halogen, —CN, —NO$_2$, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, or R; or
two $R^2$ groups are optionally taken together to form =O;

each $R^3$ is independently hydrogen or $C_{1-3}$ aliphatic; or:
two $R^3$ groups are optionally taken together to form =O;
two $R^3$ groups are optionally taken together to form =CH$_2$;
two $R^3$ groups are optionally taken together with their intervening atoms to form a 5-8 membered saturated spirocyclic ring having 0-2 heteroatoms independently selected from nitrogen, oxygen or sulfur; or
two $R^3$ groups are optionally taken together with their intervening atoms to form a 5-8 membered saturated bridged bicyclic ring having 0-2 heteroatoms independently selected from nitrogen, oxygen or sulfur;

each R is independently hydrogen or an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

X is —O—, —N(R)—, —N(S(O)$_2$(R))—, —S—, —S(O)—, —S(O)$_2$—, —CH$_2$—, —CH(R$^3$)—, or —C(R$^3$)$_2$—;
m is 0, 1, or 2;
n is 0, 1, 2, 3, 4 or 5; and
p is 0, 1, or 2.

In one aspect, the present invention provides a compound of formula I':

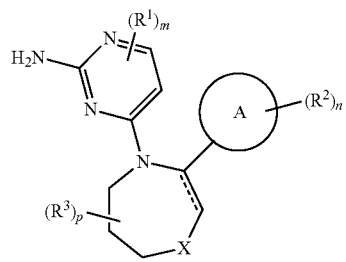

or a pharmaceutically acceptable salt thereof, wherein:
Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur; or an 8-10 membered bicyclic heteroaromatic ring having 1-5 heteroatoms independently selected from nitrogen, oxygen, or sulfur;

each $R^1$ is independently hydrogen, or $C_{1-3}$ aliphatic optionally substituted by 1-6 halogen; or
two $R^1$ groups are optionally taken together with their intervening atoms to form a 5-8 membered partially unsaturated fused carbocyclic ring;

each of $R^2$ is independently hydrogen, halogen, —CN, —NO$_2$, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, —S(O)$_2$NR$_2$, or R; or
two $R^2$ groups are optionally taken together to form =O; or
two $R^2$ groups are optionally taken together with their intervening atoms to form a 3-8 membered saturated spirocyclic ring having 0-2 heteroatoms independently selected from nitrogen, oxygen or sulfur;

each $R^3$ is independently hydrogen, —OH, or $C_{1-3}$ aliphatic; or
two $R^3$ groups are optionally taken together to form =O; or
two $R^3$ groups are optionally taken together to form =CH$_2$; or
two $R^3$ groups are optionally taken together with their intervening atoms to form a 3-8 membered saturated spirocyclic ring having 0-2 heteroatoms independently selected from nitrogen, oxygen or sulfur; or
two $R^3$ groups are optionally taken together with their intervening atoms to form a 5-8 membered saturated bridged bicyclic ring having 0-2 heteroatoms independently selected from nitrogen, oxygen or sulfur;

each R is independently hydrogen or an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

===== is a single bond or a double bond;

X is —O—, —N(R)—, —N(S(O)₂(R))—, —S—, —S(O)—, —S(O)₂—, —CH₂—, —CH(R³)—, or —C(R³)₂—;

m is 0, 1, or 2;
n is 0, 1, 2, 3, 4 or 5; and
p is 0, 1, or 2.

As defined generally above, ===== is a single bond or a double bond.

In some embodiments, ===== is a single bond. In some embodiments, ===== is a double bond.

In some embodiments, ===== is selected from those depicted in Tables 1, 2, and 2A, below.

As defined generally above, Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, Ring A is phenyl. In some embodiments, Ring A is a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, Ring A is a 5-7 membered saturated or partially unsaturated carbocyclic ring. In some embodiments, Ring A is a 8-12 membered saturated or partially unsaturated bicyclic heterocyclic ring having 1-2 heteroatoms independently selected from nitrogen, oxygen, or sulfur. In some embodiments, Ring A is a 5-6 membered heteroaromatic ring having 1-4 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is phenyl or

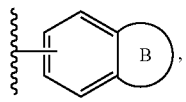

wherein Ring B is 5-7 membered partially unsaturated heterocyclic ring having 1-2 heteroatoms independently selected from nitrogen, oxygen, or sulfur, or Ring B is 5-6 membered heteroaromatic ring having 1-4 heteroatoms independently selected from nitrogen, oxygen, or sulfur. In some embodiments, Ring B is selected from:

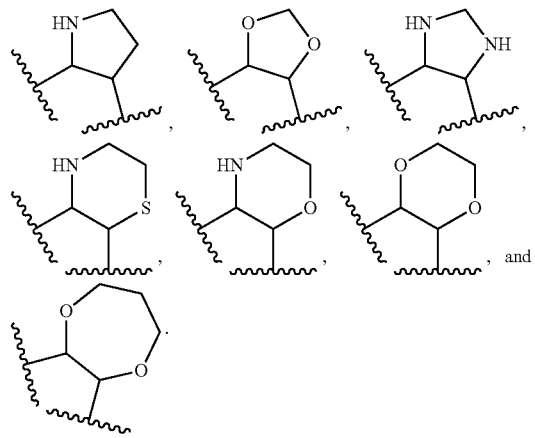

In some embodiments, Ring B is

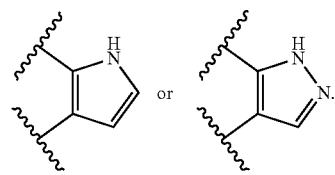 [SMILES: *c1cc[nH]c1* ; *c1cn[nH]c1*]

In some embodiments, Ring A is selected from:

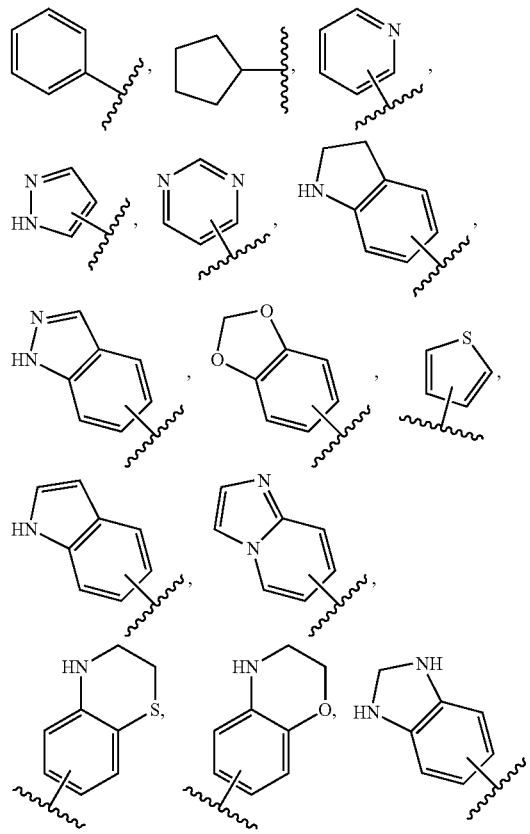

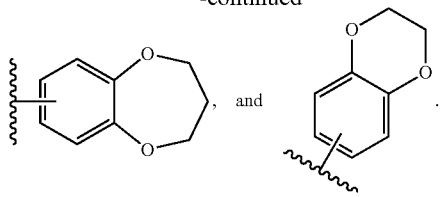
In some embodiments, Ring A is
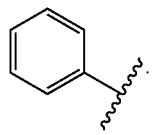
In some embodiments, Ring A is
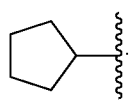
In some embodiments, Ring A is selected from:
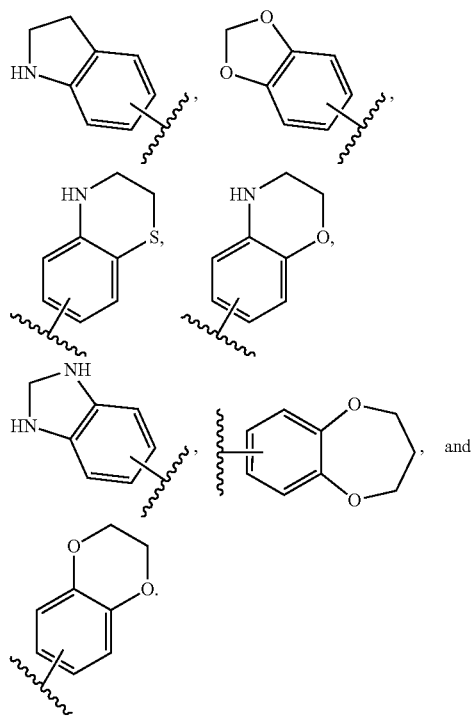
In some embodiments, Ring A is
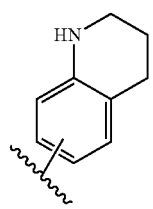
In some embodiments, Ring A is selected from:
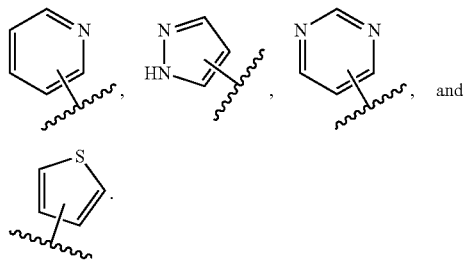
In some embodiments, Ring A is
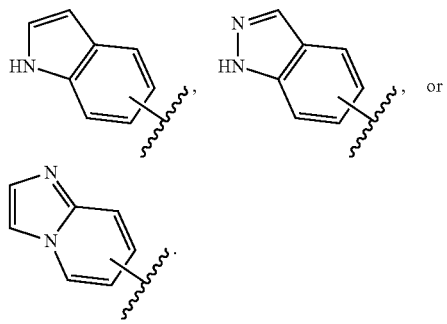
In some embodiments, Ring A is selected from:
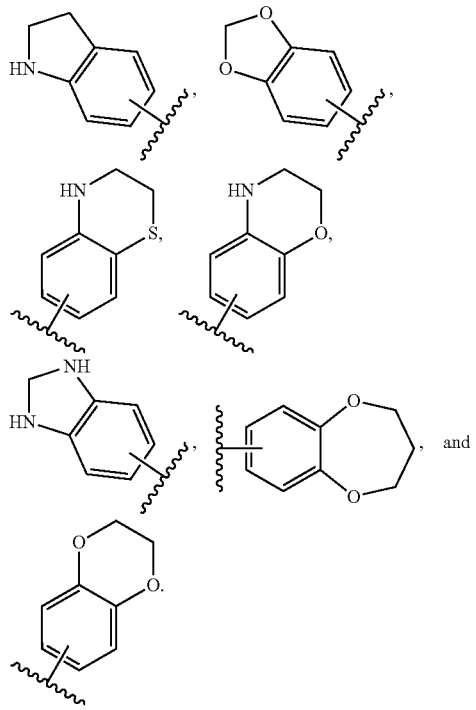
In some embodiments, Ring A is
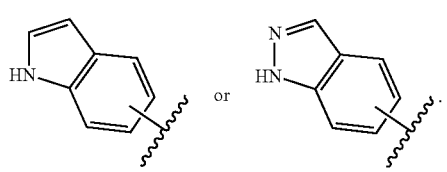

In some embodiments, Ring A is selected from:
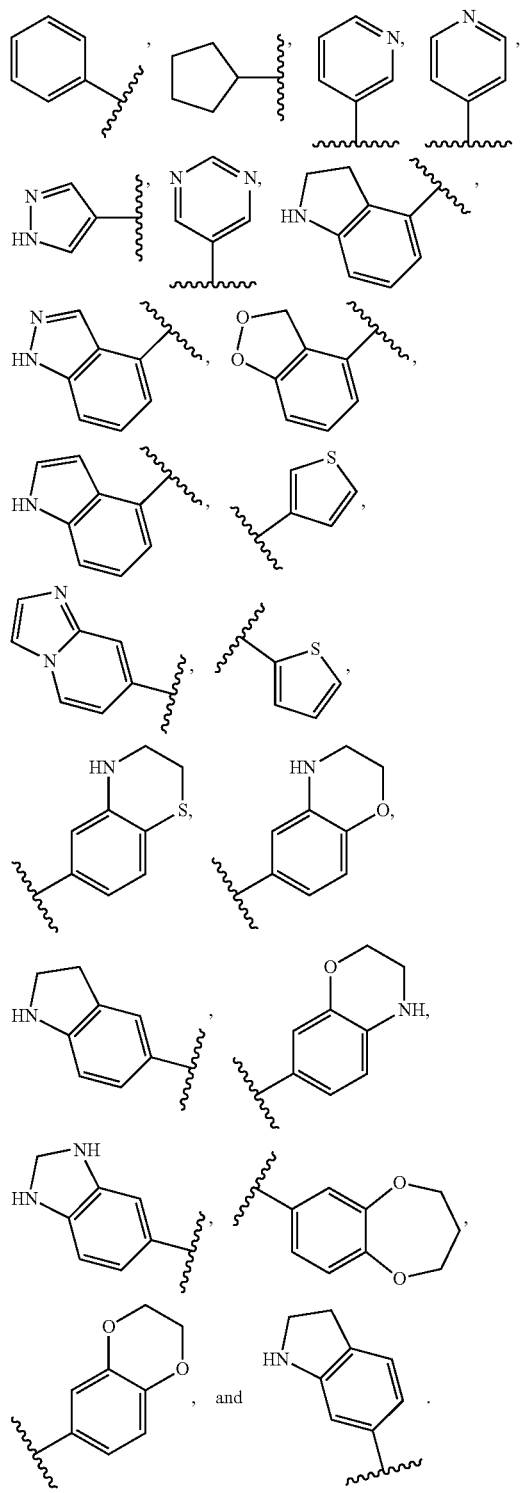
In some embodiments, Ring A is selected from:
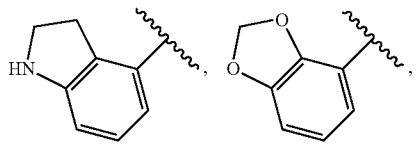
In some embodiments, Ring A is selected from:
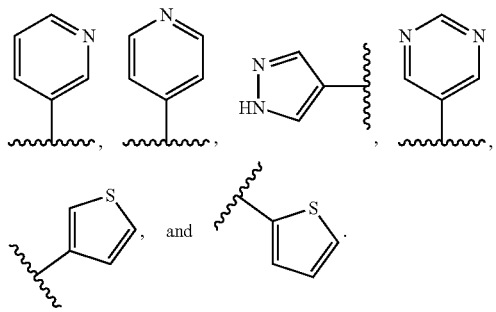
In some embodiments, Ring A is selected from:
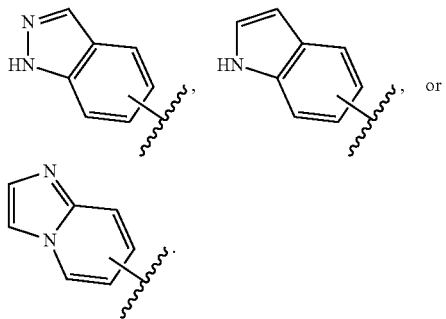
In some embodiments, Ring A is selected from:
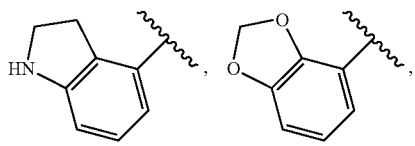

-continued

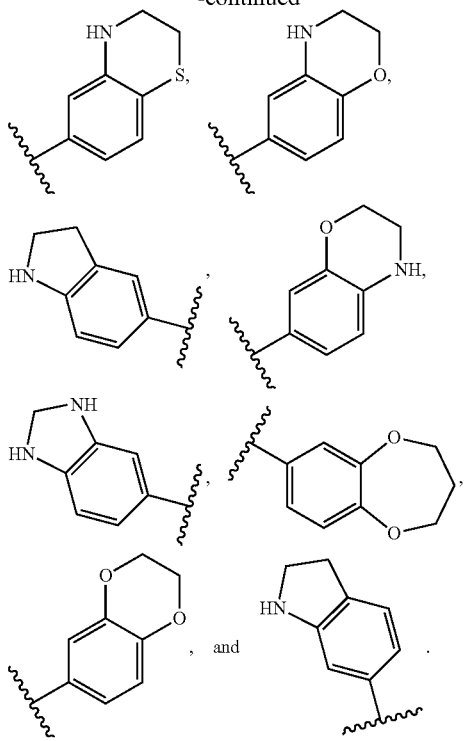

In some embodiments, Ring A is

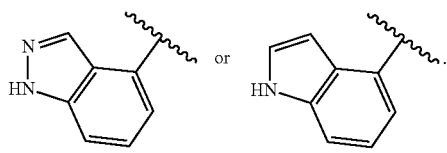 [SMILES: *c1cccc2[nH]ncc12 ; *c1cccc2[nH]ccc12]

In some embodiments, Ring A is

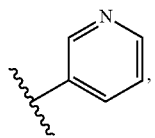

one $R^2$ is —OH, and

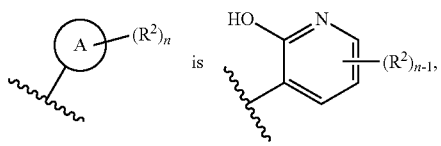

which can also be in the tautomeric form:

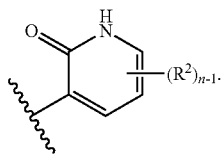

In some embodiments, Ring A is selected from those depicted in Tables 1 and 2, below.

In some embodiments, Ring A is selected from those depicted in Table 2A, below.

As defined generally above, each $R^1$ is independently hydrogen or $C_{1-3}$ aliphatic; or two $R^1$ groups are optionally taken together with their intervening atoms to form a 5-8 membered partially unsaturated fused carbocyclic ring.

In some embodiments, $R^1$ is hydrogen. In some embodiments, $R^1$ is $C_{1-3}$ aliphatic. In some embodiments, two $R^1$ groups are optionally taken together with their intervening atoms to form a 5-8 membered partially unsaturated fused carbocyclic ring.

In some embodiments, $R^1$ is methyl. In some embodiments, $R^1$ is ethyl. In some embodiments, $R^1$ is propyl. In some embodiments, $R^1$ is isopropyl.

In some embodiments, $R^1$ is attached to position 5 of the pyrimidine. In some embodiments, $R^1$ is attached to position 6 of the pyrimidine.

In some embodiments, two $R^1$ groups are optionally taken together with their intervening atoms to form a 5-8 membered partially unsaturated fused carbocyclic ring. In some embodiments, two $R^1$ groups are optionally taken together with their intervening atoms to form a 5 membered partially unsaturated fused carbocyclic ring. In some embodiments, two $R^1$ groups are optionally taken together with their intervening atoms to form a 6 membered partially unsaturated fused carbocyclic ring. In some embodiments, two $R^1$ groups are optionally taken together with their intervening atoms to form a 7 membered partially unsaturated fused carbocyclic ring. In some embodiments, two $R^1$ groups are optionally taken together with their intervening atoms to form a 8 membered partially unsaturated fused carbocyclic ring.

In some embodiments, $R^1$ is $C_{1-3}$ aliphatic optionally substituted 1-6 times by halogen. In some embodiments, $R^1$ is $C_{1-3}$ alkyl optionally substituted 1-6 times by halogen. In some embodiments, $R^1$ is $C_{1-3}$ alkyl optionally substituted 1-6 times by fluoride. In some embodiments, $R^1$ is $C_{1-3}$ alkyl optionally substituted 1-3 times by fluoride. In some embodiments, $R^1$ is —$CF_3$.

In some embodiments, $R^1$ is selected from those depicted in Tables 1 and 2, below.

In some embodiments, $R^1$ is selected from those depicted in Table 2A, below.

As defined generally above, each of $R^2$ is independently hydrogen, halogen (F, Cl, Br, or I), —CN, —$NO_2$, —C(O)OR, —C(O)$NR_2$, —$NR_2$, —NRC(O)R, —NRC(O)OR, —NRS(O)$_2$R, —OR, —P(O)$R_2$, —SR, —S(O)R, —S(O)$_2$R, —S(O)(NH)R, or R; or two $R^2$ groups are optionally taken together to form =O.

In some embodiments, $R^2$ is hydrogen. In some embodiments, each of $R^2$ is independently halogen, —CN, —$NO_2$, —C(O)OR, —C(O)$NR_2$, —$NR_2$, —NRC(O)R, —NRC(O)OR, —NRS(O)$_2$R, —OR, —P(O)$R_2$, —SR, —S(O)R, —S(O)$_2$R, —S(O)(NH)R, or R; or two $R^2$ groups are optionally taken together to form =O.

In some embodiments, $R^2$ is halogen. In some embodiments, $R^2$ is Cl. In some embodiments, $R^2$ is —CN. In some embodiments, $R^2$ is —$NO_2$. In some embodiments, $R^2$ is —C(O)OR. In some embodiments, $R^2$ is —C(O)$NR_2$. In some embodiments, $R^2$ is —$NR_2$. In some embodiments, $R^2$ is —NRC(O)R. In some embodiments, $R^2$ is —NRC(O)OR. In some embodiments, $R^2$ is —NRS(O)$_2$R. In some embodiments, $R^2$ is independently —OR. In some embodiments, $R^2$ is —P(O)$R_2$. In some embodiments, $R^2$ is —SR. In some embodiments, $R^2$ is —S(O)R. In some embodiments, $R^2$ is —S(O)$_2$R. In some embodiments, $R^2$ is —S(O)(NH)R. In some embodiments, $R^2$ is R. In some embodiments, two $R^2$ groups are optionally taken together to form =O.

In some embodiments, $R^2$ is —S(O)$_2NR_2$. In some embodiments, $R^2$ is —S(O)$_2NH_2$.

In some embodiments, $R^2$ is $C_{1-6}$ aliphatic. In some embodiments, $R^2$ is a 3-8 membered saturated monocyclic carbocyclic ring. In some embodiments, $R^2$ is a 7-10 membered saturated spirobicyclic heterocyclic ring having 1-2 heteroatoms independently selected from nitrogen, oxygen, or sulfur. In some embodiments, $R^2$ is a 7-10 membered saturated fused bicyclic heterocyclic ring having 1-2 heteroatoms independently selected from nitrogen, oxygen, or sulfur. In some embodiments, $R^2$ is a 4-8 membered saturated monocyclic heterocyclic ring having 1-2 heteroatoms independently selected from nitrogen, oxygen, or sulfur. In some embodiments, $R^2$ is a 5-6 membered monocyclic heteroaromatic ring having 1-4 heteroatoms independently selected from nitrogen, oxygen, or sulfur.

In some embodiments, each of $R^2$ is independently selected from:

halogen (e.g., Cl), —NH₂, —CH₃, —CF₃,

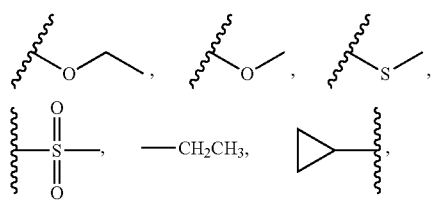

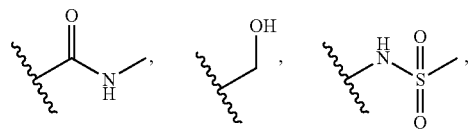

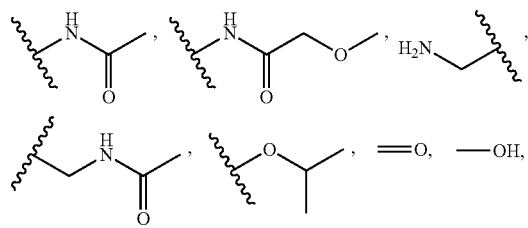

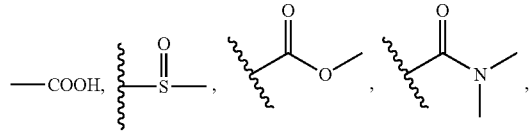

=O, —OH,

—COOH,

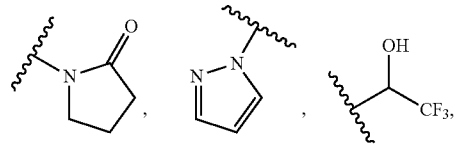

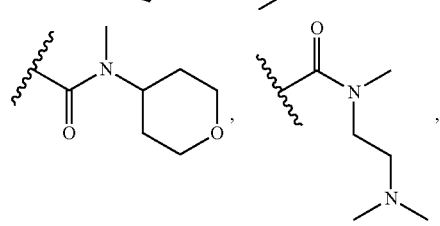

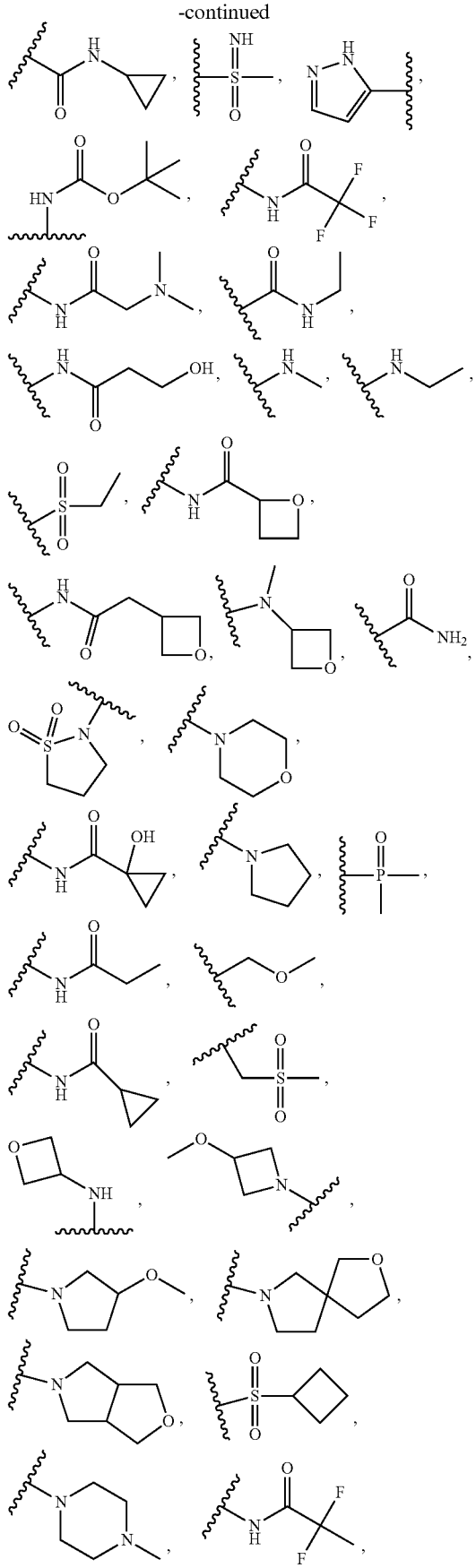

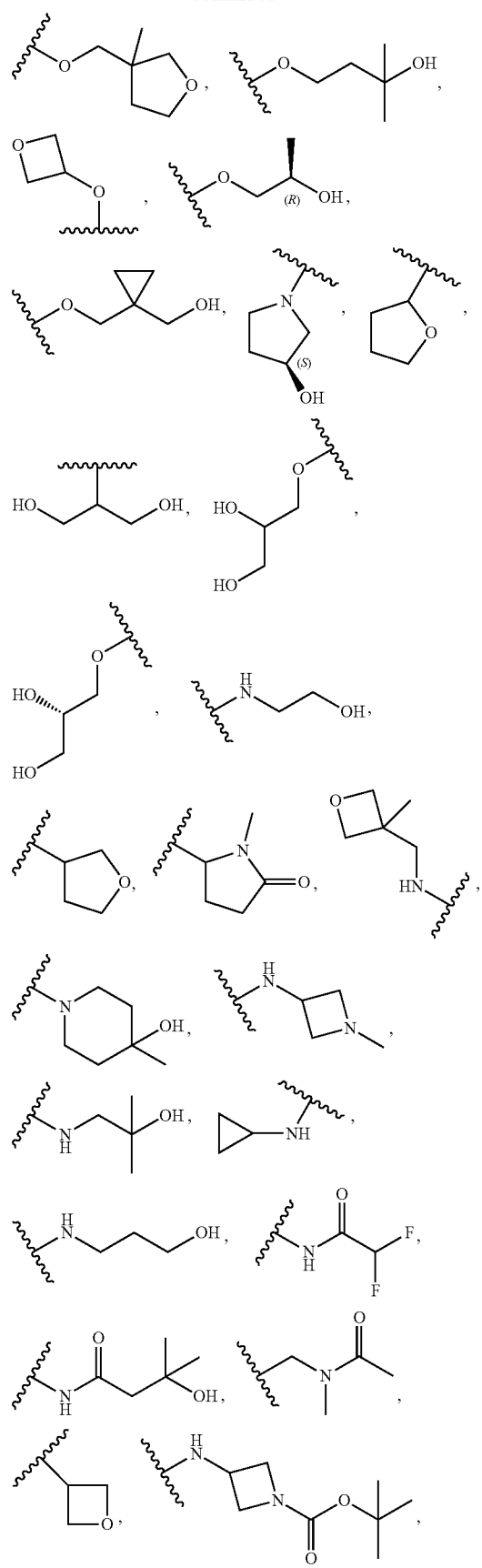
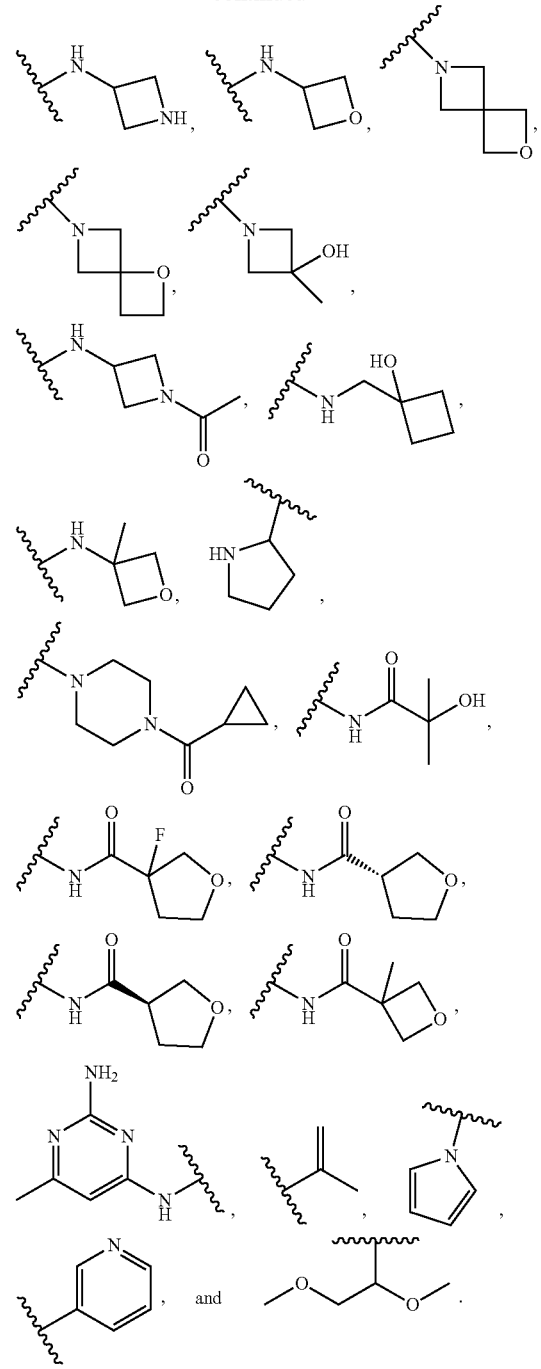
In some embodiments, $R^2$ is selected from —S(O)$_2$NH$_2$, —OCHF$_2$, —OCF$_3$, —C≡CH, —O—
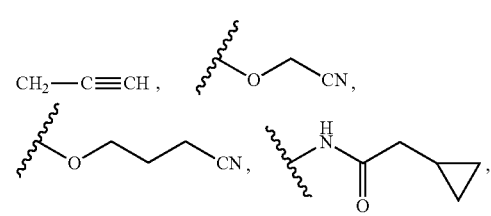

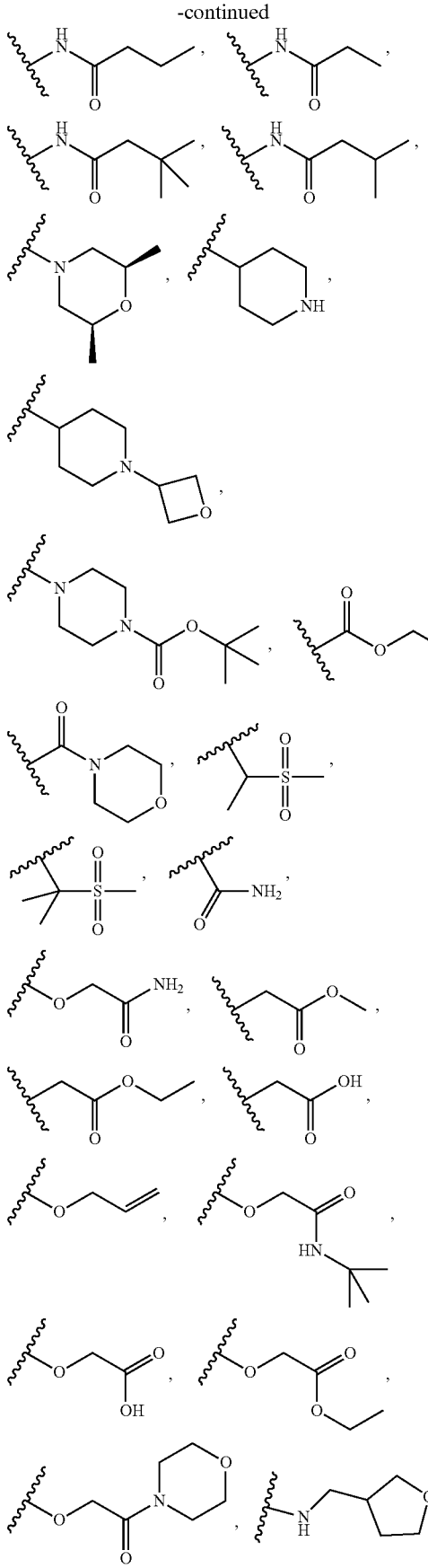

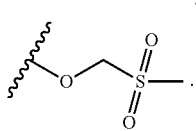

In some embodiments, $R^2$ is $C_{1-6}$ aliphatic, optionally substituted 1-4 times by halogen, —OH, $NH_2$, —$OCH_3$, —NHC(O)$CH_3$, —S(O)$_2$$CH_3$, or —N($CH_3$)C(O)$CH_3$. In some embodiments, $R^2$ is selected from $CH_3$, —$CF_3$, —$CH_2CH_3$,

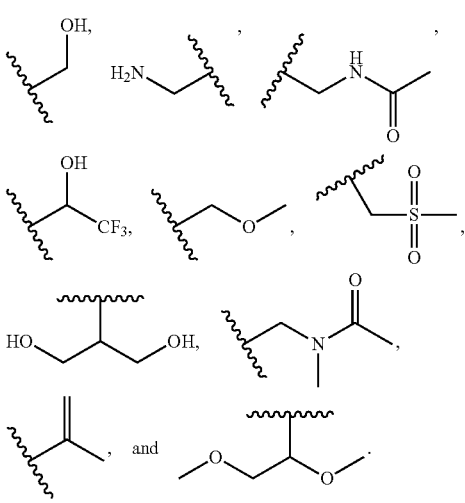

In some embodiments, $R^2$ is $C_{1-6}$ aliphatic, optionally substituted 1-4 times by halogen, —OH, $NH_2$, —$OCH_3$, —NHC(O)$CH_3$, —S(O)$_2$$CH_3$, —COOH, —$CO_2CH_3$, —$CO_2C_2H_5$, or —N($CH_3$)C(O)$CH_3$. In some embodiments, $R^2$ is

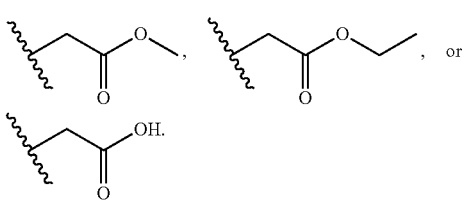

In some embodiments, $R^2$ is $C_{1-6}$ aliphatic, optionally substituted by a —S(O)$_2$—(CH$_2$)$_{0-6}$ group, wherein (CH$_2$)$_{0-6}$ is optionally substituted 1-4 times by halogen, —OH, $NH_2$, or —$OCH_3$. In some embodiments, $R^2$ is $C_{1-6}$ aliphatic, optionally substituted by a —S(O)$_2$—(CH$_2$)$_{0-6}$ group, wherein (CH$_2$)$_{0-6}$ is unsubstituted. In some embodiments, $R^2$ is $C_{1-6}$ aliphatic, optionally substituted by —S(O)$_2$—$CH_3$ or —S(O)$_2$—$CH_2$—$CH_3$. In some embodiments, $R^2$ is $C_{1-6}$ aliphatic, optionally substituted by —S(O)$_2$—$CH_3$. In some embodiments, $R^2$ is —$CH_2$—S(O)$_2$—$CH_3$. In some embodiments, $R^2$ is —$CH_2$—S(O)$_2$—$CH_2$—$CH_3$. In some embodiments, $R^2$ is —$CH_2$—$CH_2$—S(O)$_2$—$CH_3$. In some embodiments, $R^2$ is —$CH_2$—$CH_2$—S(O)$_2$—$CH_2$—$CH_3$. In some embodiments, $R^2$ is selected from

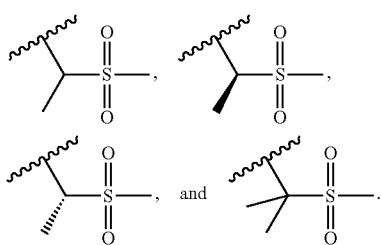

In some embodiments, R² is unsubstituted C₁₋₆ aliphatic. In some embodiments, R² is —C≡CH.

In some embodiments, R² is a 3-6 membered saturated monocyclic carbocyclic ring. In some embodiments, R² is

In some embodiments, R² is a 7-10 membered saturated spirobicyclic heterocyclic ring having 1-2 heteroatoms independently selected from nitrogen or oxygen. In some embodiments, R² is selected from

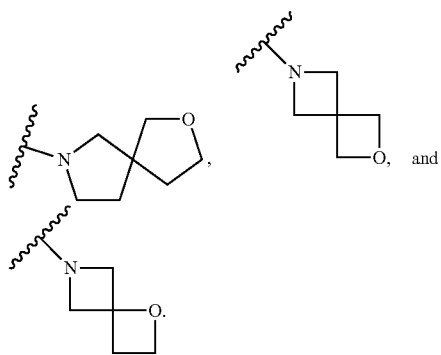

In some embodiments, R² is a 7-10 membered saturated fused bicyclic heterocyclic ring having 1-2 heteroatoms independently selected from nitrogen or oxygen. In some embodiments, R² is

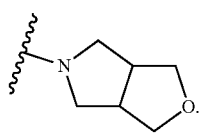 [SMILES: *N1CC2COCC2C1]

In some embodiments, R² is a 4-6 membered saturated monocyclic heterocyclic ring having 1-2 heteroatoms independently selected from nitrogen, oxygen, or sulfur, optionally substituted 1-4 times by halogen, —OH, —CH₃, —OCH₃, =O, or

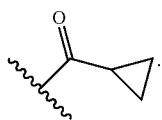

In some embodiments, R² is selected from

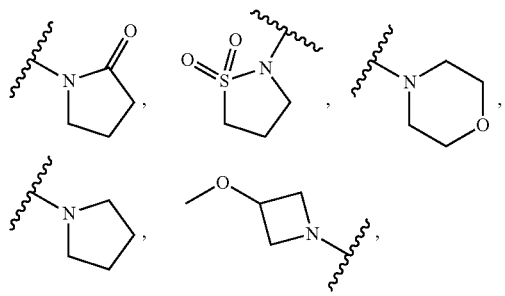

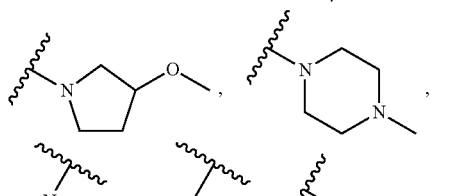

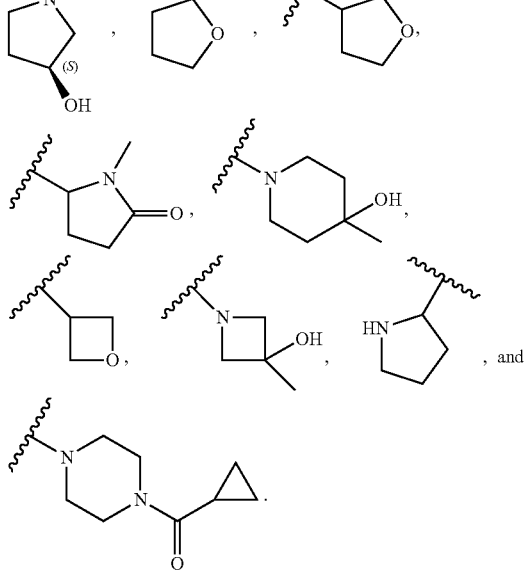

In some embodiments, R² is a 4-6 membered saturated monocyclic heterocyclic ring having 1-2 heteroatoms independently selected from nitrogen, oxygen, or sulfur, optionally substituted 1-4 times by halogen, —OH, —CH₃, —OCH₃, =O,

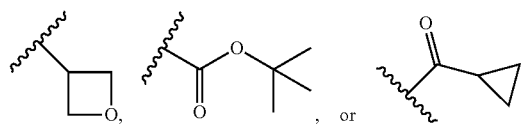

In some embodiments, R² is selected from

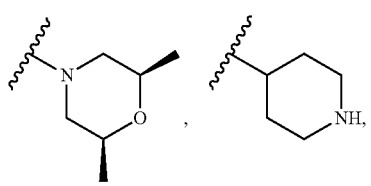

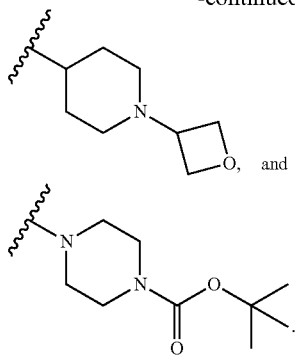

In some embodiments, $R^2$ is a 5-6 membered monocyclic heteroaromatic ring having 1-2 heteroatoms independently selected from nitrogen, oxygen, or sulfur. In some embodiments, $R^2$ is selected from

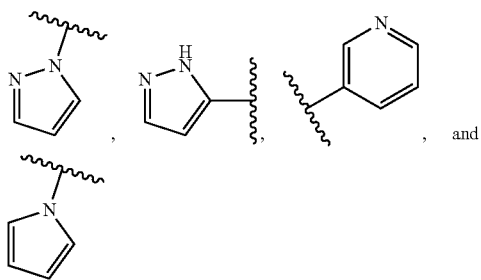

In some embodiments, $R^2$ is —C(O)OR, wherein R is hydrogen or $C_{1-6}$ aliphatic. In some embodiments, $R^2$ is —C(O)OH. In some embodiments, $R^2$ is —C(O)OC$_{1-6}$ aliphatic, wherein the $C_{1-6}$ aliphatic is unsubstituted. In some embodiments, $R^2$ is

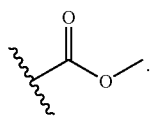 [SMILES: *C(=O)OC]

In some embodiments, $R^2$ is

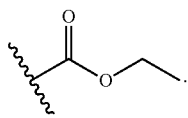 [SMILES: *C(=O)OCC]

In some embodiments, $R^2$ is —C(O)NR$_2$, wherein each of R is independently hydrogen, $C_{1-6}$ aliphatic which is optionally substituted by a —N(CH$_3$)$_2$, unsubstituted 3-6 membered saturated monocyclic carbocyclic ring, or unsubstituted 4-6 membered saturated monocyclic heterocyclic ring having 1-2 heteroatoms independently selected from nitrogen or oxygen, or two R taken together with their intervening atoms to form a 4-7 membered saturated and unsubstituted heteroaryl ring. In some embodiments, $R^2$ is selected from

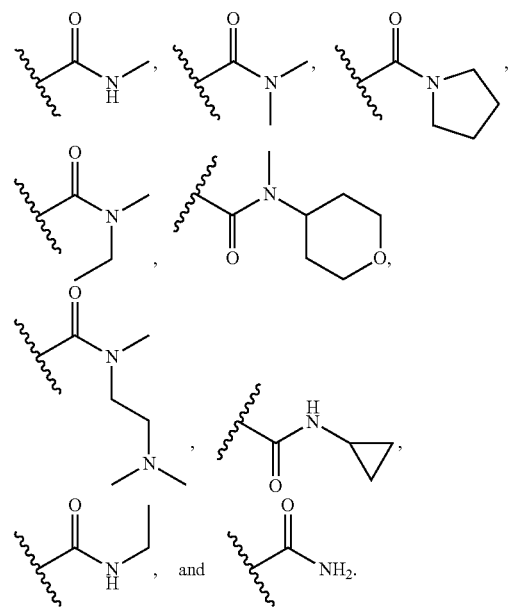

In some embodiments, $R^2$ is —C(O)NR$_2$, wherein two R taken together with their intervening atoms to form a 4-7 membered saturated ring having 0-3 heteroatoms, in addition to the nitrogen, independently selected from nitrogen, oxygen and sulfur, optionally substituted with 1-2 oxo groups. In some embodiments, $R^2$ is —C(O)NR$_2$, wherein two R taken together with their intervening atoms to form a 4-7 membered saturated and unsubstituted ring having 0-3 heteroatoms, in addition to the nitrogen, independently selected from nitrogen, oxygen and sulfur. In some embodiments, $R^2$ is

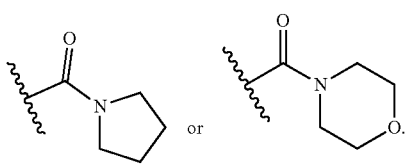 [SMILES: *C(=O)N1CCCC1 ; *C(=O)N1CCOCC1]

In some embodiments, $R^2$ is —NR$_2$, wherein each of R is independently:

hydrogen;

$C_{1-6}$ aliphatic which is optionally substituted 1-2 times by —OH,

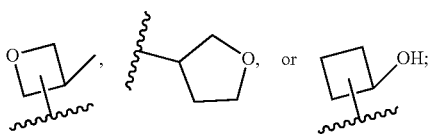

unsubstituted 3-6 membered saturated monocyclic carbocyclic ring;

4-6 membered saturated monocyclic heterocyclic ring having 1-2 heteroatoms independently selected from nitrogen or oxygen, which is optionally substituted 1-2 times by CH$_3$, —OH, —C(O)OC(CH$_3$)$_3$, or —C(O)CH$_3$; or 6 membered monocyclic heteroaromatic ring having 1-2 heteroatoms independently selected from nitrogen, oxygen, or sulfur which is optionally substituted 1-2 times by —CH₃ or —NH₂.

In some embodiments, R² is selected from

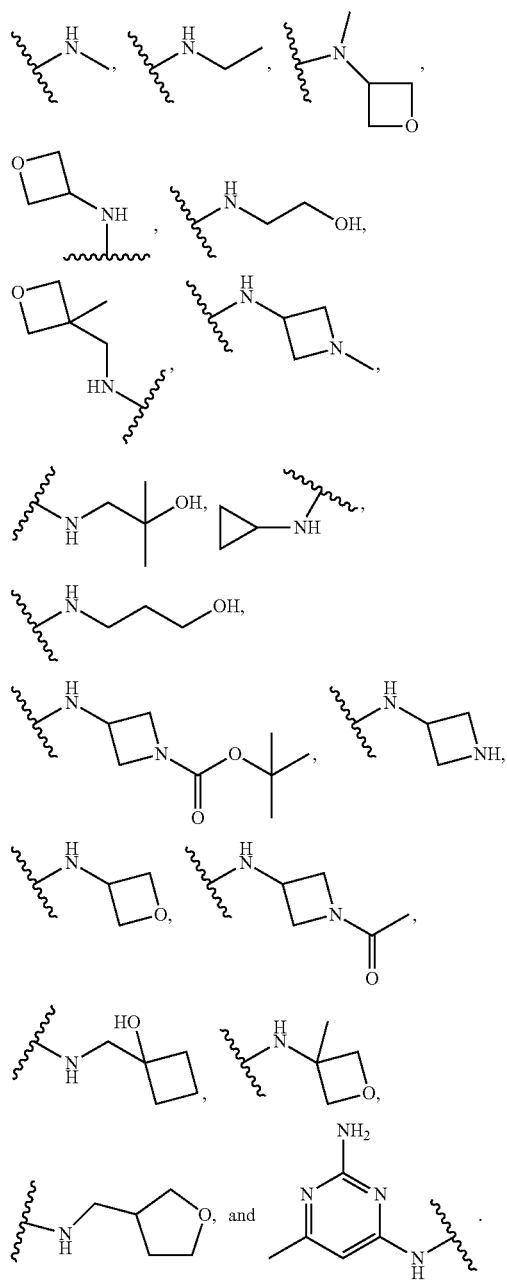

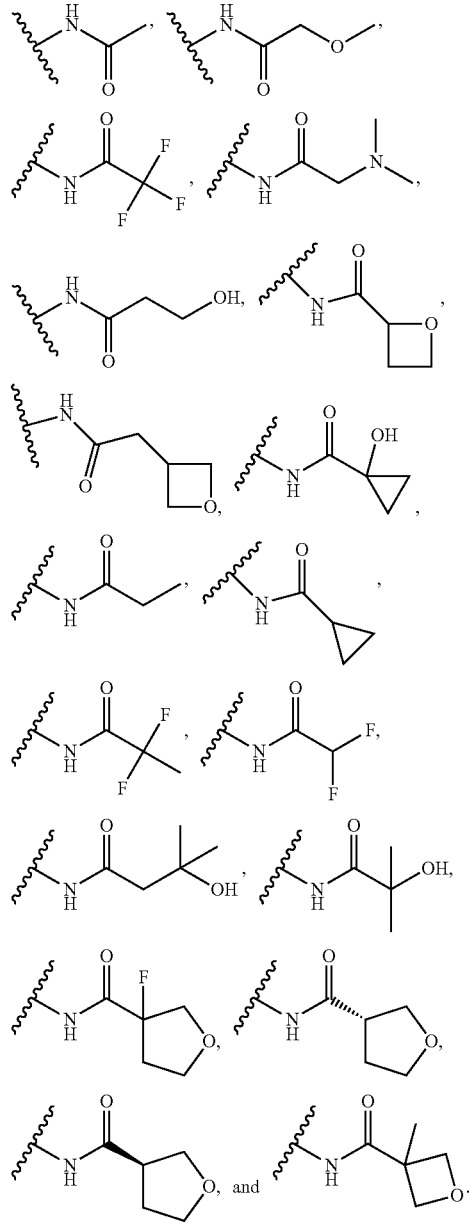

In some embodiments, R² is —NHC(O)R, wherein R is C₁₋₆ aliphatic optionally substituted 1-3 times by halogen, —OCH₃, —N(CH₃)₂, or —OH, 3-6 membered saturated monocyclic carbocyclic ring optionally substituted 1-2 times by halogen or —OH, or 4-6 membered saturated monocyclic heterocyclic ring having 1-2 heteroatoms independently selected from nitrogen, oxygen or sulfur optionally substituted 1-2 times by halogen, —OH, or —CH₃. In some embodiments, R² is selected from In some embodiments, R² is —NHC(O)R, wherein R is C₁₋₆ aliphatic optionally substituted 1-3 times by halogen, —OCH₃, —N(CH₃)₂, or —OH. In some embodiments, C₁₋₆ aliphatic is a straight-chain (i.e., unbranched) or branched, substituted or unsubstituted saturated hydrocarbon chain. In some embodiments, C₁₋₆ aliphatic is a straight-chain (i.e., unbranched) or branched, substituted or unsubstituted hydrocarbon chain comprising a monocyclic hydrocarbon. In some embodiments, C₁₋₆ aliphatic is selected from

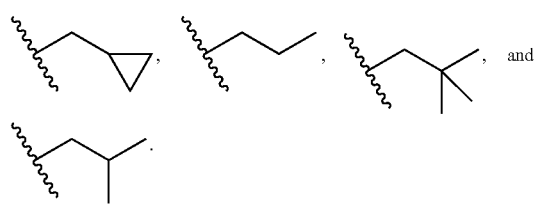

In some embodiments, $R^2$ is selected from

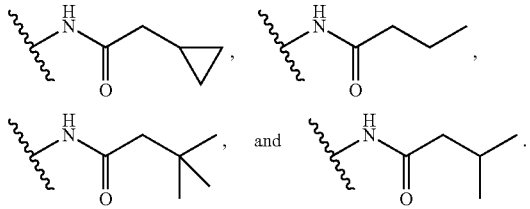

In some embodiments, $R^2$ is —NHC(O)OR, wherein R is unsubstituted $C_{1-6}$ aliphatic. In some embodiments, $R^2$ is

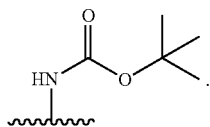

In some embodiments, $R^2$ is —NHS(O)$_2$R, wherein R is unsubstituted $C_{1-6}$ aliphatic. In some embodiments, $R^2$ is

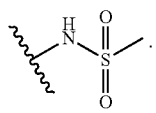

In some embodiments, $R^2$ is —OR, wherein R is H; $C_{1-6}$ aliphatic optionally substituted by a halogen, —OH,

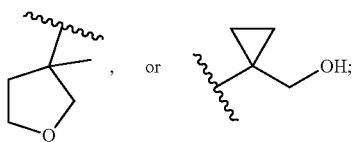

or 4-6 membered saturated monocyclic heterocyclic ring having 1-2 heteroatoms independently selected from nitrogen or oxygen. In some embodiments, $R^2$ is selected from —OH,

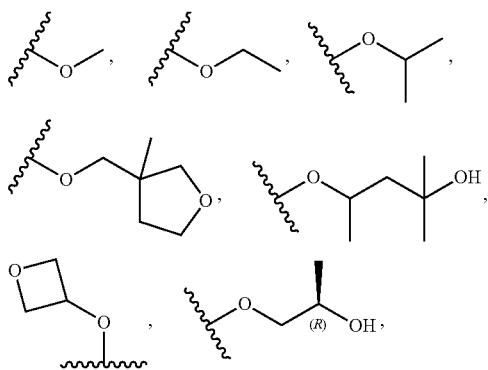

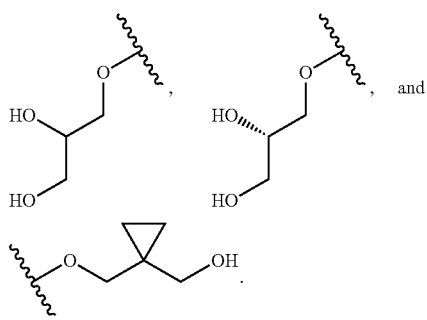

In some embodiments, $R^2$ is —OR, wherein R is $C_{1-6}$ aliphatic optionally substituted by a halogen, —OH,

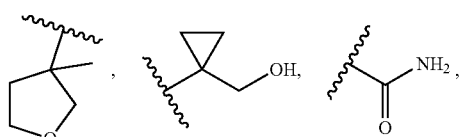

—C(O)NHC$_{1-4}$aliphatic, —COOH, —C(O)OC$_{1-4}$aliphatic, —CN, —SO$_2$C$_{1-4}$aliphatic, or

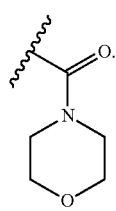 [SMILES: *C(=O)N1CCOCC1]

In some embodiments, $R^2$ is selected from

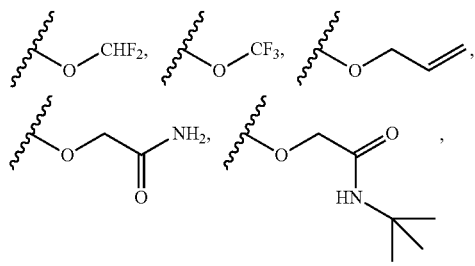

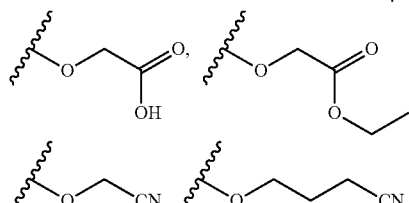

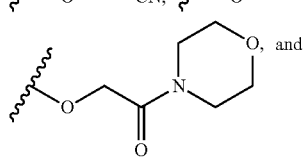

-continued

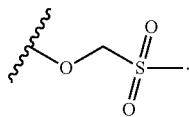

In some embodiments, $R^2$ is —OR, wherein R is unsubstituted $C_{1-6}$ aliphatic. In some embodiments, $R^2$ is —O—CH$_2$—C≡CH.

In some embodiments, $R^2$ is —P(O)R$_2$, wherein each of R is independently unsubstituted $C_{1-6}$ aliphatic. In some embodiments, $R^2$ is

In some embodiments, $R^2$ is —SR, wherein R is unsubstituted $C_{1-6}$ aliphatic. In some embodiments, $R^2$ is

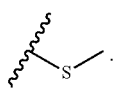

In some embodiments, $R^2$ is —S(O)R, wherein R is unsubstituted $C_{1-6}$ aliphatic. In some embodiments, $R^2$ is

In some embodiments, $R^2$ is —S(O)$_2$R, where R is unsubstituted $C_{1-6}$ aliphatic or 3-6 membered saturated monocyclic carbocyclic ring. In some embodiments, $R^2$ is selected from

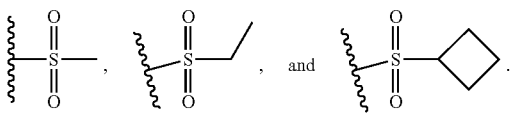

In some embodiments, $R^2$ is —S(O)(NH)R, wherein R is unsubstituted $C_{1-6}$ aliphatic. In some embodiments, $R^2$ is

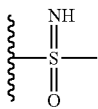

In some embodiments, $R^2$ is a group that increases hydrophilicity. In some embodiments, $R^2$ is selected from the group consisting of —NO$_2$, —C(O)OR, —C(O)NR$_2$, —NR$_2$, —NRC(O)R, —NRC(O)OR, —NRS(O)$_2$R, —OR, —P(O)R$_2$, —SR, —S(O)R, —S(O)$_2$R, —S(O)(NH)R, or a $C_{1-6}$ aliphatic group wherein one or more methylene unit is replaced by —C(O)—, —S(O)—, —S(O)$_2$—, —P(O)—, or —P(O)$_2$—. In some embodiments, $R^2$ is a $C_{1-6}$ aliphatic group wherein one or more methylene unit is replaced by —C(O)—, —S(O)—, —S(O)$_2$—, —P(O)—, or —P(O)$_2$—. In some embodiments, $R^2$ is a $C_{1-6}$ aliphatic group wherein one or more methylene unit is replaced by —S(O)$_2$—. In some embodiments, $R^2$ is selected form the group consisting of

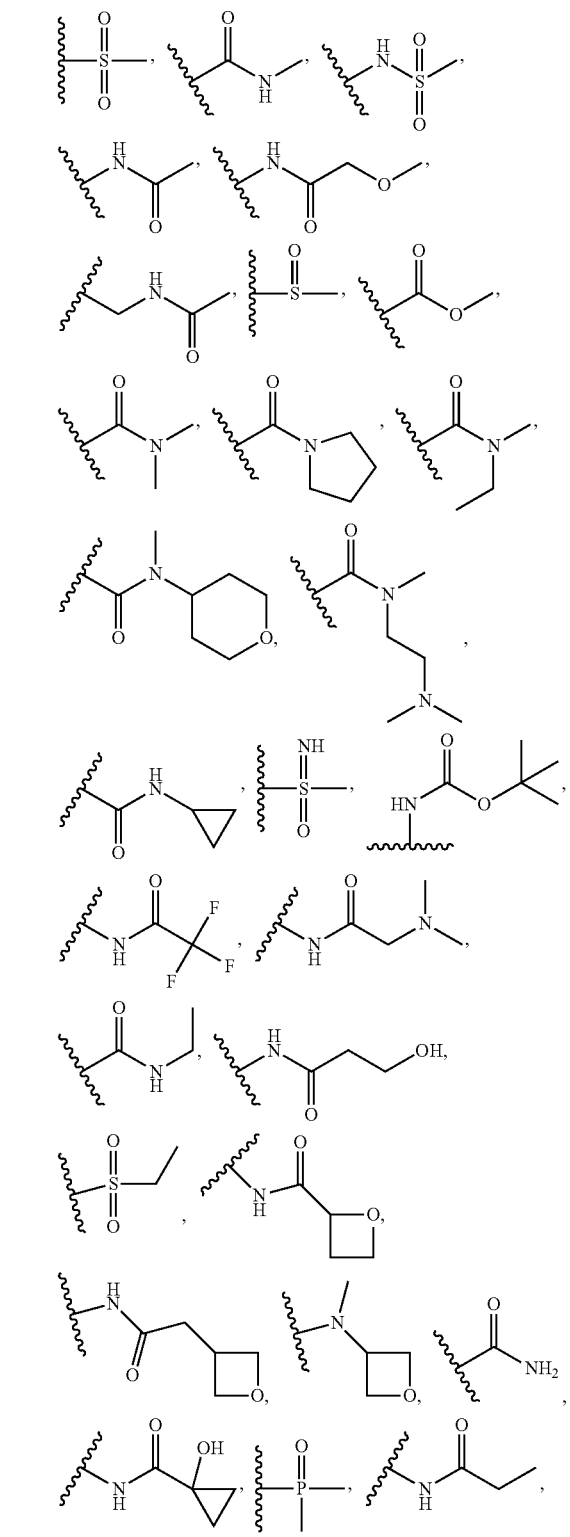

-continued

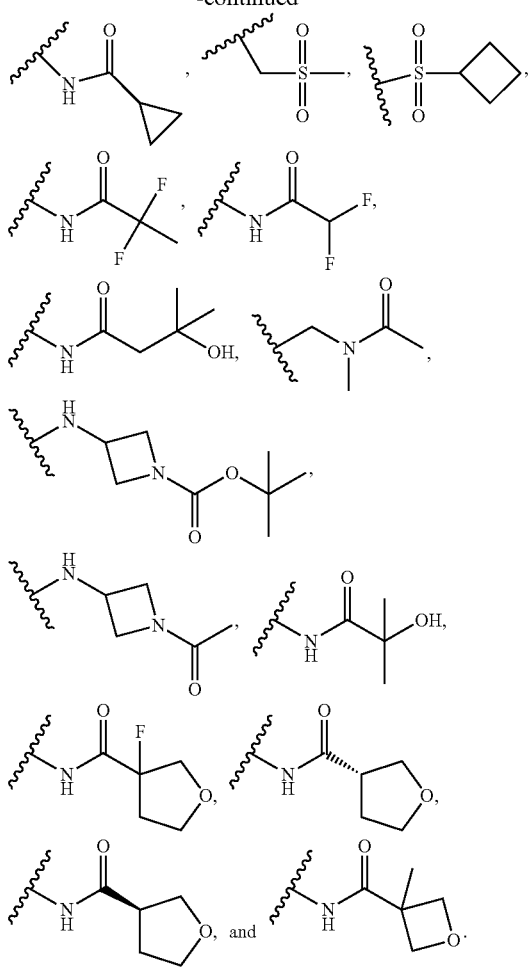

In some embodiments, $R^2$ is selected from the group consisting of

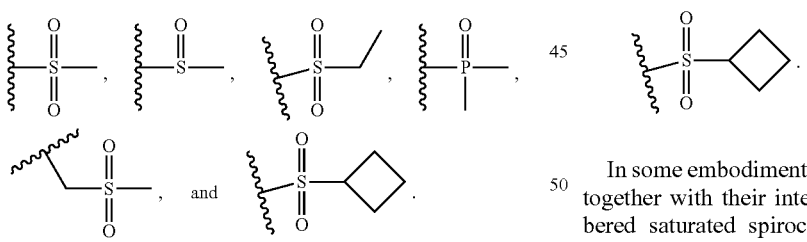

In some embodiments, $R^2$ is selected from the group consisting of

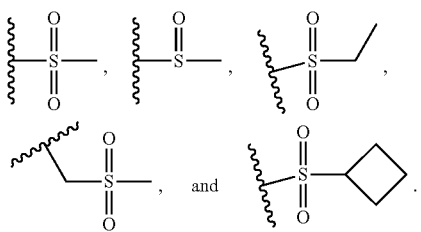

In some embodiments, $R^2$ is selected from the group consisting of

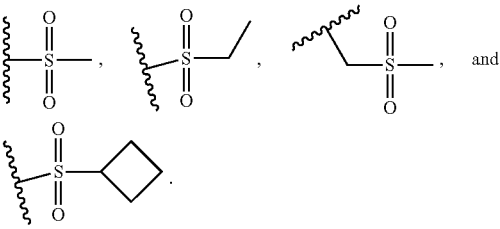

In some embodiments, $R^2$ is

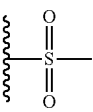

In some embodiments, $R^2$ is

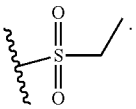

In some embodiments, $R^2$ is

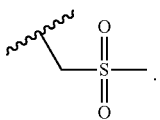 [SMILES: *CS(C)(=O)=O]

In some embodiments, $R^2$ is

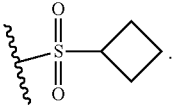 [SMILES: *S(=O)(=O)C1CCC1]

In some embodiments, two $R^2$ groups are optionally taken together with their intervening atoms to form a 3-8 membered saturated spirocyclic ring having 0-2 heteroatoms independently selected from nitrogen, oxygen or sulfur. In some embodiments, two $R^2$ groups are optionally taken together with their intervening atoms to form a 3-8 membered saturated spirocyclic carbocyclic ring. In some embodiments, two $R^2$ groups are optionally taken together with their intervening atoms to form a 3-membered saturated spirocyclic carbocyclic ring. In some embodiments, two $R^2$ groups are optionally taken together with their intervening atoms to form a 4-, 5-, or 6-membered saturated spirocyclic carbocyclic ring.

In some embodiments, two $R^2$ groups are attached at the same position. In some embodiments, two $R^2$ groups are attached to a carbon atom. In some embodiments, each of two $R^2$ groups attached to a carbon atom is independently an optionally substituted $C_{1-6}$ aliphatic group, as described herein. In some embodiments, each of two $R^2$ groups attached to a carbon atom is independently unsubstituted $C_{1-6}$ aliphatic. In some embodiments, each of two $R^2$ groups attached to a carbon atom is independently unsubstituted $C_{1-6}$ alkyl. In some embodiments, each of two $R^2$ groups attached to a carbon atom is methyl.

In some embodiments, $R^2$ is selected from those depicted in Tables 1 and 2, below.

In some embodiments, $R^2$ is selected from those depicted in Table 2A, below.

As defined generally above, each $R^3$ is independently hydrogen or $C_{1-3}$ aliphatic; or:
  two $R^3$ groups are optionally taken together to form =O;
  two $R^3$ groups are optionally taken together to form =CH$_2$;
  two $R^3$ groups are optionally taken together with their intervening atoms to form a 5-8 membered saturated spirocyclic ring having 0-2 heteroatoms independently selected from nitrogen, oxygen or sulfur; or
  two $R^3$ groups are optionally taken together with their intervening atoms to form a 5-8 membered saturated bridged bicyclic ring having 0-2 heteroatoms independently selected from nitrogen, oxygen or sulfur.

In some embodiments, $R^3$ is hydrogen. In some embodiments, $R^3$ is $C_{1-3}$ aliphatic; or:
  two $R^3$ groups are optionally taken together to form =O;
  two $R^3$ groups are optionally taken together to form =CH$_2$;
  two $R^3$ groups are optionally taken together with their intervening atoms to form a 5-8 membered saturated spirocyclic ring having 0-2 heteroatoms independently selected from nitrogen, oxygen or sulfur; or
  two $R^3$ groups are optionally taken together with their intervening atoms to form a 5-8 membered saturated bridged bicyclic ring having 0-2 heteroatoms independently selected from nitrogen, oxygen or sulfur.

In some embodiments, $R^3$ is $C_{1-3}$ aliphatic. In some embodiments, two $R^3$ groups are optionally taken together to form =O. In some embodiments, two $R^3$ groups are optionally taken together to form =CH$_2$. In some embodiments, two $R^3$ groups are optionally taken together with their intervening atoms to form a 5-8 membered saturated spirocyclic ring having 0-2 heteroatoms independently selected from nitrogen, oxygen or sulfur. In some embodiments, two $R^3$ groups are optionally taken together with their intervening atoms to form a 5-8 membered saturated bridged bicyclic ring having 1-2 heteroatoms independently selected from nitrogen, oxygen or sulfur.

In some embodiments, $R^3$ is methyl. In some embodiments, $R^3$ is ethyl. In some embodiments, $R^3$ is propyl. In some embodiments, $R^3$ is isopropyl.

In some embodiments, two $R^3$ groups are optionally taken together with their intervening atoms to form a 5 membered saturated spirocyclic ring having 0-2 heteroatoms independently selected from nitrogen, oxygen or sulfur. In some embodiments, two $R^3$ groups are optionally taken together with their intervening atoms to form a 5 membered saturated spirocyclic ring having 0-2 oxygen atoms. In some embodiments, two $R^3$ groups are optionally taken together with their intervening atoms to form

which forms a spirocyclic ring on the carbon atom at position 2.

In some embodiments, two $R^3$ groups are optionally taken together with their intervening atoms to form a 5-8 membered saturated bridged bicyclic ring having 1-2 heteroatoms independently selected from nitrogen and oxygen. In some embodiments, two $R^3$ groups are optionally taken together with their intervening atoms to form a saturated bridged bicyclic ring having 1-2 nitrogen atoms, wherein the saturated bridged bicyclic ring comprises a 6 membered ring and a 7 membered ring. In some embodiments, two $R^3$ groups together with

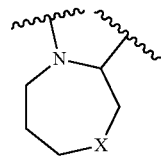

optionally form

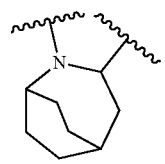

In some embodiments, $R^3$ is —OH.

In some embodiments, two $R^3$ groups are optionally taken together with their intervening atoms to form a 3-8 membered saturated spirocyclic ring having 0-2 heteroatoms independently selected from nitrogen, oxygen or sulfur. In some embodiments, two $R^3$ groups are optionally taken together with their intervening atoms to form a 3- or 4-membered saturated spirocyclic ring having 0-2 heteroatoms independently selected from nitrogen, oxygen or sulfur. In some embodiments, two $R^3$ groups are optionally taken together with their intervening atoms to form a 3- or 4-membered saturated spirocyclic carbocyclic ring. In some embodiments, two $R^3$ groups are optionally taken together with their intervening atoms to form a 3-membered saturated spirocyclic carbocyclic ring.

In some embodiments, $R^3$ is selected from those depicted in Tables 1 and 2, below.

In some embodiments, $R^3$ is selected from those depicted in Table 2A, below.

As defined generally above, each R is independently hydrogen or an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups.

In some embodiments, R is hydrogen. In some embodiments, each R is independently an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups.

In some embodiments, R is an optionally substituted $C_{1-6}$ aliphatic. In some embodiments, R is an optionally substituted 3-8 membered saturated or partially unsaturated monocyclic carbocyclic ring. In some embodiments, R is an optionally substituted phenyl. In some embodiments, R is an optionally substituted 7-10 membered saturated spirobicyclic heterocyclic ring having 1-2 heteroatoms independently selected from nitrogen, oxygen, or sulfur. In some embodiments, R is an optionally substituted 7-10 membered saturated or partially unsaturated fused bicyclic heterocyclic ring having 1-2 heteroatoms independently selected from nitrogen, oxygen, or sulfur. In some embodiments, R is an optionally substituted 4-8 membered saturated or partially unsaturated monocyclic heterocyclic ring having 1-2 heteroatoms independently selected from nitrogen, oxygen, or sulfur. In some embodiments, R is an optionally substituted 5-6 membered monocyclic heteroaromatic ring having 1-4 heteroatoms independently selected from nitrogen, oxygen, or sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups.

In some embodiments, R is selected from those depicted in Tables 1 and 2, below.

In some embodiments, R is selected from those depicted in Table 2A, below.

As defined generally above, X is —O—, —N(R)—, —N(S(O)$_2$(R))—, —S—, —S(O)—, —S(O)$_2$—, —CH$_2$—, —CH(R$^3$)—, or —C(R$^3$)$_2$—.

In some embodiments, X is —O—. In some embodiments, X is —N(R)—. In some embodiments, X is —N(S(O)$_2$(R))—. In some embodiments, X is S. In some embodiments, X is —S(O)—. In some embodiments, X is —S(O)$_2$—. In some embodiments, X is —CH$_2$—. In some embodiments, X is —CH(R$^3$)—. In some embodiments, X is —C(R$^3$)$_2$—.

In some embodiments, X is —N(S(O)$_2$(R))—, wherein R is $C_{1-6}$ aliphatic. In some embodiments, X is —N(S(O)$_2$CH$_3$)—. In some embodiments, X is —CH(R$^3$)—, wherein R$^3$ is $C_{1-6}$ aliphatic. In some embodiments, X is —CH(CH$_3$)—. In some embodiments, X is —C(R$^3$)$_2$—, wherein R$^3$ is $C_{1-6}$ aliphatic. In some embodiments, X is —C(CH$_3$)$_2$—.

In some embodiments, X is selected from those depicted in Tables 1 and 2, below.

In some embodiments, X is selected from those depicted in Table 2A, below.

As defined generally above, m is 0, 1, or 2.

In some embodiments, m is 0. In some embodiments, m is 1. In some embodiments, m is 2.

In some embodiments, m is selected from those depicted in Tables 1 and 2, below.

In some embodiments, m is selected from those depicted in Table 2A, below.

As defined generally above, n is 0, 1, 2, 3, 4 or 5.

In some embodiments, n is 0. In some embodiments, n is 1. In some embodiments, n is 2. In some embodiments, n is 3. In some embodiments, n is 4. In some embodiments, n is 5.

In some embodiments, n is selected from those depicted in Tables 1 and 2, below.

In some embodiments, n is selected from those depicted in Table 2A, below.

As defined generally above, p is 0, 1, or 2.

In some embodiments, p is 0. In some embodiments, p is 1. In some embodiments, p is 2.

In some embodiments, p is selected from those depicted in Tables 1 and 2, below.

In some embodiments, p is selected from those depicted in Table 2A, below.

In some embodiments, the present invention provides a compound of Formulae I-a or I-b:

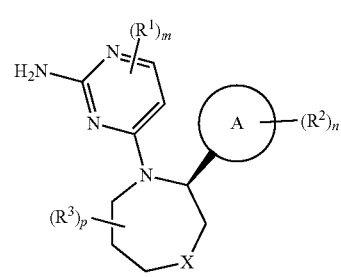

I-a

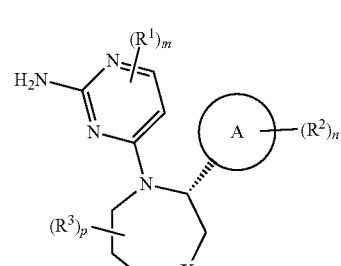

I-b or a pharmaceutically acceptable salt thereof, wherein each of Ring A, $R^1$, $R^2$, $R^3$, R, X, m, n, and p is as defined above and described in embodiments herein, both singly and in combination.

In some embodiments, the present invention provides a compound of Formula II:

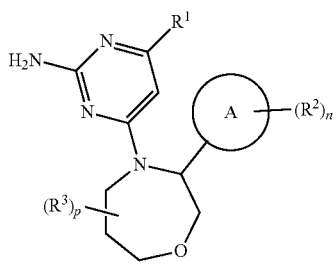

II or a pharmaceutically acceptable salt thereof, wherein each of Ring A, $R^1$, $R^2$, $R^3$, R, n, and p is as defined above and described in embodiments herein, both singly and in combination.

In some embodiments, the present invention provides a compound of Formulae II-a or II-b:

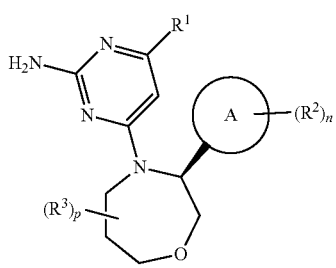

II-a

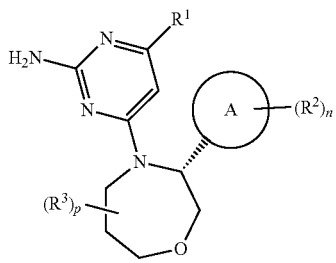

II-b or a pharmaceutically acceptable salt thereof, wherein each of Ring A, $R^1$, $R^2$, $R^3$, R, n, and p is as defined above and described in embodiments herein, both singly and in combination.

In some embodiments, the present invention provides a compound of Formula III

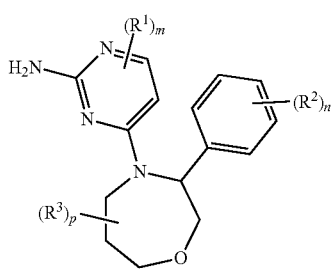

III or a pharmaceutically acceptable salt thereof, wherein each of $R^1$, $R^2$, $R^3$, R, m, n, and p is as defined above and described in embodiments herein, both singly and in combination.

In some embodiments, the present invention provides a compound of Formulae III-a or III-b:

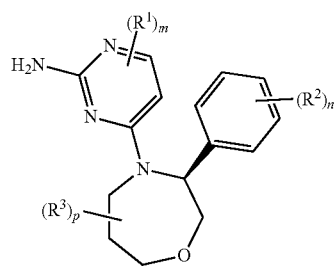

III-a

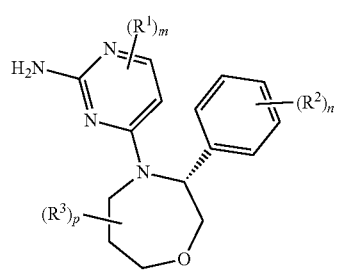

III-b or a pharmaceutically acceptable salt thereof, wherein each of $R^1$, $R^2$, $R^3$, R, m, n, and p is as defined above and described in embodiments herein, both singly and in combination.

In some embodiments, the present invention provides a compound of Formula IV

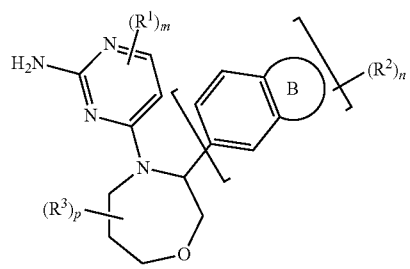

IV or a pharmaceutically acceptable salt thereof, wherein each of Ring B, $R^1$, $R^2$, $R^3$, R, m, n, and p is as defined above and described in embodiments herein, both singly and in combination.

In some embodiments, the present invention provides a compound of Formulae IV-a or IV-b:

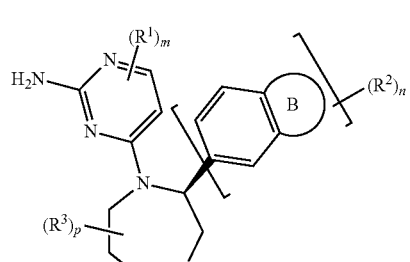

IV-a

-continued

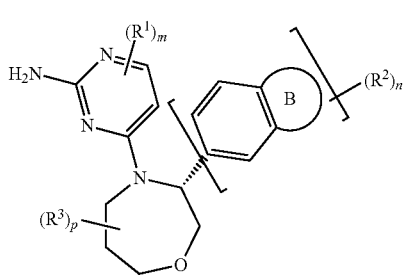

IV-b or a pharmaceutically acceptable salt thereof, wherein each of Ring B, $R^1$, $R^2$, $R^3$, R, m, n, and p is as defined above and described in embodiments herein, both singly and in combination.

In some embodiments, the present invention provides a compound of Formula V

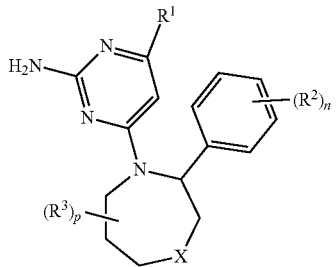

V or a pharmaceutically acceptable salt thereof, wherein each of $R^1$, $R^2$, $R^3$, R, X, n, and p is as defined above and described in embodiments herein, both singly and in combination.

In some embodiments, the present invention provides a compound of Formulae V-a or V-b:

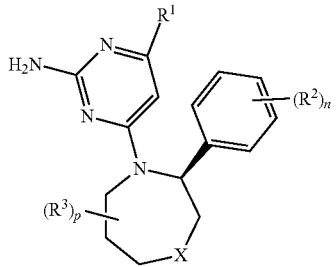

V-a


V-b or a pharmaceutically acceptable salt thereof, wherein each of $R^1$, $R^2$, $R^3$, R, X, n, and p is as defined above and described in embodiments herein, both singly and in combination.

In some embodiments, the present invention provides a compound of Formula VI

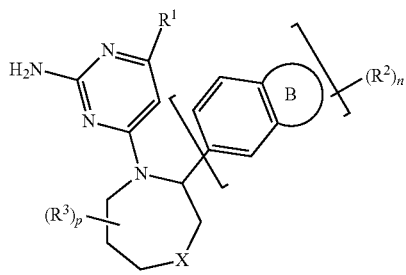

VI or a pharmaceutically acceptable salt thereof, wherein each of Ring B, $R^1$, $R^2$, $R^3$, R, X, n, and p is as defined above and described in embodiments herein, both singly and in combination.

In some embodiments, the present invention provides a compound of Formulae VI-a or VI-b:

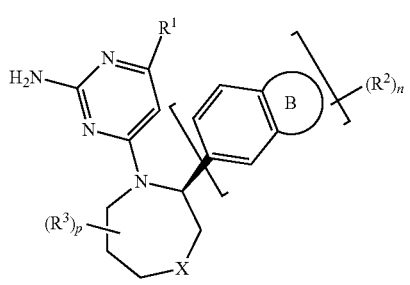

VI-a

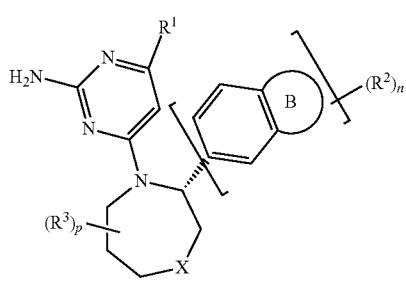

VI-b or a pharmaceutically acceptable salt thereof, wherein each of Ring B, $R^1$, $R^2$, $R^3$, R, X, n, and p is as defined above and described in embodiments herein, both singly and in combination.

In some embodiments, the present invention provides a compound of Formula VII

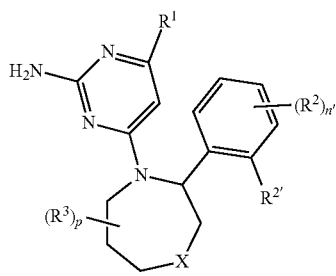

VII or a pharmaceutically acceptable salt thereof, wherein n' is 1 or 2, and $R^{2'}$ is halogen or —$OC_{1-3}$ aliphatic, and wherein each of $R^1$, $R^2$, $R^3$, R, X, and p is as defined above and described in embodiments herein, both singly and in combination. In some embodiments, n' is 1. In some embodiments, n' is 2. In some embodiments, $R^{2'}$ is F. In some embodiments, $R^{2'}$ is Cl. In some embodiments, $R^{2'}$ is Br. In some embodiments, $R^{2'}$ is I. In some embodiments, $R^{2'}$ is —$OCH_3$. In some embodiments, $R^{2'}$ is —$OC_2H_5$. In some embodiments, $R^{2'}$ is —$OCH_2CH_2CH_3$. In some embodiments, $R^{2'}$ is —$OCH(CH_3)_2$.

In some embodiments, n is selected from those depicted in tables 1, 2, and 2A, below.

In some embodiments, $R^{2'}$ is selected from those depicted in tables 1, 2, and 2A, below.

In some embodiments, the present invention provides a compound of Formulae VII-a or VII-b:

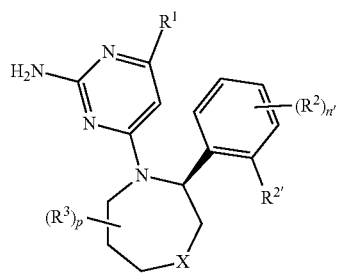

VII-a

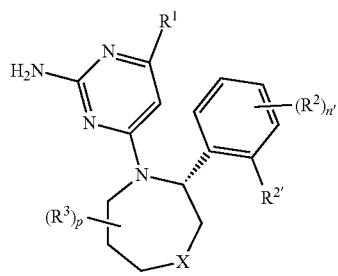

VII-b or a pharmaceutically acceptable salt thereof, wherein each of $R^1$, $R^2$, $R^{2'}$, $R^3$, R, X, p, and n' is as defined above and described in embodiments herein, both singly and in combination.

In some embodiments, the present invention provides a compound of Formula VIII:

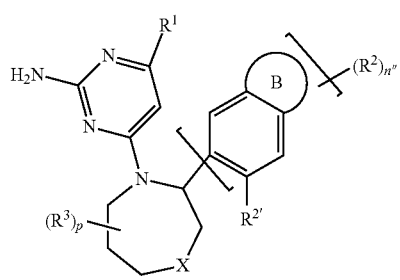

VIII or a pharmaceutically acceptable salt thereof, wherein n" is 0, 1, 2, 3, or 4, and wherein each of Ring B, $R^1$, $R^2$, $R^{2'}$, $R^3$, R, X, and p is as defined above and described in embodiments herein, both singly and in combination.

In some embodiments, n" is 0. In some embodiments, n" is 1. In some embodiments, n" is 2. In some embodiments, n" is 3. In some embodiments, n" is 4.

In some embodiments, n" is selected from those depicted in tables 1, 2, and 2A, below.

In some embodiments, the present invention provides a compound of Formulae VIII-a or VIII-b:

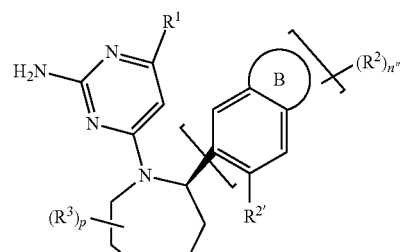

VIII-a

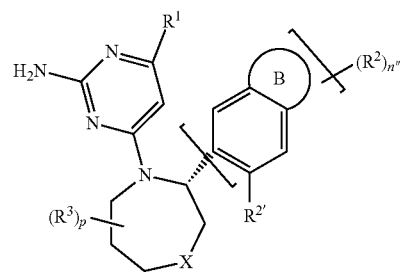

VIII-b or a pharmaceutically acceptable salt thereof, wherein each of Ring B, $R^1$, $R^2$, $R^{2'}$, $R^3$, R, X, p, and n" is as defined above and described in embodiments herein, both singly and in combination.

In some embodiments, the present invention provides a compound of Formula IX:

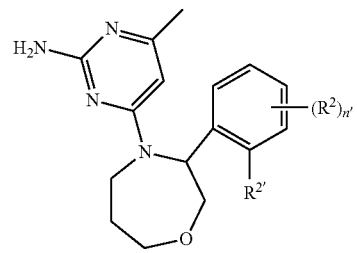

IX or a pharmaceutically acceptable salt thereof, wherein $R^{2'}$ is halogen, and each of $R^2$ and n' is as defined above and described in embodiments herein, both singly and in combination.

In some embodiments, the present invention provides a compound of Formulae IX-a or IX-b:

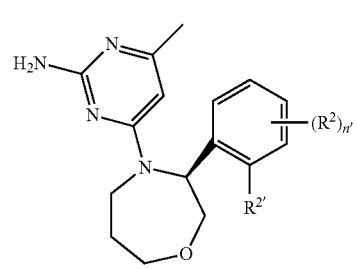

IX-a

-continued

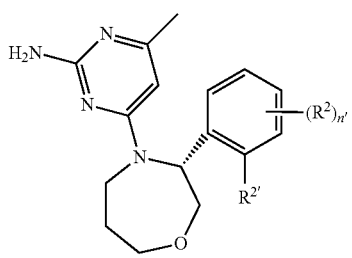
IX-b

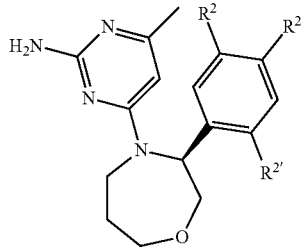
X-a

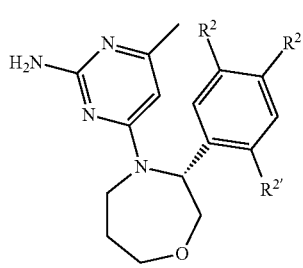
X-b or a pharmaceutically acceptable salt thereof, wherein $R^{2'}$ is halogen, and each of $R^2$ and n' is as defined above and described in embodiments herein, both singly and in combination.

In some embodiments, the present invention provides a compound of Formulas X, XI, or XII:

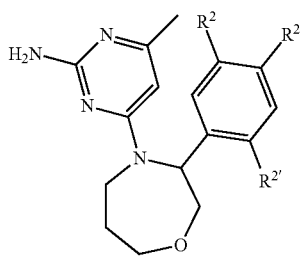
X

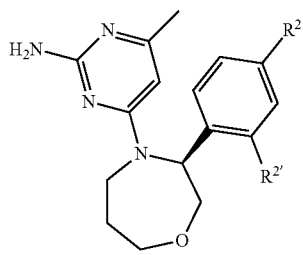
XI-a

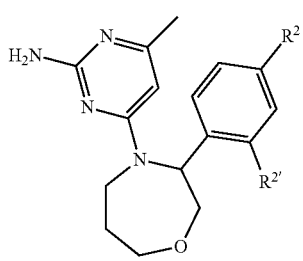
XI

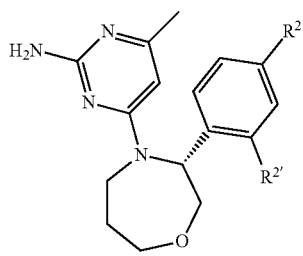
XI-b

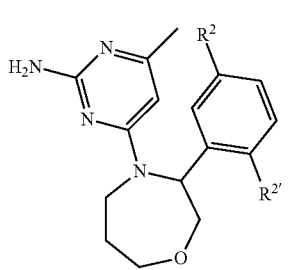
XII

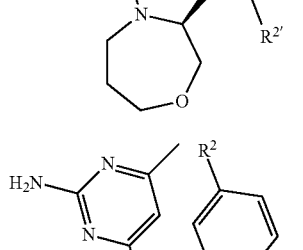
XII-a or a pharmaceutically acceptable salt thereof, wherein $R^{2'}$ is halogen, and each of $R^2$ is as defined above and described in embodiments herein, both singly and in combination.

In some embodiments, the present invention provides a compound of Formulae X-a, X-b, XI-a, XI-b, XII-a, or XII-b:

XII-b or a pharmaceutically acceptable salt thereof, wherein $R^{2'}$ is halogen, and each of $R^2$ is as defined above and described in embodiments herein, both singly and in combination.

In some embodiments, the present invention provides a compound of Formulae X, XI, XII, X-a, X-b, XI-a, XI-b, XII-a, or XII-b, as shown above, wherein $R^{2'}$ is Cl and each of $R^2$ is selected from the group consisting of halogen (e.g., Cl), $-NH_2$, $-CH_3$, $-CF_3$,
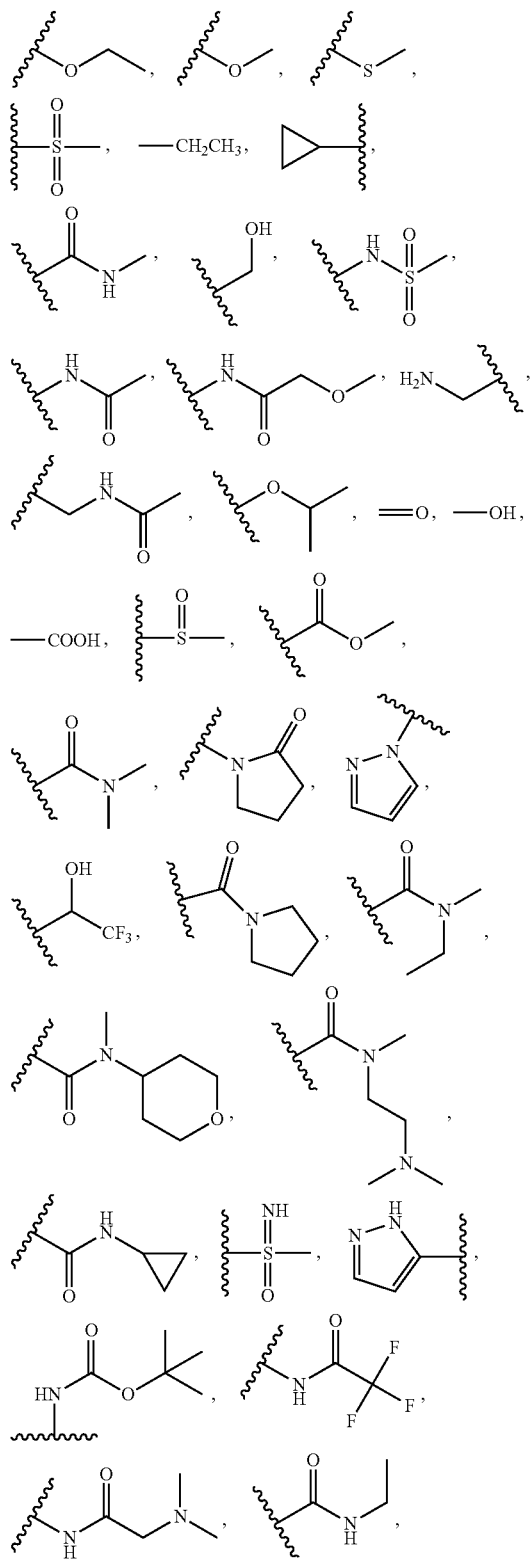
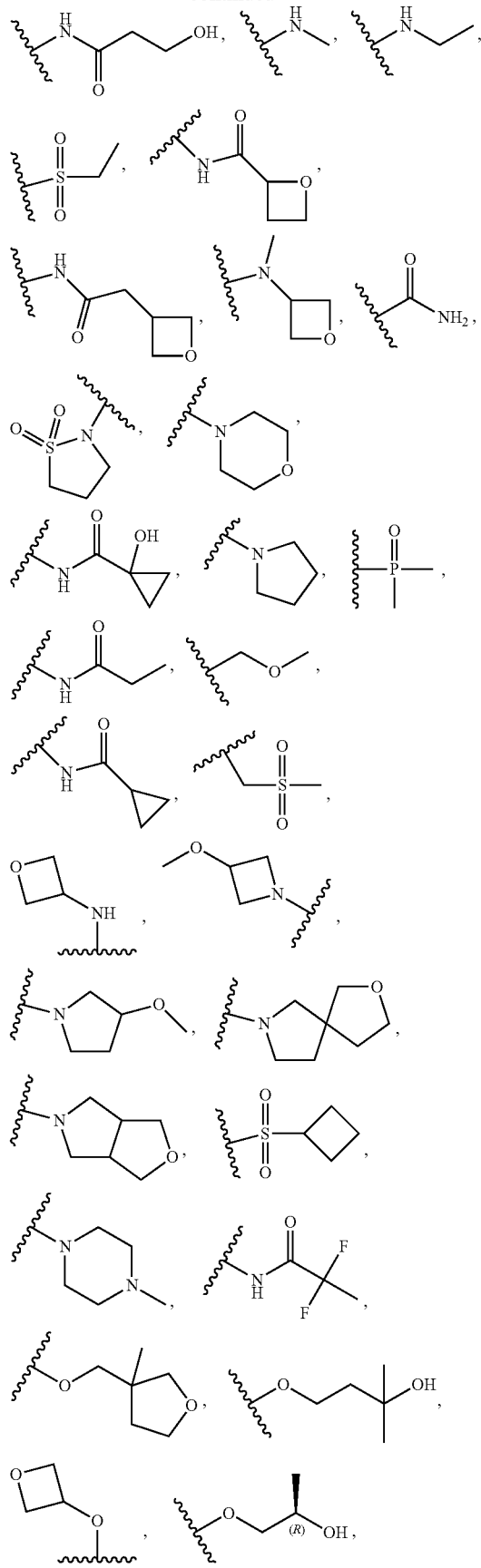

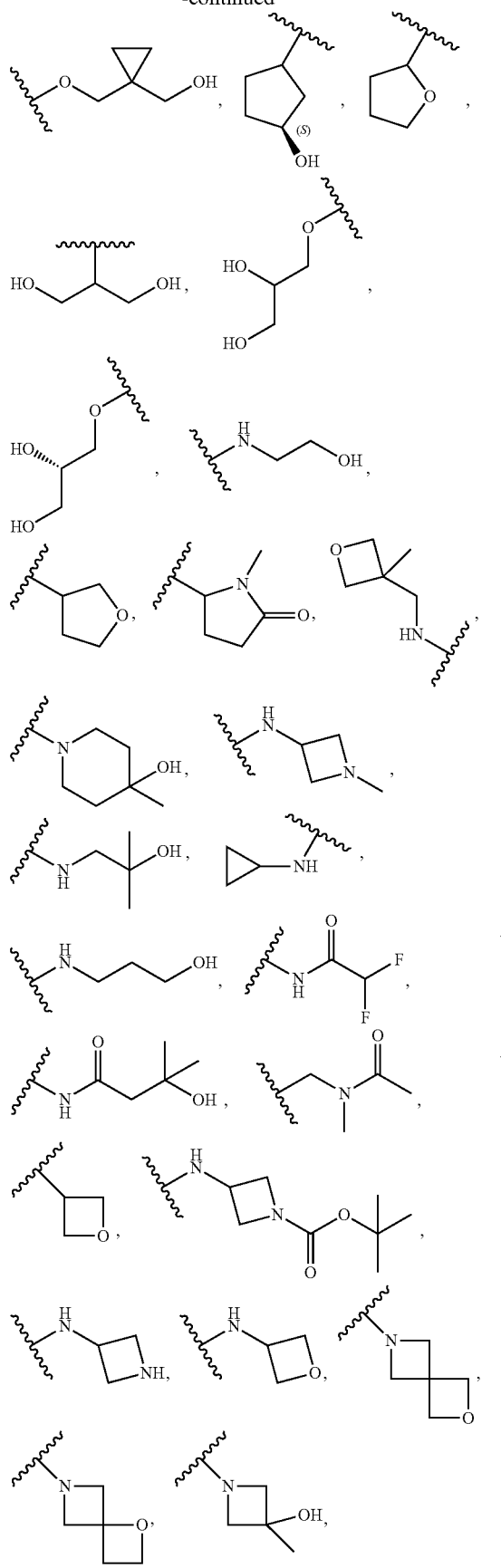
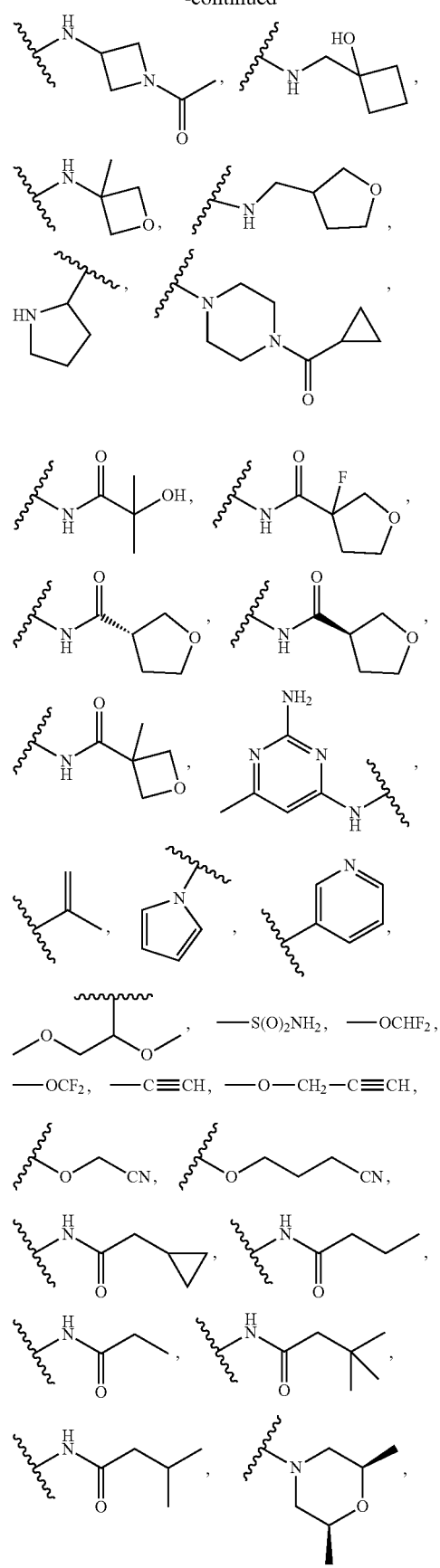

55
-continued

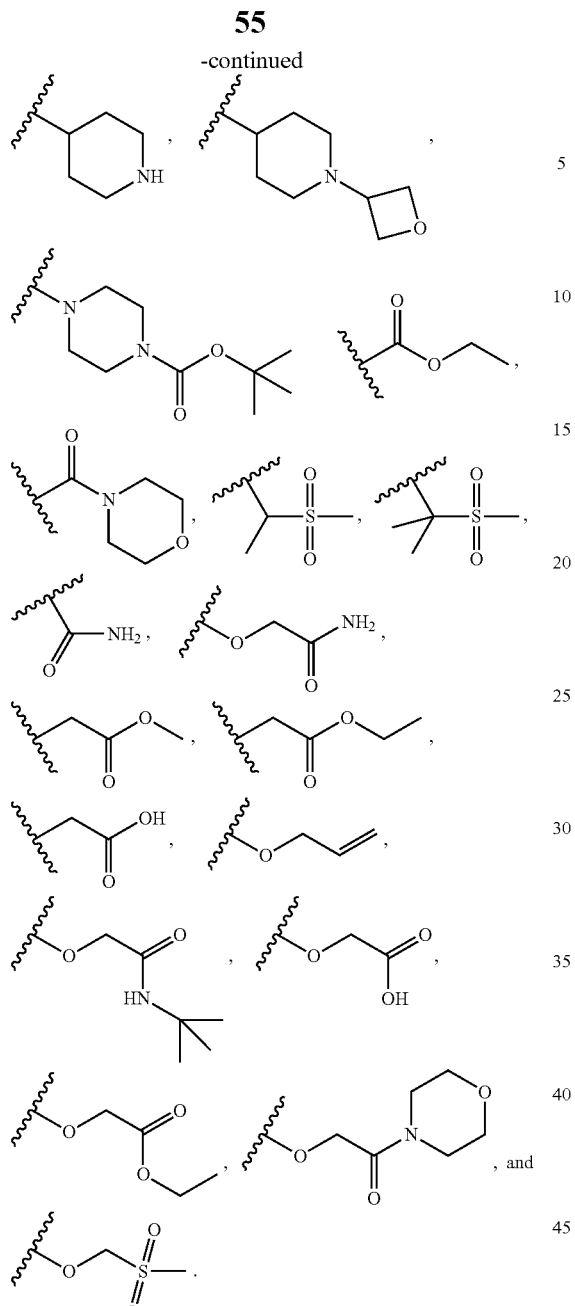

, and

In some embodiments, Exemplary compounds of the invention are set forth in Tables 1 and 2, below.

In some embodiments, Exemplary compounds of the invention are set forth in Table 2A, below.

In some embodiments, the present invention provides a compound selected from those listed in Table 1, or a pharmaceutically acceptable salt thereof.

In some embodiments, the present invention provides a compound selected from those listed in Table 2, or a pharmaceutically acceptable salt thereof.

In some embodiments, the present invention provides a compound selected from those listed in Table 2A, or a pharmaceutically acceptable salt thereof.

In some embodiments, the present invention provides a trifluoroacetate salt of compound D-150.

TABLE 1

Exemplary Compounds

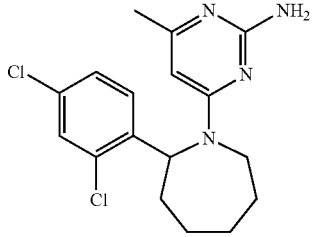 [SMILES: Cc1cc(N2CCCCCC2c2ccc(Cl)cc2Cl)nc(N)n1] I-1

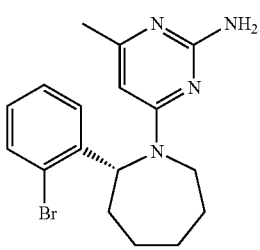 [SMILES: Cc1cc(N2CCCCC[C@@H]2c2ccccc2Br)nc(N)n1] I-2

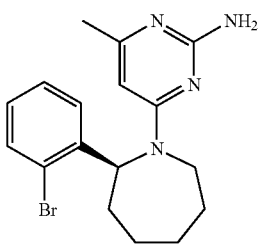 [SMILES: Cc1cc(N2CCCCC[C@H]2c2ccccc2Br)nc(N)n1] I-3

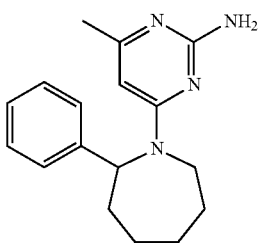 [SMILES: Cc1cc(N2CCCCCC2c2ccccc2)nc(N)n1] I-4

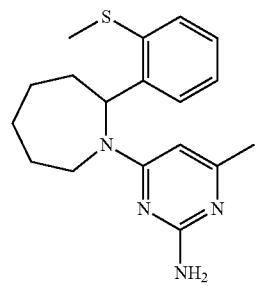 [SMILES: CSc1ccccc1C1CCCCCN1c1cc(C)nc(N)n1] I-5

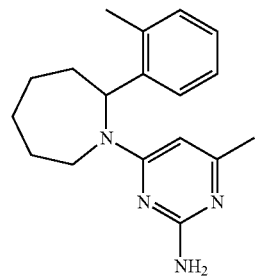 [SMILES: Cc1cc(N2CCCCCC2c2ccccc2C)nc(N)n1] I-6

TABLE 1-continued
Exemplary Compounds
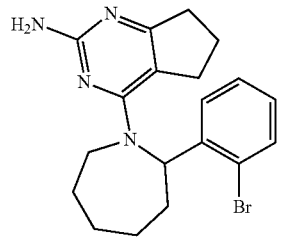 I-7
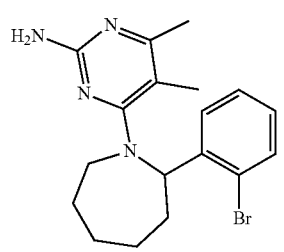 [SMILES: Cc1nc(N)nc(N2CCCCCC2c2ccccc2Br)c1C] I-8
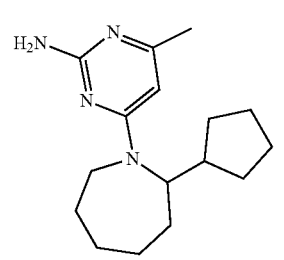 [SMILES: Cc1cc(N2CCCCCC2C2CCCC2)nc(N)n1] I-9
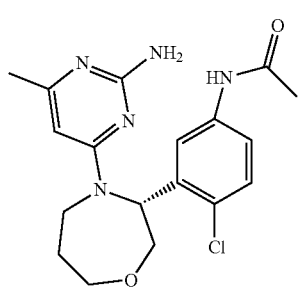 I-10
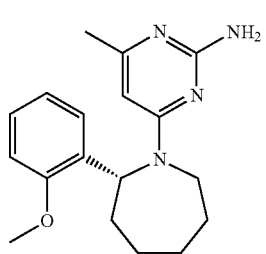 [SMILES: COc1ccccc1[C@H]1CCCCCN1c1cc(C)nc(N)n1] I-11
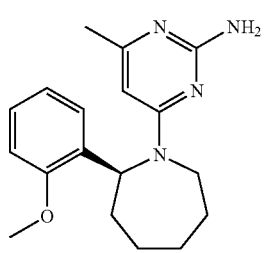 [SMILES: COc1ccccc1[C@@H]1CCCCCN1c1cc(C)nc(N)n1] I-12
TABLE 1-continued
Exemplary Compounds
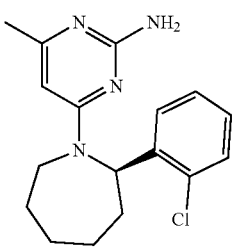 [SMILES: Cc1cc(N2CCCCC[C@@H]2c2ccccc2Cl)nc(N)n1] I-13
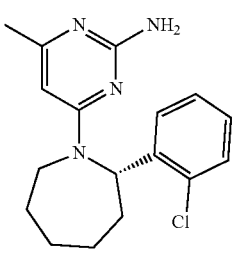 [SMILES: Cc1cc(N2CCCCC[C@H]2c2ccccc2Cl)nc(N)n1] I-14
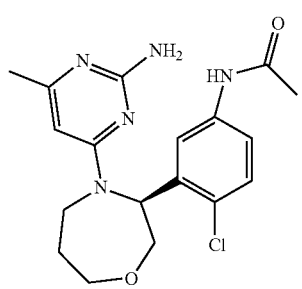 [SMILES: CC(=O)Nc1ccc(Cl)c([C@H]2COCCCN2c2cc(C)nc(N)n2)c1] I-15
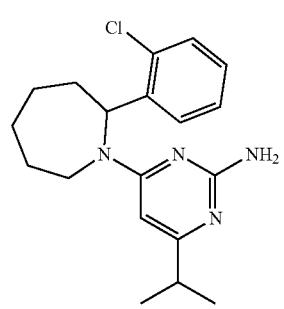 [SMILES: CC(C)c1cc(N2CCCCCC2c2ccccc2Cl)nc(N)n1] I-16
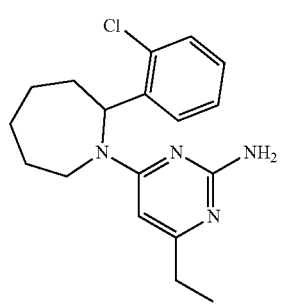 [SMILES: CCc1cc(N2CCCCCC2c2ccccc2Cl)nc(N)n1] I-17

TABLE 1-continued
Exemplary Compounds
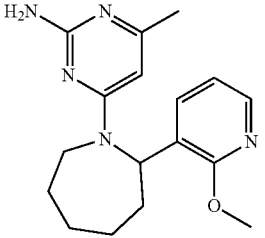 [SMILES: COc1ncccc1C1CCCCCN1c1cc(C)nc(N)n1] I-18
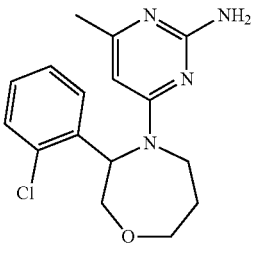 [SMILES: Cc1cc(N2CCCOCC2c2ccccc2Cl)nc(N)n1] I-19
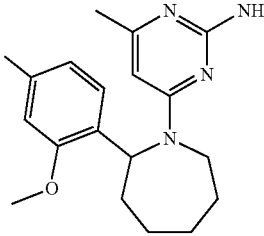 I-20
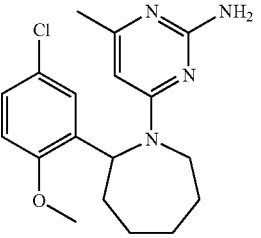 [SMILES: COc1ccc(Cl)cc1C1CCCCCN1c1cc(C)nc(N)n1] I-21
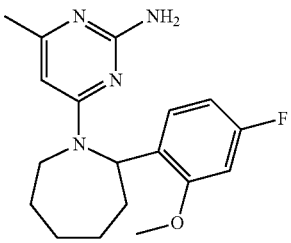 [SMILES: COc1cc(F)ccc1C1CCCCCN1c1cc(C)nc(N)n1] I-22
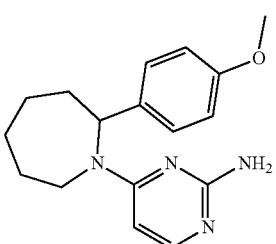 I-23
TABLE 1-continued
Exemplary Compounds
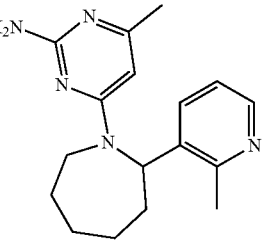 I-24
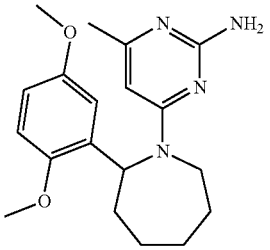 [SMILES: COc1ccc(OC)c(C2CCCCCN2c2cc(C)nc(N)n2)c1] I-25
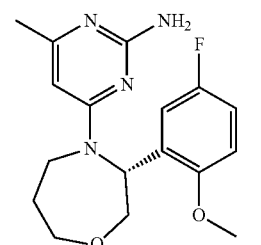 I-26
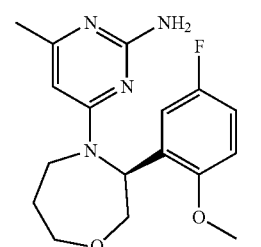 I-27
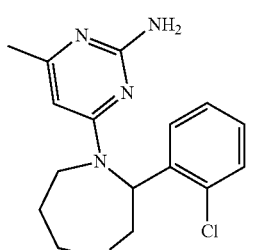 I-28
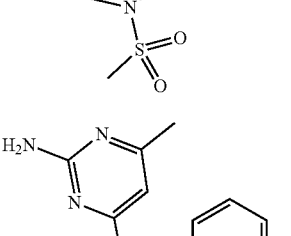 I-29

TABLE 1-continued

Exemplary Compounds

| Compound | ID |
|---|---|
| (structure) | I-30 |
| (structure) | I-31 |
| (structure) | I-32 |
| (structure) | I-33 |
| (structure) | I-34 |
| (structure) | I-35 |
| (structure) | I-36 |
| (structure) | I-37 |
| (structure) | I-38 |
| (structure) | I-39 |
| (structure) | I-40 |
| (structure) | I-41 |

TABLE 1-continued
Exemplary Compounds
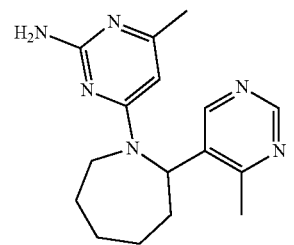 [SMILES: Cc1cc(N2CCCCCC2c2cncnc2C)nc(N)n1] I-42
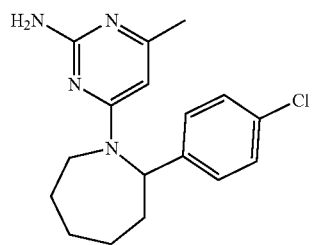 [SMILES: Cc1cc(N2CCCCCC2c2ccc(Cl)cc2)nc(N)n1] I-43
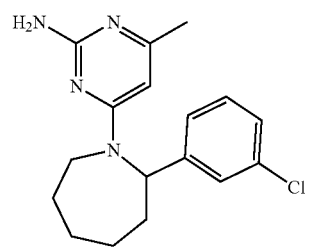 [SMILES: Cc1cc(N2CCCCCC2c2cccc(Cl)c2)nc(N)n1] I-44
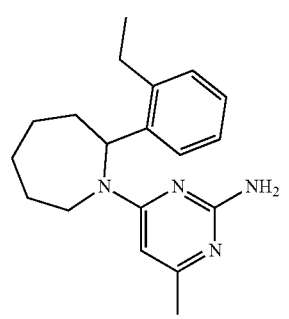 [SMILES: CCc1ccccc1C1CCCCCN1c1cc(C)nc(N)n1] I-45
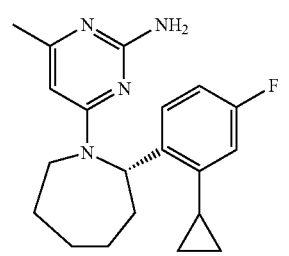 [SMILES: Cc1cc(N2CCCCC[C@H]2c2ccc(F)cc2C2CC2)nc(N)n1] I-46
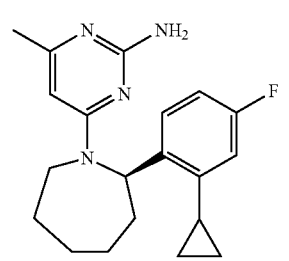 [SMILES: Cc1cc(N2CCCCC[C@@H]2c2ccc(F)cc2C2CC2)nc(N)n1] I-47
TABLE 1-continued
Exemplary Compounds
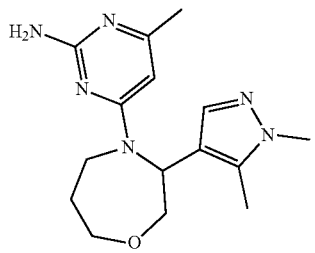 [SMILES: Cc1cc(N2CCCOCC2c2cnn(C)c2C)nc(N)n1] I-48
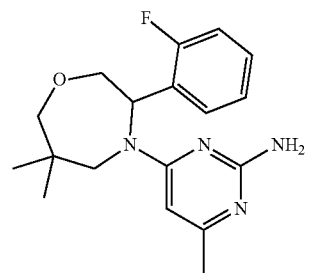 [SMILES: Cc1cc(N2CC(C)(C)COCC2c2ccccc2F)nc(N)n1] I-49
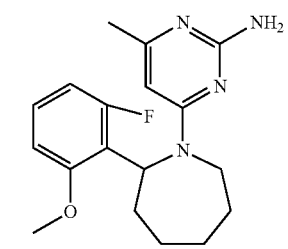 [SMILES: COc1cccc(F)c1C1CCCCCN1c1cc(C)nc(N)n1] I-50
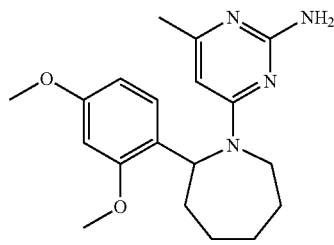 [SMILES: COc1ccc(C2CCCCCN2c2cc(C)nc(N)n2)c(OC)c1] I-51
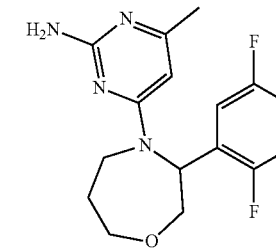 I-52
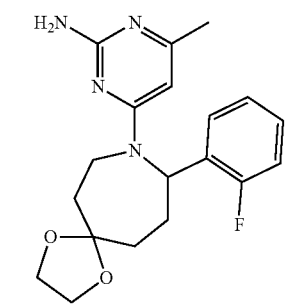 [SMILES: Cc1cc(N2CCC3(CCC2c2ccccc2F)OCCO3)nc(N)n1] I-53

TABLE 1-continued
Exemplary Compounds
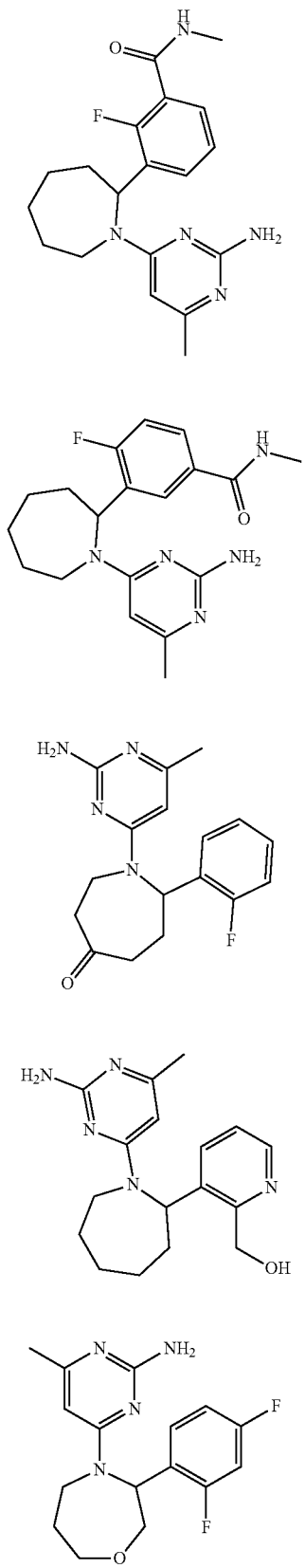
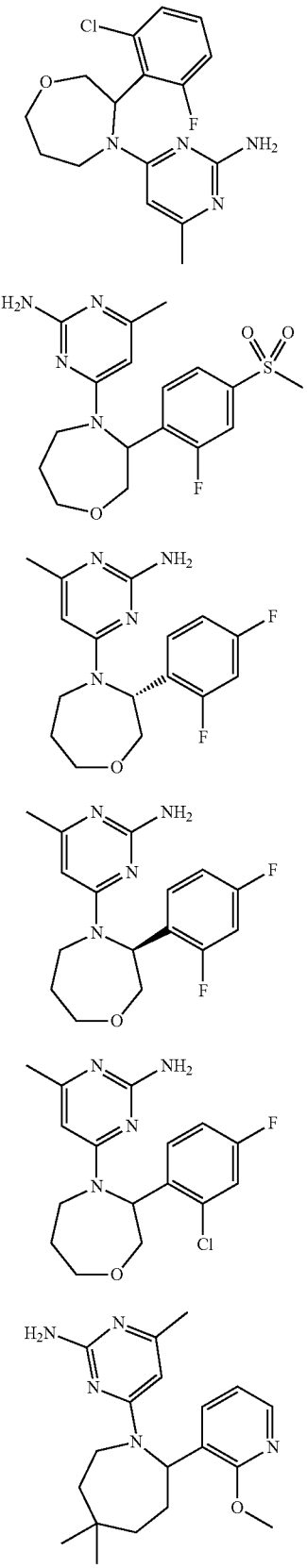

TABLE 1-continued
Exemplary Compounds
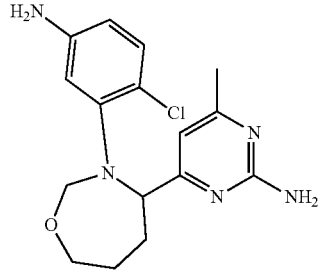 [SMILES: Cc1cc(C2CCCOCN2c2cc(N)ccc2Cl)nc(N)n1] I-65
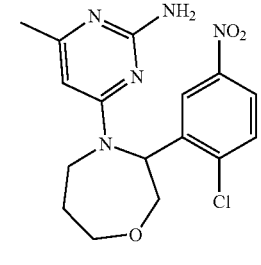 [SMILES: Cc1cc(N2CCCOCC2c2cc([N+](=O)[O-])ccc2Cl)nc(N)n1] I-66
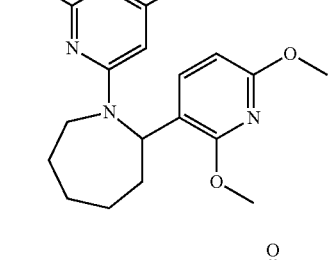 I-67
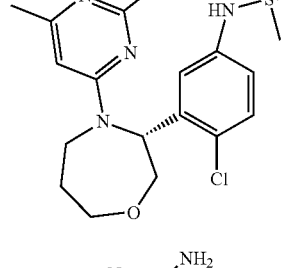 I-68
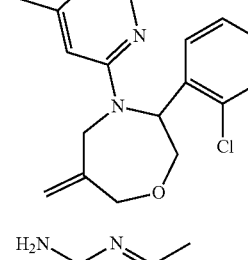 I-69
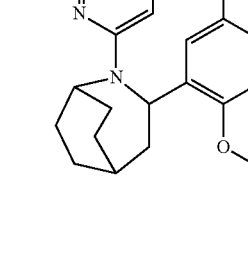 I-70
TABLE 1-continued
Exemplary Compounds
I-71
I-72
I-73
I-74
I-75
I-76

TABLE 1-continued
Exemplary Compounds
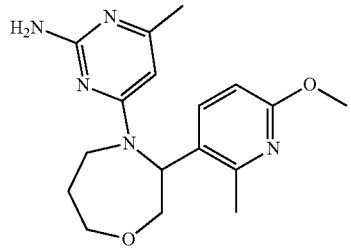 [SMILES: COc1ccc(C2COCCCN2c2cc(C)nc(N)n2)c(C)n1] I-77
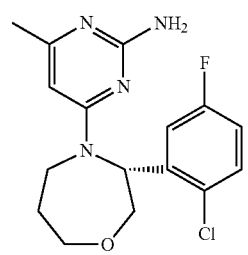 [SMILES: Cc1cc(N2CCCOC[C@H]2c2cc(F)ccc2Cl)nc(N)n1] I-78
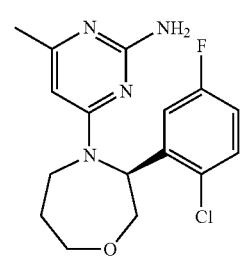 [SMILES: Cc1cc(N2CCCOC[C@@H]2c2cc(F)ccc2Cl)nc(N)n1] I-79
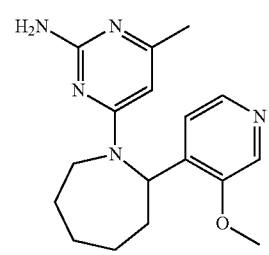 [SMILES: COc1cnccc1C1CCCCCN1c1cc(C)nc(N)n1] I-80
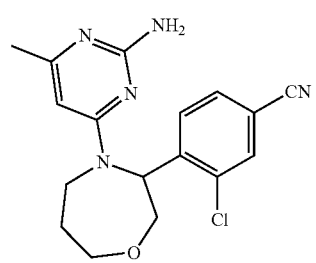 [SMILES: Cc1cc(N2CCCOCC2c2ccc(C#N)cc2Cl)nc(N)n1] I-81
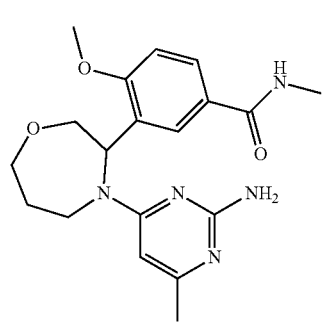 [SMILES: CNC(=O)c1ccc(OC)c(C2COCCCN2c2cc(C)nc(N)n2)c1] I-82
TABLE 1-continued
Exemplary Compounds
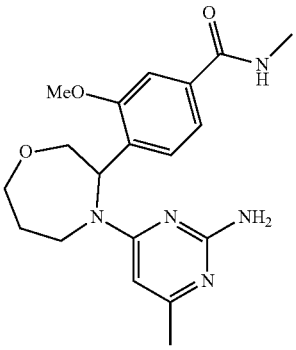 [SMILES: CNC(=O)c1ccc(C2COCCCN2c2cc(C)nc(N)n2)c(OC)c1] I-83
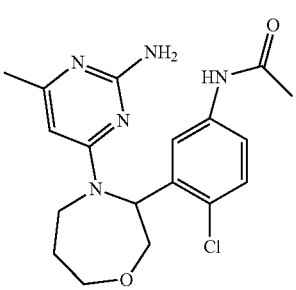 [SMILES: CC(=O)Nc1ccc(Cl)c(C2COCCCN2c2cc(C)nc(N)n2)c1] I-84
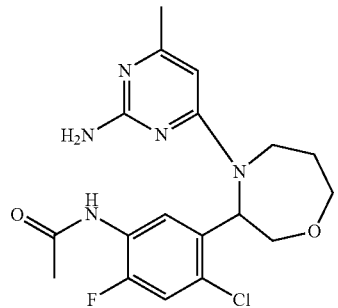 [SMILES: CC(=O)Nc1cc(C2COCCCN2c2cc(C)nc(N)n2)c(Cl)cc1F] I-85
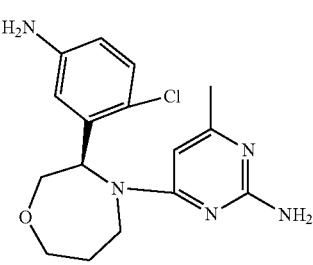 [SMILES: Cc1cc(N2CCCOC[C@H]2c2cc(N)ccc2Cl)nc(N)n1] I-86
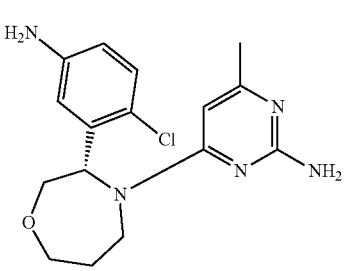 [SMILES: Cc1cc(N2CCCOC[C@@H]2c2cc(N)ccc2Cl)nc(N)n1] I-87

TABLE 1-continued
Exemplary Compounds
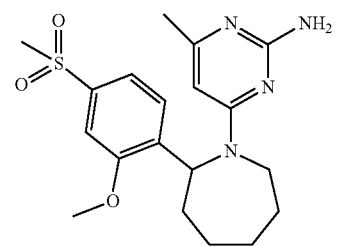 I-88
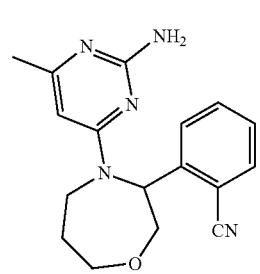 [SMILES: Cc1cc(N2CCCOCC2c2ccccc2C#N)nc(N)n1] I-89
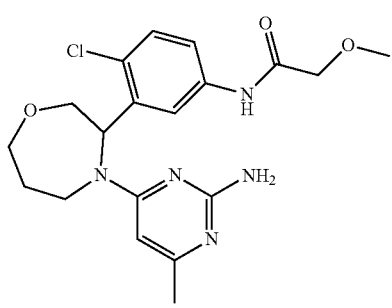 [SMILES: COCC(=O)Nc1ccc(Cl)c(C2COCCCN2c2cc(C)nc(N)n2)c1] I-90
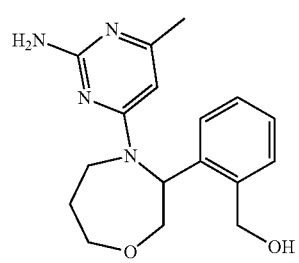 I-91
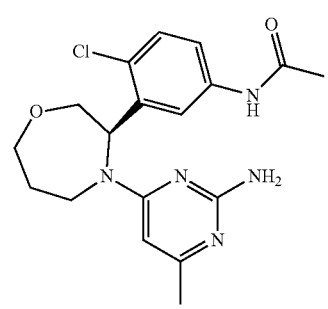 [SMILES: CC(=O)Nc1ccc(Cl)c([C@@H]2COCCCN2c2cc(C)nc(N)n2)c1] I-92
TABLE 1-continued
Exemplary Compounds
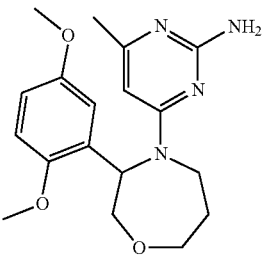 [SMILES: COc1ccc(OC)c(C2COCCCN2c2cc(C)nc(N)n2)c1] I-93
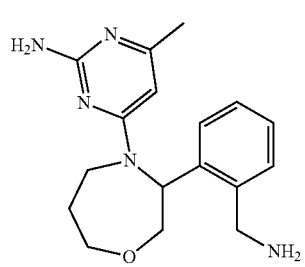 [SMILES: Cc1cc(N2CCCOCC2c2ccccc2CN)nc(N)n1] I-94
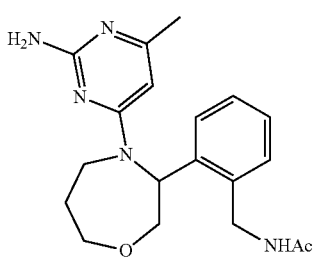 [SMILES: CC(=O)NCc1ccccc1C1COCCCN1c1cc(C)nc(N)n1] I-95
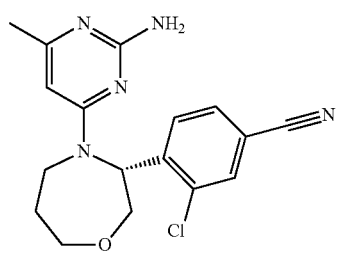 [SMILES: Cc1cc(N2CCCOC[C@H]2c2ccc(C#N)cc2Cl)nc(N)n1] I-96
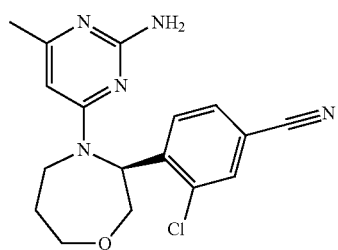 [SMILES: Cc1cc(N2CCCOC[C@@H]2c2ccc(C#N)cc2Cl)nc(N)n1] I-97
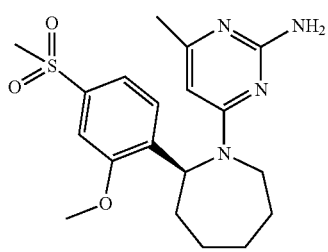 [SMILES: COc1cc(S(C)(=O)=O)ccc1[C@@H]1CCCCCN1c1cc(C)nc(N)n1] I-98

TABLE 1-continued

Exemplary Compounds

| Compound |
|---|
| I-99 |
| I-100 |
| I-101 |
| I-102 |
| I-103 |
| I-104 |
| I-105 |
| I-106 |
| I-107 |
| I-108 |
| I-109 |

TABLE 1-continued
Exemplary Compounds
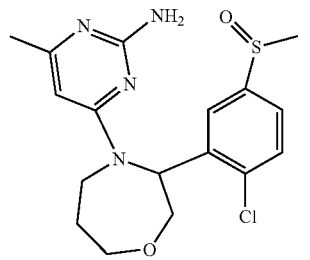 I-110
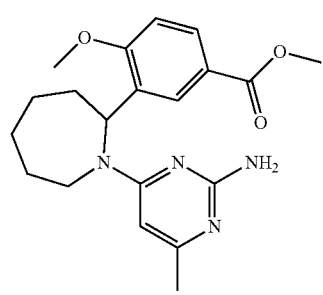 [SMILES: COC(=O)c1ccc(OC)c(C2CCCCCN2c2cc(C)nc(N)n2)c1] I-111
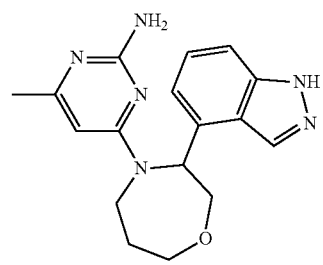 [SMILES: Cc1cc(N2CCCOCC2c2cccc3[nH]ncc23)nc(N)n1] I-112
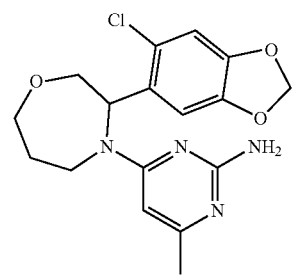 [SMILES: Cc1cc(N2CCCOCC2c2cc3c(cc2Cl)OCO3)nc(N)n1] I-113
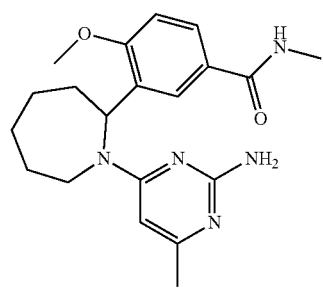 [SMILES: CNC(=O)c1ccc(OC)c(C2CCCCCN2c2cc(C)nc(N)n2)c1] I-114
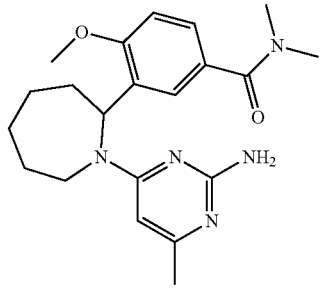 [SMILES: COc1ccc(C(=O)N(C)C)cc1C1CCCCCN1c1cc(C)nc(N)n1] I-115
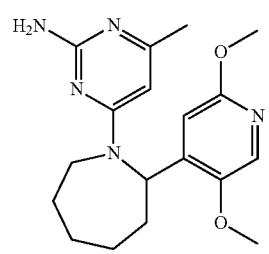 [SMILES: COc1cc(C2CCCCCN2c2cc(C)nc(N)n2)c(OC)cn1] I-116
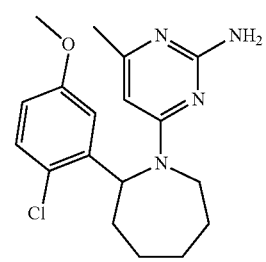 [SMILES: COc1ccc(Cl)c(C2CCCCCN2c2cc(C)nc(N)n2)c1] I-117
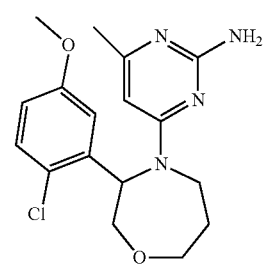 [SMILES: COc1ccc(Cl)c(C2COCCCN2c2cc(C)nc(N)n2)c1] I-118
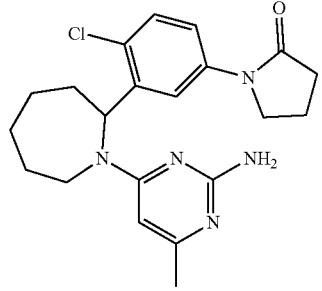 [SMILES: Cc1cc(N2CCCCCC2c2cc(N3CCCC3=O)ccc2Cl)nc(N)n1] I-119

TABLE 1-continued
Exemplary Compounds
| | |
|---|---|
| 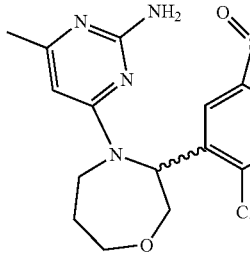 | I-120 |
| 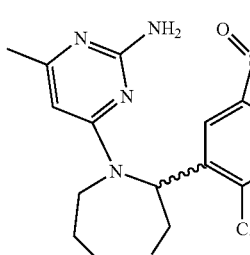 | I-121 |
| 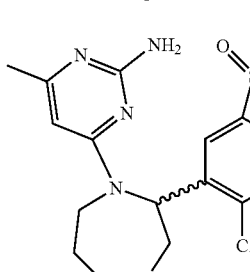 | I-122 |
| 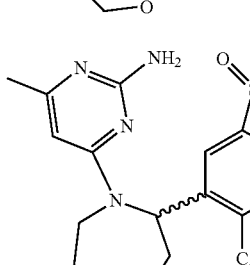 | I-123 |
| 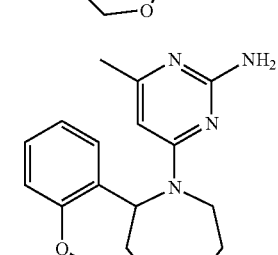 | I-124 |
| 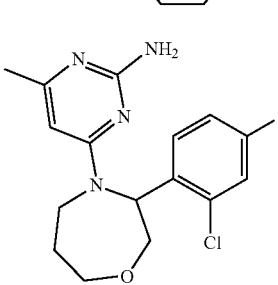 | I-125 |
TABLE 1-continued
Exemplary Compounds
| | |
|---|---|
| | I-126 |
| | I-127 |
| | I-128 |
| | I-129 |
| | I-130 |

TABLE 1-continued

Exemplary Compounds

TABLE 1-continued
Exemplary Compounds
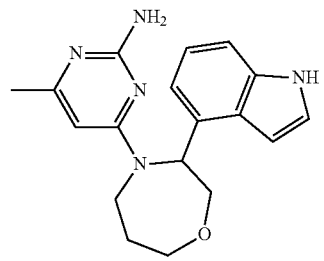 [SMILES: Cc1cc(N2CCCOCC2c2cccc3[nH]ccc23)nc(N)n1] I-142
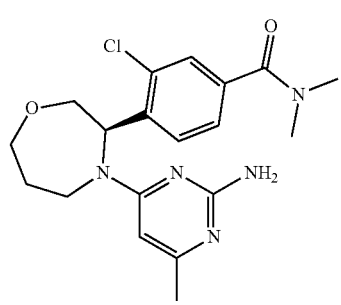 [SMILES: Cc1cc(N2CCCOC[C@H]2c2ccc(C(=O)N(C)C)cc2Cl)nc(N)n1] I-143
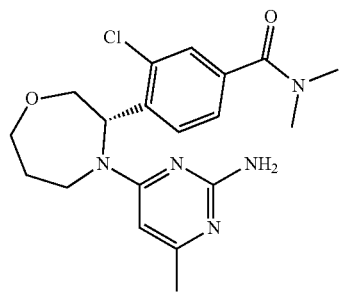 [SMILES: Cc1cc(N2CCCOC[C@@H]2c2ccc(C(=O)N(C)C)cc2Cl)nc(N)n1] I-144
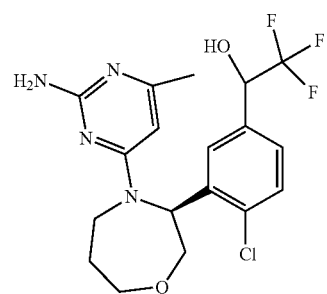 [SMILES: Cc1cc(N2CCCOC[C@@H]2c2cc(C(O)C(F)(F)F)ccc2Cl)nc(N)n1] I-145
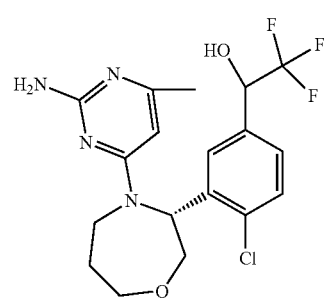 [SMILES: Cc1cc(N2CCCOC[C@H]2c2cc(C(O)C(F)(F)F)ccc2Cl)nc(N)n1] I-146
TABLE 1-continued
Exemplary Compounds
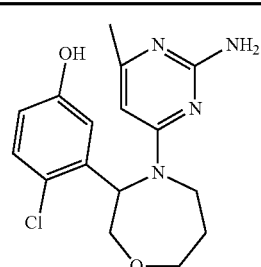 I-147
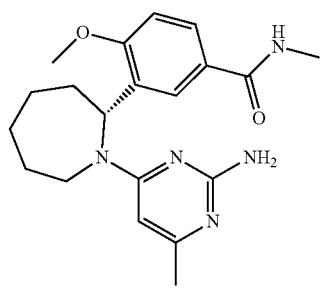 [SMILES: CNC(=O)c1ccc(OC)c([C@H]2CCCCCN2c2cc(C)nc(N)n2)c1] I-148
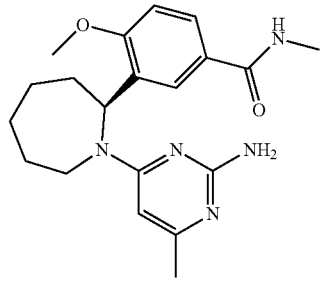 [SMILES: CNC(=O)c1ccc(OC)c([C@@H]2CCCCCN2c2cc(C)nc(N)n2)c1] I-149
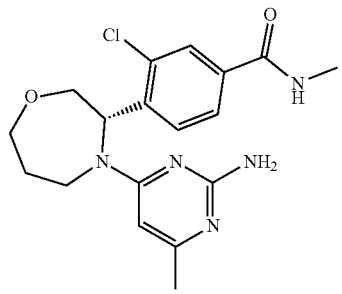 [SMILES: CNC(=O)c1ccc([C@H]2COCCCN2c2cc(C)nc(N)n2)c(Cl)c1] I-150
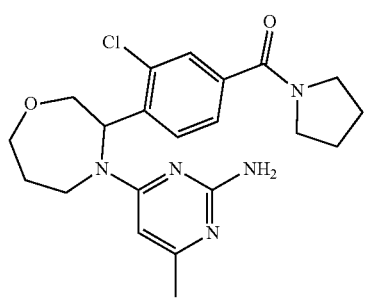 [SMILES: Cc1cc(N2CCCOCC2c2ccc(C(=O)N3CCCC3)cc2Cl)nc(N)n1] I-151

TABLE 1-continued

Exemplary Compounds

I-152

I-153

I-154

I-155

I-156

I-157

I-158

I-159

I-160

I-161

TABLE 1-continued
Exemplary Compounds
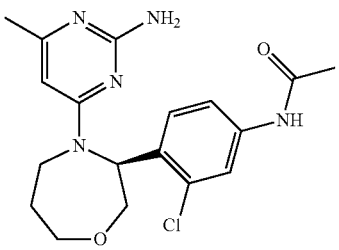 [SMILES: CC(=O)Nc1ccc([C@H]2COCCCN2c2cc(C)nc(N)n2)c(Cl)c1] I-162
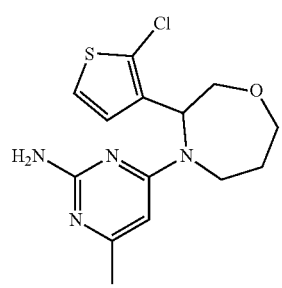 [SMILES: Cc1cc(N2CCCOCC2c2ccsc2Cl)nc(N)n1] I-163
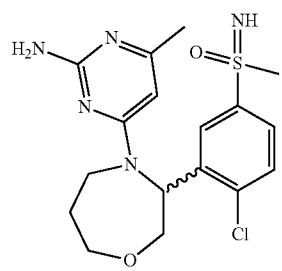 [SMILES: Cc1cc(N2CCCOCC2c2cc(S(C)(=N)=O)ccc2Cl)nc(N)n1] I-164
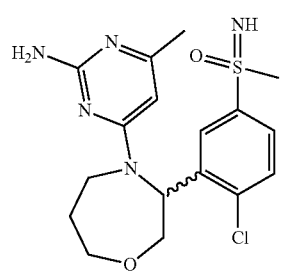 [SMILES: Cc1cc(N2CCCOCC2c2cc(S(C)(=N)=O)ccc2Cl)nc(N)n1] I-165
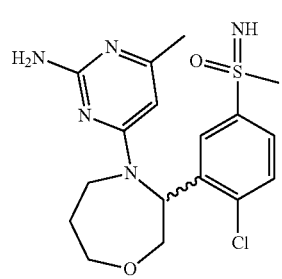 [SMILES: Cc1cc(N2CCCOCC2c2cc(S(C)(=N)=O)ccc2Cl)nc(N)n1] I-166
TABLE 1-continued
Exemplary Compounds
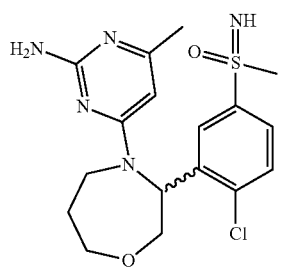 I-167
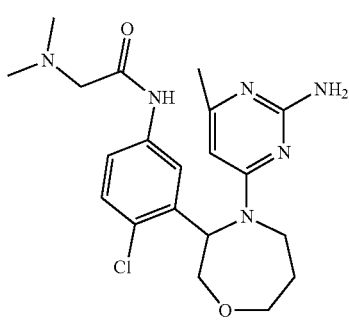 [SMILES: Cc1cc(N2CCCOCC2c2cc(NC(=O)CN(C)C)ccc2Cl)nc(N)n1] I-168
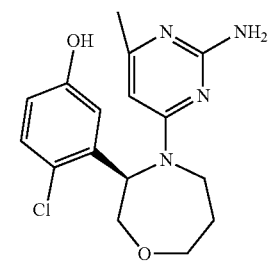 [SMILES: Cc1cc(N2CCCOC[C@H]2c2cc(O)ccc2Cl)nc(N)n1] I-169
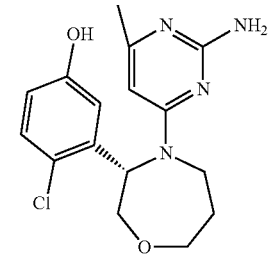 [SMILES: Cc1cc(N2CCCOC[C@@H]2c2cc(O)ccc2Cl)nc(N)n1] I-170
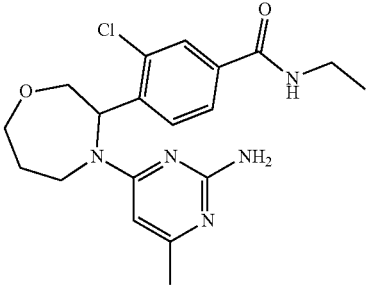 [SMILES: CCNC(=O)c1ccc(C2COCCCN2c2cc(C)nc(N)n2)c(Cl)c1] I-171

TABLE 1-continued
Exemplary Compounds
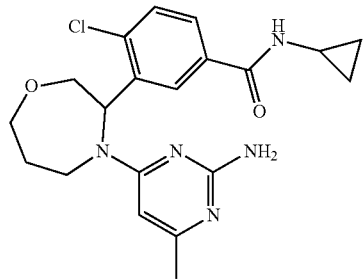 [SMILES: Cc1cc(N2CCCOCC2c2cc(C(=O)NC3CC3)ccc2Cl)nc(N)n1]
I-172
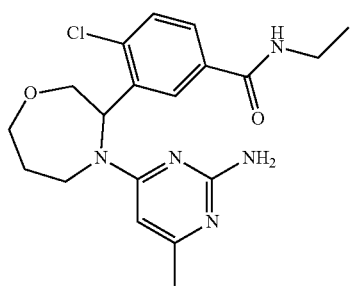 [SMILES: CCNC(=O)c1ccc(Cl)c(C2COCCCN2c2cc(C)nc(N)n2)c1]
I-173
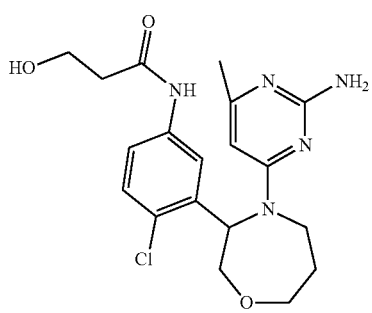 [SMILES: Cc1cc(N2CCCOCC2c2cc(NC(=O)CCO)ccc2Cl)nc(N)n1]
I-174
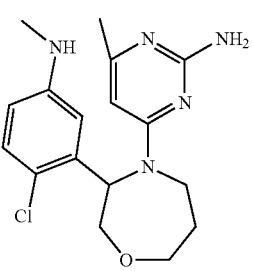 [SMILES: CNc1ccc(Cl)c(C2COCCCN2c2cc(C)nc(N)n2)c1]
I-175
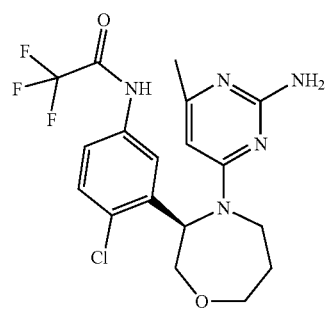 [SMILES: Cc1cc(N2CCCOC[C@H]2c2cc(NC(=O)C(F)(F)F)ccc2Cl)nc(N)n1]
I-176
TABLE 1-continued
Exemplary Compounds
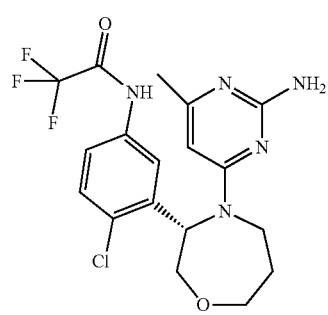 [SMILES: Cc1cc(N2CCCOC[C@@H]2c2cc(NC(=O)C(F)(F)F)ccc2Cl)nc(N)n1]
I-177
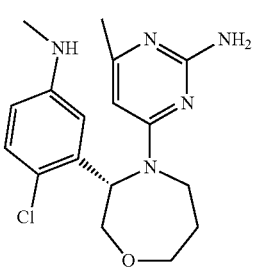 [SMILES: CNc1ccc(Cl)c([C@H]2COCCCN2c2cc(C)nc(N)n2)c1]
I-178
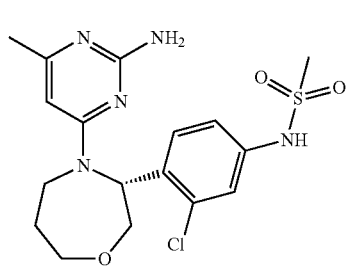 [SMILES: Cc1cc(N2CCCOC[C@H]2c2ccc(NS(C)(=O)=O)cc2Cl)nc(N)n1]
I-179
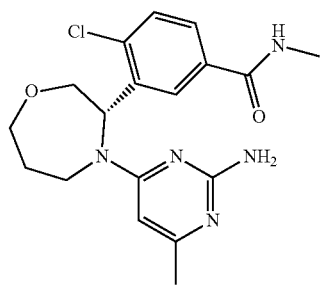 [SMILES: CNC(=O)c1ccc(Cl)c([C@H]2COCCCN2c2cc(C)nc(N)n2)c1]
I-180
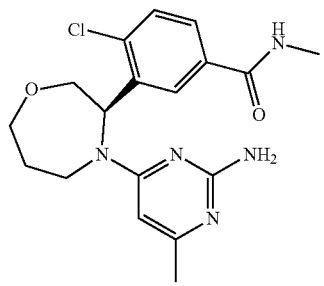 [SMILES: CNC(=O)c1ccc(Cl)c([C@@H]2COCCCN2c2cc(C)nc(N)n2)c1]
I-181

TABLE 1-continued
Exemplary Compounds
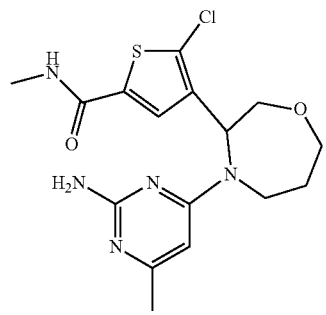 [SMILES: CNC(=O)c1cc(C2COCCCN2c2cc(C)nc(N)n2)c(Cl)s1]
I-182
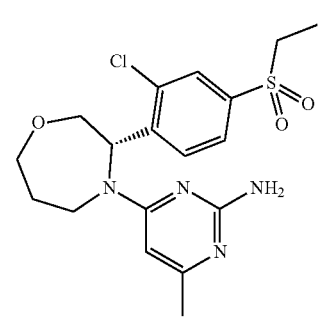
I-183
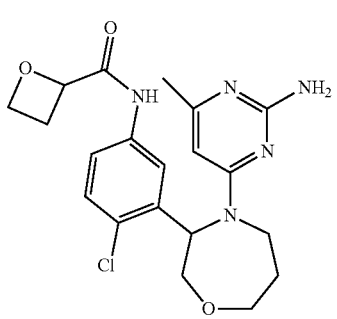 [SMILES: Cc1cc(N2CCCOCC2c2cc(NC(=O)C3CCO3)ccc2Cl)nc(N)n1]
I-184
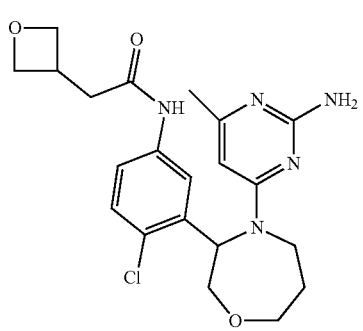 [SMILES: Cc1cc(N2CCCOCC2c2cc(NC(=O)CC3COC3)ccc2Cl)nc(N)n1]
I-185
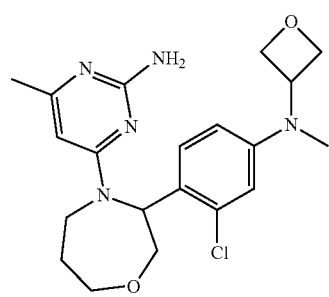
I-186
TABLE 1-continued
Exemplary Compounds
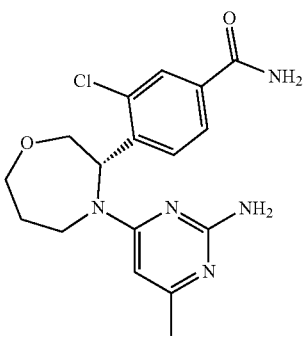 [SMILES: Cc1cc(N2CCCOC[C@@H]2c2ccc(C(N)=O)cc2Cl)nc(N)n1]
I-187
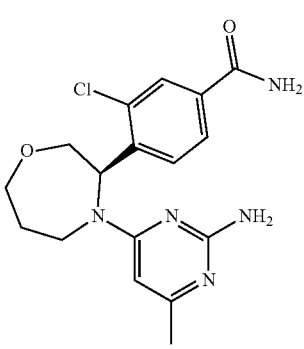 [SMILES: Cc1cc(N2CCCOC[C@H]2c2ccc(C(N)=O)cc2Cl)nc(N)n1]
I-188
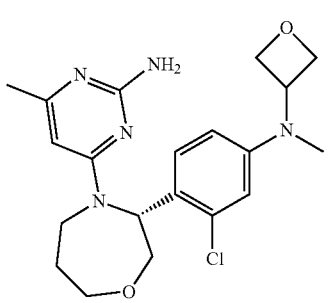
I-189
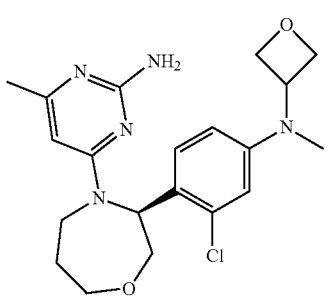
I-190
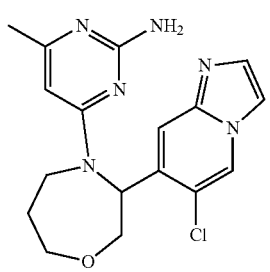 [SMILES: Cc1cc(N2CCCOCC2c2cc3nccn3cc2Cl)nc(N)n1]
I-191

TABLE 1-continued
Exemplary Compounds
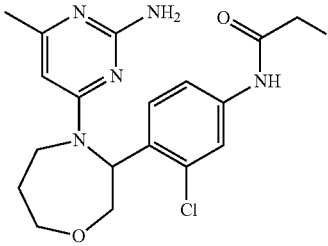 I-192
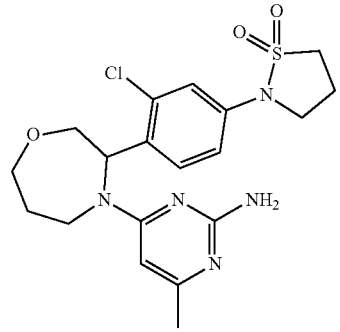 [SMILES: Cc1cc(N2CCCOCC2c2ccc(N3CCCS3(=O)=O)cc2Cl)nc(N)n1] I-193
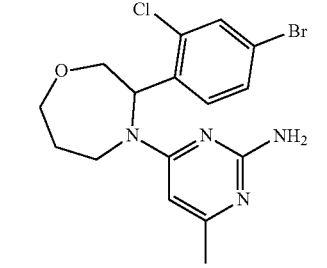 [SMILES: Cc1cc(N2CCCOCC2c2ccc(Br)cc2Cl)nc(N)n1] I-194
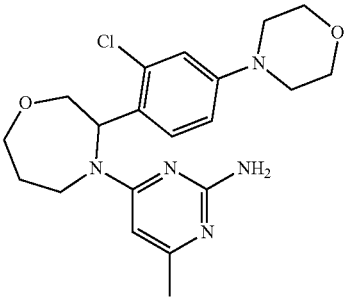 [SMILES: Cc1cc(N2CCCOCC2c2ccc(N3CCOCC3)cc2Cl)nc(N)n1] I-195
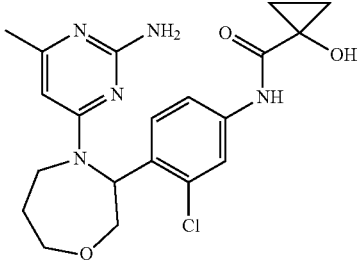 [SMILES: Cc1cc(N2CCCOCC2c2ccc(NC(=O)C3(O)CC3)cc2Cl)nc(N)n1] I-196
TABLE 1-continued
Exemplary Compounds
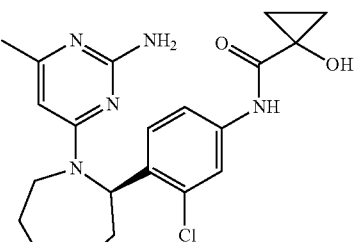 I-197
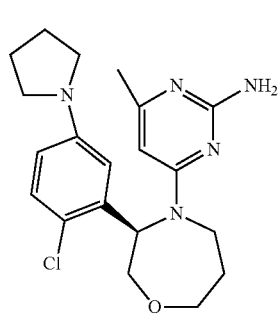 [SMILES: Cc1cc(N2CCCOC[C@H]2c2cc(N3CCCC3)ccc2Cl)nc(N)n1] I-198
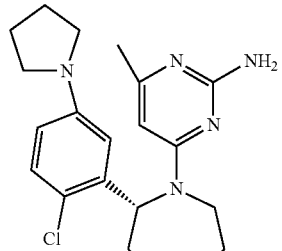 I-199
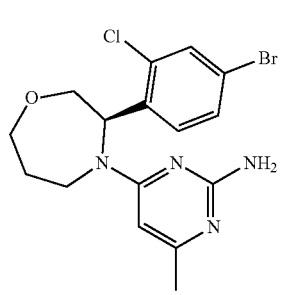 [SMILES: Cc1cc(N2CCCOC[C@H]2c2ccc(Br)cc2Cl)nc(N)n1] I-200
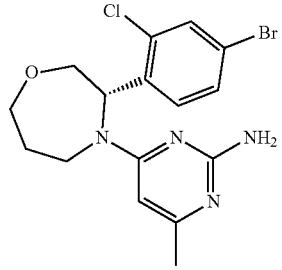 [SMILES: Cc1cc(N2CCCOC[C@@H]2c2ccc(Br)cc2Cl)nc(N)n1] I-201

TABLE 1-continued
Exemplary Compounds
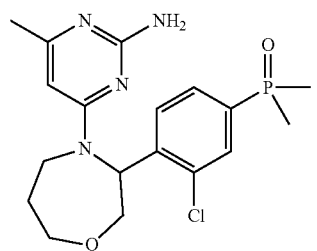 I-202
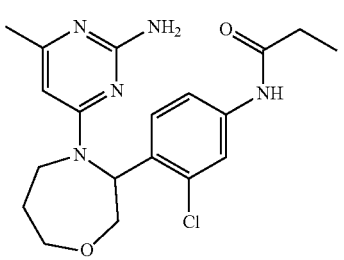 [SMILES: CCC(=O)Nc1ccc(C2COCCCN2c2cc(C)nc(N)n2)c(Cl)c1] I-203
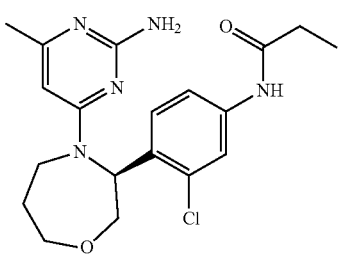 [SMILES: CCC(=O)Nc1ccc([C@H]2COCCCN2c2cc(C)nc(N)n2)c(Cl)c1] I-204
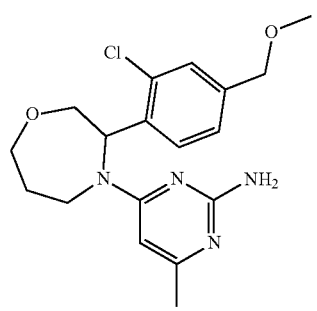 [SMILES: COCc1ccc(C2COCCCN2c2cc(C)nc(N)n2)c(Cl)c1] I-205
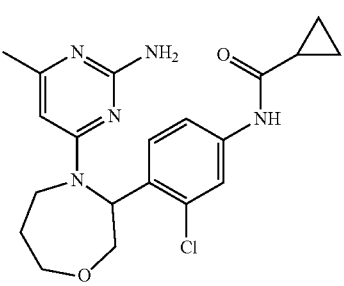 [SMILES: Cc1cc(N2CCCOCC2c2ccc(NC(=O)C3CC3)cc2Cl)nc(N)n1] I-206
TABLE 1-continued
Exemplary Compounds
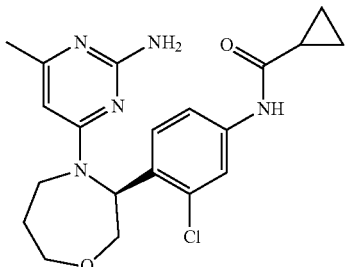 I-207
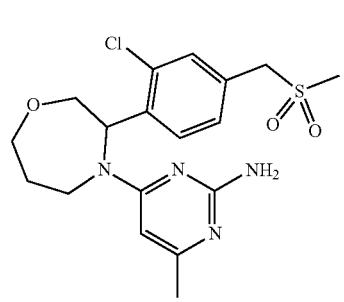 [SMILES: Cc1cc(N2CCCOCC2c2ccc(CS(C)(=O)=O)cc2Cl)nc(N)n1] I-208
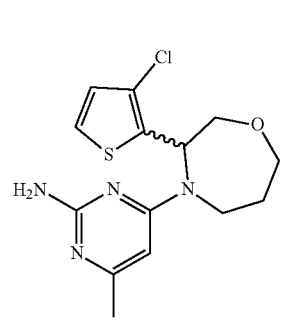 [SMILES: Cc1cc(N2CCCOCC2c2sccc2Cl)nc(N)n1] I-209
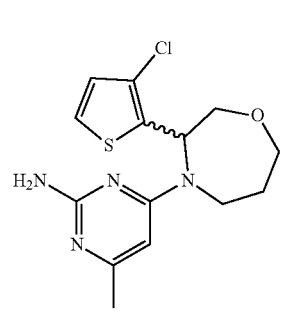 I-210
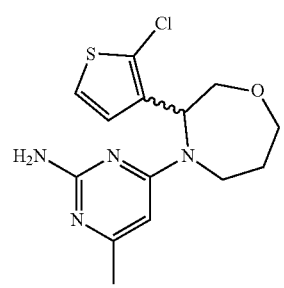 [SMILES: Cc1cc(N2CCCOCC2c2ccsc2Cl)nc(N)n1] I-211

TABLE 1-continued
Exemplary Compounds
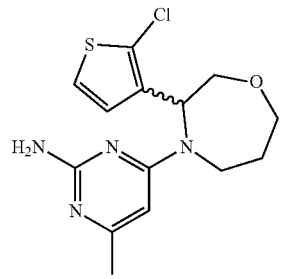 [SMILES: Cc1cc(N2CCCOCC2c2ccsc2Cl)nc(N)n1]
I-212
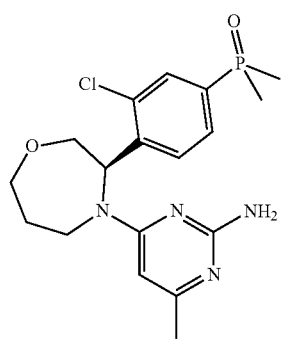 [SMILES: Cc1cc(N2CCCOC[C@H]2c2ccc(P(C)(C)=O)cc2Cl)nc(N)n1]
I-213
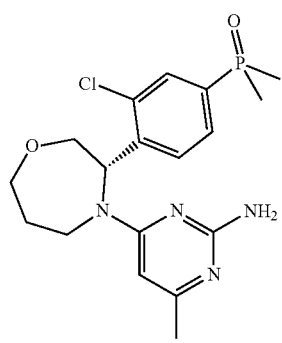 [SMILES: Cc1cc(N2CCCOC[C@@H]2c2ccc(P(C)(C)=O)cc2Cl)nc(N)n1]
I-214
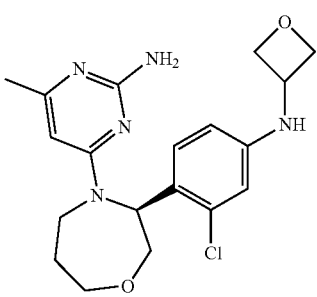 [SMILES: Cc1cc(N2CCCOC[C@@H]2c2ccc(NC3COC3)cc2Cl)nc(N)n1]
I-215
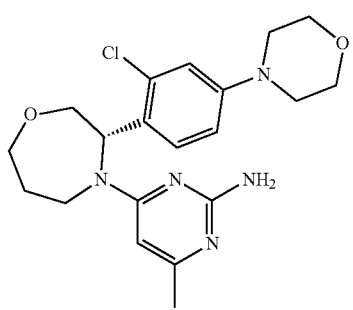 [SMILES: Cc1cc(N2CCCOC[C@@H]2c2ccc(N3CCOCC3)cc2Cl)nc(N)n1]
I-216
TABLE 1-continued
Exemplary Compounds
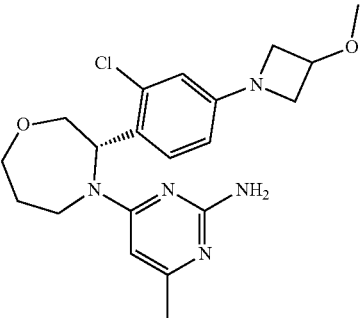 [SMILES: COC1CN(c2ccc([C@H]3COCCCN3c3cc(C)nc(N)n3)c(Cl)c2)C1]
I-217
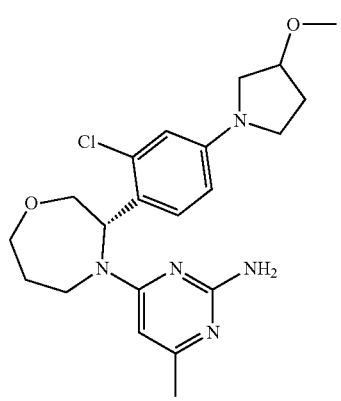 [SMILES: COC1CCN(c2ccc([C@H]3COCCCN3c3cc(C)nc(N)n3)c(Cl)c2)C1]
I-218
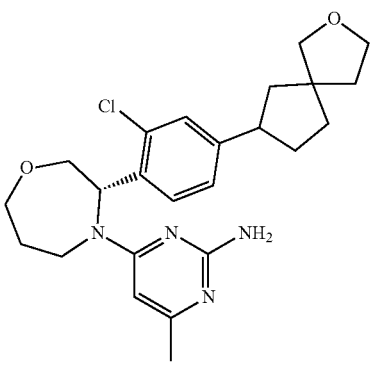 [SMILES: Cc1cc(N2CCCOC[C@@H]2c2ccc(C3CCC4(CCOC4)C3)cc2Cl)nc(N)n1]
I-219
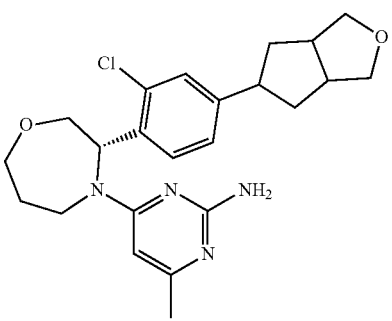 [SMILES: Cc1cc(N2CCCOC[C@@H]2c2ccc(C3CC4COCC4C3)cc2Cl)nc(N)n1]
I-220

TABLE 1-continued
Exemplary Compounds
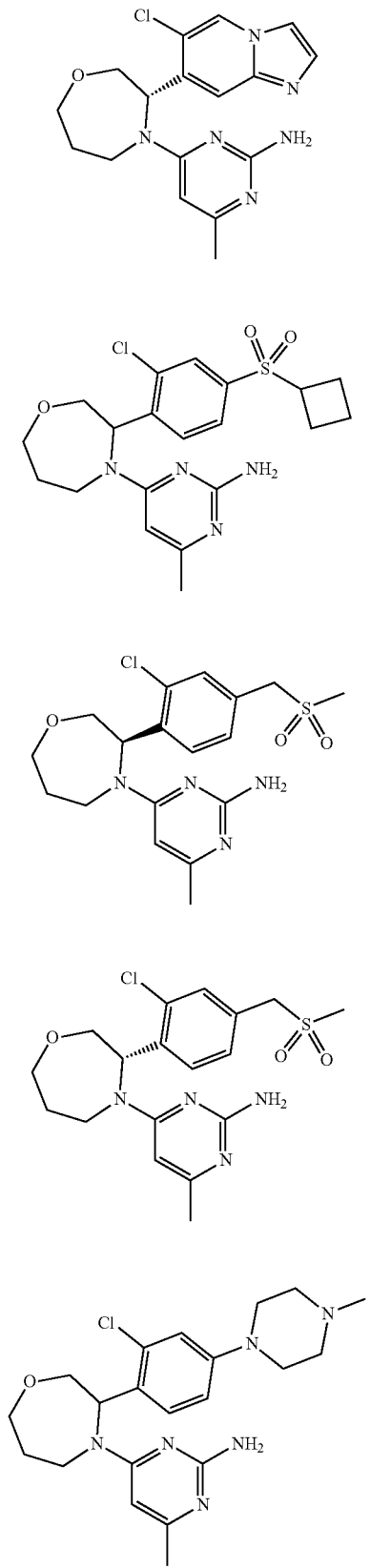
I-221
I-222
I-223
I-224
I-225
I-226
I-227
I-228
I-229

TABLE 1-continued
Exemplary Compounds
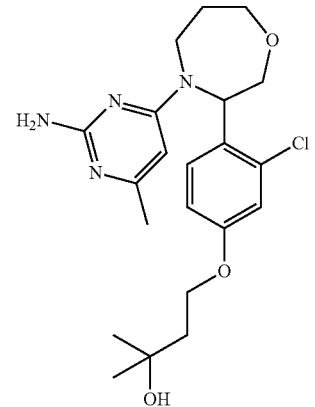 [SMILES: Cc1cc(N2CCCOCC2c2ccc(OCCC(C)(C)O)cc2Cl)nc(N)n1]
I-230
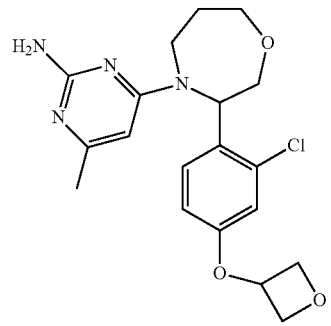 [SMILES: Cc1cc(N2CCCOCC2c2ccc(OC3COC3)cc2Cl)nc(N)n1]
I-231
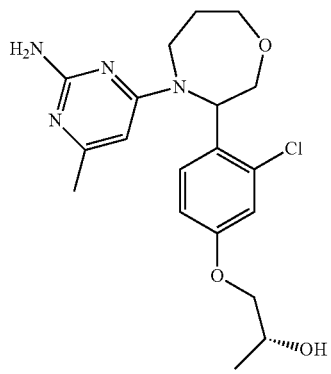
I-232
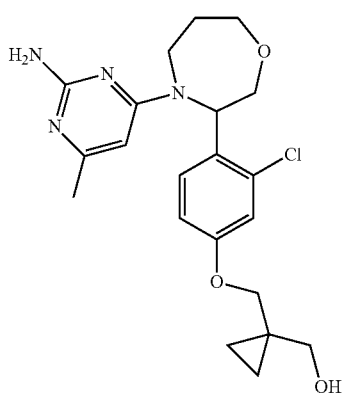 [SMILES: Cc1cc(N2CCCOCC2c2ccc(OCC3(CO)CC3)cc2Cl)nc(N)n1]
I-233
TABLE 1-continued
Exemplary Compounds
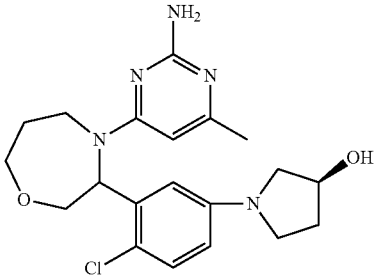 [SMILES: Cc1cc(N2CCCOCC2c2cc(N3CC[C@H](O)C3)ccc2Cl)nc(N)n1]
I-234
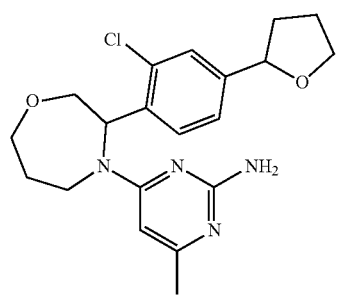 [SMILES: Cc1cc(N2CCCOCC2c2ccc(C3CCCO3)cc2Cl)nc(N)n1]
I-235
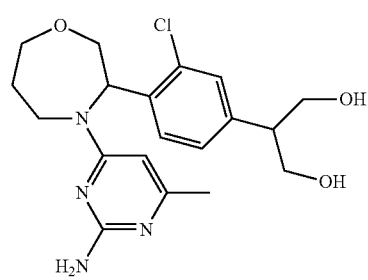 [SMILES: Cc1cc(N2CCCOCC2c2ccc(C(CO)CO)cc2Cl)nc(N)n1]
I-236
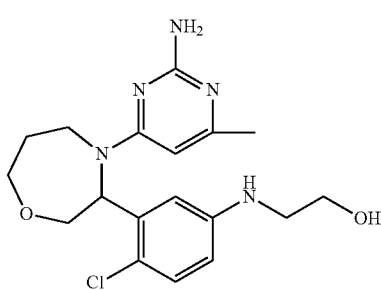 [SMILES: Cc1cc(N2CCCOCC2c2cc(NCCO)ccc2Cl)nc(N)n1]
I-237
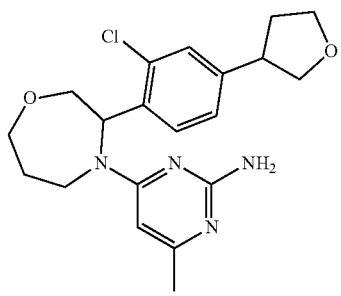 [SMILES: Cc1cc(N2CCCOCC2c2ccc(C3CCOC3)cc2Cl)nc(N)n1]
I-238

TABLE 1-continued
Exemplary Compounds
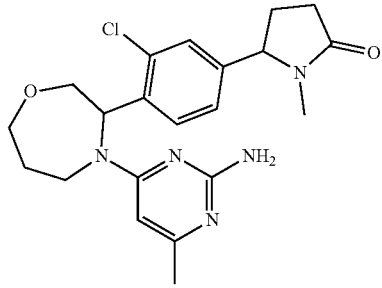 [SMILES: Cc1cc(N2CCCOCC2c2ccc(C3CCC(=O)N3C)cc2Cl)nc(N)n1] I-239
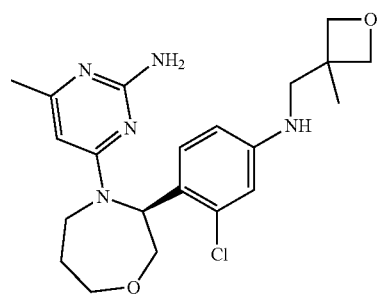 [SMILES: Cc1cc(N2CCCOC[C@@H]2c2ccc(NCC3(C)COC3)cc2Cl)nc(N)n1] I-240
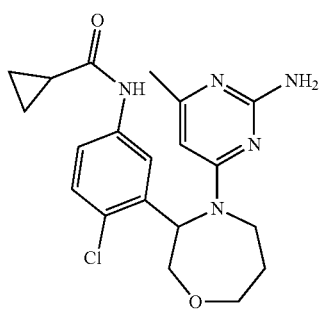 [SMILES: Cc1cc(N2CCCOCC2c2cc(NC(=O)C3CC3)ccc2Cl)nc(N)n1] I-241
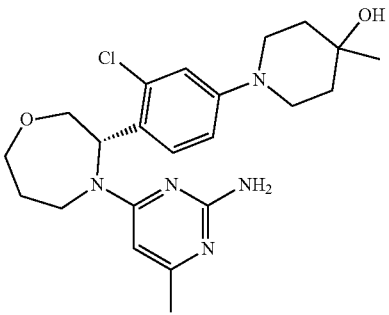 [SMILES: Cc1cc(N2CCCOC[C@@H]2c2ccc(N3CCC(C)(O)CC3)cc2Cl)nc(N)n1] I-242
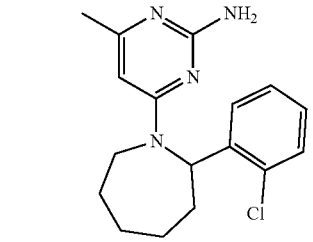 [SMILES: Cc1cc(N2CCCCCC2c2ccccc2Cl)nc(N)n1] I-243
TABLE 1-continued
Exemplary Compounds
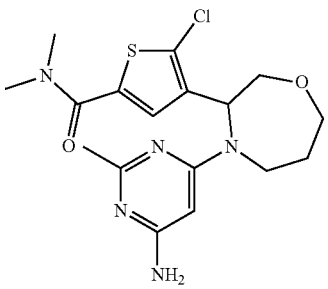 [SMILES: Cc1nc(N)cc(N2CCCOCC2c2cc(C(=O)N(C)C)sc2Cl)n1] I-244
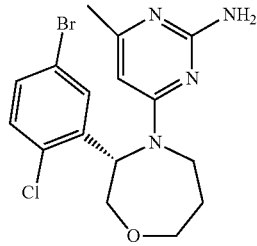 [SMILES: Cc1cc(N2CCCOC[C@@H]2c2cc(Br)ccc2Cl)nc(N)n1] I-245
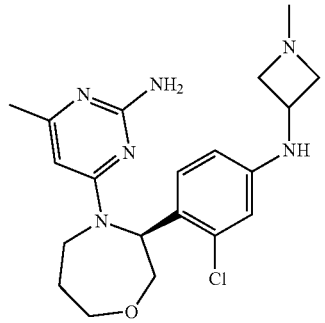 [SMILES: Cc1cc(N2CCCOC[C@@H]2c2ccc(NC3CN(C)C3)cc2Cl)nc(N)n1] I-246
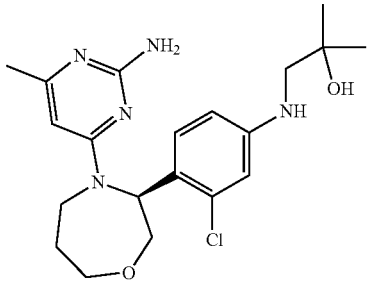 [SMILES: Cc1cc(N2CCCOC[C@@H]2c2ccc(NCC(C)(C)O)cc2Cl)nc(N)n1] I-247
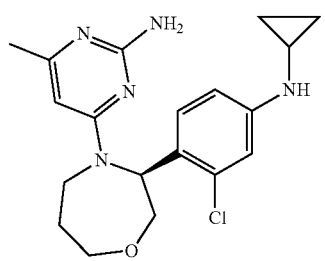 [SMILES: Cc1cc(N2CCCOC[C@@H]2c2ccc(NC3CC3)cc2Cl)nc(N)n1] I-248

TABLE 1-continued
Exemplary Compounds
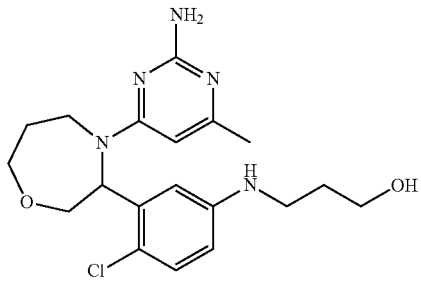 [SMILES: Cc1cc(N2CCCOCC2c2cc(NCCCO)ccc2Cl)nc(N)n1] I-249
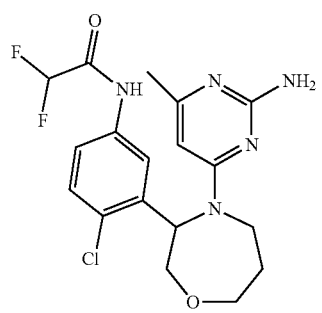 [SMILES: Cc1cc(N2CCCOCC2c2cc(NC(=O)C(F)F)ccc2Cl)nc(N)n1] I-250
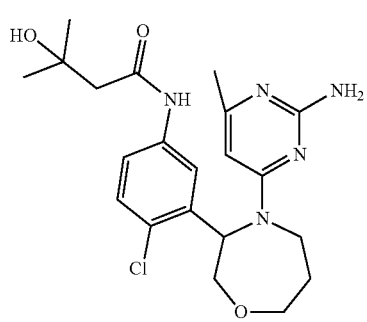 [SMILES: Cc1cc(N2CCCOCC2c2cc(NC(=O)CC(C)(C)O)ccc2Cl)nc(N)n1] I-251
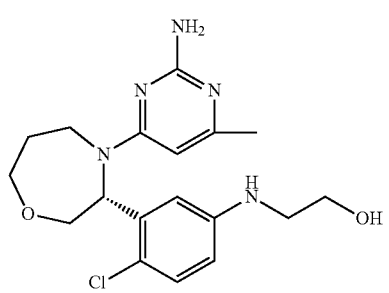 [SMILES: Cc1cc(N2CCCOC[C@H]2c2cc(NCCO)ccc2Cl)nc(N)n1] I-252
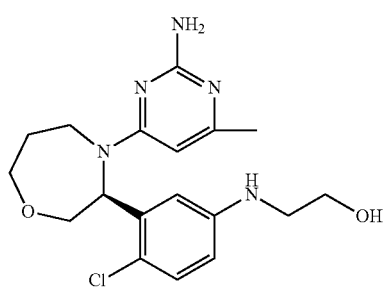 [SMILES: Cc1cc(N2CCCOC[C@@H]2c2cc(NCCO)ccc2Cl)nc(N)n1] I-253
TABLE 1-continued
Exemplary Compounds
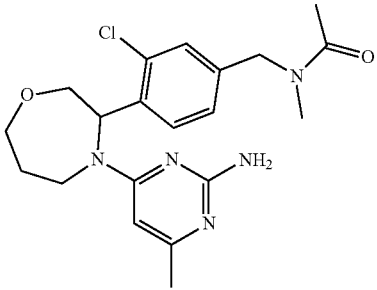 [SMILES: CC(=O)N(C)Cc1ccc(C2COCCCN2c2cc(C)nc(N)n2)c(Cl)c1] I-254
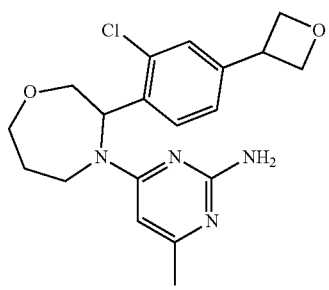 [SMILES: Cc1cc(N2CCCOCC2c2ccc(C3COC3)cc2Cl)nc(N)n1] I-255
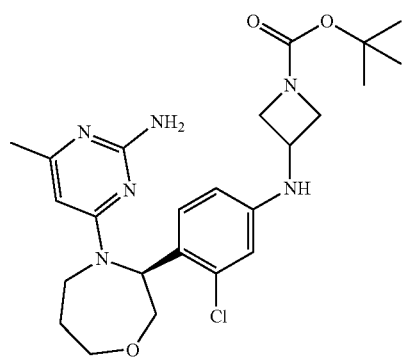 [SMILES: Cc1cc(N2CCCOC[C@@H]2c2ccc(NC3CN(C(=O)OC(C)(C)C)C3)cc2Cl)nc(N)n1] I-256
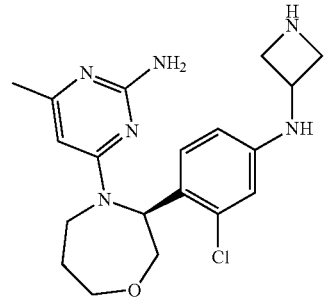 [SMILES: Cc1cc(N2CCCOC[C@@H]2c2ccc(NC3CNC3)cc2Cl)nc(N)n1] I-257
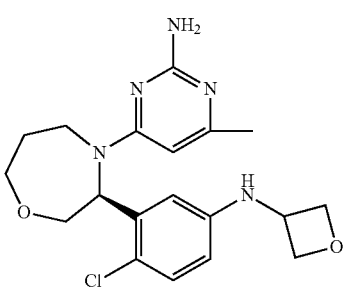 [SMILES: Cc1cc(N2CCCOC[C@@H]2c2cc(NC3COC3)ccc2Cl)nc(N)n1] I-258

TABLE 1-continued
Exemplary Compounds
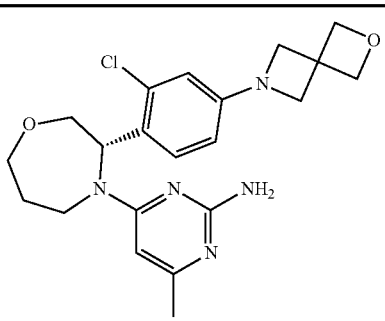
I-259
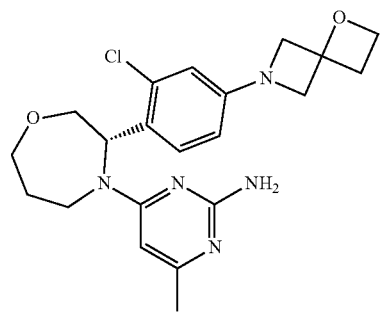 [SMILES: Cc1cc(N2CCCOC[C@@H]2c2ccc(N3CC4(CCO4)C3)cc2Cl)nc(N)n1]
I-260

I-261
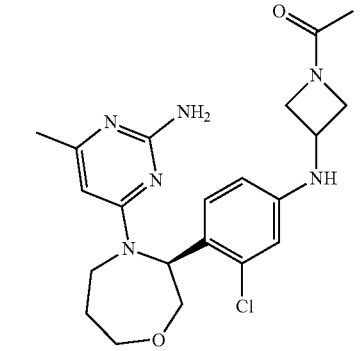 [SMILES: CC(=O)N1CC(Nc2ccc([C@H]3COCCCN3c3cc(C)nc(N)n3)c(Cl)c2)C1]
I-262
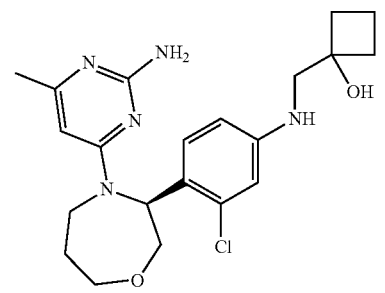 [SMILES: Cc1cc(N2CCCOC[C@@H]2c2ccc(NCC3(O)CCC3)cc2Cl)nc(N)n1]
I-263
TABLE 1-continued
Exemplary Compounds
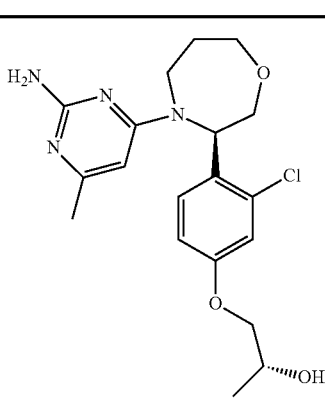
I-264
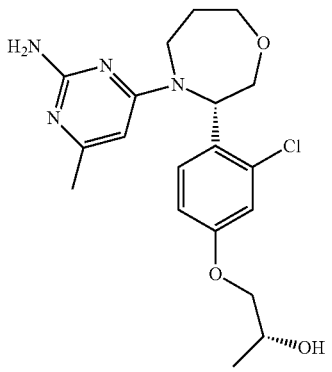 [SMILES: Cc1cc(N2CCCOC[C@@H]2c2ccc(OC[C@@H](C)O)cc2Cl)nc(N)n1]
I-265
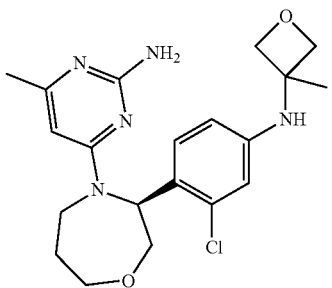
I-266
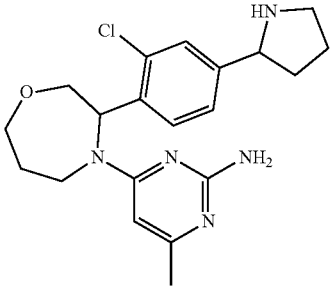 [SMILES: Cc1cc(N2CCCOCC2c2ccc(C3CCCN3)cc2Cl)nc(N)n1]
I-267

TABLE 1-continued
Exemplary Compounds
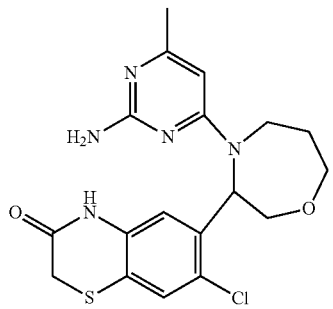 [SMILES: Cc1cc(N2CCCOCC2c2cc3c(cc2Cl)SCC(=O)N3)nc(N)n1] I-268
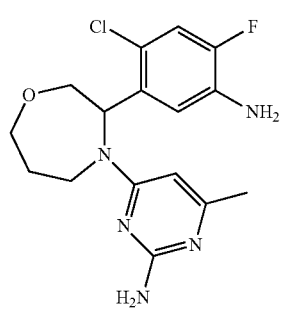 [SMILES: Cc1cc(N2CCCOCC2c2cc(N)c(F)cc2Cl)nc(N)n1] I-269
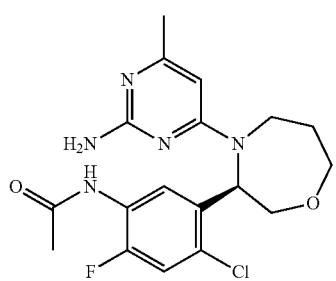 [SMILES: CC(=O)Nc1cc([C@@H]2COCCCN2c2cc(C)nc(N)n2)c(Cl)cc1F] I-270
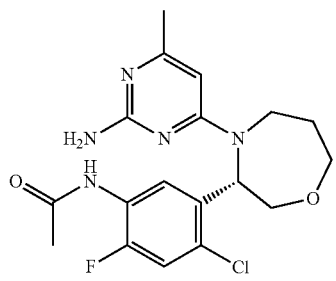 [SMILES: CC(=O)Nc1cc([C@H]2COCCCN2c2cc(C)nc(N)n2)c(Cl)cc1F] I-271
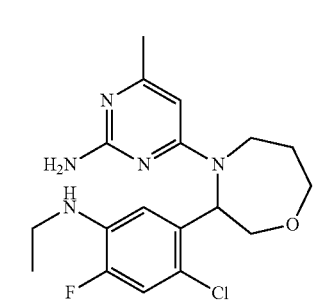 [SMILES: CCNc1cc(C2COCCCN2c2cc(C)nc(N)n2)c(Cl)cc1F] I-272
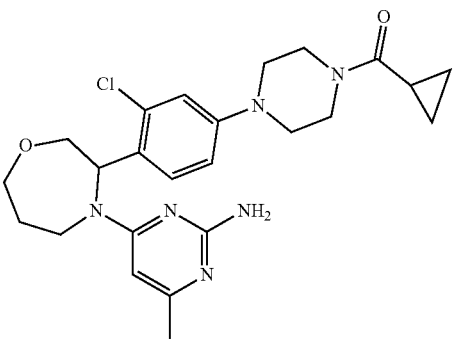 [SMILES: Cc1cc(N2CCCOCC2c2ccc(N3CCN(C(=O)C4CC4)CC3)cc2Cl)nc(N)n1] I-273
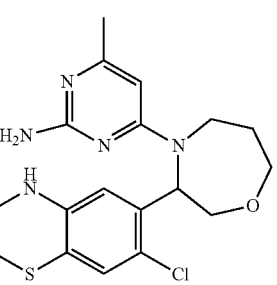 I-274
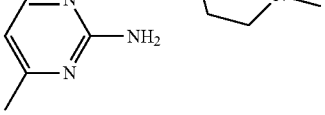 I-275
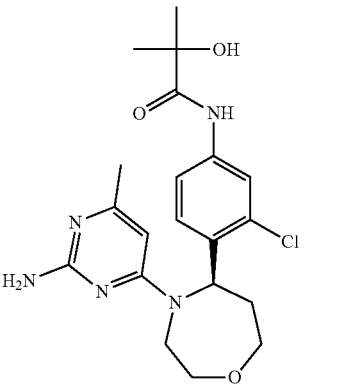 [SMILES: Cc1cc(N2CCOCC[C@@H]2c2ccc(NC(=O)C(C)(C)O)cc2Cl)nc(N)n1] I-276
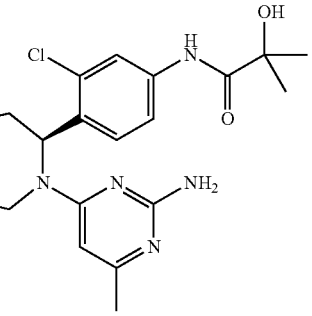 I-277

TABLE 1-continued
Exemplary Compounds
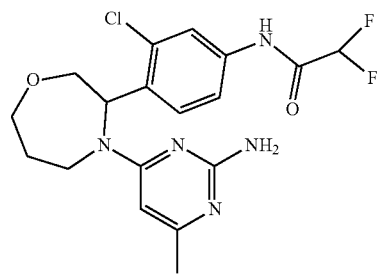 [SMILES: Cc1cc(N2CCCOCC2c2ccc(NC(=O)C(F)F)cc2Cl)nc(N)n1] I-278
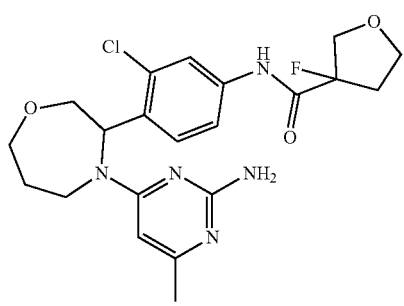 [SMILES: Cc1cc(N2CCCOCC2c2ccc(NC(=O)C3(F)CCOC3)cc2Cl)nc(N)n1] I-279
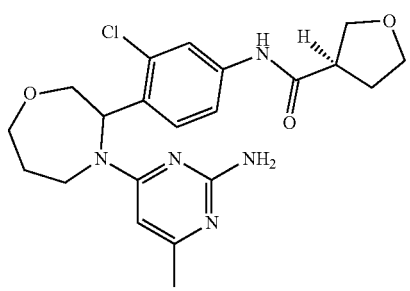 [SMILES: Cc1cc(N2CCCOCC2c2ccc(NC(=O)[C@@H]3CCOC3)cc2Cl)nc(N)n1] I-280
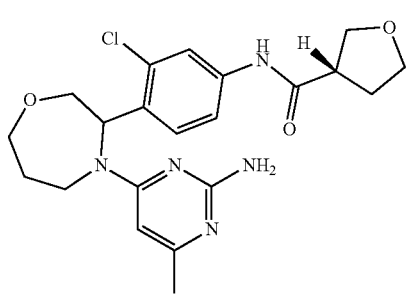 [SMILES: Cc1cc(N2CCCOCC2c2ccc(NC(=O)[C@H]3CCOC3)cc2Cl)nc(N)n1] I-281
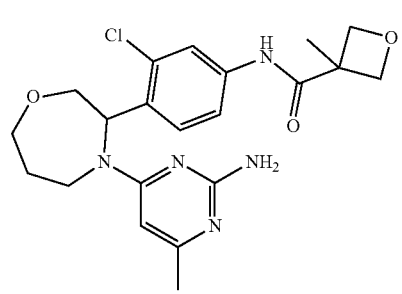 [SMILES: Cc1cc(N2CCCOCC2c2ccc(NC(=O)C3(C)COC3)cc2Cl)nc(N)n1] I-282
TABLE 1-continued
Exemplary Compounds
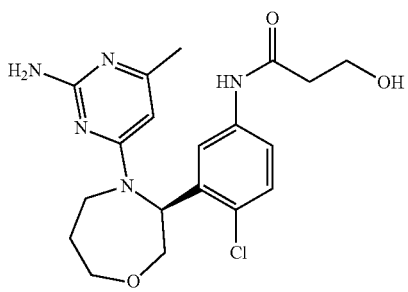 [SMILES: Cc1cc(N2CCCOC[C@@H]2c2cc(NC(=O)CCO)ccc2Cl)nc(N)n1] I-283
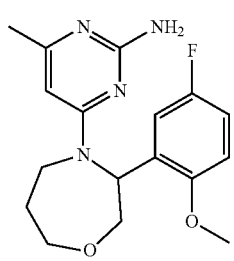 I-284
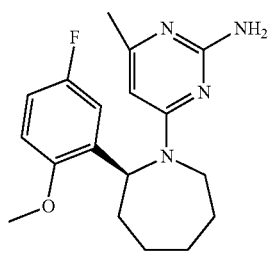 [SMILES: COc1ccc(F)cc1[C@@H]1CCCCCN1c1cc(C)nc(N)n1] I-285
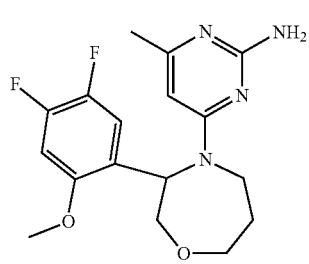 [SMILES: COc1cc(F)c(F)cc1C1COCCCN1c1cc(C)nc(N)n1] I-286
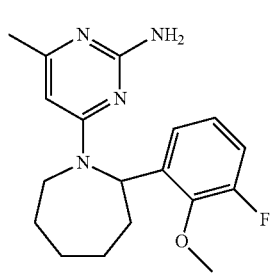 [SMILES: COc1c(F)cccc1C1CCCCCN1c1cc(C)nc(N)n1] I-287

TABLE 1-continued
Exemplary Compounds
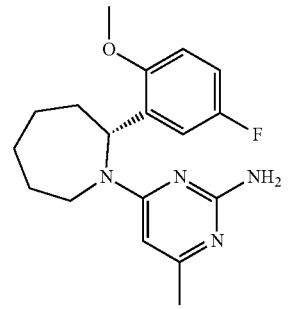 [SMILES: COc1ccc(F)cc1[C@H]1CCCCCN1c1cc(C)nc(N)n1]
I-288
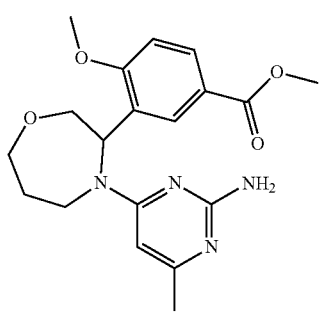 [SMILES: COC(=O)c1ccc(OC)c(C2COCCCN2c2cc(C)nc(N)n2)c1]
I-289
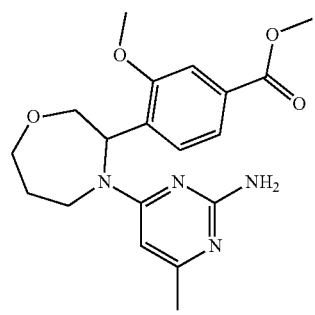 [SMILES: COC(=O)c1ccc(C2COCCCN2c2cc(C)nc(N)n2)c(OC)c1]
I-290
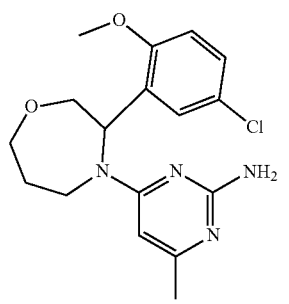 [SMILES: COc1ccc(Cl)cc1C1COCCCN1c1cc(C)nc(N)n1]
I-291
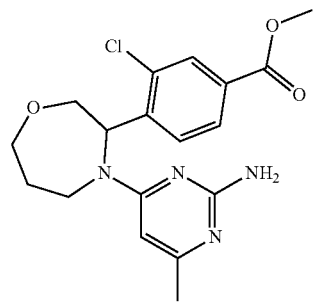 [SMILES: COC(=O)c1ccc(C2COCCCN2c2cc(C)nc(N)n2)c(Cl)c1]
I-292
TABLE 1-continued
Exemplary Compounds
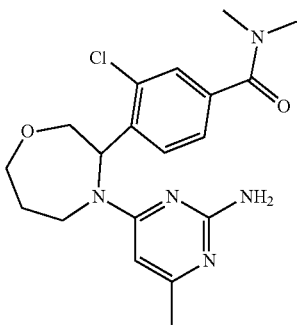 [SMILES: Cc1cc(N2CCCOCC2c2ccc(C(=O)N(C)C)cc2Cl)nc(N)n1]
I-293
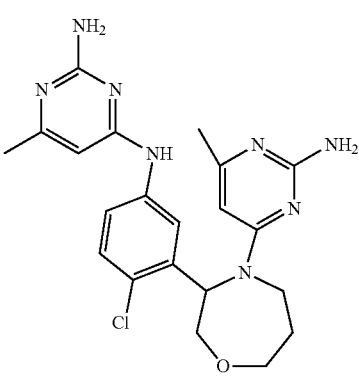 [SMILES: Cc1cc(Nc2ccc(Cl)c(C3COCCCN3c3cc(C)nc(N)n3)c2)nc(N)n1]
I-294
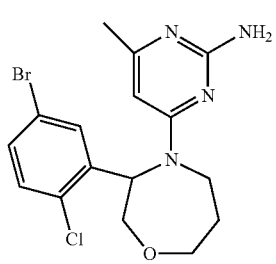 [SMILES: Cc1cc(N2CCCOCC2c2cc(Br)ccc2Cl)nc(N)n1]
I-295
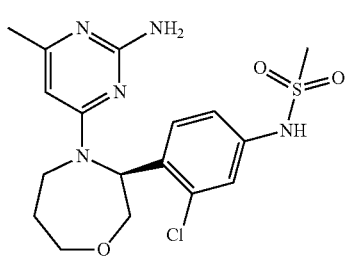 [SMILES: Cc1cc(N2CCCOC[C@@H]2c2ccc(NS(C)(=O)=O)cc2Cl)nc(N)n1]
I-296
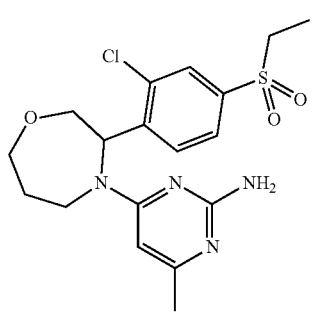 [SMILES: CCS(=O)(=O)c1ccc(C2COCCCN2c2cc(C)nc(N)n2)c(Cl)c1]
I-297

TABLE 1-continued
Exemplary Compounds
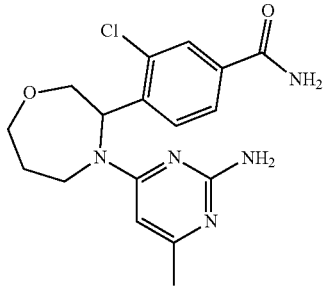 [SMILES: Cc1cc(N2CCCOCC2c2ccc(C(N)=O)cc2Cl)nc(N)n1] I-298
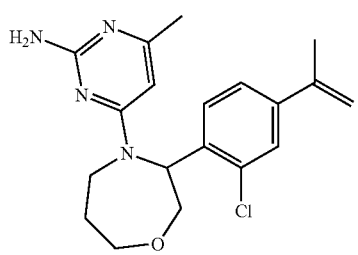 [SMILES: C=C(C)c1ccc(C2COCCCN2c2cc(C)nc(N)n2)c(Cl)c1] I-299
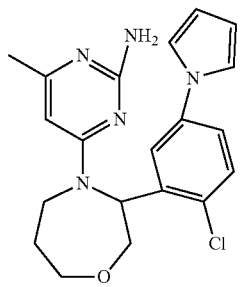 [SMILES: Cc1cc(N2CCCOCC2c2cc(-n3cccc3)ccc2Cl)nc(N)n1] I-300
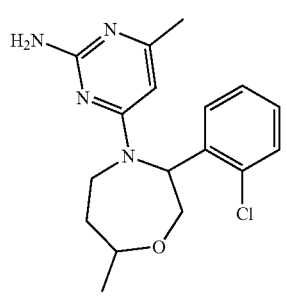 [SMILES: Cc1cc(N2CCC(C)OCC2c2ccccc2Cl)nc(N)n1] I-301
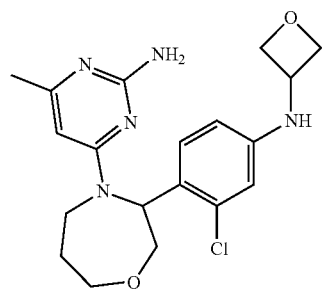 [SMILES: Cc1cc(N2CCCOCC2c2ccc(NC3COC3)cc2Cl)nc(N)n1] I-302
TABLE 1-continued
Exemplary Compounds
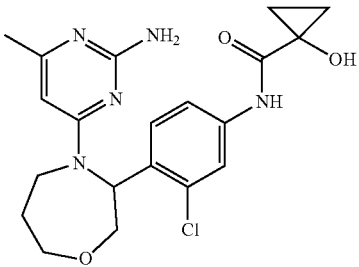 [SMILES: Cc1cc(N2CCCOCC2c2ccc(NC(=O)C3(O)CC3)cc2Cl)nc(N)n1] I-303
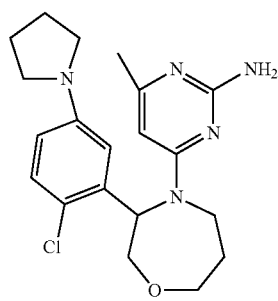 [SMILES: Cc1cc(N2CCCOCC2c2cc(N3CCCC3)ccc2Cl)nc(N)n1] I-304
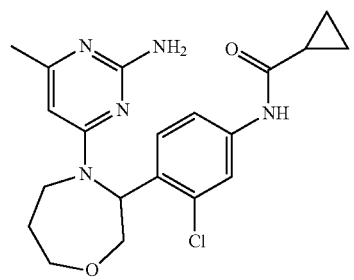 [SMILES: Cc1cc(N2CCCOCC2c2ccc(NC(=O)C3CC3)cc2Cl)nc(N)n1] I-305
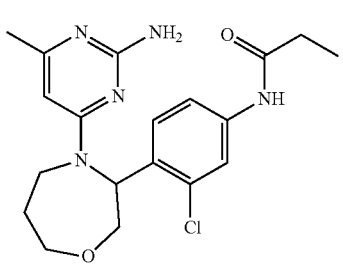 [SMILES: CCC(=O)Nc1ccc(C2COCCCN2c2cc(C)nc(N)n2)c(Cl)c1] I-306
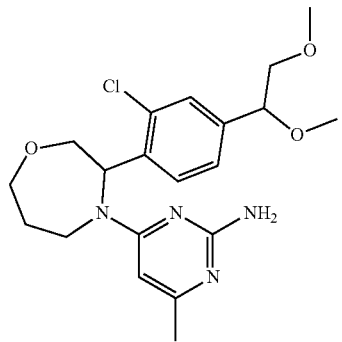 [SMILES: COCC(OC)c1ccc(C2COCCCN2c2cc(C)nc(N)n2)c(Cl)c1] I-307

TABLE 1-continued
Exemplary Compounds
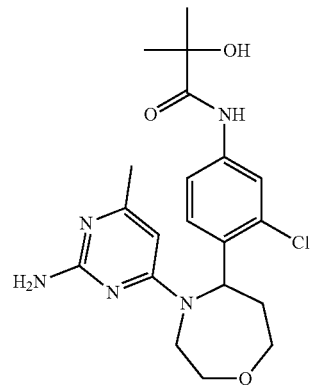 [SMILES: Cc1cc(N2CCOCCC2c2ccc(NC(=O)C(C)(C)O)cc2Cl)nc(N)n1]
I-308
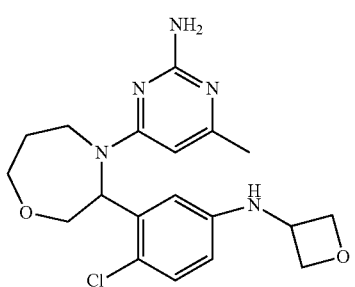 [SMILES: Cc1cc(N2CCCOCC2c2cc(NC3COC3)ccc2Cl)nc(N)n1]
I-309
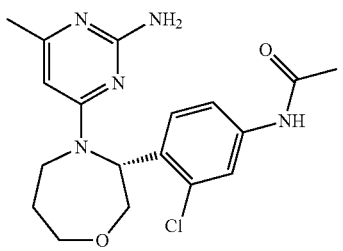
I-310
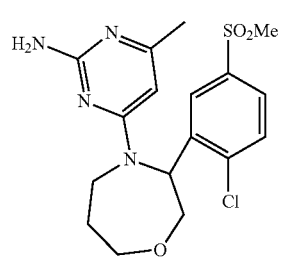
I-311
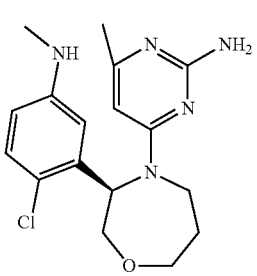 [SMILES: CNc1ccc(Cl)c([C@@H]2COCCCN2c2cc(C)nc(N)n2)c1]
I-312
TABLE 1-continued
Exemplary Compounds
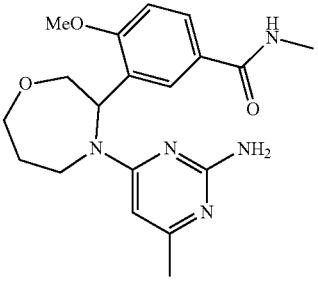 [SMILES: CNC(=O)c1ccc(OC)c(C2COCCCN2c2cc(C)nc(N)n2)c1]
I-313
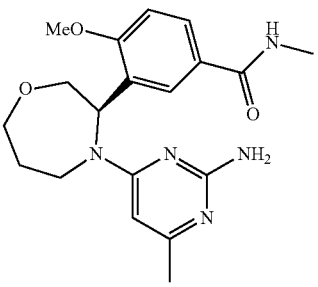 [SMILES: CNC(=O)c1ccc(OC)c([C@@H]2COCCCN2c2cc(C)nc(N)n2)c1]
I-314
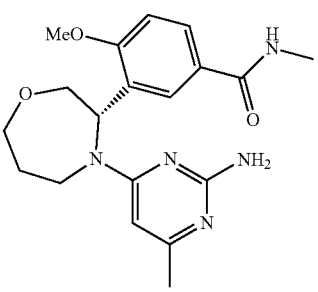 [SMILES: CNC(=O)c1ccc(OC)c([C@H]2COCCCN2c2cc(C)nc(N)n2)c1]
I-315
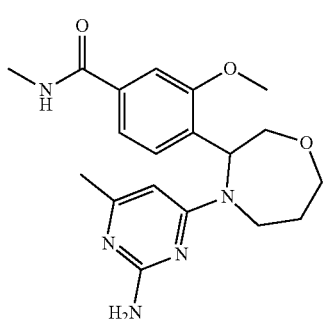
I-316
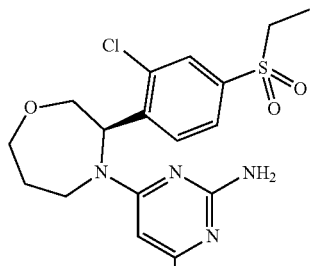
I-317
Compounds I-120 to I-123 are stereoisomers of the following formulas:

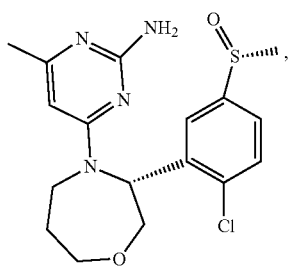

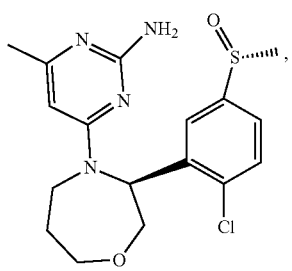

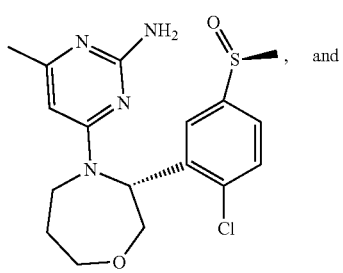

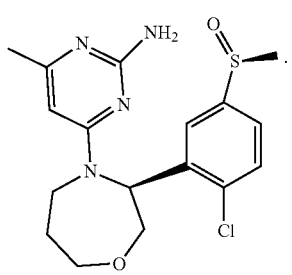

Compounds I-120 to I-123 can be separated by chrial purification (see, for example, Example 18). Accordingly, in some embodiments, the present invention provides a stereoisomer selected from compounds I-120 to I-123, or a pharmaceutically acceptable salt thereof.

Compounds I-164 to I-167 are stereoisomers of the following formulas:

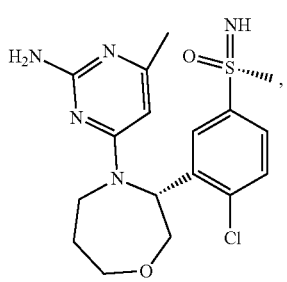

-continued

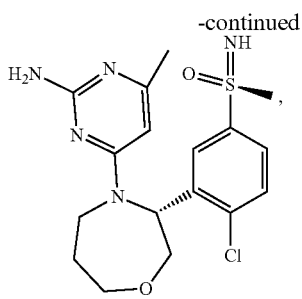

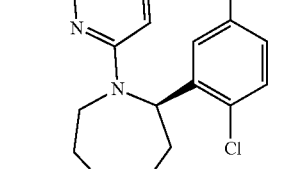

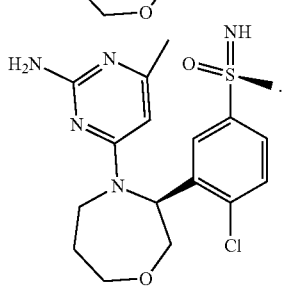

Compounds I-164 to I-167 can be separated by chrial purification (see, for example, Example 41). Accordingly, in some embodiments, the present invention provides a stereoisomer selected from compounds I-164 to I-167, or a pharmaceutically acceptable salt thereof.

Compounds I-209 and I-210 are stereoisomers of the following formulas:

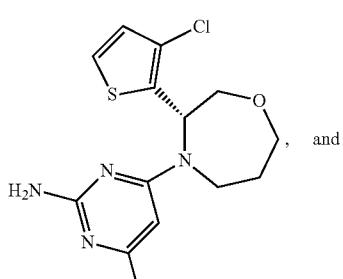

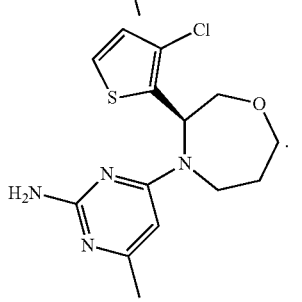

Compounds I-209 and I-210 can be separated by chrial purification (see, for example, Example 52). Accordingly, in some embodiments, the present invention provides a stereoisomer selected from compounds I-209 to I-210, or a pharmaceutically acceptable salt thereof.

Compounds I-211 and I-212 are stereoisomers of the following formulas:

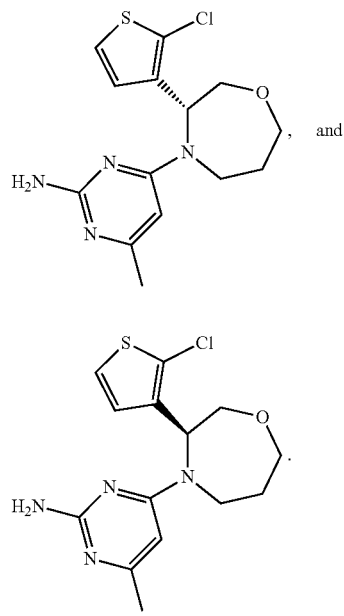

and

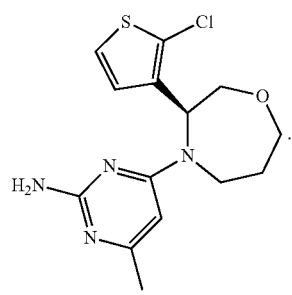

.

Compounds I-211 and I-212 can be separated by chrial purification (see, for example, Example 52). Accordingly, in some embodiments, the present invention provides a stereoisomer selected from compounds I-211 to I-212, or a pharmaceutically acceptable salt thereof.

TABLE 2

Exemplary compounds

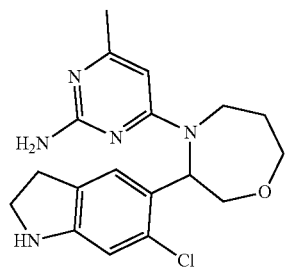 [SMILES: Cc1cc(N2CCCOCC2c2cc3c(cc2Cl)NCC3)nc(N)n1]

C-1

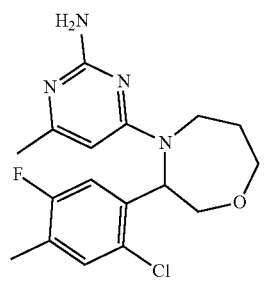 [SMILES: Cc1cc(N2CCCOCC2c2cc(F)c(C)cc2Cl)nc(N)n1]

C-2

TABLE 2-continued

Exemplary compounds

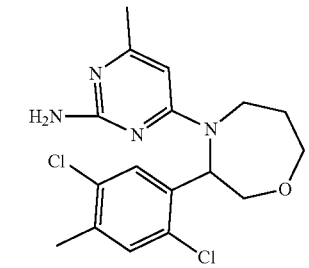 [SMILES: Cc1cc(N2CCCOCC2c2cc(Cl)c(C)cc2Cl)nc(N)n1]

C-3

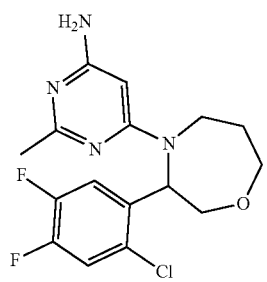

C-4

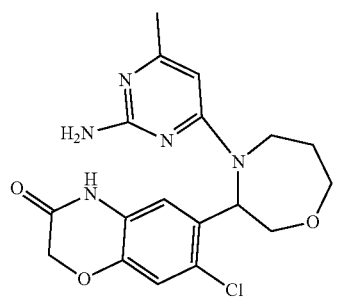 [SMILES: Cc1cc(N2CCCOCC2c2cc3c(cc2Cl)OCC(=O)N3)nc(N)n1]

C-5

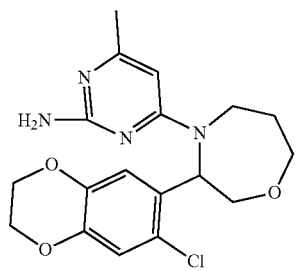 [SMILES: Cc1cc(N2CCCOCC2c2cc3c(cc2Cl)OCCO3)nc(N)n1]

C-6

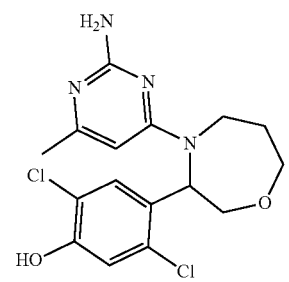 [SMILES: Cc1cc(N2CCCOCC2c2cc(Cl)c(O)cc2Cl)nc(N)n1]

C-7

TABLE 2-continued
Exemplary compounds
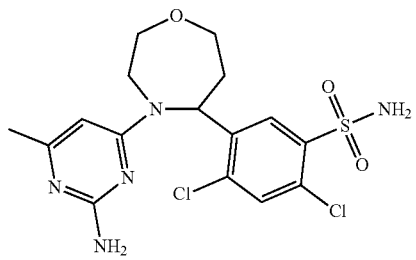 [SMILES: Cc1cc(N2CCOCCC2c2cc(S(N)(=O)=O)c(Cl)cc2Cl)nc(N)n1] C-8
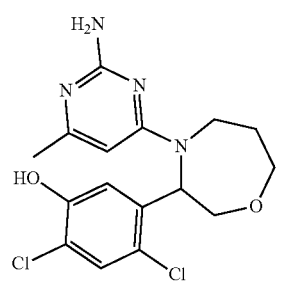 [SMILES: Cc1cc(N2CCCOCC2c2cc(O)c(Cl)cc2Cl)nc(N)n1] C-9
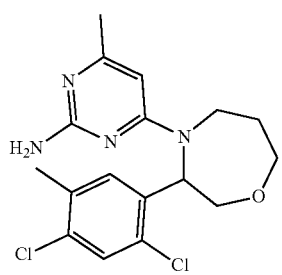 [SMILES: Cc1cc(N2CCCOCC2c2cc(C)c(Cl)cc2Cl)nc(N)n1] C-10
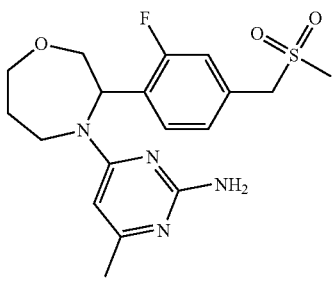 C-11
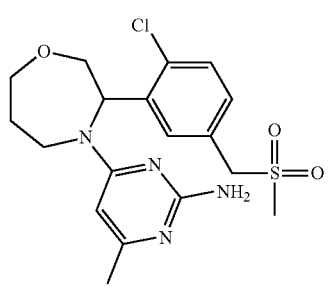 [SMILES: Cc1cc(N2CCCOCC2c2cc(CS(C)(=O)=O)ccc2Cl)nc(N)n1] C-12
TABLE 2-continued
Exemplary compounds
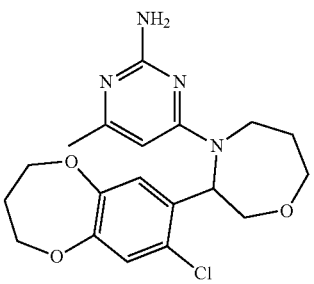 [SMILES: Cc1cc(N2CCCOCC2c2cc3c(cc2Cl)OCCCO3)nc(N)n1] C-13
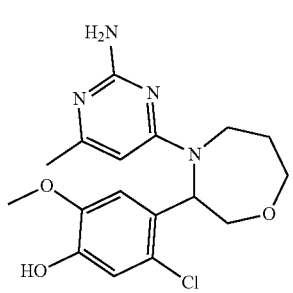 [SMILES: COc1cc(C2COCCCN2c2cc(C)nc(N)n2)c(Cl)cc1O] C-14
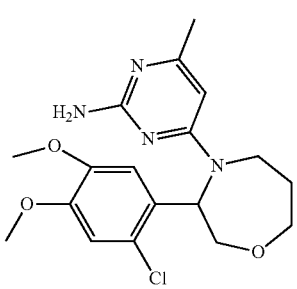 [SMILES: COc1cc(Cl)c(C2COCCCN2c2cc(C)nc(N)n2)cc1OC] C-15
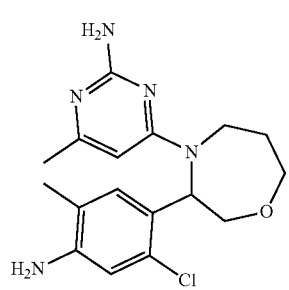 [SMILES: Cc1cc(N2CCCOCC2c2cc(C)c(N)cc2Cl)nc(N)n1] C-16
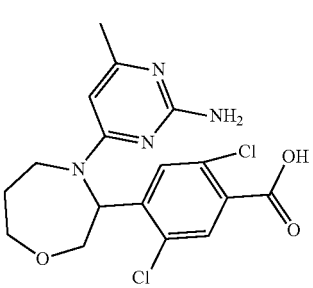 [SMILES: Cc1cc(N2CCCOCC2c2cc(Cl)c(C(=O)O)cc2Cl)nc(N)n1] C-17

TABLE 2-continued
Exemplary compounds
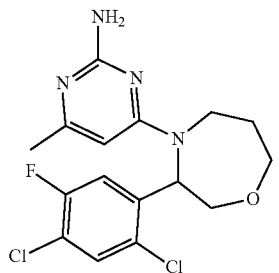 [SMILES: Cc1cc(N2CCCOCC2c2cc(F)c(Cl)cc2Cl)nc(N)n1]  C-18
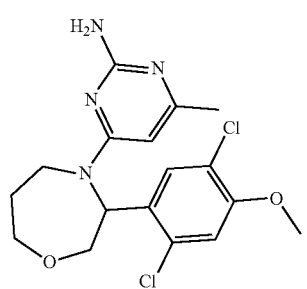  C-19
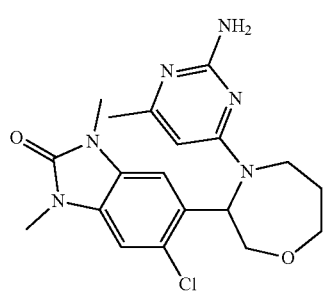 [SMILES: Cc1cc(N2CCCOCC2c2cc3c(cc2Cl)n(C)c(=O)n3C)nc(N)n1]  C-20
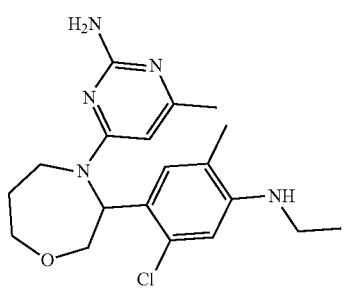 [SMILES: CCNc1cc(Cl)c(C2COCCCN2c2cc(C)nc(N)n2)cc1C]  C-21
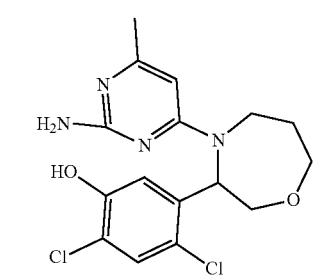 [SMILES: Cc1cc(N2CCCOCC2c2cc(O)c(Cl)cc2Cl)nc(N)n1]  C-22
TABLE 2-continued
Exemplary compounds
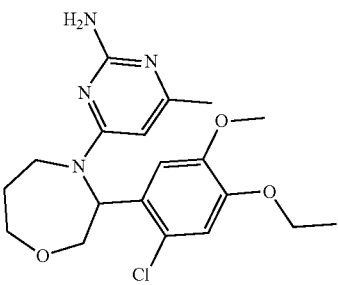 [SMILES: CCOc1cc(Cl)c(C2COCCCN2c2cc(C)nc(N)n2)cc1OC]  C-23
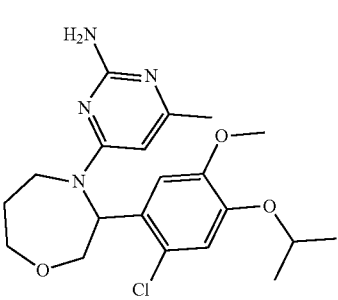 [SMILES: COc1cc(C2COCCCN2c2cc(C)nc(N)n2)c(Cl)cc1OC(C)C]  C-24
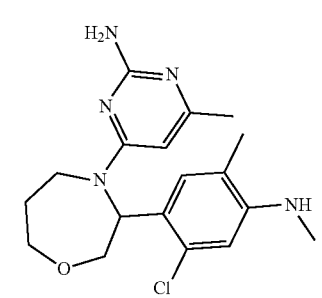 [SMILES: CNc1cc(Cl)c(C2COCCCN2c2cc(C)nc(N)n2)cc1C]  C-25
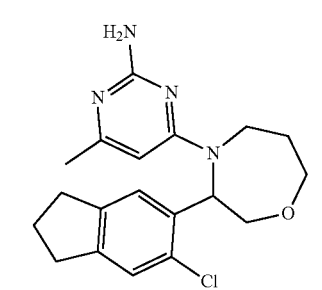 [SMILES: Cc1cc(N2CCCOCC2c2cc3c(cc2Cl)CCC3)nc(N)n1]  C-26
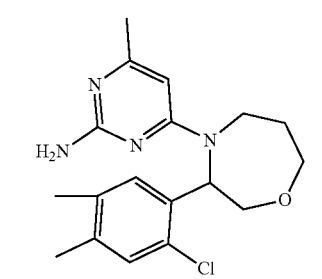 [SMILES: Cc1cc(N2CCCOCC2c2cc(C)c(C)cc2Cl)nc(N)n1]  C-27

TABLE 2-continued
Exemplary compounds
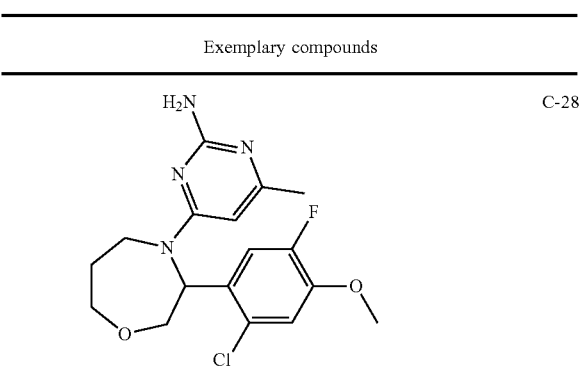
C-28
C-29
C-30
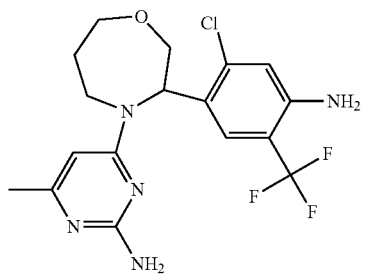 [SMILES: Cc1cc(N2CCCOCC2c2cc(C(F)(F)F)c(N)cc2Cl)nc(N)n1]
C-31
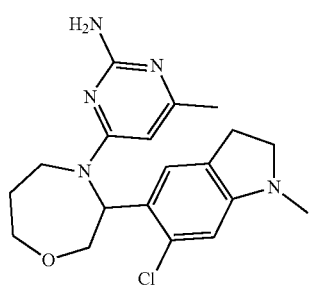 [SMILES: Cc1cc(N2CCCOCC2c2cc3c(cc2Cl)N(C)CC3)nc(N)n1]
C-32
TABLE 2-continued
Exemplary compounds
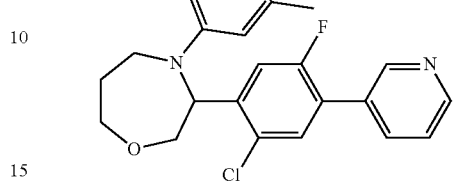
C-33
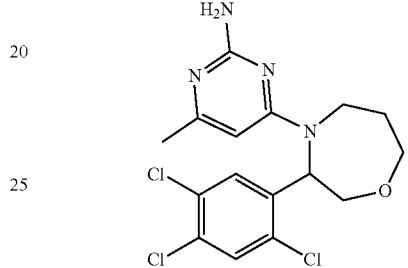
C-34
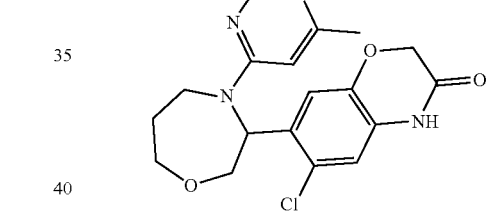
C-35
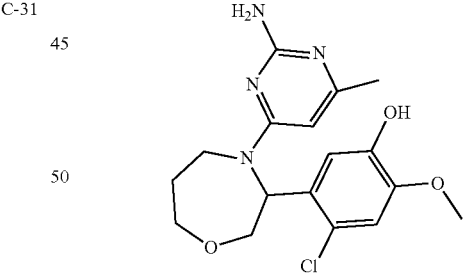
C-36
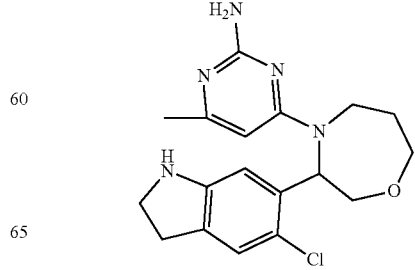
C-37

TABLE 2-continued
Exemplary compounds
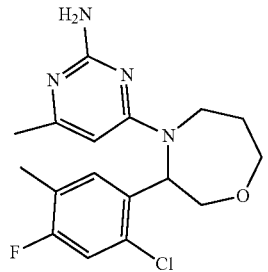
C-38
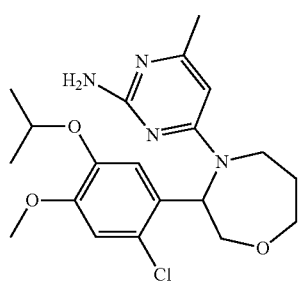 [SMILES: COc1cc(Cl)c(C2COCCCN2c2cc(C)nc(N)n2)cc1OC(C)C]
C-39
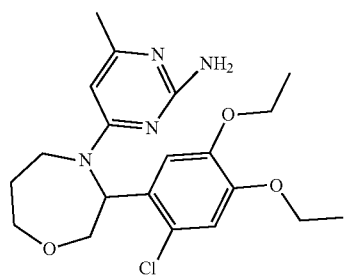 [SMILES: CCOc1cc(Cl)c(C2COCCCN2c2cc(C)nc(N)n2)cc1OCC]
C-40
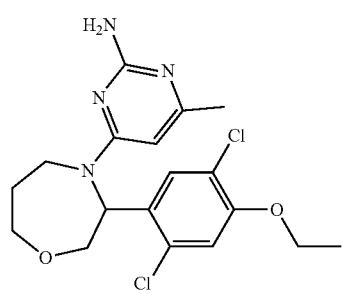 [SMILES: CCOc1cc(Cl)c(C2COCCCN2c2cc(C)nc(N)n2)cc1Cl]
C-41
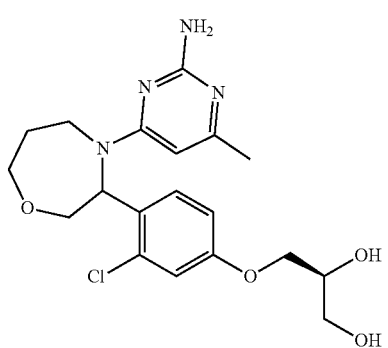 [SMILES: Cc1cc(N2CCCOCC2c2ccc(OC[C@@H](O)CO)cc2Cl)nc(N)n1]
C-42
TABLE 2-continued
Exemplary compounds
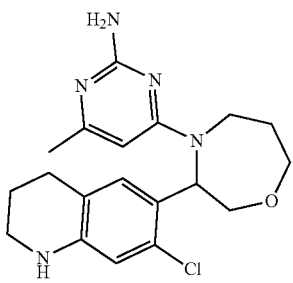 [SMILES: Cc1cc(N2CCCOCC2c2cc3c(cc2Cl)NCCC3)nc(N)n1]
C-43
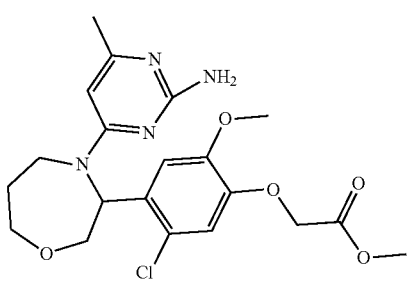 [SMILES: COC(=O)COc1cc(Cl)c(C2COCCCN2c2cc(C)nc(N)n2)cc1OC]
C-44
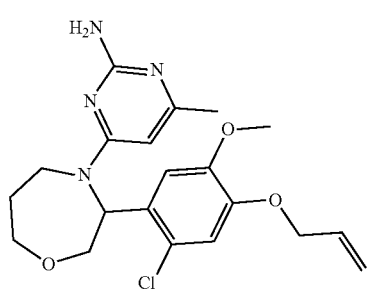 [SMILES: C=CCOc1cc(Cl)c(C2COCCCN2c2cc(C)nc(N)n2)cc1OC]
C-45
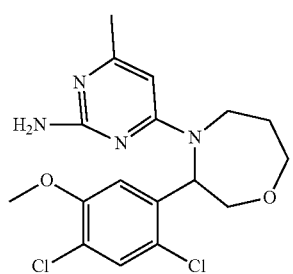 [SMILES: COc1cc(C2COCCCN2c2cc(C)nc(N)n2)c(Cl)cc1Cl]
C-46
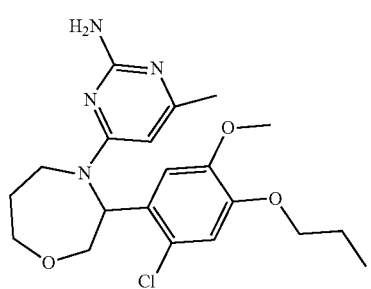 [SMILES: CCCOc1cc(Cl)c(C2COCCCN2c2cc(C)nc(N)n2)cc1OC]
C-47

TABLE 2-continued

Exemplary compounds

C-48, C-49, C-50, C-51, C-52, C-53, C-54, C-55, C-56, C-57

TABLE 2-continued

Exemplary compounds

C-58, C-59, C-60, C-61, C-62, C-63, C-64, C-65, C-66, C-67

TABLE 2-continued
Exemplary compounds
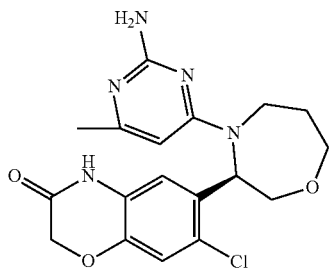 [SMILES: Cc1cc(N2CCCOC[C@H]2c2cc3c(cc2Cl)OCC(=O)N3)nc(N)n1] C-68
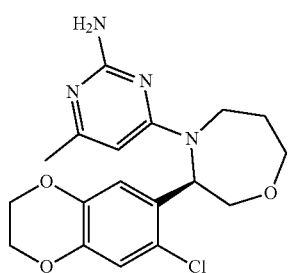 [SMILES: Cc1cc(N2CCCOC[C@H]2c2cc3c(cc2Cl)OCCO3)nc(N)n1] C-69
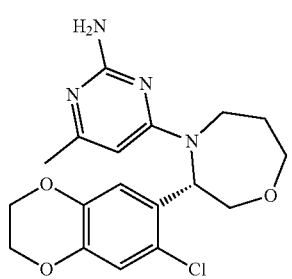 [SMILES: Cc1cc(N2CCCOC[C@@H]2c2cc3c(cc2Cl)OCCO3)nc(N)n1] C-70
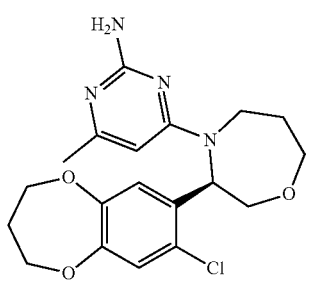 [SMILES: Cc1cc(N2CCCOC[C@H]2c2cc3c(cc2Cl)OCCCO3)nc(N)n1] C-71
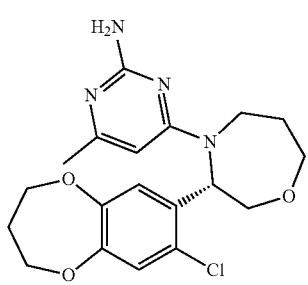 [SMILES: Cc1cc(N2CCCOC[C@@H]2c2cc3c(cc2Cl)OCCCO3)nc(N)n1] C-72
TABLE 2-continued
Exemplary compounds
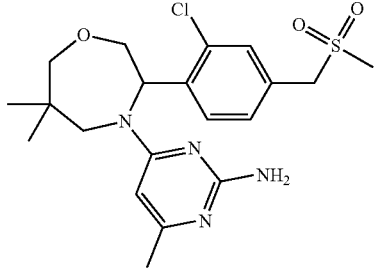 C-73
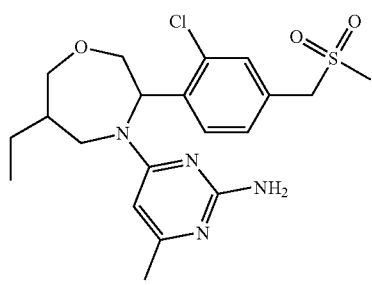 [SMILES: CCC1COCC(c2ccc(CS(C)(=O)=O)cc2Cl)N(c2cc(C)nc(N)n2)C1] C-74
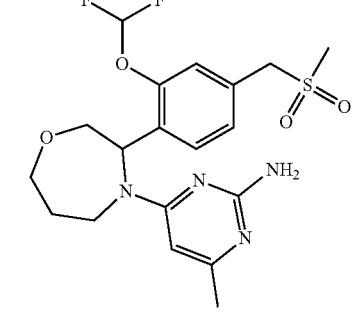 C-75
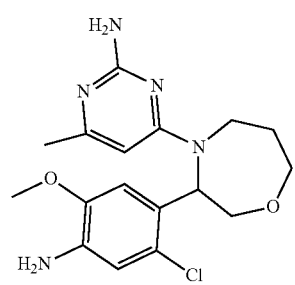 [SMILES: COc1cc(C2COCCCN2c2cc(C)nc(N)n2)c(Cl)cc1N] C-76
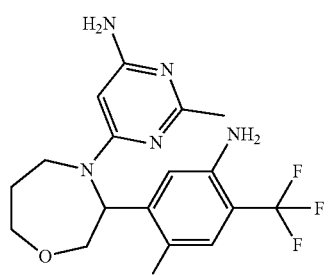 C-77

TABLE 2-continued
Exemplary compounds
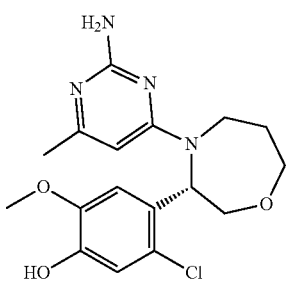 [SMILES: COc1cc([C@H]2COCCCN2c2cc(C)nc(N)n2)c(Cl)cc1O] C-78
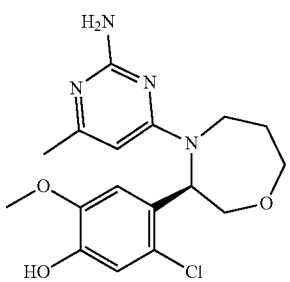 [SMILES: COc1cc([C@@H]2COCCCN2c2cc(C)nc(N)n2)c(Cl)cc1O] C-79
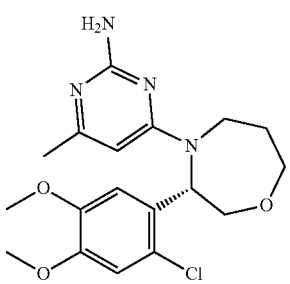 [SMILES: COc1cc(Cl)c([C@H]2COCCCN2c2cc(C)nc(N)n2)cc1OC] C-80
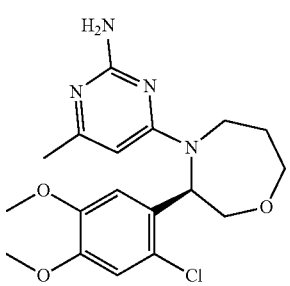 [SMILES: COc1cc(Cl)c([C@@H]2COCCCN2c2cc(C)nc(N)n2)cc1OC] C-81
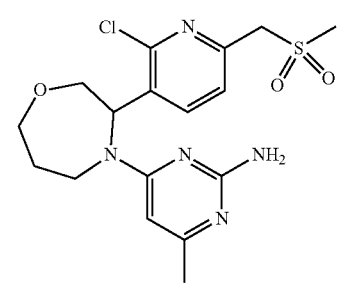 [SMILES: Cc1cc(N2CCCOCC2c2ccc(CS(C)(=O)=O)nc2Cl)nc(N)n1] C-82
TABLE 2-continued
Exemplary compounds
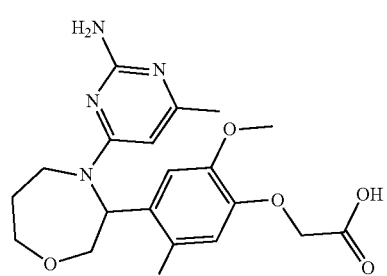 C-83
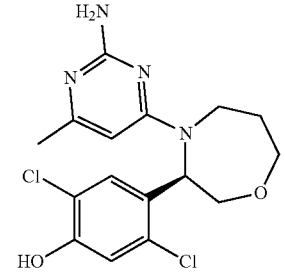 [SMILES: Cc1cc(N2CCCOC[C@H]2c2cc(Cl)c(O)cc2Cl)nc(N)n1] C-84
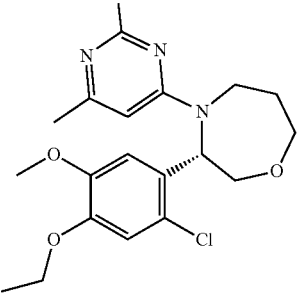 C-85
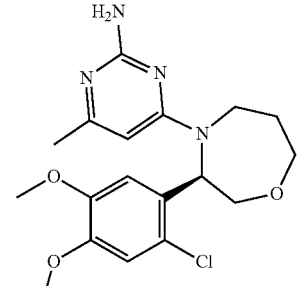 C-86
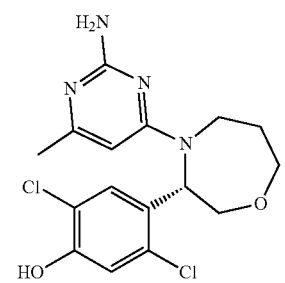 [SMILES: Cc1cc(N2CCCOC[C@@H]2c2cc(Cl)c(O)cc2Cl)nc(N)n1] C-87

TABLE 2-continued
Exemplary compounds
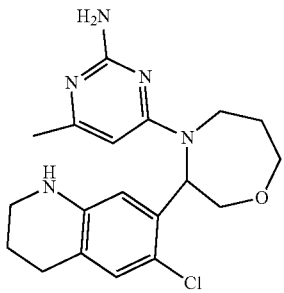 [SMILES: Cc1cc(N2CCCOCC2c2cc3c(cc2Cl)CCCN3)nc(N)n1] C-88
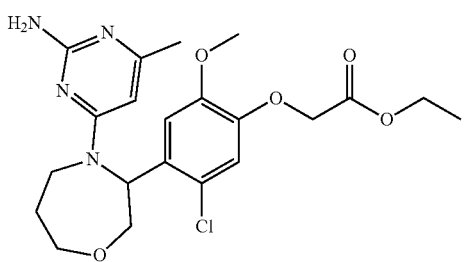 [SMILES: CCOC(=O)COc1cc(Cl)c(C2COCCCN2c2cc(C)nc(N)n2)cc1OC] C-89
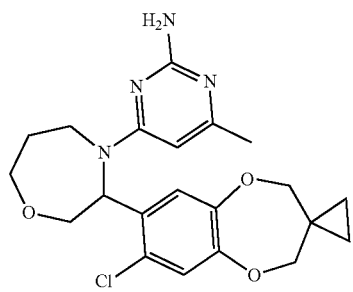 [SMILES: Cc1cc(N2CCCOCC2c2cc3c(cc2Cl)OCC2(CC2)CO3)nc(N)n1] C-90
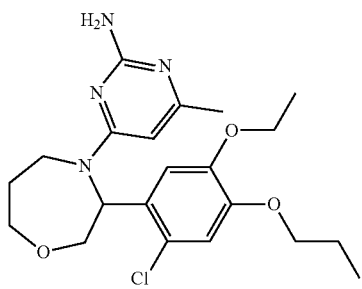 [SMILES: CCCOc1cc(Cl)c(C2COCCCN2c2cc(C)nc(N)n2)cc1OCC] C-91
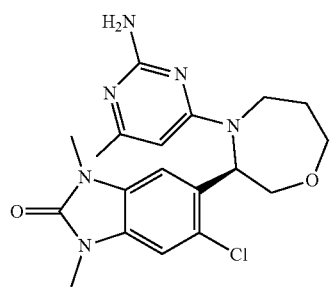 [SMILES: Cc1cc(N2CCCOC[C@H]2c2cc3c(cc2Cl)n(C)c(=O)n3C)nc(N)n1] C-92
TABLE 2-continued
Exemplary compounds
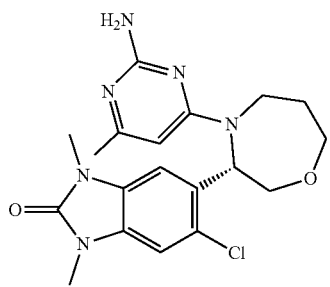 [SMILES: Cc1cc(N2CCCOC[C@@H]2c2cc3c(cc2Cl)n(C)c(=O)n3C)nc(N)n1] C-93
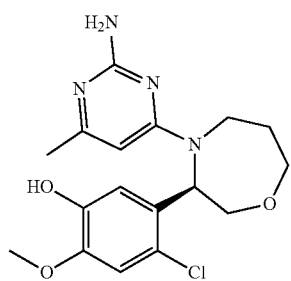 [SMILES: COc1cc(Cl)c([C@@H]2COCCCN2c2cc(C)nc(N)n2)cc1O] C-94
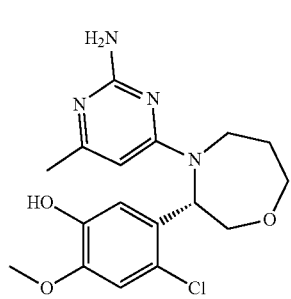 [SMILES: COc1cc(Cl)c([C@H]2COCCCN2c2cc(C)nc(N)n2)cc1O] C-95
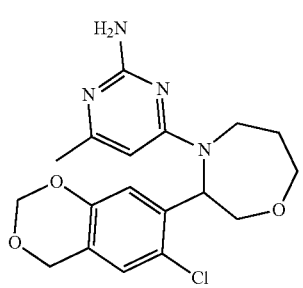 [SMILES: Cc1cc(N2CCCOCC2c2cc3c(cc2Cl)COCO3)nc(N)n1] C-96
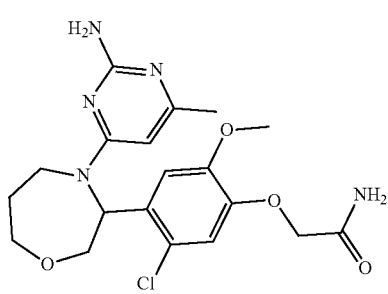 [SMILES: COc1cc(C2COCCCN2c2cc(C)nc(N)n2)c(Cl)cc1OCC(N)=O] C-97

TABLE 2-continued

Exemplary compounds

C-98, C-99, C-100, C-101, C-102, C-103, C-104, C-105, C-106, C-107

TABLE 2-continued

Exemplary compounds

| | |
|---|---|
| C-108 | C-113 |
| C-109 | C-114 |
| C-110 | C-115 |
| C-111 | C-116 |
| C-112 | C-117 |

TABLE 2-continued
Exemplary compounds
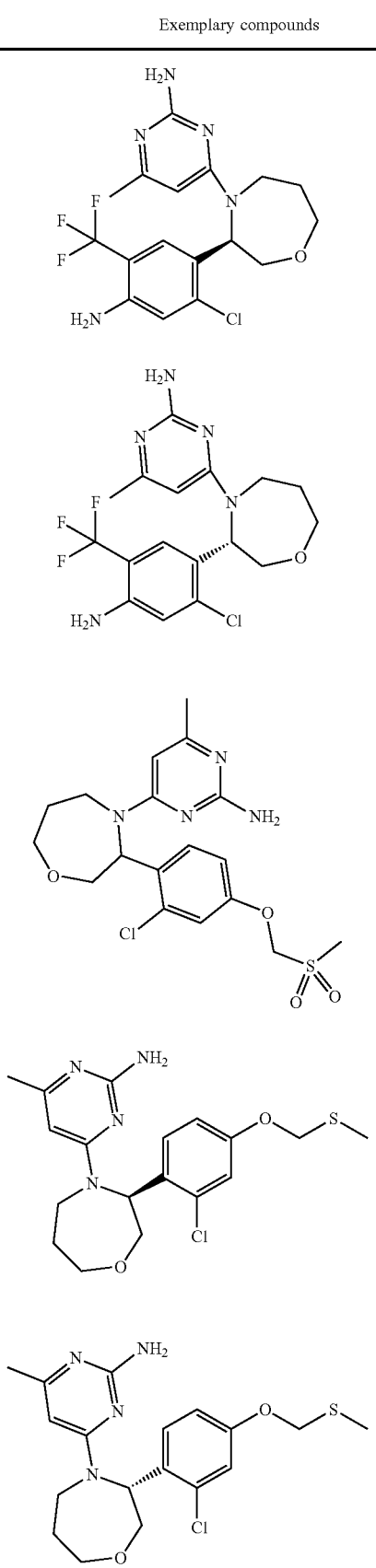
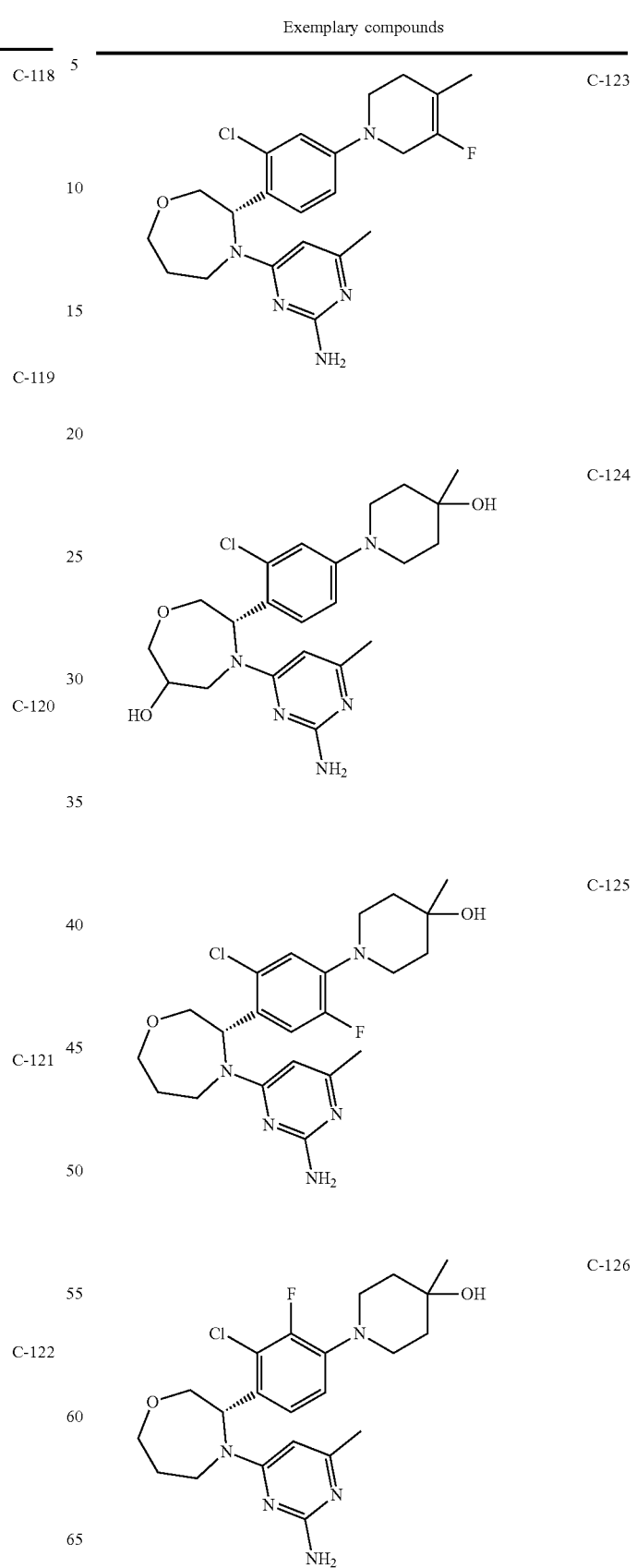

TABLE 2-continued

Exemplary compounds

C-127, C-128, C-129, C-130, C-131, C-132, C-133, C-134, C-135, C-136

TABLE 2-continued
Exemplary compounds
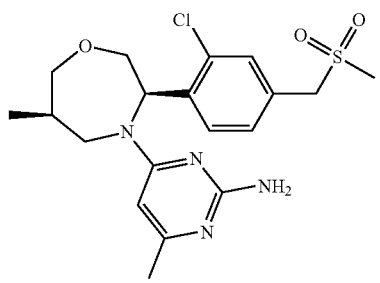 C-137
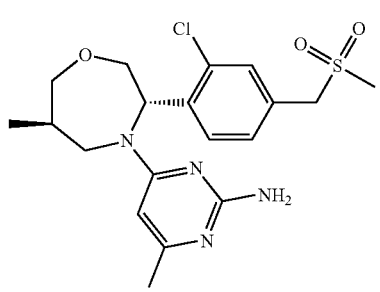 C-138
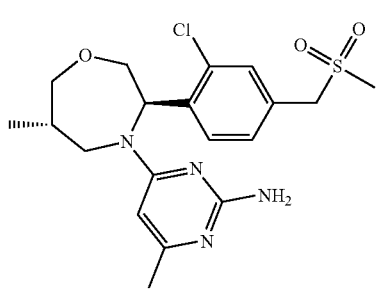 C-139
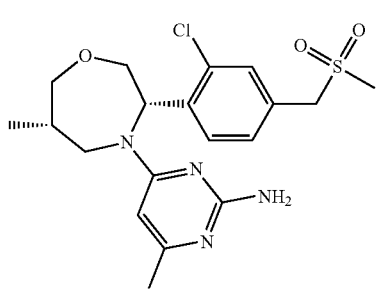 C-140
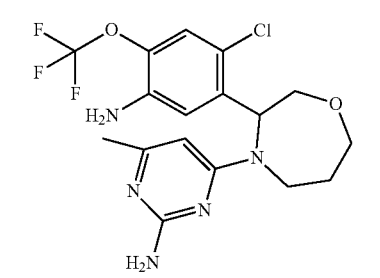 [SMILES: Cc1cc(N2CCCOCC2c2cc(N)c(OC(F)(F)F)cc2Cl)nc(N)n1] C-141
TABLE 2-continued
Exemplary compounds
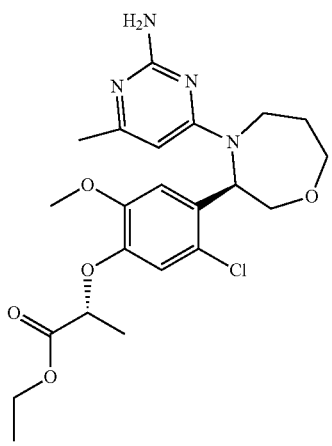 [SMILES: CCOC(=O)[C@@H](C)Oc1cc(Cl)c([C@@H]2COCCCN2c2cc(C)nc(N)n2)cc1OC] C-142
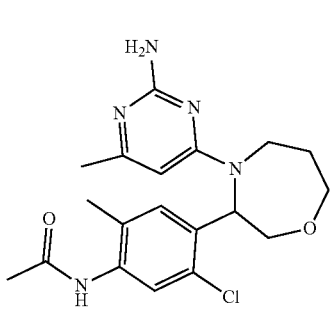 [SMILES: CC(=O)Nc1cc(Cl)c(C2COCCCN2c2cc(C)nc(N)n2)cc1C] C-143
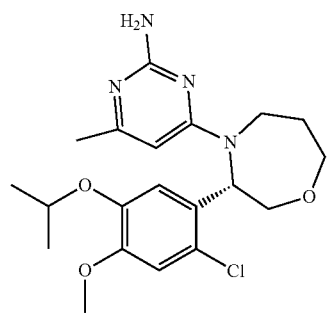 [SMILES: COc1cc(Cl)c([C@H]2COCCCN2c2cc(C)nc(N)n2)cc1OC(C)C] C-144
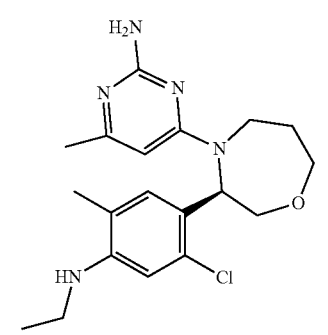 [SMILES: CCNc1cc(Cl)c([C@@H]2COCCCN2c2cc(C)nc(N)n2)cc1C] C-145

TABLE 2-continued
Exemplary compounds
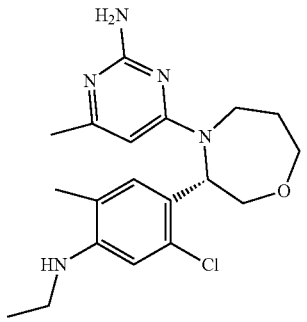 [SMILES: CCNc1cc(Cl)c([C@H]2COCCCN2c2cc(C)nc(N)n2)cc1C] C-146
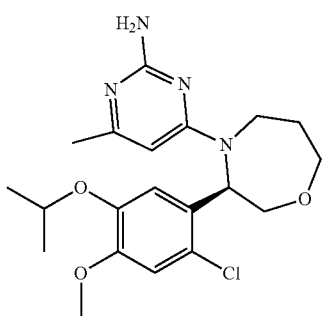 [SMILES: COc1cc(Cl)c([C@@H]2COCCCN2c2cc(C)nc(N)n2)cc1OC(C)C] C-147
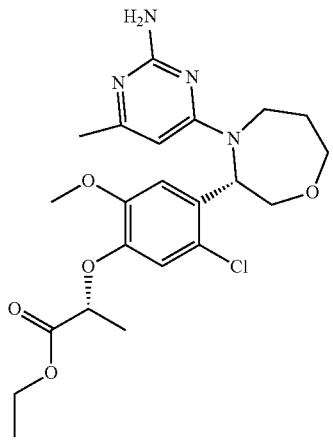 [SMILES: CCOC(=O)[C@@H](C)Oc1cc(Cl)c([C@H]2COCCCN2c2cc(C)nc(N)n2)cc1OC] C-148
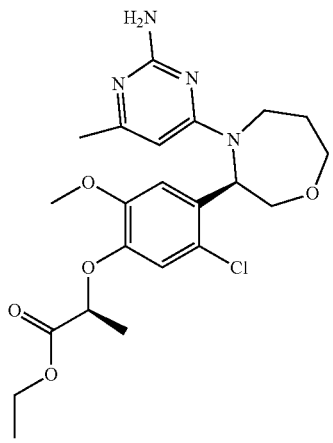 [SMILES: CCOC(=O)[C@H](C)Oc1cc(Cl)c([C@@H]2COCCCN2c2cc(C)nc(N)n2)cc1OC] C-149
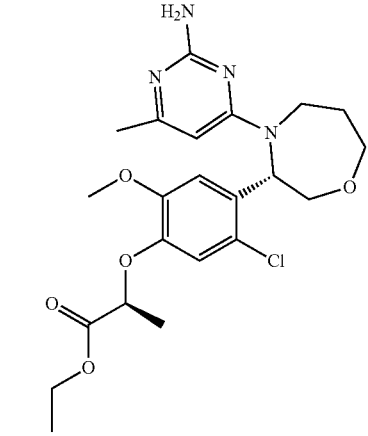 [SMILES: CCOC(=O)[C@H](C)Oc1cc(Cl)c([C@H]2COCCCN2c2cc(C)nc(N)n2)cc1OC] C-150
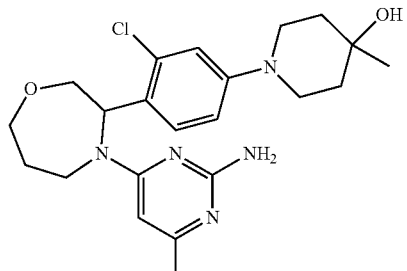 C-151
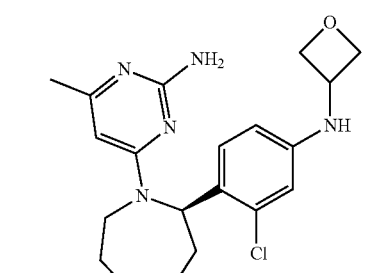 C-152
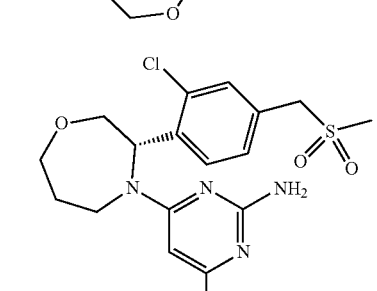 C-153
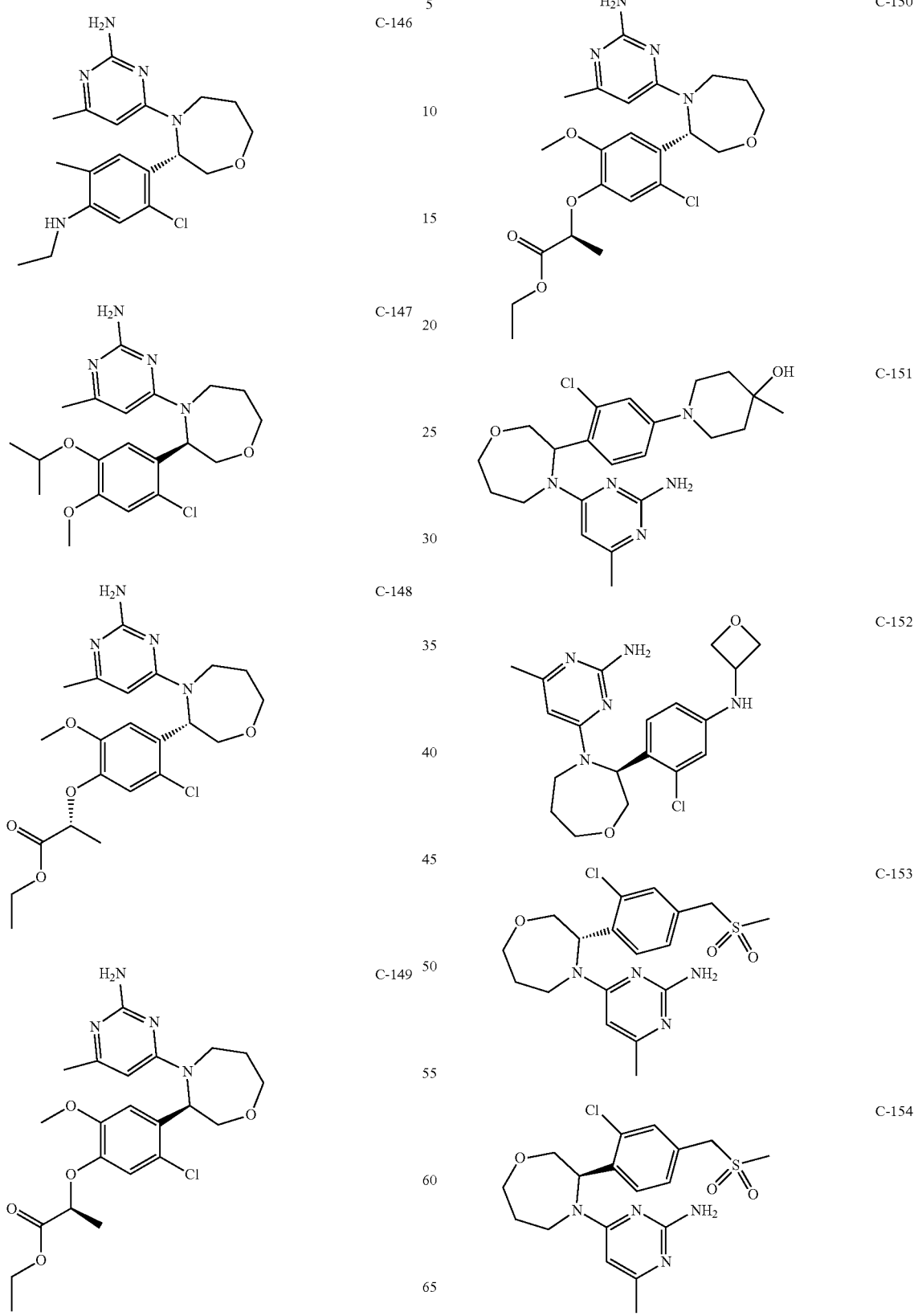 C-154

TABLE 2-continued

Exemplary compounds

C-155

TABLE 2A

Exemplary Compounds

D-1

D-2

D-3

D-4

TABLE 2A-continued

Exemplary Compounds

D-5

D-6

D-7

D-8

D-9

TABLE 2A-continued

Exemplary Compounds

TABLE 2A-continued
Exemplary Compounds
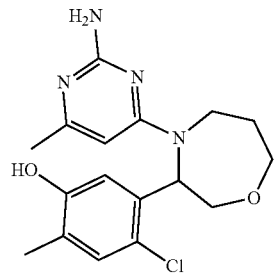 D-20
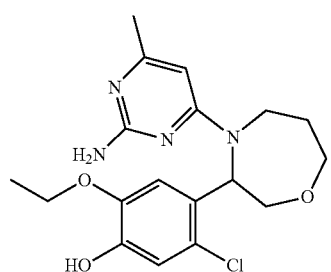 [SMILES: CCOc1cc(C2COCCCN2c2cc(C)nc(N)n2)c(Cl)cc1O] D-21
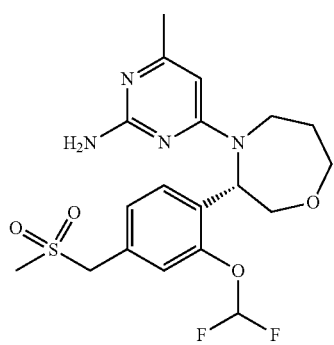 [SMILES: Cc1cc(N2CCCOC[C@@H]2c2ccc(CS(C)(=O)=O)cc2OC(F)F)nc(N)n1] D-22
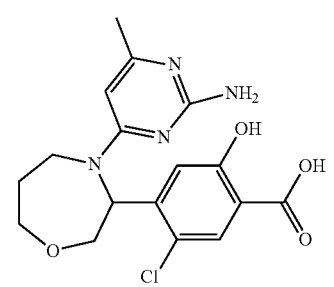 [SMILES: Cc1cc(N2CCCOCC2c2cc(O)c(C(=O)O)cc2Cl)nc(N)n1] D-23
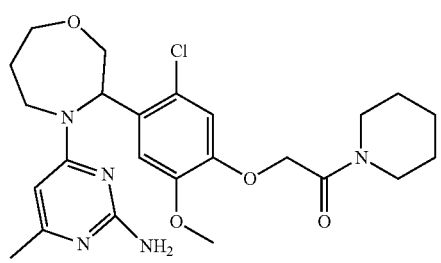 [SMILES: COc1cc(C2COCCCN2c2cc(C)nc(N)n2)c(Cl)cc1OCC(=O)N1CCCCC1] D-24
TABLE 2A-continued
Exemplary Compounds
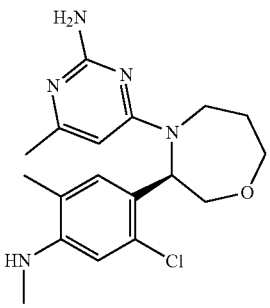 [SMILES: CNc1cc(Cl)c([C@@H]2COCCCN2c2cc(C)nc(N)n2)cc1C] D-25
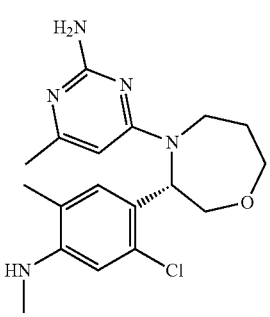 [SMILES: CNc1cc(Cl)c([C@H]2COCCCN2c2cc(C)nc(N)n2)cc1C] D-26
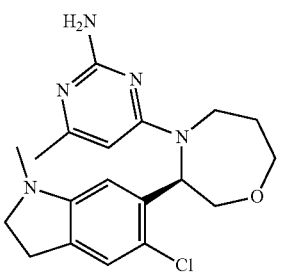 [SMILES: Cc1cc(N2CCCOC[C@H]2c2cc3c(cc2Cl)CCN3C)nc(N)n1] D-27
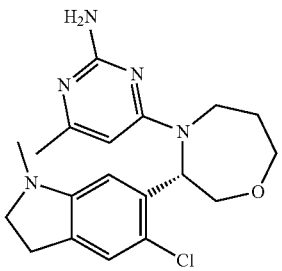 [SMILES: Cc1cc(N2CCCOC[C@@H]2c2cc3c(cc2Cl)CCN3C)nc(N)n1] D-28
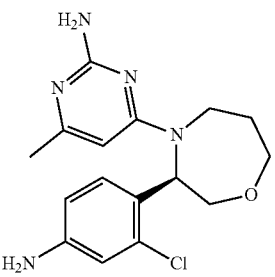 [SMILES: Cc1cc(N2CCCOC[C@H]2c2ccc(N)cc2Cl)nc(N)n1] D-29

TABLE 2A-continued
Exemplary Compounds
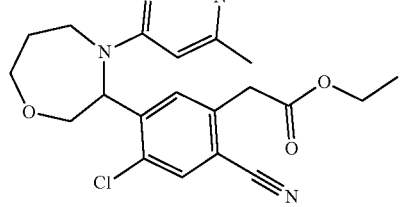

TABLE 2A-continued
Exemplary Compounds
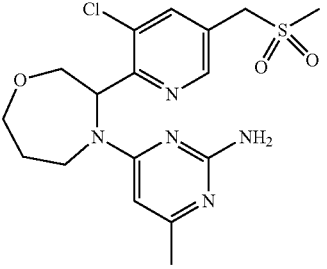 [SMILES: Cc1cc(N2CCCOCC2c2ncc(CS(C)(=O)=O)cc2Cl)nc(N)n1] D-40
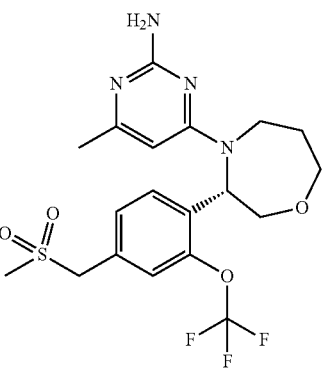 [SMILES: Cc1cc(N2CCCOC[C@@H]2c2ccc(CS(C)(=O)=O)cc2OC(F)(F)F)nc(N)n1] D-41
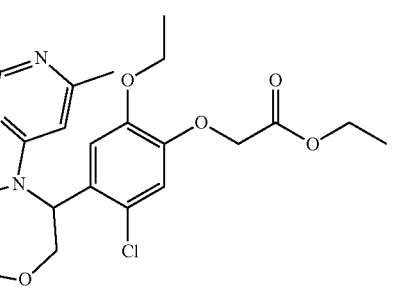 D-42
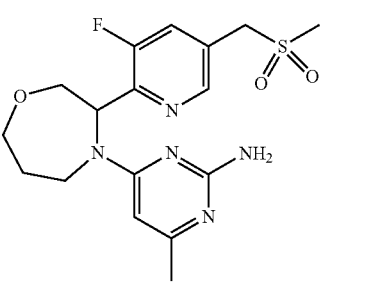 [SMILES: Cc1cc(N2CCCOCC2c2ncc(CS(C)(=O)=O)cc2F)nc(N)n1] D-43
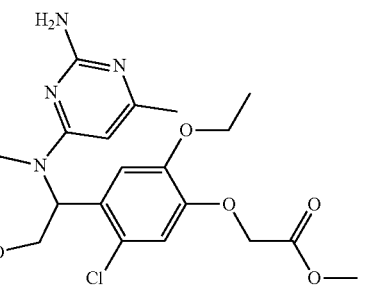 D-44
TABLE 2A-continued
Exemplary Compounds
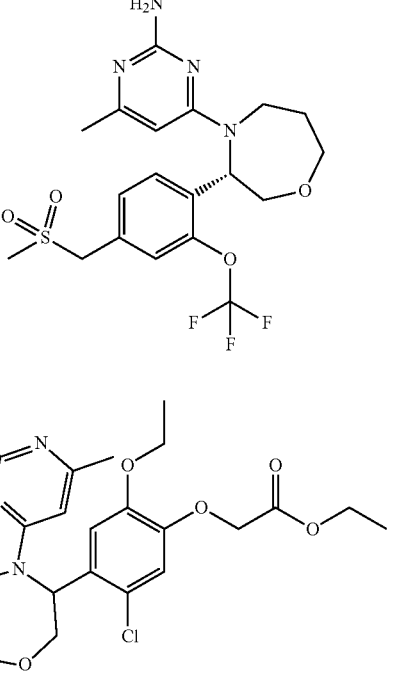 D-45
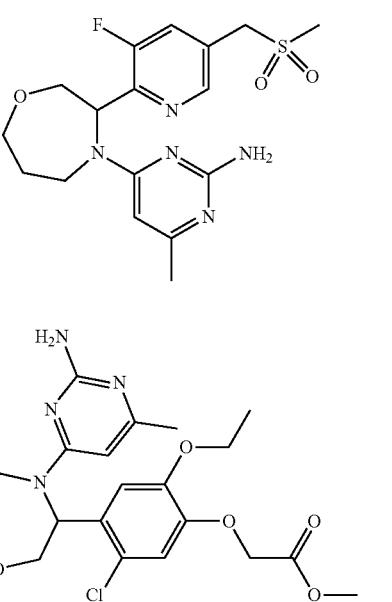 D-46
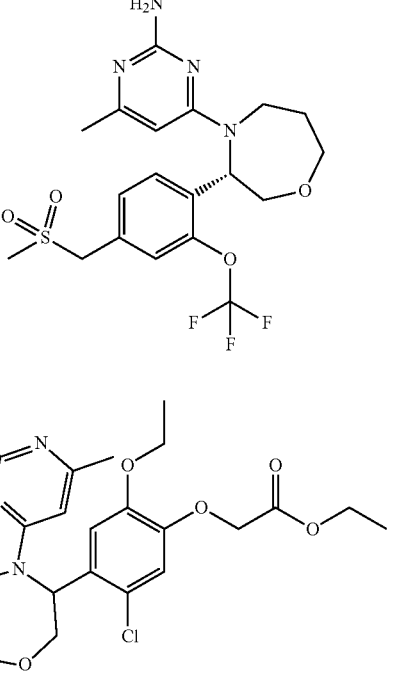 D-47
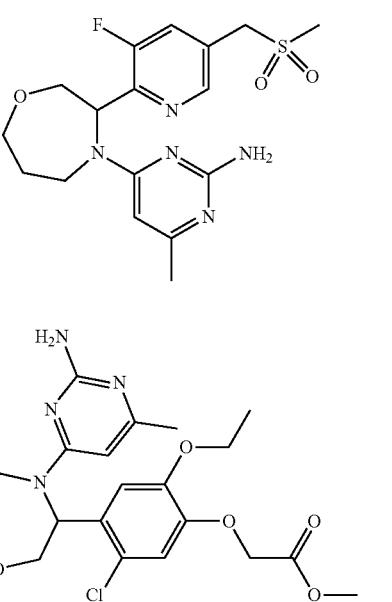 D-48
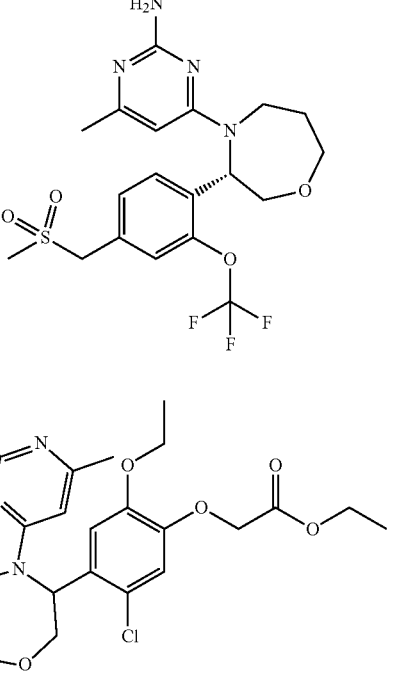 D-49

TABLE 2A-continued
Exemplary Compounds
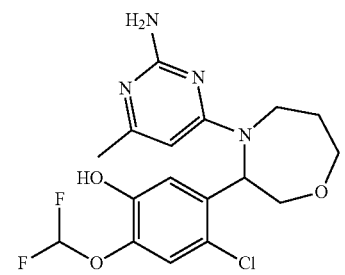 [SMILES: Cc1cc(N2CCCOCC2c2cc(O)c(OC(F)F)cc2Cl)nc(N)n1] D-50
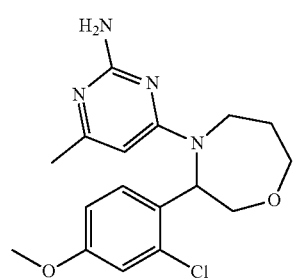 [SMILES: COc1ccc(C2COCCCN2c2cc(C)nc(N)n2)c(Cl)c1] D-51
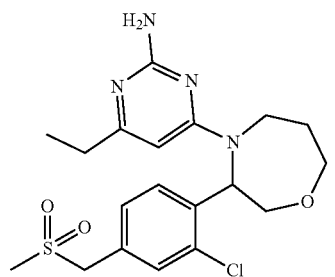 [SMILES: CCc1cc(N2CCCOCC2c2ccc(CS(C)(=O)=O)cc2Cl)nc(N)n1] D-52
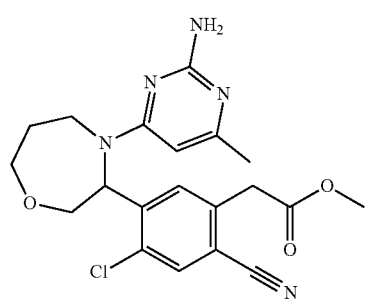 [SMILES: COC(=O)Cc1cc(C2COCCCN2c2cc(C)nc(N)n2)c(Cl)cc1C#N] D-53
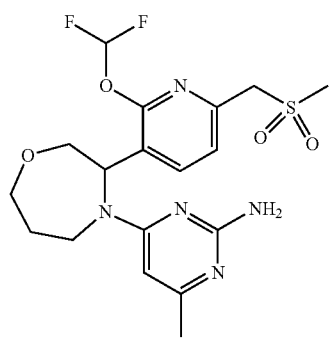 [SMILES: Cc1cc(N2CCCOCC2c2ccc(CS(C)(=O)=O)nc2OC(F)F)nc(N)n1] D-54
TABLE 2A-continued
Exemplary Compounds
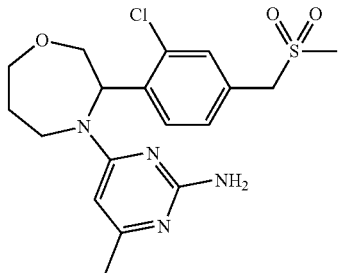 [SMILES: Cc1cc(N2CCCOCC2c2ccc(CS(C)(=O)=O)cc2Cl)nc(N)n1] D-55
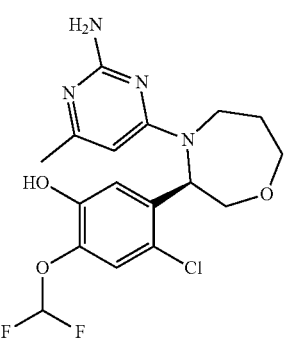 [SMILES: Cc1cc(N2CCCOC[C@H]2c2cc(O)c(OC(F)F)cc2Cl)nc(N)n1] D-56
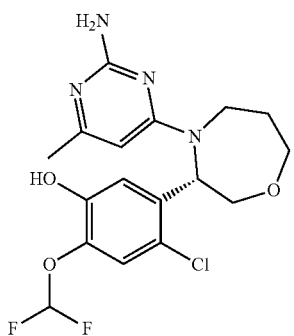 [SMILES: Cc1cc(N2CCCOC[C@@H]2c2cc(O)c(OC(F)F)cc2Cl)nc(N)n1] D-57
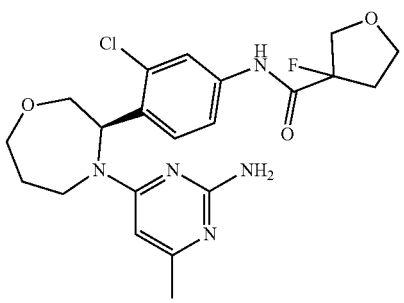 [SMILES: Cc1cc(N2CCCOC[C@H]2c2ccc(NC(=O)C3(F)CCOC3)cc2Cl)nc(N)n1] D-58
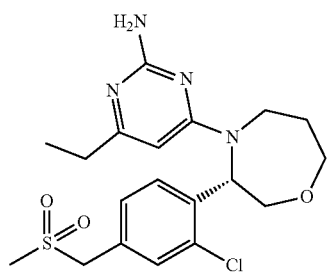 [SMILES: CCc1cc(N2CCCOC[C@@H]2c2ccc(CS(C)(=O)=O)cc2Cl)nc(N)n1] D-59

TABLE 2A-continued
Exemplary Compounds
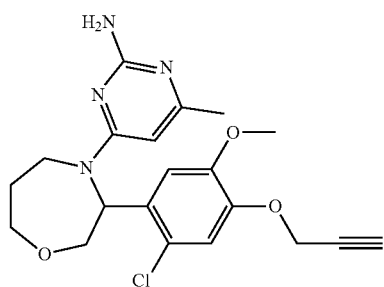 [SMILES: C#CCOc1cc(Cl)c(C2COCCCN2c2cc(C)nc(N)n2)cc1OC] D-60
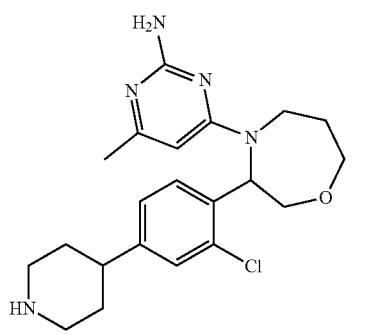 [SMILES: Cc1cc(N2CCCOCC2c2ccc(C3CCNCC3)cc2Cl)nc(N)n1] D-61
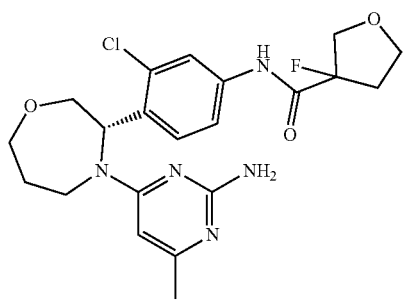 [SMILES: Cc1cc(N2CCCOC[C@@H]2c2ccc(NC(=O)C3(F)CCOC3)cc2Cl)nc(N)n1] D-62
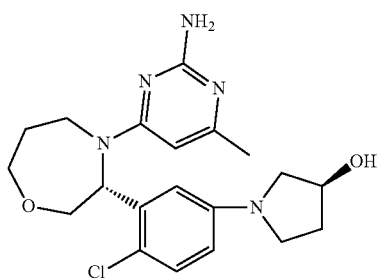 [SMILES: Cc1cc(N2CCCOC[C@H]2c2cc(N3CC[C@H](O)C3)ccc2Cl)nc(N)n1] D-63
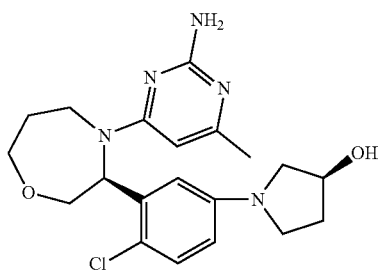 [SMILES: Cc1cc(N2CCCOC[C@@H]2c2cc(N3CC[C@H](O)C3)ccc2Cl)nc(N)n1] D-64
TABLE 2A-continued
Exemplary Compounds
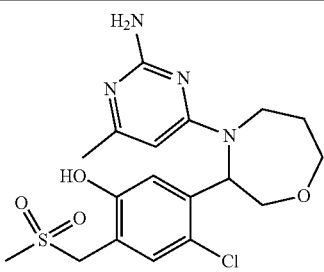 D-65
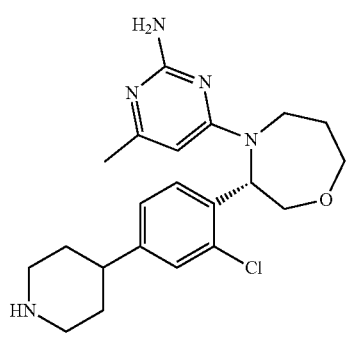 D-66
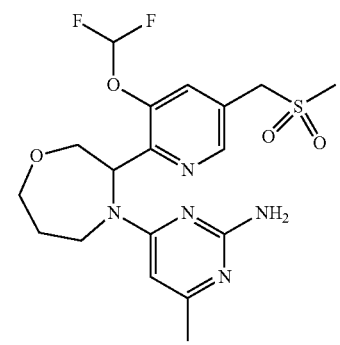 [SMILES: Cc1cc(N2CCCOCC2c2ncc(CS(C)(=O)=O)cc2OC(F)F)nc(N)n1] D-67
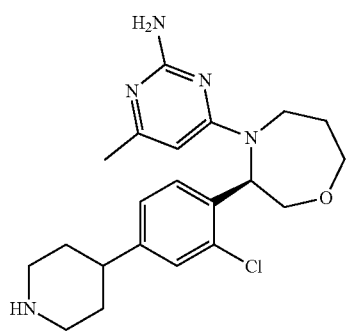 [SMILES: Cc1cc(N2CCCOC[C@H]2c2ccc(C3CCNCC3)cc2Cl)nc(N)n1] D-68

TABLE 2A-continued

Exemplary Compounds

TABLE 2A-continued
Exemplary Compounds
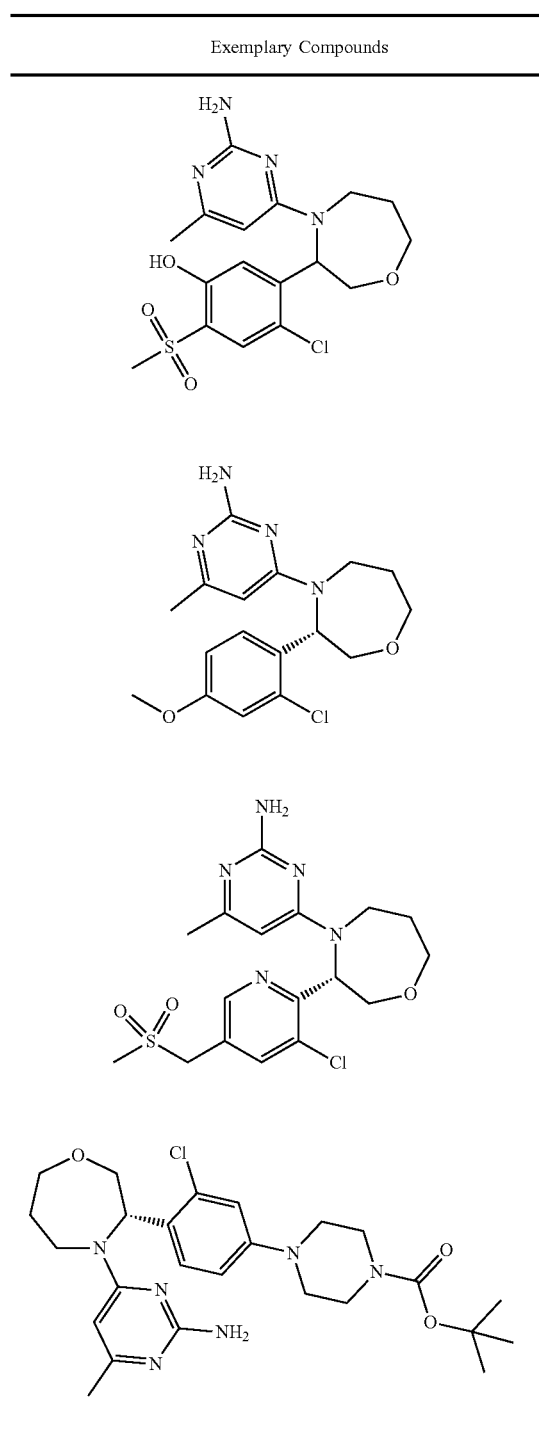
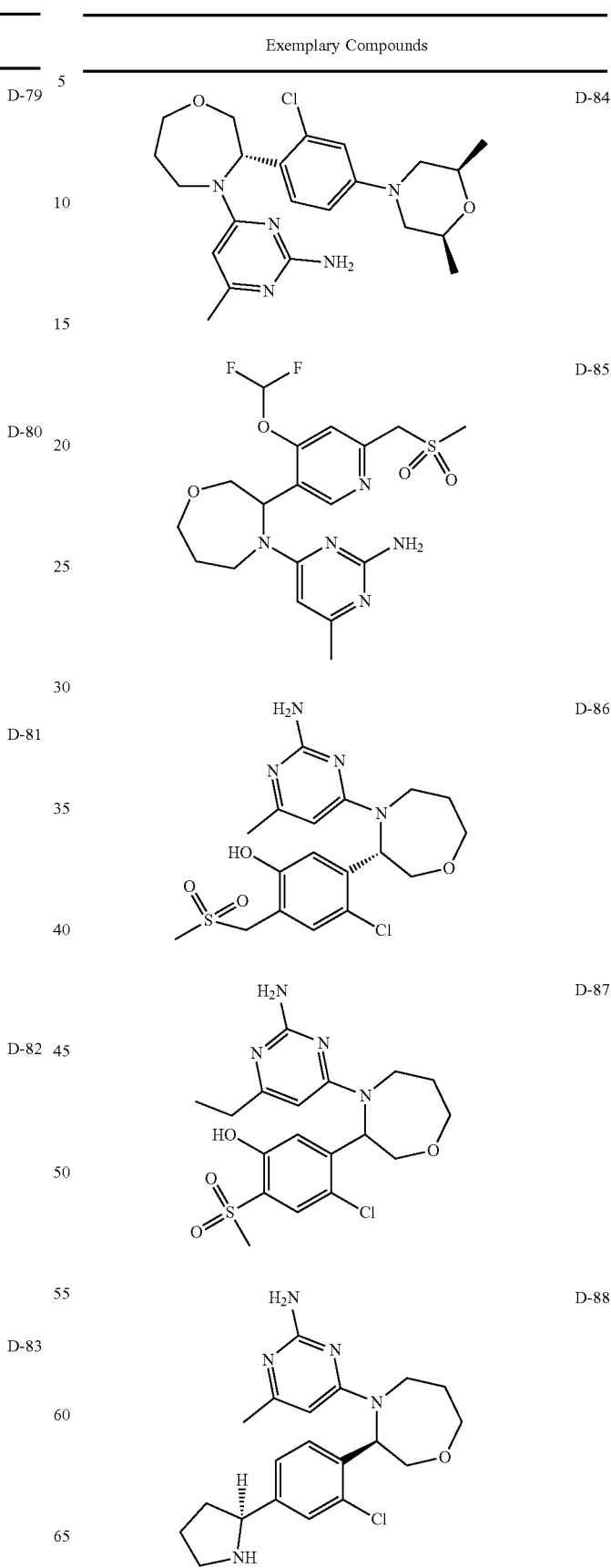

TABLE 2A-continued
Exemplary Compounds
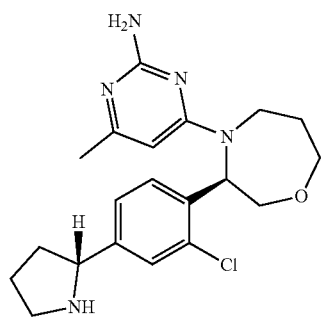 [SMILES: Cc1cc(N2CCCOC[C@H]2c2ccc([C@H]3CCCN3)cc2Cl)nc(N)n1] D-89
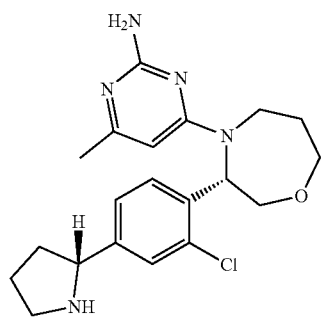 [SMILES: Cc1cc(N2CCCOC[C@@H]2c2ccc([C@H]3CCCN3)cc2Cl)nc(N)n1] D-90
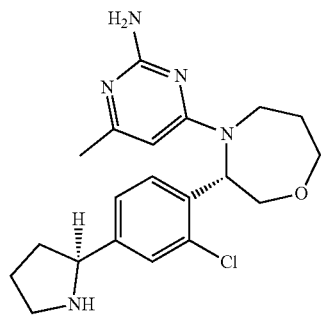 [SMILES: Cc1cc(N2CCCOC[C@@H]2c2ccc([C@@H]3CCCN3)cc2Cl)nc(N)n1] D-91
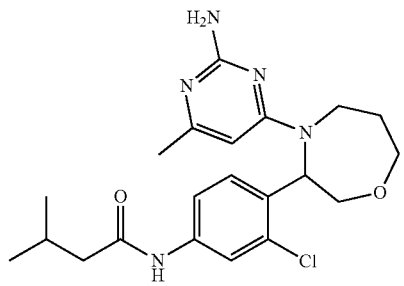 [SMILES: Cc1cc(N2CCCOCC2c2ccc(NC(=O)CC(C)C)cc2Cl)nc(N)n1] D-92
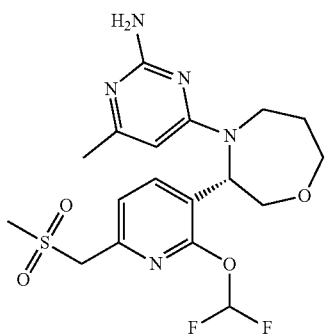 [SMILES: Cc1cc(N2CCCOC[C@@H]2c2ccc(CS(C)(=O)=O)nc2OC(F)F)nc(N)n1] D-93
TABLE 2A-continued
Exemplary Compounds
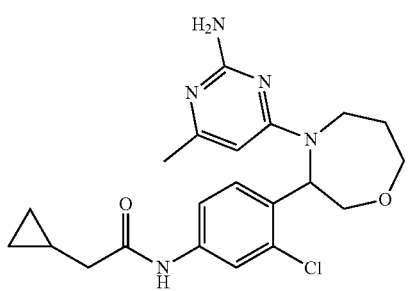 [SMILES: Cc1cc(N2CCCOCC2c2ccc(NC(=O)CC3CC3)cc2Cl)nc(N)n1] D-94
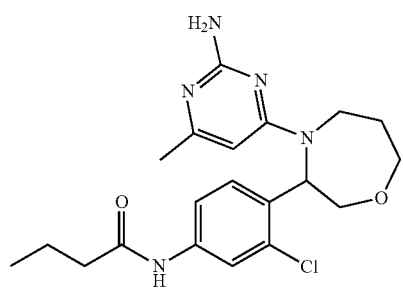 [SMILES: CCCC(=O)Nc1ccc(C2COCCCN2c2cc(C)nc(N)n2)c(Cl)c1] D-95
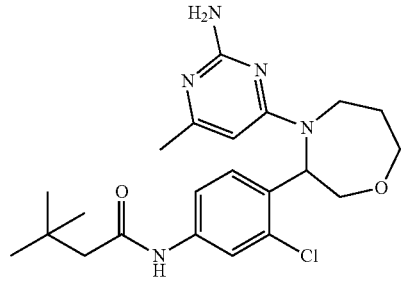 [SMILES: Cc1cc(N2CCCOCC2c2ccc(NC(=O)CC(C)(C)C)cc2Cl)nc(N)n1] D-96
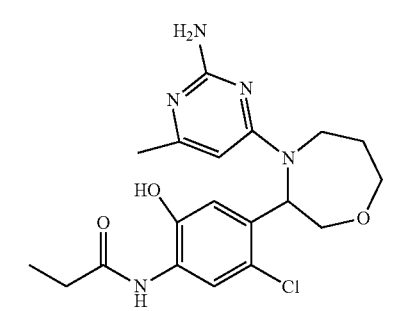 [SMILES: CCC(=O)Nc1cc(Cl)c(C2COCCCN2c2cc(C)nc(N)n2)cc1O] D-97
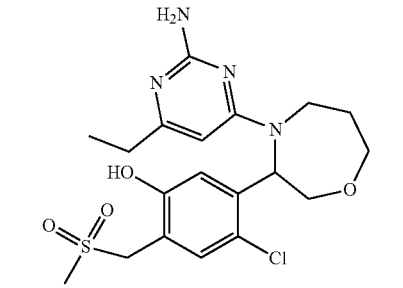 [SMILES: CCc1cc(N2CCCOCC2c2cc(O)c(CS(C)(=O)=O)cc2Cl)nc(N)n1] D-98

TABLE 2A-continued
Exemplary Compounds
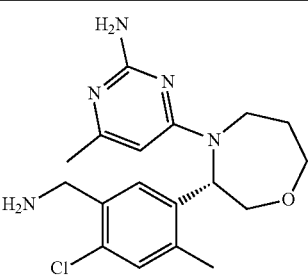 D-99
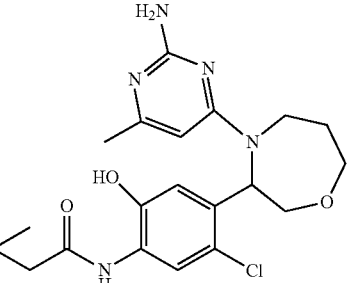 D-100
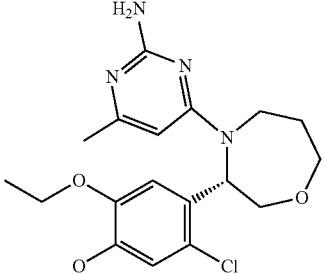 D-101
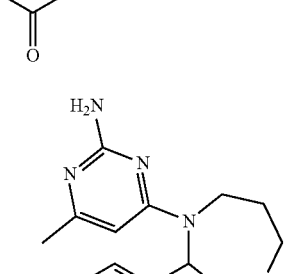 D-102
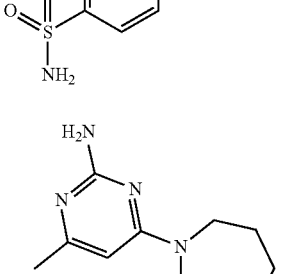 D-103
TABLE 2A-continued
Exemplary Compounds
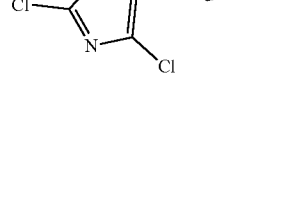 D-104
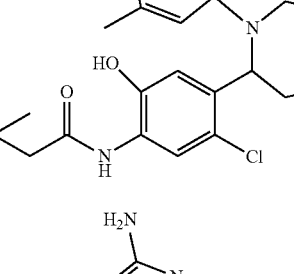 D-105
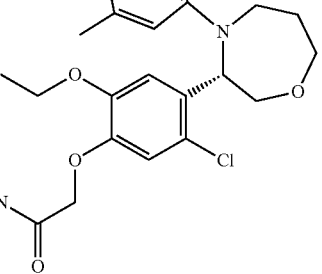 D-106
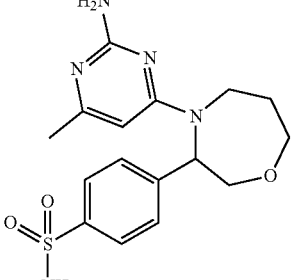 D-107
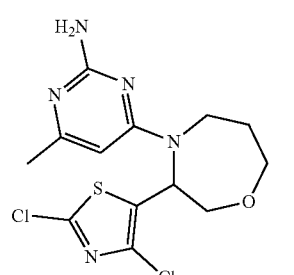 D-108

TABLE 2A-continued

Exemplary Compounds

D-109, D-110, D-111, D-112, D-113, D-114, D-115, D-116, D-117, D-118

TABLE 2A-continued
Exemplary Compounds
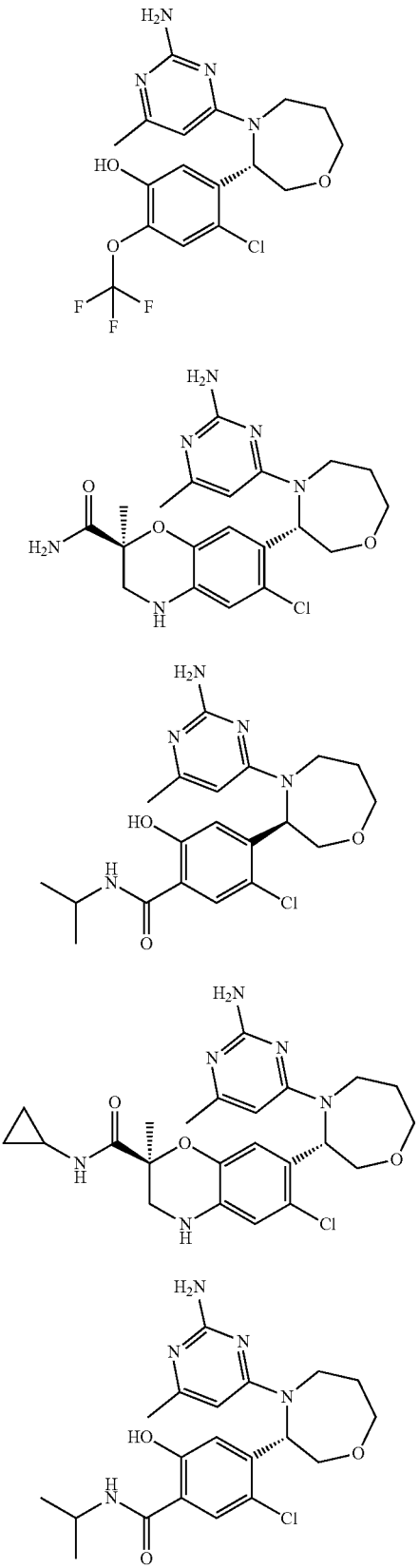
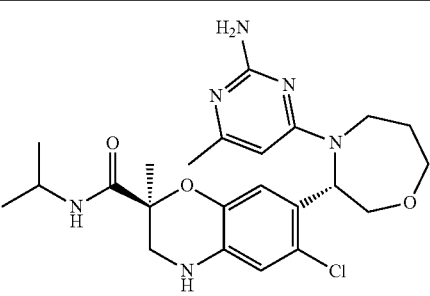

TABLE 2A-continued
Exemplary Compounds
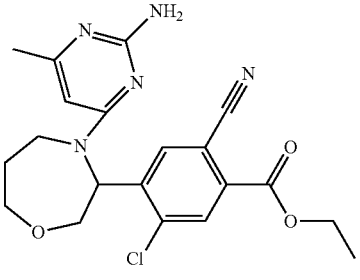 [SMILES: CCOC(=O)c1cc(Cl)c(C2COCCCN2c2cc(C)nc(N)n2)cc1C#N] D-129
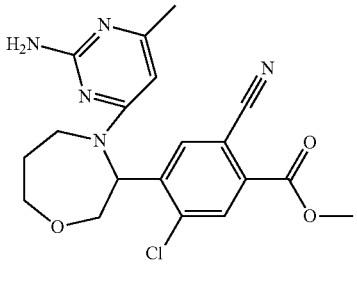 [SMILES: COC(=O)c1cc(Cl)c(C2COCCCN2c2cc(C)nc(N)n2)cc1C#N] D-130
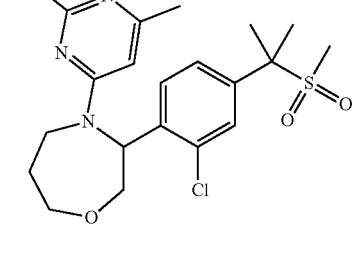 D-131
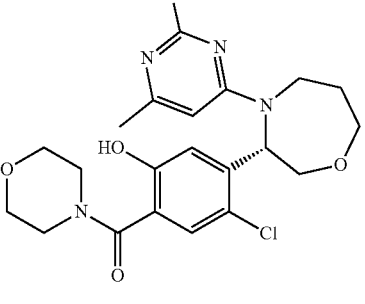 D-132
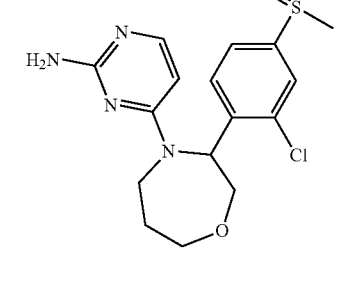 D-133
 D-134
D-135
D-136
D-137
D-138

TABLE 2A-continued
Exemplary Compounds
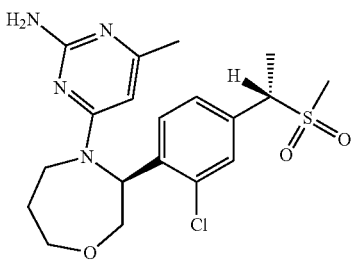 [SMILES: Cc1cc(N2CCCOC[C@@H]2c2ccc([C@H](C)S(C)(=O)=O)cc2Cl)nc(N)n1] D-139
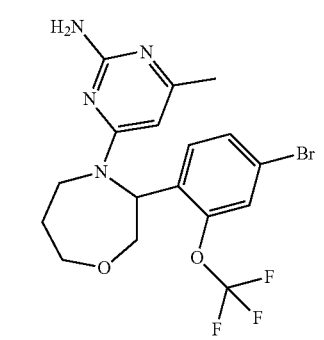 [SMILES: Cc1cc(N2CCCOCC2c2ccc(Br)cc2OC(F)(F)F)nc(N)n1] D-140
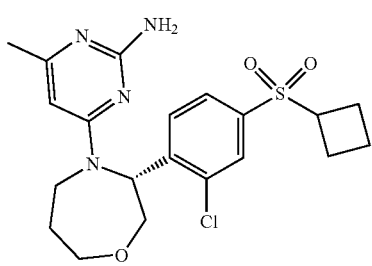 [SMILES: Cc1cc(N2CCCOC[C@H]2c2ccc(S(=O)(=O)C3CCC3)cc2Cl)nc(N)n1] D-141
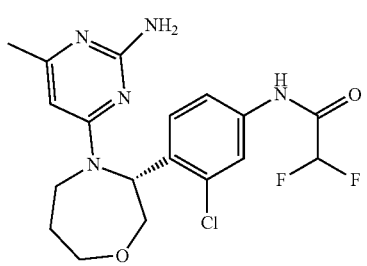 [SMILES: Cc1cc(N2CCCOC[C@H]2c2ccc(NC(=O)C(F)F)cc2Cl)nc(N)n1] D-142
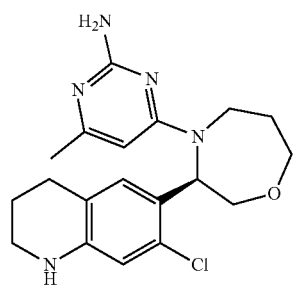 [SMILES: Cc1cc(N2CCCOC[C@H]2c2cc3c(cc2Cl)NCCC3)nc(N)n1] D-143
TABLE 2A-continued
Exemplary Compounds
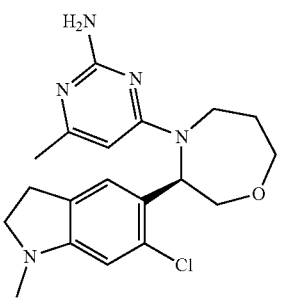 [SMILES: Cc1cc(N2CCCOC[C@H]2c2cc3c(cc2Cl)N(C)CC3)nc(N)n1] D-144
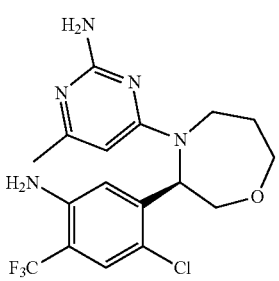 [SMILES: Cc1cc(N2CCCOC[C@H]2c2cc(N)c(C(F)(F)F)cc2Cl)nc(N)n1] D-145
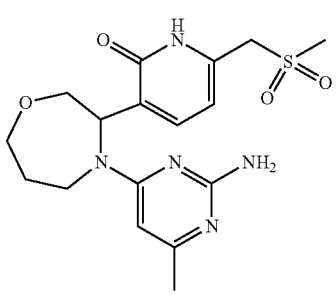 [SMILES: Cc1cc(N2CCCOCC2c2ccc(CS(C)(=O)=O)[nH]c2=O)nc(N)n1] D-146
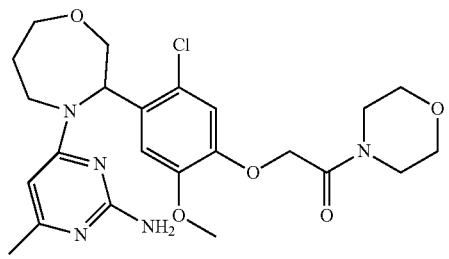 [SMILES: COc1cc(C2COCCCN2c2cc(C)nc(N)n2)c(Cl)cc1OCC(=O)N1CCOCC1] D-147
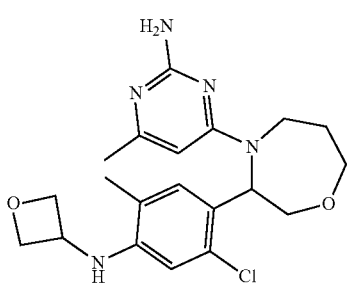 [SMILES: Cc1cc(N2CCCOCC2c2cc(C)c(NC3COC3)cc2Cl)nc(N)n1] D-148

TABLE 2A-continued

Exemplary Compounds

D-149, D-150, D-151, D-152, D-153, D-154, D-155, D-156, D-157, D-158

TABLE 2A-continued

Exemplary Compounds

TABLE 2A-continued

Exemplary Compounds

D-169, D-170, D-171, D-172, D-173, D-174, D-175, D-176, D-177, D-178

TABLE 2A-continued

Exemplary Compounds

TABLE 2A-continued

Exemplary Compounds

D-189

D-190

D-191

D-192

D-193

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, New York, 1994, the entireties of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl) ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, New York, 1994, the entireties of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below.

In one aspect, the present invention provides a method for synthesizing a compound of Formula I, or subformulae thereof, or a salt thereof, comprising reacting a compound of formula:

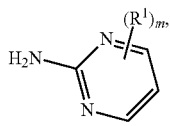

or a salt thereof, and a compound of formula

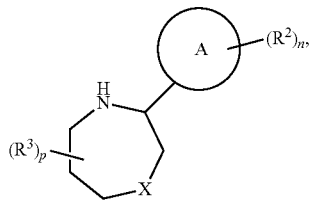

or a salt thereof, wherein each of Ring A, $R^1$, $R^2$, $R^3$, R, X, m, n, and p is as defined above and described in embodiments herein, both singly and in combination.

In some embodiments, the present invention provides a compound of formula:

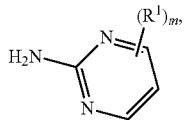

or a salt thereof, wherein each of $R^1$, R, and m is as defined above and described in embodiments herein, both singly and in combination.

In some embodiments, the present invention provides a compound of formula:

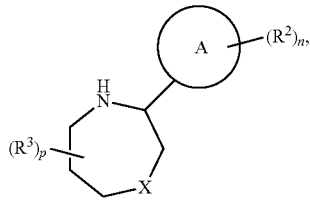

or a salt thereof, wherein each of Ring A, $R^2$, $R^3$, R, X, n, and p is as defined above and described in embodiments herein, both singly and in combination.

In one aspect, the present invention provides a method for synthesizing a compound of Formula I', or subformulae thereof, or a salt thereof, comprising reacting a compound of formula:

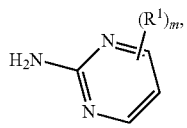

or a salt thereof, and a compound of formula:

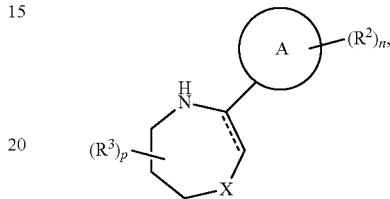

or a salt thereof, wherein each of Ring A, $R^1$, $R^2$, $R^3$, ======, R, X, m, n, and p is as defined above and described in embodiments herein, both singly and in combination.

In some embodiments, the present invention provides a compound of formula:

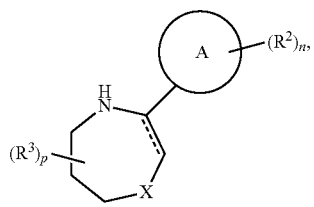

or a salt thereof, wherein each of Ring A, $R^2$, $R^3$, ======, R, X, n, and p is as defined above and described in embodiments herein, both singly and in combination.

In some embodiments, the present invention provides a method for synthesizing a compound of Formula VII, or a salt thereof, comprising reacting a compound of formula:

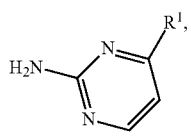

or a salt thereof, and a compound of formula:

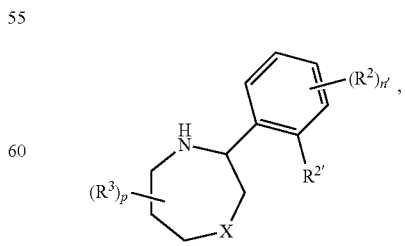

or a salt thereof, wherein each of $R^1$, $R^2$, $R^{2'}$, $R^3$, R, X, p, and n' is as defined above and described in embodiments herein, both singly and in combination.

In some embodiments, the present invention provides a method for synthesizing a compound of Formula VIII, or a salt thereof, comprising reacting a compound of formula:

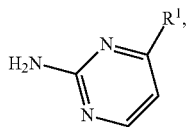

or a salt thereof, and a compound of formula:

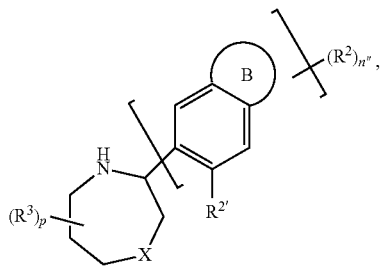

or a salt thereof, wherein each of Ring B, $R^1$, $R^2$, $R^{2'}$, $R^3$, R, X, p, and n" is as defined above and described in embodiments herein, both singly and in combination.

In some embodiments, the present invention provides a compound of formula:

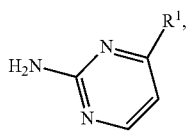

or a salt thereof, wherein each of $R^1$ and R is as defined above and described in embodiments herein, both singly and in combination.

In some embodiments, the present invention provides a compound of formula:

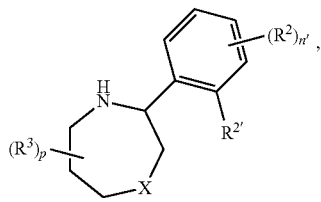

or a salt thereof, wherein each of $R^2$, $R^{2'}$, $R^3$, R, X, p, and n' is as defined above and described in embodiments herein, both singly and in combination.

In some embodiments, the present invention provides a compound of formula:

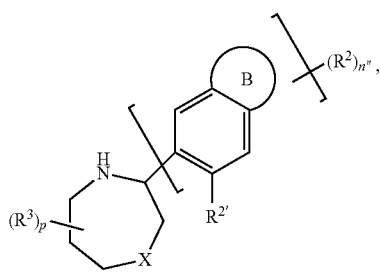

or a salt thereof, wherein each of Ring B, $R^2$, $R^{2'}$, $R^3$, R, X, p, and n" is as defined above and described in embodiments herein, both singly and in combination.

5. Uses, Formulation and Administration

Pharmaceutically Acceptable Compositions

According to another embodiment, the invention provides a composition comprising a compound of this invention, or a pharmaceutically acceptable derivative thereof, and a pharmaceutically acceptable carrier, adjuvant, or vehicle. In certain embodiments, the amount of compound in compositions of this invention is such that is effective to cause cancer cell death in a biological sample or in a patient. In certain embodiments, the amount of compound in compositions of this invention is such that is effective to induce UPR in cancer cells in a biological sample or in a patient. In certain embodiments, the amount of compound in compositions of this invention is such that is effective to induce ER stress in cancer cells in a biological sample or in a patient. In certain embodiments, the amount of compound in compositions of this invention is such that is effective to induce calcium release from the ER via WFS1 in cancer cells in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof also results in cell death.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for treatment of cellular proliferative disorders. As provided above, the compounds described herein have been found capable of causing calcium release from the endoplasmic reticulum (ER) via a putative $Ca^{2+}$ channel known as Wolframin (WFS1), inducing ER stress and the "unfolded protein response" (UPR), and resulting cell death.

In some embodiments, the present invention provides a method for treating a cellular proliferative disorder in a patient comprising administering to said patient a compound of the present invention, or a composition comprising said compound. In some embodiments, the present invention provides a compound of the present invention, or a composition comprising said compound, for use in the treatment of a cellular proliferative disorder. Such disorders are described in detail herein. In some embodiments, a cellular proliferative disorder is a cancer characterized by Wolframin (WFS1) overexpression in the cancer cells. In some embodiments, a cancer characterized by Wolframin (WFS1) overexpression is selected from non-small cell lung cancer (NSCLC), myeloma, multiple myeloma, hepatocellular carcinoma (HCC), breast cancer, bladder cancer, kidney cancer, and melanoma. In some embodiments, a method for treating a cellular proliferative disorder as described herein further comprises determining the Wolframin (WFS1) expression level. In some embodiments, the Wolframin (WFS1) expression level is determined by immunohistochemistry and/or microarray probe intensity.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for inducing ER stress in a patient in need thereof, comprising administering a compound of the present invention, or a composition comprising said compound. In some embodiments, the present invention provides a method for inducing the "unfolded protein response" (UPR) in a patient in need thereof, comprising administering a compound of the present invention, or a composition comprising said compound. In some embodiments, the present invention provides a method for causing calcium release from the endoplasmic reticulum (ER) via a putative $Ca^{2+}$ channel known as Wolframin (WFS1) in a patient in need thereof, comprising administering a compound of the present invention, or a composition comprising said compound.

In some embodiments, the present invention provides a compound of any one of Formulas I-VIII, or a composition comprising said compound, for use in causing calcium release from the endoplasmic reticulum (ER) via a putative $Ca^{2+}$ channel known as Wolframin (WFS1) in a subject in need thereof. In some embodiments, the present invention provides a compound of any one of Formulas I-VIII, or a composition comprising said compound, for use in inducing ER stress in a subject in need thereof. In some embodiments, the present invention provides a compound of any one of Formulas I-VIII, or a composition comprising said compound, for use in inducing the "unfolded protein response" (UPR) in a subject in need thereof.

In some embodiments, the present invention provides a compound of Formula I', or a composition comprising said compound, for use in causing calcium release from the endoplasmic reticulum (ER) via a putative $Ca^{2+}$ channel known as Wolframin (WFS1) in a subject in need thereof. In some embodiments, the present invention provides a compound of Formula I', or a composition comprising said compound, for use in inducing ER stress in a subject in need thereof. In some embodiments, the present invention provides a compound of Formula I, or a composition comprising said compound, for use in inducing the "unfolded protein response" (UPR) in a subject in need thereof The activity of a compound utilized in this invention as an inhibitor of cell proliferation may be assayed in vitro or in vivo. Detailed conditions for assaying a compound in this invention are set forth in the Examples below.

Cellular Proliferative Disorders

The present invention features methods and compositions for the diagnosis and prognosis of cellular proliferative disorders (e.g., cancer) and the treatment of these disorders. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the present invention provides a method for treating a cancer that presents as a solid tumor, such as a sarcoma, carcinoma, or lymphoma, comprising the step of administering a disclosed compound, or a pharmaceutically acceptable salt thereof, to a patient in need thereof. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/ study/NCT02488759; see also https://clinicaltrials.gov/ct2/show/study/NCT0240886; https://clinicaltrials.gov/ct2/show/NCT02426892)

In some embodiments, the present invention provides a method for treating a cancer in a patient in need thereof, comprising administering to the patient any of the compounds, salts or pharmaceutical compositions described herein. In some embodiments, the cancer is selected from the cancers described herein. In some embodiments, the cancer is melanoma cancer. In some embodiments, the cancer is breast cancer. In some embodiments, the cancer is lung cancer. In some embodiments, the cancer is small cell lung cancer (SCLC). In some embodiments, the cancer is non-small cell lung cancer (NSCLC). In some embodiments, the cancer is myeloma. In some embodiments, the cancer is multiple myeloma. In some embodiments, the cancer is bladder cancer. In some embodiments, the cancer is kidney cancer. In some embodiments, the cancer is hepatocellular carcinoma (HCC). In some embodiments, the cancer is melanoma. In some embodiments, the cancer is colorectal cancer. In some embodiments, the cancer is endometrial cancer. In some embodiments, the cancer is cancer of the esophagus. In some embodiments, the cancer is pancreatic cancer. In some embodiments, the cancer is renal cell carcinoma.

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

The compounds and compositions, according to the method of the present invention, may be administered using any amount and any route of administration effective for treating or lessening the severity of a cellular proliferative disorder. The exact amount required will vary from subject to subject, depending on the species, age, and general condition of the subject, the severity of the disease or condition, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiment, the invention relates to a method of inducing ER stress in a biological sample comprising the step of contacting said biological sample with a compound of this invention, or a composition comprising said compound.

In some embodiment, the invention relates to a method of inducing the "unfolded protein response" (UPR) in a biological sample comprising the step of contacting said biological sample with a compound of this invention, or a composition comprising said compound.

In certain embodiments, the invention relates to a method of causing calcium release from the endoplasmic reticulum (ER) via a putative $Ca^{2+}$ channel known as Wolframin (WFS1) in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Co-Administration of Additional Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

In some embodiments, the additional therapeutic agent is selected from an immunostimulatory therapeutic compound. In some embodiments, the immunostimulatory therapeutic compound is selected from elotuzumab, mifamurtide, an agonist or activator of a toll-like receptor, or an activator of RORγt.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, an immunostimulatory therapeutic compound, and an immune checkpoint inhibitor.

Other checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck & Co.), an agonistic anti-OX40 antibody, in Phase 1 cancer trials (NCT02528357); MEDI0562 (Medimmune/AstraZeneca), an agonistic anti-OX40 antibody, in advanced solid tumors (NCT002318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Other checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Other checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Other checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck & Co.), an agonistic anti-GITR antibody, in solid tumors (NCT02132754) and MEDI11873 (Medimmune/AstraZeneca), an agonistic hexameric GITR-ligand molecule with a human IgG1 Fc domain, in advanced solid tumors (NCT02583165).

Other checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck & Co.), an agonistic anti-ICOS antibody, in Phase 1 (NCT02723955); JTX-2011 (Jounce Therapeutics), an agonistic anti-ICOS antibody, in Phase 1 (NCT02904226).

Other checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Other checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Other checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Other checkpoint inhibitors that may be used in the present invention include agonists of stimulator of interferon genes protein (STING, also known as transmembrane protein 173, or TMEM173). Agonists of STING that are being studied in clinical trials include MK-1454 (Merck & Co.), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Other checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Other checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor.

In some embodiments, the IDO inhibitor is selected from epacadostat, indoximod, capmanitib, GDC-0919, PF-06840003, BMS:F001287, Phy906/KD108, or an enzyme that breaks down kynurenine.

In some embodiments, the PARP inhibitor is selected from olaparib, rucaparib, niraparib, iniparib, talazoparib, or veliparib.

In some embodiments, the HDAC inhibitor is selected from vorinostat, romidepsin, panobinostat, belinostat, entinostat, or chidamide.

In some embodiments, the CDK 4/6 inhibitor is selected from palbociclib, ribociclib, abemaciclib or trilaciclib.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor, and a third therapeutic agent selected from an immune checkpoint inhibitor. In some embodiments, the immune checkpoint inhibitor is selected from nivolumab, pembrolizumab, ipilimumab, avelumab, durvalumab, atezolizumab, or pidilizumab.

Another immunostimulatory therapeutic that may be used in the present invention is recombinant human interleukin 15 (rhIL-15). rhIL-15 has been tested in the clinic as a therapy for melanoma and renal cell carcinoma (NCT01021059 and NCT01369888) and leukemias (NCT02689453). Another immunostimulatory therapeutic that may be used in the present invention is recombinant human interleukin 12 (rhIL-12). Another suitable IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). Recombinant human interleukin 12 (rhIL-12) has been tested in the clinic for many oncological indications, for example, as a therapy for lymphoma (NM-IL-12, Neumedicines, Inc.), (NCT02544724 and NCT02542124).

In some embodiments, the PI3K inhibitor is selected from idelalisib, alpelisib, taselisib, pictilisib, copanlisib, duvelisib, PQR309, or TGR1202.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from a platinum-based therapeutic, a taxane, a nucleoside inhibitor, or a therapeutic agent that interferes with normal DNA synthesis, protein synthesis, cell replication, or will otherwise inhibit rapidly proliferating cells.

In some embodiments, the platinum-based therapeutic is selected from cisplatin, carboplatin, oxaliplatin, nedaplatin, picoplatin, or satraplatin.

In some embodiments, the taxane is selected from paclitaxel, docetaxel, albumin-bound paclitaxel, cabazitaxel, or SID530.

In some embodiments, the therapeutic agent that interferes with normal DNA synthesis, protein synthesis, cell replication, or will otherwise interfere with the replication of rapidly proliferating cells is selected from trabectedin, mechlorethamine, vincristine, temozolomide, cytarabine, lomustine, azacitidine, omacetaxine mepesuccinate, asparaginase Erwinia chrysanthemi, eribulin mesylate, capacetrine, bendamustine, ixabepilone, nelarabine, clorafabine, trifluridine, or tipiracil.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from a platinum-based therapeutic, a taxane, a nucleoside inhibitor, or a therapeutic agent that interferes with normal DNA synthesis, protein synthesis, cell replication, or will otherwise inhibit rapidly proliferating cells, and a third therapeutic agent selected from an immune checkpoint inhibitor.

In some embodiments, the immune checkpoint inhibitor is selected from nivolumab, pembrolizumab, ipilimumab, avelumab, durvalumab, atezolizumab, or pidilizumab.

In some embodiments, any one of the foregoing methods further comprises the step of obtaining a biological sample from the patient and measuring the amount of a disease-related biomarker.

In some embodiments, the biological sample is a blood sample.

In some embodiments, the disease-related biomarker is selected from circulating CD8+ T cells or the ratio of CD8+ T cells:Treg cells.

In one aspect, the present invention provides a method of treating an advanced cancer, comprising administering a compound disclosed herein or a pharmaceutically acceptable salt thereof or pharmaceutical composition thereof, either as a single agent (monotherapy), or in combination with a chemotherapeutic, a targeted therapeutic, such as a kinase inhibitor, and/or an immunomodulatory therapy, such as an immune checkpoint inhibitor. In some embodiments, the immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the additional therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaeculticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, the additional therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In some embodiments, the additional therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In some embodiments, the additional therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the additional therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, the additional therapeutic agent is a histone deacetylase (HDAC) inhibitor. Approved HDAC inhibitors useful in the present invention include vorinostat (Zolinza®, Merck & Co.); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In some embodiments, the additional therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In some embodiments, the additional therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In some embodiments, the additional therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, the additional therapeutic agent is an aromatase inhibitor. Approved aromatase inhibitors which may be used in the present invention include exemestane (Aromasin®, Pfizer); anastazole (Arimidex®, AstraZeneca) and letrozole (Femara®, Novartis).

In some embodiments, the additional therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, the additional therapeutic agent is a folic acid inhibitor. Approved folic acid inhibitors useful in the present invention include pemetrexed (Alimta®, Eli Lilly).

In some embodiments, the additional therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, the additional therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, the additional therapeutic agent is an arginase inhibitor. Arginase inhibitors being studied which may be used in the present invention include AEB 1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, the additional therapeutic agent is a glutaminase inhibitor. Glutaminase inhibitors being studied which may be used in the present invention include CB-839 (Calithera Biosciences).

In some embodiments, the additional therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, the additional therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, the additional therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck & Co.); cytarabine injection (ara-C, antimetabolic cytidine analog, Pfizer); lomustine (alkylating agent, CeeNU®, Bristol-Myers Squibb; Gleostine®, Next-Source Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, the additional therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In some embodiments, the additional therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In some embodiments, the additional therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, the present invention provides a method of treating prostate cancer comprising administering to a patient in need thereof an effective amount of a compound disclosed herein or a pharmaceutically acceptable salt thereof or pharmaceutical composition thereof in combination with an additional therapeutic agent that interferes with the synthesis or activity of androgens. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, the additional therapeutic agent is a selective estrogen receptor modulator (SERM), which interferes with the synthesis or activity of estrogens. Approved SERMs useful in the present invention include raloxifene (Evista®, Eli Lilly).

In some embodiments, the additional therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, the additional therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, the additional therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978.

Additional Co-Administered Therapeutic Agents—Targeted Therapeutics and Immunomodulatory Drugs In some embodiments, the additional therapeutic agent is selected from a targeted therapeutic or immunomodulatory drug. Adjuvant therapies with targeted therapeutics or immunomodulatory drugs have shown promising effectiveness when administered alone but are limited by the development of tumor immunity over time or evasion of the immune response.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a targeted therapeutic or an immunomodulatory drug. In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In other embodiments, the immunomodulatory therapeutic is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, the additional therapeutic agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$ T cell response.

In some embodiments, the present invention comprises administering to said patient a compound disclosed herein or a pharmaceutically acceptable salt thereof in combination with a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

Additional Co-Administered Therapeutic Agents—Immunostimulatory Drugs

In some embodiments, the additional therapeutic agent is an immunostimulatory drug. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med.

8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a immunostimulatory drug, such as an immune checkpoint inhibitor. In some embodiments, the compound and the checkpoint inhibitor are administered simultaneously or sequentially. In some embodiments, a compound disclosed herein is administered prior to the initial dosing with the immune checkpoint inhibitor. In certain embodiments, the immune checkpoint inhibitor is administered prior to the initial dosing with the compound disclosed herein.

In certain embodiments, the immune checkpoint inhibitor is selected from a PD-1 antagonist, a PD-L1 antagonist, or a CTLA-4 antagonist. In some embodiments, a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck & Co.); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech).

Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Another paradigm for immune-stimulation is the use of oncolytic viruses. In some embodiments, the present invention provides a method for treating a patient by administering a compound disclosed herein or a pharmaceutically acceptable salt thereof or pharmaceutical composition thereof in combination with an immunostimulatory therapy such as oncolytic viruses. Approved immunostimulatory oncolytic viruses which may be used in the present invention include talimogene laherparepvec (live, attenuated herpes simplex virus, Imlygic®, Amgen).

In some embodiments, the additional therapeutic agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. An activator of RORγt, that is being studied which may be used in the present invention is LYC-55716 (Lycera), which is currently being evaluated in clinical trials for the treatment of solid tumors (NCT02929862).

In some embodiments, the additional therapeutic agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other checkpoint inhibitors that may be used in the present invention include inhibitors of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

Other checkpoint inhibitors that may be used in the present invention include inhibitors of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

Checkpoint inhibitors that may be used in the present invention also include inhibitors of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Other immune-oncology agents that may be used in the present invention in combination with a compound disclosed herein include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

Other additional therapeutic agents that may be used in the present invention include glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

A compound of the current invention may also be used to advantage in combination with other antiproliferative compounds. Such antiproliferative compounds include, but are not limited to checkpoint inhibitors; aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signalling processes should proceed.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, $\gamma\delta$, and memory $CD8^+$ ($\alpha\beta$) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™.

Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4- pyridylmethyl)phthalazine succinate; Angiostatin™; Endostatin™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

EXEMPLIFICATION

General Synthetic Methods

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Abbreviations equiv or eq: molar equivalents
o/n: overnight
rt: room temperature
UV: ultra violet
HPLC: high pressure liquid chromatography
Rt: retention time
LCMS or LC-MS: liquid chromatography-mass spectrometry
NMR: nuclear magnetic resonance
CC: column chromatography
TLC: thin layer chromatography
sat: saturated
aq: aqueous
Ac: acetyl
DCM: dichloromethane
DCE: dichloroethane
DEA: diethylamine
DMF: dimethylformamide
DMSO: dimethylsulfoxide
ACN or MeCN: acetonitrile
DIPEA: diisopropylethylamine
EA or EtOAc: ethyl acetate
BINAP: (±)-2,2'-Bis(diphenylphosphino)-1,1'-binaphthalene
TEA: triethylamine
THF: tetrahydrofuran
TBS: tert-butyldimethylsilyl
KHMDS: potassium hexamethyl disilylazide
Tf: trifluoromethanesulfonate
Ms: methanesulfonyl
NBS: N-bromosuccinimide
PE: petroleum ether
TFA: trifluoroacetic acid
FA: formic acid
MMPP: magnesium monoperoxyphthalate
HATU: 1-[Bis(dimethylamino)methylene]-1H-1,2,3-triazolo[4,5-b]pyridinium 3-oxide Hexafluorophosphate
Cy: cyclohexyl
Tol: toluene
DMP: Dess-Martin periodinane
IBX: 2-iodoxybenzoic acid
PMB: p-methoxybenzyl
SEM: [2-(Trimethylsilyl)ethoxy]methyl
XPhos or X-Phos: 2-Dicyclohexylphosphino-2',4',6'-triisopropylbiphenyl General Information:

All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All $^1$H NMR spectra were recorded on a Bruker 400 (400 MHz) spectrometer. $^1$H chemical shifts are reported in δ values in parts per million (ppm) with the deuterated solvent as the internal standard. Data are reported as follows: chemical shift, multiplicity (s=singlet, d=doublet, t=triplet, q=quartet, br=broad, m=multiplet), coupling constant (Hz), integration (i.e. number of protons). LCMS spectra were obtained on an Agilent 1200 series 6110 or 6120 mass spectrometer with electrospray ionization and except as otherwise indicated, the general LCMS condition was as follows: Waters X Bridge C18 column (50 mm*4.6 mm*3.5 μm), Flow Rate: 2.0 mL/min, the column temperature: 40° C.

Example 1

Synthetic Scheme 1: (R)—N-(3-(4-(2-amino-6-methylpyrimidin-4-yl)-1,4-oxazepan-3-yl)-4-chlorophenyl)acetamide (6) I-10 and (S)—N-(3-(4-(2-amino-6-methylpyrimidin-4-yl)-1,4-oxazepan-3-yl)-4-chlorophenyl)acetamide (7) I-15

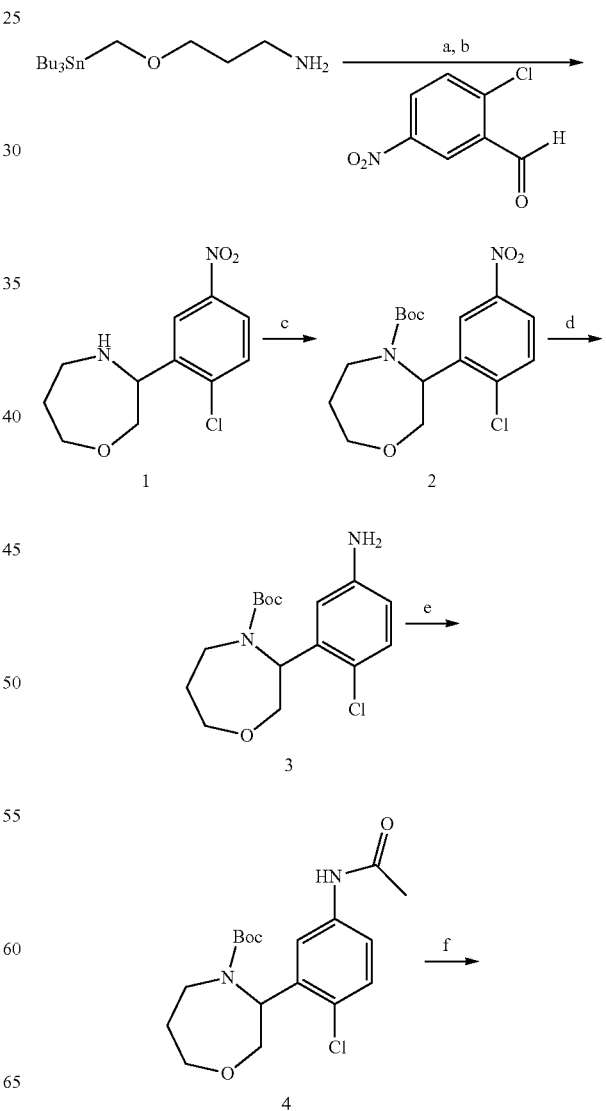

-continued

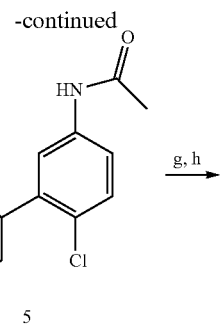

(a) 4 A mol sieves, 2-chloro-5-nitrobenzaldehyde, CH₂Cl₂; (b) 2,6-lutidine, Cu(OTf)₂, hexafluoroisopropanol, CH₂Cl₂; (c) Boc₂O, Et₃N, THF; (d) zinc, NH₄Cl, 2% TPGS-750-M in water, 75° C.; (e) AcCl, Et₃N, CH₂Cl₂; (f) TFA, CH₂Cl₂; (g) 2-amino-4-chloro-6-methylpyrimidine, NMP, 150° C.; (h) SFC chiral separation Formation of (+/−)-3-(2-chloro-5-nitrophenyl)-1,4-oxazepane (1)

To a solution of 3-(tributylstannylmethoxy)propan-1-amine (3.06 g, 8.09 mmol) in anhydrous dichloromethane (15 mL) was added 2-chloro-5-nitrobenzaldehyde (1.50 g, 8.08 mmol) followed by 4 A molecular sieves. The mixture was stirred overnight at room temperature, filtered to remove the sieves, and diluted with dichloromethane (75 mL). In a separate flask containing hexafluoroisopropanol (22 mL) was added 2,6-lutidine (0.94 mL, 8.10 mmol) followed by Cu(OTf)₂ (2.93 g, 8.10 mmol). The mixture was stirred for 1 hour then the imine solution prepared above was added in one portion. The reaction was stirred overnight at room temperature. The mixture was diluted with 150 mL of 2:1 aqueous saturated NaHCO₃ solution and 10% ammonium hydroxide. After stirring for 20 minutes, the organic layer was removed and washed with aqueous saturated NaHCO₃ solution, then brine. The organic layer was passed through a phase separator funnel and concentrated in vacuo. Purification by reverse phase silica gel chromatography using an ISCO—100 gram c18-aq column—running with 0.2% formic acid/H₂O and 0.2% formic acid/CH₃CN to afford 700 mg of the desired product as orange-red residue which was used without further purification: ¹H NMR (d6-DMSO) δ 8.48 (d, J=2.9 Hz, 1H), 8.11 (dd, J=8.8, 2.9 Hz, 1H), 7.73 (d, 1H), 4.38-4.21 (m, 1H), 3.90-3.66 (m, 3H), 3.34 (dd, J=12.4, 8.5 Hz, 1H), 3.18-2.86 (m, 2H), 1.95-1.84 (m, 2H); ESI-MS m/z calc. 256.06146, found 257.13 (M+1)⁺. Retention time: 0.52 minutes.

Formation of (+/−)-tert-butyl 3-(2-chloro-5-nitrophenyl)-1,4-oxazepane-4-carboxylate (2)

A mixture of 3-(2-chloro-5-nitro-phenyl)-1,4-oxazepane (0.50 g, 1.93 mmol) and triethylamine (0.27 mL, 1.94 mmol) in THF (7 mL) was added di-tert-butyldicarbonate (0.42 g, 1.93 mmol). The reaction mixture was stirred overnight at room temperature. The reaction mixture was diluted into aqueous saturated NH₄Cl solution and extracted with dichloromethane. The organic phase was passed through a phase separator funnel and concentrated in vacuo. The crude residue was purified by silica gel chromatography using a 40 g ISCO Gold column (0-20% EtOAc/CH₂Cl₂ gradient) to give 376 mg of the desired product as an off-white solid: ESI-MS m/z calc. 356.1139, found 356.82 (M+1)⁺. Retention time: 0.92 minutes.

Formation of tert-butyl 3-(5-amino-2-chlorophenyl)-1,4-oxazepane-4-carboxylate (3)

A suspension of tert-butyl 3-(2-chloro-5-nitro-phenyl)-1,4-oxazepane-4-carboxylate (1.98 g, 5.55 mmol), NH₄Cl (1.20 g, 22.43 mmol) and zinc (2.00 g, 30.58 mmol) was stirred in 2% TPGS-750-M in water (50 mL). The reaction mixture was stirred vigorously and heated to 75° C. for 23 hours. The mixture was diluted into aqueous saturated NaHCO₃ solution and extracted with dichloromethane. The organic phase was dried (MgSO₄), filtered and concentrated in vacuo. The crude residue was purified via silica gel chromatography with 80 g isco column using 10-50% (20% MeOH—CH₂Cl₂/CH₂Cl₂ gradient) to afford 2 grams of desired product as a light yellow solid that was used without further purification; ESI-MS m/z calc. 356.1139, found 227.14 (M-Boc)⁺. Retention time: 0.64 minutes.

Formation of (+/−)-tert-butyl 3-(5-acetamido-2-chlorophenyl)-1,4-oxazepane-4-carboxylate (4)

To a solution of tert-butyl 3-(5-amino-2-chloro-phenyl)-1,4-oxazepane-4-carboxylate, 3, (0.25 g, 0.69 mmol) and triethylamine (0.15 mL, 1.04 mmol) in dichloromethane (3 mL) was added dropwise a solution of acetyl chloride (0.05 mL, 0.75 mmol) in dichloromethane (1 mL). The reaction mixture was stirred at room temperature for 1 hour. The mixture was quenched by adding aqueous saturated NaHCO₃ solution and extracted twice with dichloromethane. The combined organic phases were filtered through a phase separator and concentrated in vacuo. The crude residue was purified via silica gel chromatography with 40 g isco GOLD column using 0-30% (20% MeOH—CH₂Cl₂/CH₂Cl₂) gradient to afford 185 mg of a white solid, clean by LCMS ESI-MS m/z calc. 368.15, found 369.42 (M+1)⁺. Retention time: 0.8 minutes.

Formation of (+/−)-N-(4-chloro-3-(1,4-oxazepan-3-yl)phenyl)acetamide (5)

To a solution of tert-butyl 3-(5-acetamido-2-chloro-phenyl)-1,4-oxazepane-4-carboxylate, 4, (0.18 g, 0.47 mmol) in dichloromethane (2 mL) was added trifluoroacetic acid (1.5 mL). Stirred reaction mixture at room temperature for 30 minutes and then concentrated in vacuo. The residue was diluted with dichloromethane and neutralized with aqueous saturated NaHCO$_3$ solution. The organic phase was passed through a phase separator and the resulting filtrate was concentrated in vacuo to afford 70 mg of product as white solid that was used without further purification: ESI-MS m/z calc. 268.09, found 269.20 (M+1)$^+$. Retention time: 0.5 minutes; $^1$H NMR (400 MHz, DMSO-d6) δ 10.04 (s, 1H), 7.72 (d, J=2.6 Hz, 1H), 7.64 (dd, J=8.7, 2.7 Hz, 1H), 7.29 (d, J=8.7 Hz, 1H), 4.18 (dd, J=9.2, 3.1 Hz, 1H), 3.90-3.73 (m, 2H), 3.67 (dt, J=11.9, 6.5 Hz, 1H), 3.20 (dd, J=12.2, 9.1 Hz, 1H), 3.07 (s, 1H), 2.94-2.80 (m, 1H), 2.70-2.57 (m, 1H), 2.02 (s, 3H), 1.91-1.80 (m, 2H).

Formation of N-(3-(4-(2-amino-6-methylpyrimidin-4-yl)-1,4-oxazepan-3-yl)-4-chlorophenyl)acetamide (R)-isomer (6) and (S)-isomer (7)

To a solution of N-[4-chloro-3-(1,4-oxazepan-3-yl)phenyl]acetamide, 5, (0.067 g, 0.224 mmol) in NMP (3 mL) was added 4-chloro-6-methyl-pyrimidin-2-amine (0.040 g, 0.279 mmol). The reaction mixture was heated to 150° C. for 18 hours. The mixture was cooled to room temperature and loaded directly onto a 50 g ISCO c18-aq column and purified by reverse phase running with 0.1% TFA/H$_2$O and 0.1% TFA/CH$_3$CN. The pure fractions were concentrated in vacuo. The residue was diluted with dichloromethane, neutralized with aqueous saturated NaHCO$_3$ solution. The organic phase was passed through a phase separator and concentrated in vacuo to afford 69 mg of light orange solid: high temperature (360 K) $^1$H NMR (d6-DMSO) δ 9.75 (s, 1H), 7.72-7.39 (m, 3H), 7.43-7.18 (m, 1H), 5.64-5.19 (m, 3H), 4.85-4.45 (m, 1H), 4.31-4.07 (m, 1H), 4.04-3.84 (m, 1H), 3.80-3.28 (m, 3H), 3.02 (s, 3H), 2.00 (s, 3H), 1.91-1.72 (m, 2H); ESI-MS m/z calc. 375.15, found 376.31 (M+1)$^+$. Retention time: 0.56 minutes. The racemic mixture was submitted to chiral SFC purification to obtain the individual enantiomers.

Peak A (R)—N-[3-[4-(2-amino-6-methyl-pyrimidin-4-yl)-1,4-oxazepan-3-yl]-4-chloro-phenyl]acetamide: high temperature (360 K) $^1$H NMR (400 MHz, DMSO-d6) δ 9.70 (s, 1H), 7.56 (dd, J=8.6, 2.6 Hz, 1H), 7.50 (d, J=2.6 Hz, 1H), 7.31 (d, J=8.7 Hz, 1H, 5.55 (s, 1H), 5.44 (s, 2H), 5.34 (s, 1H), 4.67 (d, J=15.1 Hz, 1H), 4.13 (dd, J=13.5, 5.0 Hz, 1H), 3.92-3.85 (m, 1H), 3.67 (dd, J=13.5, 10.2 Hz, 1H), 3.63-3.49 (m, 1H), 3.40 (q, J=7.0 Hz, 1H), 1.99 (d, J=4.4 Hz, 6H), 1.84-1.73 (m, 2H); ESI-MS m/z calc. 375.14, found 376.27 (M+1)$^+$. Retention time: 0.56 minutes.

Peak B (S)—N-[3-[4-(2-amino-6-methyl-pyrimidin-4-yl)-1,4-oxazepan-3-yl]-4-chloro-phenyl]acetamide: high temperature (360 K) $^1$H NMR (400 MHz, DMSO-d6) δ 9.71 (s, 1H), 7.56 (dd, J=8.6, 2.6 Hz, 1H), 7.50 (d, J=2.6 Hz, 1H), 7.31 (d, J=8.7 Hz, 1H), 5.55 (s, 1H), 5.44 (s, 2H), 5.34 (s, 1H), 4.67 (d, J=15.1 Hz, 1H), 4.13 (dd, J=13.5, 5.0 Hz, 1H), 3.95-3.86 (m, 1H), 3.67 (dd, J=13.5, 10.2 Hz, 1H), 3.63-3.49 (m, 1H), 3.40 (q, J=7.0 Hz, 1H), 1.99 (d, J=4.4 Hz, 6H), 1.84-1.73 (m, 2H); ESI-MS m/z calc. 375.14, found 376.27 (M+1)$^+$. Retention time: 0.56 minutes. [α]$_D$=+41.2°.

The following analogs were prepared according to Synthetic Scheme 1:

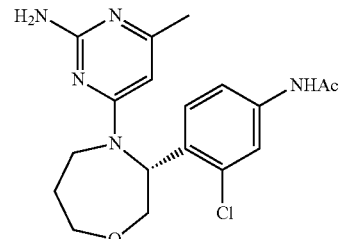

8

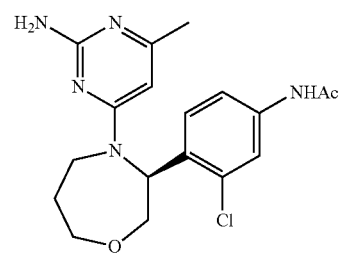

9

(+/−)-N-(4-(4-(2-amino-6-methylpyrimidin-4-yl)-1,4-oxazepan-3-yl)-3-chlorophenyl)acetamide I-141 high temperature (360 K) $^1$H NMR (400 MHz, DMSO-d6) δ 9.77 (s, 1H), 7.77 (s, 1H), 7.35 (m, 1H), 7.21 (d, J=8.0 Hz, 1H), 5.56 (s, 1H), 5.43 (s, 2H), 5.36-5.30 (m, 1H), 4.63-4.59 (m, 1H), 4.05 (m, 1H), 3.87 (m, 1H), 3.75-3.48 (m, 3H), 2.02 (s, 3H), 2.00 (s, 3H), 1.78-1.74 (m, 2H). ESI-MS m/z calc. 375.15, found 376.27 (M+1)$^+$. Retention time: 0.55 minutes.

Racemic material was submitted for SFC chiral separation.

Peak A: (R)—N-(4-(4-(2-amino-6-methylpyrimidin-4-yl)-1,4-oxazepan-3-yl)-3-chlorophenyl)acetamide (8) [α]$_D$=−19.49 (c=4.1 mg/0.8 mL MeOH); high temperature (360 K) $^1$H NMR (400 MHz, DMSO-d6) δ 9.83 (s, 1H), 7.99-7.73 (m, 1H), 7.54-7.33 (m, 1H), 7.34-7.12 (m, 1H), 5.83-5.23 (m, 4H), 4.88-4.54 (m, 1H), 4.28-4.02 (m, 1H), 4.07-3.85 (m, 1H), 3.85-3.45 (m, 3H), 2.20-1.93 (m, 6H), 1.95-1.65 (m, 2H); ESI-MS m/z calc. 375.15, found 376.31 (M+1)$^+$. Retention time: 0.55 minutes. I-310.

Peak B: (S)—N-(4-(4-(2-amino-6-methylpyrimidin-4-yl)-1,4-oxazepan-3-yl)-3-chlorophenyl)acetamide (9) [α]$_D$=+13.75 (c=4.3 mg/0.8 mL MeOH); high temperature (360 K) $^1$H NMR (400 MHz, DMSO-d6) δ 9.79 (s, 1H), 7.77 (d, J=2.2 Hz, 1H), 7.35 (dd, J=8.7, 2.1 Hz, 1H), 7.21 (d, J=8.5 Hz, 1H), 5.61 (d, J=39.5 Hz, 1H), 5.46 (s, 2H), 5.34 (s, 1H), 4.62 (s, 1H), 4.08 (dd, J=13.4, 5.2 Hz, 1H), 3.89 (d, J=12.3 Hz, 1H), 3.78-3.47 (m, 3H), 2.01 (d, J=8.1 Hz, 6H), 1.83-1.46 (m, 2H); ESI-MS m/z calc. 375.15, found 376.31 (M+1)$^+$. Retention time: 0.55 minutes. I-162.

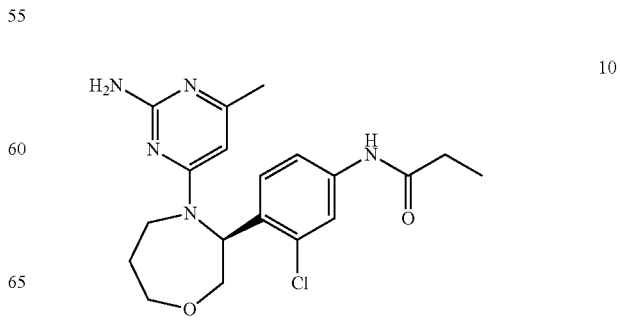

10

(S)—N-(4-(4-(2-amino-6-methylpyrimidin-4-yl)-1,4-oxazepan-3-yl)-3-chlorophenyl)propionamide (10) I-204

Peak B from SFC chiral separation: 99.8% ee; ¹H NMR (400 MHz, MeOD) δ 7.83 (s, 1H), 7.40 (dd, J=8.5, 2.1 Hz, 1H), 7.23 (d, J=8.5 Hz, 1H), 6.01-4.90 (br s, 3H), 4.31-4.23 (m, 1H), 4.04 (d, J=8.4 Hz, 1H), 3.79-3.58 (m, 3H), 2.39 (q, J=7.6 Hz, 2H), 2.10 (s, 3H), 2.00-1.78 (m, 2H), 1.24-1.16 (m, 3H). ESI-MS m/z calc. 389.2, found 390.4 (M+1)⁺. Retention time: 0.58 minutes.

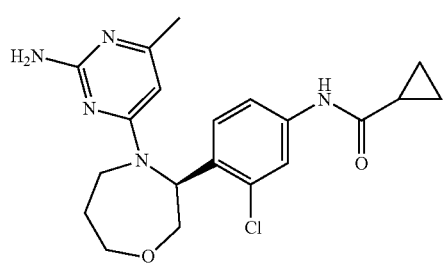

(S)—N-(4-(4-(2-amino-6-methylpyrimidin-4-yl)-1,4-oxazepan-3-yl)-3-chlorophenyl)propionamide (11) I-207

Peak B from SFC chiral separation: 99.8% ee; heated (360K) ¹H NMR (400 MHz, d6-DMSO) δ 10.03 (s, 1H), 7.80 (d, J=2.0 Hz, 1H), 7.37 (dd, J=8.5, 2.1 Hz, 1H), 7.21 (d, J=8.5 Hz, 1H), 5.56 (s, 1H), 5.46 (s, 2H), 5.33 (s, 1H), 4.63 (d, J=14.1 Hz, 1H), 4.08 (dd, J=13.5, 5.0 Hz, 1H), 3.89 (d, J=12.0 Hz, 1H), 3.70 (dd, J=13.4, 10.2 Hz, 1H), 3.66-3.50 (m, 2H), 2.00 (s, 3H), 1.76-1.72 (m, 3H), 0.83-0.75 (m, 4H); ESI-MS m/z calc. 401.2, found 402.3 (M+1)⁺. Retention time: 0.59 minutes.

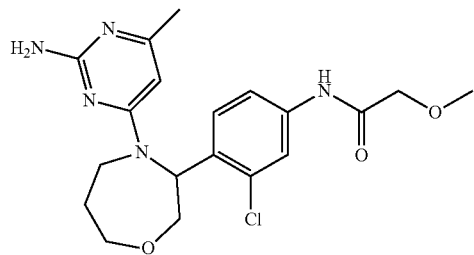

(+/−)-N-[4-[4-(2-amino-6-methyl-pyrimidin-4-yl)-1,4-oxazepan-3-yl]-3-chloro-phenyl]-2-methoxy-acetamide (12) I-192 heated (360K) ¹H NMR (400 MHz, MeOD) δ 7.74 (s, 1H), 7.35 (d, J=8.5 Hz, 1H), 7.12 (d, J=8.5 Hz, 1H), 5.50 (br s, 3H), 4.14 (dd, J=13.6, 5.1 Hz, 1H), 3.91 (s, 3H), 3.68-3.43 (m, 3H), 3.35 (s, 3H), 1.97 (s, 3H), 1.75 (m, 2H); ESI-MS m/z calc. 405.2, found 406.3 (M+1)⁺. Retention time: 0.56 minutes.

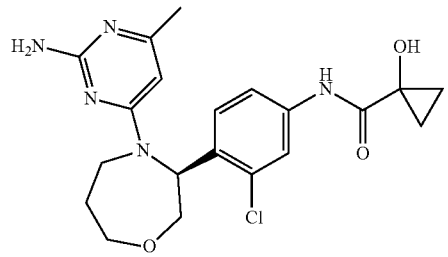

(S)—N-(4-(4-(2-amino-6-methylpyrimidin-4-yl)-1,4-oxazepan-3-yl)-3-chlorophenyl)propionamide (13) I-197

Peak B from SFC chiral separation: 99.4% ee; ¹H NMR (400 MHz, MeOD) δ 7.75 (s, 1H), 7.38-7.31 (m, 1H), 7.12 (d, J=8.5 Hz, 1H), 5.45 (s, 3H), 4.15 (dd, J=13.8, 4.9 Hz, 1H), 3.91 (d, J=9.0 Hz, 1H), 3.68-3.45 (m, 3H), 1.97 (s, 3H), 1.75 (dd, J=41.1, 11.5 Hz, 2H), 1.17 (dd, J=7.7, 4.5 Hz, 2H), 0.94 (dd, J=7.7, 4.5 Hz, 2H); ESI-MS m/z calc. 417.2, found 418.3 (M+1)⁺. Retention time: 0.56 minutes.

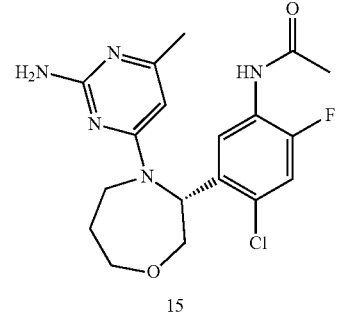

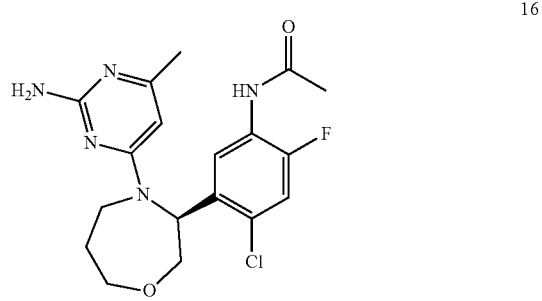

(+/−)-N-[5-[4-(2-amino-6-methyl-pyrimidin-4-yl)-1,4-oxazepan-3-yl]-4-chloro-2-fluoro-phenyl]acetamide (14) I-85

$^1$H NMR (300 MHz, CDCl$_3$) δ 8.36 (d, J=8.2 Hz, 1H), 7.51 (s, 1H), 7.18 (dd, J=19.2, 10.3 Hz, 1H), 6.02-5.77 (m, 1H), 5.28-5.09 (m, 1H), 4.28 (dt, J=13.7, 5.1 Hz, 1H), 4.20-3.95 (m, 2H), 3.84-3.49 (m, 4H), 2.42-2.27 (m, 3H), 2.22 (d, J=0.9 Hz, 3H), 2.03-1.82 (m, 2H); ESI-MS m/z calc. 393.1, found 394.1 (M+1)$^+$. Retention time: 0.59 minutes.

Racemic material was submitted for SFC chiral separation. conditions: 20×250 mm IC column, mobile phase: 40% MeOH (5 mM Ammonia), 60% CO$_2$ Peak A: N-[5-[(3R)-4-(2-amino-6-methyl-pyrimidin-4-yl)-1,4-oxazepan-3-yl]-4-chloro-2-fluoro-phenyl]acetamide (15): $^1$H NMR (300 MHz, Methanol-d4) δ 8.00 (d, J=8.2 Hz, 1H), 7.33 (d, J=10.4 Hz, 1H), 5.65 (s, 2H), 4.28 (dd, J=13.6, 5.1 Hz, 1H), 4.05 (dd, J=12.0, 4.5 Hz, 1H), 3.88-3.54 (m, 3H), 2.15 (s, 3H), 2.12 (s, 3H), 1.90 (d, J=18.8 Hz, 2H); ESI-MS m/z calc. 393.1, found 394.1 (M+1)$^+$. Retention time: 0.59 minutes; Optical rotation: 5 mg/1 mL of MeOH, C=1, [α]=−62.24°. I-270.

Peak B: N-[5-[(3 S)-4-(2-amino-6-methyl-pyrimidin-4-yl)-1,4-oxazepan-3-yl]-4-chloro-2-fluoro-phenyl]acetamide (16): $^1$H NMR (300 MHz, Methanol-d4) δ 8.00 (d, J=8.2 Hz, 1H), 7.33 (d, J=10.4 Hz, 1H), 5.65 (s, 2H), 4.28 (dd, J=13.6, 5.1 Hz, 1H), 4.05 (dd, J=12.0, 4.5 Hz, 1H), 3.88-3.54 (m, 3H), 2.15 (s, 3H), 2.12 (s, 3H), 1.90 (d, J=18.8 Hz, 2H); ESI-MS m/z calc. 393.1, found 394.2 (M+1)$^+$. Optical rotation: 5 mg/1 mL of MeOH, C=1, [α]=59.6°. I-271.

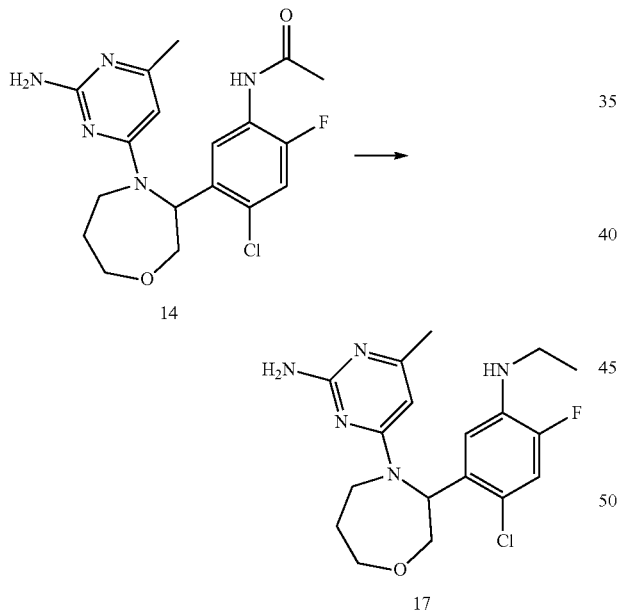

(+/−)-4-[3-[2-chloro-5-(ethylamino)-4-fluoro-phenyl]-1,4-oxazepan-4-yl]-6-methyl-pyrimidin-2-amine (17) I-272

To a solution of N-[5-[4-(2-amino-6-methyl-pyrimidin-4-yl)-1,4-oxazepan-3-yl]-4-chloro-2-fluoro-phenyl]acetamide, 14, (0.05 g, 0.12 mmol) in tetrahydrofuran (5 mL) was added lithium aluminum hydride (0.08 mL of 2 M, 0.16 mmol) in THF. The cloudy solution was stirred at room temperature overnight. Additional lithium aluminum hydride (0.10 mL) was added and the reaction mixture was heated to 60° C. overnight. The mixture was diluted with water (0.25 mL) and stirred for 10 minutes. Dichloromethane (10 mL) was added and the resulting white solid was filtered and washed with dichloromethane. The combined organic phases were concentrated in vacuo. The resulting residue was purified by silica gel chromatography using a 4 g ISCO column eluting a 0-10% MeOH/dichloromethane gradient to provide desired product as white solid: $^1$H NMR (300 MHz, Chloroform-d) δ 7.02 (d, J=10.9 Hz, 1H), 6.45 (d, J=9.0 Hz, 1H), 5.56 (s, 1H), 4.95 (s, 3H), 4.30 (dd, J=13.6, 5.0 Hz, 1H), 4.10 (dd, J=10.8, 6.6 Hz, 1H), 3.83-3.39 (m, 5H), 3.10 (qd, J=7.1, 5.2 Hz, 2H), 2.17 (s, 3H), 2.09-1.91 (m, 1H), 1.89-1.76 (m, 1H), 1.24 (d, J=7.2 Hz, 3H); ESI-MS m/z calc. 379.2, found 379.8 (M+1)$^+$. Retention time: 0.66 minutes.

Example 2

Synthetic Scheme 2: (+/−)-4-(3-(2-chloro-4-(methylsulfonyl)phenyl)-1,4-oxazepan-4-yl)-6-methylpyrimidin-2-amine (19) I-66

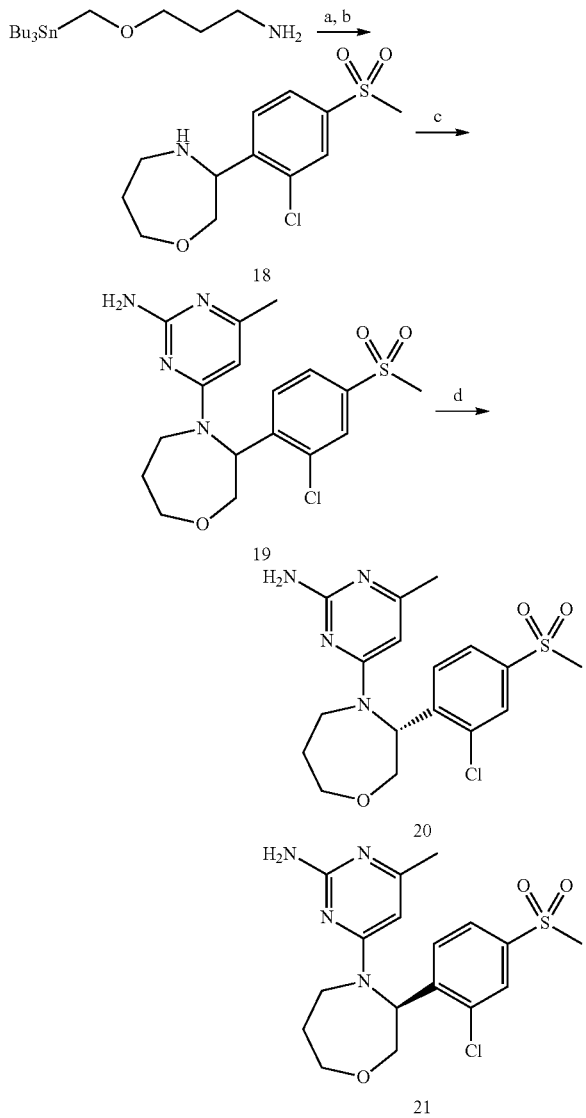

(a) 4 A mol sieves, 2-chloro-4-(methylsulfonyl)benzaldehyde, CH$_2$Cl$_2$; (b) 2,6-lutidine, Cu(OTf)$_2$, hexafluoroisopropanol, CH₂Cl₂; c) 2-amino-4-chloro-6-methylpyrimidine, NMP, 150° C.; (d) SFC chiral separation Formation of (+/−)-3-(2-chloro-4-(methylsulfonyl)phenyl)-1,4-oxazepane (18)

To a solution of 3-(tributylstannylmethoxy)propan-1-amine (2.69 g, 7.11 mmol) in dichloromethane (11 mL) was added 2-chloro-5-methylsulfonyl-benzaldehyde (1.00 g, 4.57 mmol) followed by 4 angstrom molecular sieves. The mixture was stirred for 14 h, filtered to remove the sieves and washed and diluted with dichloromethane (50 mL).

In a separate flask containing hexafluoroisopropanol (15 mL) was added 2,6-lutidine (0.53 mL, 4.58 mmol) followed by Cu(OTf)₂ (1.65 g, 4.56 mmol). The mixture was stirred for 1 h, then the imine solution prepared above was added in one portion. The reaction was stirred overnight at room temperature. The mixture was diluted with 2:1 mixture of aqueous saturated NaHCO₃ solution and 10% ammonium hydroxide. After stirring for 10 minutes, the organic layer was removed and washed with aqueous saturated NaHCO₃ solution, then brine. The organic layer was passed through a phase separator funnel and the filtrate was concentrated in vacuo. The residue was purified by reverse phase chromatography using an ISCO—100 gram c18-aq column—running with formic acid/H₂O and formic acid/CH₃CN gradient. The residue was diluted with dichloromethane, neutralized with aqueous saturated NaHCO₃ solution. The organic phase was passed through a phase separator and concentrated in vacuo to afford 688 mg of desired product: ¹H NMR (400 MHz, DMSO-d6) δ 7.93 (dd, J=1.6, 0.7 Hz, 1H), 7.90-7.87 (m, 2H), 4.31 (dd, J=8.7, 3.3 Hz, 1H), 3.92-3.77 (m, 2H), 3.71 (dt, J=12.2, 6.2 Hz, 1H), 3.35-3.27 (m, 1H), 3.26 (s, 3H), 3.10 (dt, J=13.7, 5.1 Hz, 1H), 2.89 (dt, J=13.3, 6.4 Hz, 2H), 1.93-1.81 (m, 2H). ESI-MS m/z calc. 289.05396, found 290.05 (M+1)⁺. Retention time: 0.5 minutes.

Formation of (R)-4-(3-(2-chloro-4-(methylsulfonyl)phenyl)-1,4-oxazepan-4-yl)-6-methylpyrimidin-2-amine (20) I-67 and (S)-4-(3-(2-chloro-4-(methylsulfonyl)phenyl)-1,4-oxazepan-4-yl)-6-methylpyrimidin-2-amine (21) I-68

To a solution of 3-(2-chloro-4-(methylsulfonyl)phenyl)-1,4-oxazepane, 18, (0.67 g, 2.31 mmol) in NMP (7.5 mL) was added 4-chloro-6-methyl-pyrimidin-2-amine (0.40 g, 2.79 mmol). The reaction mixture was heated to 150° C. overnight. The mixture was cooled to room temperature and loaded directly onto a 100 g ISCO c18-aq column and purified by reverse phase running with 0.1% TFA/H₂O and 0.1% TFA/CH₃CN. The pure fractions were concentrated in vacuo. The resulting residue was diluted with dichloromethane, neutralized with aqueous saturated NaHCO₃ solution. The mixture was passed through a phase separator and the organic phase concentrated in vacuo to afford 550 mg of desired product. The racemic mixture was submitted for SFC chiral purification to afford 155 mg of stereoisomer A and 153 mg of stereoisomer B:

Peak A: (R)-4-(3-(2-chloro-4-(methylsulfonyl)phenyl)-1,4-oxazepan-4-yl)-6-methylpyrimidin-2-amine (20), heated ¹H NMR (360K) (400 MHz, DMSO-d6) δ 7.97 (t, J=1.9 Hz, 1H), 7.84 (dt, J=8.2, 1.9 Hz, 1H), 7.60 (dd, J=8.1, 2.0 Hz, 1H), 5.78-5.65 (m, 1H), 5.65-5.51 (m, 1H), 5.46 (s, 2H), 4.60-4.41 (m, 1H), 4.25-4.07 (m, 1H), 4.02-3.87 (m, 1H), 3.85-3.68 (m, 2H), 3.68-3.44 (m, 1H), 3.24 (s, 3H), 2.10-1.99 (m, 3H), 1.89-1.70 (m, 2H); ESI-MS m/z calc. 396.10, found 397.16 (M+1)⁺. Retention time: 0.57 minutes; [□]D=−71.67 (c=5.4 mg/1.5 mL MeOH). I-67.

Peak B: (S)-4-(3-(2-chloro-4-(methylsulfonyl)phenyl)-1,4-oxazepan-4-yl)-6-methylpyrimidin-2-amine (21), heated ¹H NMR (360K) (400 MHz, DMSO-d6) δ 7.94 (d, J=2.0 Hz, 1H), 7.80 (dd, J=8.1, 2.0 Hz, 1H), 7.56 (d, J=8.2 Hz, 1H), 5.72-5.63 (m, 1H), 5.63-5.52 (m, 1H), 5.43 (s, 2H), 4.58-4.37 (m, 1H), 4.14 (dd, J=13.5, 4.8 Hz, 1H), 3.97-3.85 (m, 1H), 3.85-3.64 (m, 2H), 3.57 (dt, J=12.4, 7.4 Hz, 1H), 3.21 (s, 3H), 2.03 (s, 3H), 1.90-1.70 (m, 2H); ESI-MS m/z calc. 396.10, found 397.16 (M+1)⁺. Retention time: 0.56 minutes; [□]D=+58.36 (c=5.3 mg/1.5 mL MeOH). I-68.

The following analogs were according to Synthetic Scheme 2:

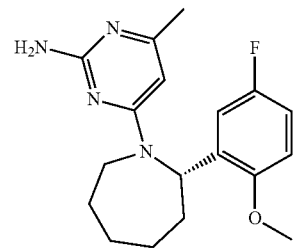

22

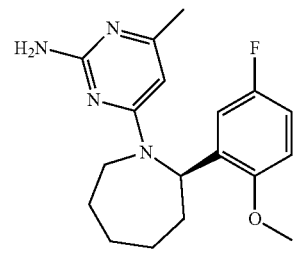

23

(R)-4-(2-(2-fluoro-5-methoxyphenyl)azepan-1-yl)-6-methylpyrimidin-2-amine (22) I-26 and (S)-4-(2-(2-fluoro-5-methoxyphenyl)azepan-1-yl)-6-methylpyrimidin-2-amine (23) I-27

The racemic mixture was synthesized in the same fashion and then submitted to chiral SFC purification to obtain the individual enantiomers:

Peak A; 98.6% ee; high temperature (360 K) ¹H NMR (400 MHz, DMSO-d6) δ 7.10-6.94 (m, 2H), 6.84 (dd, J=9.5, 2.8 Hz, 1H), 5.59 (s, 1H), 5.54-5.29 (m, 3H), 4.70-4.47 (m, 1H), 4.16 (dd, J=13.2, 5.1 Hz, 1H), 3.99-3.77 (m, 4H), 3.72-3.40 (m, 3H), 2.00 (s, 3H), 1.86-1.61 (m, 2H); [□]ᴰ=−34.12 (c=19 mg/3 mL MeOH). I-26

Peak B; 97.4% ee; high temperature (360 K) ¹H NMR (400 MHz, DMSO-d6) δ 7.08-6.93 (m, 2H), 6.84 (dd, J=9.4, 2.8 Hz, 1H), 5.59 (s, 1H), 5.48 (s, 2H), 5.44-5.31 (m, 1H), 4.68-4.50 (m, 1H), 4.16 (dd, J=13.3, 5.1 Hz, 1H), 3.96-3.77 (m, 4H), 3.72-3.38 (m, 3H), 2.00 (s, 3H), 1.89-1.60 (m, 2H); [□]ᴰ=+40.44 (c=19 mg/3 mL MeOH); ESI-MS m/z calc. 333.21, found 333.18 (M+1)⁺. Retention time: 0.61 minutes. I-27.

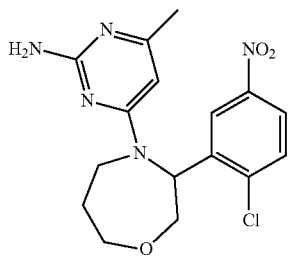

4-(3-(2-chloro-5-nitrophenyl)-1,4-oxazepan-4-yl)-6-methylpyrimidin-2-amine (24) I-72 high temperature (360 K) ¹H NMR (400 MHz, DMSO-d6) δ 8.14-8.01 (m, 2H), 7.73 (d, J=8.7 Hz, 1H), 5.73 (s, 1H), 5.68-5.53 (m, 1H), 5.44 (s, 2H), 4.56-4.39 (m, 1H), 4.12 (dd, J=13.6, 4.8 Hz, 1H), 3.95-3.69 (m, 3H), 3.68-3.53 (m, 1H), 2.04 (s, 3H), 1.85-1.73 (m, 2H); ESI-MS m/z calc. 363.11, found 364.16 (M+1)⁺. Retention time: 0.61 minutes.

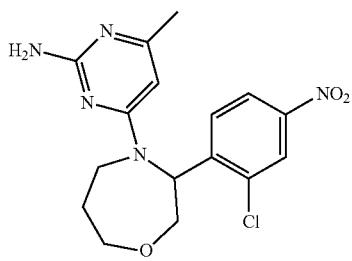

(+/−)-4-[3-(2-chloro-4-nitro-phenyl)-1,4-oxazepan-4-yl]-6-methyl-pyrimidin-2-amine (25) I-125 high temperature (360 K) ¹H NMR (400 MHz, DMSO-d6) δ 8.22 (d, J=2.3 Hz, 1H), 8.08 (dd, J=8.6, 2.4 Hz, 1H), 7.58 (d, J=8.6 Hz, 1H), 5.69 (s, 1H), 5.59 (dd, J=9.9, 4.7 Hz, 1H), 5.41 (s, 2H), 4.46 (d, J=15.7 Hz, 1H), 4.14 (dd, J=13.5, 4.8 Hz, 1H), 3.90 (dt, J=11.5, 3.6 Hz, 1H), 3.77 (ddd, J=16.3, 13.0, 8.2 Hz, 3H), 3.63-3.53 (m, 1H), 2.03 (s, 3H), 1.85-1.77 (m, 2H); ESI-MS m/z calc. 363.11, found 364.25 (M+1)⁺. Retention time: 0.6 minutes.

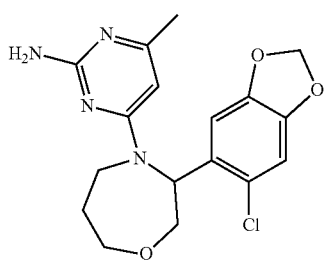

(+/−)-4-[3-(6-chloro-1,3-benzodioxol-5-yl)-1,4-oxazepan-4-yl]-6-methyl-pyrimidin-2-amine (26) I-113 heated (360K) ¹H NMR (400 MHz, DMSO-d6) δ 7.00 (s, 1H), 6.79 (s, 1H), 6.09 (s, 2H), 6.01 (s, 2H), 5.73 (s, 1H), 5.37 (s, 1H), 4.68-4.50 (m, 1H), 4.05 (dd, J=13.6, 4.9 Hz, 1H), 3.93-3.51 (m, 4H), 2.09 (s, 3H), 1.78 (p, J=4.5, 3.9 Hz, 2H); ESI-MS m/z calc. 362.1, found 363.0 (M+1)⁺. Retention time: 0.71 minutes.

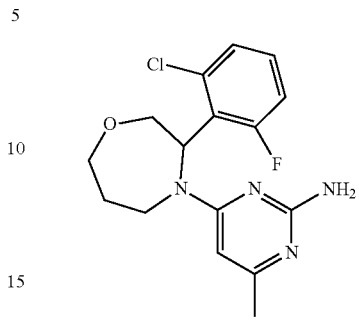

(+/−)-4-(3-(2-chloro-6-fluorophenyl)-1,4-oxazepan-4-yl)-6-methylpyrimidin-2-amine (27) I-59

¹H NMR (400 MHz, DMSO-d6) (heated 360K) δ 7.30 (td, J=3.8, 2.7 Hz, 2H), 7.10 (ddd, J=11.3, 6.1, 3.4 Hz, 1H), 5.71 (s, 1H), 5.54 (dd, J=10.6, 5.6 Hz, 1H), 5.41 (s, 2H), 4.48 (d, J=15.6 Hz, 1H), 4.00-3.88 (m, 3H), 3.71 (dd, J=15.6, 11.2 Hz, 1H), 3.53 (td, J=12.1, 3.1 Hz, 1H), 2.02 (s, 3H), 1.82-1.57 (m, 2H); ESI-MS m/z calc. 336.12, found 337.0 (M+1)⁺. Retention time: 0.7 minutes.

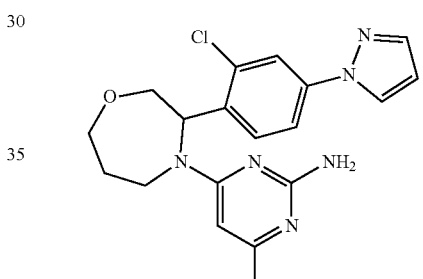

(+/−)-4-(3-(2-chloro-4-(1H-pyrazol-1-yl)phenyl)-1,4-oxazepan-4-yl)-6-methylpyrimidin-2-amine (28) I-133

¹H NMR (400 MHz, DMSO-d6) (heated 360K) δ 8.42 (d, J=2.5 Hz, 1H), 7.91 (d, J=2.3 Hz, 1H), 7.79-7.67 (m, 2H), 7.43 (d, J=8.5 Hz, 1H), 6.51 (dd, J=2.6, 1.8 Hz, 1H), 6.06 (s, 2H), 5.80 (s, 1H), 5.54 (d, J=7.6 Hz, 1H), 4.58 (d, J=15.2 Hz, 1H), 4.15 (dd, J=13.5, 4.9 Hz, 1H), 3.96-3.80 (m, 2H), 3.80-3.69 (m, 1H), 3.68-3.55 (m, 1H), 2.09 (s, 3H), 1.88-1.75 (m, 2H); ESI-MS m/z calc. 384.15, found 385.0 (M+1)⁺. Retention time: 0.72 minutes.

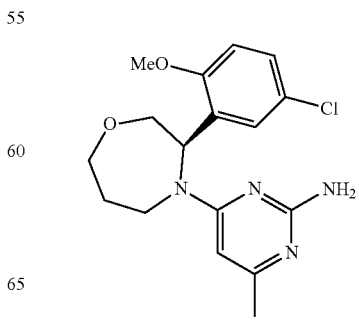

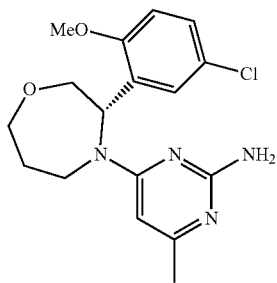

(R)-4-(3-(5-chloro-2-methoxyphenyl)-1,4-oxazepan-4-yl)-6-methylpyrimidin-2-amine (29) I-131

$^1$H NMR (400 MHz, DMSO-d6) (heated 360K) δ 7.29 (dd, J=8.8, 2.7 Hz, 1H), 7.11 (d, J=2.7 Hz, 1H), 7.07 (d, J=8.8 Hz, 1H), 6.97 (s, 2H), 5.95 (d, J=35.3 Hz, 1H), 5.55 (s, 1H), 4.55 (s, 1H), 4.17 (dd, J=13.4, 5.2 Hz, 1H), 3.87 (s, 4H), 3.82-3.68 (m, 2H), 3.57 (ddd, J=12.2, 8.3, 5.7 Hz, 1H), 2.19 (s, 3H), 1.79 (h, J=3.9 Hz, 2H). ESI-MS m/z calc. 348.14, found 349.0 (M+1)$^+$. Retention time: 0.72 minutes.

(S)-4-(3-(5-chloro-2-methoxyphenyl)-1,4-oxazepan-4-yl)-6-methylpyrimidin-2-amine (30) I-132

$^1$H NMR (400 MHz, DMSO-d6) (heated 360K) δ 7.29 (dd, J=8.8, 2.7 Hz, 1H), 7.11 (d, J=2.7 Hz, 1H), 7.07 (d, J=8.8 Hz, 1H), 6.97 (s, 2H), 5.95 (d, J=35.3 Hz, 1H), 5.55 (s, 1H), 4.55 (s, 1H), 4.17 (dd, J=13.4, 5.2 Hz, 1H), 3.87 (s, 4H), 3.82-3.68 (m, 2H), 3.57 (ddd, J=12.2, 8.3, 5.7 Hz, 1H), 2.19 (s, 3H), 1.79 (h, J=3.9 Hz, 2H); ESI-MS m/z calc. 348.14, found 349.0 (M+1)$^+$. Retention time: 0.72 minutes.

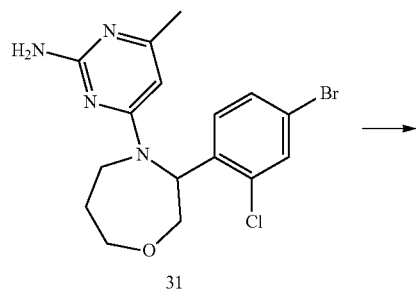

31

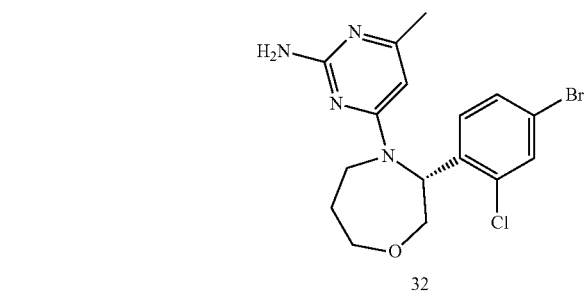

32

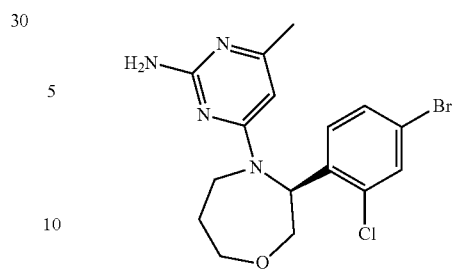

(+/−)-4-(3-(4-bromo-2-chlorophenyl)-1,4-oxazepan-4-yl)-6-methylpyrimidin-2-amine (31) I-194 high temperature (360 K) $^1$H NMR (400 MHz, DMSO-d6) δ 7.70 (d, J=2.1 Hz, 1H), 7.52 (dd, J=8.4, 2.1 Hz, 1H), 7.31 (t, J=6.8 Hz, 3H), 4.15 (dd, J=13.6, 5.0 Hz, 1H), 3.96-3.72 (m, 3H), 3.64 (s, 1H), 2.25 (s, 3H), 1.85 (s, 2H); ESI-MS m/z calc. 396.0, found 397.0 (M+1)$^+$. Retention time: 0.64 minutes.

Racemic material was submitted for SFC chiral separation.

Peak A: ESI-MS m/z calc. 396.0, found 399.0 (M+1)$^+$. Retention time: 0.8 minutes; (R)-4-(3-(4-bromo-2-chlorophenyl)-1,4-oxazepan-4-yl)-6-methylpyrimidin-2-amine (32). I-200.

Peak B: $^1$H NMR (400 MHz, DMSO-d6) δ 7.69 (d, J=2.0 Hz, 1H), 7.50 (dd, J=8.4, 2.1 Hz, 1H), 7.29 (d, J=8.4 Hz, 1H), 6.87 (s, 3H), 6.01 (s, 1H), 5.59 (s, 1H), 4.49 (d, J=14.9 Hz, 1H), 4.13 (dd, J=13.6, 4.9 Hz, 1H), 3.91-3.78 (m, 3H), 3.62 (ddd, J=12.2, 9.4, 4.9 Hz, 1H), 2.19 (s, 4H), 1.82 (dp, J=10.1, 3.6, 3.1 Hz, 2H); ESI-MS m/z calc. 396.0, found 397.0 (M+1)$^+$. Retention time: 0.8 minutes; [α]=+79.9 (c=1, MeOH) 7.1 mg/mL; (S)-4-(3-(4-bromo-2-chlorophenyl)-1,4-oxazepan-4-yl)-6-methylpyrimidin-2-amine (33). I-201

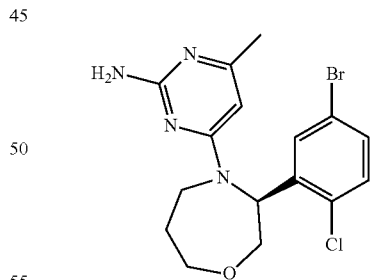

4-[(3S)-3-(5-bromo-2-chloro-phenyl)-1,4-oxazepan-4-yl]-6-methyl-pyrimidin-2-amine I-245

$^1$H NMR (300 MHz, DMSO-d6) δ 7.47 (m, 3H), 6.52 (brs, 1H), 5.99 (brs, 1H), 3.90 (m, 4H), 3.66 (br, 2H), 2.30 (s, 3H), 1.89 (m, 2H); ESI-MS m/z calc. 396.03, found 397.01 (M+1)$^+$. Retention time: 0.65 minutes; [α]$_D$=+66.68° (c=0.5, MeOH).

Example 3

Synthetic Scheme 3: (R)-4-(2-(2-chlorophenyl)azepan-1-yl)-6-methylpyrimidin-2-amine and (S)-4-(2-(2-chlorophenyl)azepan-1-yl)-6-methylpyrimidin-2-amine)

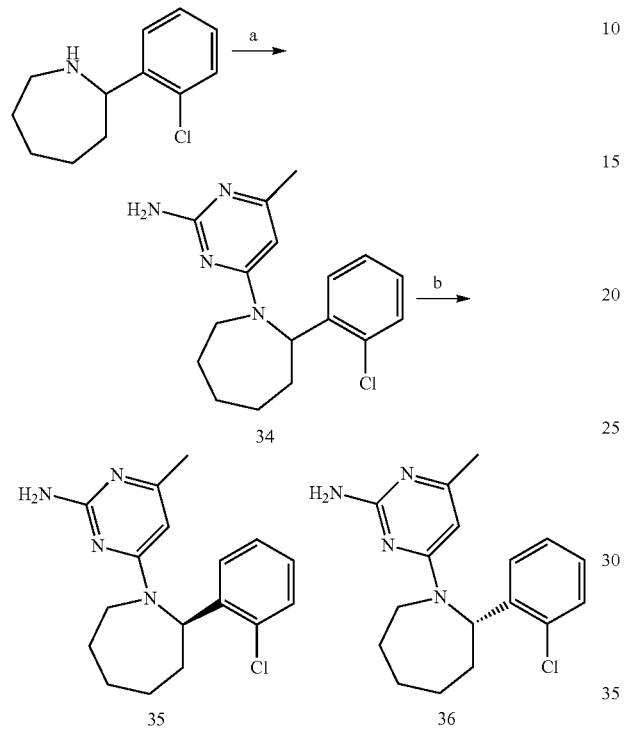

(a) 2-amino-4-chloro-6-methylpyrimidine, nBuOH, 200° C., microwave; (b) Chiral HPLC separation Formation of (+/−)-(2-(2-chlorophenyl)azepan-1-yl)-6-methylpyrimidin-2-amine (34)

A suspension of 4-chloro-6-methyl-pyrimidin-2-amine (3.02 g, 21.03 mmol), 2-(2-chlorophenyl)azepane (3.99 g, 19.01 mmol) in n-butanol (15 mL) was sealed in a microwave tube and irradiated at 200° C. for 2 hours. The crude mixture was concentrated in vacuo and diluted with aqueous saturated $KHCO_3$ solution and extracted twice with dichloromethane. The organic phase was concentrated in vacuo. The residue was then recrystallized from isopropanol and ether to afford 3.61 g of racemic product: $^1$H NMR (400 MHz, CDCl$_3$) δ 7.37 (d, J=8.5 Hz, 1H), 7.16 (d, J=13.9 Hz, 3H), 5.47 (s, 1H), 4.91 (s, 1H), 4.57 (s, 2H), 3.32 (s, 1H), 2.58-2.45 (m, 1H), 2.17 (d, J=22.1 Hz, 2H), 2.03 (s, 1H), 1.91 (d, J=10.7 Hz, 2H), 1.66 (s, 1H), 1.63 (s, 3H), 1.50-1.33 (m, 2H); ESI-MS m/z calc. 316.15, found 317.2 (M+1)$^+$. Retention time: 0.8 minutes.

The racemic mixture was separated by Analytical Chiral HPLC (AD-H, 4.6×100 mm, 40% MeOH, 5 mM ammonia, 60% $CO_2$, at 5 ml/min isocratic injection 10 uM in 1 mg/mL methanol. 120 bar. UV 254 nM). RT Peak A 0.432 min, ee 97.2%, Peak B at 0.479 min.

Peak A: 2.10 g, 97.2% ee; optical rotation: $[ ]_D$=−0.096 (c=1.04, MeOH); $^1$H NMR (400 MHz, CDCl$_3$) δ 7.36 (s, 1H), 7.17 (s, 3H), 5.81 (s, 1H), 5.44 (s, 1H), 4.90 (s, 1H), 4.68 (s, 2H), 4.03-3.20 (m, 1H), 2.63-2.43 (m, 1H), 2.11 (s, 3H), 2.02 (s, 1H), 1.97-1.82 (m, 2H), 1.76-1.51 (m, 2H), 1.51-1.31 (m, 2H); ESI-MS m/z calc. 316.15, found 317.24 (M+1)$^+$. Retention time: 0.83 minutes. (R)-4-(2-(2-chlorophenyl)azepan-1-yl)-6-methylpyrimidin-2-amine (35) I-13.

Peak B: 2.09 g, 96% ee; optical rotation: $[ ]_D$=+1.373 (c=1.02, MeOH); $^1$H NMR (400 MHz, CDCl$_3$) δ 1.46-1.31 (m, 2H), 1.72-1.53 (m, 2H), 1.96-1.82 (m, 2H), 2.04 (d, J=18.8 Hz, 1H), 2.39-2.05 (m, 3H), 2.61-2.42 (m, 1H), 4.08-3.22 (m, 1H), 4.72 (s, 2H), 4.89 (s, 1H), 5.43 (s, 1H), 5.82 (s, 1H), 7.16 (s, 3H), 7.35 (s, 1H); ESI-MS m/z calc. 316.15, found 317.2 (M+1)$^+$. Retention time: 0.82 minutes. (S)-4-(2-(2-chlorophenyl)azepan-1-yl)-6-methylpyrimidin-2-amine (36) I-14.

The following analogs were prepared according to Synthetic Scheme 3:

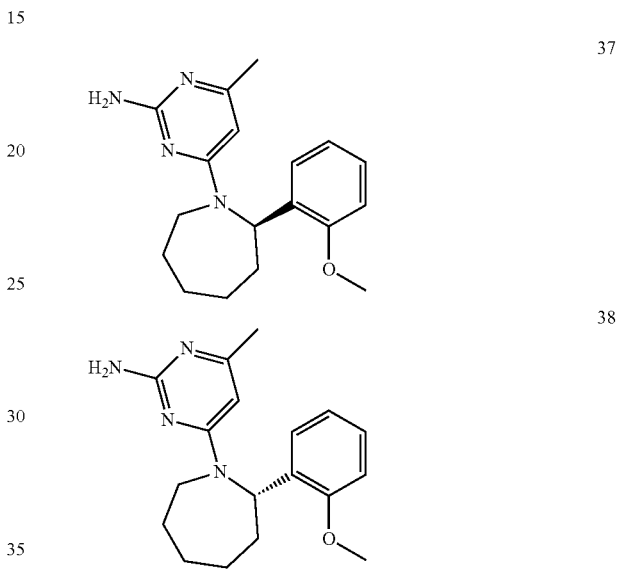

(R)-4-(2-(2-methoxyphenyl)azepan-1-yl)-6-methyl-pyrimidin-2-amine (37) I-11 and (S)-4-(2-(2-methoxyphenyl)azepan-1-yl)-6-methylpyrimidin-2-amine (38) I-12

Peak A from SFC chiral separation: $^1$H NMR (400 MHz, CDCl$_3$) δ 7.01 (dd, J=118.6, 38.8 Hz, 4H), 5.60 (2 s, 1H), 5.24-4.44 (m, 3H), 3.82 (s, 3H), 3.32 (dd, J=63.5, 46.9 Hz, 1H), 2.49 (2 s, 1H), 2.30-1.91 (m, 3H), 1.94-0.56 (m, 9H); ESI-MS m/z calc. 312.20, found 313.13 (M+1)$^+$. Retention time: 0.78 minutes. (38) I-12.

Peak B from SFC chiral separation: $^1$H NMR (400 MHz, CDCl$_3$) δ 9.03-6.27 (m, 4H), 5.59 (2 s, 1H), 5.29-4.36 (m, 3H), 3.82 (s, 3H), 3.54-2.79 (m, 1H), 2.33 (d, J=61.8 Hz, 1H), 2.00 (s, 3H), 1.93-0.44 (m, 10H); ESI-MS m/z calc. 312.12, found 313.13 (M+1)$^+$. Retention time: 0.8 minutes. (37) I-11.

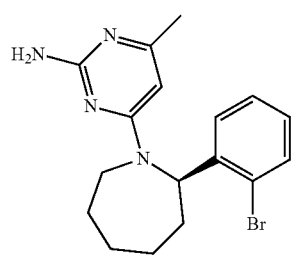

42

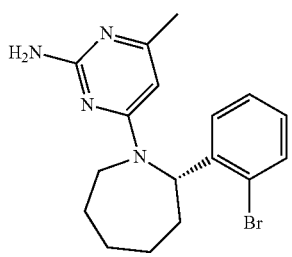

(R)-4-(2-(2-bromo)azepan-1-yl)-6-methylpyrimidin-2-amine (41) I-2 and (S)-4-(2-(2-bromo)azepan-1-yl)-6-methylpyrimidin-2-amine (42) I-3

Peak A from SFC chiral separation: $^1$H NMR (400 MHz, CDCl$_3$) δ 7.46 (d, J=7.4 Hz, 1H), 7.08 (d, J=42.6 Hz, 3H), 5.95-5.43 (m, 1H), 5.34 (s, 1H), 4.77 (d, J=37.2 Hz, 3H), 3.98-3.08 (m, 2H), 2.46-2.32 (m, 1H), 2.08 (d, J=40.4 Hz, 3H), 1.94 (s, 1H), 1.89-1.75 (m, 2H), 1.65-1.44 (m, 2H), 1.42-1.26 (m, 2H); ESI-MS m/z calc. 360.09, found 361.12 (M+1)$^+$. Retention time: 0.91 minutes. (41) I-2.

Peak B from SFC chiral separation: $^1$H NMR (400 MHz, CDCl$_3$) δ 7.46 (s, 1H), 6.99 (t, J=70.7 Hz, 3H), 6.02-5.47 (m, 1H), 5.21 (t, J=62.8 Hz, 4H), 4.78 (d, J=17.2 Hz, 1H), 3.96-3.17 (m, 2H), 2.48-2.33 (m, 1H), 2.27-2.03 (m, 3H), 1.96-1.72 (m, 3H), 1.68-1.42 (m, 2H), 1.42-1.23 (m, 2H); ESI-MS m/z calc. 360.09, found 361.12 (M+1)$^+$. Retention time: 0.93 minutes. (42) I-3.

43

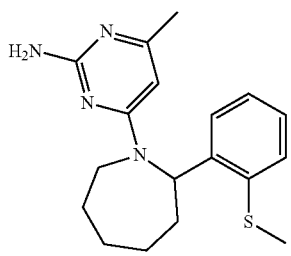

(+/−)-4-methyl-6-(2-(2-(methylthio)phenyl)azepan-1-yl)pyrimidin-2-amine (43) I-5

$^1$H NMR (400 MHz, MeOD) δ 7.33 (d, J=7.8 Hz, 1H), 7.23 (s, 1H), 7.08 (d, J=5.7 Hz, 2H), 5.45 (s, 1H), 3.41 (s, 1H), 2.58 (s, 3H), 2.38 (d, J=17.3 Hz, 1H), 2.02 (d, J=6.2 Hz, 3H), 1.96-1.81 (m, 2H), 1.72 (d, J=6.7 Hz, 1H), 1.62-1.50 (m, 1H), 1.50-1.27 (m, 2H); ESI-MS m/z calc. 328.17, found 329.11 (M+1)$^+$. Retention time: 0.75 minutes.

44

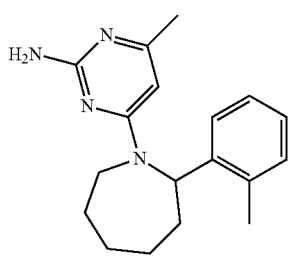

(+/−)-4-methyl-6-(2-(2-(methyl)phenyl)azepan-1-yl)pyrimidin-2-amine (44) I-6

$^1$H NMR (400 MHz, Methanol-d4) δ 7.19-6.99 (m, 4H), 2.46 (s, 3H), 2.27 (ddd, J=14.3, 8.4, 5.1 Hz, 1H), 2.22-1.96 (m, 4H), 1.95-1.82 (m, 3H), 1.81-1.68 (m, 1H), 1.59 (d, J=12.0 Hz, 1H), 1.42 (dtt, J=23.7, 12.2, 6.3 Hz, 2H); ESI-MS m/z calc. 296.20, found 297.14 (M+1)$^+$. Retention time: 0.74 minutes.

45

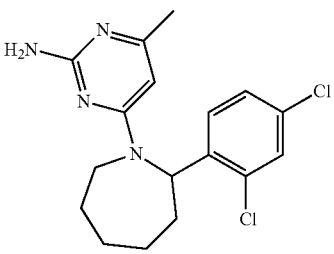

(+/−)-4-(2-(2,4-dichlorophenyl)azepan-1-yl)-6-methylpyrimidin-2-amine (45) I-1

$^1$H NMR (400 MHz, MeOD) δ 7.71-7.07 (m, 3H), 6.53-5.02 (m, 2H), 4.28-3.43 (m, 2H), 2.66-2.37 (m, 1H), 2.25 (2 s 3H), 2.17-1.28 (m, 7H); ESI-MS m/z calc. 350.11, found 351.11 (M+1)$^+$. Retention time: 3.13 minutes.

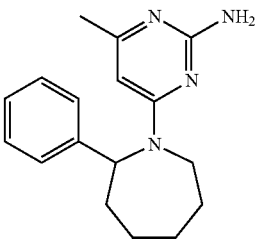 [SMILES: Cc1cc(N2CCCCCC2c2ccccc2)nc(N)n1]

(+/−)-4-methyl-6-(2-phenylazepane-1-yl)pyrimidin-2-amine (45) I-4

$^1$H NMR (400 MHz, MeOD) δ 7.48-7.17 (m, 5H), 6.39-5.94 (2 s, 1H), 4.04-3.36 (m, 1H), 2.52 (td, J=14.5, 6.2 Hz, 1H), 2.27 (d, J=61.1 Hz, 3H), 2.04-1.79 (m, 4H), 1.76-1.05 (m, 3H).

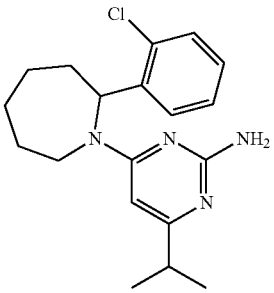 [SMILES: CC(C)c1cc(N2CCCCCC2c2ccccc2Cl)nc(N)n1]

(+/−)-4-(2-(2-chlorophenyl)azepan-1-yl)-6-isopropylpyrimidin-2-amine I-16

$^1$H NMR (400 MHz, DMSO-d6) δ 7.47-7.34 (m, 1H), 7.34-7.17 (m, 3H), 5.57 (s, 1H), 5.46 (s, 2H), 5.21 (s, 1H), 4.55 (d, J=14.9 Hz, 1H), 3.55-3.40 (m, 1H), 2.57-2.52 (m, 1H), 2.34 (ddd, J=13.8, 8.1, 5.0 Hz, 1H), 1.98 (t, J=11.2 Hz, 1H), 1.92-1.64 (m, 3H), 1.61-1.18 (m, 3H), 1.08 (d, J=6.9 Hz, 3H), 1.04 (d, J=6.9 Hz, 3H); ESI-MS m/z found 345.

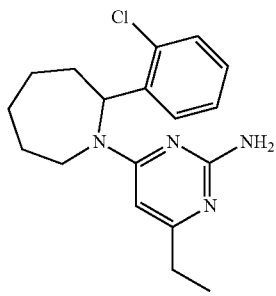 [SMILES: CCc1cc(N2CCCCCC2c2ccccc2Cl)nc(N)n1]

(+/−)-4-(2-(2-chlorophenyl)azepan-1-yl)-6-ethylpyrimidin-2-amine I-17

$^1$H NMR (400 MHz, DMSO-d6) δ 7.45-7.32 (m, 1H), 7.28-7.13 (m, 3H), 5.56 (s, 1H), 5.41 (s, 2H), 5.21 (d, J=12.0 Hz, 1H), 4.49 (d, J=14.7 Hz, 1H), 3.51-3.38 (m, 1H), 2.52-2.49 (m, 1H), 2.38-2.22 (m, 3H), 2.01-1.64 (m, 2H), 1.59-1.21 (m, 4H), 1.03 (t, J=7.5 Hz, 3H); ESI-MS m/z found 331.

Example 4

Synthetic Scheme 4: (+/−)-4-(3-(5-amino-2-chlorophenyl)-1,4-oxazepan-4-yl)-6-methylpyrimidin-2-amine (46) I-71

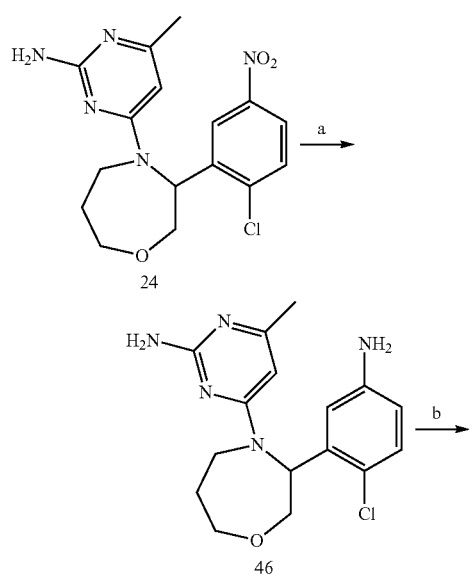

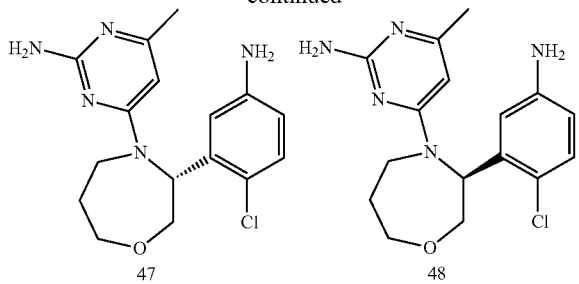

(a) zinc, NH$_4$Cl, 2% TPGS-750-M in water, 75° C.; (b) SFC chiral separation

Formation of (R)-4-(3-(5-amino-2-chlorophenyl)-1,4-oxazepan-4-yl)-6-methylpyrimidin-2-amine (47) and (S)-4-(3-(5-amino-2-chlorophenyl)-1,4-oxazepan-4-yl)-6-methylpyrimidin-2-amine (48)

4-[3-(2-chloro-5-nitro-phenyl)-1,4-oxazepan-4-yl]-6-methyl-pyrimidin-2-amine, 24, (1.00 g, 2.75 mmol), NH$_4$Cl (0.31 g, 5.85 mmol) and Zn (0.87 g, 13.36 mmol) were stirred in 2% TPGS-750-M in water (28 mL). The reaction mixture was stirred vigorously and heated to 75° C. for 24 hours. The mixture was cooled to room temperature and diluted into aqueous saturated NaHCO$_3$ solution and dichloromethane. The organic phase was dried (MgSO$_4$), filtered and concentrated in vacuo. The crude residue was purified via silica gel chromatography with 40 g isco GOLD column using 0-50% (20% MeOH—CH$_2$Cl$_2$/CH$_2$Cl$_2$) to afford 390 mg of compound 46 as a racemic mixture. The racemic mixture was submitted for SFC chiral separation: prepped at 50% IPA, 50% Hexanes, 0.2% diethylamine on AD-H to afford the individual stereoisomers.

Peak A—99% pure by chiral HPLC; (R)-4-[3-(5-amino-2-chloro-phenyl)-1,4-oxazepan-4-yl]-6-methyl-pyrimidin-2-amine (47): high temperature (360 K) $^1$H NMR (400 MHz, DMSO-d6) δ 7.01 (d, J=8.5 Hz, 1H), 6.52 (d, J=2.7 Hz, 1H), 6.47 (dd, J=8.5, 2.7 Hz, 1H), 5.51 (s, 1H), 5.43 (s, 2H), 5.26-5.10 (m, 1H), 4.94 (s, 2H), 4.82-4.64 (m, 1H), 4.10 (dd, J=13.5, 5.0 Hz, 1H), 3.95-3.84 (m, 1H), 3.69-3.46 (m, 3H), 1.99 (s, 2H), 1.82-1.65 (m, 2H). ESI-MS m/z calc. 333.14, found 334.26 (M+1)$^+$. Retention time: 0.51 minutes; [□]$^D$=−118.67 (c=12 mg/4 mL MeOH). I-86.

Peak B—99.9% pure by chiral HPLC; (S)-4-[3-(5-amino-2-chloro-phenyl)-1,4-oxazepan-4-yl]-6-methyl-pyrimidin-2-amine (48): high temperature (360 K) $^1$H NMR (400 MHz, DMSO-d6) δ 7.01 (dd, J=8.5, 1.5 Hz, 1H), 6.52 (d, J=2.5 Hz, 1H), 6.47 (dt, J=8.5, 2.1 Hz, 1H), 5.51 (s, 1H), 5.44 (s, 2H), 5.26-5.07 (m, 1H), 4.94 (s, 2H), 4.84-4.66 (m, 1H), 4.11 (ddd, J=13.4, 5.0, 1.5 Hz, 1H), 3.97-3.84 (m, 1H), 3.69-3.42 (m, 3H), 2.05-1.92 (m, 3H), 1.83-1.66 (m, 2H). ESI-MS m/z calc. 333.14, found 334.26 (M+1)$^+$. Retention time: 0.51 minutes; [□]$^D$=+175 (c=8 mg/4 mL MeOH). I-87.

249

The following analog was prepared according to Synthetic Scheme 4:

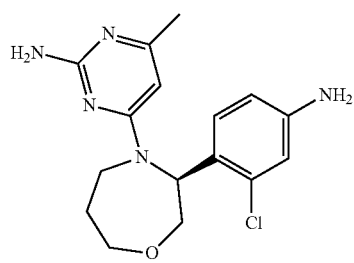

(+/−)-4-[3-(4-amino-2-chloro-phenyl)-1,4-oxazepan-4-yl]-6-methyl-pyrimidin-2-amine (49) I-140 high temperature (360 K) $^1$H NMR (400 MHz, DMSO-d6) δ 7.01 (m, 3H), 6.65 (d, J=2.3 Hz, 1H), 6.52 (dd, J=8.5, 2.3 Hz, 1H), 5.95 (br s, 1H), 5.49-5.36 (m, 2H), 4.70-4.49 (m, 1H), 4.04 (dd, J=13.5, 5.0 Hz, 1H), 3.83 (dd, J=10.4, 5.8 Hz, 2H), 3.75-3.58 (m, 3H), 2.19 (s, 3H), 1.86-1.75 (m, 2H). ESI-MS m/z calc. 333.14, found 334.26 (M+1)$^+$. Retention time: 0.51 minutes.

Example 5

Synthetic Scheme 5: (+/−)-N-[4-[4-(2-amino-6-methyl-pyrimidin-4-yl)-1,4-oxazepan-3-yl]-3-chloro-phenyl]methanesulfonamide I-139, I-179, and I-296

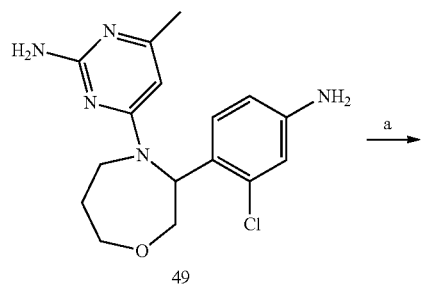

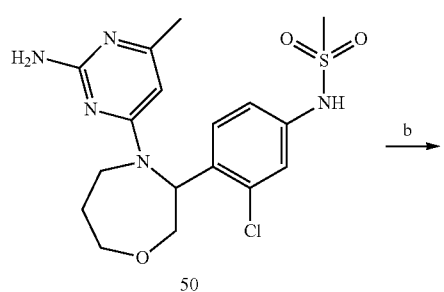

250

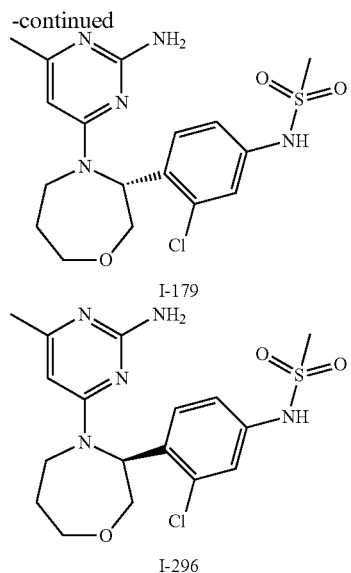

(a) Methanesulfonyl chloride, NEt$_3$, THF; (b) SFC chiral separation

Formation of (+/−)-3-(2-chloro-5-nitrophenyl)-1,4-oxazepane (50) I-139

To a solution of 4-[3-(4-amino-2-chloro-phenyl)-1,4-oxazepan-4-yl]-6-methyl-pyrimidin-2-amine, 49, (0.034 g, 0.103 mmol) and triethylamine (0.050 mL, 0.360 mmol) in THF (1.5 mL) was added methanesulfonyl chloride (0.009 mL, 0.113 mmol). The reaction mixture was stirred overnight at room temperature. An additional 5 uL of methanesulfonyl chloride was added. After 20 minutes, the reaction mixture was concentrated in vacuo. Purification was carried out on a reverse phase 50 g ISCO c18-aq column, running with 0.1% TFA/H$_2$O and 0.1% TFA/CH$_3$CN. The pure fractions were concentrated in vacuo and then dissolved in MeOH and passed through two SPE bicarbonate cartridges (Agilent Stratospheres 100 mg/6 mL) arranged in series and concentrated to give 7.3 mg of the desired product: high temperature (360 K) $^1$H NMR (400 MHz, DMSO-d6) δ 9.97-9.55 (br s, 1H), 7.25-7.21 (m, 2H), 7.09 (dd, J=8.5, 2.1 Hz, 1H), 5.59 (s, 1H), 5.42 (s, 2H), 5.36 (s, 1H), 4.60 (d, J=13.2 Hz, 1H), 4.08 (dd, J=13.5, 5.0 Hz, 1H), 3.88 (d, J=12.3 Hz, 1H), 3.70 (dd, J=13.5, 10.2 Hz, 1H), 3.66-3.50 (m, 3H), 2.01 (s, 3H), 1.76 (s, 3H); ESI-MS m/z calc. 411.11, found 412.24 (M+1)$^+$. Retention time: 0.56 minutes.

Chiral HPLC separation afforded individual enantiomers

Peak A: $^1$H NMR (400 MHz, DMSO-d6) δ 9.66 (s, 1H), 7.28-7.23 (m, 2H), 7.13 (dd, J=8.5, 2.2 Hz, 1H), 5.59 (s, 1H), 5.46 (s, 2H), 5.39 (s, 1H), 4.59 (d, J=14.9 Hz, 1H), 4.09 (dd, J=13.5, 5.0 Hz, 1H), 3.93-3.85 (m, 1H), 3.71 (dd, J=13.5, 10.1 Hz, 1H), 3.66-3.49 (m, 2H), 2.99 (s, 3H), 2.01 (s, 3H), 1.81-1.70 (m, 2H). I-179

Peak B: $^1$H NMR (400 MHz, DMSO-d6) δ 7.33-7.22 (m, 2H), 7.13 (dd, J=8.5, 2.2 Hz, 1H), 5.59 (s, 1H), 5.46 (s, 2H), 5.44-5.34 (m, 1H), 4.59 (d, J=15.2 Hz, 1H), 4.09 (dd, J=13.4, 5.0 Hz, 1H), 3.93-3.84 (m, 1H), 3.71 (dd, J=13.5, 10.1 Hz, 1H), 3.67-3.49 (m, 2H), 2.99 (s, 3H), 2.01 (s, 3H), 1.77 (ddt, J=10.2, 8.0, 3.4 Hz, 2H). I-296

Example 6

Synthetic Scheme 6: (+/−)-N-[4-[4-(2-amino-6-methyl-pyrimidin-4-yl)-1,4-oxazepan-3-yl]-3-chloro-phenyl]methanesulfonamide (51) I-282

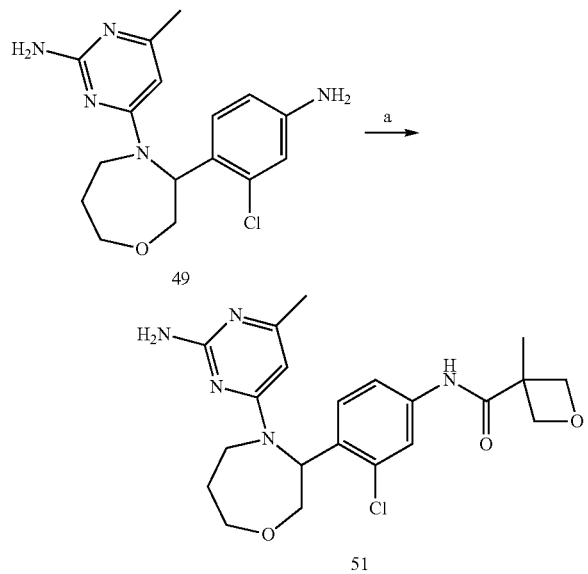

(a) 3-methyloxetane-3-carboxylic acid, iPr₂NEt, HATU, DMF.

Formation of (+/−)-N-(4-(4-(2-amino-6-methylpyrimidin-4-yl)-1,4-oxazepan-3-yl)-3-chlorophenyl)-3-methyloxetane-3-carboxamide (51) I-282

To a solution of 4-[3-(4-amino-2-chloro-phenyl)-1,4-oxazepan-4-yl]-6-methyl-pyrimidin-2-amine (0.05 g, 0.15 mmol), 3-methyloxetane-3-carboxylic acid (0.02 g, 0.16 mmol) and N,N-diisopropylethylamine (0.05 mL, 0.30 mmol) in DMF (1 mL) was added N-[(dimethylamino)-1H-1,2,3-triazolo-[4,5-b]pyridin-1-ylmethylene]-N-methyl-methanaminium hexafluorophosphate N-oxide (HATU) (0.08 g, 0.21 mmol). The reaction mixture was stirred at room temperature overnight. The resulting residue was purified by reverse phase preparatory HPLC (CH₃CN/0.1% TFA aq). The fractions containing desired product were basified with an aqueous saturated NaHCO₃ solution wash and extracted with dichloromethane. The organic phase was passed through a phase separator, concentrated in vacuo to afford the desired product The following analogs were prepared according to Synthetic Scheme 6:

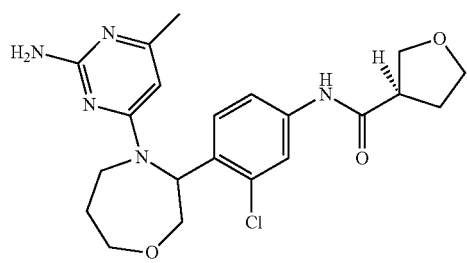

(3R)—N-(4-(4-(2-amino-6-methylpyrimidin-4-yl)-1,4-oxazepan-3-yl)-3-chlorophenyl)-tetrahydrofuran-3-carboxamide (52) I-280

(racemic mixture on oxazepane 3-position) ¹H NMR (400 MHz, CDCl₃) δ 7.74 (s, 1H), 7.54 (s, 1H), 7.30-7.21 (m, 1H), 7.15 (d, J=8.4 Hz, 1H), 5.53 (s, 1H), 4.66 (s, 2H), 4.29 (dd, J=13.6, 5.0 Hz, 1H), 4.10-3.97 (m, 3H), 3.99-3.75 (m, 2H), 3.66-3.43 (m, 3H), 3.11-2.95 (m, 1H), 2.32-2.22 (m, 2H), 2.12 (s, 3H), 2.02-1.89 (m, 1H), 1.80 (d, J=14.3 Hz, 3H).- ESI-MS m/z calc. 431.17, found 432.18 (M+1)⁺. Retention time: 0.57 minutes.

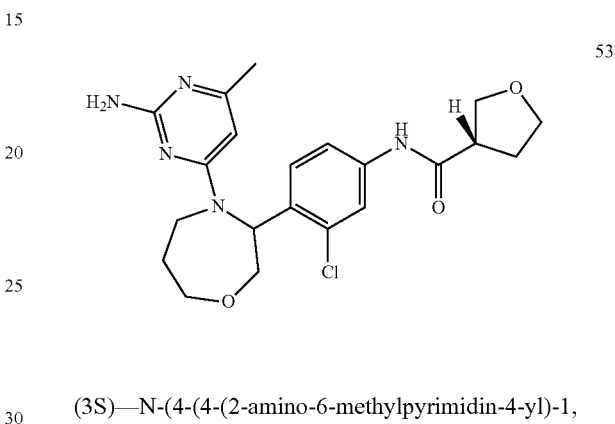

(3S)—N-(4-(4-(2-amino-6-methylpyrimidin-4-yl)-1,4-oxazepan-3-yl)-3-chlorophenyl)-tetrahydrofuran-3-carboxamide (53) I-281

(racemic mixture on oxazepane 3-position) 7.74 (s, 1H), 7.54 (s, 1H), 7.30-7.21 (m, 1H), 7.15 (d, J=8.4 Hz, 1H), 5.53 (s, 1H), 4.64 (s, 2H), 4.30 (dd, J=13.6, 5.0 Hz, 1H), 4.11-3.99 (m, 3H), 3.95-3.79 (m, 2H), 3.65-3.43 (m, 3H), 3.11-2.95 (m, 1H), 2.32-2.19 (m, 2H), 2.12 (s, 3H), 2.04-1.89 (m, 1H), 1.87-1.72 (m, 3H).- ESI-MS m/z calc. 431.17, found 432.14 (M+1)⁺. Retention time: 0.57 minutes.

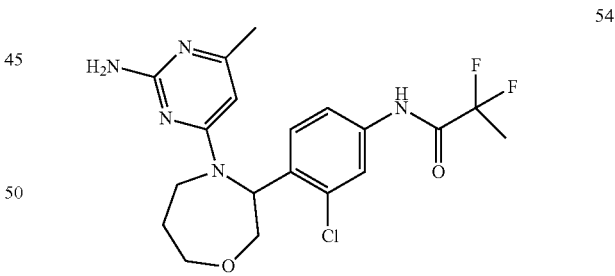

(+/−)-N-(4-(4-(2-amino-6-methylpyrimidin-4-yl)-1,4-oxazepan-3-yl)-3-chlorophenyl)-2,2-difluoropropanamide (54) I-228

¹H NMR (400 MHz, CDCl₃) δ 7.91 (s, 1H), 7.78 (s, 1H), 7.36-7.31 (m, 1H), 7.22 (d, J=8.4 Hz, 1H), 5.53 (s, 1H), 4.60 (s, 2H), 4.31 (dd, J=13.6, 5.0 Hz, 2H), 4.06 (d, J=12.5 Hz, 1H), 3.65-3.47 (m, 4H), 2.13 (s, 3H), 1.89 (t, J=19.3 Hz, 5H); ESI-MS m/z calc. 425.1, found 426.2 (M+1)⁺. Retention time: 0.64 minutes.

55

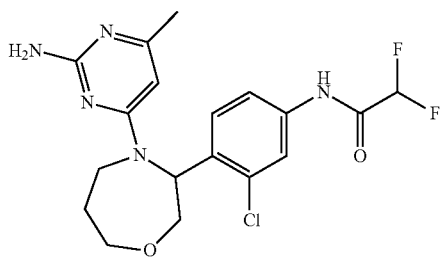

(+/−)-N-(4-(4-(2-amino-6-methylpyrimidin-4-yl)-1,4-oxazepan-3-yl)-3-chlorophenyl)-2,2-difluoroacetamide (55) I-278

$^1$H NMR (400 MHz, CDCl$_3$) δ 7.90 (s, 1H), 7.77 (s, 1H), 7.35 (dd, J=8.5, 2.2 Hz, 1H), 7.23 (d, J=8.4 Hz, 1H), 6.01 (t, J=54.2 Hz, 1H), 5.53 (s, 1H), 4.64 (s, 2H), 4.31 (dd, J=13.6, 4.9 Hz, 1H), 4.15-4.01 (m, 1H), 3.68-3.46 (m, 3H), 2.13 (s, 3H), 2.06-1.91 (m, 2H), 1.88-1.76 (m, 2H); ESI-MS m/z calc. 411.1, found 412.1 (M+1)$^+$. Retention time: 0.6 minutes.

56

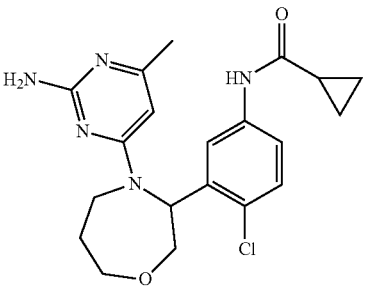

(+/−)-N-(4-(4-(2-amino-6-methylpyrimidin-4-yl)-1,4-oxazepan-3-yl)-3-chlorophenyl)-3-fluorotetrahydrofuran-3-carboxamide (56) I-279

$^1$H NMR (400 MHz, CDCl$_3$) δ 8.17 (d, J=7.9 Hz, 1H), 7.81 (d, J=7.8 Hz, 1H), 7.32 (td, J=8.3, 2.2 Hz, 1H), 7.20 (d, J=8.5 Hz, 1H), 5.53 (s, 1H), 4.61 (s, 2H), 4.30 (dd, J=13.6, 5.0 Hz, 1H), 4.19-4.02 (m, 6H), 3.68-3.49 (m, 3H), 2.77-2.56 (m, 1H), 2.44-2.27 (m, 1H), 2.12 (s, 3H), 2.03-1.90 (m, 1H), 1.88-1.74 (m, 2H); ESI-MS m/z calc. 449.2, found 450.1 (M+1)$^+$. Retention time: 0.6 minutes.

The following analogs were prepared according to Scheme 6 using 4-(3-(5-amino-2-chlorophenyl)-1,4-oxazepan-4-yl)-6-methylpyrimidin-2-amine 46 as starting material:

57

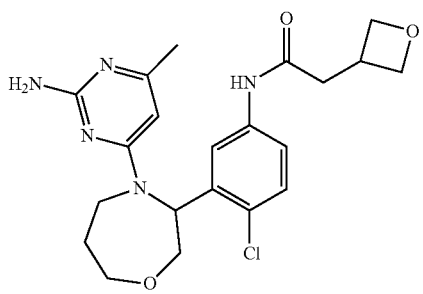

(+/−)-N-[3-[4-(2-amino-6-methyl-pyrimidin-4-yl)-1,4-oxazepan-3-yl]-4-chloro-phenyl]-2-(oxetan-3-yl)acetamide (57) I-185

$^1$H NMR (300 MHz, Methanol-d4) δ 6.07-5.93 (m, 1H), 5.75 (br, 2H), 5.26 (s, 1H), 4.27 (s, 1H), 3.87 (br, 2H), 2.80 (m, 4H), 2.52-2.21 (m, 5H), 1.74-1.35 (m, 2H), 0.83 (s, 3H), 0.56 (m, 2H); ESI-MS m/z calc. 431.2, found 432.1 (M+1)$^+$. Retention time: 0.55 minutes.

58

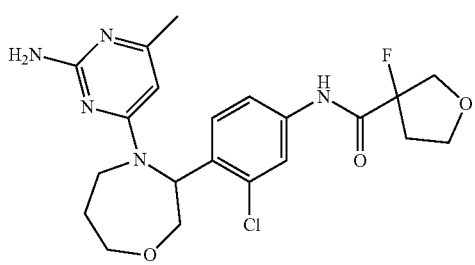

(+/−)-N-[3-[4-(2-amino-6-methyl-pyrimidin-4-yl)-1,4-oxazepan-3-yl]-4-chloro-phenyl]cyclopropanecarboxamide (58) I-241 heated (360K) $^1$H NMR (300 MHz, DMSO-d6) δ 10.38 (s, 1H), 7.96 (s, 2H), 7.74-7.30 (m, 8H), 6.65 (s, 1H), 5.95 (dd, J=10.3, 5.4 Hz, 1H), 5.56 (s, 1H), 5.18 (dd, J=10.1, 4.9 Hz, 1H), 5.10-4.93 (m, 1H), 4.34-4.10 (m, 3H), 4.02-3.55 (m, 7H), 2.29 (s, 3H), 2.00-1.63 (m, 6H), 0.79 (d, J=7.3 Hz, 6H); ESI-MS m/z calc. 401.2, found 402.2 (M+1)$^+$. Retention time: 0.62 minutes.

59

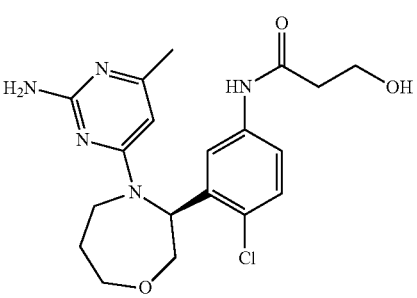

(S)—N-[3-[(3S)-4-(2-amino-6-methyl-pyrimidin-4-yl)-1,4-oxazepan-3-yl]-4-chloro-phenyl]-3-hydroxypropanamide (59) I-283

Racemic material obtained using similar procedure and then submitted for chiral HPLC purification (column (OJ-H 20×250 m), mobile phase (80% hexanes/20% IPA/0.2% diethylamine), flow 20 mL/min).

Peak B: ee: 91%; [α]$_D$ (c=0.5, MeOH) +32.4; $^1$H NMR (300 MHz, Methanol-d4) δ 7.63 (d, J=2.6 Hz, 1H), 7.49 (d, J=8.8 Hz, 1H), 7.35 (d, J=8.7 Hz, 1H), 5.46 (br, 3H), 4.30 (dd, J=13.6, 5.0 Hz, 1H), 4.11-3.97 (m, 1H), 3.85 (t, J=6.2 Hz, 2H), 3.79-3.48 (m, 3H), 2.53 (t, J=6.1 Hz, 2H), 2.07 (s, 3H), 1.87 (m, 2H); ESI-MS m/z calc. 405.2, found 406.2 (M+1)$^+$. Retention time: 0.58 minutes.

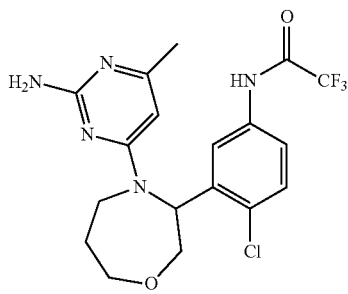

N-(3-(4-(2-amino-6-methylpyrimidin-4-yl)-1,4-oxazepan-3-yl)-4-chlorophenyl)-2,2,2-trifluoroacetamide (60) I-177

Racemic material obtained using similar procedure and then submitted for chiral HPLC purification (column (OJ-H 20×250 m), mobile phase (80% hexanes/20% IPA/0.2% diethylamine), flow 20 mL/min).

Peak B: ee: 99%; [α]$_D$ (c=0.5, MeOH) +157.3; $^1$H NMR (300 MHz, Methanol-d4) δ 6.35 (d, J=2.5 Hz, 2H), 6.16 (d, J=9.2 Hz, 1H), 4.22 (br, 1H), 3.02 (dd, J=13.6, 5.1 Hz, 1H), 2.88-2.67 (m, 1H), 2.56-2.23 (m, 3H), 2.03 (m, 2H), 0.59 (m, 2H); ESI-MS m/z calc. 429.1, found 429.9 (M+1)$^+$. Retention time: 0.65 minutes.

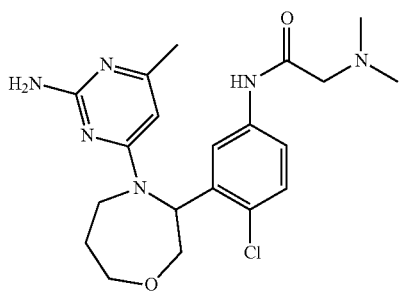

(+/−)-N-[3-[4-(2-amino-6-methyl-pyrimidin-4-yl)-1,4-oxazepan-3-yl]-4-chloro-phenyl]-2-(dimethylamino)acetamide (61) I-168 heated (360K) $^1$H NMR (300 MHz, DMSO-d6) δ 9.90 (s, 1H), 7.73 (d, J=8.7 Hz, 1H), 7.63 (d, J=2.6 Hz, 1H), 7.38 (d, J=8.7 Hz, 1H), 5.96 (brs, 2H), 5.03 (br, 2H), 4.11 (s, 1H), 3.94 (m, 1H), 3.74-3.47 (m, 3H), 3.33 (s, 6H), 3.04 (s, 2H), 2.25 (s, 3H), 1.98 (br, 2H); ESI-MS m/z calc. 418.2, found 419.1 (M+1)$^+$. Retention time: 0.58 minutes.

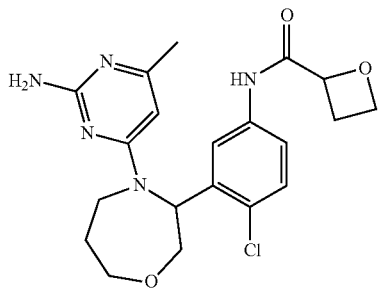 [SMILES: Cc1cc(N2CCCOCC2c2cc(NC(=O)C3CCO3)ccc2Cl)nc(N)n1]

(+/−)-N-[3-[4-(2-amino-6-methyl-pyrimidin-4-yl)-1,4-oxazepan-3-yl]-4-chloro-phenyl]oxetane-2-carboxamide (62) I-184

$^1$H NMR (300 MHz, Methanol-d4) δ 8.60 (s, 1H), 6.59-6.42 (m, 1H), 6.37-6.19 (m, 1H), 6.10 (dd, J=22.6, 8.7 Hz, 1H), 5.20 (s, 0.5H), 4.76 (dd, J=10.2, 5.2 Hz, 0.5H), 4.34 (s, 0.5H), 4.04 (dd, J=10.2, 5.0 Hz, 0.5H), 3.78 (dd, J=9.1, 6.7 Hz, 1H), 3.48-3.29 (m, 2H), 3.16-2.91 (m, 2H), 2.81-2.26 (m, 4H), 1.85-1.25 (m, 2H), 1.02 (s, 1.5H), 0.89 (d, J=0.8 Hz, 1.5H), 0.61 (m, 2H); ESI-MS m/z calc. 417.2, found 418.0 (M+1)$^+$. Retention time: 0.6 minutes.

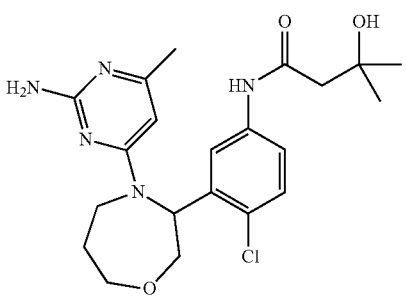

(+/−)-N-[3-[4-(2-amino-6-methyl-pyrimidin-4-yl)-1,4-oxazepan-3-yl]-4-chloro-phenyl]-3-hydroxy-3-methyl-butanamide (63) I-251

$^1$H NMR (300 MHz, Methanol-d4) δ 7.75 (t, J=10.0 Hz, 1H), 7.48-7.40 (m, 1H), 7.39-7.29 (m, 1H), 6.52 (s, 0.5H), 6.08 (dd, J=10.3, 5.3 Hz, 0.5H), 5.65 (d, J=3.3 Hz, 0.5H), 5.35 (dd, J=10.5, 5.1 Hz, 0.5H), 5.20 (d, J=14.4 Hz, 0.5H), 4.46-4.19 (m, 1.5H), 4.14-3.55 (m, 4H), 2.48 (d, J=1.4 Hz, 1.5H), 2.34 (d, J=0.8 Hz, 1H), 2.21 (t, J=0.9 Hz, 1.5H), 2.09 (d, J=1.1 Hz, 1H), 1.47-1.21 (m, 6H); ESI-MS m/z calc. 433.2, found 434.2 (M+1)$^+$. Retention time: 0.59 minutes.

Example 7

Synthetic Scheme 7: (+/−)-N-(4-(4-(2-amino-6-methylpyrimidin-4-yl)-1,4-oxazepan-3-yl)-3-chlorophenyl)-2-hydroxy-2-methylpropanamide I-277

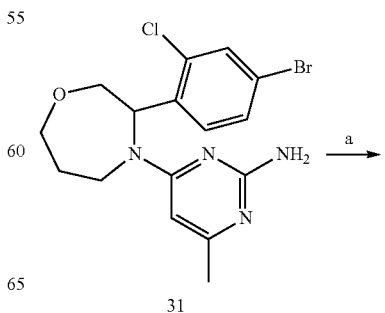

31

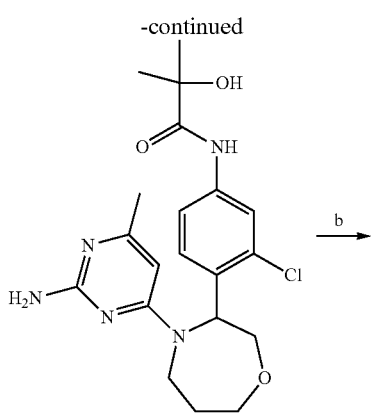

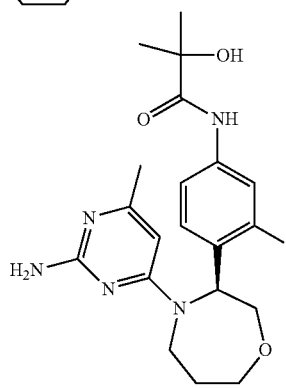

64

(a) 2-hydroxy-2-methylpropanamide, NaOtBu, tBuXPhos Pd G3, tBuOH, 60° C.; (b) SFC chiral separation Formation of (S)—N-(4-(4-(2-amino-6-methylpyrimidin-4-yl)-1,4-oxazepan-3-yl)-3-chlorophenyl)-2-hydroxy-2-methylpropanamide (64) I-276

In a microwave tube, a mixture of 4-[3-(4-bromo-2-chloro-phenyl)-1,4-oxazepan-4-yl]-6-methyl-pyrimidin-2-amine, 31, (0.77 g, 1.86 mmol), 2-hydroxy-2-methyl-propanamide (0.45 g, 4.36 mmol), sodium tert-butoxide (0.56 g, 5.78 mmol), and [2-(2-aminophenyl)phenyl]-methylsulfonyloxy-palladium;ditert-butyl-[2-(2,4,6-triisopropylphenyl)phenyl]phosphane (tBuXPhos Pd G3) (0.06 g, 0.08 mmol) in 2-methyl-2-propanol (14 mL) was evacuated and backfilled with nitrogen three times. The tube was then heated to 60° C. for 3 hours. The reaction mixture was diluted with dichloromethane and washed with water, brine, dried over sodium sulfate, filtered and concentrated in vacuo. The resulting residue was purified via reverse phase silica gel chromatography using C-18 (150 g) ISCO column eluting with 0-90% CH$_3$CN/H$_2$O (ammonium formate modifier). The pure fractions were concentrated in vacuo, diluted with dichloromethane and washed with water. The organic phases were passed through a phase separator and concentrated in vacuo to afford 207 mg of desired product. The racemic mixture was submitted for SFC chiral purification (column-IA, 20×250 mm mobile phase—20% MeOH (5 mM ammonia), 80% CO$_2$ flow—80 mL/min).

Peak B: $^1$H NMR (400 MHz, CDCl$_3$) δ 8.68 (s, 1H), 7.83 (s, 1H), 7.31 (dd, J=8.4, 2.2 Hz, 1H), 7.16 (d, J=8.5 Hz, 1H), 5.53 (s, 1H), 4.60 (s, 2H), 4.30 (dd, J=13.6, 5.0 Hz, 1H), 4.08 (d, J=15.8 Hz, 1H), 3.64-3.45 (m, 4H), 2.12 (s, 3H), 1.80 (d, J=14.3 Hz, 4H), 1.54 (s, 6H); ESI-MS m/z calc. 419.2, found 420.2 (M+1)$^+$. Retention time: 0.58 minutes.

Example 8

Synthetic Scheme 8: (+/−)-4-(3-(2-chloro-5-(methylsulfonyl)phenyl)-1,4-oxazepan-4-yl)-6-methylpyrimidin-2-amine (69) I-311

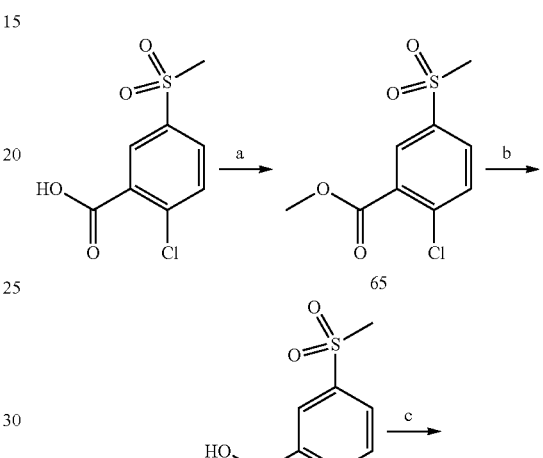

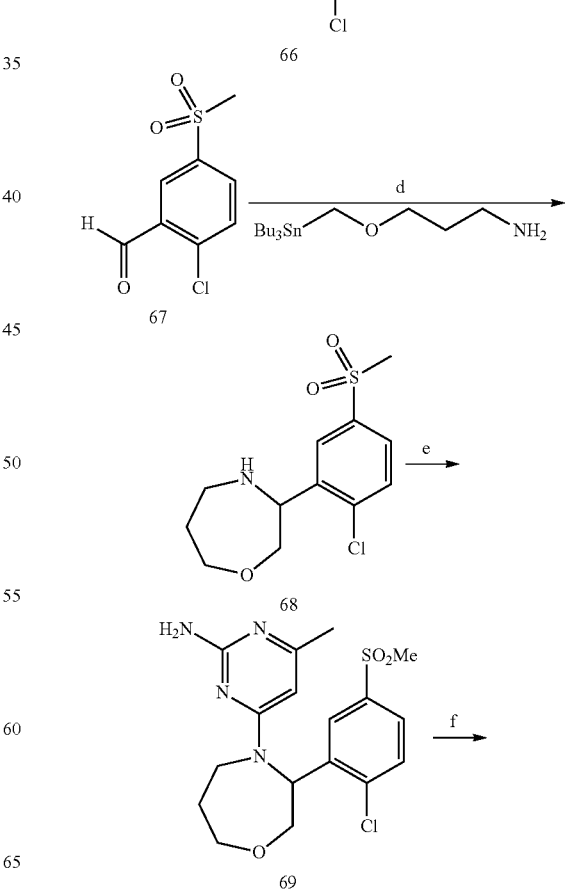

-continued

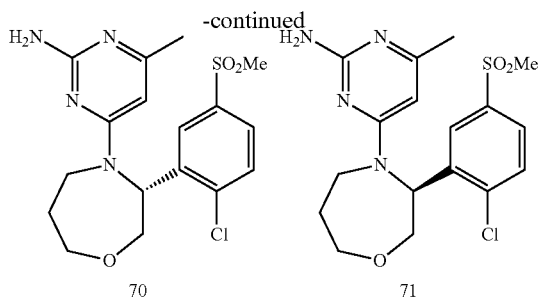

(a) TMS-diazomethane, toluene, methanol: (b) NaBH4, MeOH; (c) Dess-Martin periodinane, dichloromethane; (d) 4 A mol sieves, 3-((tributylstannyl)methoxy)propan-1-amine, $CH_2Cl_2$; then 2,6-lutidine, $Cu(OTf)_2$, hexafluoroisopropanol, $CH_2Cl_2$; (e) 2-amino-4-chloro-6-methylpyrimidine, NMP, 150° C.; (f) SFC chiral separation Formation of methyl 2-chloro-5-(methylsulfonyl)benzoate (65)

To a solution of 2-chloro-5-methylsulfonyl-benzoic acid (3.0 g, 12.8 mmol) in toluene (45 mL) and MeOH (10 mL) was added dropwise TMS-diazomethane (10.7 mL of 2 M in hexane, 21.4 mmol). The reaction mixture was stirred for 3 hours and the solvent was concentrated in vacuo to give 3 grams of desired product as tan fluffy solid that was used without further purification: $^1$H NMR (400 MHz, DMSO-d6) δ 8.32 (d, J=2.3 Hz, 1H), 8.10 (dd, J=8.4, 2.4 Hz, 1H), 7.90 (d, J=8.5 Hz, 1H), 3.92 (s, 3H), 3.30 (s, 6H); ESI-MS m/z calc. 247.99, found 249.12 (M+1)$^+$. Retention time: 0.71 minutes.

Formation of (2-chloro-5-(methylsulfonyl)phenyl)methanol (66)

To a suspension of methyl 2-chloro-5-methylsulfonyl-benzoate, 65, (3.0 g, 12.1 mmol) in EtOH (45 mL) was added NaBH$_4$ (1.83 g, 48.4 mmol). The reaction mixture was stirred at room temperature for 1 hour, then heated to 50° C. to solubilize the mixture. After 3 hours, the mixture was quenched by slow addition into aqueous saturated NH$_4$Cl solution. The aqueous phase was extracted twice with EtOAc. The combined organic phases were washed with aqueous saturated NaHCO$_3$ solution, dried (MgSO$_4$), filtered and concentrated in vacuo to give 2.5 grams of desired product as an orange oil. The crude residue was purified via silica gel chromatography with 40 g isco column using 0-30% EtOAc/CH2Cl2 gradient to afford 2.0 grams of product as a white solid: ESI-MS m/z calc. 219.99, found 221.06 (M+1)$^+$. Retention time: 0.61 minutes.

Formation of 2-chloro-5-(methylsulfonyl)benzaldehyde (67)

(2-chloro-5-methylsulfonyl-phenyl)methanol, 66, (1.00 g, 4.50 mmol) was dissolved in methylene chloride (23 mL). Dess-Martin periodinane (2.49 g, 5.87 mmol) was added and the reaction mixture was stirred at room temperature for 16 hours. The solution was diluted into aqueous saturated NaHCO$_3$ solution and extracted twice with EtOAc. The combined organic phases were washed with aqueous saturated NaHCO$_3$ solution, dried (MgSO$_4$), filtered and concentrated in vacuo. The crude residue was purified via silica gel chromatography with 40 g isco column using 0-20% EtOAc/CH$_2$Cl$_2$ gradient to afford 760 mg of desired product:

$^1$H NMR (400 MHz, DMSO-d6) δ 10.36 (s, 1H), 8.31 (d, J=2.4 Hz, 1H), 8.20 (dd, J=8.4, 2.4 Hz, 1H), 7.94 (d, J=8.4 Hz, 1H), 3.32 (s, 3H).

Formation of 3-(2-chloro-5-(methylsulfonyl)phenyl)-1,4-oxazepane (68)

To a solution of 3-(tributylstannylmethoxy)propan-1-amine (0.88 g, 2.33 mmol) in dichloromethane (6 mL) was added 2-chloro-5-methylsulfonyl-benzaldehyde, 67, (0.51 g, 2.33 mmol) followed by 4 A molecular sieves. The mixture was stirred overnight, filtered to remove the sieves, and diluted with dichloromethane (25 mL).

In a separate flask containing hexafluoroisopropanol (7 mL) was added 2,6-lutidine (0.28 mL, 2.39 mmol) followed by Cu(OTf)$_2$ (0.85 g, 2.34 mmol). The mixture was stirred for 1 hour, then the imine solution prepared above was added in one portion. The reaction was stirred for 3 days at room temperature. The mixture was diluted with 60 mL of 2:1 mixture of aqueous saturated NaHCO$_3$ solution and 10% ammonium hydroxide. After stirring for 30 minutes, the organic layer was removed and washed twice with aqueous saturated NaHCO$_3$ solution, then brine. The organic layer was passed through a phase separator funnel and concentrated in vacuo. The resulting residue was purified by reverse phase silica gel chromatography using an ISCO—100 gram c18-aq column—running with 01.% TFA/H$_2$O and 0.1% TFA/CH$_3$CN. The fractions containing product were concentrated in vacuo and the residue was diluted with dichloromethane and neutralized with aqueous saturated NaHCO$_3$ solution. The organic phase was passed through a phase separator and concentrated in vacuo. $^1$H NMR shows desired product plus additional impurity. Used product without further purification: $^1$H NMR (400 MHz, DMSO-d6) δ 8.16 (d, J=2.4 Hz, 1H), 7.81 (dd, J=8.4, 2.4 Hz, 1H), 7.70 (d, J=8.4 Hz, 1H), 7.54 (t, J=7.6 Hz, 1H), 4.29 (dd, J=9.0, 3.1 Hz, 1H), 3.91-3.76 (m, 2H), 3.76-3.63 (m, 1H), 3.22 (s, 3H), 3.12 (dd, J=12.7, 8.7 Hz, 1H), 2.89 (dt, J=13.6, 6.8 Hz, 2H), 1.93-1.78 (m, 2H); ESI-MS m/z calc. 390.05, found 390.09 (M+1)$^+$. Retention time: 0.50 minutes.

Formation of 4-(3-(2-chloro-5-(methylsulfonyl)phenyl)-1,4-oxazepan-4-yl)-6-methylpyrimidin-2-amine (69)

To a solution of 3-(2-chloro-5-methylsulfonyl-phenyl)-1,4-oxazepane, 68, (0.200 g, 0.690 mmol) in NMP (6 mL) was added 4-chloro-6-methyl-pyrimidin-2-amine (0.123 g, 0.857 mmol). The reaction mixture was heated to 150° C. for 18 hours. The reaction mixture was cooled to room temperature and loaded material directly onto a 50 g ISCO c18-aq column and purified by reverse phase silica gel chromatography using a 50 gram ISCO column running with 0.1% TFA/H$_2$O and 0.1% TFA/CH$_3$CN. The pure fractions were combined and concentrated in vacuo. The residue was diluted with dichloromethane, neutralized with aqueous saturated NaHCO$_3$ solution, passed through a phase separator and the resulting organic phase was concentrated in vacuo to afford 84 mg of brown solid: high temperature (360 K) $^1$H NMR (400 MHz, DMSO-d6) δ 7.85-7.73 (m, 2H), 7.71 (d, J=8.3 Hz, 1H), 5.75-5.54 (m, 2H), 5.50-5.34 (m, 2H), 4.48 (d, J=14.9 Hz, 1H), 4.11 (dd, J=13.5, 4.9 Hz, 1H), 3.92-3.65 (m, 3H), 3.67-3.50 (m, 1H), 3.18-3.11 (m, 3H), 2.03 (d, J=5.4 Hz, 3H), 1.80 (s, 2H).

The racemic mixture was submitted for SFC chiral separation: prepped at 50% IPA, 50% Hexanes, 0.2% diethylamine on AD-H Peak A: (R)-4-(3-(2-chloro-5-(methylsulfonyl)phenyl)-1,4-oxazepan-4-yl)-6-methylpyrimidin-2-amine (70), 96.4% ee by HPLC; heated (360K) $^1$H NMR (400 MHz, DMSO-d6) δ 7.81 (ddd, J=8.3, 2.3, 1.1 Hz, 1H), 7.78 (d, J=2.3 Hz, 1H), 7.71 (dd, J=8.3, 1.2 Hz, 1H), 5.70 (s, 1H), 5.62 (dd, J=9.9, 4.8 Hz, 1H), 5.43 (s, 2H), 4.48 (d, J=15.4 Hz, 1H), 4.11 (dd, J=13.4, 4.9 Hz, 1H), 3.97-3.68 (m, 3H), 3.66-3.52 (m, 1H), 3.16 (d, J=1.2 Hz, 3H), 2.04 (d, J=1.0 Hz, 3H), 1.89-1.70 (m, 2H); ESI-MS m/z calc. 396.10, found 397.25 (M+1)⁺. Retention time: 0.56 minutes; [□]$_D$=−42.40 (c=5 mg/2 mL MeOH). I-102.

Peak B (S)-4-(3-(2-chloro-5-(methylsulfonyl)phenyl)-1,4-oxazepan-4-yl)-6-methylpyrimidin-2-amine (71), 98+% ee by HPLC; heated (360K) ¹H NMR (400 MHz, DMSO-d6) δ 7.81 (dd, J=8.3, 2.3 Hz, 1H), 7.78 (d, J=2.2 Hz, 1H), 7.71 (d, J=8.3 Hz, 1H), 5.70 (s, 1H), 5.62 (dd, J=9.9, 4.9 Hz, 1H), 5.42 (s, 2H), 4.48 (d, J=15.2 Hz, 1H), 4.11 (dd, J=13.5, 4.9 Hz, 1H), 3.94-3.70 (m, 3H), 3.60 (ddd, J=12.0, 9.5, 4.7 Hz, 1H), 3.15 (s, 3H), 2.04 (s, 3H), 1.80 (dt, J=8.3, 4.2 Hz, 2H); ESI-MS m/z calc. 396.10, found 397.20 (M+1)⁺. Retention time: 0.55 minutes; [□]$_D$=+77.82 (c=5.5 mg/2 mL MeOH). I-103.

The following analog was prepared according to Synthetic Scheme 8:

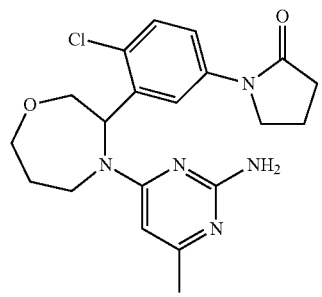

1-(3-(4-(2-amino-6-methylpyrimidin-4-yl)-1,4-oxazepan-3-yl)-4-chlorophenyl)pyrrolidin-2-one (72) I-119

¹H NMR (400 MHz, DMSO-d6) δ 7.76 (d, J=2.7 Hz, 1H), 7.45 (dd, J=8.7, 2.7 Hz, 1H), 7.39 (d, J=8.8 Hz, 1H), 5.59 (s, 1H), 5.42 (s, 3H), 4.63 (d, J=15.1 Hz, 1H), 4.12 (dd, J=13.4, 5.0 Hz, 1H), 3.91 (dt, J=11.5, 3.8 Hz, 1H), 3.81-3.73 (m, 2H), 3.72-3.52 (m, 3H), 2.47-2.40 (m, 2H), 2.08-2.01 (m, 2H), 2.00 (s, 3H), 1.80 (ddt, J=10.9, 7.5, 4.2 Hz, 2H); ESI-MS m/z calc. 401.16, found 402.0 (M+1)⁺. Retention time: 0.65 minutes.

Example 9

Synthetic Scheme 9: (+/−)-4-(2-(2,5-dimethoxyphenyl)azepan-1-yl)-6-methylpyrimidin-2-amine (77) I-25

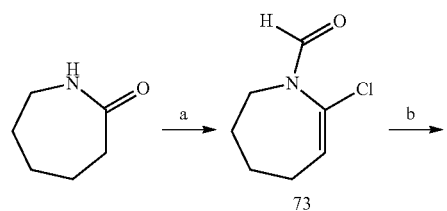

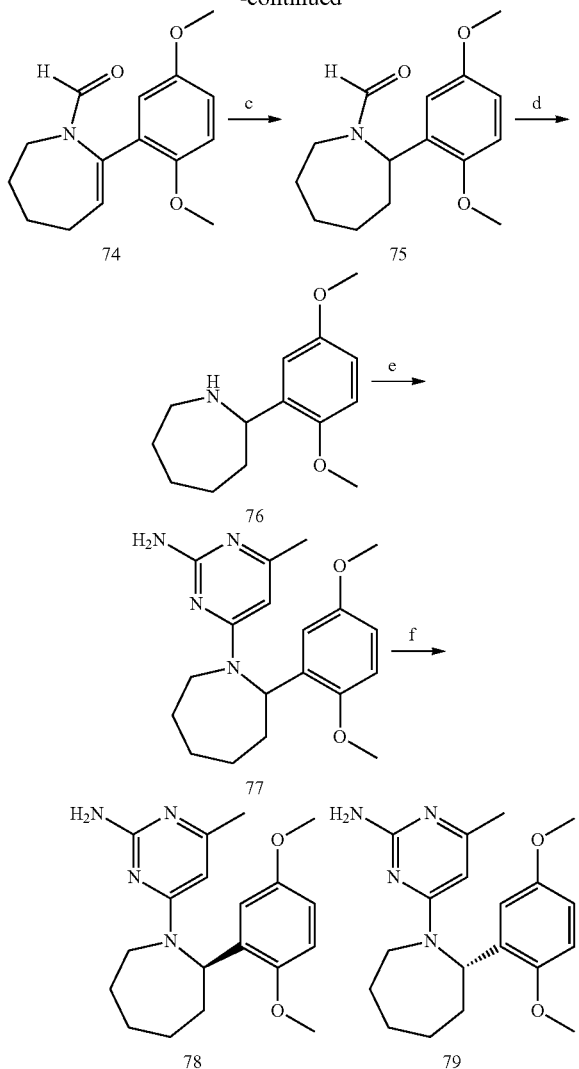

(a) DMF, POCl₃, CH₂Cl₂, 0° C. to 40° C.; (b) 2,5-dimethoxyphenylboronic acid, Pd(Ph₃P)₂Cl₂, DME, 50° C.; (c) Pd/C, HOAc, EtOAc, MeOH; (d) EtMgBr, THF, 0° C.; (e) 2-amino-4-chloro-6-methylpyrimidine, NMP, 150° C.; (f) SFC chiral separation Formation of 7-chloro-2,3,4,5-tetrahydro-1H-azepine-1-carbaldehyde (73)

A 3-neck 3 L round bottom flask equipped with overhead stirrer, temperature probe, addition funnel, nitrogen inlet and reflux condenser was charged with DMF (360 mL, 4.65 mol) in dichloromethane (500 mL) and stirred for 5 minutes and then cooled to 0° C. POCl₃ (220 mL, 2.36 mol) in dichloromethane (300 mL) was added over 60 minutes while maintaining the internal temperature below 7° C. The reaction mixture was warmed to 40° C. (observed colorless solution turn to pale orange) stirred at this temperature for 45 minutes. Added azepan-2-one (85 g, 751.2 mmol) in dichloromethane (450 mL) over 45 minutes under reflux (observed T max 45° C.). The resulting reaction mixture was stirred at this temperature for 3 h at which time HPLC-analysis revealed consumption of the starting material. The reaction mixture was cooled to ambient temperature, poured into crushed ice (3 L) and then allowed to ambient temperature over 12 h. The aqueous layer was separated, basified with solid K₂CO₃ until pH 9, allowed to warm to ambient temperature and stirred at this temperature for 18 h. The mixture was diluted with dichloromethane (2 L) and the organic layer was separated. Aqueous layer was extracted with dichloromethane (1 L) and the combined organic extracts were washed with water (100 mL), brine (200 mL), dried over Na₂SO₄, filtered and concentrated under reduced pressure. The residue was purified by silica gel plug using 0%→30% ethyl acetate/heptane-which contained 1% Et₃N, fractions which contained desired product were collected, concentrated under reduced pressure to afford 7-chloro-2,3,4,5-tetrahydroazepine-1-carbaldehyde (110 g, 92%) as a clear, colorless oil.

Formation of 7-(2,5-dimethoxyphenyl)-2,3,4,5-tetrahydro-1H-azepine-1-carbaldehyde (74)

Charged a 2-necked round bottom flask under nitrogen with 7-chloro-2,3,4,5-tetrahydroazepine-1-carbaldehyde, 73, (3.00 g, 18.80 mmol), (2,6-dimethoxyphenyl)boronic acid (4.45 g, 24.44 mmol), DME (24.67 mL) and bis(triphenylphosphine)palladium(II) chloride (0.53 g, 0.75 mmol). The reaction mixture was stirred overnight at 50° C. The mixture was diluted with water and dichloromethane. The layers were separated through a phase separator and the organic phase was concentrated in vacuo. The crude residue was purified by silica gel chromatography using a ISCO 12 g GOLD column; 10-100% EtOAc in heptane) as a pale yellow oil. ¹H NMR (300 MHz, DMSO-d6) δ 7.79 (s, 1H), 7.27 (t, J=8.4 Hz, 1H), 6.67 (d, J=8.4 Hz, 2H), 5.41 (t, J=6.1 Hz, 1H), 3.74 (s, 6H), 3.69-3.48 (m, 2H), 2.31-2.12 (m, 2H), 1.83-1.48 (m, 4H); ESI-MS m/z calc. 261.14, found 262.15 (M+1)⁺. Retention time: 0.84 minutes.

Formation of 2-(2,5-dimethoxyphenyl)azepane-1-carbaldehyde (75)

To a solution of 7-(2,6-dimethoxyphenyl)-2,3,4,5-tetrahydroazepine-1-carbaldehyde, 74, (3.00 g, 11.48 mmol) in MeOH (30 mL) and EtOAc (30 mL) was added HOAc (9 mL) and Pd/C (0.24 g, 2.30 mmol). The flask was charged with a hydrogen balloon after purging three times with vacuum. The mixture was stirred at room temperature overnight. The mixture was filtered through celite and evaporated the solvent. The resulting crude oil was used without further purification.

Formation of (+/−)-2-(2,5-dimethoxyphenyl)azepane (76)

To a solution of 2-(2,4-dimethoxyphenyl)azepane-1-carbaldehyde, 75, (1.80 g, 6.51 mmol) in THF (50 mL) was added ethylmagnesium bromide (2.21 g, 2.17 mL of 3 M solution in ether, 6.51 mmol) at 0° C. The mixture was stirred at 0° C. for 3 hours. The mixture was carefully quenched by addition of 2N NaOH solution and then extracted with EtOAc. The combined organic layers were washed with brine, and dried over MgSO₄, filtered and concentrated in vacuo. The crude residue was purified by ISCO eluting with methanol/dichloromethane gradient.

Formation of (R)-4-(2-(2,5-dimethoxyphenyl)azepan-1-yl)-6-methylpyrimidin-2-amine (78) and (S)-4-(2-(2,5-dimethoxyphenyl)azepan-1-yl)-6-methylpyrimidin-2-amine (79)

To a mixture of solids 4-chloro-6-methyl-pyrimidin-2-amine (0.15 g, 1.02 mmol) and 2-(2,4-dimethoxyphenyl)azepane, 76, (0.24 g, 1.02 mmol) in a vial was added EtOH (2 mL). The vial was placed on the hot plate and heated at 180° C. without cover for 2 hrs. The crude residue was purified by silica gel chromatography 40 g ISCO column eluting with 20% MeOH-dichloromethane/dichloromethane gradient to afford 32 mg of the desired product: ¹H NMR (300 MHz, DMSO-d6) δ 7.19 (s, 2H), 6.91 (dd, J=36.7, 8.5 Hz, 1H), 6.61 (s, 1H), 6.52-6.36 (m, 2H), 5.70 (s, 1H), 4.78 (dd, J=67.0, 11.7 Hz, 2H), 3.88 (s, 3H), 3.73 (d, J=2.4 Hz, 5H), 3.62-3.14 (m, 6H), 2.18 (d, J=39.5 Hz, 5H), 1.95-1.70 (m, 5H), 1.34 (dd, J=49.7, 10.8 Hz, 3H); ESI-MS m/z calc. 342.21, found 343.32 (M+1)⁺. Retention time: 0.72 minutes.

The racemate (4.0 g) was submitted for SFC separation (Column: IC, 4.6×100 mm IC, 20×250 mm Mobile phase: 40% EtOH (5 mM Ammonia), 60% CO2 40% EtOH (5 mM Ammonia), 60% CO₂ to afford:

Peak A: 1.61 grams of (R)-4-(2-(2,5-dimethoxyphenyl) azepan-1-yl)-6-methylpyrimidin-2-amine (78): ee=98%; [α]_D (c=1.0, MeOH) +111.98; ¹H NMR (300 MHz, DMSO-d6) δ 6.94 (br, 1H), 6.75 (br, 1H), 6.48 (s, 1H), 5.89 (s, 3H), 4.76 (brs, 1H), 3.83 (s, 3H), 3.64 (s, 3H), 3.32 (brs, 2H), 1.94 (br, 3H), 1.81-0.95 (m, 8H); ESI-MS m/z calc. 342.21, found 343.27 (M+1)⁺. Retention time: 0.74 minutes. I-40.

Peak B: 1.21 grams of (S)-4-(2-(2,5-dimethoxyphenyl) azepan-1-yl)-6-methylpyrimidin-2-amine (79): ee=96%; [α]_D (c=1.0, MeOH) −147.32; ¹H NMR (300 MHz, DMSO-d6) δ 7.56-7.10 (br, 2H), 6.89 (br, 2H), 6.64-6.39 (m, 1H), 5.86-5.65 (m, 1H), 4.83 (br, 1H), 4.05 (d, J=15.3 Hz, 0.5H), 3.83 (s, 3H), 3.67 (s, 3H), 3.59-3.41 (m, 1.5H), 2.22 (d, J=37.7 Hz, 3H), 2.00-0.94 (m, 8H); ESI-MS m/z calc. 342.21, found 343.32 (M+1)⁺. Retention time: 0.76 minutes. I-41.

The following analogs were prepared according to Synthetic Scheme 9:

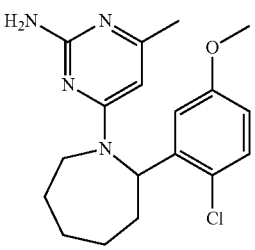

80

(+/−)-4-(2-(2-chloro-5-methoxyphenyl)azepan-1-yl)-6-methylpyrimidin-2-amine (80) I-117

¹H NMR (300 MHz, DMSO-d6) δ 7.77 (s, 1H), 7.52-7.28 (m, 2H), 6.90 (ddd, J=20.8, 8.8, 2.8 Hz, 1H), 6.58 (s, OH), 5.82-5.46 (m, 1H), 5.03-4.69 (m, 1H), 4.13 (d, J=15.2 Hz, 1H), 3.58-3.25 (m, 12H), 2.28 (s, 2H), 2.04-1.08 (m, 9H); ESI-MS m/z calc. 346.16, found 347.17 (M+1)⁺. Retention time: 0.72 minutes.

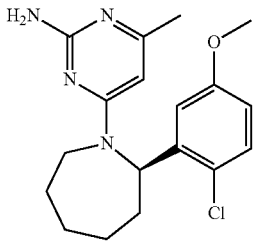

81

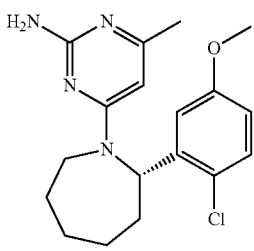

82

(R)-4-(2-(2-chloro-5-methoxyphenyl)azepan-1-yl)-6-methylpyrimidin-2-amine (81) I-135 and (S)-4-(2-(2-chloro-5-methoxyphenyl)azepan-1-yl)-6-methyl-pyrimidin-2-amine (81) I-136

4-[2-(2-chloro-5-methoxy-phenyl)azepan-1-yl]-6-methyl-pyrimidin-2-amine (450 mg, 1.289 mmol) was submitted for SFC separation. SFC conditions: Column: IC, 20×250 mm; Mobile phase: 30% MeOH (5 mM Ammonia), 70% CO₂; Flow: 75 mL/min; Concentrations: ~40 mg/mL (MeOH); Injection Volume: 500 µL; Wavelength: 214 nm; Method Type Isocratic Peak A: [α]$_D$ (c=0.5, MeOH) +74.56; 99.4% ee (R)-4-[2-(2-chloro-5-methoxy-phenyl)azepan-1-yl]-6-methyl-pyrimidin-2-amine (81): ¹H NMR (300 MHz, DMSO-d6) δ 7.36 (d, J=8.8 Hz, 1H), 6.85 (d, J=8.2 Hz, 1H), 6.62 (s, 1H), 6.07 (br, 2H), 4.78 (brs, 1H), 3.70 (s, 3H), 3.29 (br, 2H), 1.99 (s, 3H), 1.88-1.09 (m, 8H); ESI-MS m/z calc. 346.16, found 347.2 (M+1)⁺. Retention time: 0.72 minutes. I-135.

Peak B: [α]$_D$ (c=0.5, MeOH) −76.80; 99% ee (S)-4-[2-(2-chloro-5-methoxy-phenyl)azepan-1-yl]-6-methyl-pyrimidin-2-amine (82) (200 mg, 89%): ¹H NMR (300 MHz, DMSO-d6) δ 7.78 (s, 1H), 7.39 (m, 2H), 7.01-6.77 (m, 1H), 6.62 (d, 3.0 Hz, 1H), 6.49 (s, 0.5H), 5.72 (dd, J=12.5, 5.1 Hz, 0.5H), 5.55 (s, 0.5H), 5.07-4.89 (m, 0.5H), 4.79 (d, J=13.8 Hz, 0.5H), 4.13 (d, J=15.3 Hz, 0.5H), 3.73 (d, J=3.3 Hz, 3H), 3.57 (t, J=11.9 Hz, 1H), 3.18 (s, 1H), 2.28 (s, 1.5H), 2.15 (s, 1.5H), 2.05-0.97 (m, 8H); ESI-MS m/z calc. 346.16, found 347.15 (M+1)⁺. Retention time: 0.72 minutes. I-136.

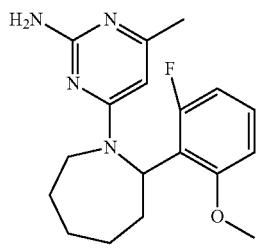 [SMILES: COc1cccc(F)c1C1CCCCCN1c1cc(C)nc(N)n1]

(+/−)-4-[2-(2-fluoro-6-methoxy-phenyl)azepan-1-yl]-6-methyl-pyrimidin-2-amine (83) I-50

¹H NMR (300 MHz, DMSO-d6) δ 7.44-6.59 (m, 5H), 5.68 (s, 1H), 5.04 (d, J=11.0 Hz, 0.5H), 4.67 (d, J=14.2 Hz, 0.5H), 3.94 (s, 3H), 3.60-3.10 (m, 2H), 2.29-1.69 (m, 8H), 1.53-0.87 (m, 3H); ESI-MS m/z calc. 330.19, found 331.29 (M+1)⁺. Retention time: 0.72 minutes.

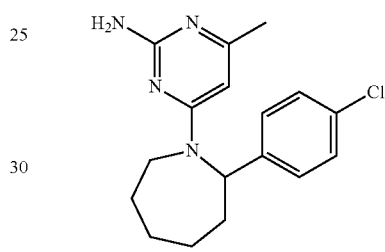

(+/−)-4-[2-(4-chlorophenyl)azepan-1-yl]-6-methyl-pyrimidin-2-amine (I-43)

¹H NMR (300 MHz, DMSO-d6) δ 7.37 (d, J=8.2 Hz, 2H), 7.28 (d, J=8.3 Hz, 2H), 6.84 (s, 2H), 5.81 (s, 1H), 4.76 (br, 1H), 4.00-2.99 (m, 2H), 2.20 (s, 3H), 1.95-0.97 (m, 8H); ESI-MS m/z calc. 316.15, found 317.24 (M+1)⁺. Retention time: 0.72 minutes.

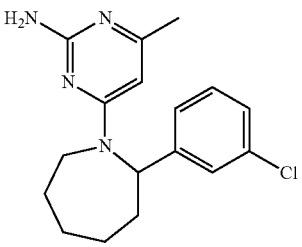 [SMILES: Cc1cc(N2CCCCCC2c2cccc(Cl)c2)nc(N)n1]

(+/−)-4-[2-(3-chlorophenyl)azepan-1-yl]-6-methyl-pyrimidin-2-amine (I-44)

¹H NMR (300 MHz, DMSO-d6) δ 7.78-7.12 (m, 5H), 6.29 (s, 2H), 6.10-5.47 (m, 1H), 4.43-3.61 (m, 1H), 3.34-2.92 (m, 2H), 2.14 (s, 3H), 1.98-0.89 (m, 8H); ESI-MS m/z calc. 316.15, found 317.19 (M+1)⁺. Retention time: 0.72 minutes.

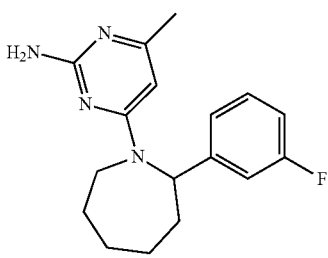 [SMILES: Cc1cc(N2CCCCCC2c2cccc(F)c2)nc(N)n1]

(+/−)-4-[2-(3-fluorophenyl)azepan-1-yl]-6-methyl-pyrimidin-2-amine I-29 high temperature (360 K) $^1$H NMR (400 MHz, DMSO-d6) δ 7.31 (dd, J=14.4, 7.7 Hz, 1H), 7.06 (d, J=7.8 Hz, 1H), 6.95 (dd, J=14.0, 5.8 Hz, 2H), 5.74 (s, 1H), 5.43 (br s, 3H), 4.07 (br s, 1H), 3.16 (dd, J=13.4, 11.5 Hz, 1H), 2.46-2.35 (m, 1H), 2.04 (s, 3H), 1.88-1.62 (m, 4H), 1.62-1.50 (m, 1H), 1.41-1.21 (m, 2H). ESI-MS m/z calc. 300.18, found 301.21 (M+1)$^+$. Retention time: 0.64 minutes.

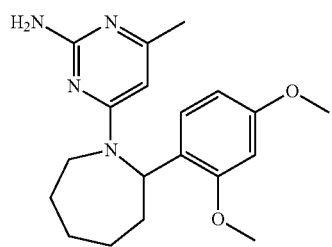 [SMILES: COc1ccc(C2CCCCCN2c2cc(C)nc(N)n2)c(OC)c1]

(+/−)-4-[2-(2,4-dimethoxyphenyl)azepan-1-yl]-6-methyl-pyrimidin-2-amine (84) I-51

$^1$H NMR (300 MHz, DMSO-d6) δ 7.19 (s, 2H), 6.91 (dd, J=36.7, 8.5 Hz, 1H), 6.61 (s, 1H), 6.52-6.36 (m, 2H), 5.70 (s, 1H), 4.78 (dd, J=67.0, 11.7 Hz, 2H), 3.88 (s, 3H), 3.73 (d, J=2.4 Hz, 5H), 3.62-3.14 (m, 6H), 2.18 (d, J=39.5 Hz, 5H), 1.95-1.70 (m, 5H), 1.34 (dd, J=49.7, 10.8 Hz, 3H); ESI-MS m/z calc. 342.20, found 343.32 (M+1)$^+$. Retention time: 0.72 minutes.

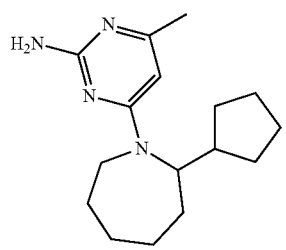 [SMILES: Cc1cc(N2CCCCCC2C2CCCC2)nc(N)n1]

(+/−)-4-(2-cyclopentylazepane-1-yl)-6-methylpyrimidin-2-amine I-9

A suspension of 4-chloro-6-methyl-pyrimidin-2-amine (0.094 g, 0.657 mmol), 2-cyclopentylazepane (0.100 g, 0.598 mmol) and $^i$Pr$_2$NEt (0.230 mL, 1.320 mmol) in IPA (0.6 mL) was sealed in a microwave tube and irradiated at 160° C. for 2 hours. The mixture was concentrated in vacuo and purified by reverse phase chromatography (0.1% TFA/acetonitrile). The material was converted to HCl salt to afford 46 mg of desired product: $^1$H NMR (400 MHz, MeOD) δ 6.31 (2 s, 1H), 5.06-4.91 (m, 1H), 4.48-3.34 (m, 2H), 2.35-2.27 (m, 3H), 2.27-2.15 (m, 1H), 2.02 (qd, J=16.7, 8.3 Hz, 1H), 1.92-1.15 (m, 14H), 1.14-0.96 (m, 1H); ESI-MS m/z calc. 274.22, found 275.18 (M+1)$^+$. Retention time: 2.84 minutes.

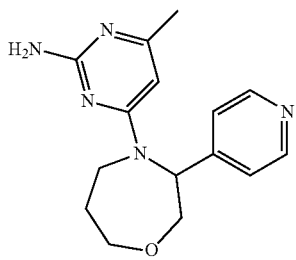 [SMILES: Cc1cc(N2CCCOCC2c2ccncc2)nc(N)n1]

(+/−)-4-methyl-6-[2-(4-pyridyl)azepan-1-yl]pyrimidin-2-amine I-35

ESI-MS m/z calc. 283.18, found 284.22 (M+1)$^+$. Retention time: 2.14 minutes.

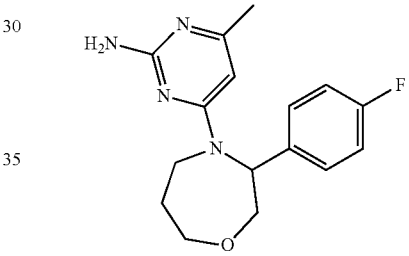

(+/−)-4-[2-(4-fluorophenyl)azepan-1-yl]-6-methyl-pyrimidin-2-amine I-34 high temperature (360 K) $^1$H NMR (400 MHz, DMSO-d6) δ 7.28-7.21 (m, 2H), 7.05 (m, 2H), 5.72 (s, 1H), 5.65 (s, 2H), 5.42 (m, 3H), 4.03 (s, 1H), 3.15 (dd, J=13.3, 11.6 Hz, 1H), 2.44-2.34 (m, 1H), 2.03 (s, 3H), 1.90-1.65 (m, 4H), 1.63-1.48 (m, 1H), 1.42-1.21 (m, 2H). ESI-MS m/z calc. 300.18, found 301.22 (M+1)$^+$. Retention time: 2.97 minutes.

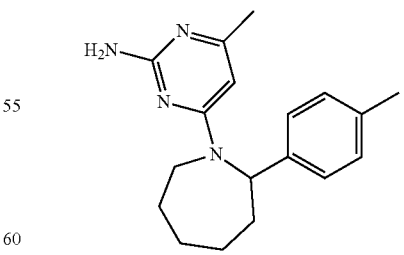

(+/−)-4-methyl-6-[2-(p-tolyl)azepan-1-yl]pyrimidin-2-amine I-33 high temperature (360 K) $^1$H NMR (400 MHz, DMSO-d6) δ 7.12-7.04 (m, 4H), 5.70 (s, 1H), 5.65 (s, 2H), 5.39 (s, 1H), 5.39-5.20 (m, 1H), 4.08 (s, 1H), 3.18-3.07 (m, 1H), 2.42-2.32 (m, 1H), 2.24 (s, 3H), 2.02 (s, 3H), 1.88-1.66 (m, 4H), 1.63-1.50 (m, 1H), 1.31 (m, 2H). ESI-MS m/z calc. 296.20, found 297.25 (M+1)⁺. Retention time: 3.07 minutes.

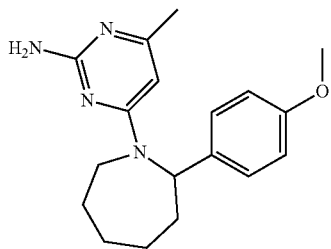 [SMILES: COc1ccc(C2CCCCCN2c2cc(C)nc(N)n2)cc1]

(+/−)-4-[2-(4-methoxyphenyl)azepan-1-yl]-6-methyl-pyrimidin-2-amine I-23 high temperature (360 K) $^1$H NMR (400 MHz, DMSO-d6) δ 7.12-7.04 (m, 4H), 5.70 (s, 1H), 5.65 (s, 2H), 5.39 (s, 1H), 5.39-5.20 (m, 1H), 4.08 (s, 1H), 3.18-3.07 (m, 1H), 2.42-2.32 (m, 1H), 2.24 (s, 3H), 2.02 (s, 3H), 1.88-1.66 (m, 4H), 1.63-1.50 (m, 1H), 1.31 (m, 2H); ESI-MS m/z calc. 296.20, found 297.25 (M+1)⁺. Retention time: 3.07 minutes.

Example 10

Synthetic Scheme 10: (+/−)-4-[2-(2,5-dimethoxy-4-pyridyl)azepan-1-yl]-6-methyl-pyrimidin-2-amine (88) I-116

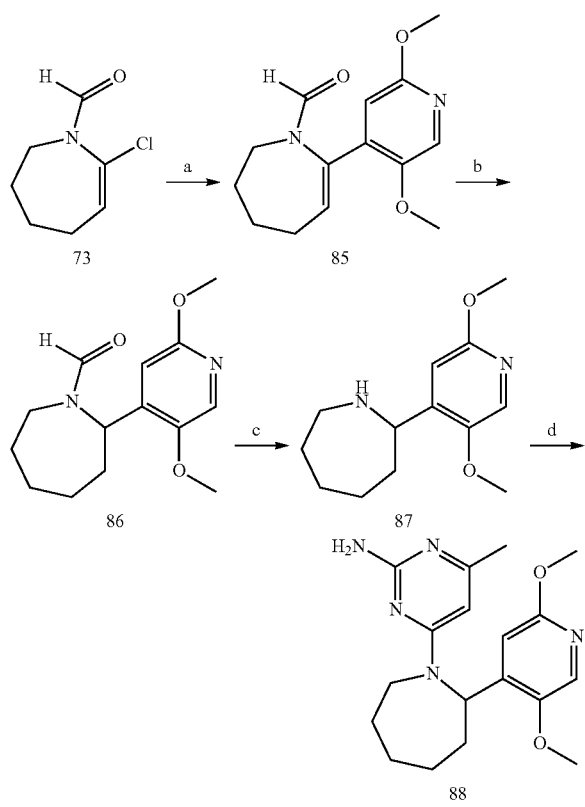

(a) (2,5-dimethoxy-4-pyridyl)boronic acid, Pd(Ph₃P)₂Cl₂, NaHCO₃, DME, water, 60° C.; (c) Pd/C, formic acid, EtOAc, MeOH; (d) nBuLi, THF, −78° C.; (e) 2-amino-4-chloro-6-methylpyrimidine, NMP, 150° C.; (f) SFC chiral separation Formation of 7-(2,5-dimethoxy-4-pyridyl)-2,3,4,5-tetrahydroazepine-1-carbaldehyde (85)

A 2-necked rb flask under nitrogen was charged with 7-chloro-2,3,4,5-tetrahydroazepine-1-carbaldehyde, 73, (0.79 g, 4.95 mmol), (2,5-dimethoxy-4-pyridyl)boronic acid (1.00 g, 5.46 mmol) in DME (10 mL), followed by NaHCO₃ (8 mL of 1.2 M solution, 9.6 mmol) and bis(triphenylphosphine) palladium(II) chloride (0.14 g, 0.20 mmol). Stirred overnight at 60° C. Added water and dichloromethane. The layers were separated through a phase separator and the organics concentrated in vacuo after a second extraction. Purification by silica gel chromatography (40 g GOLD column; 10-100% EtOAc/heptanes gradient) afforded 1 g (47%) of desired product: $^1$H NMR (300 MHz, CDCl₃) δ 7.94 (s, 1H), 7.75 (s, 1H), 7.28 (d, J=1.1 Hz, 1H), 6.64 (s, 1H), 3.91 (s, 3H), 3.84 (s, 3H), 3.80-3.69 (m, 2H), 2.43-2.29 (m, 2H), 1.87 (dd, J=8.5, 3.8 Hz, 2H), 1.71-1.64 (m, 2H); ESI-MS m/z calc. 262.13, found 263.07 (M+1)⁺. Retention time: 0.75 minutes.

Formation of 2-(2,5-dimethoxy-4-pyridyl)azepane-1-carbaldehyde (86)

To a solution of 7-(2,5-dimethoxy-4-pyridyl)-2,3,4,5-tetrahydroazepine-1-carbaldehyde, 85, (1.0 g, 3.8 mmol) in MeOH (20 mL) and EtOAc (20 mL) was added formic acid (1.7 g, 37.0 mmol) and Pd/C (40 mg, 0.4 mmol) under N₂ atmosphere. The reaction mixture was then charged with H₂ (balloon) and stirred at room temperature over night. Filtered through celite, the solvent was evaporated. the residue was purified by silica gel column (40 g) in ISCO eluting 0% to 50% EtOAc/heptanes gradient. The desired fractions were collected and evaporated to afford 1.0 grams (51%) of desired product: ESI-MS m/z calc. 264.15, found 265.14 (M+1)⁺. Retention time: 0.72 minutes.

Formation of 2-(2,5-dimethoxy-4-pyridyl)azepane (87)

To a solution of 2-(2,5-dimethoxy-4-pyridyl)azepane-1-carbaldehyde, 86, (1.00 g, 3.78 mmol) in THF (20 mL) was added n-butyllithium (5.0 mL of 1.6 M, 8.00 mmol) at −78° C. The mixture was stirred at −78° C. for 2 hours. The reaction mixture was carefully quenched by the addition of MeOH. To the mixture was added 2N HCl solution until pH=2 was achieved. The resulting solution was then basified by adding 6N NaOH until pH=10 was achieved. The aqueous solution was extracted with EtOAc and the combined organic layers were washed with brine, dried over MgSO₄, filtered and concentrated in vacuo to afford 230 mg of desired product: ESI-MS m/z calc. 236.15, found 237.15 (M+1)⁺. Retention time: 0.58 minutes.

Formation of 4-[2-(2,5-dimethoxy-4-pyridyl)azepan-1-yl]-6-methyl-pyrimidin-2-amine (88) I-116

To a mixture of solids 4-chloro-6-methyl-pyrimidin-2-amine (0.12 g, 0.81 mmol) and 2-(2,5-dimethoxy-4-pyridyl) azepane (0.23 g, 0.90 mmol) in a vial was added EtOH (2 mL). The vial was placed on the hot plate and heated at 160° C. without cover for 2 hours. The crude solid was purified by silica gel chromatography (40 g) in ISCO eluting with 20% MeOH/dichloromethane—dichloromethane to afford 6.5 mg of desired product: ¹H NMR (300 MHz, DMSO-d6) δ 7.85 (s, 1H), 7.56 (br, 2H), 6.48 (s, 0.5H), 6.30 (s, 0.5H), 5.69 (s, 1H), 4.81 (m, 1H), 3.88 (s, 3H), 3.75 (s, 3H), 3.61-3.25 (m, 2H), 2.28 (s, 3H), 1.99-1.07 (m, 8H); ESI-MS m/z calc. 343.20, found 344.16 (M+1)⁺. Retention time: 0.65 minutes.

The following analogs were prepared according to Synthetic Scheme 10:

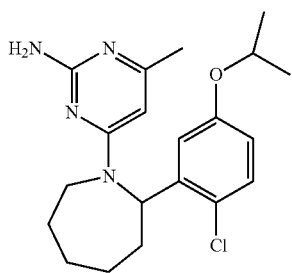

4-[2-(2-chloro-5-isopropoxy-phenyl)azepan-1-yl]-6-methyl-pyrimidin-2-amine (89) I-104

¹H NMR (300 MHz, DMSO-d6) δ 7.78 (s, 1H), 7.50-7.25 (m, 2H), 6.88 (ddd, J=20.5, 8.8, 2.8 Hz, 1H), 6.68-6.39 (m, 1H), 5.81-5.46 (m, 1H), 5.09-4.72 (m, 1H), 4.56 (m, 1H), 4.13 (d, J=14.6 Hz, 1H), 3.87-3.46 (m, 1H), 2.22 (s, 3H), 2.05-1.34 (m, 8H), 1.23 (d, J=5.4 Hz, 6H); ESI-MS m/z calc. 374.19, found 375.07 (M+1)⁺. Retention time: 0.76 minutes.

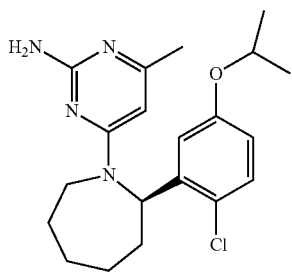

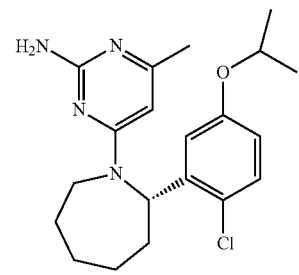

(R)-4-[2-(2-chloro-5-isopropoxy-phenyl)azepan-1-yl]-6-methyl-pyrimidin-2-amine (90) I-108

SFC conditions: column: IC, 4.6×00 mm IC, 20×250 mm; Mobile phase: 40% EtOH (5 mM Ammonia), 60% CO₂.

Peak A: [α]_D (c=0.5, MeOH) +58.56; 99% ee; (R)-4-[2-(2-chloro-5-isopropoxy-phenyl)azepan-1-yl]-6-methyl-pyrimidin-2-amine (90): ¹H NMR (300 MHz, DMSO-d6) δ 7.31 (s, 1H), 6.82 (d, J=8.9 Hz, 1H), 6.54 (s, 1H), 5.76 (br, 3H), 5.00-4.37 (m, 3H), 4.01-3.81 (m, 1H), 1.95 (s, 3H), 1.86-1.29 (m, 8H), 1.21 (m, 6H); ESI-MS m/z calc. 374.19, found 375.07 (M+1)⁺. Retention time: 0.75 minutes. I-108.

Peak B: [α]_D (c=0.5, MeOH) −70.52; 98.4% ee; (S)-4-[2-(2-chloro-5-isopropoxy-phenyl)azepan-1-yl]-6-methyl-pyrimidin-2-amine (91): ¹H NMR (300 MHz, DMSO-d6) δ 7.32 (brs, 1H), 6.83 (brs, 1H), 6.55 (s, 1H), 5.83 (br, 3H), 4.96-4.43 (m, 2H), 4.02 (br, 2H), 3.17 (s, 3H), 1.95 (s, 3H), 1.86-1.31 (m, 8H), 1.26-1.15 (m, 6H); ESI-MS m/z calc. 374.19, found 375.12 (M+1)⁺. Retention time: 0.77 minutes. I-109.

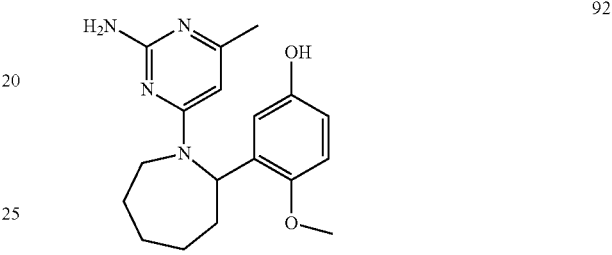

3-[1-(2-amino-6-methyl-pyrimidin-4-yl)azepan-2-yl]-4-methoxy-phenol (92) I-107

¹H NMR (300 MHz, DMSO-d6) δ 8.99 (br, 1H), 7.79 (s, 1H), 7.54 (s, 1H), 6.85 (dd, J=20.5, 8.7 Hz, 1H), 6.69-6.57 (m, 1H), 6.53-6.43 (m, 1H), 6.31 (d, J=2.8 Hz, 0.5H), 5.77 (s, 0.5H), 5.70 (s, 1H), 5.09-4.57 (m, 1H), 4.00 (m, 1H), 3.82 (s, 3H), 3.49 (m, 1H), 2.15 (s, 3H), 1.98-1.01 (m, 8H); ESI-MS m/z calc. 328.19, found 329.17 (M+1)⁺. Retention time: 0.67 minutes.

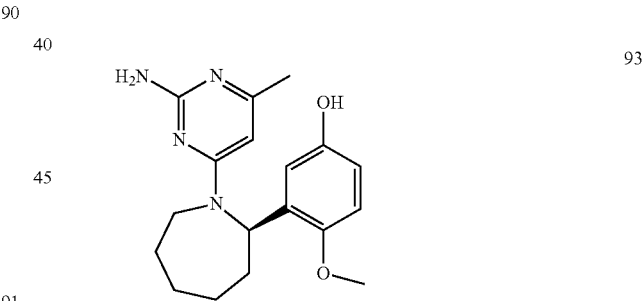

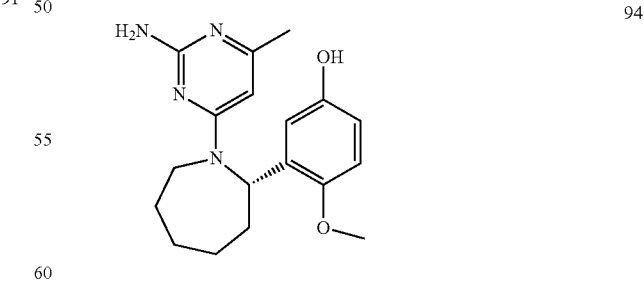

(R)-3-[1-(2-amino-6-methyl-pyrimidin-4-yl)azepan-2-yl]-4-methoxy-phenol (93) I-127

SFC conditions: column: IC, 4.6×100 mm IC, 20×250 mm; Mobile phase: 30% MeOH (5 mM Ammonia), 70% CO₂.

Peak A: [α]_D (c=0.5, MeOH) +100.16; 87.6% ee

3-[1-(2-amino-6-methyl-pyrimidin-4-yl)azepan-2-yl]-4-methoxy-phenol (93): ¹H NMR (300 MHz, DMSO-d6) δ 8.84 (br, 1H), 6.81 (s, 1H), 6.55 (s, 1H), 6.39 (s, 1H), 5.80 (s, 2H), 5.32 (s, 1H), 4.74 (s, 1H), 3.79 (m, 3H), 3.30 (m, 2H), 1.92 (s, 3H), 1.82-0.64 (m, 8H); ESI-MS m/z calc. 328.19, found 329.25 (M+1)⁺. Retention time: 0.65 minutes. I-127.

Peak B: [α]_D (c=0.5, MeOH) −98.32; 94% ee

3-[1-(2-amino-6-methyl-pyrimidin-4-yl)azepan-2-yl]-4-methoxy-phenol (94): ¹H NMR (300 MHz, DMSO-d6) δ 8.85 (br, 1H), 6.82 (s, 1H), 6.56 (s, 1H), 6.40 (s, 1H), 5.80 (s, 2H), 5.32 (s, 1H), 4.74 (s, 1H), 3.79 (s, 3H), 3.30 (m, 2H), 1.92 (s, 3H), 1.83-0.84 (m, 8H); ESI-MS m/z calc. 328.19, found 329.1 (M+1)⁺. Retention time: 0.65 minutes. I-128.

95

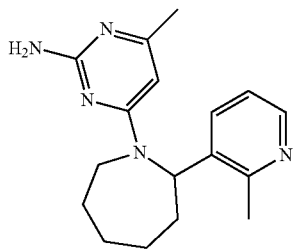

(+/−)-4-methyl-6-(2-(2-methylpyridin-3-yl)azepan-1-yl)pyrimidin-2-amine (95) I-24

¹H NMR (400 MHz, DMSO-d6) δ 8.30 (d, J=4.6 Hz, 1H), 7.42 (d, J=7.9 Hz, 1H), 7.12 (dd, J=7.8, 4.7 Hz, 1H), 6.94 (s, 2H), 6.18-6.00 (m, 1H), 5.38 (s, 1H), 4.29 (s, 2H), 3.63 (s, 1H), 2.63 (s, 3H), 2.32-2.22 (m, 1H), 2.21 (s, 3H), 2.00-1.73 (m, 3H), 1.56-1.28 (m, 4H); ESI-MS m/z calc. 297.2, found 298.2 (M+1)⁺. Retention time: 0.49 minutes.

96

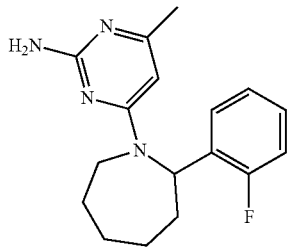

4-(2-(2-fluorophenyl)azepan-1-yl)-6-methylpyrimidin-2-amine (96) I-36

¹H NMR (300 MHz, DMSO-d6) δ 7.28 (m, 2H), 7.20-7.06 (m, 3H), 6.30 (s, 2H), 6.20-5.62 (m, 1H), 3.48-3.07 (m, 2H), 2.10 (brs, 3H), 1.98-1.18 (m, 8H); ESI-MS m/z calc. 300.2, found 301.2 (M+1)⁺. Retention time: 0.7 minutes.

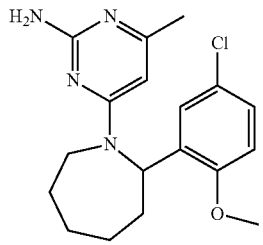 [SMILES: COc1ccc(Cl)cc1C1CCCCCN1c1cc(C)nc(N)n1]

4-(2-(5-chloro-2-methoxyphenyl)azepan-1-yl)-6-methylpyrimidin-2-amine I-21

¹H NMR (300 MHz, DMSO-d6) δ 7.46 (brs, 1H), 7.37-7.23 (m, 2H), 7.17-6.96 (m, 2H), 6.87 (s, 0.5H), 6.43 (s, 0.5H), 5.84-5.59 (m, 1H), 4.96 (d, J=10.2 Hz, 1H), 4.06 (d, J=15.4 Hz, 1H), 3.88 (d, J=15.1 Hz, 3H), 3.55 (dt, J=42.6, 12.7 Hz, 1H), 2.20 (d, J=38.7 Hz, 3H), 2.01-1.03 (m, 8H); ESI-MS m/z calc. 346.16, found 347.23 (M+1)⁺. Retention time: 0.73 minutes.

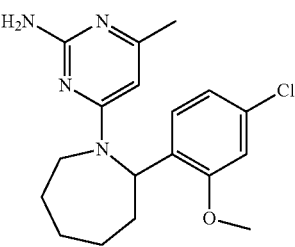

4-(2-(4-chloro-2-methoxyphenyl)azepan-1-yl)-6-methylpyrimidin-2-amine I-20

¹H NMR (300 MHz, DMSO-d6) δ 7.44-6.85 (m, 6H), 6.39 (s, 0.5H), 5.62 (s, 0.5H), 4.81 (dd, J=71.0, 12.5 Hz, 1H), 4.18-3.80 (m, 4H), 3.68-3.23 (m, 4H), 2.18 (d, J=39.0 Hz, 4H), 2.01-1.07 (m, 7H); ESI-MS m/z calc. 346.16, found 347.23 (M+1)⁺. Retention time: 0.74 minutes.

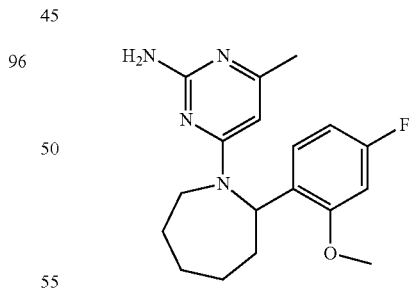

4-(2-(4-fluoro-2-methoxyphenyl)azepan-1-yl)-6-methylpyrimidin-2-amine I-22

¹H NMR (400 MHz, DMSO-d6) δ 6.98 (dd, J=8.4, 6.9 Hz, 1H), 6.84 (dd, J=11.2, 2.5 Hz, 1H), 6.61 (td, J=8.5, 2.5 Hz, 1H), 5.56 (s, 1H), 5.35 (s, 2H), 5.14 (s, 1H), 4.38 (s, 1H), 3.36-3.26 (m, 1H), 2.39-2.29 (m, 1H), 1.98 (s, 3H), 1.81 (d, J=47.9 Hz, 3H), 1.69-1.44 (m, 2H), 1.40-1.18 (m, 2H); ESI-MS m/z calc. 330.2, found 331.2 (M+1)⁺. Retention time: 0.67 minutes.

Example 11

Synthetic Scheme 11: (+/−)-4-(2-(2-methoxy-4-(methylsulfonyl)phenyl)azepan-1-yl)-6-methylpyrimidin-2-amine (100) I-88

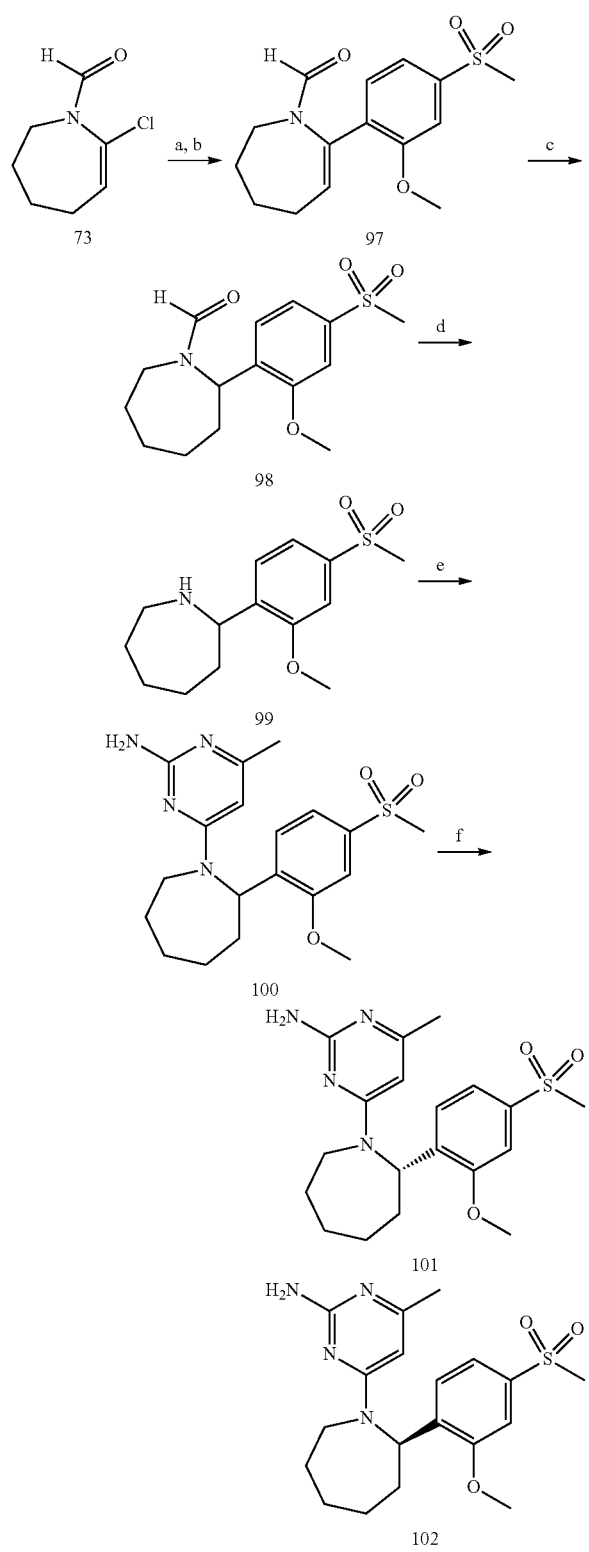

(a) 1-bromo-2-methoxy-4-methylsulfonyl-benzene, bis(pinocalatodiboron), PdCl$_2$(Ph$_3$P)$_2$, KOAc, dioxane, water, 85° C.; (b) (c) Pd/C, formic acid, EtOAc, MeOH; (d) nBuLi, THF, −78° C.; (e) 2-amino-4-chloro-6-methylpyrimidine, NMP, 150° C.; (f) SFC chiral separation

Formation of 7-(2-methoxy-4-methylsulfonyl-phenyl)-2,3,4,5-tetrahydroazepine-1-carbaldehyde (97)

Step-1: To a solution of 1-bromo-2-methoxy-4-methylsulfonyl-benzene (1.00 g, 3.77 mmol) in dioxane (50 mL) was added bis(pinocalatodiboron) (1.44 g, 5.66 mmol), potassium acetate (1.11 g, 11.32 mmol). The mixture was purged with nitrogen for 15 minutes and added dichloro-bis (triphenylphosphoranyl)-palladium (0.27 g, 0.37 mmol) was added. The reaction was heated to 85° C. for 18 hours. The mixture was diluted with EtOAc and filtered through celite washing with EtOAc (60 mL). The organic phase was concentrated in vacuo. The resulting dark brown solid was used without further purification.

Step-2: The above crude product was dissolved in DME (30 mL). 7-chloro-2,3,4,5-tetrahydroazepine-1-carbaldehyde, 73, (0.60 g, 3.77 mmol) was added followed by NaHCO$_3$ (6.3 mL of 1.2 M solution, 7.54 mmol). The mixture was bubbled with nitrogen, and Pd(dppf)Cl$_2$ catalyst was added. The flask was covered and heated at 80° C. for 12 hours. The residue was purified by silica gel chromatography using (40 g ISCO column) 20% MeOH-dichloromethane/dichloromethane gradient. The desired fractions were collected and evaporated. The fractions were collected and used for the next step directly.

Formation of 2-(2-methoxy-4-methylsulfonyl-phenyl)azepane-1-carbaldehyde (98)

To a solution of 7-(2-methoxy-4-methylsulfonyl-phenyl)-2,3,4,5-tetrahydroazepine-1-carbaldehyde, 97, (1.00 g, 3.23 mmol) in MeOH (10 mL) and EtOAc (10 mL) was added acetic acid (1 mL). Under an atmosphere of nitrogen, 10% Pd/C (10 mol %) was added. The reaction mixture was purged 3 times with hydrogen and then stirred under an atmosphere of hydrogen for 14 hours. LCMS indicated poor conversion to desired product. The mixture was filtered through celite and the solvent was partially concentrated in vacuo. The above procedure was repeated, except using formic acid to replace acetic acid. After overnight stirring, the starting material was converted to the desired product. The mixture was filtered through celite and the filtrate was concentrated in vacuo. The resulting residue was purified by silica gel chromatography (40 g ISCO column) eluting with EtOAc/heptanes (0-75%) gradient to afford 760 mg of desired product: $^1$H NMR (300 MHz, CDCl$_3$) δ 8.20 (s, s, 1H), 7.63-7.38 (m, 2H), 7.35-7.16 (m, 1H), 5.41 (dd, J=12.3, 4.7 Hz, 0.6H), 5.00 (dd, J=11.7, 5.6 Hz, 0.4H), 4.35 (d, J=13.7 Hz, 0.4H), 3.96 (s, 3H), 3.91-3.79 (m, 0.6H), 3.56 (dd, J=14.9, 11.3 Hz, 0.6H), 3.06 (s, 3H), 3.01-2.85 (m, 0.4H), 2.46 (m, 1H), 2.19-1.17 (m, 7H).

Formation of 2-(2-methoxy-4-methylsulfonyl-phenyl)azepane (99)

To a solution of 2-(2-methoxy-4-methylsulfonyl-phenyl)azepane-1-carbaldehyde, 98, (0.76 g, 2.44 mmol) in MeOH (20 mL) was added HCl (10 mL of 12 M, 120 mmol). The mixture was heated at 100° C. for 4 hours. The solvent was concentrated in vacuo to afford 600 mg of desired product that was used without further purification: $^1$H NMR (300

MHz, DMSO-d6) δ 9.49 (br, 2H), 7.82 (d, J=8.0 Hz, 1H), 7.65-7.48 (m, 2H), 4.59 (t, J=9.2 Hz, 1H), 3.97 (s, 3H), 3.27 (s, 3H), 3.19-3.08 (m, 2H), 2.34-1.51 (m, 8H); ESI-MS m/z calc. 283.12, found 284.27 (M+1)⁺. Retention time: 0.56 minutes.

Formation of (+/−)-4-[2-(2-methoxy-4-methylsulfonyl-phenyl)azepan-1-yl]-6-methyl-pyrimidin-2-amine (100) I-88

To a mixture of solids 4-chloro-6-methyl-pyrimidin-2-amine (0.10 g, 0.68 mmol) and 2-(2-methoxy-4-methylsulfonyl-phenyl)azepane-HCl, 99, (0.25 g, 0.78 mmol) in a vial was added EtOH (2 mL). The vial was placed on the hot plate and heated at 170° C. without cover for 2 hours. The crude solid was purified by silica gel chromatography (40 g ISCO column) eluting with 20% MeOH-dichloromethane/dichloromethane to afford 182 mg of desired product: ¹H NMR (300 MHz, DMSO-d6) δ 7.59-7.38 (m, 2H), 7.22 (s, 1H), 6.06-5.23 (m, 3H), 4.82 (brs, 1H), 4.00 (s, 3H), 3.31 (brs, 2H), 3.22 (s, 3H), 1.94 (s, 3H), 1.87-1.01 (m, 8H); ESI-MS m/z calc. 390.17, found 391.09 (M+1)⁺. Retention time: 0.66 minutes.

The racemic mixture (182 mg) was submitted for SFC chiral separation.

SFC conditions: Column: AD-H, 4.6×100 mm AD-H, 10×250 mm; Mobile phase: 40% EtOH (5 mM Ammonia), 60% CO2

I-98 Peak A: [α]$_D$ (c=0.5, MeOH) −72.39; ee=99%
4-[2-(2-methoxy-4-methylsulfonyl-phenyl)azepan-1-yl]-6-methyl-pyrimidin-2-amine (101): ¹H NMR (400 MHz, DMSO-d6) δ 7.59-7.40 (m, 2H), 7.26 (d, J=8.0 Hz, 1H), 5.64 (s, 1H), 5.40 (br, 2H), 4.39 (brs, 1H), 4.01 (s, 3H), 3.57-3.34 (m, 1H), 3.17 (s, 3H), 2.48-2.29 (m, 1H), 2.03 (s, 3H), 1.93-1.04 (m, 8H). ESI-MS m/z calc. 390.17, found 391.09 (M+1)⁺. Retention time: 0.67 minutes.

I-99 Peak B: [α]$_D$ (c=0.5, MeOH) +86.51; ee=99.6%
4-[2-(2-methoxy-4-methylsulfonyl-phenyl)azepan-1-yl]-6-methyl-pyrimidin-2-amine (102): ¹H NMR (400 MHz, DMSO-d6) δ 7.39 (d, J=1.6 Hz, 1H), 7.36-7.26 (m, 1H), 7.16 (d, J=7.9 Hz, 1H), 5.54 (s, 1H), 5.30 (s, 2H), 4.28 (brs, 1H), 3.92 (s, 3H), 3.35-3.20 (m, 1H), 3.07 (s, 3H), 2.40-2.26 (m, 1H), 1.93 (s, 3H), 1.87-1.10 (m, 8H); ESI-MS m/z calc. 390.17, found 391.05 (M+1)⁺. Retention time: 0.66 minutes.

The following analogs were prepared according to Synthetic Scheme 11:

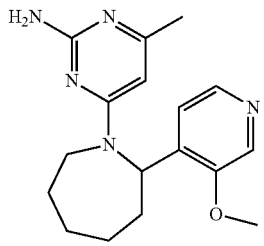 [SMILES: COc1ncccc1C1CCCCCN1c1cc(C)nc(N)n1]

103

(+/−)-4-[2-(3-methoxy-4-pyridyl)azepan-1-yl]-6-methyl-pyrimidin-2-amine (103) I-80

¹H NMR (400 MHz, DMSO-d6) δ 8.57 (d, J=5.9 Hz, 1H), 8.34 (d, J=5.3 Hz, 1H), 7.62 (s, 2H), 7.36 (d, J=5.3 Hz, 1H), 6.52 (s, 1H), 5.69 (m, 1H), 4.06 (s, 3H), 3.78-3.37 (m, 2H), 2.28 (s, 3H), 2.03-1.14 (m, 8H); ESI-MS m/z calc. 313.19, found 314.14 (M+1)⁺. Retention time: 0.56 minutes.

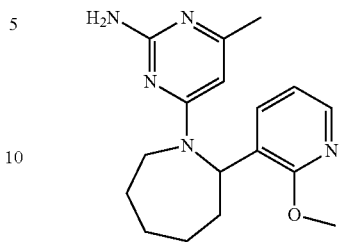

(+/−)-4-(2-(2-methoxypyridin-3-yl)azepan-1-yl)-6-methylpyrimidin-2-amine I-18

¹H NMR (400 MHz, DMSO-d6) δ 8.00 (dd, J=4.9, 1.8 Hz, 1H), 7.34 (dd, J=7.2, 1.6 Hz, 1H), 6.86 (dd, J=7.3, 4.9 Hz, 1H), 5.61 (s, 1H), 5.36 (s, 2H), 5.19 (s, 1H), 4.32 (s, 1H), 3.96 (s, 3H), 3.37-3.28 (m, 1H), 2.96 (s, 5H), 2.45-2.35 (m, 1H), 2.00 (s, 3H), 1.88 (s, 1H), 1.75 (s, 2H), 1.70-1.44 (m, 3H), 1.41-1.20 (m, 2H); ESI-MS m/z calc. 313.2, found 314.2 (M+1)⁺. Retention time: 0.61 minutes.

Example 12

Synthetic Scheme 12: (+/−)-4-(2-(2-ethylphenyl)azepan-1-yl)-6-methylpyrimidin-2-amine (107) I-45

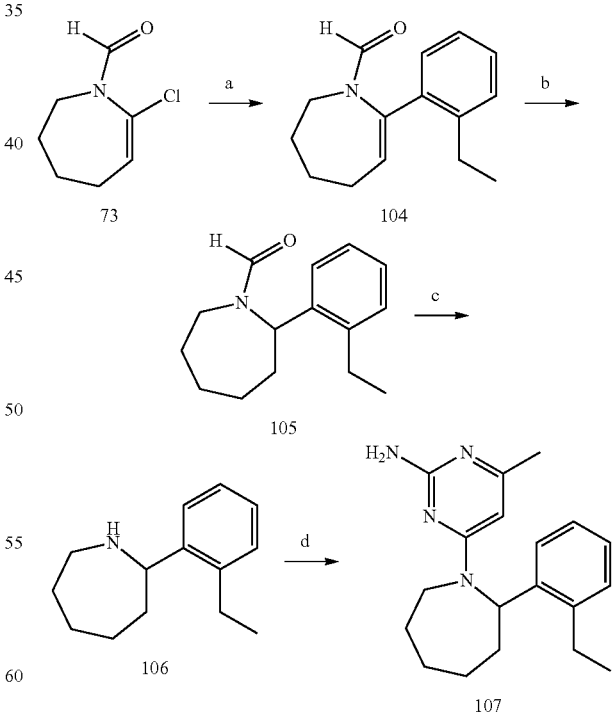

(a) (2-ethylphenyl)boronic acid, PdCl₂(dppf), NaHCO₃, DMF, water, 85° C.; (b) Pd/C, formic acid, EtOAc, MeOH; (c) nBuLi, THF, −78° C.; (d) 2-amino-4-chloro-6-methyl-pyrimidine, NMP, 150° C.; (e) SFC chiral separation

Formation of 7-(2-ethylphenyl)-2,3,4,5-tetrahydro-1H-azepine-1-carbaldehyde (104)

A mixture of 7-chloro-2,3,4,5-tetrahydroazepine-1-carbaldehyde, 73, (1.5 g, 9.4 mmol), (2-ethylphenyl)boronic acid (1.4 g, 9.4 mmol), and PdCl$_2$(dppf) (0.4 g, 0.5 mmol) in DMF (30 mL) and aqueous saturated NaHCO$_3$ solution (10 mL) was heated with microwave irradiation at 80° C. for 30 minutes. The mixture was filtered over Celite, diluted with EtOAc, and washed with water. The organic layer was dried over magnesium sulfate, filtered and concentrated in vacuo. The resulting residue was purified via silica gel chromatography eluting with 0-50% EtOAc/heptane. Pure fractions were combined and concentrated to afford 1.68 g of desired product as a colorless oil: $^1$H NMR (400 MHz, CDCl$_3$) δ 7.94 (s, 1H), 7.29 (ddd, J=7.7, 6.3, 2.2 Hz, 1H), 7.23-7.14 (m, 3H), 5.39 (t, J=5.7 Hz, 1H), 3.96-3.87 (m, 2H), 2.57 (q, J=7.5 Hz, 2H), 2.39-2.32 (m, 2H), 1.92 (tt, J=6.2, 5.2 Hz, 2H), 1.84-1.74 (m, 2H), 1.20 (t, J=7.6 Hz, 3H); ESI-MS m/z calc. 229.1, found 230.0 (M+1)$^+$. Retention time: 1.05 minutes.

Formation of (+/−)-2-(2-ethylphenyl)azepane-1-carbaldehyde (105)

A mixture of 7-(2-ethylphenyl)-2,3,4,5-tetrahydro-1H-azepine-1-carbaldehyde, 104, (1.68 g, 7.33 mmol) and wet Pd/C (0.79 g, 0.37 mmol) in ethyl acetate (25 mL) and MeOH (25 mL) was shaken overnight under 55 psi of hydrogen. The reaction mixture was filtered through Celite and the filter pad was rinsed with EtOAc. The filtrate was dried over magnesium sulfate, filtered, and concentrated in vacuo to give 1.47 g light yellow oil: $^1$H NMR (400 MHz, DMSO-d6) δ 8.06 (d, J=55.7 Hz, 1H), 7.22-7.05 (m, 4H), 5.04 (ddd, J=106.0, 12.0, 4.9 Hz, 1H), 4.13-4.00 (m, 0.5H), 3.90-3.78 (m, 1H), 3.63-3.50 (m, 1H), 3.25-3.15 (m, 0.5H), 2.84-2.63 (m, 2H), 2.22-1.66 (m, 5H), 1.49-1.11 (m, 6H); ESI-MS m/z calc. 231.2, found 232.0 (M+1)$^+$. Retention time: 1.03 minutes.

Formation of (+/−)-2-(2-ethylphenyl)azepane (106)

A solution of 2-(2-ethylphenyl)azepane-1-carbaldehyde, 105, (1.47 g, 6.35 mmol) in MeOH (5 mL) and concentrated HCl (5 mL of 12.1 M solution, 60.50 mmol) was refluxed overnight. The resulting mixture was concentrated to dryness, dissolved in minimal MeOH and dropped into cold diethyl ether while stirring vigorously. The resulting white precipitate was filtered and dried to give 1.15 g of the desired product as an HCl salt: $^1$H NMR (300 MHz, DMSO-d6) δ 9.72 (s, 1H), 9.26 (s, 1H), 7.76-7.61 (m, 1H), 7.41-7.18 (m, 3H), 4.43 (d, J=10.6 Hz, 1H), 3.42-3.02 (m, 2H), 2.72 (ddt, J=19.3, 14.6, 7.3 Hz, 2H), 2.33-1.45 (m, 6H), 1.16 (t, J=7.5 Hz, 3H); ESI-MS m/z calc. 203.2, found 204.0 (M+1)$^+$. Retention time: 0.67 minutes.

Formation of (+/−)-4-(2-(2-ethylphenyl)azepan-1-yl)-6-methylpyrimidin-2-amine (107) I-45

A mixture of 2-(2-ethylphenyl)azepane-HCl, 106, (0.15 g, 0.63 mmol), 4-chloro-6-methyl-pyrimidin-2-amine (0.09 g, 0.63 mmol) and triethylamine (0.17 mL, 1.25 mmol) in NMP (2 mL) was stirred for 5 hours in a sealed tube at 150° C. The crude reaction mixture was purified by reverse phase silica gel chromatography by injecting directly onto a 50 g C18 aqueous ISCO column and eluting with 5-50% MeCN in water with 0.1% TFA. Pure fractions were combined, neutralized with saturated sodium bicarbonate, and extracted with EtOAc. The organic layer was dried over magnesium sulfate, filtered, concentrated in vacuo and lyophilized to afford 45 mg of desired product: $^1$H NMR (400 MHz, DMSO-d6) δ 7.18 (d, J=7.5 Hz, 1H), 7.15-7.09 (m, 1H), 7.09-7.04 (m, 2H), 5.67 (s, 1H), 5.54 (s, 2H), 5.27 (s, 1H), 4.33 (d, J=14.8 Hz, 1H), 3.54-3.40 (m, 1H), 2.88-2.69 (m, 2H), 2.16 (ddd, J=14.2, 8.2, 5.1 Hz, 1H), 2.01 (s, 3H), 1.96-1.67 (m, 3H), 1.52 (q, J=12.9, 12.4 Hz, 1H), 1.46-1.33 (m, 2H), 1.33-1.24 (m, 4H); ESI-MS m/z calc. 310.2, found 311.0 (M+1)$^+$. Retention time: 0.84 minutes.

The following analog was prepared according to Synthetic Scheme 12:

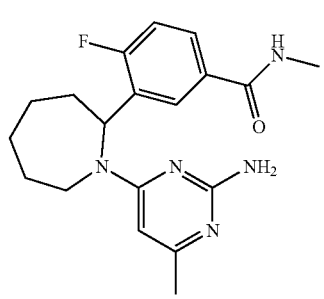

108

3-(1-(2-amino-6-methylpyrimidin-4-yl)azepan-2-yl)-4-fluoro-N-methylbenzamide (108) I-55

$^1$H NMR (400 MHz, DMSO-d6) δ 8.14-8.06 (m, 1H), 7.71 (ddd, J=8.5, 5.0, 2.3 Hz, 1H), 7.62 (dd, J=7.4, 2.3 Hz, 1H), 7.19-7.13 (m, 1H), 5.80 (s, 1H), 5.68 (s, 2H), 5.41 (d, J=35.0 Hz, 1H), 4.25 (m, 1H), 3.49-3.42 (m, 1H), 2.76 (d, J=4.5 Hz, 3H), 2.32 (dt, J=14.3, 7.1 Hz, 1H), 2.06 (s, 3H), 1.95-1.69 (m, 4H), 1.55 (p, J=11.5 Hz, 1H), 1.45-1.22 (m, 2H); ESI-MS m/z calc. 357.2, found 358.0 (M+1)$^+$. Retention time: 0.67 minutes.

Example 13

Synthetic Scheme 13: (+/−)-3-[4-(2-amino-6-methyl-pyrimidin-4-yl)-1,4-oxazepan-3-yl]-4-chloro-phenol (112) I-147

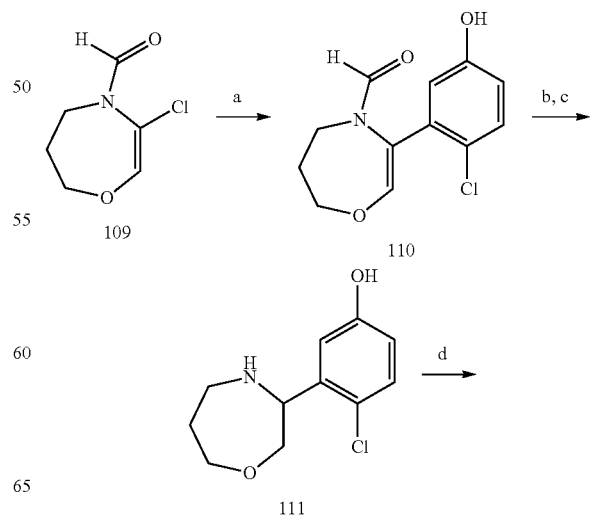

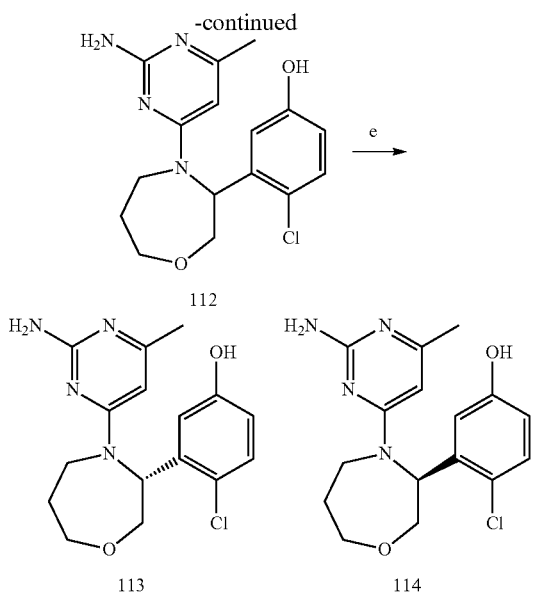

(a) 2,5-dimethoxyphenylboronic acid, Pd(Ph₃P)₂Cl₂, DME, 50° C.; (b) nBuLi, THF, −78° C.; (c) NaBH₄, MeOH; (d) 2-amino-4-chloro-6-methylpyrimidine, EtOH, 160° C.; (e) SFC chiral separation Formation of 3-chloro-6,7-dihydro-1,4-oxazepine-4(5H)-carbaldehyde (109)

Intermediate, 109, was prepared according to Synthetic Scheme 9 using 1,4-oxazepan-3-one instead of azepan-2-one.

Formation of 3-(2-chloro-5-hydroxyphenyl)-6,7-dihydro-1,4-oxazepine-4(5H)-carbaldehyde (110)

Charged a 2-necked rb flask under nitrogen with 3-chloro-6,7-dihydro-5H-1,4-oxazepine-4-carbaldehyde, 109, (0.46 g, 2.80 mmol), NaHCO₃ (6.0 mL of 1.2 M solution, 7.2 mmol) and (2-chloro-5-hydroxy-phenyl)boronic acid (0.50 g, 2.90 mmol) in dimethoxyethane (10 mL). Then bis(triphenyl-phosphine)palladium(II)chloride (0.10 g, 0.14 mmol) was added the reaction mixture was heated overnight at 60° C. The mixture was diluted into water and dichloromethane. The layers were separated through a phase separator and the organics concentrated in vacuo after a second extraction. Purification by silica gel chromatography (40 g GOLD column; 10-100% EtOAc/heptanes gradient) afforded 650 mg of desired product: ¹H NMR (300 MHz, CDCl₃) δ 7.93 (s, 1H), 7.28 (s, OH), 7.20 (d, J=8.4 Hz, 1H), 6.81 (d, J=2.7 Hz, 1H), 6.13 (s, 1H), 4.25 (t, J=5.8 Hz, 2H), 4.11 (t, J=6.3 Hz, 3H), 2.15 (t, J=6.2 Hz, 2H); ESI-MS m/z calc. 253.05, found 252.29 (M+1)⁺. Retention time: 0.55 minutes.

Formation of (+/−)-4-chloro-3-(1,4-oxazepan-3-yl)phenol (111)

To a cold (−78° C.) solution of 3-(2-chloro-5-hydroxyphenyl)-6,7-dihydro-5H-1,4-oxazepine-4-carbaldehyde, 110, (0.65 g, 1.55 mmol) in THF (10 mL) was added n-butyllithium (3 mL of 1.6 M solution, 4.80 mmol). The mixture was stirred at this temp for 50 minutes. The reaction mixture was quenched carefully by addition of methanol. More MeOH (30 mL) was added and the solution was warmed to room temperature. The resulting solution was used directly for the next step; ESI-MS m/z calc. 225.06, found 226.08 (M+1)⁺. Retention time: 0.54 minutes.

To the above solution was added NaBH₄ (0.09 g, 2.38 mmol). The mixture was stirred at room temperature overnight. The reaction was quenched by the addition of MeOH and then 2N HCl solution. The acidic solution was then basified with 6N NaOH and the aqueous phase was extracted with EtOAc three times. The combined organic phases were washed with brine, dried over MgSO₄, filtered and evaporated. The crude product (300 mg, 77%) was obtained and used directly; ESI-MS m/z calc. 227.07, found 228.09 (M+1)⁺. Retention time: 0.54 minutes.

Formation of (+/−)-3-(4-(2-amino-6-methylpyrimidin-4-yl)-1,4-oxazepan-3-yl)-4-chlorophenol (112) I-147

To a mixture of solids 4-chloro-6-methyl-pyrimidin-2-amine (0.30 g, 2.04 mmol) and 4-chloro-3-(1,4-oxazepan-3-yl)phenol, 111, (1.43 g, 2.22 mmol) in a vial was added EtOH (2 mL). The vial was placed on the hot plate and heated at 160° C. without cover for 2 hours. The crude solid was purified by silica gel column (40 g) in ISCO eluting with 20% MeOH-DCM/DCM gradient (0% B to 50% B) to afford 192 mg of desired product: ¹H NMR (300 MHz, DMSO-d6) δ 9.80 (s, 1H), 7.72 (brs, 1H), 7.48-7.18 (m, 2H), 6.90-6.54 (m, 2.5H), 5.93 (br, 0.5H), 5.59 (s, 0.5H), 5.26-5.07 (m, 0.5H), 4.99 (m, 0.5H), 4.43-4.04 (m, 1.5H), 3.86 (m, 3H), 3.62 (t, J=10.2 Hz, 1H), 2.18 (s, 3H), 1.84 (m, 2H); ESI-MS m/z calc. 334.12, found 335.10 (M+1)⁺. Retention time: 0.6 minutes. The racemic mixture (180 mg) was submitted to chiral SFC purification to obtain the individual enantiomers. SFC conditions: Column: Cellulose-2, 20×250 mm; Mobile phase: 30% EtOH (5 mM Ammonia), 70% CO₂; Flow: 80 mL/min; Concentrations: ~18 mg/mL (MeOH); Injection Volume: 250 µL; Wavelength: 220 nm.

(I-169) Peak A: 96.8% ee [α]_D (c=0.5, MeOH) −85.10

(R)-3-[4-(2-amino-6-methyl-pyrimidin-4-yl)-1,4-oxazepan-3-yl]-4-chloro-phenol (113): ¹H NMR (300 MHz, DMSO-d6) δ 9.73 (s, 1H), 7.25 (d, J=8.6 Hz, 1H), 6.75-6.60 (m, 2H), 6.40 (s, 2H), 5.01 (s, 1H), 4.68-4.54 (m, 1H), 4.12 (br, 1H), 3.99-3.86 (m, 2H), 3.83-3.48 (m, 3H), 2.04 (brs, 3H), 1.76 (m, 2H); ESI-MS m/z calc. 334.12, found 335.11 (M+1)⁺. Retention time: 0.61 minutes.

(I-170) Peak B: 95.4% ee [α]_D (c=0.5, MeOH) +79.40

(S)-3-[4-(2-amino-6-methyl-pyrimidin-4-yl)-1,4-oxazepan-3-yl]-4-chloro-phenol (114): ¹H NMR (300 MHz, DMSO-d6) δ 9.75 (s, 1H), 7.25 (d, J=8.5 Hz, 1H), 6.79-6.63 (m, 2H), 6.57 (s, 1.5H), 5.34 (brs, 0.5H), 5.01 (brs, 1H), 4.71-4.53 (m, 1H), 4.13 (br, 1H), 3.91 (m, 2H), 3.83-3.48 (m, 3H), 2.06 (br, 3H), 1.77 (m, 2H); ESI-MS m/z calc. 334.12, found 335.10 (M+1)⁺. Retention time: 0.63 minutes.

The following analogs were prepared according to Synthetic Scheme 13:

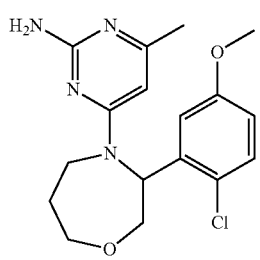

115

(+/−)-4-(3-(2-chloro-5-methoxyphenyl)-1,4-oxaze-
pan-4-yl)-6-methylpyrimidin-2-amine (115) I-118

¹H NMR (300 MHz, DMSO-d6) δ 7.95 (brs, 1H), 7.59 (s, 1H), 7.43 (dd, J=24.4, 8.7 Hz, 1H), 7.07-6.88 (m, 1H), 6.84-6.72 (m, 1H), 6.07-5.47 (m, 1H), 5.09 (dd, J=58.8, 11.2 Hz, 1H), 4.38-4.05 (m, 2H), 4.01-3.48 (m, 7H), 2.29 (s, 3H), 1.84 (br, 2H). ESI-MS m/z calc. 348.13, found 349.11 (M+1)⁺. Retention time: 0.67 minutes.

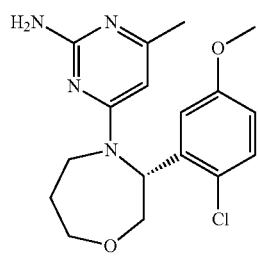

116

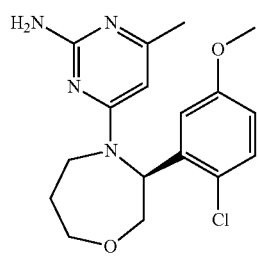

117

(+/−)-4-(3-(2-chloro-5-methoxyphenyl)-1,4-oxaze-
pan-4-yl)-6-methylpyrimidin-2-amine (115) I-118

The racemic mixture 115 was submitted to chiral SFC purification to obtain the individual enantiomers.

SFC conditions: Column: AD-H, 20×250 mm; Mobile phase: 30% IPA (5 mM Ammonia), 70% CO₂; Flow: 75 mL/min; Concentrations: ~75 mg/mL (MeOH); Injection Volume: 500 μL; Wavelength: 214 nm.

Peak A: white solid, ee 99.4%; [α]_D (c=0.5, MeOH) −67.96 (R)-4-[3-(2-chloro-5-methoxy-phenyl)-1,4-oxaze-pan-4-yl]-6-methyl-pyrimidin-2-amine (116): ¹H NMR (300 MHz, DMSO-d6) δ 7.94 (s, 1H), 7.59 (s, 1H), 7.52-7.16 (m, 1H), 7.09-6.88 (m, 1H), 6.86-6.75 (m, 1H), 6.58 (s, 0.5H), 5.95 (br, 0.5H), 5.60 (s, 0.5H), 5.17 (s, 0.5H), 4.99 (br, 0.5H), 4.22 (m, 1H), 4.17-4.03 (m, 0.5H), 3.88 (m, 2H), 3.75 (s, 3H), 3.61 (m, 2H), 2.23 (s, s, 3H), 1.84 (br, 2H); ESI-MS m/z calc. 348.13, found 349.15 (M+1)⁺. Retention time: 0.64 minutes. I-137.

Peak B: white solid, ee 99.2%; [α]_D (c=0.5, MeOH) +60.08 (S)-4-[3-(2-chloro-5-methoxy-phenyl)-1,4-oxaze-pan-4-yl]-6-methyl-pyrimidin-2-amine (117) ¹H NMR (300 MHz, DMSO-d6) δ 7.39 (d, J=8.5 Hz, 1H), 6.91 (dd, J=8.7, 3.0 Hz, 1H), 6.75 (t, J=2.3 Hz, 1H), 6.27 (s, 2H), 4.32 (s, 1H), 4.11 (d, J=13.3 Hz, 1H), 3.92 (d, J=11.8 Hz, 1H), 3.85-3.66 (m, 5H), 3.57 (d, J=12.3 Hz, 1H), 3.25 (d, J=43.7 Hz, 1H), 2.05 (s, 3H), 1.77 (s, 2H); ESI-MS m/z calc. 348.14, found 349.15 (M+1)⁺. Retention time: 0.64 minutes. I-138.

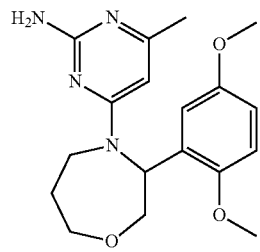

118

(+/−)-4-[3-(2,5-dimethoxyphenyl)-1,4-oxazepan-4-
yl]-6-methyl-pyrimidin-2-amine (118) I-93

¹H NMR (300 MHz, DMSO-d6) δ 7.61-7.24 (br, 2H), 7.10-6.77 (m, 2H), 6.77-6.42 (br, 1H), 5.84 (br, 1H), 5.04 (br, 1H), 4.22 (br, 1H), 4.00-3.44 (m, 12H), 2.34-1.62 (m, 3H), 1.75 (br, 2H); ESI-MS m/z calc. 344.18, found 345.06 (M+1)⁺. Retention time: 0.65 minutes.

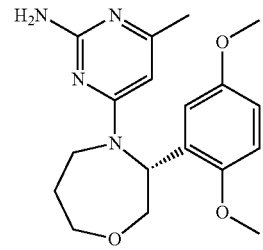

119

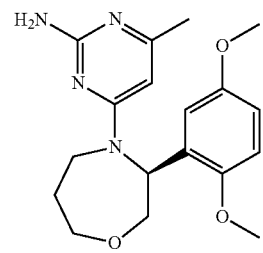

120

The racemic mixture was submitted to chiral SFC purification to obtain the individual enantiomers. SFC conditions: Column: AD-H, 10×250 mm; Mobile phase: 30% EtOH (5 mM Ammonia), 70% CO₂; Flow: 15 mL/min; Concentrations: ~40 mg/mL (MeOH); Injection Volume: 100 μL; Wavelength: 214 nm.

Peak A: white solid, ee 97.6%; [α]_D (c=0.5, MeOH) −96.56 (R)-4-[3-(2,5-dimethoxyphenyl)-1,4-oxazepan-4-yl]-6-methyl-pyrimidin-2-amine (119): ¹H NMR (400 MHz, DMSO-d6) δ 6.99 (d, J=8.9 Hz, 1H), 6.84 (dd, J=8.9, 3.1 Hz, 1H), 6.69 (s, 1H), 6.24 (s, 3H), 5.81 (s, 2H), 5.46 (s, 1H), 4.67 (s, 1H), 4.18 (dd, J=13.1, 5.2 Hz, 1H), 3.94 (d, J=12.5 Hz, 2H), 3.85 (s, 1H), 3.77-3.66 (m, 7H), 3.60-3.48 (m, 2H), 2.11 (s, 2H), 1.89-1.70 (m, 3H); ESI-MS m/z calc. 344.18, found 345.06 (M+1)⁺. Retention time: 0.65 minutes. I-100.

Peak B: white solid, ee 99.6%; [α]_D (c=0.5, MeOH) +98.16; (S)-4-[3-(2,5-dimethoxyphenyl)-1,4-oxazepan-4-yl]-6-methyl-pyrimidin-2-amine (120): ¹H NMR (400 MHz, DMSO-d6) δ 6.95 (d, J=8.9 Hz, 1H), 6.79 (dd, J=8.9, 3.1 Hz, 1H), 6.64 (d, J=3.1 Hz, 1H), 5.68 (s, 2H), 5.64 (s, 1H), 5.37 (s, 1H), 4.65 (d, J=14.8 Hz, 1H), 4.15 (dd, J=13.3, 5.2 Hz, 1H), 3.98-3.87 (m, 1H), 3.82 (s, 3H), 3.71-3.58 (m, 2H), 3.65 (s, 3H), 3.50 (td, J=11.5, 4.0 Hz, 1H), 2.02 (s, 3H), 1.75 (m, 2H). ESI-MS m/z calc. 344.18, found 345.1 (M+1)⁺. Retention time: 0.65 minutes. I-101.

Example 14

Synthetic Scheme 14: (+/−)-4-[3-(2-chlorophenyl)-1,4-oxazepan-4-yl]-6-methyl-pyrimidin-2-amine (121) I-19

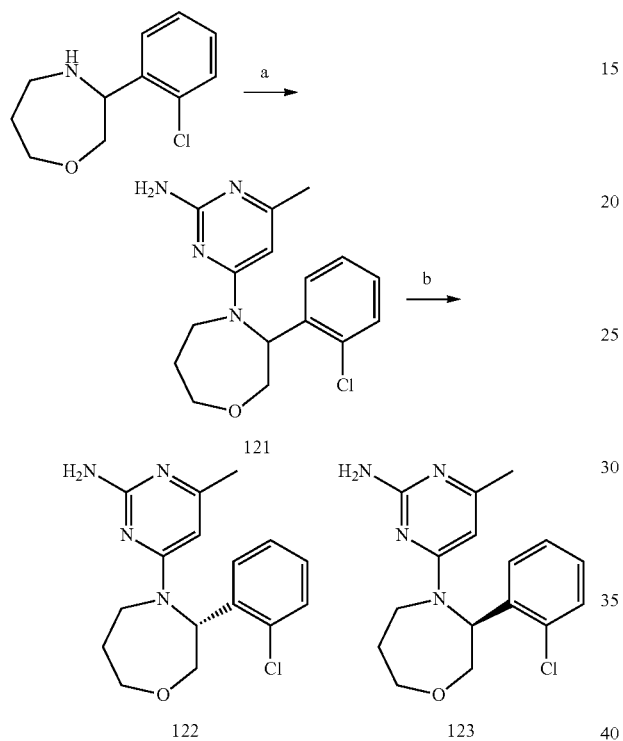

(a) 4-chloro-6-methyl-pyrimidin-2-amine, EtOH, 160° C.;
(b) SFC chiral purification Formation of (+/−)-4-[3-(2-chlorophenyl)-1,4-oxazepan-4-yl]-6-methyl-pyrimidin-2-amine (121) I-19

To a mixture of solids 4-chloro-6-methyl-pyrimidin-2-amine (0.45 g, 3.07 mmol) and 3-(2-chlorophenyl)-1,4-oxazepane (0.65 g, 3.07 mmol) in a vial was added EtOH (9 mL). The vial was placed on the hot plate and heated at 160° C. without cover for 2 hours. The crude solid was purified by silica gel chromatography (40 g) in ISCO eluting with 20% MeOH-dichloromethane/dichloromethane. The desired fractions were collected and concentrated in vacuo. The racemic mixture was submitted to chiral SFC purification to obtain the individual enantiomers. SFC conditions: Column: Cellulose-2, 20×250 mm; Mobile phase: 40% EtOH (5 mM Ammonia), 60% CO₂; Flow: 80 mL/min; Concentrations: ~30 mg/mL (MeOH); Wavelength: 254 nm; Method Type Isocratic.

Peak A: 97% ee; [α]$_D$ (c=1.0, MeOH) −16.26.

(R)-4-[3-(2-chlorophenyl)-1,4-oxazepan-4-yl]-6-methyl-pyrimidin-2-amine (122): ¹H NMR (300 MHz, DMSO-d6) δ 7.48 (dd, J=6.2, 3.1 Hz, 1H), 7.32 (m, 3H), 6.58 (br, 2H), 4.61 (br, 0.5H), 4.15 (br, 1H), 3.93 (br, 1H), 3.84-3.69 (m, 2H), 3.66-3.53 (m, 1H), 3.44 (m, 0.5H), 2.09 (s, 3H), 1.78 (br, 2H);

ESI-MS m/z calc. 318.12, found 319.13 (M+1)⁺. Retention time: 0.64 minutes. I-30.

Peak B: 89% ee; [α]$_D$ (c=1.0, MeOH) +39.92.

(S)-4-[3-(2-chlorophenyl)-1,4-oxazepan-4-yl]-6-methyl-pyrimidin-2-amine (123) ¹H NMR (300 MHz, DMSO-d6) δ 7.83-7.23 (m, 6H), 6.59 (s, 0.5H), 6.00 (brs, 0.5H), 5.59 (s, 0.5H), 5.24 (brs, 0.5H), 4.98 (br, 0.5H), 4.58 (br, 0.5H), 4.04 (m, 4H), 3.61 (td, J=11.3, 3.9 Hz, 1H), 2.22 (br, 3H), 1.84 (s, 2H).

ESI-MS m/z calc. 318.12, found 319.13 (M+1)⁺. Retention time: 0.64 minutes. I-31.

The following analogs were prepared according to Synthetic Scheme 14:

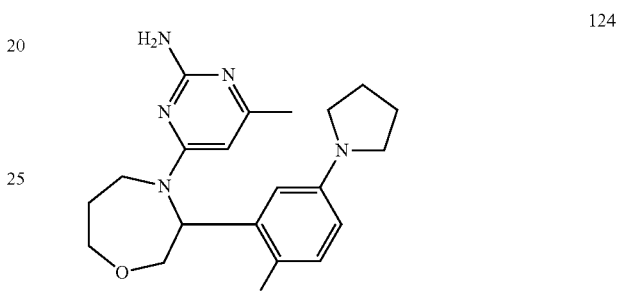

(+/−)-4-[3-(2-chloro-5-pyrrolidin-1-yl-phenyl)-1,4-oxazepan-4-yl]-6-methyl-pyrimidin-2-amine (124) I-199

¹H NMR (300 MHz, Methanol-d4) δ 7.16 (d, J=8.8 Hz, 1H), 6.46 (dd, J=8.8, 2.9 Hz, 1H), 6.35 (d, J=2.9 Hz, 1H), 5.52 (brs, 1H), 5.20 (br, 1H), 4.28 (dd, J=13.6, 4.9 Hz, 1H), 4.03 (dd, J=12.4, 4.8 Hz, 1H), 3.80-3.50 (m, 3H), 3.30-3.04 (m, 5H), 2.05 (s, 3H), 2.02-1.94 (m, 4H), 1.91-1.64 (m, 2H); ESI-MS m/z calc. 387.2, found 388.33 (M+1)⁺. Retention time: 0.71 minutes.

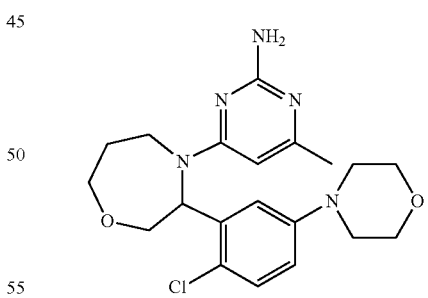

(+/−)-4-(3-(2-chloro-5-morpholinophenyl)-1,4-oxazepan-4-yl)-6-methylpyrimidin-2-amine I-226

¹H NMR (300 MHz, Methanol-d4) δ 7.29 (dd, J=18.3, 8.8 Hz, 2H), 6.91 (ddd, J=16.6, 8.9, 2.9 Hz, 1H), 6.78 (dd, J=26.7, 3.0 Hz, 0.5H), 6.48 (s, 1H), 6.10 (dd, J=9.5, 5.1 Hz, 0.5H), 5.68 (s, 1H), 5.39-5.10 (m, 2H), 4.42-4.17 (m, 1H), 4.09-3.59 (m, 11H), 3.09 (t, J=4.9 Hz, 6H), 2.28 (dd, J=40.8, 0.8 Hz, 5H), 2.09-1.84 (m, 4H); ESI-MS m/z calc. 403.18, found 404.21 (M+1)⁺. Retention time: 0.62 minutes.

Example 15

Synthetic Scheme 15: (+/−)-4-[3-[2-chloro-5-(methylamino)phenyl]-1,4-oxazepan-4-yl]-6-methyl-pyrimidin-2-amine (129) I-175

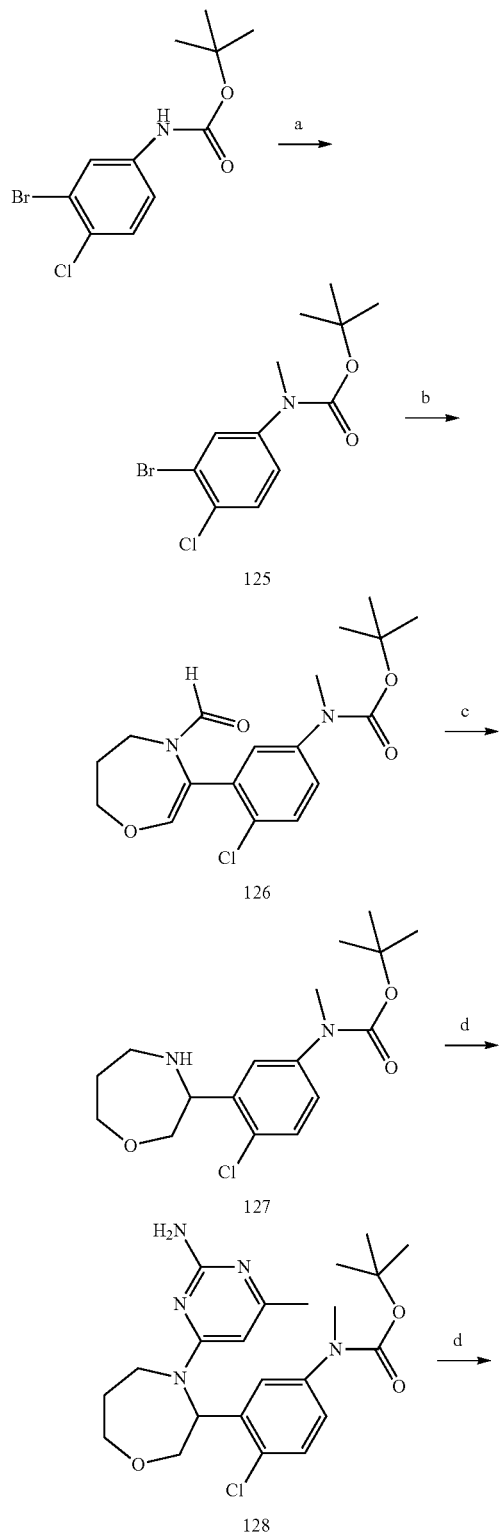

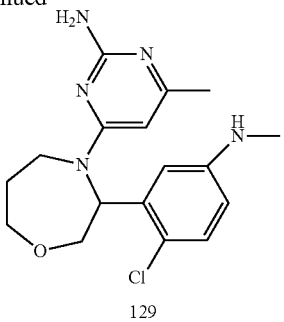

(a) NaH, DMF, 0° C.; (b) bis(pinocalatodiboron), Pd(Ph₃P)₂Cl₂, KOAc, dioxane, 85° C.; (c) nBuLi, THF, −78° C.; (d) 2-amino-4-chloro-6-methyl pyrimidine, MeOH, 125° C.; (e) TFA, CH₂Cl₂

Formation of tert-butyl (3-bromo-4-chlorophenyl)(methyl)carbamate (125)

To a solution of tert-butyl N-(3-bromo-4-chloro-phenyl)carbamate (2.00 g, 6.20 mmol) in DMF (20 mL) was added NaH (0.30 g, 7.50 mmol) at 0° C. The mixture was stirred 0° C. for 30 minutes. Methyl iodide (0.47 mL, 7.55 mmol) was added to the reaction mixture. The reaction mixture was diluted into water and extracted with EtOAc. The organic phase was dried (MgSO₄), filtered and concentrated in vacuo to afford 1.5 grams of desired product: $^1$H NMR (300 MHz, CDCl₃) δ 7.55 (d, J=2.5 Hz, 1H), 7.40 (d, J=8.7 Hz, 1H), 7.24-7.12 (m, 1H), 3.25 (s, 3H), 1.48 (s, 9H); ESI-MS m/z calc. 319.0, found 320.0 (M+1)⁺. Retention time: 1.06 minutes.

Formation of tert-butyl (4-chloro-3-(4-formyl-4,5,6,7-tetrahydro-1,4-oxazepin-3-yl)phenyl)-(methyl)carbamate (126)

Step-1: To a solution of tert-butyl N-(3-bromo-4-chloro-phenyl)-N-methyl-carbamate, 125, (1.5 g, 4.7 mmol) in dioxane (75 mL) was added bis(pinocalatodiboron) (1.5 g, 5.9 mmol), potassium acetate (1.4 g, 14.0 mmol). To this mixture was purged with nitrogen for 15 minutes and added dichloro-bis(triphenylphosphoranyl)palladium (0.3 g, 0.5 mmol). The reaction was heated to 85° C. for 18 hours. The reaction mixture was diluted with EtOAc and filtered through celite with EtOAc wash (60 mL). The organic phases were concentrated in vacuo. The resulting dark brown solid was used without further purification: ESI-MS m/z calc. 367.2, found 367.6 (M+1)⁺. Retention time: 1.0 minutes.

Step-2: To the above crude product dissolved in DME (45 mL) was added 3-chloro-6,7-dihydro-5H-1,4-oxazepine-4-carbaldehyde, 109, (0.76 g, 4.70 mmol) followed by aqueous NaHCO₃ (8 mL of 1.2 M, 9.60 mmol). The mixture was bubbled with nitrogen and PdCl₂(dppf) was added to the reaction mixture. The flask was covered and heated at 80° C. for 12 hrs. The mixture was concentrated in vacuo and purified by silica gel chromatography (40 g ISCO column eluting with 20% MeOH/dichloromethane. The desired fractions were collected and concentrated in vacuo to afford 500 mg of desired product: ESI-MS m/z calc. 366.1, found 367.1 (M+1)⁺. Retention time: 0.92 minutes.

Formation of (+/−)-tert-butyl (4-chloro-3-(1,4-oxazepan-3-yl)phenyl)(methyl)carbamate (127)

To a solution of tert-butyl N-[4-chloro-3-(4-formyl-6,7-dihydro-5H-1,4-oxazepin-3-yl)phenyl]-N-methyl-carbamate, 126, (0.40 g, 1.09 mmol) in THF (10 mL) was added nBuLi (2.1 mL of 1.6 M solution, 3.3 mmol) at −78° C. The reaction mixture was stirred at −78° C. for 50 minutes. To this mixture was carefully added MeOH to quench the reaction. Additional MeOH (30 mL) was added and the solution was warmed to room temperature: ESI-MS m/z calc. 338.1, found 339.1 (M+1)⁺. Retention time: 0.63 minutes. To this solution was added NaBH₄ (0.07 g, 1.81 mmol). The reaction mixture was stirred at room temperature overnight. The mixture was diluted into water and extracted twice with EtOAc. The combined organic phases were dried (MgSO₄), filtered and concentrated in vacuo to afford 200 mg of desired product that was used without further purification: ESI-MS m/z calc. 340.1, found 341.2 (M+1)⁺. Retention time: 0.64 minutes.

Formation of (+/−)-tert-butyl (3-(4-(2-amino-6-methylpyrimidin-4-yl)-1,4-oxazepan-3-yl)-4-chlorophenyl)(methyl)carbamate (128)

A mixture of 4-chloro-6-methyl-pyrimidin-2-amine (0.08 g, 0.54 mmol) and tert-butyl N-[4-chloro-3-(1,4-oxazepan-3-yl)phenyl]-N-methyl-carbamate, 127, (0.30 g, 0.77 mmol) was mixed in a small amount of methanol. The resulting suspension was heated at 125° C. in an open flask for 16 hours so as to allow solvent to evaporate. The resulting solid was dissolved in MeOH and purified by silica gel chromatography (40 g ISCO column) eluting with 20% MeOH-dichloromethane/dichloromethane. The desired fractions were collected and evaporated to afford 220 mg of desired product: ¹H NMR (300 MHz, DMSO-d6) δ 7.45 (d, J=8.5 Hz, 1H), 7.25 (d, J=8.7 Hz, 1H), 7.16 (s, 1H), 6.95 (br, 2H), 6.46 (br, 1H), 5.95 (br, 1H), 5.11 (br, 1H), 4.15 (br, 2H), 4.02-3.70 (m, 3H), 3.57 (td, J=11.4, 4.0 Hz, 1H), 3.15 (s, 3H), 2.15 (br, 3H), 1.80 (m, 2H), 1.28 (s, 9H); ESI-MS m/z calc. 447.2, found 448.1 (M+1)⁺. Retention time: 0.68 minutes.

Formation of (+/−)-4-[3-[2-chloro-5-(methylamino) phenyl]-1,4-oxazepan-4-yl]-6-methyl-pyrimidin-2-amine (129)

To a solution of tert-butyl N-[3-[4-(2-amino-6-methyl-pyrimidin-4-yl)-1,4-oxazepan-3-yl]-4-chloro-phenyl]-N-methyl-carbamate, 128, (0.25 g, 0.53 mmol) in dichloromethane (10 mL) was added trifluoroacetic acid (0.74 g, 6.49 mmol). The mixture was stirred at room temperature for 12 hours and the solvent evaporated in vacuo. The resulting residue was purified by reverse ISCO eluting with 0.1% TFA-acetonile/0.1% TFA-water to afford 183 mg of desired product: ¹H NMR (300 MHz, DMSO-d6) δ 7.82 (s, 1H), 7.49 (s, 1H), 7.17 (dd, J=19.2, 8.6 Hz, 1H), 6.73-6.34 (m, 2H), 5.93 (dd, J=10.1, 5.4 Hz, 0H), 5.16-5.07 (m, OH), 5.06-4.90 (m, 10H), 4.35-4.05 (m, 1H), 4.00-3.47 (m, 3H), 2.62 (d, J=1.9 Hz, 3H), 2.23 (d, J=35.1 Hz, 2H), 1.94-1.67 (m, 2H); ESI-MS m/z calc. 347.2, found 348.2 (M+1)⁺. Retention time: 0.57 minutes. I-175.

SFC chiral separation afforded individual enantiomers. Column: Cellulose-2, 20×250 mm Mobile phase: 30% MeOH (5 mM Ammonia), 70% C02; Flow: 80 mL/min. Concentrations: ~40 mg/mL (MeOH) Injection Volume: 250 μL Wavelength: 220 nm; Method Type Isocratic Peak A: ee: 97% [α]_D (c=0.5, MeOH) −296.96 I-312
4-[3-[2-chloro-5-(methylamino)phenyl]-1,4-oxazepan-4-yl]-6-methyl-pyrimidin-2-amine (38.5 mg, 47%) 1H NMR (300 MHz, Methanol-d4) δ 5.64 (d, J=8.7 Hz, 1H), 5.05-4.96 (m, 2H), 4.89 (d, J=2.8 Hz, 1H), 4.13 (d, J=1.0 Hz, 1H), 3.78-3.61 (m, 2H), 2.78 (ddd, J=27.1, 13.7, 5.1 Hz, 2H), 2.57-2.03 (m, 4H), 1.16 (s, 3H), 0.67 (d, J=0.8 Hz, 3H), 0.37 (td, J=9.1, 7.4, 4.1 Hz, 3H). ESI-MS m/z calc. 347.15128, found 348.15 (M+1)⁺. Retention time: 0.57 minutes.

Peak B: ee: 95.4% [α]_D (c=0.5, MeOH) +254.02 I-178
4-[3-[2-chloro-5-(methylamino)phenyl]-1,4-oxazepan-4-yl]-6-methyl-pyrimidin-2-amine (36.0 mg, 44%) 1H NMR (300 MHz, Methanol-d4) δ 5.84 (d, J=8.6 Hz, 1H), 5.29-5.07 (m, 2H), 4.21 (br, 1H), 3.78 (br, 2H), 2.99 (dd, J=13.6, 5.0 Hz, 1H), 2.75 (dd, J=12.2, 4.8 Hz, 1H), 2.54-2.20 (m, 3H), 1.39 (s, 3H), 0.78 (s, 3H), 0.68-0.41 (m, 2H). ESI-MS m/z calc. 347.15128, found 348.15 (M+1)⁺. Retention time: 0.57 minutes.

Example 16

Synthetic Scheme 16: (+/−)-4-methyl-6-(2-(2-methyl-4-(methylsulfonyl)phenyl)azepan-1-yl)pyrimidin-2-amine (132) I-37

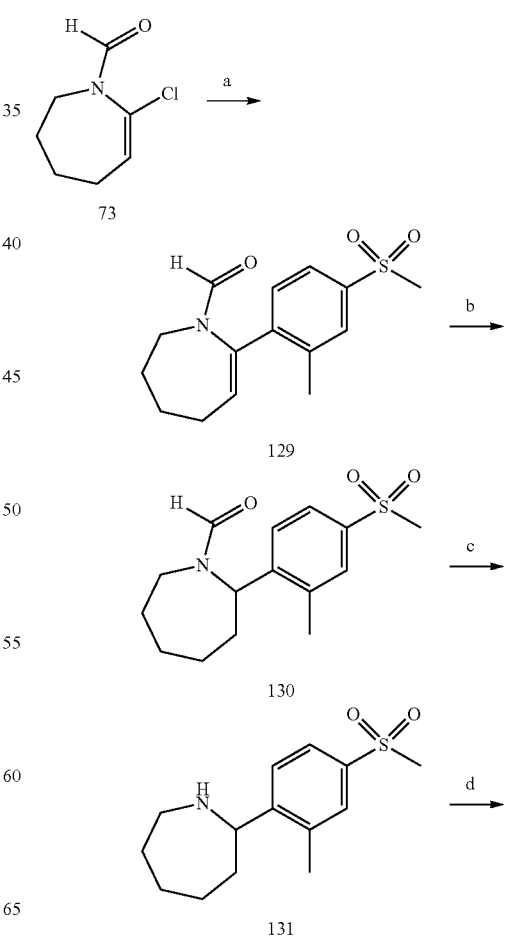

-continued

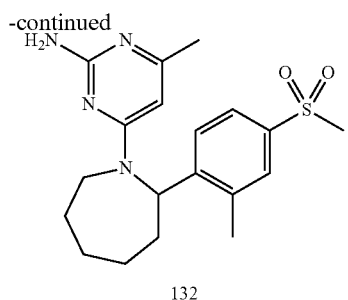

132

(a) (2-methyl-4-methyl sulfonyl-phenyl)boronic acid, Pd(Ph₃P)₂Cl₂, Et₃N, DMF; (b) Pd/C, HOAc, EtOAc, MeOH; (c) nBuLi, THF, −78° C.; (d) 2-amino-4-chloro-6-methylpyrimidine, NMP, 150° C.

Formation of 7-(2-methyl-4-(methylsulfonyl)phenyl)-2,3,4,5-tetrahydro-1H-azepine-1-carbaldehyde (129)

Charged a rb flask under nitrogen with 7-chloro-2,3,4,5-tetrahydroazepine-1-carbaldehyde, 73, (0.60 g, 3.76 mmol), (2-methyl-4-methylsulfonyl-phenyl)boronic acid (1.00 g, 4.67 mmol), DMF (3.5 mL), triethylamine (2.5 mL, 17.9 mmol) then bis(triphenylphosphine)palladium II chloride (0.11 g, 0.15 mmol). The mixture was flushed with stream of nitrogen and heated at 50° C. for 7 hours. Added water and extracted twice with EtOAc. The combined organic phases were washed twice with brine, dried (MgSO₄), filtered and concentrated in vacuo. The resulting residue was purified by column chromatography (40 g gold ISCO column; 0-30% EtOAc/CH₂Cl₂ gradient) to afford 161 mg of desired product: $^1$H NMR (400 MHz, DMSO-d6) δ 7.83-7.58 (m, 3H), 7.57-7.33 (m, 1H), 5.82-5.50 (m, 1H), 3.83-3.60 (m, 2H), 3.20 (s, 3H), 2.39-2.31 (m, 2H), 2.28 (s, 3H), 1.87-1.73 (m, 2H), 1.73-1.62 (m, 2H); ESI-MS m/z calc. 293.1, found 294.1 (M+1)⁺. Retention time: 0.71 minutes.

Formation of (+/−)-2-(2-methyl-4-(methylsulfonyl)phenyl)azepane-1-carbaldehyde (130)

A mixture of 7-(2-methyl-4-methylsulfonyl-phenyl)-2,3,4,5-tetrahydroazepine-1-carbaldehyde, 129, (0.162 g, 0.552 mmol) and palladium on carbon (0.056 g, 0.526 mmol) in ethyl acetate (3 mL), methanol (3 mL) and acetic acid (1 mL) was stirred under an atmosphere of hydrogen gas. After 21 hours, the mixture was filtered through a small pad of fluorosil and washed with EtOAc. The filtrate was concentrated in vacuo to afford 190 mg of the desired product as an oil that was used without further purification: ESI-MS m/z calc. 295.12, found 296.17 (M+1)⁺. Retention time: 0.69 minutes peak RT=0.69 (M+H) 296 is desired product.

Formation of (+/−)-2-(2-methyl-4-(methylsulfonyl)phenyl)azepane (131)

To a cold (−78° C.) solution of 2-(2-methyl-4-methylsulfonyl-phenyl)azepane-1-carbaldehyde, 130, (0.170 g, 0.576 mmol) in THF (4 mL) was added n-butyllithium (0.450 mL of 1.6 M solution in hexanes, 0.720 mmol). After 30 minutes, added another 0.4 mL of nBuLi solution. After an additional 10 minutes, stopped reaction by slow addition of reaction mixture into water. The aqueous phase was extracted twice with EtOAc. The combined organic phases were dried (MgSO₄), filtered and concentrated in vacuo to afford 90 mg of crude orange oil that was used in next step without further purification: ESI-MS m/z calc. 267.13, found 268.16 (M+1)⁺. Retention time: 0.69 minutes peak RT=0.69 (M+H) 296 is desired product.

Formation of (+/−)-4-methyl-6-(2-(2-methyl-4-(methylsulfonyl)phenyl)azepan-1-yl)pyrimidin-2-amine (132) I-37

To a solution of 2-(2-methyl-4-methylsulfonyl-phenyl)azepane, 131, (0.090 g, 0.337 mmol) in NMP (2 mL) was added 4-chloro-6-methyl-pyrimidin-2-amine (0.048 g, 0.337 mmol). The reaction mixture was heated reaction to 150° C. overnight in a sealable vial with teflon septum. After 15 hours, the mixture was cooled to room temperature and loaded directly onto a 15 g ISCO c18-aq column and purified by reverse phase silica gel chromatography running with 0.1% TFA/H₂O and 0.1% TFA/CH₃CN. The combined fractions containing desired product were concentrated in vacuo and the resulting residue was diluted with dichloromethane and neutralized with aqueous saturated NaHCO₃ solution. The mixture was passed through a phase separator and the resulting organic phase was concentrated in vacuo to afford 46 mg of the desired product as a light brown solid: high temperature (360 K) $^1$H NMR (400 MHz, DMSO-d6) δ 7.71-7.53 (m, 3H), 7.31 (d, J=8.2 Hz, 1H), 5.34 (s, 2H), 4.24 (s, 1H), 3.57-3.44 (m, 1H), 3.15-3.05 (m, 1H), 3.10 (s, 3H), 2.55 (s, 3H), 2.51-2.40 (m, 1H), 2.29-2.08 (m, 1H), 2.01 (s, 3H), 1.98-1.88 (m, 1H), 1.88-1.59 (m, 2H), 1.59-1.13 (m, 3H); ESI-MS m/z calc. 374.18, found 375.23 (M+1)⁺. Retention time: 0.61 minutes.

The following analog was prepared in the same fashion:

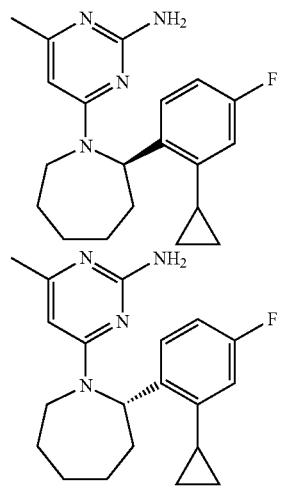

(R)-4-(2-(2-cyclopropyl-4-fluorophenyl)azepan-1-yl)-6-methylpyrimidin-2-amine I-47 and (S)-4-(2-(2-cyclopropyl-4-fluorophenyl)azepan-1-yl)-6-methylpyrimidin-2-amine I-46

Peak A: $^1$H NMR (400 MHz, DMSO-d6) δ 7.06 (dd, J=8.7, 6.1 Hz, 1H), 6.83 (td, J=8.6, 2.8 Hz, 1H), 6.69 (dd, J=10.7, 2.8 Hz, 1H), 5.63 (d, J=15.1 Hz, 1H), 5.46-5.19 (m, 3H), 4.39 (s, 1H), 3.42 (dd, J=14.6, 11.1 Hz, 1H), 2.33 (dt, J=14.1, 6.4 Hz, 1H), 2.22 (p, J=8.3 Hz, 1H), 1.99 (s, 3H), 1.96-1.84 (m, 1H), 1.84-1.60 (m, 3H), 1.52 (d, J=12.7 Hz, 1H), 1.44-1.18 (m, 2H), 1.13-0.91 (m, 2H), 0.78 (dtd, J=13.8, 10.6, 10.0, 4.6 Hz, 2H); ESI-MS m/z found 341.24 (M+1)$^+$. Retention time: 0.70 minutes; [α]$_D$=−12.57 (c=21 mg/3 mL).

Peak B: $^1$H NMR (400 MHz, DMSO-d6) δ 7.13-6.98 (m, 1H), 6.83 (td, J=8.6, 3.0 Hz, 1H), 6.75-6.64 (m, 1H), 5.62 (s, 1H), 5.49-5.25 (m, 3H), 4.40 (s, 1H), 3.70 (s, 1H), 3.42 (dd, J=14.7, 11.0 Hz, 1H), 2.41-2.25 (m, 1H), 2.28-2.11 (m, 1H), 2.04-1.95 (m, 3H), 1.92 (s, 1H), 1.88-1.62 (m, 3H), 1.61-1.44 (m, 1H), 1.44-1.18 (m, 2H), 1.14-0.94 (m, 2H), 0.87-0.64 (m, 2H); ESI-MS m/z found 341.24 (M+1)$^+$. Retention time: 0.70 minutes; [α]$_D$=+31.94 (c=23 mg/3 mL).

Example 17

Synthetic Scheme 17: (+/−)-4-(3-(2-fluoro-4-(methylsulfonyl)phenyl)-1,4-oxazepan-4-yl)-6-methyl-pyrimidin-2-amine (135) I-60

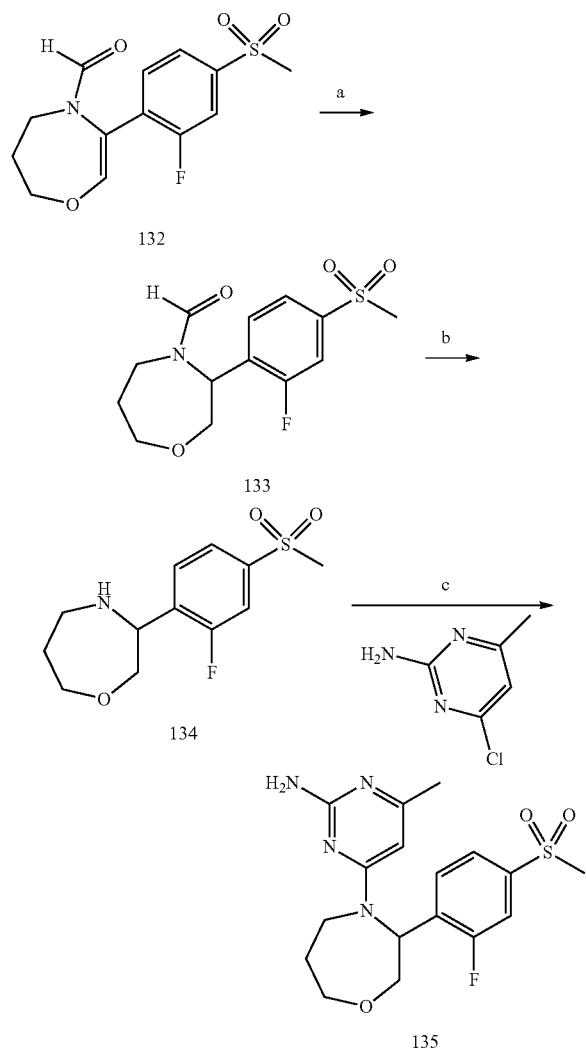

(a) Pd/C, HOAc, EtOAc, MeOH; (b) HCl, MeOH, reflux; (c) 2-amino-4-chloro-6-methylpyrimidine, NMP, 150° C.

Formation of 3-(2-fluoro-4-(methylsulfonyl)phenyl)-6,7-dihydro-1,4-oxazepine-4(5H)-carbaldehyde (133)

Intermediate 132 was prepared to Synthetic Scheme 13 using 2-fluoro-4-(methylsulfonyl)-benzaldehyde instead of 2-chloro-5-hydroxybenzaldehyde.

Formation of (+/−)-3-(2-fluoro-4-(methylsulfonyl) phenyl)-1,4-oxazepane-4-carbaldehyde (133)

A mixture of 3-(2-fluoro-4-methylsulfonyl-phenyl)-6,7-dihydro-5H-1,4-oxazepine-4-carbaldehyde, 132, (0.73 g, 2.30 mmol), palladium on carbon (0.23 g, 2.18 mmol) in EtOAc (6 mL) and MeOH (6 mL) and acetic acid (3 mL) was stirred under an atmosphere of hydrogen gas. After 8 days, the reaction was stopped. The mixture was filtered through a small pad of florosil and washed with EtOAc. The organic phase was neutralized by washing with aqueous saturated NaHCO$_3$ solution, dried (MgSO$_4$), filtered and concentrated filtrate in vacuo to afford 280 mg colorless oil. The resulting residue was used without further purification.

Formation of (+/−)-3-(2-fluoro-4-(methylsulfonyl) phenyl)-1,4-oxazepane (134)

A solution of 3-(2-fluoro-4-methylsulfonyl-phenyl)-1,4-oxazepane-4-carbaldehyde, 133, (0.28 g, 0.93 mmol) in methanol (6 mL) and concentrated HCl (5.5 mL of 12.1 M, 66.55 mmol) was heated to reflux for 2.5 hours. The mixture was cooled to room temperature and diluted into water. The mixture was neutralized by addition of aqueous saturated NaHCO$_3$ solution and then extracted three times with EtOAc. The organic phase was dried (MgSO$_4$), filtered and concentrated in vacuo to afford the desired product. ESI-MS m/z calc. 274, found 274 (M+1)$^+$. Retention time: 0.48 minutes.

Formation of (+/−)-4-(3-(2-fluoro-4-(methylsulfonyl)phenyl)-1,4-oxazepan-4-yl)-6-methyl-pyrimidin-2-amine (135) I-60

To a solution of 3-(2-fluoro-4-methylsulfonyl-phenyl)-1,4-oxazepane (0.25 g, 0.81 mmol) in NMP (10 mL) was added triethylamine (1.00 mL, 8.89 mmol) and 4-chloro-6-methyl-pyrimidin-2-amine (0.13 g, 0.87 mmol). The reaction mixture was heated to 150° C. After 17 hours, cooled mixture to room temperature and loaded material directly onto 100 g ISCO c18-aq column and purified by reverse phase running with 0.1% TFA/H$_2$O and 0.1% TFA/CH$_3$CN. Pure fractions containing desired product were concentrated in vacuo, diluted with dichloromethane. The mixture was passed through a phase separator and the organic phase was concentrated in vacuo to afford 69 mg of the desired product as a light brown solid: high temperature (360 K) $^1$H NMR (400 MHz, DMSO-d6) δ 7.71-7.56 (m, 2H), 7.52-7.40 (m, 1H), 5.71 (s, 1H), 5.66-5.59 (m, 1H), 5.40 (s, 2H), 4.32-4.16 (m, 1H), 4.09 (dd, J=13.4, 5.2 Hz, 1H), 3.88-3.78 (m, 1H), 3.74 (dd, J=13.3, 10.0 Hz, 1H), 3.63-3.38 (m, 2H), 3.11 (s, 3H), 1.97 (s, 3H), 1.84-1.60 (m, 2H).

The following analog was prepared according to Synthetic Scheme 17:

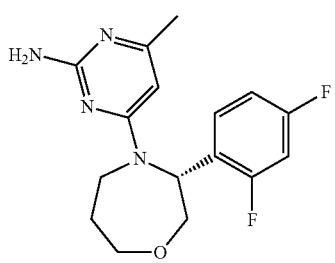

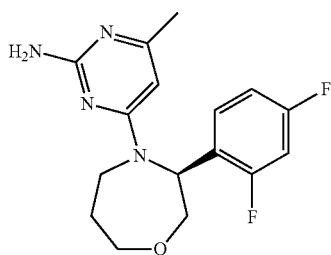

4-[3-(2,4-difluorophenyl)-1,4-oxazepan-4-yl]-6-methyl-pyrimidin-2-amine (136) I-58 high temperature (360 K) ¹H NMR (400 MHz, DMSO-d6) δ 7.36-7.27 (m, 1H), 7.13-7.05 (m, 1H), 6.97 (td, J=8.2, 1.9 Hz, 1H), 5.73 (s, 1H), 5.58-5.50 (m, 1H), 5.45 (s, 2H), 4.37 (d, J=15.7 Hz, 1H), 4.10 (dd, J=12.9, 5.7 Hz, 1H), 3.92-3.85 (m, 1H), 3.78 (dd, J=13.3, 10.0 Hz, 1H), 3.62-3.51 (m, 2H), 2.04 (s, 3H), 1.89-1.68 (m, 2H); ESI-MS m/z calc. 320.14, found 321.11 (M+1)⁺. Retention time: 0.6 minutes. The racemic mixture was submitted for SFC chiral separation.

Peak A; (R)-4-[3-(2,4-difluorophenyl)-1,4-oxazepan-4-yl]-6-methyl-pyrimidin-2-amine (137); 99.5% ee; high temperature (360 K) ¹H NMR (400 MHz, DMSO-d6) δ 7.36-7.27 (m, 1H), 7.13-7.05 (m, 1H), 6.97 (td, J=8.2, 1.9 Hz, 1H), 5.73 (s, 1H), 5.58-5.50 (m, 1H), 5.45 (s, 2H), 4.37 (d, J=15.7 Hz, 1H), 4.10 (dd, J=12.9, 5.7 Hz, 1H), 3.92-3.85 (m, 1H), 3.78 (dd, J=13.3, 10.0 Hz, 1H), 3.62-3.51 (m, 2H), 2.04 (s, 3H), 1.89-1.68 (m, 2H); ESI-MS m/z calc. 320.14, found 321.13 (M+1)⁺. Retention time: 0.6 minutes. I-61.

Peak B; (S)-4-[3-(2,4-difluorophenyl)-1,4-oxazepan-4-yl]-6-methyl-pyrimidin-2-amine (138); 99.5% ee; high temperature (360 K) ¹H NMR (400 MHz, DMSO-d6) δ 7.36-7.27 (m, 1H), 7.13-7.05 (m, 1H), 6.97 (td, J=8.2, 1.9 Hz, 1H), 5.73 (s, 1H), 5.58-5.50 (m, 1H), 5.45 (s, 2H), 4.37 (d, J=15.7 Hz, 1H), 4.10 (dd, J=12.9, 5.7 Hz, 1H), 3.92-3.85 (m, 1H), 3.78 (dd, J=13.3, 10.0 Hz, 1H), 3.62-3.51 (m, 2H), 2.04 (s, 3H), 1.89-1.68 (m, 2H). ESI-MS m/z calc. 320.14, found 321.16 (M+1)⁺. Retention time: 0.6 minutes. I-62.

Example 18

Synthetic Scheme 18: (+/−)-4-(3-(2-chloro-5-(methylsulfinyl)phenyl)-1,4-oxazepan-4-yl)-6-methylpyrimidin-2-amine (143) I-110

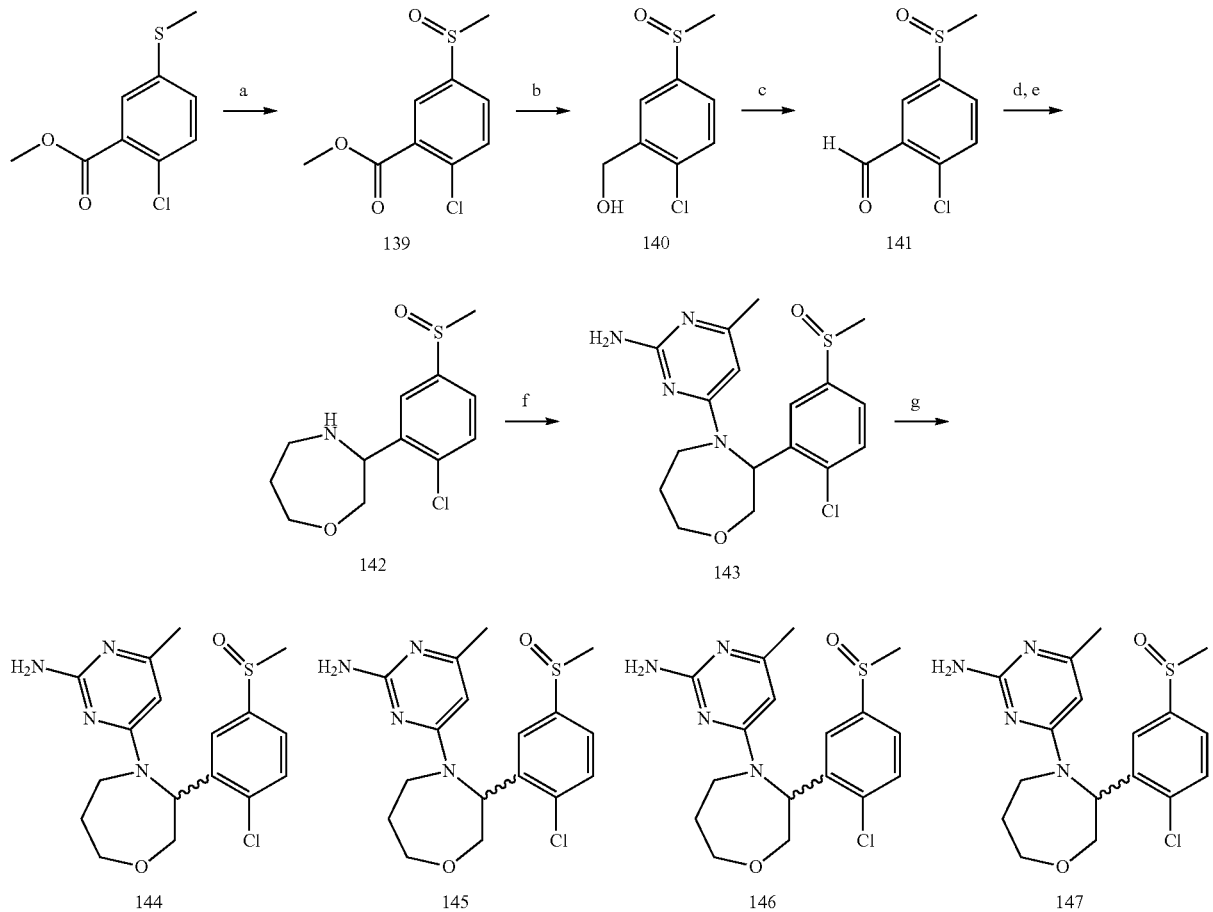

(a) mCPBA, CH$_2$Cl$_2$, 0° C.; (b) NaBH$_4$, EtOH; (c) Dess-Martin periodinane, CH$_2$Cl$_2$; (d) 4 A mol sieves, 3-((tributylstannyl)methoxy)propan-1-amine, CH$_2$Cl$_2$; (e) 2,6-lutidine, Cu(OTf)$_2$, hexafluoroisopropanol, CH$_2$Cl$_2$; (f) 2-amino-4-chloro-6-methylpyrimidine, NMP, 150° C.; (g) SFC chiral separation Formation of methyl
2-chloro-5-(methylsulfinyl)benzoate (139)

To a cold (0° C.) solution of methyl 2-chloro-5-methylsulfanyl-benzoate (2.0 g, 9.2 mmol) in dichloromethane (40 mL) was added 3-chloroperoxybenzoic acid (2.1 g of 77% w/w, 9.4 mmol). The reaction mixture was slowly warmed to room temperature over 3 hours. After 3.5 hours, the reaction mixture was diluted into aqueous saturated NaHCO$_3$ solution and extracted twice with dichloromethane. Combined organic phases were washed twice with aqueous saturated NaHCO$_3$ solution and then passed through a phase separator. The resulting filtrate was concentrated in vacuo. The crude residue was purified via silica gel chromatography using an 80 g isco column using 0-30% EtOAc/CH$_2$Cl$_2$ gradient to afford 1.8 g as a white solid: $^1$H NMR (400 MHz, DMSO-d6) δ 8.11 (dd, J=2.2, 0.4 Hz, 1H), 7.88 (dd, J=8.3, 2.2 Hz, 1H), 7.80 (dd, J=8.4, 0.4 Hz, 1H), 3.90 (s, 3H), 2.80 (s, 3H); ESI-MS m/z calc. 232.00, found 233.08 (M+1)$^+$. Retention time: 0.63 minutes.

Formation of
(2-chloro-5-(methylsulfinyl)phenyl)methanol (140)

To a solution of methyl 2-chloro-5-methylsulfinyl-benzoate, 139, (0.88 g, 3.79 mmol) in EtOH (15 mL) was added NaBH$_4$ (0.57 g, 15.09 mmol) in portions. The reaction was stirred at room temperature for 30 minutes and then heated to 50° C. After 3 hours, the reaction mixture was quenched by slow addition into aqueous saturated NaHCO$_3$ solution and extracted twice with EtOAc. The combined organic phases were washed with aqueous saturated NH$_4$Cl solution, dried (MgSO$_4$), filtered and concentrated in vacuo to give 486 mg of desired product: $^1$H NMR (400 MHz, DMSO-d6) δ 7.92-7.81 (m, 1H), 7.69-7.53 (m, 2H), 5.58 (t, J=5.6 Hz, 1H), 4.62 (dt, J=5.6, 0.8 Hz, 2H), 2.74 (s, 3H); ESI-MS m/z calc. 204.00, found 205.07 (M+1)$^+$. Retention time: 0.55 minutes.

Formation of
2-chloro-5-(methylsulfinyl)benzaldehyde (141)

(2-chloro-5-methylsulfinyl-phenyl)methanol, 140, (0.48 g, 2.35 mmol) was dissolved in methylene chloride (9.6 mL). Dess-Martin periodinane (1.20 g, 2.83 mmol) was added and the reaction solution was stirred at room temperature for 16 hours. The solution was diluted into aqueous saturated NaHCO$_3$ solution and extracted twice with CH$_2$Cl$_2$. The combined organic phases were filtered through a phase separator and concentrated in vacuo. The crude residue was purified via silica gel chromatography with 40 g isco column using 0-20% EtOAc/CH$_2$Cl$_2$ gradient to afford 429 mg of desired product: $^1$H NMR (400 MHz, DMSO-d6) δ 10.37 (s, 1H), 8.17-8.15 (m, 1H), 7.99 (dd, J=8.3, 2.3 Hz, 1H), 7.87-7.83 (m, 1H), 2.81 (s, 3H); ESI-MS m/z calc. 202.0, found 203.0 (M+1)$^+$, Retention time: 0.59 minutes.

Formation of 3-(2-chloro-5-(methylsulfinyl)phenyl)-
1,4-oxazepane (142)

To a solution of 3-(tributylstannylmethoxy)propan-1-amine, 141, (0.78 g, 2.05 mmol) in dichloromethane (5 mL) was added 2-chloro-5-methylsulfinyl-benzaldehyde (0.42 g, 1.99 mmol) followed by 4 angstrom molecular sieves. The mixture was stirred overnight, filtered to remove the sieves and washed with dichloromethane (20 mL).

In a separate flask containing hexafluoroisopropanol (5.5 mL) was added 2,6-lutidine (0.24 mL, 2.05 mmol) followed by Cu(OTf)$_2$ (0.72 g, 2.00 mmol). The mixture was stirred for 1 hour. Then the imine solution prepared above was added in one portion. The reaction was stirred at room temperature. After 3 days, the mixture was diluted with 60 mL of 2:1 aqueous saturated NaHCO$_3$ solution and 10% ammonium hydroxide. After stirring for 30 minutes, the organic layer was removed and washed twice with aqueous saturated NaHCO$_3$ solution, then brine. The organic layer was passed through a phase separator funnel and concentrated in vacuo. The crude residue, which contains hexafluoroisopropanol, was loaded directly onto a 100 gram c18-aq column and purification via reverse phase chromatography eluting with 0.1% TFA/H$_2$O and 0.1% TFA/CH$_3$CN. The fractions containing product were concentrated in vacuo, diluted with dichloromethane and neutralized with aqueous saturated NaHCO$_3$ solution. The mixture was passed through a phase separator and the organic filtrated was concentrated in vacuo to afford 110 mg of desired product: ESI-MS m/z calc. 270.06, found 271.11 (M+1)$^+$. Retention time: 0.46 minutes.

Formation of (+/−)-3-(2-chloro-5-(methylsulfinyl)
phenyl)-1,4-oxazepane (143)

To a solution of 3-(2-chloro-5-methylsulfinyl-phenyl)-1,4-oxazepane, 142, (0.11 g, 0.40 mmol) in NMP (5 mL) was added 4-chloro-6-methyl-pyrimidin-2-amine (0.08 g, 0.52 mmol). The reaction mixture was heated to 150° C. for 17 hours. The mixture was cooled to room temperature and loaded directly onto 50 g ISCO c18-aq column and the crude was purified by reverse phase eluting with 0.1% TFA/H$_2$O and 0.1% TFA/CH$_3$CN gradient. The fractions containing desired product were concentrated in vacuo, diluted with dichloromethane, neutralized with aqueous saturated NaHCO$_3$ solution and the mixture was passed through a phase separator. The organic phase concentrated in vacuo to afford 50 mg of desired product as a mixture of 4 stereoisomers: high temperature (360 K) $^1$H NMR (400 MHz, DMSO-d6) δ 7.69-7.48 (m, 3H), 5.66 (s, 1H), 5.58-5.50 (m, 1H), 5.43 (s, 2H), 4.60-4.46 (m, 1H), 4.18-4.04 (m, 1H), 3.95-3.85 (m, 1H), 3.85-3.66 (m, 2H), 3.65-3.49 (m, 1H), 2.68 (d, J=4.9 Hz, 3H), 2.02 (d, J=2.4 Hz, 3H), 1.86-1.67 (m, 2H). ESI-MS m/z calc. 380.11, found 381.22 (M+1)$^+$. Retention time: 0.53 minutes.

The mixture (34 mg) was submitted for SFC chiral separation to afford 4 stereoisomers:

Peak A: (144) high temperature (360 K) $^1$H NMR (400 MHz, DMSO-d6) δ 7.72-7.50 (m, 3H), 5.66 (s, 1H), 5.62-5.50 (m, 1H), 5.44 (s, 2H), 4.64-4.45 (m, 1H), 4.12 (dd, J=13.3, 5.2 Hz, 1H), 3.98-3.86 (m, 1H), 3.84-3.49 (m, 3H), 2.69 (s, 3H), 2.03 (d, J=1.6 Hz, 3H), 1.89-1.67 (m, 2H); ESI-MS m/z calc. 380.11, found 381.22 (M+1)$^+$. Retention time: 0.53 minutes. I-120.

Peak B: (145) high temperature (360 K) $^1$H NMR (400 MHz, DMSO-d6) δ 7.68-7.47 (m, 3H), 5.65 (s, 1H), 5.62-5.50 (m, 1H), 5.42 (s, 2H), 4.61-4.46 (m, 1H), 4.13 (dd, J=13.4, 4.9 Hz, 1H), 3.99-3.66 (m, 3H), 3.64-3.47 (m, 1H), 2.70-2.67 (m, 3H), 2.02 (s, 3H), 1.85-1.69 (m, 2H); ESI-MS m/z calc. 380.11, found 381.22 (M+1)$^+$. Retention time: 0.53 minutes. I-121.

Peak C: (146) high temperature (360 K) $^1$H NMR (400 MHz, DMSO-d6) δ 7.68-7.47 (m, 3H), 5.65 (s, 1H), 5.62-5.50 (m, 1H), 5.42 (s, 2H), 4.61-4.46 (m, 1H), 4.13 (dd, J=13.4, 4.9 Hz, 1H), 3.99-3.66 (m, 3H), 3.64-3.47 (m, 1H), 2.70-2.67 (m, 3H), 2.02 (s, 3H), 1.85-1.69 (m, 2H); ESI-MS m/z calc. 380.11, found 381.22 (M+1)$^+$. Retention time: 0.53 minutes. I-122.

Peak D: (147) high temperature (360 K) $^1$H NMR (400 MHz, DMSO-d6) δ 7.68-7.48 (m, 3H), 5.65 (s, 1H), 5.61-5.49 (m, 1H), 5.43 (s, 2H), 4.59-4.42 (m, 1H), 4.12 (dd, J=13.5, 5.0 Hz, 1H), 4.00-3.65 (m, 3H), 3.65-3.45 (m, 1H), 2.72-2.66 (m, 3H), 2.02 (s, 3H), 1.86-1.68 (m, 2H); ESI-MS m/z calc. 380.11, found 381.22 (M+1)$^+$. Retention time: 0.53 minutes. I-123.

Example 19

Synthetic Scheme 19: (+/−)-1-(3-(4-(2-amino-6-methylpyrimidin-4-yl)-1,4-oxazepan-3-yl)-4-chlorophenyl)-2,2,2-trifluoroethan-1-ol (154) I-134

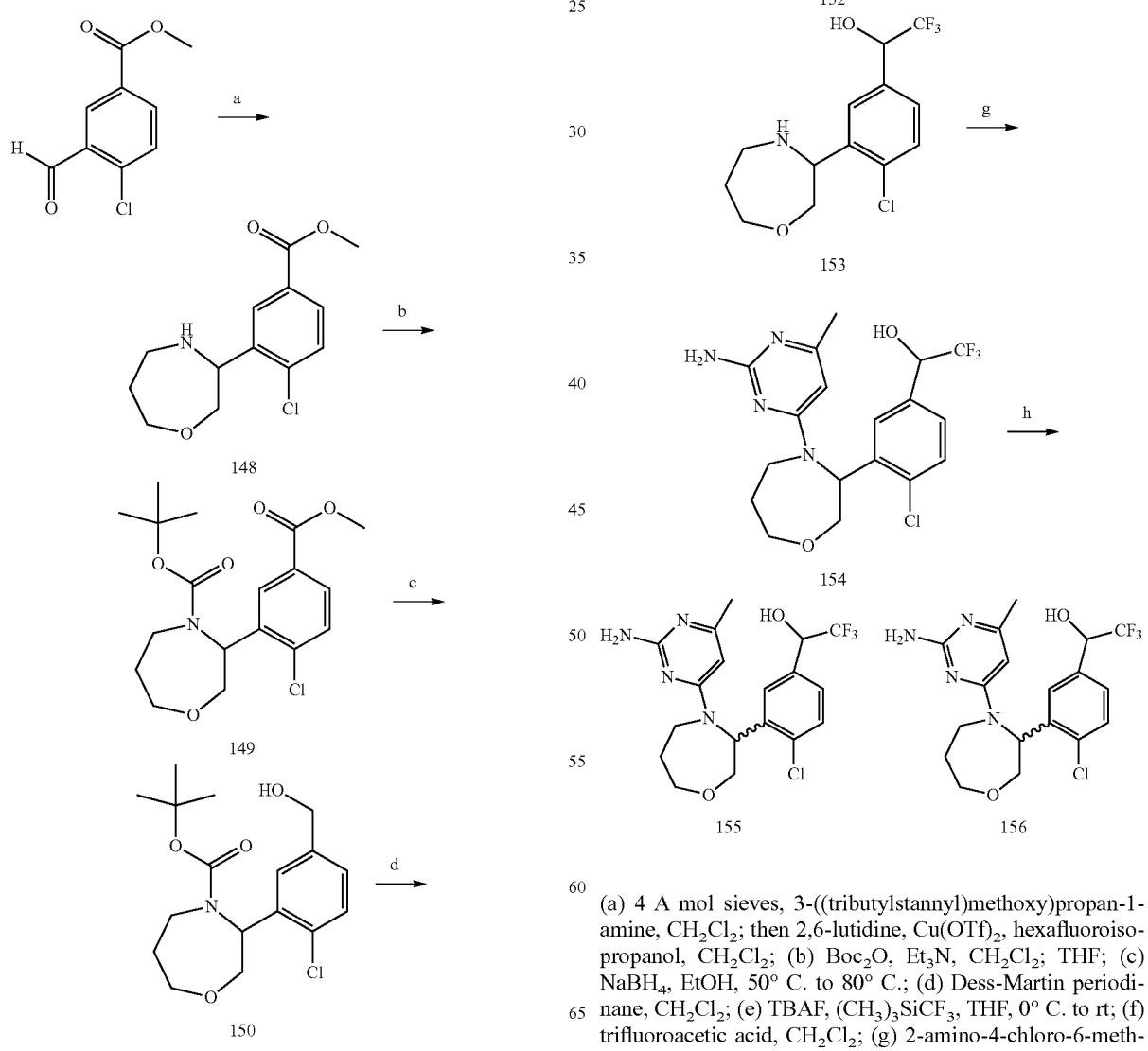

(a) 4 A mol sieves, 3-((tributylstannyl)methoxy)propan-1-amine, CH$_2$Cl$_2$; then 2,6-lutidine, Cu(OTf)$_2$, hexafluoroisopropanol, CH$_2$Cl$_2$; (b) Boc$_2$O, Et$_3$N, CH$_2$Cl$_2$; THF; (c) NaBH$_4$, EtOH, 50° C. to 80° C.; (d) Dess-Martin periodinane, CH$_2$Cl$_2$; (e) TBAF, (CH$_3$)$_3$SiCF$_3$, THF, 0° C. to rt; (f) trifluoroacetic acid, CH$_2$Cl$_2$; (g) 2-amino-4-chloro-6-methylpyrimidine, NMP, 150° C.; (h) SFC chiral separation

Formation of methyl 4-chloro-3-(1,4-oxazepan-3-yl)benzoate (148)

To a solution of 3-(tributylstannylmethoxy)propan-1-amine (2.09 g, 5.53 mmol) in dichloromethane (14 mL) was added methyl 4-chloro-3-formyl-benzoate (1.12 g, 5.36 mmol) followed by 4 angstrom molecular sieves. The mixture was stirred overnight, filtered to remove the sieves, washed with dichloromethane (50 mL).

In a separate flask containing hexafluoroisopropanol (14 mL) was added 2,6-lutidine (0.64 mL, 5.52 mmol) followed by Cu(OTf)$_2$ (1.95 g, 5.40 mmol). The mixture was stirred for 1 hour, then the imine solution prepared above was added in one portion. The reaction mixture turned from blue to green and the mixture was stirred over night at room temperature. The mixture was diluted with 120 mL of 2:1 aqueous saturated NaHCO$_3$ solution and 10% ammonium hydroxide. After stirring for 40 minutes, the mixture was diluted with dichloromethane (50 mL) and the organic layer was removed and washed twice with aqueous saturated NaHCO$_3$ solution. The organic layer was passed through a phase separator funnel and concentrated in vacuo. The crude residue was purified by reverse phase ISCO using a 100 gram c18-aq column eluting with 0.1% TFA/H$_2$O and 0.1% TFA/CH$_3$CN. The fractions containing desired product were concentrated in vacuo, diluted with dichloromethane, neutralized with aqueous saturated NaHCO$_3$ solution and the mixture was passed through a phase separator. The organic phase concentrated in vacuo to afford 754 mg of desired product as a yellow oil: $^1$H NMR (400 MHz, DMSO-d6) δ 8.23 (d, J=2.3 Hz, 1H), 7.82 (dd, J=8.3, 2.2 Hz, 1H), 7.56 (d, J=8.3 Hz, 1H), 4.26 (dd, J=8.9, 3.2 Hz, 1H), 3.87 (s, 4H), 3.84-3.78 (m, 2H), 3.72 (ddd, J=12.0, 6.7, 6.0 Hz, 1H), 3.26 (dd, J=12.3, 8.9 Hz, 1H), 3.10 (dt, J=13.5, 5.1 Hz, 1H), 2.88 (ddd, J=13.0, 7.2, 5.3 Hz, 2H), 1.89 (dtd, J=7.9, 6.1, 5.0 Hz, 2H); ESI-MS m/z calc. 269.08, found 270.19 (M+1)$^+$. Retention time: 0.53 minutes.

Formation of tert-butyl 3-(2-chloro-5-(methoxycarbonyl)phenyl)-1,4-oxazepane-4-carboxylate (149)

A mixture of methyl 4-chloro-3-(1,4-oxazepan-3-yl)benzoate, 148, (0.51 g, 1.80 mmol) and triethylamine (0.28 mL, 2.00 mmol) in THF (8 mL) was added tert-butoxycarbonyl tert-butyl carbonate (0.41 g, 1.90 mmol) and the mixture was stirred overnight at room temperature. The reaction mixture was diluted into aqueous saturated NH$_4$Cl solution and extracted with dichloromethane. The organic phase was passed through a phase separator funnel and concentrated in vacuo. The crude residue was purified by silica gel chromatography using 40 g ISCO column (0-20% EtOAc/CH$_2$Cl$_2$ gradient) to give 545 mg of desired product as a colorless oil: $^1$H NMR (400 MHz, DMSO-d6) δ 7.92-7.78 (m, 2H), 7.61 (d, J=8.2 Hz, 1H), 5.48-5.23 (m, 1H), 4.37-4.24 (m, 1H), 3.90 (s, 2H), 3.86 (s, 3H), 3.76-3.43 (m, 3H), 1.87-1.56 (m, 2H), 1.42-1.04 (m, 9H); ESI-MS m/z calc. 369.13, found 370.33 (M+1)$^+$. Retention time: 0.92 minutes.

Formation of tert-butyl 3-(2-chloro-5-(hydroxymethyl)phenyl)-1,4-oxazepane-4-carboxylate (150)

To a solution of tert-butyl 3-(2-chloro-5-methoxycarbonyl-phenyl)-1,4-oxazepane-4-carboxylate, 149, (0.52 g, 1.47 mmol) in EtOH (9 mL) was added NaBH$_4$ (0.22 g, 5.84 mmol) in portions. The reaction was stirred at room temperature for 15 minutes and then heated to 50° C. for 23 hours. The temperature was increased to 80° C. and stirred at this temperature for 12 hours. The reaction was quenched by slow addition into aqueous saturated NaHCO$_3$ solution. The aqueous phase was extracted twice with EtOAc. The combined organic phases were washed with aqueous saturated NH$_4$Cl solution, dried (MgSO$_4$), filtered and concentrated in vacuo. The crude residue was purified via silica gel chromatography with 40 g isco column using 0-60% (EtOAc/CH$_2$Cl$_2$) to afford 270 mg of desired product as a white solid: $^1$H NMR (400 MHz, DMSO-d6) δ 7.36 (d, J=8.1 Hz, 1H), 7.27-7.16 (m, 2H), 5.28 (dt, J=11.5, 5.2 Hz, 2H), 4.46 (d, J=5.6 Hz, 2H), 4.37-3.97 (m, 1H), 3.92 (d, J=10.7 Hz, 2H), 3.52 (dq, J=23.3, 12.7, 11.9 Hz, 3H), 1.72 (d, J=28.4 Hz, 2H), 1.52-1.03 (m, 9H).

Formation of tert-butyl 3-(2-chloro-5-formylphenyl)-1,4-oxazepane-4-carboxylate (151)

tert-Butyl 3-[2-chloro-5-(hydroxymethyl)phenyl]-1,4-oxazepane-4-carboxylate, 150, (0.27 g, 0.78 mmol) was dissolved in methylene chloride (6 mL). Dess-Martin periodinane (0.40 g, 0.93 mmol) was added and the reaction solution was stirred at room temperature for 18 hours. The mixture was diluted into aqueous saturated NaHCO$_3$ solution and extracted twice with EtOAc. The combined organic phases were dried (MgSO$_4$), filtered and concentrated in vacuo. The crude residue was purified via silica gel chromatography with a 40 g isco column using 0-30% EtOAc/CH$_2$Cl$_2$) gradient to afford 187 mg of desired product as a white solid: $^1$H NMR (400 MHz, DMSO-d6) δ 10.02 (s, 1H), 7.89-7.75 (m, 2H), 7.69 (d, J=8.7 Hz, 1H), 5.50-5.26 (m, 1H), 4.43-4.11 (m, 1H), 4.07-3.85 (m, 2H), 3.79-3.40 (m, 3H), 1.89-1.49 (m, 2H), 1.47-1.04 (m, 9H); ESI-MS m/z calc. 339.12, found 338.54 (M+1)$^+$. Retention time: 0.87 minutes.

Formation of tert-butyl 3-(2-chloro-5-(2,2,2-trifluoro-1-hydroxyethyl)phenyl)-1,4-oxazepane-4-carboxylate (152)

To a cold (0° C.) stirred solution of tert-butyl 3-(2-chloro-5-formyl-phenyl)-1,4-oxazepane-4-carboxylate, 151, (0.17 g, 0.48 mmol) and trimethyl(trifluoromethyl)silane (0.09 mL, 0.58 mmol) in THF (2 mL) was added tetrabutylammonium fluoride (0.05 mL of 1 M solution in THF, 0.05 mmol). The reaction mixture was stirred at 0° C. for 40 minutes and then at room temperature for 3 hours. The mixture was then diluted with 1 N aq. HCl (2 ml) and stirring was continued for a further 3 days. The mixture was diluted with dichloromethane and washed with aqueous saturated NaHCO$_3$. The aqueous phase was extracted again with dichloromethane. The combined organic phases were filtered through a phase separator and concentrated in vacuo. The resulting residue was purified by silica gel column chromatography using a 12 gram ISCO column eluting with 0 to 20% EtOAc/CH$_2$Cl$_2$ gradient to afford 80 mg of desired product as a white solid: $^1$H NMR (400 MHz, DMSO-d6) δ 7.56-7.30 (m, 3H), 6.90 (s, 1H), 5.43-5.13 (m, 2H), 4.42-4.07 (m, 1H), 3.98-3.80 (m, 2H), 3.65-3.34 (m, 3H), 1.85-1.48 (m, 2H), 1.43-1.03 (m, 9H).

Formation of 1-(4-chloro-3-(1,4-oxazepan-3-yl)phenyl)-2,2,2-trifluoroethan-1-ol (153)

To a solution of tert-butyl 3-[2-chloro-5-(2,2,2-trifluoro-1-hydroxy-ethyl)phenyl]-1,4-oxazepane-4-carboxylate, 152, (0.08 g, 0.18 mmol) in dichloromethane (2 mL) was added trifluoroacetic acid (2 mL). The reaction mixture was stirred at room temperature for one hour and concentrated in vacuo. The residue was dissolved in dichloromethane and neutralized by washing with aqueous saturated NaHCO₃ solution. The aqueous phase was back extracted with dichloromethane. The combined organic phases were passed through a phase separator and concentrated in vacuo to afford approximately 40 mg of desired product that was used without further purification: ESI-MS m/z calc. 309.07, found 310.17 (M+1)⁺. Retention time: 0.55 minutes.

Formation of (+/−)-1-(3-(4-(2-amino-6-methylpyrimidin-4-yl)-1,4-oxazepan-3-yl)-4-chlorophenyl)-2,2,2-trifluoroethan-1-ol (154)

To a solution of 1-[4-chloro-3-(1,4-oxazepan-3-yl)phenyl]-2,2,2-trifluoro-ethanol (0.040 g, 0.129 mmol) in NMP (1.5 mL) was added 4-chloro-6-methyl-pyrimidin-2-amine (0.024 g, 0.168 mmol). The reaction mixture was heated to 150° C. for 17 hours. After cooling the mixture to room temperature, the mixture was loaded directly onto 15 g ISCO c18-aq column and purified by reverse phase running with 0.1% TFA/H₂O and 0.1% TFA/CH₃CN. The fractions containing desired product were concentrated in vacuo, diluted with dichloromethane, neutralized with aqueous saturated NaHCO₃ solution and the mixture was passed through a phase separator. The organic phase concentrated in vacuo to afford 41 mg of desired product: heated (360K) ¹H NMR (400 MHz, DMSO-d6) δ 7.50-7.29 (m, 3H), 6.65-6.48 (m, 1H), 5.63 (d, J=19.0 Hz, 1H), 5.43 (s, 2H), 5.09 (t, J=6.8 Hz, 1H), 4.60 (d, J=15.2 Hz, 1H), 4.19-4.05 (m, 1H), 3.97-3.81 (m, OH), 3.78-3.47 (m, 3H), 2.01 (s, 3H), 1.78 (d, J=5.6 Hz, 2H); ESI-MS m/z calc. 416.12, found 417.28 (M+1)⁺. Retention time: 0.61 minutes.

The racemic product was submitted for SFC chiral separation. SFC conditions: (30% MeOH (5 mM ammonia) on Cellulose-2) to afford two separate racemic products:

Peak A, (S)-1-(3-(4-(2-amino-6-methylpyrimidin-4-yl)-1,4-oxazepan-3-yl)-4-chlorophenyl)-2,2,2-trifluoroethan-1-ol (155); 98.5% pure by HPLC: heated (360K) ¹H NMR (400 MHz, DMSO-d6) δ 7.54-7.30 (m, 3H), 6.56 (s, 1H), 5.63 (d, J=19.0 Hz, 1H), 5.55-5.37 (m, 3H), 5.09 (d, J=7.8 Hz, 1H), 4.60 (d, J=15.4 Hz, 1H), 4.12 (dd, J=13.4, 4.9 Hz, 1H), 3.89 (d, J=11.9 Hz, 1H), 3.76-3.41 (m, 3H), 2.01 (s, 3H), 1.89-1.71 (m, 2H). ESI-MS m/z calc. 416.12268, found 417.33 (M+1)⁺. Retention time: 0.6 minutes. I-145.

Peak B; (R)-1-(3-(4-(2-amino-6-methylpyrimidin-4-yl)-1,4-oxazepan-3-yl)-4-chlorophenyl)-2,2,2-trifluoroethan-1-ol (156); 99.5% pure by HPLC: heated (360K) ¹H NMR (400 MHz, DMSO-d6) δ 7.57-7.33 (m, 3H), 5.60 (s, 1H), 5.56-5.36 (m, 3H), 5.09 (q, J=7.4 Hz, 1H), 4.60 (d, J=14.9 Hz, 1H), 4.12 (dd, J=13.4, 4.9 Hz, 1H), 3.99-3.79 (m, 1H), 3.79-3.48 (m, 3H), 2.01 (s, 3H), 1.81 (d, J=19.9 Hz, 2H). I-146

The following analog was prepared according to Synthetic Scheme 19:

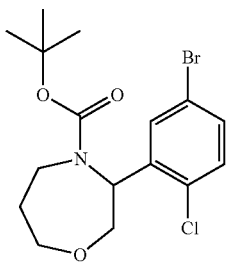

157 tert-butyl 3-(5-bromo-2-chloro-phenyl)-1,4-oxazepane-4-carboxylate (157)

¹H NMR (400 MHz, DMSO-d6) δ 7.50 (dd, J=8.5, 2.4 Hz, 1H), 7.46-7.33 (m, 2H), 5.38-5.14 (m, 1H), 4.38-4.03 (m, 1H), 3.89 (d, J=12.4 Hz, 2H), 3.75-3.52 (m, 2H), 3.49 (t, J=11.7 Hz, 1H), 1.71 (d, J=32.1 Hz, 2H), 1.45-1.05 (m, 9H); ESI-MS m/z calc. 389.04, found 390.27 (M+1)⁺. Retention time: 1.0 minutes.

Example 20

Synthetic Scheme 20: (+/−)-4-(3-(2-chloro-5-(1H-pyrazol-5-yl)phenyl)-1,4-oxazepan-4-yl)-6-methyl-pyrimidin-2-amine (159) I-157

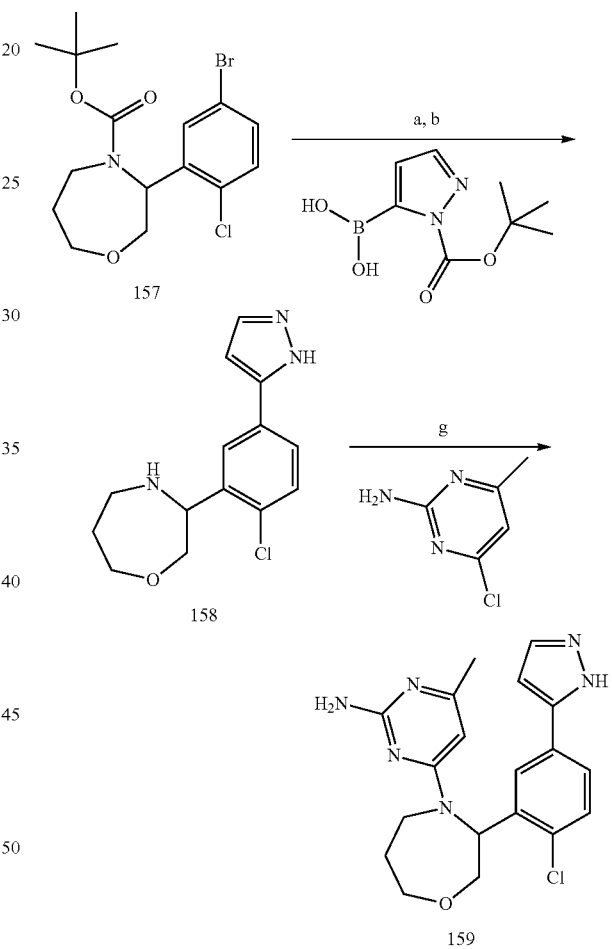

(a) (2-tert-butoxycarbonylpyrazol-3-yl)boronic acid, Pd(dppf)Cl₂—CH₂Cl₂, 1,4-dioxane, water, Na₂CO₃, 105° C., microwave; (b) dichloromethane, trifluoroacetic acid; (g) 2-amino-4-chloro-6-methylpyrimidine, NMP, 150° C.

Formation of 3-(2-chloro-5-(1H-pyrazol-5-yl)phenyl)-1,4-oxazepane (158)

To a suspension of tert-butyl 3-(5-bromo-2-chloro-phenyl)-1,4-oxazepane-4-carboxylate, 157, (0.48 g, 0.89 mmol) and (2-tert-butoxycarbonylpyrazol-3-yl)boronic acid (0.53 g, 2.48 mmol) in 1,4-dioxane (7.3 mL) and water (0.73 mL)

was added Pd(dppf)Cl₂.DCM (0.20 g, 0.25 mmol) and Na₂CO₃ (0.39 g, 3.72 mmol). The mixture was bubbled with nitrogen for 10 minutes and then heated in the microwave at 105° C. for 30 minutes. The mixture was diluted into water and extracted twice with EtOAc. The combined organic phases were washed with brine, dried (MgSO4), filtered and concentrated in vacuo. The crude material was diluted with dichloromethane (5 mL) and trifluoroacetic acid (5 mL) was added to the reaction mixture. The mixture was stirred at room temperature for 30 minutes and concentrated in vacuo. The resulting residue was loaded directly onto a 15 g ISCO c18-aq column and purified by reverse phase running with 0.1% TFA/H₂O and 0.1% TFA/CH₃CN.

Formation of (+/−)-4-(3-(2-chloro-5-(1H-pyrazol-5-yl)phenyl)-1,4-oxazepan-4-yl)-6-methyl-pyrimidin-2-amine (159) I-157

To a solution of 3-[2-chloro-5-(1H-pyrazol-5-yl)phenyl]-1,4-oxazepane, 158, (0.22 g, 0.50 mmol) in NMP (4.5 mL) was added 4-chloro-6-methyl-pyrimidin-2-amine (0.09 g, 0.65 mmol). The mixture was heated to 150° C. for 18 hours. The material was cooled to room temperature and loaded directly onto a 50 g ISCO c18-aq column and purified by reverse phase running with 0.1% TFA/H₂O and 0.1% TFA/CH₃CN. The fractions containing desired product along with an impurity were concentrated in vacuo, diluted with dichloromethane, neutralized with aqueous saturated NaHCO₃ solution and the mixture was passed through a phase separator. The organic phase concentrated in vacuo to afford 420 mg of desired product: heated (360K) ¹H NMR (400 MHz, DMSO-d6). The mixture was purified again via silica gel chromatography with 40 g isco GOLD column using 5-100% (20% MeOH—CH₂Cl₂/CH₂Cl₂) gradient to afford 5 mg of desired product: ¹H NMR (heated 360K) (400 MHz, DMSO-d6) δ 12.66 (s, 1H), 7.84-7.53 (m, 2H), 7.53-7.27 (m, 1H), 6.59 (s, 1H), 5.77-5.55 (m, 2H), 5.43 (s, 3H), 4.79-4.46 (m, 1H), 4.24-4.03 (m, 1H), 3.98-3.84 (m, 1H), 3.84-3.65 (m, 2H), 3.65-3.39 (m, 1H), 2.00 (s, 3H), 1.92-1.65 (m, 2H); ESI-MS m/z calc. 384.15, found 385.32 (M+1)⁺. Retention time: 0.57 minutes.

Example 21

Synthetic Scheme 21: (+/−)-N-(3-(4-(2-amino-6-methylpyrimidin-4-yl)-1,4-oxazepan-3-yl)-4-chlorophenyl)methanesulfonamide (164) I-74

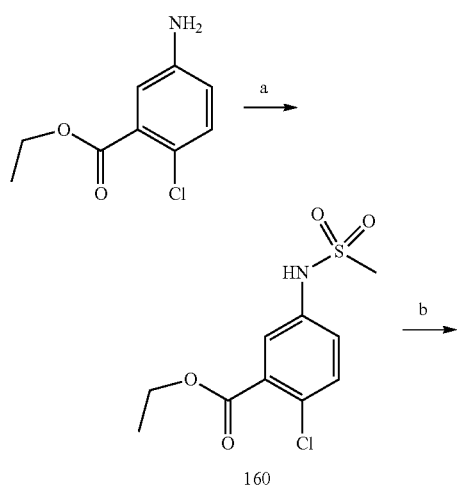
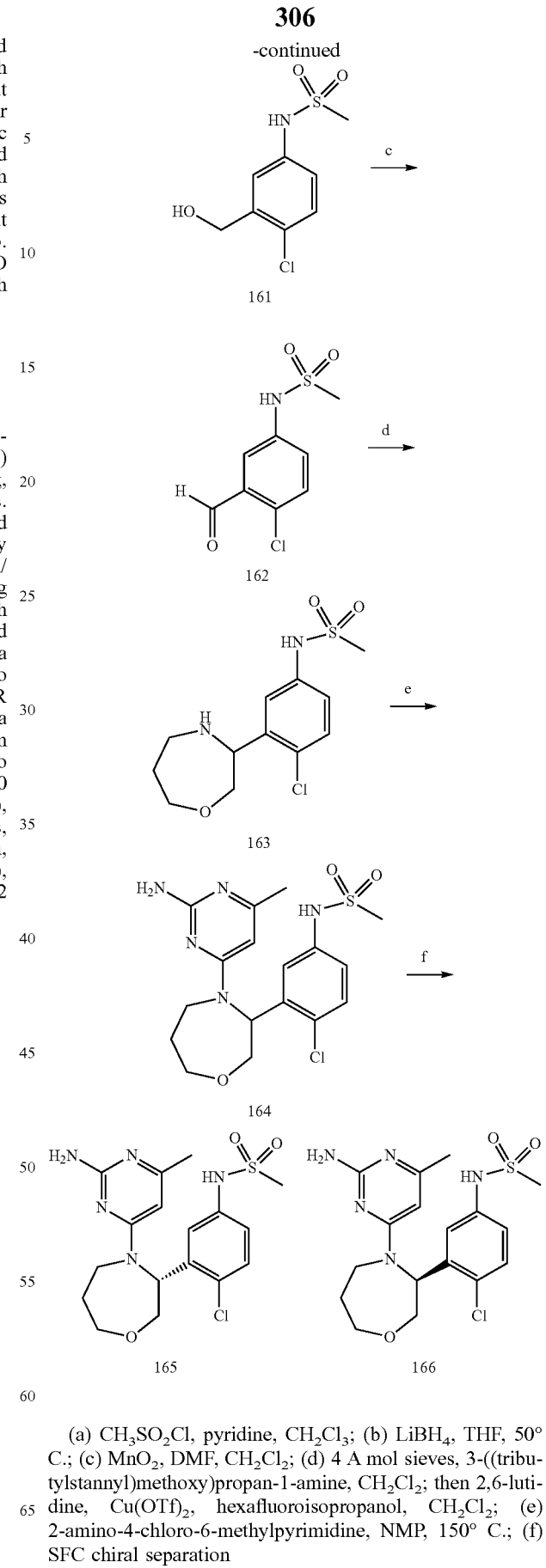

(a) CH₃SO₂Cl, pyridine, CH₂Cl₃; (b) LiBH₄, THF, 50° C.; (c) MnO₂, DMF, CH₂Cl₂; (d) 4 Å mol sieves, 3-((tributylstannyl)methoxy)propan-1-amine, CH₂Cl₂; then 2,6-lutidine, Cu(OTf)₂, hexafluoroisopropanol, CH₂Cl₂; (e) 2-amino-4-chloro-6-methylpyrimidine, NMP, 150° C.; (f) SFC chiral separation

Formation of ethyl 2-chloro-5-(methylsulfonamido)benzoate (160)

To a solution of ethyl 5-amino-2-chloro-benzoate (2.95 g, 14.80 mmol) in dichloromethane (60 mL) was added pyridine (1.32 mL, 16.30 mmol) followed by dropwise addition of methanesulfonyl chloride (1.26 mL, 16.30 mmol). The reaction mixture was stirred at room temperature for 22 hours. The mixture was diluted into aqueous saturated $NH_4Cl$ solution and extracted with EtOAc. The organic phase was dried ($MgSO_4$), filtered and concentrated in vacuo. The resulting residue was purified via silica gel chromatography with a 80 g isco GOLD column using 0-20% (EtOAc/$CH_2Cl_2$) to afford 2.6 grams of desired product: $^1$H NMR (400 MHz, DMSO-d6) δ 10.08 (s, 1H), 7.60 (d, J=2.7 Hz, 1H), 7.54 (d, J=8.8 Hz, 1H), 7.38 (dd, J=8.7, 2.8 Hz, 1H), 4.33 (q, J=7.1 Hz, 2H), 3.04 (s, 3H), 1.31 (t, J=7.1 Hz, 3H); ESI-MS m/z calc. 277.02, found 278.16 (M+1)$^+$. Retention time: 0.75 minutes.

Formation of N-(4-chloro-3-(hydroxymethyl)phenyl)methanesulfonamide (161)

To a solution of ethyl 2-chloro-5-(methanesulfonamido)benzoate, 160, (1.20 g, 4.10 mmol) in THF (20 mL) was added lithium borohydride (0.26 g, 11.80 mmol). The reaction was stirred at room temperature for 10 minutes and then heated to 50° C. for 8 hours and then room temperature for 3 days. The mixture was diluted into aqueous saturated $NH_4Cl$ solution and extracted twice with EtOAc. The combined organic phases were dried ($MgSO_4$), filtered and concentrated in vacuo to afford 900 mg of desired product as a white solid: $^1$H NMR (400 MHz, DMSO-d6) δ 9.84 (s, 1H), 7.44 (dd, J=2.8, 0.9 Hz, 1H), 7.35 (d, J=8.6 Hz, 1H), 7.11 (ddd, J=8.6, 2.8, 0.7 Hz, 1H), 5.43 (t, J=5.6 Hz, 1H), 4.52 (d, J=5.4 Hz, 2H), 2.98 (s, 3H).

Formation of N-(4-chloro-3-formylphenyl)methanesulfonamide (162)

To a solution of N-[4-chloro-3-(hydroxymethyl)phenyl]methanesulfonamide, 161, (1.8 g, 7.6 mmol) in dichloromethane (60 mL) and DMF (10 mL) was added manganese dioxide (10.9 g, 125.0 mmol). The reaction mixture was stirred at room temperature for 7 hours. The mixture was diluted with dichloromethane and filtered through a plug of celite and washed with dichloromethane. The filtrate was concentrated in vacuo. The resulting mixture was diluted into brine and extracted twice with EtOAc. The combined organic phases were washed with brine, dried ($MgSO_4$), filtered and concentrated in vacuo. The crude solid was mostly insoluble in dichloromethane and EtOAc. The solid was diluted with 50% EtOAc/dichloromethane. The filtrate was purified by silica gel chromatography with 40 g isco column using 0-30% EtOAc/$CH_2Cl_2$ gradient. The fractions containing clean product was combined with the precipitate to afford 1.08 grams of off-white solid: ESI-MS m/z calc. 232.99, found 234.03 (M+1)$^+$. Retention time: 0.69 minutes.

Formation of N-(4-chloro-3-(1,4-oxazepan-3-yl)phenyl)methanesulfonamide (163)

To a solution of 3-(tributylstannylmethoxy)propan-1-amine (1.79 g, 4.73 mmol) in dichloromethane (12 mL) was added N-(4-chloro-3-formyl-phenyl)methanesulfonamide, 162, (1.07 g, 4.58 mmol) followed by 4 angstrom molecular sieves. The mixture was stirred for 2 days, filtered to remove the sieves, and washed with dichloromethane (45 mL).

In a separate flask containing hexafluoroisopropanol (12 mL) was added 2,6-lutidine (0.55 mL, 4.72 mmol) followed by bis(trifluoromethylsulfonyloxy)copper (1.77 g, 4.89 mmol). The mixture was stirred for 1 h, then the imine solution prepared above was added in one portion. The mixture turned from blue to green. Mixture was stirred for 2 days at room temperature. The mixture was diluted with 150 mL of 2:1 aqueous saturated $NaHCO_3$ solution and 10% ammonium hydroxide. After stirring for 30 minutes, the organic layer was removed and washed twice with aqueous saturated $NaHCO_3$ solution. The organic layer was passed through a phase separator funnel and concentrated in vacuo. The crude residue was purified by reverse phase ISCO—150 gram c18-aq column—running with 0.1% TFA/$H_2O$ and 0.1% TFA/$CH_3CN$. The resulting product was purified again by reverse phase ISCO—100 gram c18-aq column—running with 0.1% TFA/$H_2O$ and 0.1% TFA/$CH_3CN$. All fractions containing product were concentrated in vacuo and the residue was diluted with aqueous saturated $NaHCO_3$ solution and extracted three times with dichloromethane and then three times with 10% MeOH/dichloromethane. The mixture was passed through a phase separator and the organic phase was concentrated in vacuo to afford 163 mg desired product: ESI-MS m/z calc. 304.06, found 305.18 (M+1)$^+$. Retention time: 0.51 minutes. LCMS still showed product in aqueous phase. The aqueous phase was concentrated in vacuo. The resulting white solid was diluted with acetonitrile and stirred vigorously for 30 minutes, filtered, washed with acetonitrile and the filtrate was concentrated in vacuo to afford 500 mg of mixture containing mostly desired product.

Formation of (R)—N-(3-(4-(2-amino-6-methylpyrimidin-4-yl)-1,4-oxazepan-3-yl)-4-chlorophenyl)methanesulfonamide (165) and (S)—N-(3-(4-(2-amino-6-methylpyrimidin-4-yl)-1,4-oxazepan-3-yl)-4-chlorophenyl)methanesulfonamide (166)

To a solution of N-[4-chloro-3-(1,4-oxazepan-3-yl)phenyl]methanesulfonamide, 163, (0.16 g, 0.53 mmol) in NMP (4 mL) was added 4-chloro-6-methyl-pyrimidin-2-amine (0.10 g, 0.69 mmol). The reaction mixture was heated to 150° C. for 16 hours. The reaction mixture was cooled to room temperature and loaded directly onto 50 g ISCO c18-aq column and purified by reverse phase running with 0.1% TFA/$H_2O$ and 0.1% TFA/$CH_3CN$. All fractions containing product were concentrated in vacuo and the resulting residue was diluted with dichloromethane, neutralized with aqueous saturated $NaHCO_3$ solution and passed through a phase separator. The organic phase was concentrated in vacuo to afford 233 mg of desired product as a light brown solid. The racemic mixture was submitted for SFC chiral separation.

Peak A: (R)—N-(3-(4-(2-amino-6-methylpyrimidin-4-yl)-1,4-oxazepan-3-yl)-4-chlorophenyl) methanesulfonamide (165); 74 mg of yellow solid. [□]$_D$=−128.77 (c=3.5 mg/0.8 mL MeOH), 99+% by chiral HPLC; 98+% ee. $^1$H NMR heated (360K) (400 MHz, DMSO-d6) δ 9.79-9.44 (m, 1H), 7.62-7.33 (m, 1H), 7.36-6.98 (m, 2H), 5.85-5.25 (m, 4H), 4.81-4.46 (m, 1H), 4.38-4.09 (m, 1H), 3.94 (s, 4H), 3.24 (s, 3H), 2.06 (s, 3H), 1.98-1.62 (m, 2H); ESI-MS m/z calc. 411.11, found 412.28 (M+1)$^+$. Retention time: 0.57 minutes. I-160.

Peak B: (S)—N-(3-(4-(2-amino-6-methylpyrimidin-4-yl)-1,4-oxazepan-3-yl)-4-chlorophenyl) methanesulfonamide (166); 65 mg of yellow solid. [☐]_D=+124.74 (c=3.1 mg/0.8 mL MeOH); 99+% by chiral HPLC; 98+% ee. ¹H NMR heated (360K) (400 MHz, DMSO-d6) δ 9.54 (s, 1H), 7.36 (dd, J=8.8, 4.4 Hz, 1H), 7.26-7.03 (m, 2H), 5.47 (t, J=40.2 Hz, 4H), 4.58 (s, 1H), 4.19-4.02 (m, 1H), 3.88 (s, 1H), 3.80-3.40 (m, 3H), 2.91 (s, 3H), 2.00 (s, 3H), 1.88-1.69 (m, 2H); ESI-MS m/z calc. 411.11, found 412.28 (M+1)⁺. Retention time: 0.57 minutes. I-161.

Example 22

Synthetic Scheme 22: (+/−)-4-(2-(2-chlorophenyl)-4-(methylsulfonyl)-1,4-diazepan-1-yl)-6-methylpyrimidin-2-amine (170) I-28

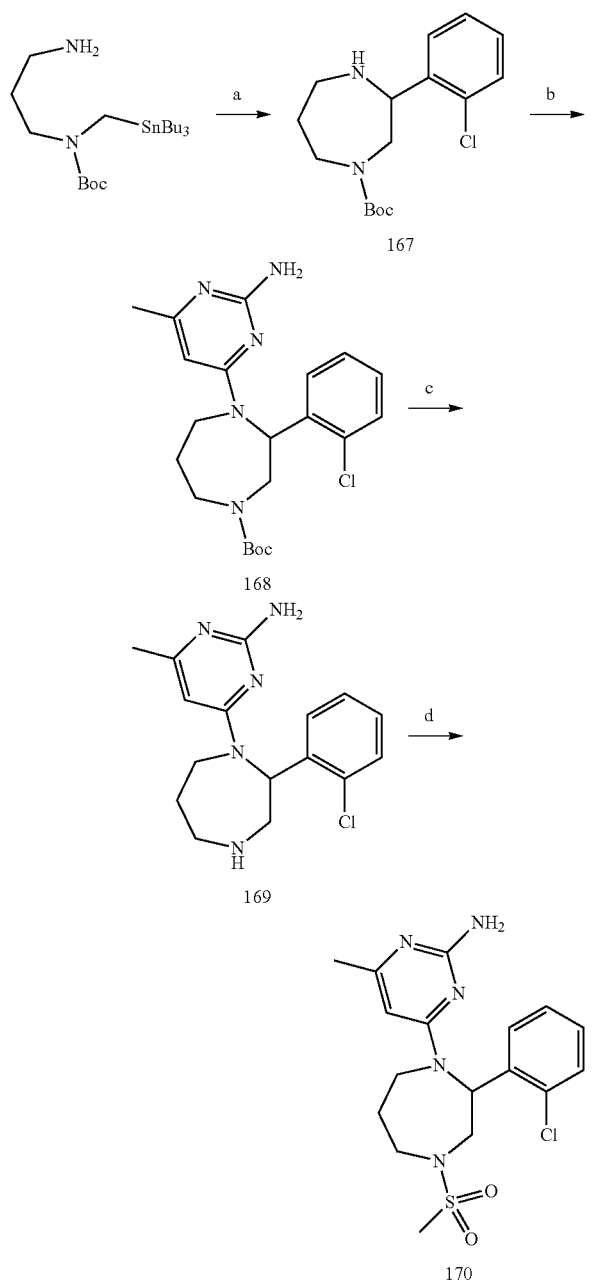

(a) 2-chlorobenzaldehyde, 4 A mol sieves, CH₂Cl₂ then 2,6-lutidine, Cu(OTf)₂, hexafluoroisopropanol, CH₂C2; (b) 2-amino-4-chloro-6-methylpyrimidine, Et₃N, NMP, 150° C.; (c) HCl, 1,4-dioxane; (d) methanesulfonyl chloride, Et₃N, CH₂Cl₂.

Formation of (+/−)-tert-butyl 3-(2-chlorophenyl)-1, 4-diazepane-1-carboxylate (167)

To a solution of tert-butyl (3-aminopropyl)((tributylstannyl)methyl)carbamate (SnAP-DA) (3.0 g, 6.3 mmol) in anhydrous dichloromethane (16 mL) was added 2-chlorobenzaldehyde (0.71 mL) followed by 4 A MS (0.64 g). The hazy yellow mixture was stirred at room temperature for 2 hours then filtered through Celite. The filter pad was rinsed with 25 mL dichloromethane and the filtrate was concentrated to dryness.

In a separate 250 mL RB flask containing hexafluoroisopropanol (25 mL) was added 2,6-lutidine (0.73 mL, 6.28 mmol) followed by Cu(OTf)₂ (0.40 g, 6.295 mmol) (Cu (OTf)₂ was dried under hi vac for 30 minutes and heated with heat gun). The suspension instantly became dark blue upon addition of Cu(OTf)₂. The mixture was stirred at room temperature for 1 h.

The imine solution prepared above was dissolved in dichloromethane (100 mL) and poured directly into the greenish/blue lutidine-Cu(OTf)₂-hexafluoroisopropanol mixture. The reaction turned very dark green immediately and was stirred overnight at room temperature. The reaction was quenched with 150 mL of a 2:1 mixture of aqueous saturated sodium bicarbonate solution and 10% ammonium hydroxide. The mixture was stirred for 15 minutes and then separated. The aqueous layer was extracted 2×150 mL dichloromethane. The combined organic phases were washed with brine, dried over magnesium sulfate, filtered and concentrated to give 13 g of an amber colored oil. The crude material was purified via silica gel chromatography eluting with 0-100% EtOAc in heptane (40 g ISCO column). TLC w/ninhydrin stain was used to identify fractions containing desired product. Fractions containing desired product were combined and concentrated to give 1.7 g of a light orange oil. The material was purified a second time via silica gel chromatography eluting with 0-75% EtOAc in heptane (40 g ISCO column). Pure fractions were combined and concentrated to give 700 mg of the desired product as a colorless oil: ¹H NMR (400 MHz, CDCl₃) δ 7.54 (ddd, J=13.2, 7.7, 1.8 Hz, 1H), 7.36 (dd, J=7.9, 1.5 Hz, 1H), 7.31-7.14 (m, 2H), 4.32 (dd, J=10.2, 3.4 Hz, 1H), 4.18-3.88 (m, 2H), 3.41-3.18 (m, 2H), 3.01-2.72 (m, 2H), 1.99-1.72 (m, 2H), 1.50 (d, J=4.4 Hz, 9H); ESI-MS m/z calc. 310.1, found 311.0 (M+1)⁺. Retention time: 0.71 minutes.

Formation of (+/−)-tert-butyl 4-(2-amino-6-methylpyrimidin-4-yl)-3-(2-chlorophenyl)-1,4-diazepane-1-carboxylate (168)

A mixture of tert-butyl 3-(2-chlorophenyl)-1,4-diazepane-1-carboxylate, 167, (0.42 g, 1.35 mmol), 4-chloro-6-methylpyrimidine-2-amine (0.19 g, 1.34 mmol), and triethylamine (0.38 mL, 2.69 mmol) in NMP (6 mL) was stirred for 1 day at 150° C. and then 3 days at room temperature. The reaction was diluted with water and extracted with EtOAc. The organic layer was dried over magnesium sulfate, filtered, and concentrated to dryness. The crude product was purified via silica gel chromatography eluting with 0-15% MeOH in dichloromethane. Pure fractions were combined and concentrated to give 163 mg of desired product as a brown oil: ¹H NMR (400 MHz, DMSO-d6) δ 7.46-7.39 (m, 1H), 7.31-7.21 (m, 3H), 5.78 (s, 1H), 5.61 (s, 1H), 5.40 (s, 2H), 4.54 (d, J=14.9 Hz, 1H), 4.33 (dd, J=14.8, 5.7 Hz, 1H), 3.99 (d, J=13.7 Hz, 1H), 3.67-3.55 (m, 1H), 3.16 (dd, J=14.9, 11.2 Hz, 1H), 2.86 (t, J=12.9 Hz, 1H), 2.00 (s, 3H), 1.87-1.52 (m, 2H), 1.38 (s, 9H); ESI-MS m/z calc. 417.2, found 418.0 (M+1)+. Retention time: 0.81 minutes.

Formation of (+/−)-4-(2-(2-chlorophenyl)-1,4-diazepan-1-yl)-6-methylpyrimidin-2-amine (169)

A solution of tert-butyl 4-(2-amino-6-methyl-pyrimidin-4-yl)-3-(2-chlorophenyl)-1,4-diazepane-1-carboxylate, 168, (0.08 g, 0.19 mmol) in HCl (3 mL of 4 M solution, 12.00 mmol) in dioxane was stirred overnight at room temperature and then concentrated to dryness. The crude residue was used without further purification: ESI-MS m/z calc. 317.1, found 318.0 (M+1)+. Retention time: 0.49 minutes.

Formation of (+/−)-4-(2-(2-chlorophenyl)-4-(methylsulfonyl)-1,4-diazepan-1-yl)-6-methylpyrimidin-2-amine (170) I-28

To a solution of 4-[2-(2-chlorophenyl)-1,4-diazepan-1-yl]-6-methyl-pyrimidin-2-amine, 169, (0.03 g, 0.09 mmol) and triethylamine (0.53 mL, 0.38 mmol) in dichloromethane (1.9 mL) was added dropwise a solution of methane sulfonyl chloride (0.008 mL, 0.0969 mmol) in dichloromethane (1.2 mL). The reaction was stirred for 5 minutes and then concentrated to dryness. The crude residue was purified by silica gel chromatography eluting with 0-10% MeOH in dichloromethane (4 g ISCO column). Pure fractions were combined, concentrated, and lyophilized to afford 15 mg of desired product: $^1$H NMR (400 MHz, DMSO-d6) δ 7.50-7.39 (m, 1H), 7.36-7.20 (m, 3H), 5.96 (s, 2H), 5.74 (s, 1H), 4.60 (d, J=15.2 Hz, 1H), 4.21 (ddd, J=15.4, 5.3, 1.2 Hz, 1H), 3.80-3.61 (m, 2H), 3.28 (dd, J=15.4, 11.1 Hz, 1H), 3.08-3.01 (m, 1H), 2.86 (s, 3H), 2.08 (s, 3H), 1.92-1.72 (m, 2H), 1.20 (t, J=7.3 Hz, 1H); ESI-MS m/z calc. 395.1, found 396.0 (M+1)+. Retention time: 0.65 minutes.

Example 23

Synthetic Scheme 23: (+/−)-N-[3-[4-(2-amino-6-methyl-pyrimidin-4-yl)-1,4-oxazepan-3-yl]-4-chloro-phenyl]-3-hydroxy-propanamide (171) I-174

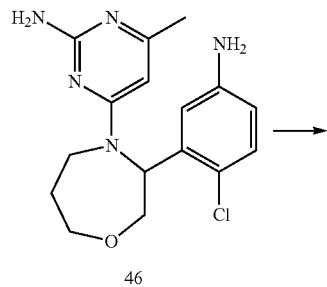

46

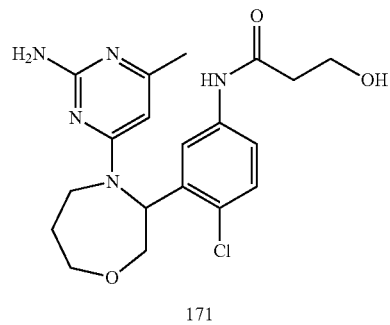

171

(+/−)-N-[3-[4-(2-amino-6-methyl-pyrimidin-4-yl)-1,4-oxazepan-3-yl]-4-chloro-phenyl]-3-hydroxy-propanamide (171) I-174

To a solution of 4-[3-(5-amino-2-chloro-phenyl)-1,4-oxazepan-4-yl]-6-methyl-pyrimidin-2-amine, 46, (0.22 g, 0.66 mmol) in DMF (18 mL) was added 3-hydroxypropanoic acid (0.08 g, 0.89 mmol), diisopropylethyl amine (0.26 g, 2.01 mmol) and HATU (0.46 g, 1.21 mmol). The mixture was stirred at room temperature for 10 hours. The crude mixture was diluted with EtOAc and washed three times with aqueous saturated NaHCO₃ solution. The organic phase was dried (MgSO₄), filtered and concentrated in vacuo. The crude product was purified by silica gel chromatography (40 g ISCO column) eluting with DCM, 10% MeOH/DCM (0% to 65% gradient) to afford 54 mg (20%): $^1$H NMR (300 MHz, DMSO-d6) δ 12.67 (br, 1H), 10.08 (d, J=14.6 Hz, 1H), 7.83 (br, 1H), 7.74-7.31 (m, 4H), 6.67 (s, 0.5H), 5.95 (dd, J=10.3, 5.4 Hz, 0.5H), 5.57 (d, J=3.0 Hz, 0.5H), 5.18 (dd, J=9.6, 4.7 Hz, 0.5H), 5.01 (d, J=13.9 Hz, 1H), 4.63 (t, J=5.9 Hz, 2H), 4.23 (ddd, J=30.9, 13.7, 5.2 Hz, 2H), 4.01-3.53 (m, 4H), 2.81 (t, J=5.9 Hz, 1H), 2.42 (t, J=6.2 Hz, 1H), 2.29 (s, 1.5H), 2.20 (s, 1.5H), 1.83 (m, 2H); ESI-MS m/z calc. 405.16, found 406.2 (M+1)+. Retention time: 0.57 minutes.

The following analogs were prepared according to Synthetic Scheme 23:

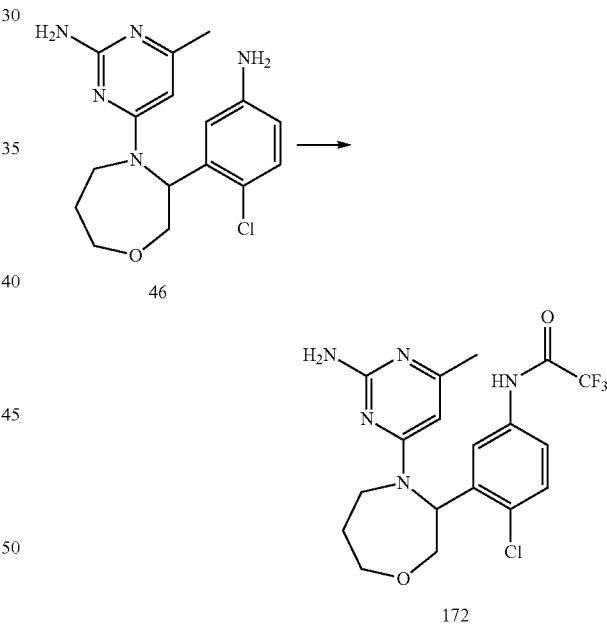

172

(+/−)-N-[3-[4-(2-amino-6-methyl-pyrimidin-4-yl)-1,4-oxazepan-3-yl]-4-chloro-phenyl]-2,2,2-trifluoro-acetamide (172) I-159 heated (360K) $^1$H NMR (400 MHz, DMSO-d6) δ 11.12 (s, 1H), 7.71 (d, J=7.3 Hz, 2H), 7.52 (d, J=9.1 Hz, 1H), 7.12 (s, 2H), 6.13 (brs, 1H), 5.66 (brs, 1H), 4.56 (br, 1H), 4.23 (dd, J=13.6, 5.1 Hz, 1H), 4.01-3.75 (m, 3H), 3.72-3.57 (m, 1H), 2.25 (s, 3H), 1.89 (d, J=14.5 Hz, 2H); ESI-MS m/z calc. 429.12, found 430.14 (M+1)+. Retention time: 0.68 minutes.

The racemic mixture was submitted for SFC chiral separation. SFC conditions: Column: IC, 20×250 mm, mobile phase: 30% MeOH (5 mM ammonia), 70% $CO_2$ flow; 75 mL/min; concentrations: ~24 mg/mL (MeOH); injection volume 250 μL; wavelength: 254 nM; method type—isocratic.

Peak A: (R)—N-[3-[4-(2-amino-6-methyl-pyrimidin-4-yl)-1,4-oxazepan-3-yl]-4-chloro-phenyl]-2,2,2-trifluoro-acetamide (173); $[\alpha]_D$ (c=0.5, MeOH) −159.04 (98% ee); ESI-MS m/z calc. 429.1, found 431.8 (M+1)$^+$. Retention time: 0.54 minutes. I-176.

Peak B: (S)—N-[3-[4-(2-amino-6-methyl-pyrimidin-4-yl)-1,4-oxazepan-3-yl]-4-chloro-phenyl]-2,2,2-trifluoro-acetamide (174); $[\alpha]_D$ (c=0.5, MeOH) +157.28 (99% ee); $^1$H NMR (300 MHz, Methanol-d4) δ 6.35 (d, J=2.5 Hz, 2H), 6.16 (d, J=9.2 Hz, 1H), 4.22 (br, 1H), 3.02 (dd, J=13.6, 5.1 Hz, 1H), 2.88-2.67 (m, 1H), 2.56-2.23 (m, 3H), 2.03 (m, 2H), 0.59 (m, 2H); ESI-MS m/z calc. 429.12, found 429.99 (M+1)$^+$. Retention time: 0.65 minutes. I-177.

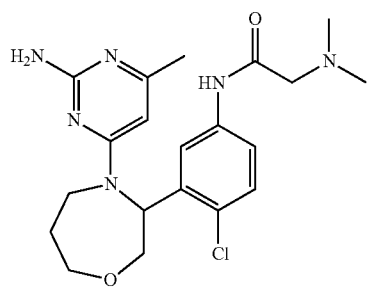

(+/−)-N-[3-[4-(2-amino-6-methyl-pyrimidin-4-yl)-1,4-oxazepan-3-yl]-4-chloro-phenyl]-2-(dimethylamino)acetamide (175) I-168

$^1$H NMR (300 MHz, DMSO-d6) δ 9.90 (s, 1H), 7.73 (d, J=8.7 Hz, 1H), 7.63 (d, J=2.6 Hz, 1H), 7.38 (d, J=8.7 Hz, 1H), 5.96 (brs, 2H), 5.03 (br, 2H), 4.11 (s, 1H), 3.94 (m, 1H), 3.74-3.47 (m, 3H), 3.33 (s, 6H), 3.04 (s, 2H), 2.25 (s, 3H), 1.98 (br, 2H); ESI-MS m/z calc. 418.19, found 419.09 (M+1)$^+$. Retention time: 0.58 minutes.

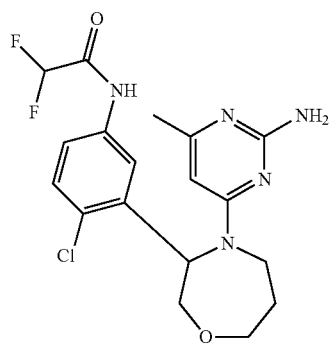 [SMILES: Cc1cc(N2CCCOCC2c2cc(NC(=O)C(F)F)ccc2Cl)nc(N)n1]

(+/−)-N-(3-(4-(2-amino-6-methylpyrimidin-4-yl)-1,4-oxazepan-3-yl)-4-chlorophenyl)-2,2-difluoroacetamide I-250

$^1$H NMR (300 MHz, Methanol-d4) δ 7.78 (dd, J=9.2, 2.5 Hz, 1H), 7.67-7.35 (m, 2H), 6.63-6.48 (m, OH), 6.36-5.91 (m, 1H), 5.65 (d, J=1.0 Hz, 1H), 5.37 (dd, J=10.2, 5.0 Hz, 1H), 5.20 (d, J=14.5 Hz, 1H), 4.47-4.21 (m, 1H), 4.12-3.53 (m, 4H), 2.35 (d, J=0.8 Hz, 1H), 2.21 (d, J=0.8 Hz, 2H), 1.96 (d, J=10.7 Hz, 2H); ESI-MS m/z calc. 411.13, found 412.23 (M+1)$^+$. Retention time: 0.62 minutes.

Example 24

Synthetic Scheme 24: (+/−)-4-[4-(2-amino-6-methyl-pyrimidin-4-yl)-1,4-oxazepan-3-yl]-3-chloro-benzonitrile (179) I-97

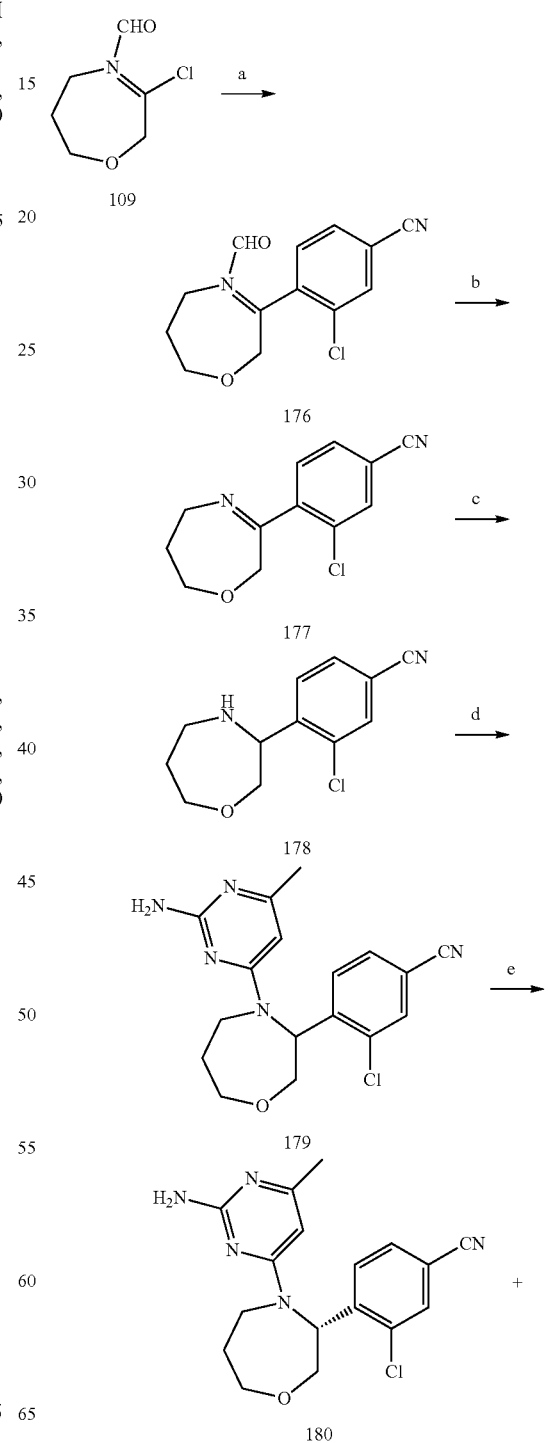

-continued

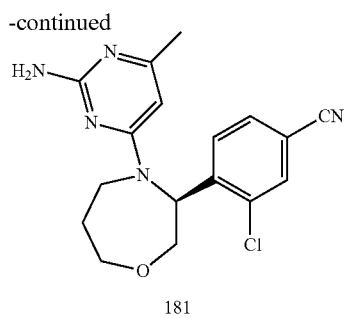

181

(a) 2-chloro-4-cyanophenylboronic acid, Pd(Ph$_3$P)$_2$Cl$_2$, DME, 50° C.; (b) MeMgBr, DME; (c) NaBH$_4$, MeOH; (d) 4-chloro-6-methyl-pyrimidin-2-amine, NMP, 150° C.; (e) chiral SFC chromatography.

Formation of (+/−)-3-chloro-4-(2,5,6,7-tetrahydro-1, 4-oxazepin-3-yl)benzonitrile (176)

Intermediate 176 was prepared according to Synthetic Scheme 13 using 2-chloro-4-cyanophenylboronic acid instead of 2-chloro-5-hydroxyphenyl boronic acid.

Formation of (+/−)-3-chloro-4-(2,5,6,7-tetrahydro-1, 4-oxazepin-3-yl)benzonitrile (177)

To a solution of 3-chloro-4-(4-formyl-6,7-dihydro-5H-1, 4-oxazepin-3-yl)benzonitrile, 176, (1.0 g, 3.8 mmol) in DME (60 mL) at −5 to 0° C. was added MeMgBr (2 mL of 2M solution in 2-MeTHF, 6.4 mmol) under nitrogen. After 15 minutes, the reaction was quenched with 1M sodium potassium tartrate and stirred vigorously for 1 hour. The reaction mixture was partially concentrated and then extracted twice with dichloromethane. The layers were separated with the aid of a phase separator and the combined organics concentrated in vacuo to give the desired product as a yellow semi-solid. The crude product was used in the next step without further purification: ESI-MS m/z calc. 252.07 found 253.12 (M+1)$^+$. Retention time: 0.55 minutes.

Formation of (+/−)-3-chloro-4-(1,4-oxazepan-3-yl)benzonitrile (178)

To a solution of 3-chloro-4-(2,5,6,7-tetrahydro-1,4-oxazepin-3-yl)benzonitrile, 177, (0.84 g, 3.59 mmol) in MeOH (10 mL) was added NaBH$_4$ (0.68 g, 18.00 mmol) at room temperature. After 1.5 hours, the mixture was heated at 50° C. After a further 3 hours, added additional 1.0 g NaBH$_4$ at 50° C. and then stirred at room temperature overnight. The reaction mixture was concentrated and extracted twice with dichloromethane. The layers were separated with the aid of a phase separator and the organics concentrated in vacuo. Purification was carried out on a reverse phase 100 g ISCO c18-aq column, running with 0.1% TFA/H$_2$O and 0.1% TFA/CH$_3$CN. The pure fractions were partially concentrated in vacuo, some 1M NaOH added and the mixture extracted with dichloromethane three times and concentrated in vacuo to give 294 mg of the desired product: $^1$H NMR (400 MHz, DMSO-d6) δ 8.00 (m, 1H), 7.81 (m, 1H), 4.28 (dd, J=8.7, 3.3 Hz, 1H), 3.85-3.78 (m, 2H), 3.75-3.60 (m, 1H), 3.30-3.26 (m, 1H), 3.13-3.03 (m, 1H), 2.92-2.84 (m, 1H), 1.91-1.81 (m, 2H). ESI-MS m/z calc. 236.07, found 237.1 (M+1)$^+$. Retention time: 0.49 minutes.

Formation of (+/−)-4-[4-(2-amino-6-methyl-pyrimidin-4-yl)-1,4-oxazepan-3-yl]-3-chloro-benzonitrile (179) I-97

A mixture of 3-chloro-4-(1,4-oxazepan-3-yl)benzonitrile (0.19 g, 0.80 mmol) and 4-chloro-6-methyl-pyrimidin-2-amine (0.10 g, 0.70 mmol) was heated in NMP (1.5 mL) at 160° C. for 3.5 h. Purification was carried out on a reverse phase 50 g ISCO c18-aq column, running with 0.1% TFA/H$_2$O and 0.1% TFA/CH$_3$CN. The pure fractions were concentrated in vacuo, triethylamine (1 mL) was added and concentrated in vacuo again. Purification by column chromatography (40 g column; 0-10% MeOH/dichloromethane) afforded 124 mg of the desired product: high temperature (360 K) $^1$H NMR (400 MHz, DMSO-d6) δ 7.96 (s, 1H), 7.73 (dd, J=8.1, 1.6 Hz, 1H), 7.50 (d, J=8.1 Hz, 1H), 6.37 (s, 2H), 5.96 (s, 1H), 5.65 (s, 1H), 4.47 (d, J=16.3 Hz, 1H), 4.16 (dd, J=13.6, 4.9 Hz, 1H), 3.93-3.76 (m, 3H), 3.65-3.57 (m, 1H), 2.15 (s, 3H), 1.87-1.79 (m, 2H); ESI-MS m/z calc. 343.12, found 344.15 (M+1)$^+$. Retention time: 0.57 minutes. The racemic mixture was submitted to chiral SFC purification to obtain the individual enantiomers.

Peak A: (R)-4-[4-(2-amino-6-methyl-pyrimidin-4-yl)-1, 4-oxazepan-3-yl]-3-chloro-benzonitrile (180); >99% ee; high temperature (360 K) $^1$H NMR (400 MHz, DMSO-d6) δ 7.93 (d, J=1.5 Hz, 1H), 7.69 (dd, J=8.1, 1.6 Hz, 1H), 7.48 (d, J=8.1 Hz, 1H), 5.66 (s, 1H), 5.54 (d, J=5.3 Hz, 1H), 5.41 (s, 2H), 4.47 (d, J=16.0 Hz, 1H), 4.12 (dd, J=13.5, 4.8 Hz, 1H), 3.89 (dd, J=8.5, 3.6 Hz, 1H), 3.73 (ddd, J=15.2, 12.9, 7.7 Hz, 2H), 3.61-3.52 (m, 1H), 2.02 (s, 3H), 1.83-1.74 (m, 2H); ESI-MS m/z calc. 343.12, found 344.17 (M+1)$^+$. Retention time: 0.58 minutes. I-96.

Peak B: (S)-4-[4-(2-amino-6-methyl-pyrimidin-4-yl)-1,4-oxazepan-3-yl]-3-chloro-benzonitrile (181); >99% ee; high temperature (360 K) $^1$H NMR (400 MHz, DMSO-d6) δ 7.93 (d, J=1.5 Hz, 1H), 7.69 (dd, J=8.1, 1.6 Hz, 1H), 7.48 (d, J=8.1 Hz, 1H), 5.66 (s, 1H), 5.54 (d, J=5.3 Hz, 1H), 5.41 (s, 2H), 4.47 (d, J=16.0 Hz, 1H), 4.12 (dd, J=13.5, 4.8 Hz, 1H), 3.89 (dd, J=8.5, 3.6 Hz, 1H), 3.73 (ddd, J=15.2, 12.9, 7.7 Hz, 2H), 3.61-3.52 (m, 1H), 2.02 (s, 3H), 1.83-1.74 (m, 2H); ESI-MS m/z calc. 343.12, found 344.17 (M+1)$^+$. Retention time: 0.58 minutes. I-97.

The following analogs were prepared according to Synthetic Scheme 24 starting from the appropriate boronic acids:

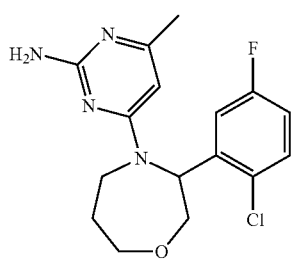

182

(+/−)-4-[3-(2-chloro-5-fluoro-phenyl)-1,4-oxazepan-4-yl]-6-methyl-pyrimidin-2-amine (182) I-70 high temperature (360 K) $^1$H NMR (400 MHz, DMSO-d6) δ 7.47 (dd, J=8.8, 5.2 Hz, 1H), 7.11 (td, J=8.2, 3.0 Hz, 1H), 7.06 (dd, J=9.6, 3.1 Hz, 1H), 5.62 (s, 1H), 5.49-5.41 (m, 3H), 4.60-4.50 (m, 1H), 4.11 (dd, J=13.5, 4.9 Hz, 1H), 3.92-3.85 (m, 1H), 3.76 (dd, J=13.5, 10.0 Hz, 1H), 3.73-3.64 (m, 1H), 3.56 (dd, J=14.4, 12.0 Hz, 1H), 2.02 (s, 3H), 1.80-1.74 (m, 2H); ESI-MS m/z calc. 336.12, found 337.14 (M+1)⁺. Retention time: 0.62 minutes. The racemic mixture was submitted to chiral SFC purification to obtain the individual enantiomers.

Peak A: (R)-4-[3-(2-chloro-5-fluoro-phenyl)-1,4-oxazepan-4-yl]-6-methyl-pyrimidin-2-amine (183); 99.9% ee; high temperature (360 K) ¹H NMR (400 MHz, DMSO-d6) δ 7.93 (d, J=1.5 Hz, 1H), 7.69 (dd, J=8.1, 1.6 Hz, 1H), 7.48 (d, J=8.1 Hz, 1H), 5.66 (s, 1H), 5.54 (d, J=5.3 Hz, 1H), 5.41 (s, 2H), 4.47 (d, J=16.0 Hz, 1H), 4.12 (dd, J=13.5, 4.8 Hz, 1H), 3.89 (dd, J=8.5, 3.6 Hz, 1H), 3.73 (ddd, J=15.2, 12.9, 7.7 Hz, 2H), 3.61-3.52 (m, 1H), 2.02 (s, 3H), 1.83-1.74 (m, 2H); ESI-MS m/z calc. 343.12, found 344.17 (M+1)⁺. Retention time: 0.58 minutes. I-78.

Peak B: (S)-4-[3-(2-chloro-5-fluoro-phenyl)-1,4-oxazepan-4-yl]-6-methyl-pyrimidin-2-amine (184); 98% ee; high temperature (360 K) ¹H NMR (400 MHz, DMSO-d6) δ 7.93 (d, J=1.5 Hz, 1H), 7.69 (dd, J=8.1, 1.6 Hz, 1H), 7.48 (d, J=8.1 Hz, 1H), 5.66 (s, 1H), 5.54 (d, J=5.3 Hz, 1H), 5.41 (s, 2H), 4.47 (d, J=16.0 Hz, 1H), 4.12 (dd, J=13.5, 4.8 Hz, 1H), 3.89 (dd, J=8.5, 3.6 Hz, 1H), 3.73 (ddd, J=15.2, 12.9, 7.7 Hz, 2H), 3.61-3.52 (m, 1H), 2.02 (s, 3H), 1.83-1.74 (m, 2H); ESI-MS m/z calc. 343.12, found 344.17 (M+1)⁺. Retention time: 0.58 minutes. I-79.

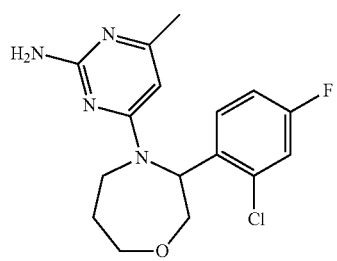

185

(+/−)-4-[3-(2-chloro-4-fluoro-phenyl)-1,4-oxazepan-4-yl]-6-methyl-pyrimidin-2-amine (185) I-63 high temperature (360 K) ¹H NMR (400 MHz, DMSO-d6) δ 7.35 (dd, J=8.8, 6.4 Hz, 2H), 7.13 (d, J=6.0 Hz, 1H), 5.59 (s, 1H), 5.47-5.41 (m, 2H), 4.58 (s, 1H), 4.08 (dd, J=13.4, 5.1 Hz, 1H), 3.87 (s, 1H), 3.75-3.50 (m, 3H), 2.01 (s, 3H), 1.77 (s, 2H); ESI-MS m/z calc. 336.12, found 337.14 (M+1)⁺. Retention time: 0.62 minutes.

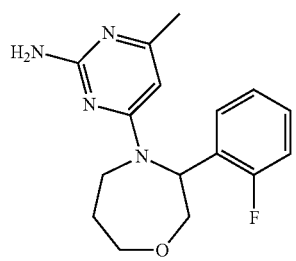

186

(+/−)-4-[3-(2-fluorophenyl)-1,4-oxazepan-4-yl]-6-methyl-pyrimidin-2-amine (186) I-32 high temperature (360 K) ¹H NMR (400 MHz, DMSO-d6) δ 7.32-7.23 (m, 2H), 7.14 (dd, J=13.0, 5.0 Hz, 2H), 5.71 (s, 1H), 5.55 (s, 1H), 5.45 (s, 2H), 4.43 (d, J=15.5 Hz, 1H), 4.15 (dd, J=13.4, 5.1 Hz, 1H), 3.90 (d, J=12.0 Hz, 1H), 3.77 (dd, J=13.3, 10.2 Hz, 1H), 3.63-3.49 (m, 2H), 2.02 (s, 3H), 1.89-1.68 (m, 2H); ESI-MS m/z calc. 302.15, found 303.19 (M+1)⁺. Retention time: 0.58 minutes.

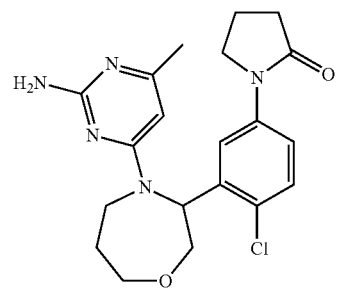

187

(+/−)-1-[3-[4-(2-amino-6-methyl-pyrimidin-4-yl)-1,4-oxazepan-3-yl]-4-chloro-phenyl]pyrrolidin-2-one (187) I-119 high temperature (360 K) ¹H NMR (400 MHz, DMSO-d6) δ 7.76 (d, J=2.7 Hz, 1H), 7.45 (dd, J=8.7, 2.7 Hz, 1H), 7.39 (d, J=8.8 Hz, 1H), 5.59 (s, 1H), 5.42 (s, 3H), 4.63 (d, J=15.1 Hz, 1H), 4.12 (dd, J=13.4, 5.0 Hz, 1H), 3.91 (dt, J=11.5, 3.8 Hz, 1H), 3.81-3.73 (m, 2H), 3.72-3.52 (m, 3H), 2.47-2.40 (m, 2H), 2.08-2.01 (m, 2H), 2.00 (s, 3H), 1.80 (ddt, J=10.9, 7.5, 4.2 Hz, 2H); ESI-MS m/z calc. 401.2, found 402.0 (M+1)⁺. Retention time: 0.65 minutes.

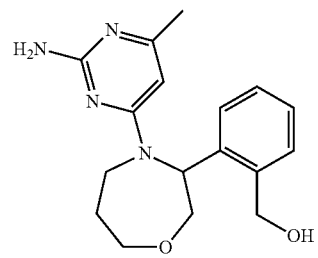 [SMILES: Cc1cc(N2CCCOCC2c2ccccc2CO)nc(N)n1]

(+/−)-(2-(4-(2-amino-6-methylpyrimidin-4-yl)-1,4-oxazepan-3-yl)phenyl)methanol-91 high temperature (360 K) ¹H NMR (400 MHz, DMSO-d6) δ 7.77 (s, 1H), 7.51 (dd, J=7.7, 0.7 Hz, 1H), 7.36 (td, J=7.4, 1.8 Hz, 1H), 7.29-7.21 (m, 2H), 6.12 (s, 1H), 5.18 (t, J=5.5 Hz, 1H), 4.41 (d, J=5.5 Hz, 2H), 4.18 (t, J=5.9 Hz, 2H), 3.93 (t, J=6.5 Hz, 2H), 2.03-1.95 (m, 2H); ESI-MS m/z calc. 233.11, found 234.17 (M+1)⁺. Retention time: 0.62 minutes.

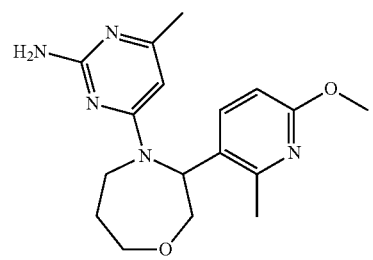 [SMILES: COc1ccc(C2COCCCN2c2cc(C)nc(N)n2)c(C)n1]

319

(+/−)-4-[3-(6-methoxy-2-methyl-3-pyridyl)-1,4-oxazepan-4-yl]-6-methyl-pyrimidin-2-amine I-77 high temperature (360 K) $^1$H NMR (400 MHz, DMSO-d6) δ 7.56 (s, 1H), 6.59 (d, J=8.5 Hz, 1H), 6.04-5.62 (m, 1H), 4.08-4.01 (m, 1H), 3.89-3.85 (m, 5H), 3.75-3.55 (m, 2H), 3.33-3.27 (m, 2H), 2.52 (s, 3H), 2.15 (s, 3H), 2.01-1.75 (m, 2H); ESI-MS m/z calc. 329.19, found 330.24 (M+1)$^+$. Retention time: 0.47 minutes. 888.

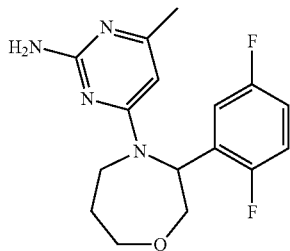 [SMILES: Cc1cc(N2CCCOCC2c2cc(F)ccc2F)nc(N)n1]

(+/−)-4-[3-(2,5-difluorophenyl)-1,4-oxazepan-4-yl]-6-methyl-pyrimidin-2-amine I-52 high temperature (360 K) $^1$H NMR (400 MHz, DMSO-d6) δ 7.23-7.15 (m, 1H), 7.12-6.98 (m, 2H), 5.75 (s, 1H), 5.58 (s, 1H), 5.47 (s, 2H), 4.36 (d, J=15.7 Hz, 1H), 4.13 (dd, J=13.3, 5.1 Hz, 1H), 3.89 (d, J=11.4 Hz, 1H), 3.80 (dd, J=13.3, 10.0 Hz, 1H), 3.65-3.50 (m, 2H), 2.04 (s, 3H), 1.87-1.68 (m, 2H); ESI-MS m/z calc. 320.14, found 321.2 (M+1)$^+$. Retention time: 0.6 minutes.

Example 25

Synthetic Scheme 25: (+/−)-4-[4-(2-amino-6-methyl-pyrimidin-4-yl)-1,4-oxazepan-3-yl]-3-chloro-N-cyclopropyl-benzamide (191) I-155

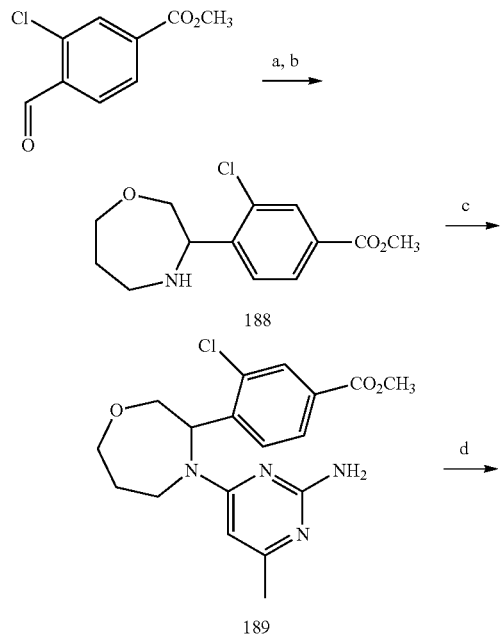

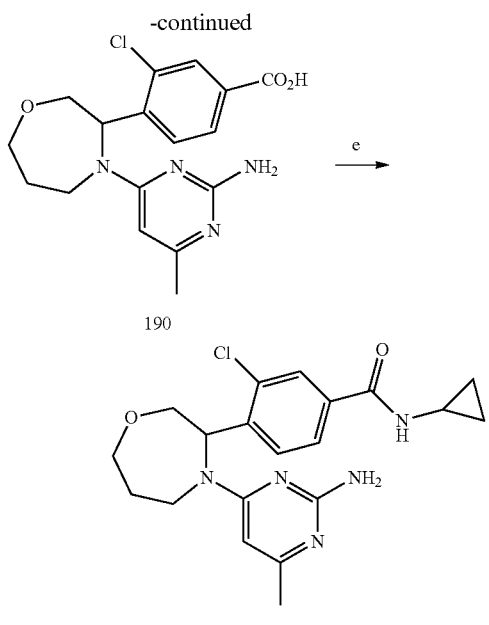

(a) 3-(tributylstannylmethoxy)propan-1-amine, 4 Å mol sieves, CH$_2$Cl$_2$; (b) 2,6-lutidine, Cu(OTf)$_2$, hexafluoroisopropanol, CH$_2$Cl$_2$; c) 2-amino-4-chloro-6-methylpyrimidine, NMP, 150° C.; (d) LiOH, MeOH, H$_2$O; (e) cyclopropyl amine, HATU, Et$_3$N, DMF.

Formation of methyl 3-chloro-4-(1,4-oxazepan-3-yl)benzoate (188)

To a solution of 3-(tributylstannylmethoxy)propan-1-amine (8.0 g, 21.0 mmol) in anhydrous dichloromethane (60 mL) was added methyl 3-chloro-4-formyl-benzoate (4.2 g, 21.0 mmol) followed by 4 Å molecular sieves (5 g). The reaction was stirred at room temperature for 2 hours, filtered over Celite, and diluted with anhydrous dichloromethane (180 mL). To a separate flask containing hexafluoroisopropanol (60 mL) was added 2,6-lutidine (2.5 mL, 21.7 mmol) followed by Cu(OTf)$_2$ (7.6 g, 21.0 mmol). The blue suspension was stirred at room temperature for 2 h, and then the imine solution prepared above was added in one portion. The reaction mixture was stirred overnight and was then quenched with 100 mL of 2:1 mixture of aqueous saturated sodium bicarbonate solution and 10% ammonium hydroxide. The mixture was stirred for 15 minutes and then separated. The organic layer was washed with aqueous saturated sodium bicarbonate solution followed by brine. The organic layer was concentrated in vacuo and purified via silica gel chromatography eluting with 0-70% EtOAc in heptane. Pure fractions were combined and concentrated in vacuo to give 2.9 g (51%) of the desired product: $^1$H NMR (400 MHz, CDCl$_3$) δ 8.01 (d, J=1.7 Hz, 1H), 7.91 (ddd, J=8.1, 1.7, 0.5 Hz, 1H), 7.68 (d, J=8.1 Hz, 1H), 4.49 (dd, J=8.9, 3.5 Hz, 1H), 4.04-3.96 (m, 2H), 3.92 (s, 3H), 3.84 (dt, J=12.3, 6.2 Hz, 1H), 3.42 (dd, J=12.4, 9.0 Hz, 1H), 3.24 (dt, J=13.6, 5.0 Hz, 1H), 3.07 (dt, J=13.6, 6.8 Hz, 1H), 2.00 (qd, J=6.4, 5.0 Hz, 2H); ESI-MS m/z calc. 269.08, found 270.0 (M+1)$^+$. Retention time: 0.58 minutes.

Formation of (+/−)-methyl 4-(4-(2-amino-6-methyl-pyrimidin-4-yl)-1,4-oxazepan-3-yl)-3-chlorobenzoate 189)

A mixture of methyl 3-chloro-4-(1,4-oxazepan-3-yl)benzoate, 188, (0.37 g, 1.35 mmol) and 4-chloro-6-methylpyrimidin-2-amine (0.19 g, 1.35 mmol) in NMP (4 mL) was stirred for 3 hours at 150° C. The reaction mixture was cooled to room temperature, diluted with EtOAc, and washed with water. The organic layer was concentrated to dryness and purified via silica gel chromatography eluting with 0-15% MeOH in dichloromethane to give 252 mg (47%) of the desired product: $^1$H NMR (400 MHz, DMSO-d6) δ 7.94 (d, J=1.7 Hz, 1H), 7.85 (dd, J=8.1, 1.7 Hz, 1H), 7.49 (d, J=8.1 Hz, 1H), 6.90 (s, 2H), 6.09 (d, J=26.9 Hz, 1H), 5.69 (s, 1H), 4.51 (d, J=15.6 Hz, 1H), 4.18 (dd, J=13.7, 4.9 Hz, 1H), 3.97-3.79 (m, 6H), 3.71-3.56 (m, 1H), 2.20 (s, 3H), 1.86 (d, J=5.3 Hz, 2H); ESI-MS m/z calc. 376.13, found 377.0 (M+1)$^+$. Retention time: 0.72 minutes.

Formation of (+/−)-4-[4-(2-amino-6-methyl-pyrimidin-4-yl)-1,4-oxazepan-3-yl]-3-chloro-benzoic acid-trifluoroacetate salt (190)

To a solution of methyl 4-(4-(2-amino-6-methylpyrimidin-4-yl)-1,4-oxazepan-3-yl)-3-chlorobenzoate, 189, (0.23 g, 0.61 mmol) in MeOH (4 mL) and water (4.0 mL) was added LiOH (0.10 g, 4.18 mmol). The reaction mixture was stirred at room temperature overnight, acidified with 1M aq. HCl, and concentrated to dryness. The resulting crude residue was purified by reverse phase chromatography eluting with 0-60% MeCN in water with 0.1% TFA. Fractions containing the desired product were combined and concentrated in vacuo to give 134 mg of the desired product: $^1$H NMR (400 MHz, DMSO-d6) δ 7.93 (d, J=1.7 Hz, 1H), 7.85 (dd, J=8.1, 1.7 Hz, 1H), 7.47 (d, J=8.1 Hz, 1H), 7.39 (d, J=23.9 Hz, 2H), 6.46-5.31 (m, 2H), 5.04-4.28 (m, 1H), 4.20 (dd, J=13.7, 5.0 Hz, 1H), 3.96-3.80 (m, 3H), 3.65 (ddd, J=12.2, 10.0, 4.3 Hz, 1H), 2.28-2.19 (m, 4H), 1.91-1.85 (m, 2H); ESI-MS m/z calc. 362.11, found 363.0 (M+1)$^+$. Retention time: 0.63 minutes.

Formation of (+/−)-4-[4-(2-amino-6-methyl-pyrimidin-4-yl)-1,4-oxazepan-3-yl]-3-chloro-N-cyclopropyl-benzamide (191) I-155

To a solution of 4-[4-(2-amino-6-methyl-pyrimidin-4-yl)-1,4-oxazepan-3-yl]-3-chloro-benzoic acid (Trifluoroacetate salt), 190, (0.050 g, 0.100 mmol) in DMF (0.33 mL) was added HATU (0.057 g, 0.150 mmol) followed by Et$_3$N (0.041 mL, 0.290 mmol). After stirring for 15 minutes, cyclopropylamine (0.011 mL, 0.150 mmol) was added and the mixture was stirred overnight. The reaction mixture was diluted with 0.25 mL water and extracted with 1 mL EtOAc. The organic layer was concentrated to dryness and the product was purified via silica gel chromatography eluting with 0-12% MeOH in dichloromethane. Pure fractions were combined, concentrated in vacuo and lyophilized to give 7 mg of the desired product: $^1$H NMR (400 MHz, DMSO-d6) (heated 360K) δ 8.22 (s, 1H), 7.85 (d, J=1.7 Hz, 1H), 7.70 (dd, J=8.1, 1.8 Hz, 1H), 7.37 (d, J=8.2 Hz, 1H), 6.07 (s, 2H), 5.79 (s, 1H), 5.55 (s, 1H), 4.64-4.50 (m, 1H), 4.13 (dd, J=13.6, 4.9 Hz, 1H), 3.97-3.85 (m, 1H), 3.85-3.67 (m, 2H), 3.67-3.53 (m, 1H), 2.83 (tt, J=7.7, 3.9 Hz, 1H), 2.09 (s, 3H), 1.86-1.74 (m, 2H), 0.68 (td, J=7.1, 4.6 Hz, 2H), 0.60-0.50 (m, 2H); ESI-MS m/z found 402.0 (M+1)$^+$. Retention time: 0.62 minutes.

The following analogs were prepared according to Synthetic Scheme 25:

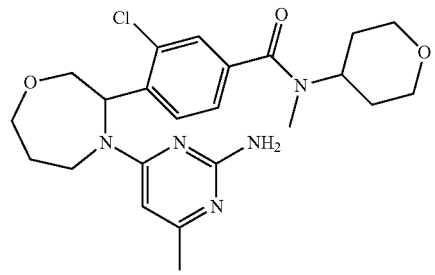

(+/−)-4-(4-(2-amino-6-methylpyrimidin-4-yl)-1,4-oxazepan-3-yl)-3-chloro-N-methyl-N-(tetrahydro-2H-pyran-4-yl)benzamide (192) I-153

$^1$H NMR (400 MHz, DMSO-d6) (heated 360K) δ 7.48-7.36 (m, 2H), 7.29 (ddd, J=8.3, 6.7, 1.7 Hz, 1H), 6.65 (s, 2H), 6.00 (s, 1H), 5.64 (s, 1H), 4.54 (d, J=14.9 Hz, 1H), 4.19 (dd, J=13.6, 5.0 Hz, 1H), 3.94-3.75 (m, 5H), 3.70-3.58 (m, 1H), 3.43-3.11 (m, 2H), 2.79 (s, 2H), 2.18 (s, 3H), 1.92-1.72 (m, 4H), 1.58 (ddt, J=13.5, 5.2, 2.7 Hz, 2H); ESI-MS m/z found 460.0 (M+1)$^+$. Retention time: 0.62 minutes.

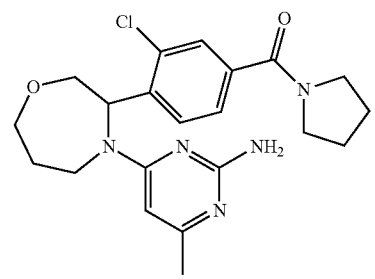

(+/−)-(4-(4-(2-amino-6-methylpyrimidin-4-yl)-1,4-oxazepan-3-yl)-3-chlorophenyl)(pyrrolidin-1-yl)methanone (193) I-151

$^1$H NMR (400 MHz, DMSO-d6) (heated 360K) δ 7.54 (d, J=1.6 Hz, 1H), 7.47-7.33 (m, 2H), 5.84 (s, 1H), 5.58 (s, 1H), 4.56 (d, J=15.0 Hz, 1H), 4.16 (dd, J=13.5, 5.0 Hz, 1H), 3.90 (dt, J=12.0, 4.1 Hz, 1H), 3.86-3.71 (m, 2H), 3.60 (dt, J=12.2, 7.4 Hz, 1H), 3.14-3.10 (m, 2H), 2.11 (s, 3H), 1.85 (dq, J=11.9, 3.6 Hz, 8H); ESI-MS m/z found 416.0 (M+1)$^+$. Retention time: 0.75 minutes.

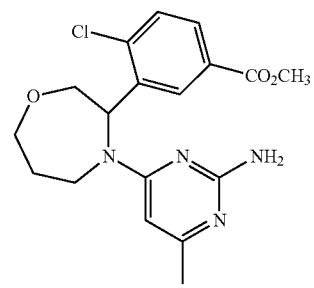

323

(+/−)-Methyl 3-(4-(2-amino-6-methylpyrimidin-4-yl)-1,4-oxazepan-3-yl)-4-chlorobenzoate (194) I-126

$^1$H NMR (400 MHz, DMSO-d6) (heated 360K) δ 7.91-7.82 (m, 2H), 7.65-7.53 (m, 1H), 6.47 (s, 2H), 5.95 (s, 1H), 5.66 (s, 1H), 4.53 (d, J=15.3 Hz, 1H), 4.14 (dd, J=13.6, 4.9 Hz, 1H), 3.92-3.85 (m, 2H), 3.84 (s, 3H), 3.82-3.75 (m, 1H), 3.65 (dt, J=12.2, 7.1 Hz, 1H), 2.15 (s, 3H), 1.85 (dq, J=8.5, 4.2 Hz, 2H); ESI-MS m/z calc. 376.13, found 377.0 (M+1)$^+$. Retention time: 0.7 minutes.

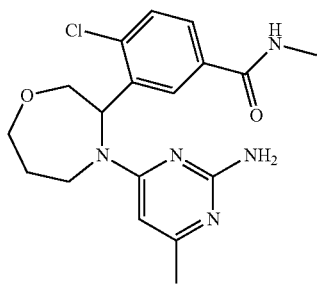

195

(+/−)-3-(4-(2-amino-6-methylpyrimidin-4-yl)-1,4-oxazepan-3-yl)-4-chloro-N-methylbenzamide (195) I-129

$^1$H NMR (400 MHz, DMSO-d6) (heated 360K) δ 8.21 (s, 1H), 7.79-7.67 (m, 2H), 7.54 (d, J=8.2 Hz, 1H), 6.89 (s, 2H), 6.07 (s, 1H), 5.67 (s, 1H), 4.57 (s, 1H), 4.16 (dd, J=13.7, 5.0 Hz, 1H), 3.89 (qd, J=9.5, 3.5 Hz, 3H), 3.64 (ddd, J=12.3, 10.3, 4.2 Hz, 1H), 2.78 (d, J=4.5 Hz, 3H), 2.21 (s, 3H), 1.85 (dt, J=17.6, 5.7 Hz, 2H); ESI-MS m/z calc. 375.15, found 376.0 (M+1)$^+$. Retention time: 0.59 minutes.

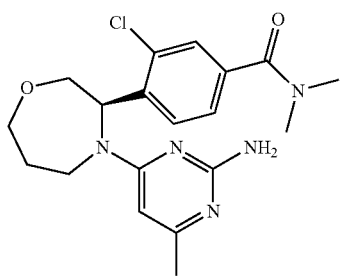

196

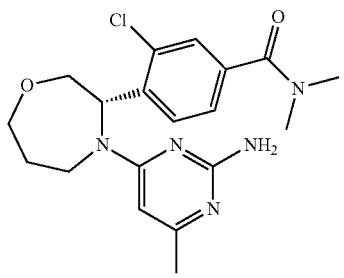

197

324

(R)-4-[4-(2-amino-6-methyl-pyrimidin-4-yl)-1,4-oxazepan-3-yl]-3-chloro-N,N-dimethyl-benzamide (196) I-143 and (S)-4-[4-(2-amino-6-methyl-pyrimidin-4-yl)-1,4-oxazepan-3-yl]-3-chloro-N,N-dimethyl-benzamide (197) I-144

Peak A: 4-[4-(2-amino-6-methyl-pyrimidin-4-yl)-1,4-oxazepan-3-yl]-3-chloro-N,N-dimethylbenzamide (196); $^1$H NMR (400 MHz, DMSO-d6) (heated 360K) δ 7.47 (d, J=1.6 Hz, 1H), 7.39 (d, J=8.0 Hz, 1H), 7.33 (dd, J=8.0, 1.7 Hz, 1H), 6.78 (s, 2H), 6.05 (s, 1H), 5.65 (s, 1H), 4.54 (d, J=14.9 Hz, 1H), 4.19 (dd, J=13.7, 5.0 Hz, 1H), 3.96-3.75 (m, 3H), 3.64 (ddd, J=12.2, 9.2, 4.9 Hz, 1H), 2.92 (s, 6H), 2.20 (s, 3H), 1.84 (dp, J=9.9, 3.7, 3.2 Hz, 2H); ESI-MS m/z calc. 389.16, found 390.0 (M+1)$^+$. Retention time: 0.61 minutes.

Peak B: 4-[4-(2-amino-6-methyl-pyrimidin-4-yl)-1,4-oxazepan-3-yl]-3-chloro-N,N-dimethyl-benzamide (197) 1H NMR (400 MHz, DMSO-d6) δ 7.47 (d, J=1.6 Hz, 1H), 7.39 (d, J=8.0 Hz, 1H), 7.33 (dd, J=8.0, 1.7 Hz, 1H), 6.78 (s, 2H), 6.05 (s, 1H), 5.65 (s, 1H), 4.54 (d, J=14.9 Hz, 1H), 4.19 (dd, J=13.7, 5.0 Hz, 1H), 3.96-3.75 (m, 3H), 3.64 (ddd, J=12.2, 9.2, 4.9 Hz, 1H), 2.92 (s, 6H), 2.20 (s, 3H), 1.84 (dp, J=9.9, 3.7, 3.2 Hz, 2H); ESI-MS m/z calc. 389.16187, found 390.0 (M+1)$^+$. Retention time: 0.61 minutes.

198

(S)-4-(4-(2-amino-6-methylpyrimidin-4-yl)-1,4-oxazepan-3-yl)-3-chloro-N-methylbenzamide (198) I-150

$^1$H NMR (400 MHz, DMSO-d6) (heated 360K) δ 8.20 (s, 1H), 7.85 (d, J=1.8 Hz, 1H), 7.70 (dd, J=8.1, 1.8 Hz, 1H), 7.37 (d, J=8.1 Hz, 1H), 5.59 (s, 1H), 5.55-5.38 (m, 2H), 4.59 (d, J=15.5 Hz, 1H), 4.12 (dd, J=13.5, 4.9 Hz, 1H), 3.90 (dt, J=11.9, 3.9 Hz, 1H), 3.81-3.64 (m, 2H), 3.64-3.51 (m, 1H), 2.77 (d, J=4.6 Hz, 3H), 2.00 (s, 3H), 1.78 (dt, J=7.8, 3.9 Hz, 2H); ESI-MS m/z calc. 375.15, found 376.0 (M+1)$^+$. Retention time: 0.58 minutes.

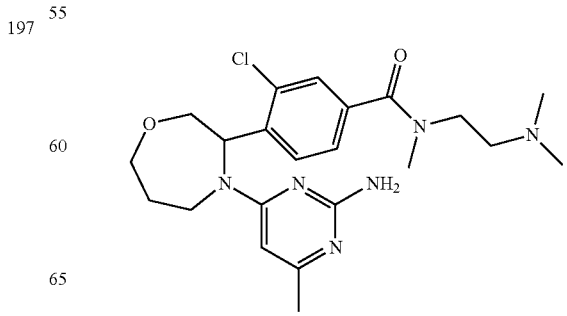

(+/−)-4-(4-(2-amino-6-methylpyrimidin-4-yl)-1,4-oxazepan-3-yl)-3-chloro-N-(2-(dimethylamino)ethyl)-N-methylbenzamide I-154

¹H NMR (400 MHz, DMSO-d6) (heated 360K) δ 7.53 (d, J=1.6 Hz, 1H), 7.42 (d, J=8.0 Hz, 1H), 7.37 (dd, J=8.0, 1.6 Hz, 1H), 6.72 (s, 2H), 6.03 (s, 1H), 5.67 (s, 1H), 4.53 (s, 1H), 4.18 (dd, J=13.6, 4.9 Hz, 1H), 3.94-3.75 (m, 3H), 3.73-3.59 (m, 3H), 3.55 (td, J=10.2, 9.3, 5.6 Hz, 1H), 3.34-3.25 (m, 1H), 2.93 (s, 3H), 2.73-2.65 (m, 6H), 2.19 (s, 3H), 1.92-1.83 (m, 2H); ESI-MS m/z found 447.0 (M+1)⁺. Retention time: 0.52 minutes.

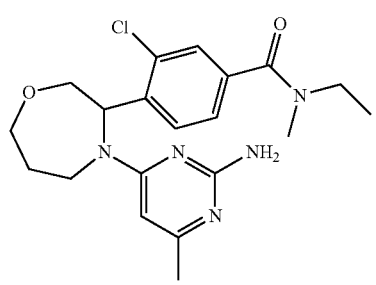 [SMILES: CCN(C)C(=O)c1ccc(C2COCCCN2c2cc(C)nc(N)n2)c(Cl)c1]

(+/−)-4-(4-(2-amino-6-methylpyrimidin-4-yl)-1,4-oxazepan-3-yl)-3-chloro-N-ethyl-N-methylbenzamide I-152

¹H NMR (400 MHz, DMSO-d6) (heated 360K) δ 7.46-7.37 (m, 2H), 7.34-7.25 (m, 1H), 6.79 (s, 2H), 6.05 (s, 1H), 5.66 (s, 1H), 4.53 (d, J=14.7 Hz, 1H), 4.19 (dd, J=13.6, 5.0 Hz, 1H), 3.95-3.77 (m, 3H), 3.64 (ddd, J=12.2, 9.3, 4.9 Hz, 1H), 3.11 (q, J=7.3 Hz, 2H), 2.92-2.86 (m, 3H), 2.20 (s, 3H), 1.89-1.79 (m, 2H), 1.21 (t, J=7.3 Hz, 3H); ESI-MS m/z found 404.0 (M+1)⁺. Retention time: 0.64 minutes.

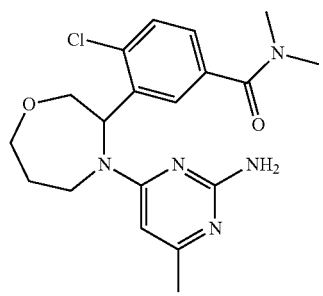 [SMILES: Cc1cc(N2CCCOCC2c2cc(C(=O)N(C)C)ccc2Cl)nc(N)n1]

(+/−)-3-(4-(2-amino-6-methylpyrimidin-4-yl)-1,4-oxazepan-3-yl)-4-chloro-N,N-dimethylbenzamide I-130

¹H NMR (400 MHz, DMSO-d6) (heated 360K) δ 7.51 (d, J=8.1 Hz, 1H), 7.39-7.28 (m, 2H), 6.71 (s, 2H), 6.03 (s, 1H), 5.65 (s, 1H), 4.52 (d, J=15.0 Hz, 1H), 4.17 (dd, J=13.6, 4.9 Hz, 1H), 3.96-3.73 (m, 3H), 3.65 (ddd, J=12.2, 9.2, 6.1 Hz, 1H), 2.89 (d, J=3.4 Hz, 6H), 2.19 (s, 3H), 1.85 (dt, J=7.6, 4.3 Hz, 2H); ESI-MS m/z calc. 389.16, found 390.0 (M+1)⁺. Retention time: 0.61 minutes.

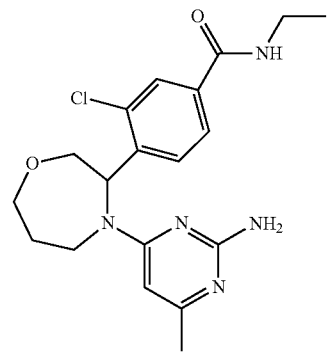 [SMILES: CCNC(=O)c1ccc(C2COCCCN2c2cc(C)nc(N)n2)c(Cl)c1]

(+/−)-4-[4-(2-amino-6-methyl-pyrimidin-4-yl)-1,4-oxazepan-3-yl]-3-chloro-N-ethyl-benzamide I-171

¹H NMR (400 MHz, DMSO-d6) (heated 360K) δ 7.51 (d, J=8.1 Hz, 1H), 7.39-7.28 (m, 2H), 6.71 (s, 2H), 6.03 (s, 1H), 5.65 (s, 1H), 4.52 (d, J=15.0 Hz, 1H), 4.17 (dd, J=13.6, 4.9 Hz, 1H), 3.96-3.73 (m, 3H), 3.65 (ddd, J=12.2, 9.2, 6.1 Hz, 1H), 2.89 (d, J=3.4 Hz, 6H), 2.19 (s, 3H), 1.85 (dt, J=7.6, 4.3 Hz, 2H); ESI-MS m/z calc. 389.16, found 390.0 (M+1)⁺. Retention time: 0.61 minutes.

(+/−)-3-(4-(2-amino-6-methylpyrimidin-4-yl)-1,4-oxazepan-3-yl)-4-chloro-N-cyclopropylbenzamide I-172

¹H NMR (400 MHz, DMSO-d6) δ 8.25 (s, 1H), 7.76-7.66 (m, 2H), 7.53 (d, J=8.2 Hz, 1H), 6.93 (s, 2H), 6.08 (s, 1H), 4.56 (s, 1H), 4.15 (dd, J=13.7, 5.0 Hz, 1H), 3.89 (ddd, J=16.0, 9.1, 3.7 Hz, 3H), 3.64 (ddd, J=12.2, 10.3, 4.2 Hz, 1H), 2.89 (s, 1H), 2.80 (tq, J=7.7, 4.0 Hz, 1H), 2.21 (s, 3H), 1.95-1.76 (m, 2H), 0.69 (td, J=7.0, 4.6 Hz, 2H), 0.56 (dt, J=6.9, 4.3 Hz, 2H); ESI-MS m/z found 402 (M+1).

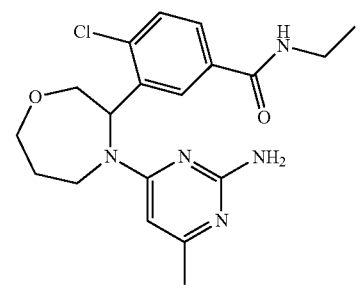 [SMILES: CCNC(=O)c1ccc(Cl)c(C2COCCCN2c2cc(C)nc(N)n2)c1]

327

(+/−)-3-[4-(2-amino-6-methyl-pyrimidin-4-yl)-1,4-oxazepan-3-yl]-4-chloro-N-ethyl-benzamide I-173

$^1$H NMR (400 MHz, DMSO-d6) δ 8.24 (s, 1H), 7.76-7.69 (m, 2H), 7.52 (dd, J=7.9, 0.7 Hz, 1H), 6.32 (s, 2H), 5.89 (s, 1H), 5.60 (s, 1H), 4.59 (d, J=15.1 Hz, 1H), 4.13 (dd, J=13.6, 5.0 Hz, 1H), 3.96-3.78 (m, 3H), 3.67-3.55 (m, 1H), 3.27 (dtd, J=8.0, 7.2, 5.9 Hz, 2H), 2.13 (s, 3H), 1.89-1.76 (m, 2H), 1.12 (t, J=7.2 Hz, 3H); ESI-MS m/z found 390.

Example 26

Synthetic Scheme 26: (+/−)-3-(4-(2-amino-6-methylpyrimidin-4-yl)-1,4-oxazepan-3-yl)-4-methoxy-N-methylbenzamide I-313

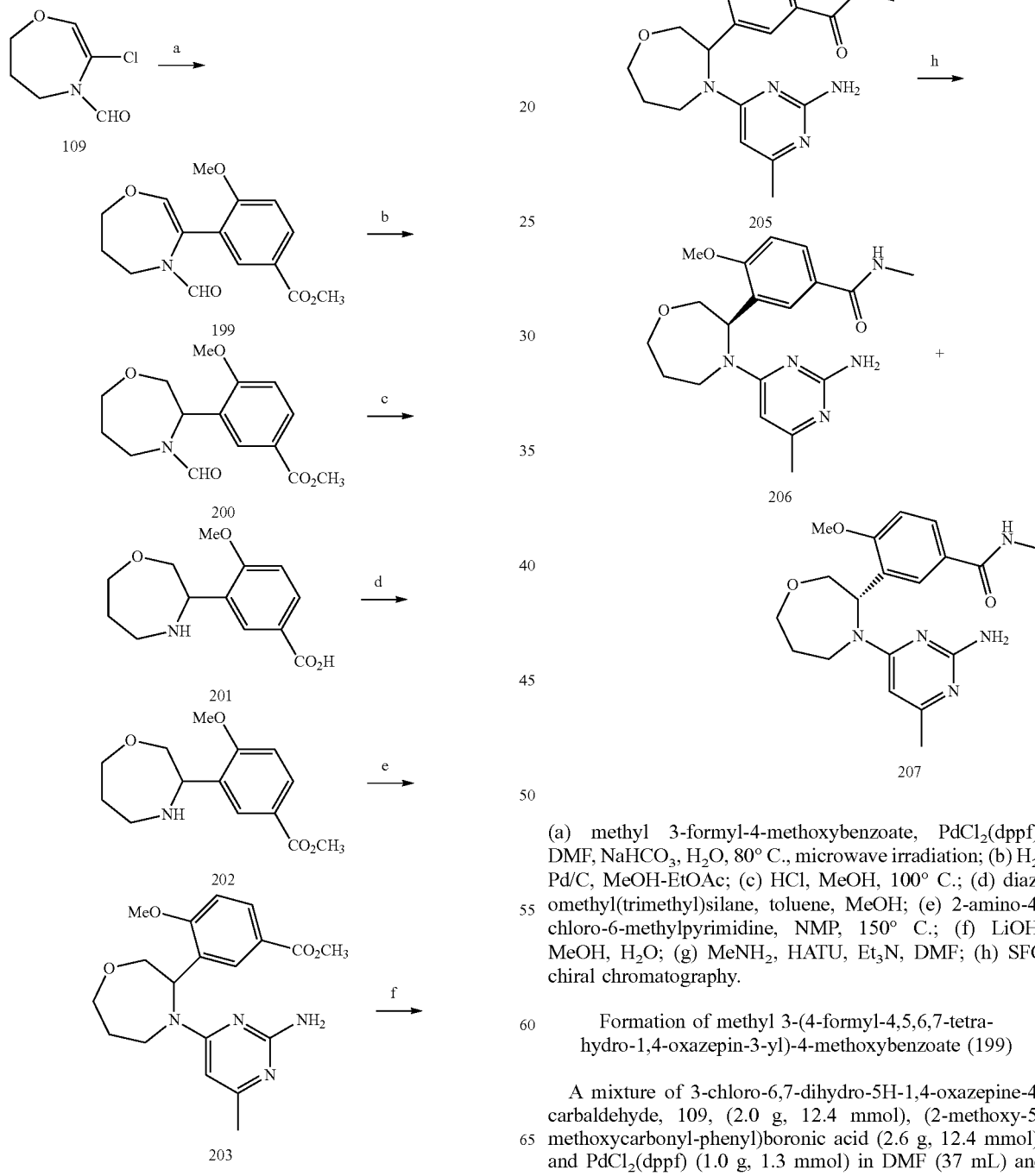

(a) methyl 3-formyl-4-methoxybenzoate, PdCl$_2$(dppf), DMF, NaHCO$_3$, H$_2$O, 80° C., microwave irradiation; (b) H$_2$, Pd/C, MeOH-EtOAc; (c) HCl, MeOH, 100° C.; (d) diazomethyl(trimethyl)silane, toluene, MeOH; (e) 2-amino-4-chloro-6-methylpyrimidine, NMP, 150° C.; (f) LiOH, MeOH, H$_2$O; (g) MeNH$_2$, HATU, Et$_3$N, DMF; (h) SFC chiral chromatography.

Formation of methyl 3-(4-formyl-4,5,6,7-tetrahydro-1,4-oxazepin-3-yl)-4-methoxybenzoate (199)

A mixture of 3-chloro-6,7-dihydro-5H-1,4-oxazepine-4-carbaldehyde, 109, (2.0 g, 12.4 mmol), (2-methoxy-5-methoxycarbonyl-phenyl)boronic acid (2.6 g, 12.4 mmol), and PdCl$_2$(dppf) (1.0 g, 1.3 mmol) in DMF (37 mL) and aqueous saturated sodium bicarbonate (12 mL) was heated in microwave reactor at 80° C. for 30 minutes. The reaction mixture was diluted with water, washed with water, and then the organic phase was concentrated to dryness. The resulting residue was purified via silica gel chromatography eluting with 40-100% EtOAc in heptanes followed by a 10% MeOH in dichloromethane flush. Fractions containing the desired product were combined and concentrated in vacuo to afford 2.4 g (63%) of the desired product as a colorless oil: $^1$H NMR (400 MHz, CDCl$_3$) δ 8.04 (dd, J=8.6, 2.2 Hz, 1H), 7.95 (s, 1H), 7.92 (d, J=2.2 Hz, 1H), 6.90 (d, J=8.6 Hz, 1H), 6.19 (s, 1H), 4.24 (dd, J=6.3, 5.3 Hz, 2H), 4.06 (t, J=6.6 Hz, 2H), 3.92 (s, 3H), 3.87 (s, 3H), 2.18-2.09 (m, 2H); ESI-MS m/z calc. 291.11, found 290.0 (M+1)$^+$. Retention time: 0.9 minutes.

Formation of (+/−)-methyl 3-(4-formyl-1,4-oxazepan-3-yl)-4-methoxybenzoate (200)

A mixture of methyl 3-(4-formyl-4,5,6,7-tetrahydro-1,4-oxazepin-3-yl)-4-methoxybenzoate, 199, (2.4 g, 8.2 mmol) and Pd/C (1.5 g, 0.7 mmol) in ethyl acetate (25 mL) and MeOH (25 mL) was shaken overnight under 55 psi hydrogen. The reaction mixture was filtered over Celite and the resulting filtrated was concentrated to dryness. The resulting residue was purified via silica gel chromatography eluting with 40-100% EtOAc in heptanes. Several mixed fractions containing the desired product were carried onto the next step as is: ESI-MS m/z calc. 293.13, found 294.0 (M+1)$^+$. Retention time: 0.77 minutes.

Formation of (+/−)-4-methoxy-3-(1,4-oxazepan-3-yl)benzoic acid hydrochloride (201)

A solution of methyl 3-(4-formyl-1,4-oxazepan-3-yl)-4-methoxybenzoate, 200, (2.4 g, 8.2 mmol) in MeOH (40 mL) and concentrated HCl (40 mL of 12.1 M solution, 484.0 mmol) was stirred overnight at 100° C. The mixture was concentrated to dryness. The product was taken up in MeOH and diluted into diethyl ether, then filtered and dried to give 2.2 g (84%) of a white solid: $^1$H NMR (400 MHz, DMSO-d6) δ 8.12 (d, J=2.1 Hz, 1H), 7.98 (ddd, J=8.7, 3.3, 2.1 Hz, 1H), 7.18 (d, J=8.7 Hz, 1H), 4.77-4.55 (m, 1H), 4.00 (dd, J=13.5, 8.9 Hz, 1H), 3.93 (d, J=1.9 Hz, 3H), 3.91-3.85 (m, 2H), 3.49-3.41 (m, 2H), 3.26 (ddd, J=13.4, 9.4, 3.4 Hz, 1H), 2.83 (ddt, J=47.7, 12.7, 7.3 Hz, 0.5H), 2.31-2.05 (m, 1H), 2.05-1.75 (m, 0.5H); ESI-MS m/z calc. 251.12, found 252.0 (M+1)$^+$. Retention time: 0.5 minutes.

Formation of (+/−)-methyl 4-methoxy-3-(1,4-oxazepan-3-yl)benzoate (202)

To a solution of 4-methoxy-3-(1,4-oxazepan-3-yl)benzoic acid hydrochloride, 201, (0.53 g, 1.65 mmol) in toluene (22 mL) and MeOH (2.5 mL) was added diazomethyl(trimethyl) silane (0.84 mL of 2 M solution, 1.69 mmol) in hexanes. The mixture was stirred for 15 minutes then concentrated to dryness to afford 487 mg of a colorless oil: ESI-MS m/z calc. 265.13, found 266.0 (M+1)$^+$. Retention time: 0.57 minutes.

Formation of (+/−)-methyl 3-(4-(2-amino-6-methylpyrimidin-4-yl)-1,4-oxazepan-3-yl)-4-methoxybenzoate (203)

A mixture of methyl 4-methoxy-3-(1,4-oxazepan-3-yl)benzoate, 202, (0.44 g, 1.65 mmol) and 4-chloro-6-methylpyrimidin-2-amine (0.26 g, 1.82 mmol) in NMP (5.5 mL) was stirred for 4 hours at 150° C. in a sealed tube. The mixture was diluted with water and extracted with EtOAc. The organic layer was concentrated to dryness and the resulting residue was purified via silica gel chromatography eluting with 0-12% MeOH in dichloromethane. Pure fractions were combined and concentrated in vacuo to give 89 mg (14%) of the desired product: $^1$H NMR (400 MHz, DMSO-d6) (heated 360K) δ 7.89 (dd, J=8.6, 2.2 Hz, 1H), 7.70 (d, J=2.2 Hz, 1H), 7.16 (d, J=8.7 Hz, 1H), 6.60 (s, 2H), 5.89 (s, 1H), 5.57 (s, 1H), 4.60 (d, J=14.7 Hz, 1H), 4.19 (dd, J=13.4, 5.2 Hz, 1H), 3.95 (s, 3H), 3.90 (dt, J=12.0, 3.8 Hz, 1H), 3.79 (s, 3H), 3.77-3.68 (m, 1H), 3.63-3.54 (m, 1H), 2.14 (s, 3H), 1.80 (dt, J=7.7, 4.2 Hz, 2H). ESI-MS m/z calc. 372.18, found 373.0 (M+1)$^+$. Retention time: 0.66 minutes.

Formation of (+/−)-3-(4-(2-amino-6-methylpyrimidin-4-yl)-1,4-oxazepan-3-yl)-4-methoxybenzoic acid trifluoroacetate salt (204)

To a solution of methyl 3-(4-(2-amino-6-methylpyrimidin-4-yl)-1,4-oxazepan-3-yl)-4-methoxybenzoate, 203, (0.090 g, 0.230 mmol) in MeOH (1 mL) and water (1 mL) was added LiOH (0.025 g, 1.044 mmol). The reaction mixture was stirred at room temperature for 3 hours, acidified with 1 M HCl and the mixture was purified by reverse phase chromatography eluting with 10-90% MeCN in water with 0.1% TFA. Pure fractions were combined, concentrated, and lyophilized to give 50 mg (58%) of the desired product: $^1$H NMR (400 MHz, DMSO-d6) (heated 360K) δ 7.92 (dd, J=8.6, 2.1 Hz, 1H), 7.72 (s, 1H), 7.41 (s, 2H), 7.17 (d, J=8.6 Hz, 1H), 4.24 (s, 1H), 3.99-3.90 (m, 4H), 3.80 (t, J=7.1 Hz, 2H), 3.64 (dt, J=12.2, 7.4 Hz, 1H), 2.33-1.65 (m, 6H); ESI-MS m/z calc. 358.16, found 359.0 (M+1)$^+$. Retention time: 0.6 minutes.

Formation of (R)-3-(4-(2-amino-6-methylpyrimidin-4-yl)-1,4-oxazepan-3-yl)-4-methoxy-N-methylbenzamide and (S)-3-(4-(2-amino-6-methylpyrimidin-4-yl)-1,4-oxazepan-3-yl)-4-methoxy-N-methylbenzamide (205)

To a solution of 3-[4-(2-amino-6-methyl-pyrimidin-4-yl)-1,4-oxazepan-3-yl]-4-chloro-benzoic acid (Trifluoroacetate salt), 204, (0.085 g, 0.180 mmol) in DMF (1 mL) was added HATU (0.102 g, 0.268 mmol) followed by Et$_3$N (0.125 mL, 0.897 mmol). After stirring for 10 minutes, methylamine (0.700 mL of 2 M, 1.40 mmol) in THF was added and the reaction was stirred overnight. The reaction mixture was diluted with water and extracted with EtOAc. The organic layer was concentrated to dryness and purified via silica gel chromatography eluting with 0-10% MeOH in dichloromethane. Pure fractions were combined, concentrated in vacuo and subjected to SFC purification to afford the racemic mixture, 205, which was then submitted to SFC chiral separation.

Peak A: (R)-3-(4-(2-amino-6-methylpyrimidin-4-yl)-1,4-oxazepan-3-yl)-4-methoxy-N-methylbenzamide (206); $^1$H NMR (400 MHz, DMSO-d6) (heated 360K) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.22, found 370.0 (M+1)$^+$. Retention time: 0.68 minutes. I-314.

Peak B: (S)-3-(4-(2-amino-6-methylpyrimidin-4-yl)-1,4-oxazepan-3-yl)-4-methoxy-N-methylbenzamide (207); $^1$H NMR (400 MHz, DMSO-d6) (heated 360K) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.22, found 370.0 (M+1)⁺. Retention time: 0.68 minutes. I-315.

The following analogs were prepared according to Synthetic Scheme 26:

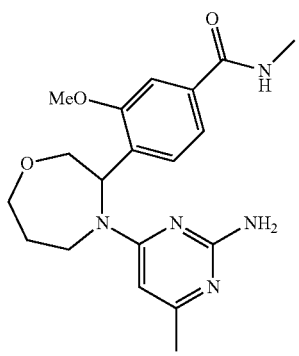

208

(+/−)-4-(4-(2-amino-6-methylpyrimidin-4-yl)-1,4-oxazepan-3-yl)-3-methoxy-N-methylbenzamide (208) I-316

¹H NMR (400 MHz, DMSO-d6) (heated 360K) δ 8.12 (s, 1H), 7.49 (d, J=1.6 Hz, 1H), 7.40 (dd, J=7.9, 1.6 Hz, 1H), 7.23 (d, J=7.9 Hz, 1H), 7.02 (s, 2H), 6.05 (s, 1H), 5.61 (s, 1H), 4.62 (s, 1H), 4.24 (dd, J=13.4, 5.2 Hz, 1H), 3.95 (s, 4H), 3.81 (dt, J=13.4, 7.9 Hz, 2H), 3.60 (ddd, J=12.1, 9.4, 5.1 Hz, 1H), 2.82 (d, J=4.5 Hz, 3H), 2.22 (s, 3H), 1.91-1.74 (m, 2H); ESI-MS m/z calc. 371.20, found 372.0 (M+1)⁺. Retention time: 0.55 minutes.

The following azepanes were made according to Synthetic Scheme 12. Amide preparation according to Synthetic Scheme 26

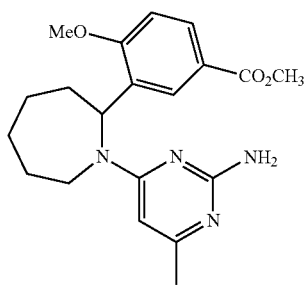

209

(+/−)-Methyl 3-(1-(2-amino-6-methylpyrimidin-4-yl)azepan-2-yl)-4-methoxybenzoate (209) I-111

¹H NMR (400 MHz, DMSO-d6) (heated 360K) δ 7.82 (dd, J=8.6, 2.2 Hz, 1H), 7.59 (d, J=2.2 Hz, 1H), 7.11 (d, J=8.6 Hz, 1H), 5.55 (d, J=45.8 Hz, 3H), 5.25 (s, 1H), 4.36 (d, J=44.7 Hz, 1H), 3.96 (s, 3H), 3.77 (s, 3H), 3.39-3.28 (m, 1H), 2.39 (dt, J=14.1, 6.9 Hz, 1H), 2.00 (s, 3H), 1.95-1.71 (m, 3H), 1.71-1.44 (m, 2H), 1.45-1.16 (m, 2H); ESI-MS m/z calc. 370.20, found 371.0 (M+1)⁺. Retention time: 0.78 minutes.

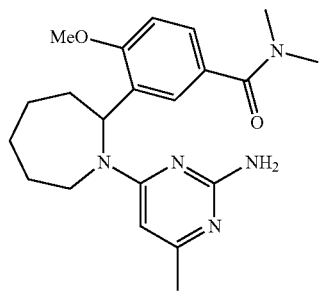

210

(+/−)-3-(1-(2-amino-6-methylpyrimidin-4-yl)azepan-2-yl)-4-methoxy-N,N-dimethylbenzamide (210) I-115

¹H NMR (400 MHz, DMSO-d6) (heated 360K) δ 7.31 (dd, J=8.4, 2.1 Hz, 1H), 7.15-6.93 (m, 4H), 6.02 (s, 1H), 3.91 (s, 3H), 3.54 (s, 1H), 2.90 (s, 6H), 2.20 (s, 3H), 2.01-1.68 (m, 4H), 1.63-1.20 (m, 3H); ESI-MS m/z calc. 383.23, found 384.0 (M+1)⁺. Retention time: 0.7 minutes.

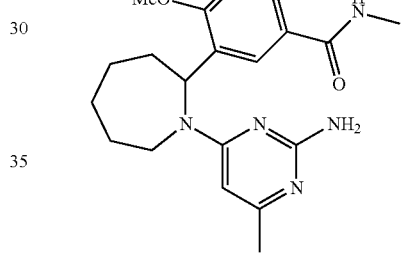

211

(+/−)-3-(1-(2-amino-6-methylpyrimidin-4-yl)azepan-2-yl)-4-methoxy-N-methylbenzamide (211) I-114

¹H NMR (400 MHz, DMSO-d6) (heated 360K) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.22, found 370.0 (M+1)⁺. Retention time: 0.68 minutes.

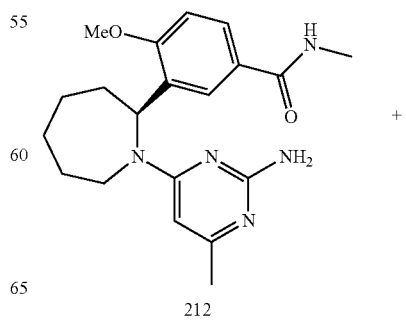

212

333
-continued

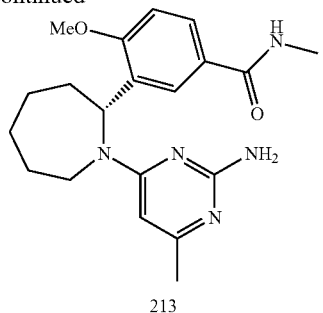

213

(S)-3-(1-(2-amino-6-methylpyrimidin-4-yl)azepan-2-yl)-4-methoxy-N-methylbenzamide (212) I-149;
(R)-3-(1-(2-amino-6-methylpyrimidin-4-yl)azepan-2-yl)-4-methoxy-N-methylbenzamide (213) I-148

(S)-3-[1-(2-amino-6-methyl-pyrimidin-4-yl)azepan-2-yl]-4-methoxy-N-methylbenzamide (212); 1H NMR (400 MHz, DMSO-d6) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.21646, found 370.0 (M+1)$^+$. Retention time: 0.68 minutes. I-149.

(R)-3-[1-(2-amino-6-methyl-pyrimidin-4-yl)azepan-2-yl]-4-methoxy-N-methylbenzamide (213); $^1$H NMR (400 MHz, DMSO-d6) (heated 360K) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.22, found 370.0 (M+1)$^+$. Retention time: 0.68 minutes. I-148.

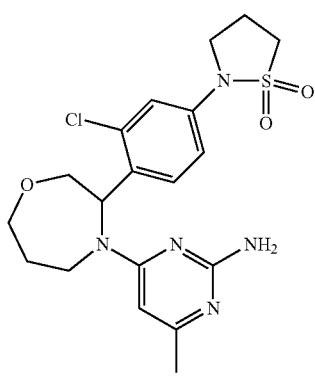

214

(+/−)-4-[3-[2-chloro-4-(1,1-dioxo-1,2-thiazolidin-2-yl)phenyl]-1,4-oxazepan-4-yl]-6-methyl-pyrimidin-2-amine (214) I-193 heated (360K) $^1$H NMR (400 MHz, DMSO-d6) δ 7.30 (d, J=8.6 Hz, 1H), 7.26 (d, J=2.4 Hz, 1H), 7.13 (dd, J=8.6, 2.4 Hz, 1H), 5.59 (s, 1H), 5.47 (s, 2H), 4.60 (d, J=15.1 Hz, 1H), 4.09 (dd, J=13.4, 5.0 Hz, 1H), 3.93-3.84 (m, 1H), 3.77-3.71 (m, 3H), 3.70-3.50 (m, 2H), 3.46 (t, J=7.4 Hz, 4H), 2.44-2.35 (m, 2H), 2.01 (s, 3H), 1.78 (tt, J=8.3, 4.3 Hz, 2H); ESI-MS m/z calc. 437.1, found 438.0 (M+1)$^+$. Retention time: 0.67 minutes.

334

Example 27

Synthetic Scheme 27: (+/−)-4-(3-(2-chloro-4-((methylsulfonyl)methyl)phenyl)-1,4-oxazepan-4-yl)-6-methylpyrimidin-2-amine (219) I-208

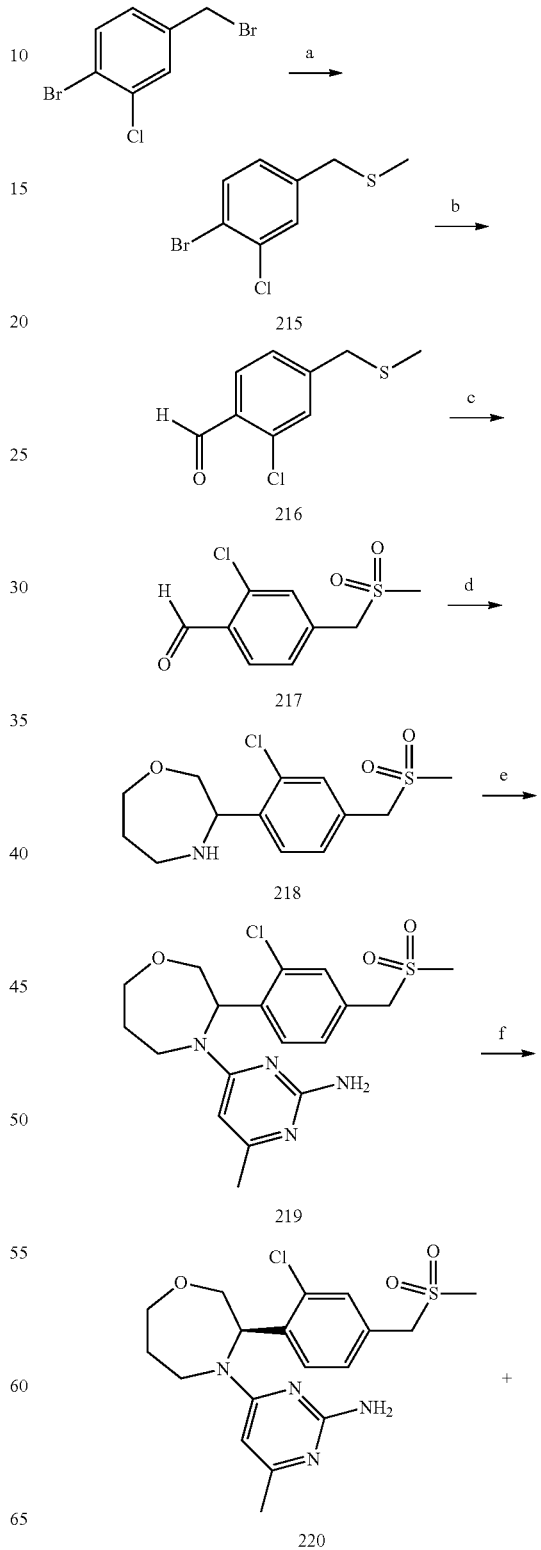

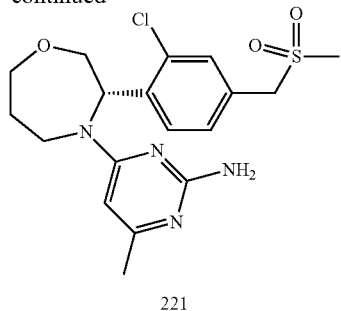

221

(a) NaSMe, MeOH, 0° C. to RT; (b) nBuLi, THF, −78° C., then DMF; (c) mCPBA, CH$_2$Cl$_2$; (d) i) 4 Å mol sieves, 3-((tributylstannyl)methoxy)propan-1-amine, CH$_2$Cl$_2$; ii) 2,6-lutidine, Cu(OTf)$_2$, hexafluoroisopropanol, CH$_2$Cl$_2$; (e) 2-amino-4-chloro-6-methylpyrimidine, nBuOH, 135° C.; (f) SFC chiral chromatography.

Formation of
(4-bromo-3-chlorobenzyl)(methyl)sulfane (215)

The 1-bromo-4-(bromomethyl)-2-chloro-benzene (120 g, 422 mmol) was dissolved in MeOH (1 L) in a 2 L round-bottomed flask equipped with an overhead stirrer, temperature probe, and a 500 mL addition funnel. The solution was cooled to 0° C. in a brine bath. The NaSMe (235 g of 15% w/w, 503 mmol) solution was added dropwise at a rate to keep the temperature below 10° C. A white solid precipitated. The solution was stirred over the weekend. The reaction was poured into 1N NaOH and extracted three times with dichloromethane. The extracts were combined, dried (MgSO$_4$), filtered and evaporated in vacuo to afford 1-bromo-2-chloro-4-(methylsulfanylmethyl)benzene (105 g, 99%) as a clear, slightly purple oil. $^1$H NMR showed the oil to be pure product and consistent with previous batches: $^1$H NMR (300 MHz, CDCl$_3$) 7.54 (d, J=8.2 Hz, 1H), 7.40 (s, 1H), 7.07 (dd, J=8.2, 1.6 Hz, 1H), 3.59 (s, 1H), 1.99 (s, 2H) ppm.

Formation of
2-chloro-4-((methylthio)methyl)benzaldehyde (216)

The 1-bromo-2-chloro-4-(methylsulfanylmethyl)benzene, 215, (2.9 g, 11.4 mmol) was dissolved in THF (75 mL) in a flame-dried 250 mL round-bottomed flask equipped with a magnetic stirbar. The yellow solution was cooled to −78° C. in a dry ice/acetone bath. The nBuLi (6.6 mL of 1.9 M solution, 12.5 mmol) was added dropwise via syringe at a rate to keep the temperature below −60° C. The reaction initially turned a reddish-orange color during the nBuLi addition but changed to a brown color after stirring for 15 minutes. The DMF (1.2 mL, 15.5 mmol) was added via syringe at a rate to keep the temperature below −60° C. The reaction was stirred for 30 minutes at −78° C. and then removed from the cooling bath and allowed to warm to room temperature. The reaction mixture was poured into 1N HCl and extracted with MTBE. The extract was dried (MgSO$_4$), filtered and evaporated in vacuo to afford 2.2 g of the crude product as a yellow oil. The product was purified via silica gel chromatography using a 120 g ISCO silica gel cartridge using an isocratic gradient of 50% dichloromethane/heptane. The fractions containing the largest peak were combined and evaporated in vacuo to afford 2-chloro-4-(methylsulfanylmethyl)benzaldehyde (1.95 g, 85%) as a slightly yellow oil.

$^1$H NMR was consistent with the product: $^1$H NMR (300 MHz, CDCl$_3$) 10.45 (s, 1H), 7.89 (d, J=8.0 Hz, 1H), 7.43 (d, J=1.3 Hz, 1H), 7.39-7.30 (m, 1H), 3.68 (s, 2H), 2.02 (s, 3H) ppm.

Formation of
2-chloro-4-((methylsulfonyl)methyl)benzaldehyde (217)

The 2-chloro-4-(methylsulfanylmethyl)benzaldehyde 2-chloro-4-(methylsulfanylmethyl) benzaldehyde, 216, (8.75 g, 43.60 mmol) was dissolved in dichloromethane (400 mL) in a 1 L round bottomed flask equipped with a magnetic stir bar. The mCPBA (22.2 g, 89.97 mmol) was added completely dissolving. After 15 minutes, a white solid precipitated. After stirring for 1 hour, the reaction mixture was poured into saturated aqueous NaHCO$_3$ solution and extracted with dichloromethane. The organic phase was dried (MgSO$_4$) and filtered over a plug of silica gel. The plug was eluted with 25% EtOAc/dichloromethane and the filtrate was evaporated in vacuo to afford 2-chloro-4-(methylsulfonylmethyl)benzaldehyde (9.1 g, 90%) as a white solid. $^1$H NMR was consistent with the product: $^1$H NMR (300 MHz, CDCl$_3$) 10.48 (s, 1H), 7.97 (d, J=8.0 Hz, 1H), 7.56 (s, 1H), 7.50-7.40 (m, 2H), 4.28 (s, 2H), 2.86 (s, 4H) ppm.

Formation of 3-(2-chloro-4-((methylsulfonyl)methyl)phenyl)-1,4-oxazepane (218)

A mixture of 3-(tributylstannylmethoxy)propan-1-amine (3.4 g, 8.9 mmol), 2-chloro-4-(methylsulfonylmethyl)benzaldehyde, 217, (2.0 g, 8.6 mmol) and 4 angstrom molecular sieves in dichloromethane (40 mL) was stirred for 20 hours. The mixture was filtered. In a separate flask containing hexafluoroisopropanol (10.0 mL) was added 2,6-lutidine (1.1 mL, 9.5 mmol) followed by Cu(OTf)$_2$ (3.3 g, 9.1 mmol) and dichloromethane (10 mL). The mixture was stirred for 3 hours at room temperature. The filtered imine solution was added in one portion to the second flask all at once. The resulting reaction mixture was stirred overnight, filtered and then treated with 100 mL of 2:1 mixture of aqueous saturated NaHCO$_3$ solution and 10% ammonium hydroxide. The organic phase was separated and washed with aqueous saturated NaHCO$_3$ solution, dried with sodium sulfate, filtered and concentrated in vacuo. The resulting residue was purified by silica gel chromatography using 80 gram ISCO column eluting with 0-15% methanol/dichloromethane to afford 1.1 grams of desired product as a yellow oil. A second purification by silica gel chromatography using 40 gram ISCO column eluting with 0-8% methanol/dichloromethane was required to afford 690 mg of pure desired product as a yellow oil: $^1$H NMR (400 MHz, CDCl$_3$) δ 7.64 (d, J=8.0 Hz, 1H), 7.43 (d, J=1.8 Hz, 1H), 7.33 (dd, J=8.0, 1.9 Hz, 1H), 4.46 (dd, J=9.0, 3.5 Hz, 1H), 4.20 (s, 2H), 4.07-3.92 (m, 2H), 3.85 (dt, J=12.3, 6.2 Hz, 1H), 3.49 (s, 2H), 3.44 (dd, J=12.4, 9.1 Hz, 3H), 3.24 (dt, J=13.6, 5.0 Hz, 1H), 3.06 (dt, J=13.7, 6.8 Hz, 1H), 2.81 (d, J=0.8 Hz, 3H), 2.00 (qd, J=6.4, 4.9 Hz, 2H), 1.81 (s, 2H); ESI-MS m/z calc. 303.8, found 304.0 (M+1)$^+$. Retention time: 0.48 minutes.

Formation of 4-(3-(2-chloro-4-((methylsulfonyl)methyl)phenyl)-1,4-oxazepan-4-yl)-6-methylpyrimidin-2-amine (219)

A solution of 3-[2-chloro-4-(methylsulfonylmethyl)phenyl]-1,4-oxazepane, 218, (1.02 g, 3.37 mmol) and 4-chloro-6-methyl-pyrimidin-2-amine (0.58 g, 4.05 mmol) in n-BuOH (15 mL) was stirred overnight in a sealed tube at 135° C. then concentrated to dryness. The residue was dissolved in EtOAc and washed with aqueous saturated sodium bicarbonate solution. The organic layer was concentrated to dryness and purified via silica gel chromatography eluting with 0-10% MeOH in dichloromethane. Pure fractions were combined and concentrated to give 830 mg of desired product: ESI-MS m/z calc. 410.1, found 411.0 (M+1)$^+$. Retention time: 0.63 minutes.

The racemic mixture was submitted for SFC purification: AD-H 20×250 mm column using 40% MeOH (5 mM ammonia) 60% $CO_2$ isocratic method. Pure fractions were concentrated to dryness and run through plug of silica eluting with 0-10% MeOH in dichloromethane. Fractions were concentrated and lyophilized.

Peak A: (R)-4-[3-[2-chloro-4-(methylsulfonylmethyl) phenyl]-1,4-oxazepan-4-yl]-6-methyl-pyrimidin-2-amine (220) $^1$H NMR (400 MHz, DMSO-d6) δ 7.50 (d, J=1.2 Hz, 1H), 7.33 (d, J=1.0 Hz, 2H), 5.59 (s, 1H), 5.46 (s, 3H), 4.59 (d, J=14.9 Hz, 1H), 4.43 (s, 2H), 4.13 (dd, J=13.5, 5.0 Hz, 1H), 3.94-3.85 (m, 1H), 3.74 (dd, J=13.6, 10.3 Hz, 1H), 3.70-3.62 (m, 1H), 3.55 (ddd, J=12.0, 9.8, 4.6 Hz, 1H), 2.88 (s, 3H), 2.00 (s, 3H), 1.82-1.72 (m, 2H); ESI-MS m/z calc. 410.1, found 411.0 (M+1)$^+$. Retention time: 0.62 minutes. I-223.

Peak B: (S)-4-[3-[2-chloro-4-(methylsulfonylmethyl)phenyl]-1,4-oxazepan-4-yl]-6-methyl-pyrimidin-2-amine (221); $^1$H NMR (400 MHz, DMSO-d6) δ 7.50 (d, J=1.2 Hz, 1H), 7.33 (d, J=1.1 Hz, 2H), 5.60 (s, 1H), 5.46 (s, 3H), 4.59 (d, J=14.8 Hz, 1H), 4.43 (s, 2H), 4.14 (dd, J=13.5, 5.0 Hz, 1H), 3.95-3.85 (m, 1H), 3.74 (dd, J=13.5, 10.2 Hz, 1H), 3.70-3.62 (m, 1H), 3.55 (ddd, J=12.0, 9.9, 4.6 Hz, 1H), 2.88 (s, 3H), 2.01 (s, 3H), 1.84-1.73 (m, 2H); ESI-MS m/z calc. 410.1, found 411.0 (M+1)$^+$. Retention time: 0.64 minutes; Optical rotation: +47.7° (3.1 mg in 1 mL MeOH). I-224.

Example 28

Synthetic Scheme 28: (S)-1-(4-(4-(2-amino-6-methylpyrimidin-4-yl)-1,4-oxazepan-3-yl)-3-chlorophenyl)-4-methylpiperidin-4-ol (222) I-242

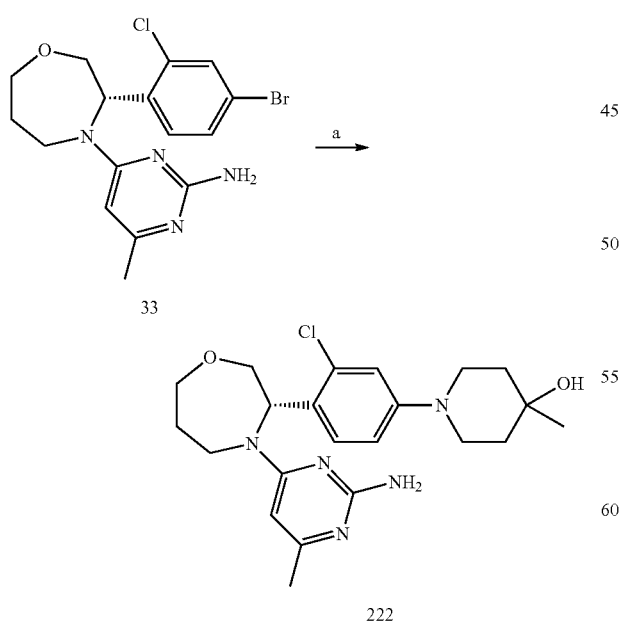

(a) 4-methylpiperidin-4-ol, NaOtBu, 2,6-lutidine, tBuXPhos palladacycle G3

Formation of 1-[4-[(3S)-4-(2-amino-6-methyl-pyrimidin-4-yl)-1,4-oxazepan-3-yl]-3-chloro-phenyl]-4-methyl-piperidin-4-ol (222)

A solution of (S)-4-[(3 S)-3-(4-bromo-2-chloro-phenyl)-1,4-oxazepan-4-yl]-6-methyl-pyrimidin-2-amine, 33, (3.1 g, 7.8 mmol), 4-methylpiperidin-4-ol (3.5 g, 30.4 mmol) and NaOtBu (3.0 g, 31.2 mmol) in 2,6-lutidine (40 mL) was degassed with nitrogen for 5 minutes. tBuXPhos palladacycle G3 (0.9 g, 1.2 mmol) was added and the reaction mixture was stirred at room temperature for 2 hours. The mixture was diluted with water and extracted 3 times with EtOAc. The combined organic phases were dried over magnesium sulfate, filtered and concentrated in vacuo. The resulting residue was purified via silica gel chromatography eluting with 0-15% MeOH in dichloromethane. Fractions containing the desired product were combined and concentrated to give a light brown oil. A second purification using reverse phase silica gel chromatography 275 g C18-aqueous column eluting with 5-60% MeCN in water with 0.1% TFA. Pure fractions were combined, neutralized with saturated aqueous sodium bicarbonate solution and extracted twice with EtOAc. The combined organic phases were dried over magnesium sulfate, filtered, concentrated in vacuo and lyophilized to afford 850 mg of product: heated (360K) $^1$H NMR (400 MHz, DMSO-d6) δ 7.07 (d, J=8.6 Hz, 1H), 6.86 (d, J=2.6 Hz, 1H), 6.79 (dd, J=8.8, 2.6 Hz, 1H), 5.70 (s, 2H), 5.60 (s, 1H), 5.28 (s, 1H), 4.63 (d, J=14.6 Hz, 1H), 4.11-3.95 (m, 2H), 3.90-3.81 (m, 1H), 3.67 (dd, J=13.4, 10.0 Hz, 1H), 3.63-3.47 (m, 2H), 3.31-3.08 (m, 4H), 2.01 (s, 3H), 1.75 (dp, J=12.3, 4.5 Hz, 2H), 1.57-1.45 (m, 4H), 1.13 (s, 3H); ESI-MS m/z calc. 431.2, found 432.0 (M+1)$^+$. Retention time: 0.58 minutes.

The following analogs were prepared according to Synthetic Scheme 28:

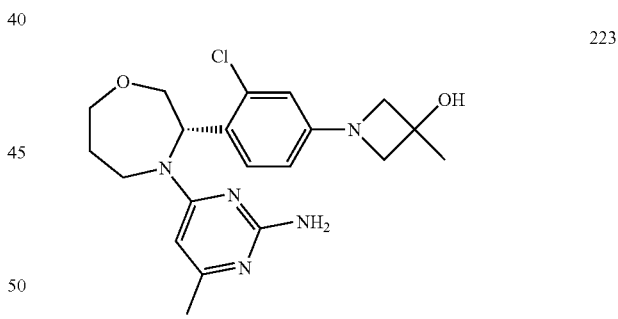

(S)-1-(4-(4-(2-amino-6-methylpyrimidin-4-yl)-1,4-oxazepan-3-yl)-3-chlorophenyl)-3-methylazetidin-3-ol (223) I-261 heated (360K) $^1$H NMR (400 MHz, DMSO-d6) δ 7.07 (d, J=8.5 Hz, 1H), 6.41 (d, J=2.3 Hz, 1H), 6.32 (dd, J=8.5, 2.4 Hz, 1H), 5.68 (s, 2H), 5.60 (s, 1H), 5.24 (d, J=22.4 Hz, 2H), 4.66 (d, J=14.8 Hz, 1H), 4.09-3.99 (m, 1H), 3.87 (dt, J=11.6, 3.6 Hz, 1H), 3.72 (d, J=7.3 Hz, 2H), 3.63 (t, J=7.5 Hz, 2H), 3.55 (ddd, J=12.4, 9.6, 5.0 Hz, 2H), 2.02 (s, 3H), 1.76 (tt, J=8.3, 3.6 Hz, 2H), 1.43 (s, 3H); ESI-MS m/z calc. 403.2, found 404.0 (M+1)$^+$. Retention time: 0.7 minutes.

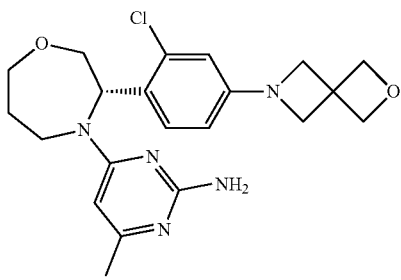

4-[(3S)-3-[2-chloro-4-(2-oxa-6-azaspiro[3.3]heptan-6-yl)phenyl]-1,4-oxazepan-4-yl]-6-methyl-pyrimidin-2-amine (224) I-259 heated (360K) 1H NMR (400 MHz, DMSO-d6) δ 7.08 (d, J=8.4 Hz, 1H), 6.43 (d, J=2.4 Hz, 1H), 6.33 (dd, J=8.5, 2.4 Hz, 1H), 5.59 (d, J=11.6 Hz, 4H), 5.26 (s, 1H), 4.68 (s, 4H), 4.02 (dd, J=13.5, 5.0 Hz, 1H), 3.91-3.83 (m, 1H), 3.67 (dd, J=13.4, 10.1 Hz, 1H), 3.63-3.50 (m, 2H), 2.01 (d, J=2.4 Hz, 3H), 1.74 (dd, J=8.4, 4.3 Hz, 3H), 1.25 (s, 3H); ESI-MS m/z calc. 415.2, found 416.0 (M+1)⁺. Retention time: 0.7 minutes.

225

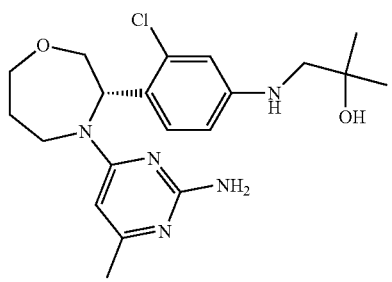

4-[(3S)-3-[2-chloro-4-[(3-methyloxetan-3-yl)amino]phenyl]-1,4-oxazepan-4-yl]-6-methyl-pyrimidin-2-amine (225) I-266

¹H NMR (400 MHz, MeOD) δ 7.00 (d, J=8.5 Hz, 1H), 6.47 (d, J=2.4 Hz, 1H), 6.32 (dd, J=8.5, 2.4 Hz, 1H), 5.56 (br s, 1H), 5.27-4.97 (br s, 2H), 4.73 (dd, J=5.9, 2.3 Hz, 2H), 4.53 (dd, J=5.9, 1.8 Hz, 2H), 4.19 (dd, J=5.1 Hz, 1H), 4.00 (d, J=8.3 Hz, 1H), 3.68 (dd, J=13.6, 10.5 Hz, 1H), 3.60 (dd, J=16.6, 7.8 Hz, 2H), 2.08 (s, 3H), 1.98-1.82 (m, 1H), 1.82-1.73 (m, 1H), 1.61 (s, 3H). ESI-MS m/z calc. 403.1775, found 404.25 (M+1)⁺. Retention time: 0.6 minutes.

226

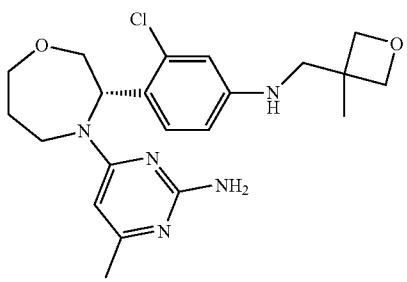

4-[(3S)-3-[2-chloro-4-[(3-methyloxetan-3-yl)methyl-amino]phenyl]-1,4-oxazepan-4-yl]-6-methyl-pyrimidin-2-amine (226) I-240

¹H NMR (400 MHz, MeOD) δ 6.99 (d, J=8.5 Hz, 1H), 6.70 (d, J=2.4 Hz, 1H), 6.57 (dd, J=8.6, 2.4 Hz, 1H), 5.75-4.80 (m, 3H), 4.53 (d, J=5.9 Hz, 2H), 4.38 (d, J=5.9 Hz, 2H), 4.19 (dd, J=13.6, 5.1 Hz, 1H), 4.00 (d, J=7.2 Hz, 1H), 3.69 (dd, J=13.6, 10.5 Hz, 1H), 3.60 (dd, J=13.7, 10.7 Hz, 2H), 3.26 (s, 2H), 2.07 (s, 3H), 1.96-1.71 (m, 2H), 1.36 (s, 3H); ESI-MS m/z calc. 417.2, found 418.3 (M+1)⁺. Retention time: 0.63 minutes.

227

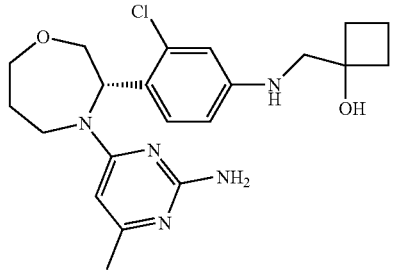

1-[4-[(3S)-4-(2-amino-6-methyl-pyrimidin-4-yl)-1,4-oxazepan-3-yl]-3-chloro-anilino]-2-methyl-propan-2-ol (227) I-247

¹H NMR (400 MHz, MeOD) δ6.97 (d, J=8.5 Hz, 1H), 6.70 (d, J=2.4 Hz, 1H), 6.57 (dd, J=8.6, 2.4 Hz, 1H), 5.57 (br s, 1H), 5.14 (br s, 2H), 4.19 (dd, J=13.6, 5.1 Hz, 1H), 4.00 (d, J=8.2 Hz, 1H), 3.75-3.52 (m, 3H), 3.03 (s, 2H), 2.07 (s, 3H), 2.00-1.70 (m, 2H), 1.23 (s, 6H); ESI-MS m/z calc. 405.2, found 406.2 (M+1)⁺. Retention time: 0.6 minutes.

228

1-[[4-[(3S)-4-(2-amino-6-methyl-pyrimidin-4-yl)-1,4-oxazepan-3-yl]-3-chloro-anilino]methyl]-cyclobutanol (228) I-263

¹H NMR (400 MHz, MeOD) δ 6.98 (d, J=8.5 Hz, 1H), 6.72 (d, J=2.4 Hz, 1H), 6.58 (dd, J=8.6, 2.4 Hz, 1H), 5.56 (br s, 1H), 5.07 (br s, 2H), 4.19 (dd, J=13.6, 5.1 Hz, 1H), 4.00 (d, J=8.7 Hz, 1H), 3.73-3.55 (m, 1H), 3.59 (t, J=12.3 Hz, 2H), 3.17 (s, 2H), 2.16-1.98 (m, 6H), 1.96-1.70 (m, 3H), 1.64-1.56 (m, 1H); ESI-MS m/z calc. 417.2, found 418.1 (M+1)⁺. Retention time: 2.72 minutes.

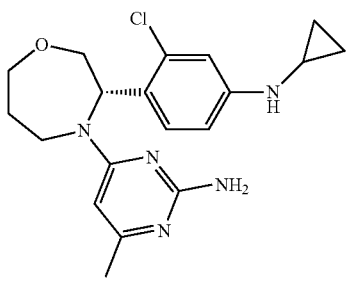

4-[(3S)-3-[2-chloro-4-(cyclopropylamino)phenyl]-1,4-oxazepan-4-yl]-6-methyl-pyrimidin-2-amine (229) I-248

$^1$H NMR (400 MHz, MeOD) δ 6.98 (d, J=8.6 Hz, 1H), 6.80 (d, J=2.3 Hz, 1H), 6.64 (dd, J=8.5, 2.3 Hz, 1H), 5.57 (br s, 1H), 5.35-4.80 (br s, 2H), 4.19 (dd, J=13.6, 5.1 Hz, 1H), 4.01 (d, J=8.0 Hz, 1H), 3.65 (ddd, J=24.2, 17.3, 11.3 Hz, 4H), 2.36-2.28 (m, 1H), 2.07 (s, 3H), 1.95-1.72 (m, 3H), 0.73-0.65 (m, 2H), 0.42 (td, J=6.6, 4.4 Hz, 2H); ESI-MS m/z calc. 373.2, found 374.2 (M+1)$^+$. Retention time: 0.65 minutes.

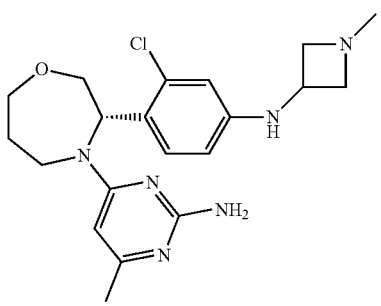

4-[(3S)-3-[2-chloro-4-[(1-methylazetidin-3-yl)amino]phenyl]-1,4-oxazepan-4-yl]-6-methyl-pyrimidin-2-amine (230) I-246

$^1$H NMR (400 MHz, MeOD) δ 7.00 (d, J=8.5 Hz, 1H), 6.57 (d, J=2.4 Hz, 1H), 6.45 (dd, J=8.5, 2.4 Hz, 1H), 5.53 (br s, 1H), 5.09 (br s, 2H), 4.18 (dd, J=13.6, 5.1 Hz, 1H), 4.05-3.95 (m, 2H), 3.82-3.74 (m, 2H), 3.68 (dd, J=13.6, 10.5 Hz, 1H), 3.59 (t, J=12.1 Hz, 2H), 3.02-2.94 (m, 2H), 2.39 (s, 3H), 2.06 (s, 3H), 1.96-1.73 (m, 2H); ESI-MS m/z calc. 402.2, found 403.3 (M+1)$^+$. Retention time: 0.53 minutes.

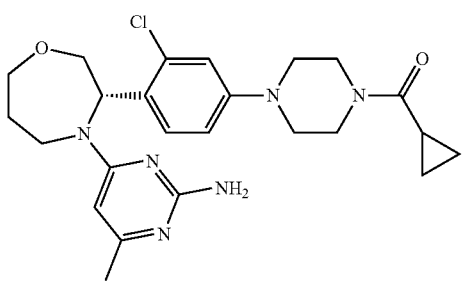

(+/−)-[4-[4-[4-(2-amino-6-methyl-pyrimidin-4-yl)-1,4-oxazepan-3-yl]-3-chloro-phenyl]piperazin-1-yl]-cyclopropyl-methanone (231) I-273

$^1$H NMR (400 MHz, CDCl$_3$) δ 7.13 (d, J=8.6 Hz, 1H), 6.92 (d, J=2.5 Hz, 1H), 6.76 (dd, J=8.7, 2.6 Hz, 1H), 5.58 (s, 1H), 4.60 (s, 2H), 4.31 (dd, J=13.5, 5.0 Hz, 1H), 4.08 (d, J=12.2 Hz, 1H), 4.01-3.05 (m, 11H), 2.15 (s, 3H), 1.92-1.62 (m, 3H), 1.14-0.98 (m, 2H), 0.91-0.65 (m, 2H); ESI-MS m/z calc. 470.2, found 471.2 (M+1)$^+$. Retention time: 2.72 minutes.

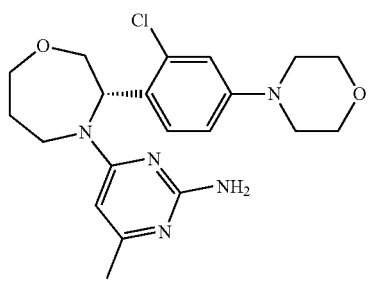

4-[(3S)-3-(2-chloro-4-morpholino-phenyl)-1,4-oxazepan-4-yl]-6-methyl-pyrimidin-2-amine (232) I-216 heated (360K) $^1$H NMR (400 MHz, DMSO-d6) δ 7.14 (d, J=8.7 Hz, 1H), 6.92 (d, J=2.6 Hz, 1H), 6.83 (dd, J=8.7, 2.6 Hz, 1H), 5.60 (s, 3H), 5.31 (s, 1H), 4.65 (d, J=14.9 Hz, 1H), 4.06 (dd, J=13.4, 5.1 Hz, 1H), 3.93-3.83 (m, 1H), 3.74-3.67 (m, 5H), 3.65-3.50 (m, 2H), 3.14-3.08 (m, 4H), 2.01 (d, J=1.8 Hz, 3H), 1.76 (dt, J=8.3, 4.1 Hz, 2H); ESI-MS m/z calc. 403.2, found 404.0 (M+1)$^+$. Retention time: 0.7 minutes.

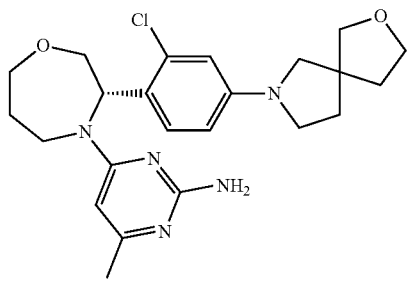

4-[(3S)-3-[2-chloro-4-(2-oxa-7-azaspiro[4.4]nonan-7-yl)phenyl]-1,4-oxazepan-4-yl]-6-methyl-pyrimidin-2-amine (233) I-219 heated (360K) $^1$H NMR (400 MHz, DMSO-d6) δ 7.07 (d, J=8.6 Hz, 1H), 6.52 (d, J=2.6 Hz, 1H), 6.45 (dd, J=8.7, 2.5 Hz, 1H), 5.56 (s, 1H), 5.49 (s, 2H), 5.24 (s, 1H), 4.69 (d, J=14.7 Hz, 1H), 4.03 (dd, J=13.4, 5.0 Hz, 1H), 3.87 (dt, J=12.0, 3.9 Hz, 1H), 3.80 (t, J=7.0 Hz, 2H), 3.67 (dd, J=13.4, 10.1 Hz, 1H), 3.59-3.49 (m, 3H), 3.29 (dddd, J=9.6, 7.3, 4.9, 2.4 Hz, 2H), 3.20 (q, J=3.0, 2.3 Hz, 2H), 1.99 (s, 3H), 1.98-1.80 (m, 4H), 1.76 (tt, J=8.3, 4.4 Hz, 2H); ESI-MS m/z calc. 443.2, found 444.0 (M+1)$^+$. Retention time: 0.74 minutes.

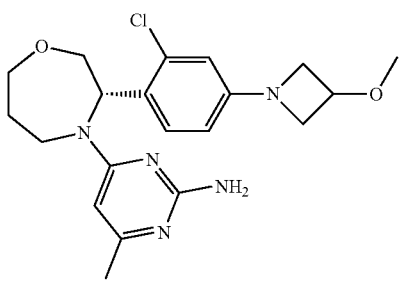

4-[(3S)-3-[2-chloro-4-(3-methoxyazetidin-1-yl)phenyl]-1,4-oxazepan-4-yl]-6-methyl-pyrimidin-2-amine (234) I-217 heated (360K) $^1$H NMR (400 MHz, DMSO-d6) δ 7.08 (d, J=8.5 Hz, 1H), 6.43 (d, J=2.4 Hz, 1H), 6.33 (dd, J=8.5, 2.4 Hz, 1H), 5.55 (d, J=7.9 Hz, 1H), 5.47 (s, 2H), 5.29 (d, J=33.3 Hz, 1H), 4.67 (d, J=14.8 Hz, 1H), 4.29 (tt, J=6.2, 4.2 Hz, 1H), 4.06-3.99 (m, 3H), 3.87 (dt, J=12.0, 4.0 Hz, 1H), 3.71-3.48 (m, 5H), 3.24 (s, 3H), 1.99 (d, J=2.8 Hz, 3H), 1.81-1.67 (m, 2H); ESI-MS m/z calc. 403.2, found 404.0 (M+1)$^+$. Retention time: 0.74 minutes.

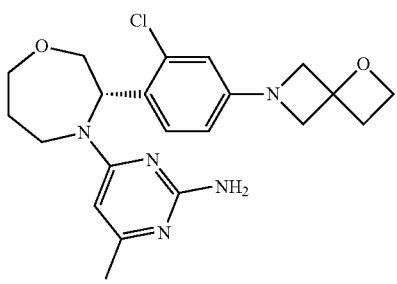

4-[(3S)-3-[2-chloro-4-(1-oxa-6-azaspiro[3.3]heptan-6-yl)phenyl]-1,4-oxazepan-4-yl]-6-methyl-pyrimidin-2-amine (235) I-260 heated (360K) $^1$H NMR (400 MHz, DMSO-d6) δ 7.08 (d, J=8.4 Hz, 1H), 6.44 (t, J=2.1 Hz, 1H), 6.34 (dt, J=8.5, 2.0 Hz, 1H), 5.70 (s, 2H), 5.60 (s, 1H), 5.28 (s, 1H), 4.65 (d, J=14.6 Hz, 1H), 4.43 (td, J=7.5, 1.5 Hz, 2H), 4.12-4.00 (m, 3H), 3.93-3.83 (m, 3H), 3.74-3.65 (m, 1H), 3.65-3.50 (m, 2H), 2.83 (td, J=7.5, 1.6 Hz, 2H), 2.02 (d, J=1.4 Hz, 3H), 1.76 (h, J=5.1, 4.4 Hz, 2H); ESI-MS m/z calc. 415.2, found 416.0 (M+1)$^+$. Retention time: 0.74 minutes.

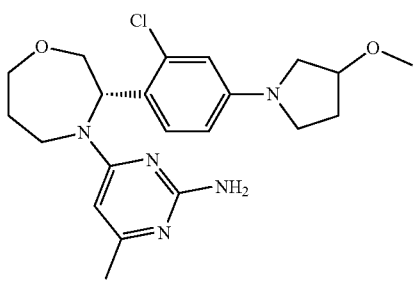

4-[(3S)-3-[2-chloro-4-(3-methoxypyrrolidin-1-yl)phenyl]-1,4-oxazepan-4-yl]-6-methyl-pyrimidin-2-amine (236) I-218 (mixture of 2 diastereomers)

heated (360K) $^1$H NMR (400 MHz, DMSO-d6) 7.07 (d, J=8.6 Hz, 1H), 6.53 (d, J=2.5 Hz, 1H), 6.46 (dd, J=8.6, 2.5 Hz, 1H), 5.55 (s, 1H), 5.48 (s, 2H), 5.27 (d, J=35.5 Hz, 1H), 4.70 (d, J=15.4 Hz, 1H), 4.10-3.99 (m, 2H), 3.87 (d, J=12.2 Hz, 1H), 3.67 (dd, J=13.4, 10.1 Hz, 1H), 3.55 (qd, J=12.0, 10.9, 3.8 Hz, 2H), 3.39 (ddd, J=10.7, 5.3, 2.5 Hz, 1H), 3.28-3.16 (m, 6H), 2.09-2.02 (m, 1H), 2.00 (d, J=3.9 Hz, 3H), 1.81-1.69 (m, 2H); ESI-MS m/z calc. 417.2, found 418.0 (M+1)$^+$. Retention time: 0.78 minutes.

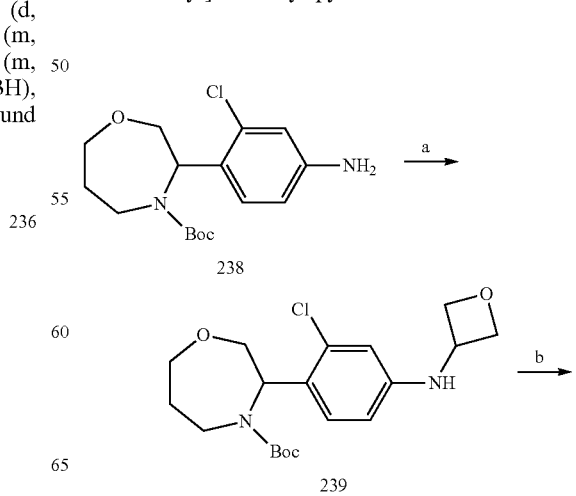

tert-butyl 3-[4-[(3S)-4-(2-amino-6-methyl-pyrimidin-4-yl)-1,4-oxazepan-3-yl]-3-chloro-anilino]azetidine-1-carboxylate (237) I-256

$^1$H NMR (400 MHz, MeOD) δ 7.02 (d, J=8.5 Hz, 1H), 6.58 (d, J=2.4 Hz, 1H), 6.46 (dd, J=8.5, 2.4 Hz, 1H), 5.54 (br s, 1H), 5.28-4.90 (m, 3H), 4.30-4.14 (m, 4H), 4.02-3.96 (m, 1H), 3.72-3.58 (m, 5H), 2.07 (s, 3H), 1.94-1.73 (m, 2H), 1.43 (s, 9H); ESI-MS m/z calc. 488.2, found 489.3 (M+1)$^+$. Retention time: 0.69 minutes.

Example 29

Synthetic Scheme 29: (+/−)-4-[3-[2-chloro-4-[methyl(oxetan-3-yl)amino]phenyl]-1,4-oxazepan-4-yl]-6-methyl-pyrimidin-2-amine I-186

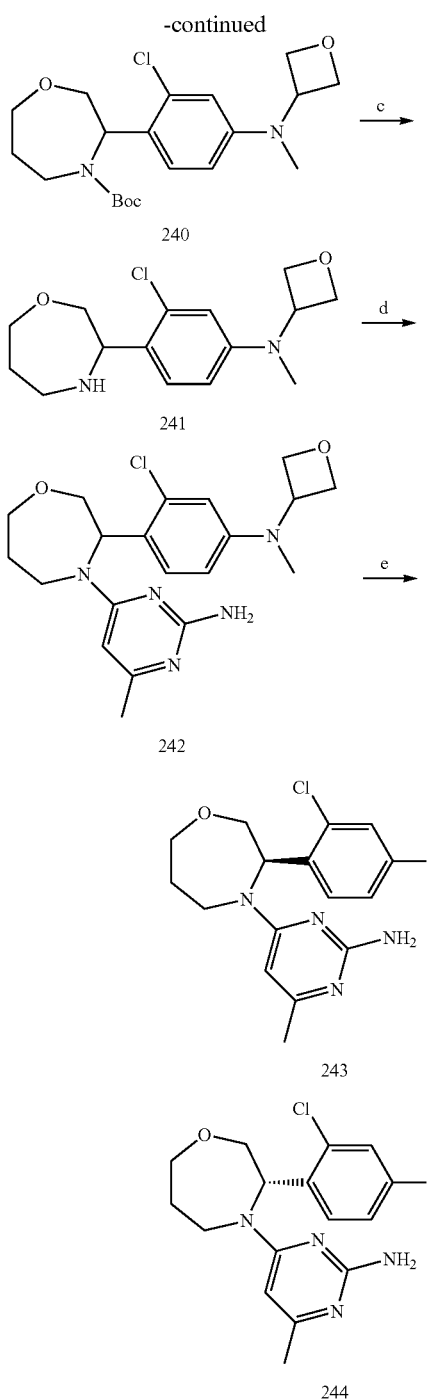

(a) oxetan-3-one, Na(OAc)₃BH, AcOH, CH₂Cl₂; (b) NaH, methyl iodide, DMF; (c) TFA, CH₂Cl₂; (d) 2-amino-4-chloro-6-methylpyrimidine, nBuOH, 130° C.; (e) SFC chiral separation Formation of tert-butyl 3-(2-chloro-4-(oxetan-3-ylamino)phenyl)-1,4-oxazepane-4-carboxylate (239)

To a solution of tert-butyl 3-(4-amino-2-chloro-phenyl)-1,4-oxazepane-4-carboxylate, 238, (0.67 g, 2.04 mmol) in dichloromethane (20 mL) was added oxetan-3-one (0.22 g, 3.05 mmol) then AcOH (0.15 mL, 2.65 mmol). After 3 minutes, sodium triacetoxyborohydride (0.65 g, 3.05 mmol) was added to the reaction mixture. After 4 hours, aqueous saturated sodium bicarbonate solution was added and the organic phase was passed through a phase separator and the resulting filtrate was concentrated in vacuo. The resulting residue was purified by silica gel chromatography (12 g ISCO column; 20-100% EtOAc in heptane) followed by a second purification by column chromatography (C18 AQ 40 g column; 0.1% TFA-water/0.1% TFA-MeCN). The fractions containing desired product were concentrated in vacuo and then diluted with MeOH and filtered off 300 mg (39%) of desired product as a white solid: ¹H NMR (400 MHz, d6-DMSO) δ 7.00 (s, 1H), 6.60 (s, 1H), 6.45 (d, J=2.0 Hz, 2H), 5.18-5.14 (m, 1H), 4.82 (t, J=6.5 Hz, 2H), 4.51 (dd, J=12.8, 6.4 Hz, 1H), 4.36 (t, J=6.0 Hz, 2H), 4.25 (d, J=14.0 Hz, 1H), 3.89 (d, J=11.7 Hz, 2H), 3.44 (m, 4H), 1.75-1.65 (m, 2H), 1.17 (s, 9H); ESI-MS m/z calc. 382.2, found 383.3 (M+1)⁺. Retention time: 0.81 minutes.

Formation of tert-butyl 3-[2-chloro-4-[methyl(oxetan-3-yl)amino]phenyl]-1,4-oxazepane-4-carboxylate (240)

To a solution of tert-butyl 3-[2-chloro-4-(oxetan-3-ylamino)phenyl]-1,4-oxazepane-4-carboxylate, 239, (0.117 g, 0.306 mmol) in DMF (2 mL) under an atmosphere of nitrogen was added NaH (0.021 g of 60% w/w, 0.525 mmol). After 20 minutes, methyl iodide (0.070 mL, 1.124 mmol) was added to the reaction mixture that was then stirred at room temperature. After 60 minutes, additional NaH (0.060 g) and methyl iodide (0.100 mL) was added to the mixture. Added water and then extracted twice with dichloromethane. The organic phases were passed through a phase separator and concentrated in vacuo. Purification by silica gel chromatography (40 g ISCO column; 20-100% EtOAc/heptanes gradient) to afford 101 mg of the desired product as a colorless oil: ESI-MS m/z calc. 396.2, found 397.34 (M+1)⁺. Retention time: 0.87 minutes.

Formation of N-[3-chloro-4-(1,4-oxazepan-3-yl)phenyl]-N-methyl-oxetan-3-amine (241)

To a solution of tert-butyl 3-[2-chloro-4-[methyl(oxetan-3-yl)amino]phenyl]-1,4-oxazepane-4-carboxylate, 240, (0.10 g, 0.25 mmol) in dichloromethane (2 mL) was added trifluoroacetic acid (1.0 mL, 12.9 mmol). The reaction mixture was stirred for 20 minutes and concentrated in vacuo. The resulting residue was diluted with methanol and then passed through a SPE bicarbonate cartridge (5 g/60 mL) and concentrated to give 71 mg of a colorless oil which was used without further purification: ESI-MS m/z calc. 296.1, found 297.3 (M+1)⁺. Retention time: 0.52 minutes.

Formation of (+/−)-4-[3-[2-chloro-4-[methyl(oxetan-3-yl)amino]phenyl]-1,4-oxazepan-4-yl]-6-methyl-pyrimidin-2-amine (242) I-186

A mixture of N-[3-chloro-4-(1,4-oxazepan-3-yl)phenyl]-N-methyl-oxetan-3-amine, 241, (0.07 g, 0.24 mmol) and 4-chloro-6-methyl-pyrimidin-2-amine (0.03 g, 0.22 mmol) in nBuOH (2 mL) was heated at 130° C. overnight. The reaction mixture was cooled to room temperature followed by purification by silica gel chromatography (C18 AQ 50 g column; 0.1% TFA-water/0.1% TFA-MeCN). The pure fractions were concentrated in vacuo and then dissolved in MeOH and passed through a SPE bicarbonate cartridge (Agilent Stratospheres 500 mg/6 mL) and concentrated in vacuo. Added ether and concentrated again to give 42 mg of product as a white solid: $^1$H NMR (400 MHz, d6-DMSO) δ 7.06 (d, J=8.4 Hz, 1H), 6.71 (s, 1H), 6.58 (d, J=8.5 Hz, 1H), 5.85 (br s, 2H), 5.45-5.26 (br s, 1H), 5.05-4.88 (br s, 1H), 4.78-4.70 (m, 3H), 4.57 (d, J=5.0 Hz, 2H), 4.10-3.95 (m, 1H), 3.90-3.82 (m, 1H), 3.70-3.46 (m, 3H), 2.86 (s, 3H), 1.97 (s, 3H), 1.72 (s, 2H); ESI-MS m/z calc. 403.2, found 404.4 (M+1)$^+$. Retention time: 0.57 minutes.

The racemic mixture was submitted for SFC chiral separation: AD-H 20×250 mm column using 40% MeOH (5 mM ammonia) 60% $CO_2$ isocratic method.

Peak A: (R)-4-[3-[2-chloro-4-[methyl(oxetan-3-yl) amino]phenyl]-1,4-oxazepan-4-yl]-6-methyl-pyrimidin-2-amine (243); 99+% ee; $^1$H NMR (400 MHz, d6-DMSO) δ 7.06 (d, J=8.4 Hz, 1H), 6.71 (s, 1H), 6.58 (d, J=8.5 Hz, 1H), 5.85 (br s, 2H), 5.45-5.26 (br s, 1H), 5.05-4.88 (br s, 1H), 4.78-4.70 (m, 3H), 4.57 (d, J=5.0 Hz, 2H), 4.10-3.95 (m, 1H), 3.90-3.82 (m, 1H), 3.70-3.46 (m, 3H), 2.86 (s, 3H), 1.97 (s, 3H), 1.72 (s, 2H); ESI-MS m/z calc. 403.2, found 404.2 (M+1)$^+$. Retention time: 0.58 minutes. I-189.

Peak B: (S)-4-[3-[2-chloro-4-[methyl(oxetan-3-yl)amino] phenyl]-1,4-oxazepan-4-yl]-6-methyl-pyrimidin-2-amine (244); 99.4% ee; $^1$H NMR (400 MHz, d6-DMSO) δ 7.06 (d, J=8.4 Hz, 1H), 6.71 (s, 1H), 6.58 (d, J=8.5 Hz, 1H), 5.85 (br s, 2H), 5.45-5.26 (br s, 1H), 5.05-4.88 (br s, 1H), 4.78-4.70 (m, 3H), 4.57 (d, J=5.0 Hz, 2H), 4.10-3.95 (m, 1H), 3.90-3.82 (m, 1H), 3.70-3.46 (m, 3H), 2.86 (s, 3H), 1.97 (s, 3H), 1.72 (s, 2H); ESI-MS m/z calc. 403.2, found 404.3 (M+1)$^+$. Retention time: 0.58 minutes. I-190.

The following analogs were prepared according to Synthetic Scheme 29:

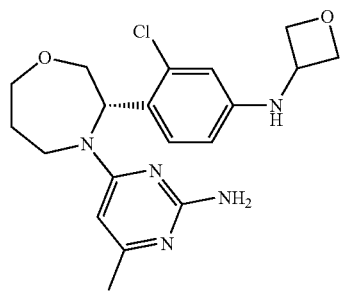

245

4-[(3S)-3-[2-chloro-4-(oxetan-3-ylamino)phenyl]-1, 4-oxazepan-4-yl]-6-methyl-pyrimidin-2-amine (245) I-215

$^1$H NMR (300 MHz, CDCl$_3$) δ 6.91 (d, J=8.4 Hz, 1H), 6.38 (d, J=2.4 Hz, 1H), 6.25 (dd, J=8.5, 2.5 Hz, 1H), 5.46 (s, 1H), 5.16 (s, 1H), 4.88 (td, J=6.3, 2.3 Hz, 2H), 4.65 (s, 2H), 4.55-4.33 (m, 3H), 4.26-4.11 (m, 2H), 4.03 (q, J=7.1 Hz, 2H), 3.58-3.26 (m, 3H), 2.04 (s, 3H), 1.83 (s, 1H), 1.73 (s, 1H); ESI-MS m/z calc. 389.2, found 390.2 (M+1)$^+$. Retention time: 0.6 minutes; Optical rotation: +32.4 (MeOH).

Example 30

Synthetic Scheme 30: (S)-1-(3-((4-(4-(2-amino-6-methylpyrimidin-4-yl)-1,4-oxazepan-3-yl)-3-chlorophenyl)amino)azetidin-1-yl)ethan-1-one (247) I-262

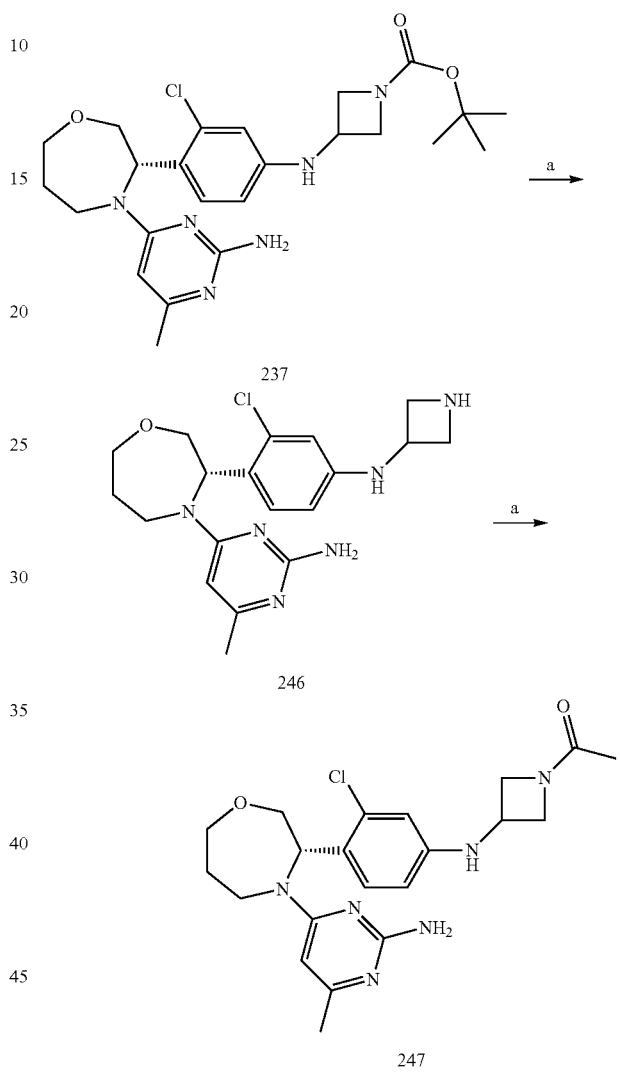

(a) TFA, $CH_2Cl_2$; (b) 2-amino-4-chloro-6-methylpyrimidine, nBuOH, 130° C.

Formation of 4-[(3S)-3-[4-(azetidin-3-ylamino)-2-chloro-phenyl]-1,4-oxazepan-4-yl]-6-methyl-pyrimidin-2-amine (246) I-257

To a solution of tert-butyl 3-[4-[(3S)-4-(2-amino-6-methyl-pyrimidin-4-yl)-1,4-oxazepan-3-yl]-3-chloro-anilino]azetidine-1-carboxylate, 237, (0.118 g, 0.239 mmol) in dichloromethane (2 mL) was added trifluoroacetic acid (1.0 mL). The reaction mixture was stirred at room temperature for 30 minutes and then partially concentrated in vacuo. 1M HCl (2 mL) was added and the mixture washed twice with dichloromethane. The aqueous layer was basified with 2M NaOH (5 mL) and then extracted with dichloromethane. The layers were separated with the aid of a phase separator. The aqueous layer was re-extracted with dichloromethane and the layers were separated through a phase separator again and the combined organic phases were concentrated in vacuo to afford 51 mg of the desired product as a white solid: $^1$H NMR (400 MHz, MeOD) δ 7.00 (d, J=8.5 Hz, 1H), 6.56 (d, J=2.4 Hz, 1H), 6.45 (dd, J=8.5, 2.4 Hz, 1H), 5.53 (br s, 1H), 5.08 (br s, 2H), 4.35-4.26 (m, 1H), 4.18 (dd, J=13.6, 5.1 Hz, 1H), 4.00 (d, J=6.8 Hz, 1H), 3.88 (t, J=7.8 Hz, 2H), 3.74-3.45 (m, 5H), 2.06 (s, 3H), 1.94-1.68 (m, 2H); ESI-MS m/z calc. 388.2, found 389.3 (M+1)$^+$. Retention time: 0.53 minutes.

Formation of 1-[3-[4-[(3S)-4-(2-amino-6-methyl-pyrimidin-4-yl)-1,4-oxazepan-3-yl]-3-chloro-anilino]azetidin-1-yl]ethanone (247)

To a suspension of 4-[(3S)-3-[4-(azetidin-3-ylamino)-2-chloro-phenyl]-1,4-oxazepan-4-yl]-6-methyl-pyrimidin-2-amine, 246, (0.040 g, 0.088 mmol) in dichloromethane (4 mL) and THF (1 mL) was added triethylamine (0.025 mL, 0.176 mmol) followed by acetyl chloride (0.007 mL, 0.097 mmol). The reaction mixture was stirred at room temperature. After 1 hour, additional acetyl chloride (0.002 mL) was added and stirring continued at room temperature overnight. The resulting precipitate was filtered and washed with minimal dichloromethane. The white solid was dried to afford 25 mg of desired product: $^1$H NMR (400 MHz, MeOD) δ 7.03 (d, J=8.5 Hz, 1H), 6.60 (dd, J=4.0, 2.4 Hz, 1H), 6.51-6.44 (m, 1H), 5.55 (br s, 1H), 4.93 (br s, 2H), 4.57-4.49 (m, 1H), 4.35-4.15 (m, 3H), 4.04-3.90 (m, 2H), 3.79-3.53 (m, 4H), 2.07 (s, 3H), 1.87 (s, 3H), 1.95-1.70 (m, 2H); ESI-MS m/z calc. 430.2, found 431.3 (M+1)$^+$. Retention time: 0.57 minutes.

Example 31

Synthetic Scheme 31: 4-[(3S)-3-[4-(1,3,3a,4,6,6a-hexahydrofuro[3,4-c]pyrrol-5-yl)-2-chloro-phenyl]-1,4-oxazepan-4-yl]-6-methyl-pyrimidin-2-amine (248) I-220

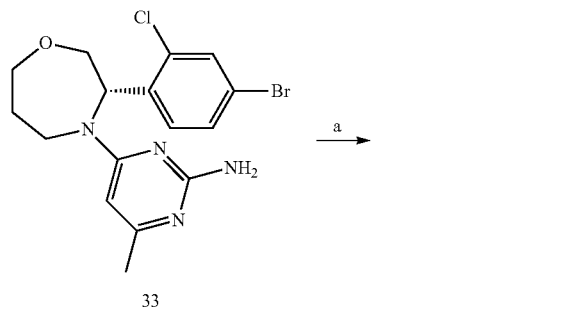

(a) CuI, (3aS,6aR)-3,3a,4,5,6,6a-hexahydro-1H-furo[3,4-c]pyrrole, K$_2$CO$_3$, N,N-dimethylglycine Formation of 4-[(3S)-3-[4-(1,3,3a,4,6,6a-hexahydro-furo[3,4-c]pyrrol-5-yl)-2-chloro-phenyl]-1,4-oxazepan-4-yl]-6-methyl-pyrimidin-2-amine (248)

A Schlenck tube was charged with 4-[(3S)-3-(4-bromo-2-chloro-phenyl)-1,4-oxazepan-4-yl]-6-methyl-pyrimidin-2-amine, 33, (0.30 g, 0.75 mmol), (3aS,6aR)-3,3a,4,5,6,6a-hexahydro-1H-furo[3,4-c]pyrrole (0.36 g, 3.19 mmol), N,N-dimethylglycine (0.05 g, 0.4364 mmol), CuI (0.10 g, 0.50 mmol), K$_2$CO$_3$ (0.63 g, 4.53 mmol) and DMSO (4 mL) in that order and vacuum/nitrogen cycles five times. The flask was heated to 90° C. After 24 hours, 10% MeOH in EtOAc was added and the mixture was filtered through Celite and concentrated (DMSO still present). Purification by silica gel chromatography (80 g GOLD ISCO column; 0-10% MeOH/dichloromethane gradient) and fractions containing product were concentrated in vacuo. The product was subjected to a second purification by silica gel chromatography (C18 aqueous 80 g ISCO column eluting with 0.1% TFA-water/0.1% TFA-MeCN): $^1$H NMR (400 MHz, MeOD) δ 7.06 (d, J=8.6 Hz, 1H), 6.67 (d, J=2.5 Hz, 1H), 6.56 (dd, J=8.6, 2.5 Hz, 1H), 5.70-4.70 (br m, 3H), 4.20 (dd, J=13.6, 5.1 Hz, 1H), 4.06-3.89 (m, 3H), 3.75-7.53 (m, 5H), 3.38 (dd, J=8.8, 7.1 Hz, 2H), 3.23-3.15 (m, 2H), 3.10-3.00 (m, 2H), 2.06 (s, 3H), 1.95-1.75 (m, 2H); ESI-MS m/z calc. 429.2, found 430.3 (M+1)$^+$. Retention time: 0.63 minutes. The following analogs were prepared according to Synthetic Scheme 31.

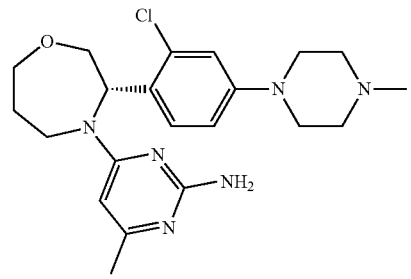

249

(+/-)-4-[3-[2-chloro-4-(4-methylpiperazin-1-yl)phenyl]-1,4-oxazepan-4-yl]-6-methyl-pyrimidin-2-amine (249) I-225 heated (360K) $^1$H NMR (400 MHz, DMSO-d6) δ 7.11 (d, J=8.7 Hz, 1H), 6.90 (d, J=2.5 Hz, 1H), 6.82 (dd, J=8.8, 2.6 Hz, 1H), 5.56 (d, J=12.9 Hz, 3H), 5.28 (s, 1H), 4.66 (d, J=14.9 Hz, 1H), 4.11-4.00 (m, 1H), 3.87 (dt, J=12.1, 3.9 Hz, 1H), 3.68 (dd, J=13.4, 10.1 Hz, 1H), 3.64-3.49 (m, 2H), 3.20-3.09 (m, 4H), 2.46-2.41 (m, 4H), 2.22 (s, 3H), 2.00 (s, 3H), 1.76 (tt, J=7.9, 3.9 Hz, 2H). ESI-MS m/z calc. 416.2, found 4170 (M+1)$^+$. Retention time: 0.56 minutes.

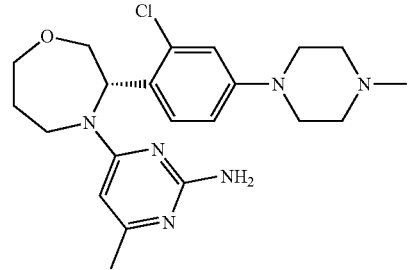

XX (S)-4-[3-[2-chloro-4-(4-methylpiperazin-1-yl)phenyl]-1,4-oxazepan-4-yl]-6-methyl-pyrimidin-2-amine (249) I-275

¹H NMR (400 MHz, Chloroform-d) δ 6.92 (d, J=8.7 Hz, 1H), 6.74 (d, J=2.5 Hz, 1H), 6.57 (dd, J=8.7, 2.6 Hz, 1H), 5.40 (s, 1H), 4.46 (s, 2H), 4.13 (dd, J=13.5, 5.0 Hz, 1H), 3.90 (d, J=12.0 Hz, 1H), 3.51-3.25 (m, 2H), 3.13-2.97 (m, 4H), 2.43-2.33 (m, 4H), 2.18 (s, 3H), 1.91-1.80 (m, 1H), 1.68-1.45 (m, 1H); ESI-MS m/z calc. 416.21, found 417.0 (M+1)⁺. Retention time: 0.51 minutes.

The following analogs were prepared according to Synthetic Scheme 31 with exception that N-methylglycine was used instead of N,N-dimethylglycine:

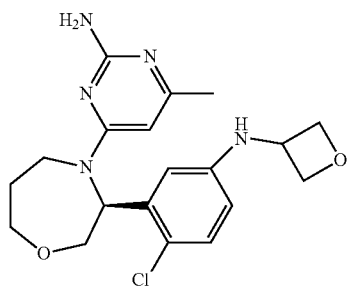

250

4-[(3S)-3-[2-chloro-5-(oxetan-3-ylamino)phenyl]-1,4-oxazepan-4-yl]-6-methyl-pyrimidin-2-amine (250) I-258

¹H NMR (400 MHz, Methanol-d4) δ 7.16 (dd, J=25.4, 8.6 Hz, 1H), 6.53-6.35 (m, 2H), 6.05 (dd, J=9.5, 5.1 Hz, 0H), 5.67 (s, 1H), 5.26 (dd, J=10.2, 4.8 Hz, 1H), 5.19 (d, J=14.4 Hz, 1H), 4.91 (dt, J=12.7, 6.3 Hz, 2H), 4.50 (ddt, J=21.1, 11.9, 4.5 Hz, 2H), 4.40-4.13 (m, 1H), 4.11-3.56 (m, 4H), 2.44-2.15 (m, 3H), 1.92 (s, 3H); ESI-MS m/z calc. 389.16187, found 390.13 (M+1)⁺. Retention time: 0.6 minutes; [α]_D=+60.6° (c=1, MeOH).

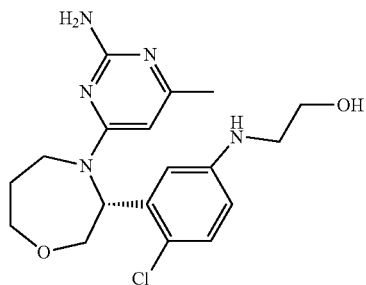

251

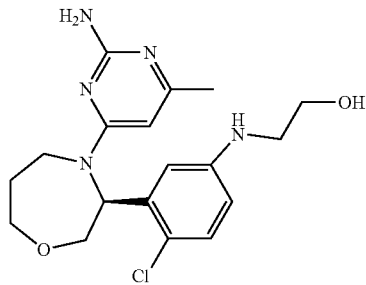

252

2-[3-[(3R)-4-(2-amino-6-methyl-pyrimidin-4-yl)-1,4-oxazepan-3-yl]-4-chloro-anilino]ethanol 251) I-252 and 2-[3-[(3S)-4-(2-amino-6-methyl-pyrimidin-4-yl)-1,4-oxazepan-3-yl]-4-chloro-anilino]ethanol (252) I-253

(racemic mixture): ¹H NMR (300 MHz, Methanol-d4) δ 7.21 (dd, J=8.5, 4.9 Hz, 1H), 6.79-6.51 (m, 2H), 6.06 (dd, J=9.8, 5.1 Hz, 0.5H), 5.76-5.58 (m, 1H), 5.32-5.09 (m, 1.5H), 4.46-4.15 (m, 2H), 4.12-3.87 (m, 2H), 3.86-3.54 (m, 5H), 3.20 (dt, J=17.0, 5.7 Hz, 2H), 2.21 (d, J=0.8 Hz, 3H), 2.05-1.81 (m, 2H); ESI-MS m/z calc. 377.2, found 378.2 (M+1)⁺. Retention time: 0.57 minutes. I-237.

SFC conditions: Column: AD-H, 20×250 mm; Mobile phase: 40% MeOH (5 mM Ammonia), 60% CO₂; Flow: 80 mL/min; Concentrations: ~50 mg/mL (MeOH)

Peak A: ee: 99.2%; [α]_D=−190.45° (c=0.5, MeOH); 2-[3-[(3R)-4-(2-amino-6-methyl-pyrimidin-4-yl)-1,4-oxazepan-3-yl]-4-chloro-anilino]ethanol (251): ¹H NMR (300 MHz, Methanol-d4) δ 7.14 (d, J=8.6 Hz, 1H), 6.63-6.46 (m, 2H), 5.54 (brs, 1H), 5.17 (brs, 1H), 4.28 (dd, J=13.7, 5.0 Hz, 1H), 4.03 (d, J=12.1 Hz, 1H), 3.82-3.53 (m, 4H), 3.14 (t, J=5.7 Hz, 2H), 2.13 (s, 3H), 1.90 (br, 2H); ESI-MS m/z calc. 377.2, found 378.2 (M+1)⁺. Retention time: 0.57 minutes. I-252.

Peak B: ee 99%; [α]_D=+172.580 (c=0.5, MeOH); 2-[3-[(3S)-4-(2-amino-6-methyl-pyrimidin-4-yl)-1,4-oxazepan-3-yl]-4-chloro-anilino]ethanol (252): ¹H NMR (300 MHz, Methanol-d4) δ 7.12 (d, J=8.4 Hz, 1H), 6.68-6.46 (m, 2H), 5.48 (brs, 1H), 5.13 (brs, 1H), 4.27 (dd, J=13.6, 5.0 Hz, 1H), 4.03 (dd, J=12.1, 4.7 Hz, 1H), 3.77-3.52 (m, 4H), 3.13 (t, J=5.7 Hz, 2H), 2.06 (s, 3H), 1.97-1.71 (m, 2H); ESI-MS m/z calc. 377.2, found 378.2 (M+1)⁺. Retention time: 0.57 minutes. I-253.

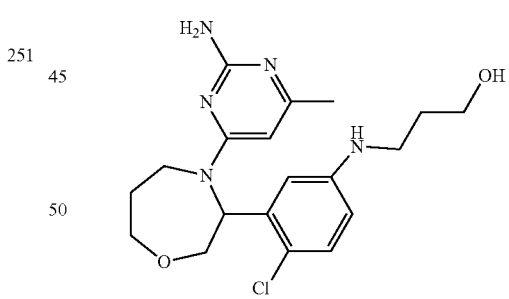

253

(+/−)-3-[3-[4-(2-amino-6-methyl-pyrimidin-4-yl)-1,4-oxazepan-3-yl]-4-chloro-anilino]propan-1-ol (253) I-249

¹H NMR (300 MHz, Methanol-d4) δ 7.18 (d, J=8.7 Hz, 1H), 6.59 (t, J=7.8 Hz, 1H), 6.48 (s, 1H), 6.05 (dd, J=9.8, 5.2 Hz, 0.5H), 5.68 (s, 1H), 5.31-5.12 (m, 1.5H), 4.32 (ddd, J=27.7, 13.8, 5.1 Hz, 2H), 4.09-3.52 (m, 7H), 2.35 (s, 1.5H), 2.21 (s, 1.5H), 2.04-1.65 (m, 4H); ESI-MS m/z calc. 391.2, found 392.2 (M+1)⁺. Retention time: 0.56 minutes.

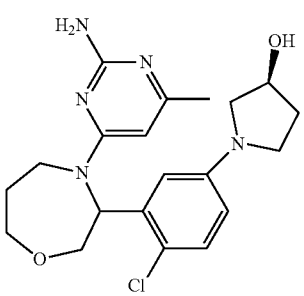

(3S)-1-[3-[4-(2-amino-6-methyl-pyrimidin-4-yl)-1,4-oxazepan-3-yl]-4-chloro-phenyl]pyrrolidin-3-ol (254) I-234

¹H NMR (300 MHz, Methanol-d4) δ 7.33-7.11 (m, 2H), 6.59-6.25 (m, 3H), 5.68 (s, 1H), 5.36-5.11 (m, 2H), 4.57-4.17 (m, 2H), 4.13-3.58 (m, 5H), 3.51-2.97 (m, 3H), 2.20 (s, 3H), 2.13-1.79 (m, 4H); ESI-MS m/z calc. 403.2, found 404.21 (M+1)⁺. Retention time: 0.62 minutes.

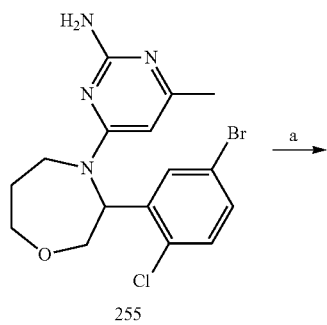

255

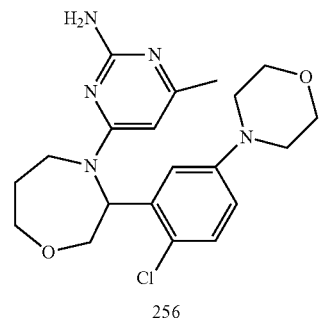

256

(a) tBuXPhos Pd G3, morpholine, dioxane, tert-BuOH, Cs₂CO₃, 75° C.

Formation of 4-(3-(5-bromo-2-chlorophenyl)-1,4-oxazepan-4-yl)-6-methylpyrimidin-2-amine (255)

Intermediate, 255, was prepared according to Synthetic Scheme 2, using intermediate tert-butyl 3-(5-bromo-2-chlorophenyl)-1,4-oxazepane-4-carboxylate, 157.

Formation of (+/−)-4-[3-(2-chloro-5-morpholino-phenyl)-1,4-oxazepan-4-yl]-6-methyl-pyrimidin-2-amine (256) I-195

A 250 mL flask was charged with 4-[3-(5-bromo-2-chloro-phenyl)-1,4-oxazepan-4-yl]-6-methyl-pyrimidin-2-amine, 255, (0.30 g, 0.75 mmol), morpholine (0.20 mL, 2.29 mmol), dioxane (7 mL) and tert-BuOH (8 mL). The reaction mixture was stirred to give a clear solution. The solution was then degassed with a stream of nitrogen for 10 minutes. [2-(2-aminophenyl)phenyl]-methylsulfonyloxy-palladium; ditert-butyl-[2-(2,4,6-triisopropylphenyl)phenyl]phosphane (0.03 g, 0.04 mmol) (tBuXPhos Pd G3) was added then nitrogen bubbling was continued for 5 minutes. Cs₂CO₃ (0.59 g, 1.81 mmol) was placed under a nitrogen atmosphere and then heated to 75° C. After 90 minutes, the reaction mixture was partitioned between EtOAc and water. The organic phase was washed with water and brine, dried (MgSO₄) filtered and concentrated in vacuo. The resulting residue was purified via silica gel chromatography using 40 gram ISCO column eluting with 0-100% EtOAc/heptanes linear gradient to afford 17 mg of desired product: ¹H NMR (300 MHz, Methanol-d4) δ 7.29 (dd, J=18.3, 8.8 Hz, 2H), 6.91 (ddd, J=16.6, 8.9, 2.9 Hz, 1H), 6.78 (dd, J=26.7, 3.0 Hz, 0.5H), 6.48 (s, 1H), 6.10 (dd, J=9.5, 5.1 Hz, 0.5H), 5.68 (s, 1H), 5.39-5.10 (m, 2H), 4.42-4.17 (m, 1H), 4.09-3.59 (m, 11H), 3.09 (t, J=4.9 Hz, 6H), 2.28 (dd, J=40.8, 0.8 Hz, 5H), 2.09-1.84 (m, 4H); ESI-MS m/z calc. 403.2, found 404.2 (M+1)⁺. Retention time: 0.62 minutes.

Example 32

Synthetic Scheme 32: (+/−)-4-[3-(2-chloro-4-pyrrolidin-1-yl-phenyl)-1,4-oxazepan-4-yl]-6-methyl-pyrimidin-2-amine (257) I-227

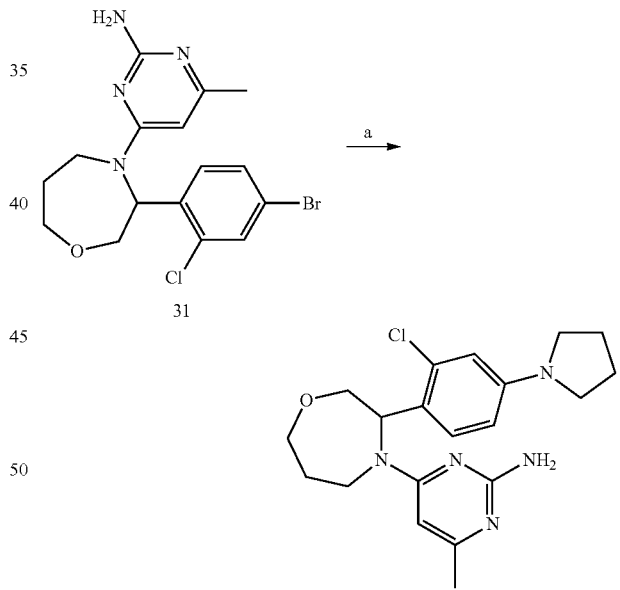

(a) Ir(dF(CF₃)ppy)₂(dtbpy)PF₆, dibromonickel; 1-methoxy-2-(2-methoxyethoxy)ethane, pyrrolidine, DABCO, dimethylacetamide, flow reactor, 30° C.

Formation of (+/−)-4-[3-(2-chloro-4-pyrrolidin-1-yl-phenyl)-1,4-oxazepan-4-yl]-6-methyl-pyrimidin-2-amine (257) I-227

A solution of 4-[3-(4-bromo-2-chloro-phenyl)-1,4-oxazepan-4-yl]-6-methyl-pyrimidin-2-amine, 31, (0.050 g, 0.120 mmol), pyrrolidine (0.015 mL, 0.180 mmol) and 1,4-diazabicyclo[2,2,2]octane (DABCO) (0.025 g, 0.223 mmol) in dimethylacetamide (2 mL) was bubbled with a stream of nitrogen. To the reaction vial was added $Ir(dF(CF_3)ppy)_2$(dtbpy)$PF_6$ (0.3 mg) in dimethylacetamide (0.1 mL) and dibromonickel; 1-methoxy-2-(2-methoxyethoxy)ethane (2.2 mg, 0.006 mmol) in dimethylacetamide (0.1 mL). The reaction was carried out in a Vapourtec flow reactor, with 0.2 mL/min at 30° C. The resulting mixture was diluted with EtOAc, washed with $H_2O$, dried over $Na_2SO_4$, filtered and concentrated in vacuo. Purified by 4 g silica gel cartridge eluting with 0-10% MeOH/dichloromethane to afford 2 mg of desired product: $^1H$ NMR (400 MHz, $CDCl_3$) δ 7.04 (t, J=7.5 Hz, 1H), 6.56 (d, J=2.5 Hz, 1H), 6.40 (dd, J=8.6, 2.5 Hz, 1H), 5.60 (s, 1H), 4.60 (s, 2H), 4.30 (dd, J=13.5, 5.1 Hz, 1H), 3.34-3.16 (m, 4H), 2.14 (s, 3H), 2.08-1.92 (m, 4H), 1.80 (d, J=14.5 Hz, 1H); ESI-MS m/z calc. 387.2, found 388.1 $(M+1)^+$. Retention time: 3.13 minutes.

Example 33

Synthetic Scheme 33: (+/−)-1-(4-(4-(2-amino-6-methylpyrimidin-4-yl)-1,4-oxazepan-3-yl)-3-chlorophenoxy)propan-2-ol (261) I-232

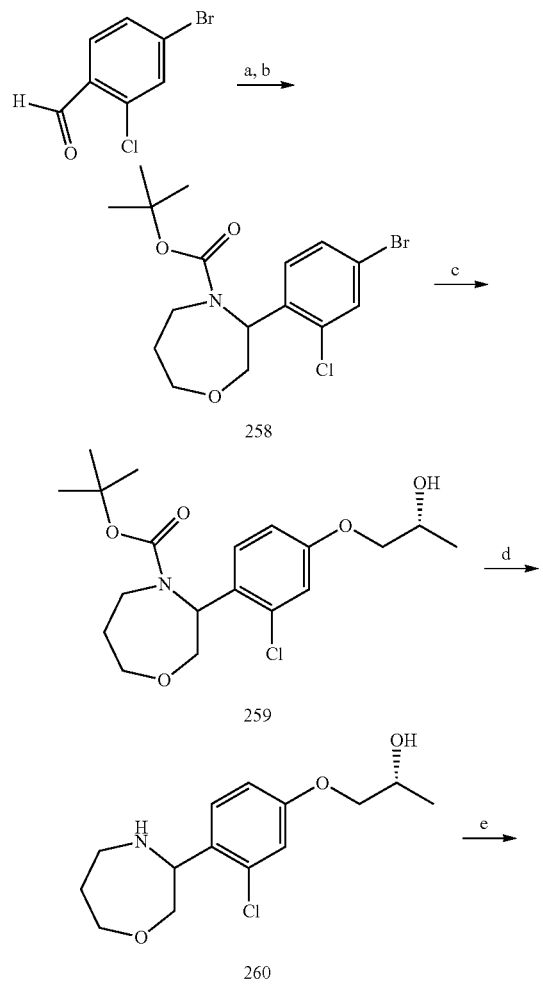

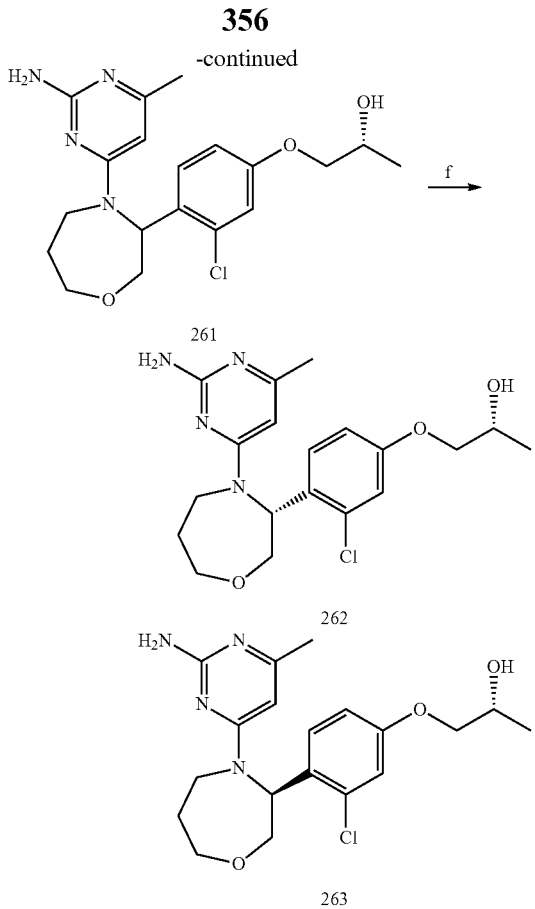

(a) 3-(tributylstannyl)methoxy)propan-1-amine 4 A mol sieves, $CH_2Cl_2$; then 2,6-lutidine, $Cu(OTf)_2$, hexafluoroisopropanol, $CH_2Cl_2$; (b) $Boc_2O$, $Et_3N$, THF; (c) di-tert-butylXPhos, $Cs_2CO_3$, (2R)-propane-1,2-diol, 100° C.; (d) TFA, $CH_2Cl_2$; (e) 2-amino-4-chloro-6-methylpyrimidine, nBuOH, 120° C.; (f) SFC chiral separation Formation of (+/−)-tert-Butyl 3-(4-bromo-2-chlorophenyl)-1,4-oxazepane-4-carboxylate (258)

A mixture of 4-bromo-2-chloro-benzaldehyde (10.0 g, 45.6 mmol), 3-(tributylstannylmethoxy)-propan-1-amine (17.2 g, 45.6 mmol), and 4 angstrom molecular sieves (5.2 g) in dichloromethane (180 mL) was stirred at room temperature for 2 hours, filtered and diluted with additional dichloromethane (540 mL). To a separate flask containing hexafluoroisopropanol (180 mL) was added 2,6-lutidine (5.3 mL, 45.6 mmol) followed by $Cu(OTf)_2$ (16.5 g, 45.7 mmol). The reaction mixture was stirred for 2 hours and then the imine solution prepared above was added in one portion. The reaction mixture was stirred overnight and then treated with a 2:1 mixture of aqueous saturated sodium bicarbonate solution and 10% ammonium hydroxide. The organic layer was separated and washed with aqueous saturated sodium bicarbonate solution, filtered through a phase separator and concentrated to dryness. The resulting residue was purified via silica gel chromatography eluting with 0-75% EtOAc/heptane. Pure fractions were combined and concentrated in vacuo to afford 6.2 g of 3-(4-bromo-2-chlorophenyl)-1,4-oxazepane as a yellow oil: $^1H$ NMR (400 MHz, $CDCl_3$) δ 7.50 (d, J=2.0 Hz, 1H), 7.47 (d, J=8.4 Hz, 1H), 7.38 (dd, J=8.5, 2.0 Hz, 1H), 4.39 (dd, J=9.0, 3.4 Hz, 1H), 4.01-3.92

(m, 2H), 3.82 (dt, J=12.3, 6.2 Hz, 1H), 3.38 (dd, J=12.4, 9.0 Hz, 1H), 3.20 (dt, J=13.5, 5.0 Hz, 1H), 3.04 (dt, J=13.6, 6.8 Hz, 1H), 1.98 (qd, J=6.4, 5.0 Hz, 2H); ESI-MS m/z calc. 289.0, found 290.0 (M+1)$^+$. Retention time 0.6 minutes.

To a solution of 3-(4-bromo-2-chloro-phenyl)-1,4-oxazepane (1.97 g, 6.78 mmol) and triethylamine (1.04 mL, 7.46 mmol) in THF (40 mL) was added Boc anhydride (1.67 g, 7.65 mmol). The reaction mixture was stirred at room temperature overnight, then diluted with EtOAc and washed with 1 M HCl. The organic layer was concentrated to dryness and purified via silica gel chromatography eluting with 0-40% EtOAc in heptane. Fractions containing the desired product were combined and concentrated to give 2.28 g of desired product, 258, as a colorless oil that solidified upon standing: $^1$H NMR (400 MHz, DMSO-d6) δ 7.63 (dt, J=6.8, 2.0 Hz, 1H), 7.56-7.48 (m, 1H), 7.26 (d, J=8.3 Hz, 1H), 5.29 (dd, J=10.4, 4.9 Hz, 1H), 4.26-4.12 (m, 1H), 4.00-3.84 (m, 2H), 3.63-3.44 (m, 3H), 1.83-1.64 (m, 2H), 1.25 (s, 7H); ESI-MS m/z calc. 389.0, found 390.0 (M+1)$^+$. Retention time: 0.69 minutes.

Formation of tert-butyl 3-(2-chloro-4-((R)-2-hydroxypropoxy)phenyl)-1,4-oxazepane-4-carboxylate (259)

tert-Butyl 3-(4-bromo-2-chloro-phenyl)-1,4-oxazepane-4-carboxylate, 258, (1.13 g, 2.89 mmol) and Cs$_2$CO$_3$ (1.40 g, 4.30 mmol) were placed in a microwave vial under nitrogen. Toluene (3.0 mL) and (2R)-propane-1,2-diol (1.10 mL, 14.98 mmol) were added. The mixture was stirred for 5 minutes. Di-tert-butyl-[6-methoxy-3-methyl-2-(2,4,6-triisopropylphenyl)-phenyl]phosphane:methanesulfonate palladium(2+);2-phenylaniline (di-tertBu-XPhos) (0.12 g, 0.14 mmol) was added. The reaction mixture was heated for 1 hour at 100° C. The mixture was diluted with water and dichloromethane. The phases were separated on a phase separator and the organic phase concentrated in vacuo. The resulting residue was purified by silica gel chromatography (Ethyl acetate/Heptanes) to afford 820 mg of desired product: ESI-MS m/z calc. 385.2, found 386.2 (M+1)$^+$. Retention time: 0.85 minutes.

Formation of (2R)-1-(3-chloro-4-(1,4-oxazepan-3-yl)phenoxy)propan-2-ol (260)

tert-Butyl 3-[2-chloro-4-[(2R)-2-hydroxypropoxy]phenyl]-1,4-oxazepane-4-carboxylate, 259, (0.82 g, 2.13 mmol) was dissolved in dichloromethane (20 mL) and trifluoroacetic acid (10 mL) was added. The volatiles were removed on a rotory evaporator. Saturated aqueous sodium bicarbonate and dichloromethane were added. The phases were separated on a phase separator. The organic phase was concentrated in vacuo. The resulting residue was purified via silica gel chromatography (Eluent: Ethyl acetate/Heptanes) to afford 330 mg of desired product: ESI-MS m/z calc. 285.1, found 286.2 (M+1)$^+$. Retention time: 0.5 minutes.

Formation of (2R)-1-(4-(4-(2-amino-6-methylpyrimidin-4-yl)-1,4-oxazepan-3-yl)-3-chlorophenoxy) propan-2-ol (261)

4-Chloro-6-methyl-pyrimidin-2-amine (0.12 g, 0.83 mmol) and (2R)-1-[3-chloro-4-(1,4-oxazepan-3-yl)phenoxy]propan-2-ol, 260, (0.33 g, 0.83 mmol) were dissolved in 1-butanol (2.4 mL). The reaction mixture was heated for 16 hours at 130° C. The volatiles were removed on a rotory evaporator. The crude residue was purified via silica gel chromatography (Eluent: methanol/dichloromethane). A second purification was carried out using an ISCO aminosilica gel column (Eluent: Ethyl acetate/Heptanes) to afford 270 mg of desired product as mixture of 2 diastereomers: $^1$H NMR (400 MHz, MeOD) δ 7.24-7.10 (m, 1H), 7.01 (t, J=6.4 Hz, 1H), 6.91-6.78 (m, 1H), 4.22 (dd, J=13.6, 5.1 Hz, 1H), 4.12-3.96 (m, 2H), 3.90-3.77 (m, 2H), 3.75-3.54 (m, 3H), 2.06 (s, 3H), 1.89 (dddd, J=35.0, 32.2, 11.8, 9.7 Hz, 2H), 1.24 (dd, J=6.4, 2.5 Hz, 3H); ESI-MS m/z calc. 392.2, found 393.2 (M+1)$^+$. Retention time: 0.59 minutes. SFC chiral separation: Column: AD-H, 20×250 mm; Mobile phase: 40% MeOH (5 mM Ammonia), 60% CO$_2$; Flow: 80 mL/min; Concentrations: ~50 mg/mL (MeOH)

Peak A: (R)-1-(4-((R)-4-(2-amino-6-methylpyrimidin-4-yl)-1,4-oxazepan-3-yl)-3-chlorophenoxy)-propan-2-ol (262) optical rotation 5.0 mg in 0.5 mL MeOH=−17.20°; $^1$H NMR (400 MHz, MeOD) δ 7.19 (d, J=8.7 Hz, 1H), 7.03 (d, J=2.5 Hz, 1H), 6.88 (dd, J=8.6, 2.4 Hz, 1H), 4.22 (dd, J=13.7, 5.0 Hz, 1H), 4.15-3.95 (m, 2H), 3.85 (ddd, J=16.2, 9.7, 5.4 Hz, 2H), 3.77-3.53 (m, 3H), 2.07 (s, 3H), 1.86 (d, J=29.4 Hz, 2H), 1.24 (d, J=6.4 Hz, 3H); ESI-MS m/z calc. 392.2, found 393.2 (M+1)$^+$. Retention time: 0.58 minutes. I-264.

Peak B: (R)-1-(4-((S)-4-(2-amino-6-methylpyrimidin-4-yl)-1,4-oxazepan-3-yl)-3-chlorophenoxy)-propan-2-ol (263): optical rotation 4.8 mg in 0.5 mL MeOH=−22.76°; $^1$H NMR (400 MHz, MeOD) δ 7.19 (d, J=8.7 Hz, 1H), 7.03 (d, J=2.4 Hz, 1H), 6.87 (d, J=8.7 Hz, 1H), 4.22 (dd, J=13.6, 5.1 Hz, 1H), 4.13-3.94 (m, 2H), 3.85 (ddd, J=16.2, 9.6, 5.4 Hz, 2H), 3.76-3.52 (m, 2H), 2.07 (s, 2H), 1.86 (d, J=33.1 Hz, 2H); ESI-MS m/z calc. 392.2, found 393.2 (M+1)$^+$. Retention time: 0.57 minutes. I-265.

The following analogs were prepared according to Synthetic Scheme 33:

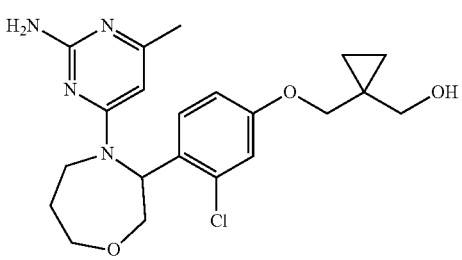

264

(+/−)-[1-[[4-[4-(2-amino-6-methyl-pyrimidin-4-yl)-1,4-oxazepan-3-yl]-3-chloro-phenoxy]methyl]-cyclopropyl]methanol (264) I-233

$^1$H NMR (400 MHz, MeOD) δ 7.20 (d, J=8.6 Hz, 1H), 7.03 (d, J=2.6 Hz, 1H), 6.88 (dd, J=8.6, 2.5 Hz, 1H), 4.23 (dd, J=13.6, 5.0 Hz, 1H), 4.05-3.45 (m, 8H), 2.17 (s, 3H), 1.89 (d, J=13.2 Hz, 2H), 0.58 (dt, J=5.2, 1.9 Hz, 4H); ESI-MS m/z calc. 418.2, found 419.3 (M+1)$^+$. Retention time: 0.62 minutes.

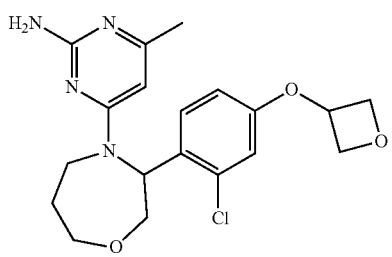

(+/−)-4-[3-[2-chloro-4-(oxetan-3-yloxy)phenyl]-1,4-oxazepan-4-yl]-6-methyl-pyrimidin-2-amine (265) I-231

¹H NMR (400 MHz, MeOD) δ 7.20 (d, J=8.6 Hz, 1H), 6.86 (d, J=2.6 Hz, 1H), 6.70 (dd, J=8.8, 2.6 Hz, 1H), 5.32-5.16 (m, 1H), 5.04-4.90 (m, 2H), 4.71-4.50 (m, 2H), 4.22 (dd, J=13.6, 5.1 Hz, 1H), 4.01 (d, J=11.9 Hz, 1H), 3.73-3.53 (m, 3H), 2.07 (s, 3H), 1.86 (d, J=34.4 Hz, 2H); ESI-MS m/z calc. 390.1, found 391.2 (M+1)⁺. Retention time: 0.61 minutes.

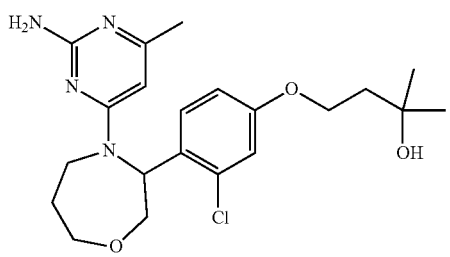

(+/−)-4-[4-[4-(2-amino-6-methyl-pyrimidin-4-yl)-1,4-oxazepan-3-yl]-3-chloro-phenoxy]-2-methyl-butan-2-ol (266) I-230

¹H NMR (400 MHz, MeOD) δ 7.19 (d, J=8.7 Hz, 1H), 6.99 (d, J=2.7 Hz, 1H), 6.85 (dd, J=8.9, 2.6 Hz, 1H), 4.22 (dd, J=13.6, 5.0 Hz, 1H), 4.10 (t, J=6.9 Hz, 2H), 4.06-3.90 (m, 1H), 3.67 (ddd, J=45.9, 13.8, 10.6 Hz, 3H), 2.09 (s, 3H), 2.00-1.71 (m, 3H), 1.26 (s, 6H); ESI-MS m/z calc. 420.2, found 421.3 (M+1)⁺. Retention time: 0.63 minutes.

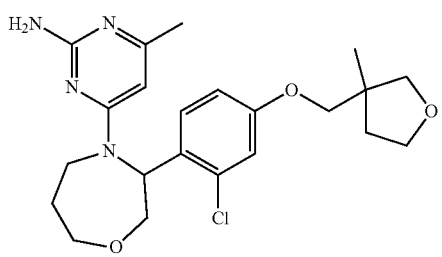

(+/−)-4-[3-[2-chloro-4-[(3-methyltetrahydrofuran-3-yl)methoxy]phenyl]-1,4-oxazepan-4-yl]-6-methyl-pyrimidin-2-amine (267) I-229

¹H NMR (400 MHz, MeOD) δ 7.19 (d, J=8.7 Hz, 1H), 7.02 (d, J=2.6 Hz, 1H), 6.87 (dd, J=8.7, 2.6 Hz, 1H), 4.22 (dd, J=13.6, 5.0 Hz, 1H), 4.01 (d, J=11.3 Hz, 1H), 3.93-3.54 (m, 8H), 3.53-3.38 (m, 2H), 2.08 (s, 3H), 2.03-1.66 (m, 4H), 1.23 (s, 3H); ESI-MS m/z calc. 432.2, found 433.3 (M+1)⁺. Retention time: 0.67 minutes.

Example 34

Synthetic Scheme 34: (+/−)-6-(4-(2-amino-6-methylpyrimidin-4-yl)-1,4-oxazepan-3-yl)-7-chloro-2H-benzo[b][1,4]thiazin-3(4H)-one (273) I-268 and (+/−)-4-(3-(7-chloro-3,4-dihydro-2H-benzo[b][1,4]thiazin-6-yl)-1,4-oxazepan-4-yl)-6-methylpyrimidin-2-amine (274) I-274

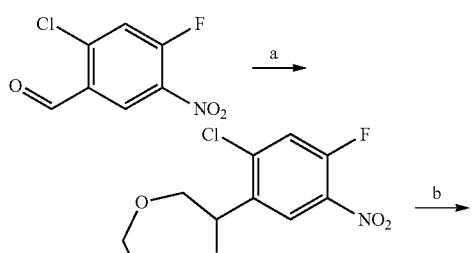

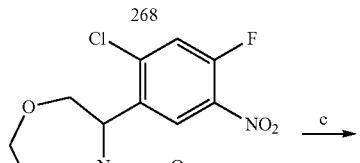

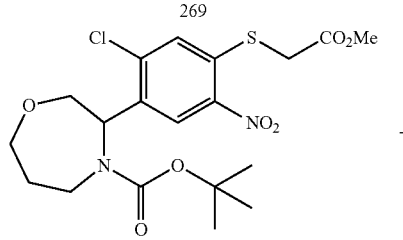

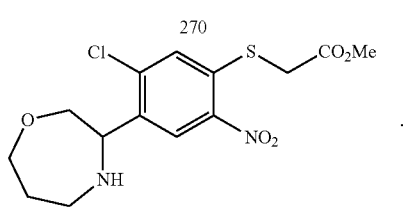

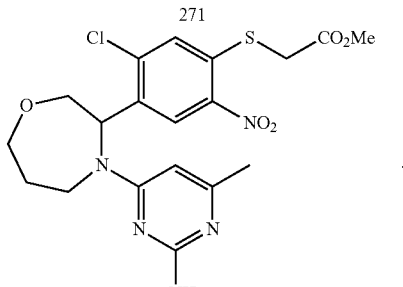

-continued

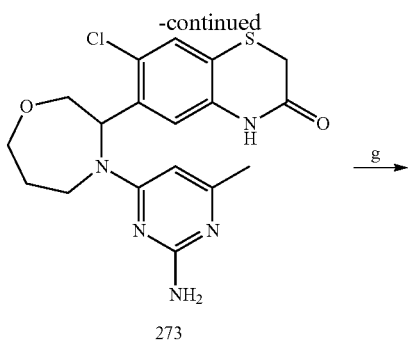

273

274

(a) 3-(tributylstannyl)methoxy)propan-1-amine, 4 Å mol sieves, CH₂Cl₂; then 2,6-lutidine Cu(OTf)₂, hexafluoroisopropanol, CH₂Cl₂; b) Boc₂O, CH₂Cl₂; c) methyl 2-sulfanylacetate, K₂CO₃, DMF, 50° C.; d) TFA, CH₂Cl₂; e) 2-amino-4-chloro-6-methylpyrimidine, nBuOH, 120° C.; f) iron, acetic acid, 60° C.; g) LiAlH₄, THF, 60° C.

Formation of 3-(2-chloro-4-fluoro-5-nitro-phenyl)-1,4-oxazepane (268)

To a solution of 2-chloro-4-fluoro-5-nitro-benzaldehyde (2.0 g, 9.8 mmol) in dichloromethane (50 mL) was added 3-(tributylstannylmethoxy)propan-1-amine (3.8 g, 9.9 mmol) and 4 angstrom molecular sieves (1.5 g). The reaction mixture was stirred at room temperature for two hours and filtered through a short layer of Celite and rinsed with dichloromethane. The filtrate was concentrated in vacuo to afford the crude imine.

To a separate solution of 2,6-lutidine (1.4 mL, 12.1 mmol) in hexafluoroisopropanol (50 mL) was added Cu(OTf)₂ (4.3 g, 11.9 mmol) (1.20 eq., preheated at 110° C. for 1 h under high vacuum) and stirred at room temperature for 1 hour. A solution of the imine in dichloromethane (160 mL) was added in one portion and the resulting mixture was stirred at room temperature for 12 hours. The reaction was quenched at room temperature with a mixture of aqueous saturated NaHCO₃ solution (40 mL) and 10% aqueous ammonium hydroxide (20 mL) and stirred vigorously for 15 minutes. The layers were separated and the aqueous layer was extracted with dichloromethane (3×50 mL). The combined organic layers were washed with water (3×5 mL) and brine (10 mL), dried over Na₂SO₄, filtered, and concentrated in vacuo. Purification by silica gel chromatography (0-6% MeOH/dichloromethane gradient) afforded 420 mg of the desired product: ¹H NMR (300 MHz, CDCl₃) δ 8.21-8.04 (m, 1H), 7.36-7.05 (m, 1H), 4.03 (ddd, J=15.7, 7.3, 4.1 Hz, 1H), 3.95-3.72 (m, 2H), 3.72-3.47 (m, 2H), 3.50-3.30 (m, 2H), 2.13-1.51 (m, 2H); ESI-MS m/z calc. 274.1, found 275.2 (M+1). Retention time: 0.84 minutes.

Formation of tert-butyl 3-(2-chloro-4-fluoro-5-nitro-phenyl)-1,4-oxazepane-4-carboxylate (269)

3-(2-Chloro-4-fluoro-5-nitro-phenyl)-1,4-oxazepane, 268, (0.42 g, 1.53 mmol) in dichloromethane (5 mL) was added Boc₂O (0.50 g, 2.29 mmol). The reaction mixture was stirred overnight at room temperature. The mixture was concentrated in vacuo and purified by silica gel chromatography (12 g ISCO column, eluting with 10-100% EtOAc/Heptanes) to afford 350 mg of the desired product as yellow crystalline solid: ¹H NMR (300 MHz, CDCl₃) δ 7.97 (t, J=6.1 Hz, 1H), 7.34 (d, J=10.1 Hz, 1H), 5.50 (ddd, J=33.9, 10.1, 4.4 Hz, 1H), 4.55-3.94 (m, 3H), 3.68-3.23 (m, 3H), 2.17-1.72 (m, 2H), 1.34 (d, J=59.9 Hz, 9H); ESI-MS m/z calc. 374.1, found 375.2. Retention time: 0.93 minutes.

Formation of tert-butyl 3-[2-chloro-4-(2-methoxy-2-oxo-ethyl)sulfanyl-5-nitro-phenyl]-1,4-oxazepane-4-carboxylate (270)

tert-Butyl 3-(2-chloro-4-fluoro-5-nitro-phenyl)-1,4-oxazepane-4-carboxylate, 269, (0.31 g, 0.83 mmol) and K₂CO₃ (0.24 g, 1.77 mmol) was dissolved in DMF (2 mL) in a small vial. Methyl 2-sulfanylacetate (0.09 mL, 0.95 mmol) was added to the mixture. The mixture was heated to 50° C. for 6 hours. After removal of DMF in vacuo, the crude was diluted with EtOAc (5 mL). The organic layer was filtered and the solvent was removed in vacuo to afford 380 mg of the desired product as a yellow solid: ESI-MS m/z calc. 460.1, found 461.10. Retention time: 0.92 minutes.

Formation of methyl 2-((5-chloro-2-nitro-4-(1,4-oxazepan-3-yl)phenyl)thio)acetate (271)

tert-Butyl 3-[2-chloro-4-(2-methoxy-2-oxo-ethyl)sulfanyl-5-nitro-phenyl]-1,4-oxazepane-4-carboxylate, 270, (50 mg, 0.1085 mmol) in dichloromethane (1.5 mL) was added trifluoroacetic acid (0.25 mL, 3.25 mmol) and stirred for 1 hour at room temperature. LCMS indicated no more starting material present. Solvent was removed in vacuo and the crude product (TFA salt) was used directly without further purification.

Formation of methyl 2-((4-(4-(2-amino-6-methylpyrimidin-4-yl)-1,4-oxazepan-3-yl)-5-chloro-2-nitrophenyl)thio)acetate (272)

In a microwave vial, methyl 2-[5-chloro-2-nitro-4-(1,4-oxazepan-3-yl)phenyl]sulfanylacetate (Trifluoroacetate salt), 271, (0.05 g) and 4-chloro-6-methyl-pyrimidin-2-amine (0.03 g, 0.17 mmol) in n-BuOH (2 mL) was heated at 120° C. overnight. LCMS indicated disappearance of the starting material. Both Methyl ester and n-Bu ester products were obtained. n-BuOH was removed to give crude product as yellow solid and used directly without further purification.

Formation of 6-[4-(2-amino-6-methyl-pyrimidin-4-yl)-1,4-oxazepan-3-yl]-7-chloro-4H-1,4-benzothiazin-3-one (273) I-268 tert-Butyl 3-[2-chloro-4-(2-methoxy-2-oxo-ethyl)sulfanyl-5-nitro-phenyl]-1,4-oxazepane-4-carboxylate, 272, (0.05 g, 0.11 mmol) and iron (0.06 g, 1.07 mmol) in a vial was added acetic acid (2 mL). The mixture was heated to 60° C. and stirred for 1 hour. Acetic acid was removed and the crude mixture was purified by silica gel chromatography (12 g ISCO column, eluting with 0-10% MeOH/dichloromethane gradient) to provide 24 mg of the desired product as white solid: $^1$H NMR (300 MHz, CDCl$_3$) δ 10.01 (s, 1H), 7.29 (s, 1H), 6.93 (d, J=52.9 Hz, 2H), 5.87 (d, J=52.3 Hz, 1H), 5.50-4.71 (m, 2H), 4.26 (dd, J=13.7, 5.0 Hz, 1H), 4.12-3.92 (m, 1H), 3.72-3.37 (m, 3H), 3.31 (d, J=1.8 Hz, 2H), 2.01 (d, J=17.2 Hz, 4H), 1.81 (s, 2H); ESI-MS m/z calc. 405.1, found 406.1 (M+1)$^+$. Retention time: 0.61 minutes.

Formation of 4-[3-(7-chloro-3,4-dihydro-2H-1,4-benzothiazin-6-yl)-1,4-oxazepan-4-yl]-6-methyl-pyrimidin-2-amine (274) I-274

At room temperature, 6-[4-(2-amino-6-methyl-pyrimidin-4-yl)-1,4-oxazepan-3-yl]-7-chloro-4H-1,4-benzothiazin-3-one, 273, (0.02 g, 0.05 mmol) in THF (2.0 mL) was added a solution of LiAlH$_4$ (0.05 mL of 2 M solution in THF, 0.10 mmol). The cloudy solution was stirred overnight. Additional LiAlH$_4$ solution (0.10 mL) was added and the mixture was heated to 60° C. overnight. Ice-water (0.25 mL) was added and the mixture was stirred for 10 minutes. Dichloromethane (10 mL) was added. The resulting white solid was filtered and washed with dichloromethane. The combined organic phases were concentrated in vacuo. The crude residue was purified by silica gel chromatography (4 g ISCO column, eluting with 0-10% MeOH/dichloromethane gradient) to afford 7.5 mg of the desired product as white solid: $^1$H NMR (300 MHz, CDCl$_3$) δ 6.92 (s, 1H), 6.27 (s, 1H), 5.49 (s, 3H), 5.06 (s, 2H), 4.23 (dd, J=13.6, 5.0 Hz, 2H), 3.98 (s, 2H), 3.61-3.35 (m, 6H), 3.00-2.85 (m, 2H), 2.11 (s, 4H), 1.74 (d, J=13.7 Hz, 2H); ESI-MS m/z calc. 391.1, found 392.1 (M+1)$^+$. Retention time: 0.67 minutes.

Example 35

Synthetic Scheme 35: (+/−)-4-[3-[2-chloro-4-(oxetan-3-yl)phenyl]-1,4-oxazepan-4-yl]-6-methyl-pyrimidin-2-amine (275) I-255

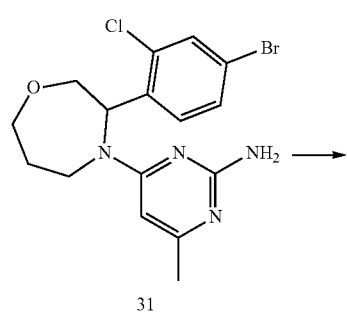

31

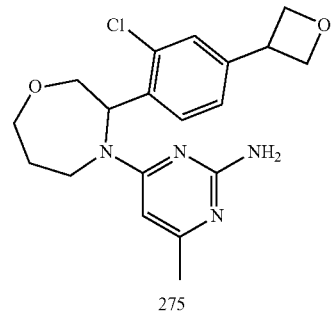

275

A Pyrex tube was charged with 3-bromooxetane (0.025 g, 0.180 mmol), NiCl$_2$ glyme (0.003 g, 0.014 mmol), 1,10-phenanthroline (0.005 g, 0.028 mmol), NaBF$_4$ (0.007 g, 0.065 mmol), manganese (0.013 g, 0.240 mmol). The tube was bubbled with nitrogen for 5 minutes. To the mixture was added MeOH (0.5 mL), 4-ethylpyridine (0.007 g, 0.060 mmol) and 4-[3-(4-bromo-2-chloro-phenyl)-1,4-oxazepan-4-yl]-6-methyl-pyrimidin-2-amine, 31, (0.050 g, 0.120 mmol). The reaction mixture was stirred overnight at 60° C. The reaction mixture was diluted with EtOAc and filtered though a layer of Celite. The filtrate was concentrated in vacuo and the residue was purified by silica gel chromatography using a 4 g ISCO column eluting with 0-10% MeOH. The product recovered has minor debromination impurity. The product was purified again by reverse phase HPLC chromatography to afford 9.0 mg of desired product: $^1$H NMR (400 MHz, CDCl$_3$) δ 7.44 (d, J=1.5 Hz, 1H), 7.28-7.22 (m, 2H), 5.71 (s, 1H), 5.58 (s, 1H), 5.07 (ddd, J=8.3, 6.1, 0.9 Hz, 2H), 4.74 (ddd, J=6.8, 6.1, 0.9 Hz, 2H), 4.63 (s, 2H), 4.35 (dd, J=13.6, 5.0 Hz, 1H), 4.26-4.02 (m, 2H), 2.15 (s, 3H), 2.10-1.95 (m, 1H), 1.90-1.79 (m, 1H); ESI-MS m/z calc. 374.2, found 375.0 (M+1)$^+$. Retention time: 2.63 minutes.

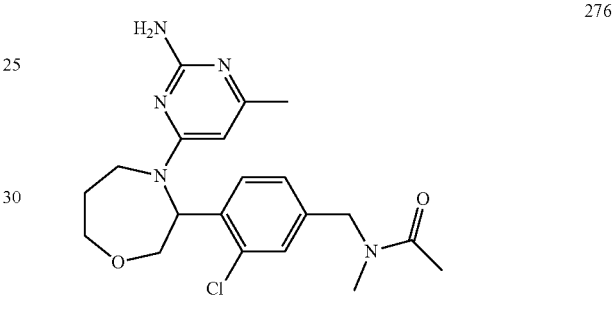

(+/−)-N-(4-(4-(2-amino-6-methylpyrimidin-4-yl)-1,4-oxazepan-3-yl)-3-chlorobenzyl)-N-methylacetamide (276) I-254

$^1$H NMR (400 MHz, CDCl$_3$) δ 7.28-7.17 (m, 2H), 7.13-6.99 (m, 1H), 5.57 (s, 2H), 4.79-4.56 (m, 3H), 4.56-4.43 (m, 2H), 4.34 (ddd, J=13.6, 5.0, 3.6 Hz, 1H), 4.10 (d, J=11.6 Hz, 1H), 3.70-3.47 (m, 1H), 2.97 (d, J=7.5 Hz, 3H), 2.17 (d, J=13.1 Hz, 7H); ESI-MS m/z calc. 403.2, found 404.0 (M+1)$^+$. Retention time: 2.55 minutes.

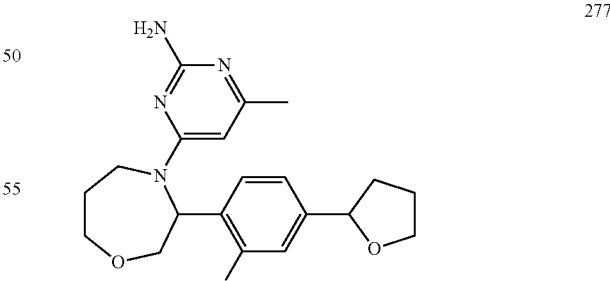

(+/−)-4-(3-(2-chloro-4-(tetrahydrofuran-2-yl)phenyl)-1,4-oxazepan-4-yl)-6-methylpyrimidin-2-amine (277) I-235

$^1$H NMR (400 MHz, CDCl$_3$) δ 7.40 (t, J=1.8 Hz, 1H), 7.24-7.10 (m, 2H), 5.56 (s, 1H), 4.85 (t, J=7.2 Hz, 1H), 4.60

(s, 2H), 4.35 (ddd, J=13.6, 5.1, 2.1 Hz, 1H), 4.10 (dtd, J=8.7, 6.8, 2.2 Hz, 2H), 4.01-3.89 (m, 1H), 3.70-3.46 (m, 3H), 2.39-2.28 (m, 1H), 2.14 (s, 3H), 2.02 (ttd, J=8.1, 6.7, 6.2, 5.3 Hz, 2H), 1.90-1.74 (m, 2H), 1.29 (d, J=6.0 Hz, 1H); ESI-MS m/z calc. 388.2, found 389.0 (M+1)$^+$. Retention time: 3.09 minutes.

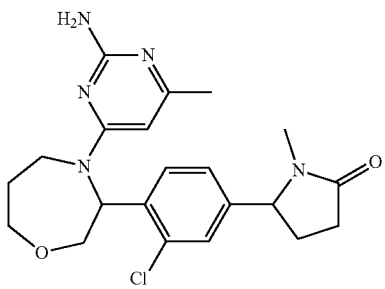

(+/−)-5-(4-(4-(2-amino-6-methylpyrimidin-4-yl)-1,4-oxazepan-3-yl)-3-chlorophenyl)-1-methylpyrrolidin-2-one (278) I-239

$^1$H NMR (400 MHz, CDCl$_3$) δ 7.30 (s, 1H), 7.28-7.22 (m, 1H), 7.18-7.03 (m, 1H), 5.68 (s, 5H), 4.60-4.26 (m, 2H), 4.21-4.02 (m, 1H), 3.65 (dd, J=26.2, 13.5 Hz, 4H), 3.32 (t, J=7.1 Hz, 1H), 2.71 (d, J=2.2 Hz, 2H), 2.64-2.34 (m, 2H), 2.35-1.76 (m, 6H); ESI-MS m/z calc. 415.2, found 416.27 (M+1)$^+$. Retention time: 0.66 minutes.

Example 36

Synthetic Scheme 36: (+/−)-4-(3-(2-chloro-4-(tetrahydrofuran-3-yl)phenyl)-1,4-oxazepan-4-yl)-6-methylpyrimidin-2-amine (279) I-238

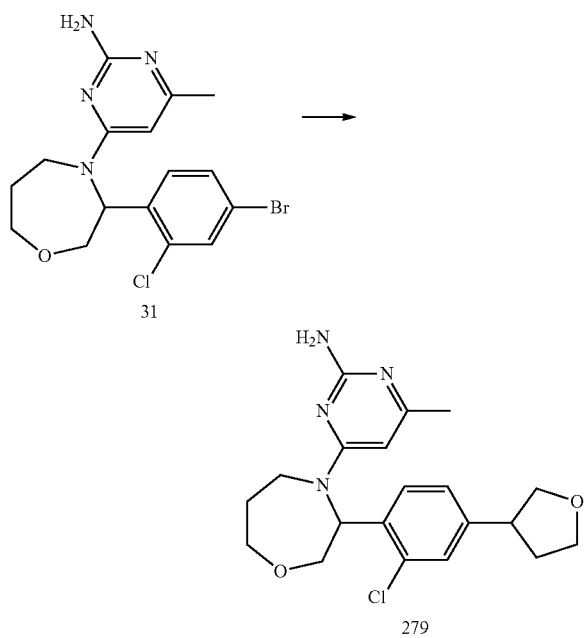

A pyrex tube was charged with 3-bromotetrahydrofuran (0.027 g, 0.179 mmol) dichloronickel; 1,2-dimethoxyethane (0.003 g, 0.014 mmol), 1,10-phenanthroline (0.005 g, 0.028 mmol), BF4 (Sodium salt) (0.007 g, 0.064 mmol), manganese (0.013 g, 0.237 mmol). The reaction mixture was bubbled with nitrogen for 5 minutes. To the mixture was added MeOH (4 mL), 4-ethylpyridine (0.007 g, 0.061 mmol) and followed with 4-[3-(4-bromo-2-chloro-phenyl)-1,4-oxazepan-4-yl]-6-methyl-pyrimidin-2-amine, 31, (0.050 g, 0.121 mmol). The mixture was stirred at 55° C. overnight. The reaction mixture was diluted with EtOAc, filtered though a layer of celite and concentrated in vacuo. The resulting residue was purified by silica gel chromatography using a 4 g ISCO silica gel cartridge eluting with 0-10% MeOH. The product recovered was repurified by reverse phase chromatography. To afford 6.7 mg of desired product: $^1$H NMR (400 MHz, CDCl$_3$) δ 7.30 (d, J=1.7 Hz, 1H), 7.24 (d, J=3.2 Hz, 1H), 7.18 (d, J=8.0 Hz, 1H), 7.11 (d, J=8.1 Hz, 1H), 5.58 (s, 1H), 4.90 (s, 2H), 4.51-4.26 (m, 1H), 4.18-4.05 (m, 2H), 3.92 (q, J=7.8 Hz, 1H), 3.73 (ddd, J=8.7, 7.0, 1.8 Hz, 1H), 3.69-3.49 (m, 3H), 3.37 (p, J=7.6 Hz, 1H), 2.45-2.27 (m, 1H), 2.17 (s, 3H), 2.08-1.95 (m, 2H); ESI-MS m/z calc. 388.2, found 389.0 (M+1)$^+$. Retention time: 3.06 minutes.

Example 37

Synthetic Scheme 37: (+/−)-4-(3-(2-chloro-4-(pyrrolidin-2-yl)phenyl)-1,4-oxazepan-4-yl)pyrimidin-2-amine (280) I-267

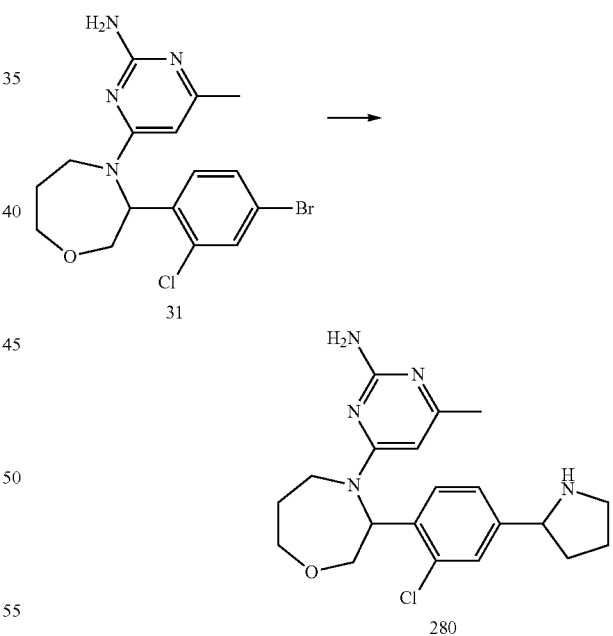

A pyrex vial was charged with NiCl$_2$-6H$_2$O (0.029 g, 0.121 mmol) and 4,7-dimethoxy-1,10-phenanthroline (0.125 mL of 0.1 M, 0.013 mmol) in DMSO (1 mL). The tube was sonicated for 5 minutes until materials were dissolved. In a reaction vial charged with 4-[3-(4-bromo-2-chloro-phenyl)-1,4-oxazepan-4-yl]-6-methyl-pyrimidin-2-amine, 31, (0.050 g, 0.121 mmol), Ir(dF(CF$_3$)ppy)$_2$(dtbpy) PF$_6$ (0.0013 g, 0.0012 mmol), tert-butyl pyrrolidine-1-carboxylate (0.050 mL, 0.285 mmol), quinuclidin-3-yl acetate (0.270 mL of 0.5 M solution, 0.135 mmol) in DMSO (0.40 mL) and 4,7-dimethoxy-1,10-phenanthroline (0.125 mL of 0.1 M solution in DMSO, 0.013 mmol). The tube was bubbled with nitrogen for 5 minutes. To the mixture was added H$_2$O (0.090 mL, 4.996 mmol). The reaction tube was exposed to a blue LED light and stirred overnight. The mixture was diluted with EtOAc, washed with H$_2$O and brine. The organic phase was dried over Na$_2$SO$_4$, filtered and concentrated in vacuo. The resulting residue was purified by silica gel chromatography using a 4 g ISCO column eluting with 0-10% MeOH/dichloromethane to afford mostly pure desired product that was used in next step without further purification.

To a solution of the above product dissolved in dichloromethane (1 mL) was added trifluoroacetic acid (0.500 mL, 6.490 mmol). The reaction mixture was stirred at room temperature for 20 minutes. The reaction mixture was submitted directly to reverse phase HPLC purification to afford 16 mg of desired product as a TFA salt. The product was converted to free base by passing through a PL-HCO$_3$ MPS PE cartridge and the filtrate was concentrated in vacuo to afford 5.6 mg of desired product: $^1$H NMR (400 MHz, CDCl$_3$) δ 7.43 (d, J=8.5 Hz, 1H), 7.24-7.15 (m, 2H), 4.59 (s, 3H), 4.35 (ddd, J=13.6, 5.0, 1.7 Hz, 1H), 4.10 (d, J=8.0 Hz, 3H), 3.69-3.49 (m, 4H), 3.27-3.14 (m, 1H), 3.04 (d, J=8.6 Hz, 1H), 2.64 (s, 6H), 2.30-2.09 (m, 4H); ESI-MS m/z calc. 387.2, found 388.2 (M+1)$^+$. Retention time: 0.5 minutes.

Example 38

Synthetic Scheme 38: (+/−)-4-(3-(2-chloro-4-(methoxymethyl)phenyl)-1,4-oxazepan-4-yl)-6-methylpyrimidin-2-amine (286) I-205

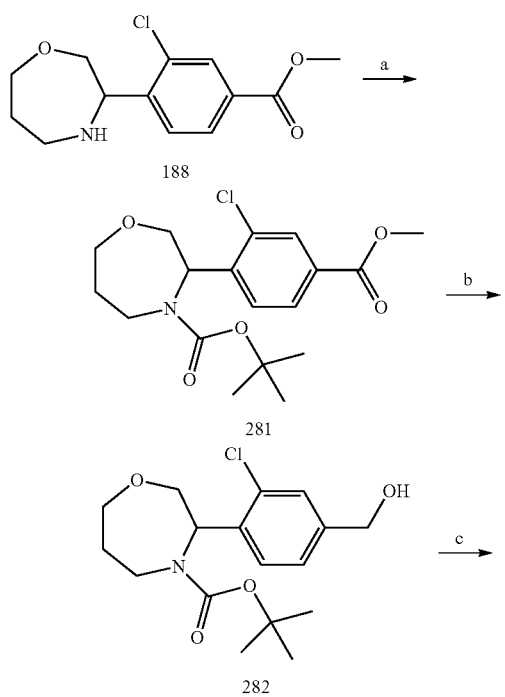

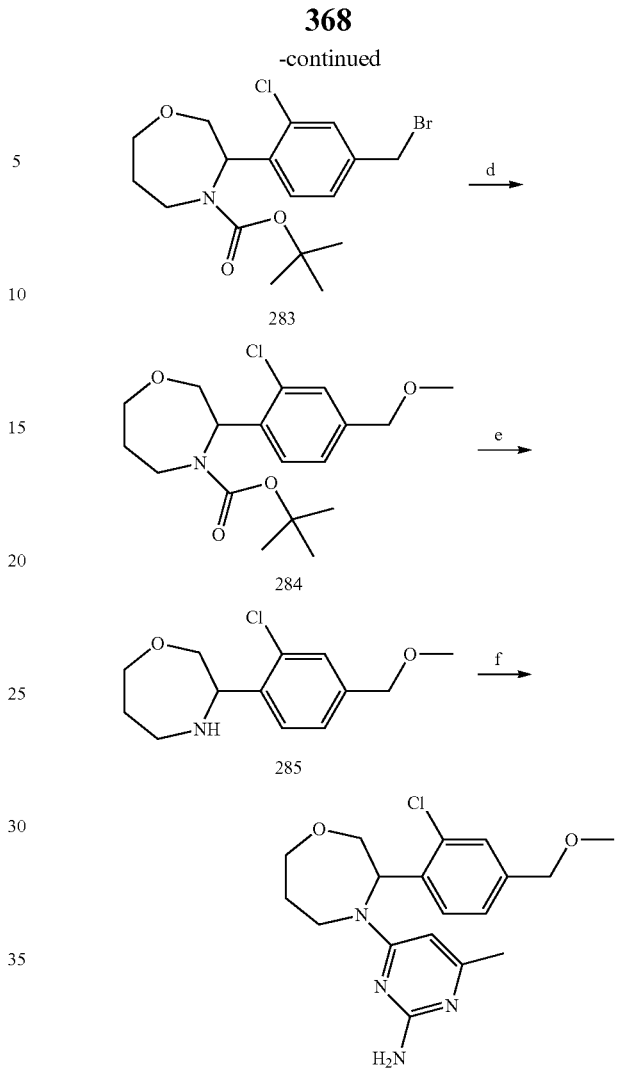

(a) Boc$_2$O, Et$_3$N, THF; (b) NaBH$_4$, EtOH; (c) NBS, Ph$_3$P, CH$_2$Cl$_2$; (d) NaOMe, MeOH, 70° C.; (e) HCl, dioxane; (f) 2-amino-4-chloro-6-methylpyrimidine, nBuOH, 120° C.

Formation of (+/−)-tert-butyl 3-(2-chloro-4-(methoxycarbonyl)phenyl)-1,4-oxazepane-4-carboxylate (281)

To a solution of methyl 3-chloro-4-(1,4-oxazepan-3-yl)benzoate, 188, (5.69 g, 21.10 mmol) and triethylamine (3.25 mL, 23.32 mmol) in THF (80 mL) was added Boc anhydride (5.07 g, 23.23 mmol). The reaction mixture was stirred at room temperature for 3 days, diluted with 1 M HCl and extracted twice with EtOAc. The combined organics were concentrated to dryness and purified via silica gel chromatography eluting with 0-50% EtOAc in heptane. Pure fractions were combined and concentrated in vacuo to give 6.27 g of the desired product as a light yellow oil: $^1$H NMR (400 MHz, CDCl$_3$) δ 8.03 (d, J=1.7 Hz, 1H), 7.90 (dd, J=8.1, 1.7 Hz, 1H), 7.34 (d, J=8.2 Hz, 1H), 5.56 (dd, J=10.6, 4.6 Hz, 1H), 4.56 (dd, J=15.0, 5.5 Hz, 1H), 4.31-4.06 (m, 2H), 3.94 (s, 3H), 3.58-3.33 (m, 3H), 2.07-1.91 (m, 1H), 1.85 (d, J=15.9 Hz, 1H), 1.22 (s, 10H).

Formation of (+/−)-tert-butyl 3-[2-chloro-4-(hydroxymethyl)phenyl]-1,4-oxazepane-4-carboxylate (282)

To a solution of tert-butyl 3-(2-chloro-4-methoxycarbonyl-phenyl)-1,4-oxazepane-4-carboxylate, 281, (6.25 g, 16.05 mmol) in EtOH (80 mL) was added NaBH$_4$ (6.07 g, 160.4 mmol). The reaction was stirred overnight at room temperature and then carefully quenched with aqueous 1M HCl to pH ~1. The product was extracted three times with EtOAc and the combined organics were concentrated to dryness and purified via silica gel chromatography eluting with 0-65% EtOAc in heptane. Pure fractions were combined and concentrated in vacuo to give 4.94 g of product: $^1$H NMR (400 MHz, CDCl$_3$) δ 7.37 (s, 1H), 7.23 (s, 2H), 5.52 (dd, J=10.8, 4.7 Hz, 1H), 4.68 (d, J=3.3 Hz, 2H), 4.54 (dd, J=15.1, 5.3 Hz, 1H), 4.12 (ddd, J=28.6, 13.6, 4.6 Hz, 2H), 3.57-3.28 (m, 3H), 2.08-1.90 (m, 2H), 1.90-1.75 (m, 1H), 1.24 (s, 9H); ESI-MS m/z calc. 341.2, found 342.0 (M+1)$^+$. Retention time: 0.96 minutes.

Formation of (+/−)-tert-butyl 3-[4-(bromomethyl)-2-chloro-phenyl]-1,4-oxazepane-4-carboxylate (283)

To a solution of tert-butyl 3-[2-chloro-4-(hydroxymethyl)phenyl]-1,4-oxazepane-4-carboxylate, 282, (4.94 g, 13.73 mmol) and triphenylphosphine (4.35 g, 16.58 mmol) in dichloromethane (50 mL) was added N-bromosuccinimide (3.75 g, 21.07 mmol). The reaction mixture was stirred for 20 minutes at room temperature and then diluted with water. The organic layer was concentrated to dryness and purified via silica gel chromatography eluting with 0-40% EtOAc in heptane. Pure fractions were combined and concentrated to give 5.0 g of desired product as a colorless oil: $^1$H NMR (400 MHz, CDCl$_3$) δ 7.43-7.36 (m, 1H), 7.32-7.18 (m, 2H), 5.51 (dd, J=10.8, 4.7 Hz, 1H), 4.60-4.48 (m, 1H), 4.44 (s, 2H), 4.35-3.98 (m, 2H), 3.48 (dddd, J=17.1, 14.3, 11.4, 3.1 Hz, 3H), 2.09-1.90 (m, 1H), 1.90-1.71 (m, 1H), 1.31-1.18 (m, 9H); ESI-MS m/z calc. 403.1, found 404.0 (M+1)$^+$. Retention time: 0.63 minutes.

Formation of (+/−)-tert-butyl 3-[2-chloro-4-(methoxymethyl)phenyl]-1,4-oxazepane-4-carboxylate (284)

A suspension of (+/−)-tert-butyl 3-[4-(bromomethyl)-2-chloro-phenyl]-1,4-oxazepane-4-carboxylate, 283, (0.37 g, 0.88 mmol) was stirred in sodium methoxide (3 mL of 25% w/v solution in MeOH, 14 mmol) at 70° C. overnight in a sealed tube. The mixture was diluted with water and extracted with EtOAc. The organic layer was concentrated to dryness and purified via silica gel chromatography eluting with 0-50% EtOAc in heptane. Fractions containing the desired product were combined and concentrated to give 161 mg colorless oil: $^1$H NMR (400 MHz, CDCl$_3$) δ 7.39-7.30 (m, 1H), 7.30-7.17 (m, 2H), 5.52 (dd, J=10.9, 4.7 Hz, 1H), 4.62-4.49 (m, 1H), 4.42 (s, 2H), 3.55-3.43 (m, 2H), 3.40 (s, 3H), 1.98 (qdd, J=11.2, 5.8, 2.2 Hz, 1H), 1.87-1.72 (m, 1H), 1.47-1.24 (m, 9H); ESI-MS m/z calc. 355.2, found 356.0 (M+1)$^+$. Retention time: 0.55 minutes.

Formation of (+/−)-3-[2-chloro-4-(methoxymethyl)phenyl]-1,4-oxazepane (285)

A solution of (+/−)-tert-butyl 3-[2-chloro-4-(methoxymethyl)phenyl]-1,4-oxazepane-4-carboxylate, 284, (0.16 g, 0.45 mmol) in HCl (3.0 mL of 4 M, 12.00 mmol) was stirred for 1 hour at room temperature. The reaction mixture was then concentrated to dryness to afford 132 mg of the desired product as an HCl salt and used in the next step without further purification: ESI-MS m/z calc. 255.1, found 256.0 (M+1)$^+$. Retention time: 0.56 minutes.

Formation of (+/−)-4-[3-[2-chloro-4-(methoxymethyl)phenyl]-1,4-oxazepan-4-yl]-6-methyl-pyrimidin-2-amine (286) I-205

A mixture of (+/−)-3-[2-chloro-4-(methoxymethyl)phenyl]-1,4-oxazepane-HCl, 285, (0.13 g, 0.45 mmol), 4-chloro-6-methyl-pyrimidin-2-amine (0.10 g, 0.70 mmol), and triethylamine (0.19 mL, 1.36 mmol) in n-BuOH (2 mL) was heated in a sealed tube at 120° C. overnight. The reaction mixture was concentrated to dryness then dissolved in EtOAc and washed with aqueous saturated sodium bicarbonate solution. The organic phase was isolated and concentrated to dryness. The resulting residue was purified via silica gel chromatography eluting with 0-10% MeOH in dichloromethane. Pure fractions were combined, concentrated, and lyophilized to afford 18 mg of desired product: $^1$H NMR (400 MHz, DMSO-d6) δ 7.36 (d, J=1.6 Hz, 1H), 7.28 (d, J=8.0 Hz, 1H), 7.21 (dd, J=8.1, 1.7 Hz, 1H), 5.57 (s, 1H), 5.46 (s, 2H), 4.63 (d, J=14.9 Hz, 1H), 4.38 (s, 2H), 4.11 (dd, J=13.5, 5.0 Hz, 1H), 3.93-3.86 (m, 1H), 3.76-3.60 (m, 2H), 3.60-3.48 (m, 1H), 3.30 (d, J=0.7 Hz, 3H), 1.99 (s, 3H), 1.77 (p, J=4.1 Hz, 2H); ESI-MS m/z calc. 362.2, found 363.0 (M+1)$^+$. Retention time: 0.7 minutes.

Example 39

Synthetic Scheme 39: (+/−)-2-(4-(4-(2-amino-6-methylpyrimidin-4-yl)-1,4-oxazepan-3-yl)-3-chlorophenyl)propane-1,3-diol (288) I-236

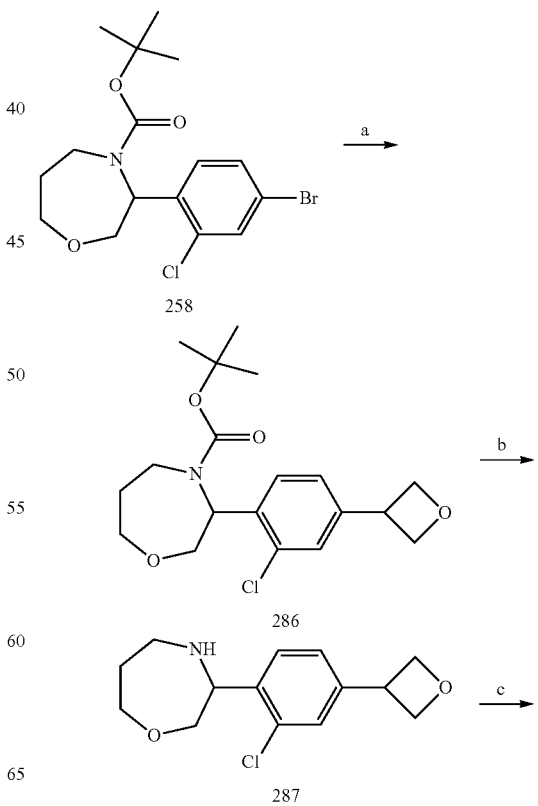

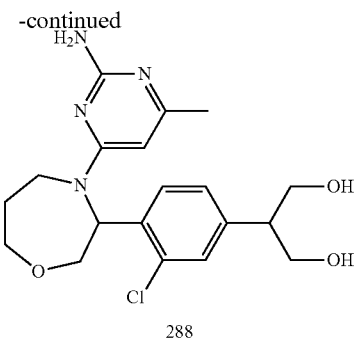

288

(a) Ir(dF(CF$_3$)ppy)$_2$(dtbpy)PF$_6$, NiCl$_2$ glyme, TTMMS, Na$_2$CO$_3$, DME, LED blue light; (b) TFA, CH$_2$Cl$_2$; (c) 2-amino-4-chloro-6-methylpyrimidine, nBuOH, 130° C.

Formation of (+/−)-tert-butyl 3-(2-chloro-4-(oxetan-3-yl)phenyl)-1,4-oxazepane-4-carboxylate (286)

To a reaction vial was added NiCl$_2$ glyme (0.003 g, 0.014 mmol), 4-tert-butyl-2-(4-tert-butyl-2-pyridyl)pyridine (0.004 g, 0.015 mmol) and DME (1 mL). The mixture was bubbled with nitrogen for 5 minutes until the solid dissolved in DME (1 mL). In another vial was added tert-butyl 3-(4-bromo-2-chloro-phenyl)-1,4-oxazepane-4-carboxylate, 258, (0.200 g, 0.510 mmol), 3-bromooxetane (0.110 g, 0.800 mmol), Ir[dF(CF3)ppy]$_2$(dtbby)PF$_6$ (0.003 g, 0.0034 mmol), TTMSS (0.170 mL, 0.550 mmol) and Na$_2$CO$_3$ (0.062 g, 0.590 mmol) and DME (2 mL). To the mixture was added NiCl$_2$glyme solution and stirred for 18 h in front of blue LED lamp. The mixture was diluted with H$_2$O, extracted with dichloromethane and the organic phase was concentrated in vacuo. The residue was purified by silica gel chromatography using a 12 g ISCO column eluting with 0-50% EtOAc/heptane to afford 80 mg of desired product: $^1$H NMR (400 MHz, CDCl$_3$) δ 7.22 (s, 1H), 7.11 (s, 2H), 5.47-5.27 (m, 1H), 4.92 (t, J=7.2 Hz, 2H), 4.57 (d, J=6.4 Hz, 1H), 4.16-3.76 (m, 3H), 3.49-3.12 (m, 4H), 1.74 (d, J=46.8 Hz, 1H), 1.41 (s, 3H), 1.08 (s, 9H).

Formation of 3-(2-chloro-4-(oxetan-3-yl)phenyl)-1,4-oxazepane (287)

To a solution of tert-butyl 3-[2-chloro-4-(oxetan-3-yl)phenyl]-1,4-oxazepane-4-carboxylate, 286, (0.080 g, 0.220 mmol) in dichloromethane (5 mL) was added trifluoroacetic acid (0.20 mL, 2.60 mmol). The reaction mixture was stirred for 1 hour at room temperature. The mixture was concentrated in vacuo. The crude TFA salt was converted to parent form by passing though a PL-HCO3 MP SPE cartridge with MeOH as solvent. The filtrate was concentrated in vacuo. The crude product was carried to next step without further purification: ESI-MS m/z calc. 267.1 found 268.2 (M+1)$^+$. Retention time: 0.66 minutes.

Formation of (+/−)-2-(4-(4-(2-amino-6-methylpyrimidin-4-yl)-1,4-oxazepan-3-yl)-3-chlorophenyl) propane-1,3-diol (288) I-236

A mixture of 3-[2-chloro-4-(oxetan-3-yl)phenyl]-1,4-oxazepane, 287, (0.050 g, 0.190 mmol) and 4-chloro-6-methylpyrimidin-2-amine (0.035 g, 0.240 mmol) in n-BuOH (5 mL) was heated overnight at 130° C. LC-MS showed oxetene ring opening product. The mixture was concentrated in vacuo. The resulting residue was purified by silica gel chromatography using a 4 g ISCO column eluting with 0-10% MeOH/dichloromethane to afford 11.4 mg of desired product: $^1$H NMR (400 MHz, CDCl$_3$) δ 7.30 (s, 1H), 7.23-7.10 (m, 2H), 5.58 (s, 1H), 4.89 (s, 2H), 4.35 (dd, J=13.6, 5.1 Hz, 1H), 4.10 (dd, J=12.3, 4.8 Hz, 1H), 4.02-3.84 (m, 4H), 3.67-3.53 (m, 2H), 3.13-2.89 (m, 1H), 2.14 (s, 3H), 2.08-1.95 (m, 1H), 1.83 (d, J=14.4 Hz, 1H), 1.38-1.14 (m, 1H); ESI-MS m/z calc. 392.2, found 393.0 (M+1)$^+$. Retention time: 2.82 minutes. The following analogs were according to Synthetic Scheme 3.

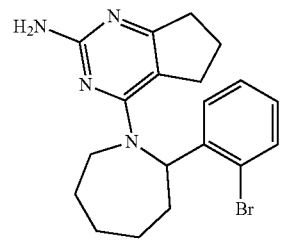 [SMILES: Nc1nc2c(c(N3CCCCCC3c3ccccc3Br)n1)CCC2]

(+/−)-4-(2-(2-bromophenyl)azepan-1-yl)-6,7-dihydro-5H-cyclopenta[d]pyrimidin-2-amine I-7

$^1$H NMR (400 MHz, MeOD) δ 7.58 (s, 1H), 7.29 (d, J=65.1 Hz, 3H), 5.61 (d, J=166.6 Hz, 2H), 4.54 (s, 1H), 3.82 (s, 1H), 3.48 (s, 1H), 3.27-3.21 (m, 1H), 3.20-1.31 (m, 12H); ESI-MS m/z calc. 272.16, found 272.92 (M+1)$^+$. Retention time: 0.58 minutes.

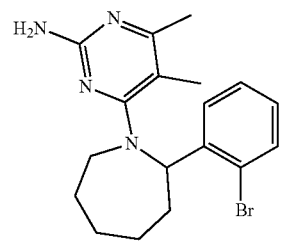 [SMILES: Cc1nc(N)nc(N2CCCCCC2c2ccccc2Br)c1C]

(+/−)-4-(2-(2-bromophenyl)azepan-1-yl)-5,6-dimethylpyrimidin-2-amine I-8

$^1$H NMR (400 MHz, MeOD) δ 7.60 (d, J=8.0 Hz, 1H), 7.33 (q, J=7.7 Hz, 2H), 7.15 (dd, J=11.3, 5.2 Hz, 1H), 5.51 (s, 1H), 4.49 (s, 1H), 3.90-3.51 (m, 1H), 2.62 (s, 1H), 2.27 (s, 3H), 2.08 (s, 3H), 1.84 (dd, J=33.6, 27.8 Hz, 5H), 1.59-1.37 (m, 2H); ESI-MS m/z calc. 375.0, found 375.1 (M+1)$^+$. Retention time: 2.95 minutes.

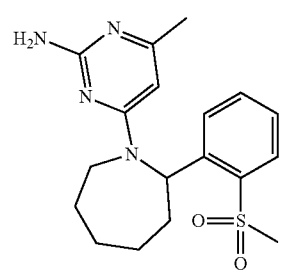 [SMILES: Cc1cc(N2CCCCCC2c2ccccc2S(C)(=O)=O)nc(N)n1]

4-methyl-6-(2-(2-(methylsulfonyl)phenyl)azepan-1-yl)pyrimidin-2-amine I-38 high temperature (360 K) ¹H NMR (400 MHz, DMSO-d6) δ 7.93 (dd, J=8.0, 1.4 Hz, 1H), 7.61 (td, J=7.6, 1.5 Hz, 1H), 7.47 (td, J=7.6, 1.3 Hz, 1H), 7.38 (dd, J=7.9, 1.3 Hz, 1H), 6.05-5.80 (m, 1H), 5.65 (d, J=11.6 Hz, 1H), 5.56-5.29 (m, 2H), 4.14-3.80 (m, 1H), 3.60 (s, 3H), 2.66-2.54 (m, 1H), 2.05 (s, 3H), 1.97-1.76 (m, 2H), 1.81-1.54 (m, 2H), 1.56-1.11 (m, 4H).

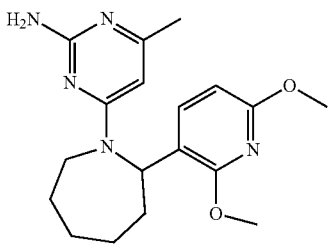 [SMILES: COc1ccc(C2CCCCCN2c2cc(C)nc(N)n2)c(OC)n1]

4-[2-(2,6-dimethoxy-3-pyridyl)azepan-1-yl]-6-methyl-pyrimidin-2-amine, I-73

¹H NMR (300 MHz, DMSO-d6) δ 7.37 (br, 1H), 7.11 (s, 2H), 6.31 (s, 1H), 5.66 (br, 1H), 4.73 (br, 1H), 4.02-3.72 (m, 6H), 3.68-3.01 (m, 2H), 2.17 (brs, 3H), 1.98-0.93 (m, 8H); ESI-MS m/z calc. 343.20, found 344.35 (M+1)⁺. Retention time: 0.72 minutes.

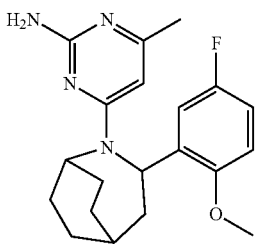 [SMILES: COc1ccc(F)cc1C1CC2CCC(CC2)N1c1cc(C)nc(N)n1]

4-(3-(5-fluoro-2-methoxyphenyl)-2-azabicyclo[3.2.2]nonan-2-yl)-6-methylpyrimidin-2-amine I-76 high temperature (360 K) ¹H NMR (400 MHz, DMSO-d6) δ 6.99 (dd, J=9.0, 4.6 Hz, 1H), 6.95-6.81 (m, 2H), 5.65 (s, 1H), 5.53-5.33 (m, 2H), 5.26-5.11 (m, 1H), 3.88 (s, 3H), 2.45-2.31 (m, 1H), 2.23-2.11 (m, 1H), 2.10-1.96 (m, 2H), 1.91 (s, 3H), 1.88-1.74 (m, 1H), 1.73-1.42 (m, 7H); ESI-MS m/z calc. 356.20, found 357.25 (M+1)⁺. Retention time: 0.68 minutes.

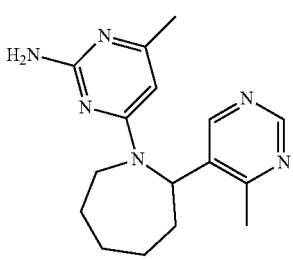 [SMILES: Cc1cc(N2CCCCCC2c2cncnc2C)nc(N)n1]

(+/-)-4-methyl-6-[2-(4-methylpyrimidin-5-yl)azepan-1-yl]pyrimidin-2-amine I-42 high temperature (360 K) ¹H NMR (400 MHz, DMSO-d6) δ 8.81 (s, 1H), 8.38 (s, 1H), 5.74 (s, 1H), 5.41-5.33 (m, 3H), 4.10 (d, J=12.0 Hz, 1H), 3.52 (dd, J=15.0, 11.0 Hz, 2H), 2.62 (s, 3H), 2.25-2.14 (m, 1H), 2.04 (s, 3H), 1.93 (s, 1H), 1.87-1.72 (m, 2H), 1.56-1.28 (m, 4H); ESI-MS m/z calc. 298.19, found 299.19 (M+1)⁺. Retention time: 0.53 minutes.

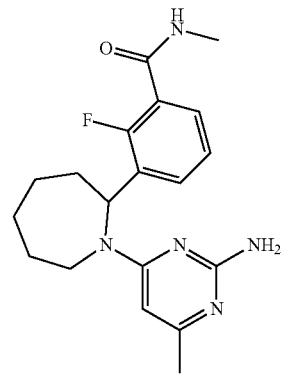 [SMILES: CNC(=O)c1cccc(C2CCCCCN2c2cc(C)nc(N)n2)c1F]

3-(1-(2-amino-6-methylpyrimidin-4-yl)azepan-2-yl)-2-fluoro-N-methylbenzamide I-54

¹H NMR (400 MHz, DMSO-d6) δ 7.87 (s, 1H), 7.43 (td, J=7.2, 1.9 Hz, 1H), 7.22 (td, J=7.5, 1.9 Hz, 1H), 7.12 (t, J=7.6 Hz, 1H), 5.72 (s, 1H), 5.40 (s, 2H), 4.20 (d, J=14.4 Hz, 1H), 3.42-3.29 (m, 1H), 2.97 (s, 1H), 2.80 (d, J=4.7 Hz, 3H), 2.43-2.29 (m, 1H), 2.03 (s, 3H), 1.97-1.71 (m, 4H), 1.67-1.23 (m, 3H). ESI-MS m/z calc. 357.1965, found 358.0 (M+1)⁺. Retention time: 0.66 minutes.

Example 40

Synthetic Scheme 40: (+/-)-4-(3-(2-chlorophenyl)-6-methylene-1,4-oxazepan-4-yl)-6-methylpyrimidin-2-amine I-75

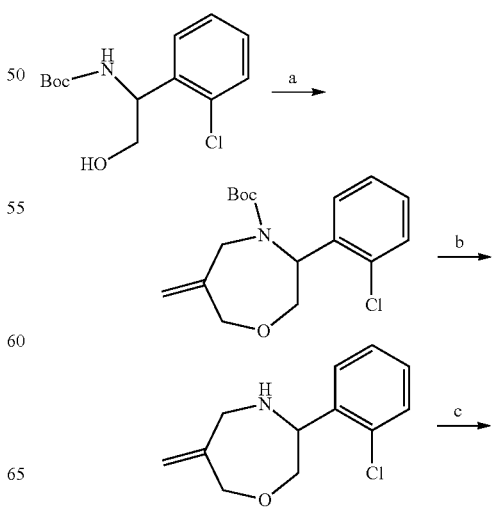

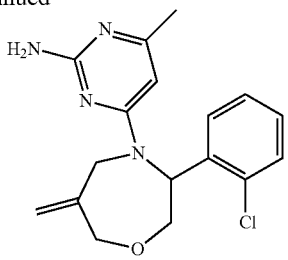

(a) 3-chloro-2-(chloromethyl)prop-1-ene, LiI, NaH, DMF, rt, then 50° C.; (b) TFA, CH$_2$Cl$_2$; (c) NH$_4$OH, CH$_3$CN, 70° C.

Formation of (+/−)-tert-butyl 3-(2-chlorophenyl)-6-methylene-1,4-oxazepane-4-carboxylate To a solution of tert-butyl N-[1-(2-chlorophenyl)-2-hydroxy-ethyl]carbamate (5.00 g, 18.40 mmol), 3-chloro-2-(chloromethyl)prop-1-ene (2.60 g, 20.80 mmol) and lithium iodide (0.11 g, 0.84 mmol) in DMF (200 mL) was added one equivalent of NaH in portions (0.75 g, 18.62 mmol). The mixture was stirred at room temperature for 15 hours. Then added the 2nd equivalent of NaH (0.75 g, 18.62 mmol). After 24 hours, heated reaction mixture to 50° C. for 3 days. The reaction mixture was diluted into aqueous saturated NH$_4$Cl solution and extracted twice with EtOAc. The combined organic phases were washed twice with brine, dried (MgSO$_4$), filtered and concentrated in vacuo. The resulting residue was purified via silica gel chromatography with 80 g ISCO column using 0-30% (EtOAc/heptanes): $^1$H NMR (400 MHz, DMSO-d6) δ 7.50-7.25 (m, 4H), 5.50-5.19 (m, 1H), 5.00 (s, 2H), 4.72-4.23 (m, 1H), 4.16 (s, 2H), 4.09-3.74 (m, 3H), 1.54-1.02 (m, 9H).

Formation of (+/−)-3-(2-chlorophenyl)-6-methylene-1,4-oxazepane

To a solution of tert-butyl 3-(2-chlorophenyl)-6-methylene-1,4-oxazepane-4-carboxylate (0.76 g, 2.23 mmol) in dichloromethane (8 mL) was added trifluoroacetic acid (6 mL). Stirred reaction mixture at room temperature for 1 hour and concentrated in vacuo. The residue was diluted with dichloromethane and neutralized with aqueous saturated NaHCO$_3$ solution. The organic phase was passed through a phase separator and the resulting filtrate was concentrated in vacuo to afford 485 mg of product as yellow oil.

Formation of (+/−)-4-(3-(2-chlorophenyl)-6-methylene-1,4-oxazepan-4-yl)-6-methylpyrimidin-2-amine I-75

To a solution of 3-(2-chlorophenyl)-6-methylene-1,4-oxazepane in (0.49 g, 2.17 mmol) in NMP (6 mL) was added 4-chloro-6-methyl-pyrimidin-2-amine (0.38 g, 2.61 mmol). The reaction mixture was heated to 150° C. for 16 hours. The mixture was cooled to room temperature and loaded directly onto 100 g ISCO c18-aq column and the crude was purified by reverse phase eluting with 0.1% TFA/H$_2$O and 0.1% TFA/CH$_3$CN gradient. The fractions containing desired product were concentrated in vacuo, diluted with dichloromethane, neutralized with aqueous saturated NaHCO$_3$ solution and the mixture was passed through a phase separator. The organic phase concentrated in vacuo to afford 575 mg of orange solid: heated $^1$H NMR (360K) (400 MHz, DMSO-d6) δ 7.69-7.52 (m, 1H), 7.50-7.36 (m, 1H), 7.36-7.20 (m, 2H), 5.76 (s, 1H), 5.73 (d, J=2.2 Hz, 1H), 5.52 (s, 2H), 5.05 (d, J=51.9 Hz, 2H), 4.72 (d, J=16.0 Hz, 1H), 4.29-4.09 (m, 2H), 4.08-3.97 (m, 2H), 3.92 (d, J=16.0 Hz, Example 41

Synthetic Scheme 41: (+/−)-(3-(4-(2-amino-6-methylpyrimidin-4-yl)-1,4-oxazepan-3-yl)-4-chlorophenyl)(imino)(methyl)-λ$^6$-sulfanone (I-156)

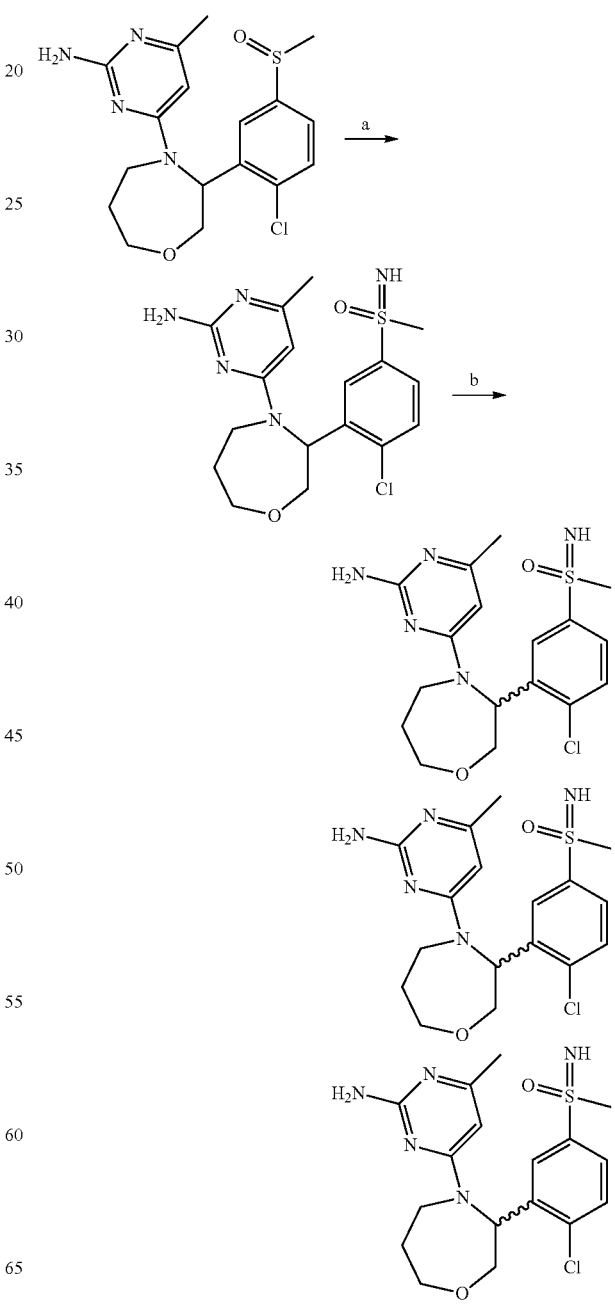

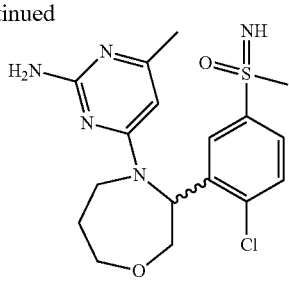

(a) PhI(OAc)₂, (NH₄)₂CO₃; MeOH; (b) SFC chiral separation

Formation of (+/−)-(3-(4-(2-amino-6-methylpyrimidin-4-yl)-1,4-oxazepan-3-yl)-4-chlorophenyl)(imino)(methyl)-λ⁶-sulfanone I-156

4-[3-(2-chloro-5-methylsulfinyl-phenyl)-1,4-oxazepan-4-yl]-6-methyl-pyrimidin-2-amine (0.25 g, 0.59 mmol), ammonium carbamate (0.18 g, 2.34 mmol) and (diacetoxyiodo)benzene (0.57 g, 1.78 mmol) were combined in a round bottom flask followed by the addition of MeOH (4 mL) and stirring continued for 75 minutes. The reaction mixture was diluted into EtOAc and washed with aqueous saturated NaHCO₃ solution. The aqueous phase was extracted with EtOAc. The combined organic phases were dried (MgSO4), filtered and concentrated in vacuo. The crude residue was purified by reverse phase silica gel chromatography with 50 g ISCO c18-aq column running with 0.1% TFA/H₂O and 0.1% TFA/CH₃CN. The pure fractions were concentrated in vacuo and residue was diluted with dichloromethane and neutralized with aqueous saturated NaHCO₃ solution. The mixture was passed through a phase separator and the filtrate was concentrated in vacuo to afford 27 mg of desired racemic product as a light yellow solid: heated NMR (360K) ¹H NMR (400 MHz, DMSO-d6) δ 7.90-7.70 (m, 2H), 7.63 (dd, J=14.2, 8.3 Hz, 1H), 6.35-5.32 (m, 4H), 4.91-4.41 (m, 1H), 4.18-3.50 (m, 5H), 3.06-3.00 (m, 3H), 2.12-1.99 (m, 3H), 1.87-1.64 (m, 2H).

The Racemic Mixture was Submitted for SFC Chiral Separation

Peak A, 2.9 mg (89.8% ee). 4-[3-[2-chloro-5-(methylsulfonimidoyl)phenyl]-1,4-oxazepan-4-yl]-6-methyl-pyrimidin-2-amine (2.9 mg, 5%): ESI-MS m/z calc. 395.12, found 396.0 (M+1)⁺. Retention time: 0.52 minutes. I-164.

Peak B, 4.3 mg (97.4% ee). 4-[3-[2-chloro-5-(methylsulfonimidoyl)phenyl]-1,4-oxazepan-4-yl]-6-methyl-pyrimidin-2-amine (4.3 mg, 7%): ESI-MS m/z calc. 395.12, found 396.0 (M+1)⁺. Retention time: 0.52 minutes. I-165.

Peak C, 3.2 mg (98% ee). 4-[3-[2-chloro-5-(methylsulfonimidoyl)phenyl]-1,4-oxazepan-4-yl]-6-methyl-pyrimidin-2-amine (3.2 mg, 5%): ESI-MS m/z calc. 395.12, found 396.0 (M+1)⁺. Retention time: 0.52 minutes. I-166.

Peak D, 4.7 mg (98% ee). 4-[3-[2-chloro-5-(methylsulfonimidoyl)phenyl]-1,4-oxazepan-4-yl]-6-methyl-pyrimidin-2-amine (4.7 mg, 8%): ESI-MS m/z calc. 395.12, found 396.0 (M+1)⁺. Retention time: 0.52 minutes. I-167.

Example 42

Synthetic Scheme 42: (+/−)-2-[4-(2-amino-6-methyl-pyrimidin-4-yl)-1,4-oxazepan-3-yl]benzonitrile, (+/−)-4-[3-[2-(aminomethyl)phenyl]-1,4-oxazepan-4-yl]-6-methyl-pyrimidin-2-amine, and (+/−)-N-[[2-[4-(2-amino-6-methyl-pyrimidin-4-yl)-1,4-oxazepan-3-yl]phenyl]methyl]acetamide

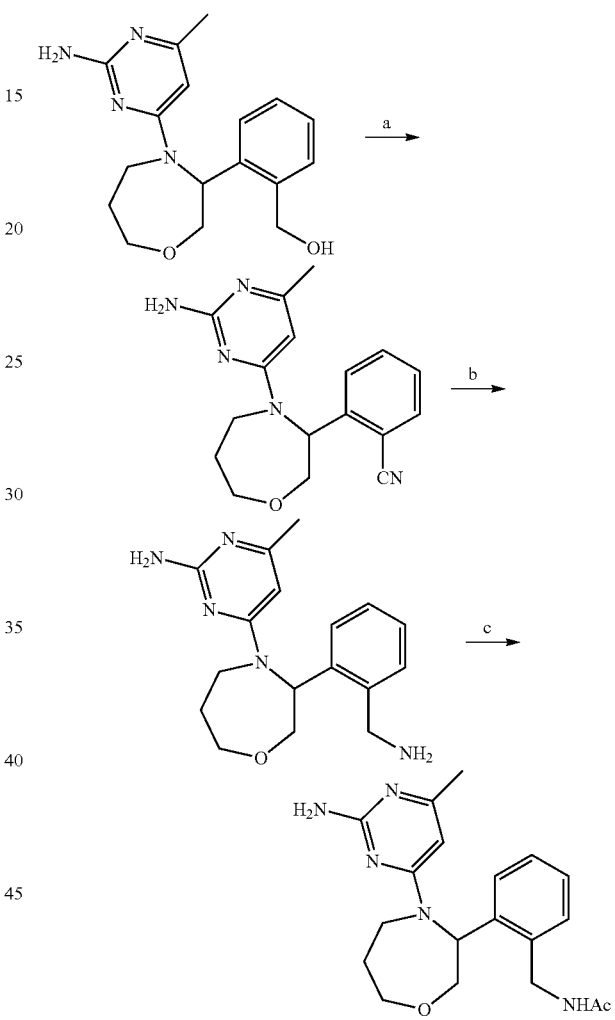

(a) MnO₂, MgSO₄, ammonia, THF; (b) LiAlH₄, THF; (c) Ac₂O, NEt₃, DCM.

Formation of (+/−)-2-[4-(2-amino-6-methyl-pyrimidin-4-yl)-1,4-oxazepan-3-yl]benzonitrile I-89

To a solution of [2-[4-(2-amino-6-methyl-pyrimidin-4-yl)-1,4-oxazepan-3-yl]phenyl]methanol (0.16 g, 0.52 mmol) in THF (3 mL) was added ammonia (2 mL of 2 M solution, 4.00 mmol) then anhydrous MgSO₄ (1.07 g, 8.89 mmol) and finally MnO₂ (135 µL, 7.78 mmol). The next morning 1 g more MgSO₄, 1g more MnO₂ and ammonia (4 mL of 2 M, 8.000 mmol) were added and the mixture heated at 45° C. After 1 h, the reaction mixture was filtered through Celite with the aid of 10% MeOH in EtOAc and concentrated in vacuo. Ether was added and 160 mg of the desired product filtered off: high temperature (360 K) ¹H NMR (400 MHz, DMSO-d6) δ 7.76 (d, J=7.7 Hz, 1H), 7.63 (t, J=7.6 Hz, 1H), 7.49 (d, J=7.5 Hz, 1H), 7.43 (t, J=7.6 Hz, 1H), 5.75 (s, 1H), 5.55 (dd, J=10.6, 5.2 Hz, 1H), 5.39 (s, 2H), 4.38 (d, J=14.8 Hz, 1H), 4.11 (dd, J=13.6, 5.1 Hz, 1H), 3.95-3.83 (m, 2H), 3.74 (dd, J=15.3, 12.7 Hz, 1H), 3.58 (dd, J=14.6, 12.1 Hz, 1H), 2.04 (s, 3H), 1.83-1.75 (m, 2H); ESI-MS m/z calc. 309.16, found 310.22 (M+1)⁺. Retention time: 0.55 minutes.

Formation of (+/−)-4-[3-[2-(aminomethyl)phenyl]-1,4-oxazepan-4-yl]-6-methyl-pyrimidin-2-amine I-94

To a solution of 2-[4-(2-amino-6-methyl-pyrimidin-4-yl)-1,4-oxazepan-3-yl]benzonitrile (0.055 g, 0.177 mmol) in THF (3 mL) with ice bath cooling was added LiAlH₄ (0.034 g, 0.873 mmol) under nitrogen and the mixture was stirred overnight at room temperature. Carefully dropwise addition of water and then added dichloromethane. Filtered the reaction mixture through Celite with the aid of aqueous saturated sodium bicarbonate solution. The layers were separated and the aqueous layer was re-extracted with dichloromethane and concentrated in vacuo. The residue was loaded directly onto a 30 g ISCO c18-aq column and purified by reverse phase running with 0.1% TFA/H₂O and 0.1% TFA/CH₃CN. The pure fractions were concentrated in vacuo and then dissolved in MeOH and passed through a SPE bicarbonate cartridge (Agilent Stratospheres 500 mg/6 mL) and concentrated in vacuo to give a pink oil. Ether was added and the mixture sonicated and 43 mg of the desired product was filtered off: high temperature (360 K) ¹H NMR (400 MHz, DMSO-d6) δ 7.37 (d, J=7.1 Hz, 1H), 7.25 (d, J=7.5 Hz, 1H), 7.17 (tt, J=7.4, 5.9 Hz, 2H), 5.82 (s, 1H), 5.54 (d, J=4.6 Hz, 1H), 5.37 (s, 2H), 4.47 (d, J=14.1 Hz, 1H), 4.08 (dd, J=13.5, 4.9 Hz, 1H), 4.00-3.80 (m, 3H), 3.75 (dd, J=13.5, 9.7 Hz, 1H), 3.59 (ddd, J=16.7, 14.1, 7.3 Hz, 2H), 2.00 (s, 3H), 1.76 (s, 4H); ESI-MS m/z calc. 313.19, found 314.23 (M+1)⁺. Retention time: 0.48 minutes.

Formation of (+/−)-N-[[2-[4-(2-amino-6-methyl-pyrimidin-4-yl)-1,4-oxazepan-3-yl]phenyl]methyl] acetamide I-95

To a solution of 4-[3-[2-(aminomethyl)phenyl]-1,4-oxazepan-4-yl]-6-methyl-pyrimidin-2-amine (0.015 g, 0.049 mmol) in dichloromethane (2 mL) was added triethylamine (0.035 mL, 0.251 mmol) then acetic anhydride (0.006 mL, 0.064 mmol) at room temperature. After 20 minutes, aqueous saturated sodium bicarbonate solution and dichloromethane were added and the layers separated. The aqueous layer was re-extracted with dichloromethane The layers were separated with the aid of a phase separator and the organics were concentrated in vacuo to give 2.8 mg of the desired product: high temperature (360 K) ¹H NMR (400 MHz, DMSO-d6) δ 8.07 (br s, 1H), 7.28-7.13 (m, 4H), 5.75 (s, 1H), 5.53 (s, 2H), 5.48-5.44 (m, 1H), 4.76 (dd, J=15.2, 5.8 Hz, 1H), 4.42-4.22 (m, 2H), 3.98 (dd, J=13.6, 4.9 Hz, 1H), 3.87 (d, J=11.8 Hz, 1H), 3.78-3.64 (m, 2H), 3.61-3.52 (m, 1H), 2.02 (s, 3H), 1.92 (s, 3H), 1.76 (dd, J=8.2, 4.2 Hz, 2H); ESI-MS m/z calc. 355.20, found 356.28 (M+1)⁺. Retention time: 0.53 minutes.

Example 43

Synthetic Scheme 43: (+/−)-3-[4-(2-amino-6-methyl-pyrimidin-4-yl)-1,4-oxazepan-3-yl]-4-chloro-benzonitrile. I-65

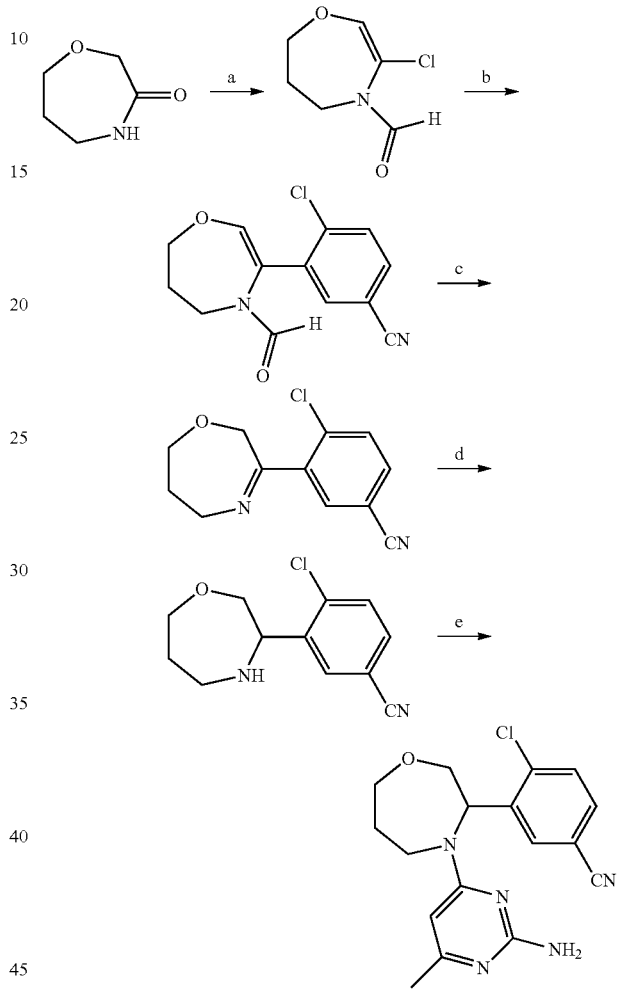

(a) DMF, POCl₃; (b) 2-chloro-5-cyanophenyl boronic acid, PdCl₂(PPh₃)₂, Et₃N, DMF, 70° C.; (c) nBuLi, 2-MeTHF, −78° C.; (d) NaBH₄, 2-MeTHF, MeOH; (e) 4-chloro-6-methyl-pyrimidin-2-amine, NMP, 160° C.

Formation of 3-chloro-6,7-dihydro-1,4-oxazepine-4 (5H)-carbaldehyde

A 3-neck 2 L round bottom flask equipped with an overhead stirrer, temperature probe, addition funnel, nitrogen inlet and reflux condenser was charged with DMF (150 mL, 1.94 mol) in dichloromethane (300 mL). The mixture was stirred for 5 minutes and then cooled to 0° C. POCl₃ (90 mL, 0.97 mol) in dichloromethane (100 mL) was added over 30 minutes while maintaining the internal temperature below 6° C. The reaction mixture was warmed to 40° C. and stirred at this temperature for 45 minutes. 1,4-oxazepan-3-one (50 g, 0.43 mol) in dichloromethane (300 mL) was added over 40 minutes, observed exotherm, maintained internal temperature ~40° C. The resulting reaction mixture was stirred at this temperature for 90 minutes at which time TLC (10% methanol in dichloromethane) and LCMS-analysis revealed consumption of the starting material, major peak RT=0.51 minutes (M+H)$^+$ 189/191 that corresponds to the amidine intermediate. Reaction mixture was cooled to ambient temperature, poured into crushed ice (1.2 L), and then allowed to warm to ambient temperature over 1 hour and stirred further for 1 hour. Separated the aqueous layer, basified with solid K$_2$CO$_3$ until pH 9, allowed to ambient temperature, stirred at this temperature for 12 hours. Reaction mixture was diluted with dichloromethane (300 mL) and the organic layer was separated. Aqueous layer was extracted with dichloromethane (2×100 mL). The combined organic extracts were dried over Na$_2$SO$_4$, filtered and concentrated under reduced pressure. The residue was purified by silica gel chromatography (330 g isco column linear gradient, 20 CV, 0%→50% ethyl acetate/heptane-which contained 1% Et$_3$N), to afford 3-chloro-6,7-dihydro-5H-1,4-oxazepine-4-carbaldehyde (40 g, 57%) as a clear colorless oil which contained traces of DMF.

Formation of 4-chloro-3-(4-formyl-4,5,6,7-tetrahydro-1,4-oxazepin-3-yl)benzonitrile Charged a 20 mL vial with pressure relief cap under nitrogen with (2-chloro-5-cyano-phenyl)boronic acid (2.98 g, 16.43 mmol), 3-chloro-6,7-dihydro-5H-1,4-oxazepine-4-carbaldehyde (2.00 g, 11.76 mmol), PdCl$_2$(PPh$_3$)$_2$ (0.40 g, 0.58 mmol), DMF (9 mL) and triethylamine (5.0 mL, 35.9 mmol). The mixture was heated at 70° C. overnight. Added water, brine and EtOAc and then separated layers. The aqueous layer was re-extracted with EtOAc and the combined organics were washed with water (×3), dried (MgSO$_4$), filtered and concentrated in vacuo. Purification by silica gel chromatography (120 g ISCO column; 0-100% EtOAc in heptane) to afford desired product as a pale green solid (1.5 g, 49%): $^1$H NMR (400 MHz, ACN) δ 7.85 (s, 1H), 7.77 (d, J=2.0 Hz, 1H), 7.68 (dd, J=8.3, 2.1 Hz, 1H), 7.60-7.57 (m, 1H), 6.19 (s, 1H), 4.28-4.24 (m, 2H), 4.00 (t, J=6.6 Hz, 2H), 2.11-2.05 (m, 2H); ESI-MS m/z calc. 262.05, found 263.08 (M+1)$^+$. Retention time: 0.74 minutes.

Formation of 4-chloro-3-(2,5,6,7-tetrahydro-1,4-oxazepin-3-yl)benzonitrile

To a solution of 4-chloro-3-(4-formyl-6,7-dihydro-5H-1,4-oxazepin-3-yl)benzonitrile (1.5 g, 5.7 mmol) in 2-MeTHF (23 mL) at −78° C. was added nBuLi (4.7 mL of 1.6 M, 7.5 mmol) under nitrogen atmosphere over 2 minutes. Added water and then removed cold bath. Extracted with dichloromethane, separated the layers with the aid of a phase separator. The aqueous layer was re-extracted with dichloromethane and the layers were separated through a phase separator again and the combined organics concentrated to afford desired product (1.34 g, 100%): ESI-MS m/z calc. 234.06, found 235.11 (M+1)$^+$. Retention time: 0.74 minutes.

Formation of (+/−)-4-chloro-3-(1,4-oxazepan-3-yl)benzonitrile and (+/−)-3-(1,4-oxazepan-3-yl)benzonitrile To a solution of 4-chloro-3-(2,5,6,7-tetrahydro-1,4-oxazepin-3-yl)benzonitrile (1.34 g, 5.71 mmol) in 2-MeTHF (15 mL) was added NaBH$_4$ (2.16 g, 57.10 mmol) at room temperature overnight. The reaction mixture was cooled in an ice bath and MeOH (5 mL) was added. After 10 minutes, the cold bath was removed and stirring continued at room temperature. The reaction was heated at 50° C. overnight. Water and excess solid K$_2$CO$_3$ were added and the mixture partially concentrated. Dichloromethane was added and stirring continued overnight. The layers were separated with the aid of a phase separator. The aqueous layer was re-extracted with dichloromethane and the layers were separated through a phase separator again and the combined organics concentrated in vacuo. The crude residue was purified via silica gel chromatography with a 40 g isco column using 0-100% EtOAc/heptane gradient followed by 0-30% MeOH/dichloromethane to afford 283 mg of the desired product as a pale yellow oil: $^1$H NMR (400 MHz, DMSO-d6) δ 8.01 (d, J=2.1 Hz, 1H), 7.75 (dt, J=6.2, 3.1 Hz, 1H), 7.64 (d, J=8.3 Hz, 1H), 4.26 (d, J=5.8 Hz, 1H), 3.84-3.78 (m, 2H), 3.71 (m, 1H), 3.33 (m, 1H), 3.08 (m, 1H), 2.92-2.83 (m, 1H) 1.86 (m, 2H); ESI-MS m/z calc. 236.07, found 237.14 (M+1)$^+$. Retention time: 0.52 minutes.

A side product, 3-(1,4-oxazepan-3-yl)benzonitrile was also isolated after re-purification of some of the fractions: 100 g ISCO c18-aq reverse phase column running with 0.1% TFA/H$_2$O and 0.1% TFA/CH$_3$CN and the pure fractions were concentrated in vacuo. The residue was dissolved in MeOH and passed through a SPE bicarbonate cartridge (Agilent Stratospheres 500 mg/6 mL) and concentrated to give 64 mg of the desired product as a colorless oil. $^1$H NMR (400 MHz, DMSO-d6) δ 7.81 (d, J=1.7 Hz, 1H), 7.72-7.67 (m, 2H), 7.51 (t, J=7.7 Hz, 1H), 3.93 (dd, J=9.0, 3.4 Hz, 1H), 3.85-3.79 (m, 2H), 3.69 (dd, J=12.4, 6.1 Hz, 1H), 3.35 (dd, J=12.2, 9.1 Hz, 1H), 3.08-3.01 (m, 1H), 2.87-2.79 (m, 1H), 1.85 (m, 2H); ESI-MS m/z calc. 202.11, found 203.14 (M+1)$^+$. Retention time: 0.5 minutes.

Formation of (+/−)-3-[4-(2-amino-6-methyl-pyrimidin-4-yl)-1,4-oxazepan-3-yl]-4-chloro-benzonitrile I-65

A mixture of 4-chloro-3-(1,4-oxazepan-3-yl)benzonitrile (0.078 g, 0.333 mmol) and 4-chloro-6-methyl-pyrimidin-2-amine (0.047 g, 0.330 mmol) in NMP (0.60 mL) was heated at 160° C. in a scintillation vial on a heating block. The mixture was cooled to room temperature and loaded directly onto a 50 g ISCO c18-aq column and purified by reverse phase running with 0.1% TFA/H$_2$O and 0.1% TFA/CH$_3$CN. The pure fractions were partially concentrated in vacuo. 1M NaOH was added and the mixture extracted with dichloromethane twice. The layers were separated with the aid of a phase separator and the organics concentrated in vacuo. Trituration with ether gave 64 mg of the desired product as a white solid: high temperature (360 K) $^1$H NMR (400 MHz, DMSO-d6) δ 7.72-7.61 (m, 3H), 5.69 (s, 1H), 5.55 (dd, J=9.9, 4.9 Hz, 1H), 5.41 (s, 2H), 4.46 (d, J=15.8 Hz, 1H), 4.08 (dd, J=13.5, 4.9 Hz, 1H), 3.92-3.85 (m, 1H), 3.84-3.72 (m, 2H), 3.61-3.53 (m, 1H), 2.03 (s, 3H), 1.83-1.75 (m, 2H); ESI-MS m/z calc. 343.12, found 344.17 (M+1)$^+$. Retention time: 0.59 minutes.

Example 44

Synthetic Scheme 44: (+/−)-4-[2-(2-methoxy-3-pyridyl)-5,5-dimethyl-azepan-1-yl]-6-methyl-pyrimidin-2-amine I-64

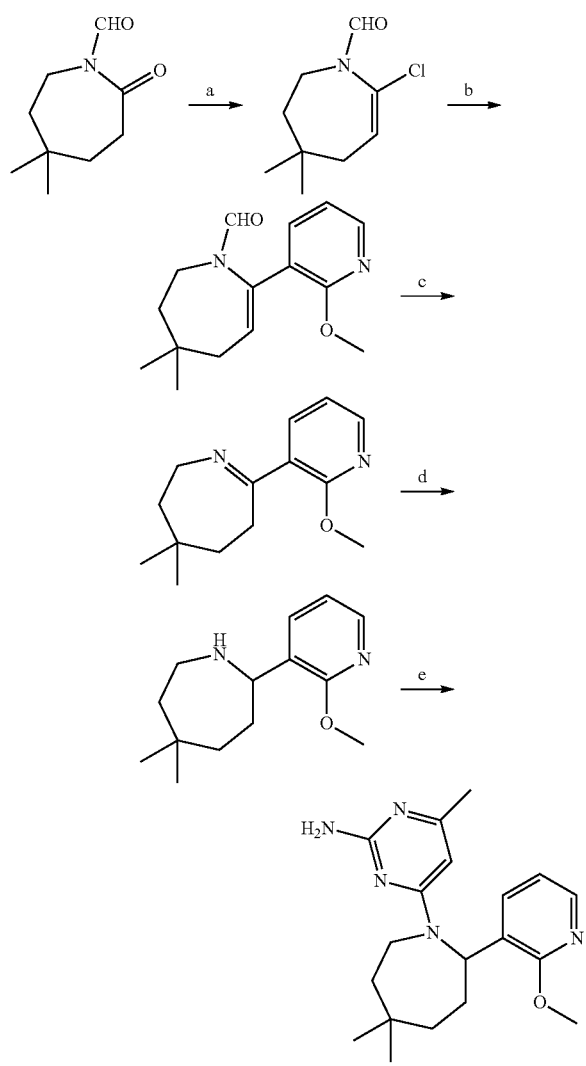

(a) POCl₃, CH₂Cl₂; (b) (2-methoxy-3-pyridyl)boronic acid, PdCl₂(PPh₃)₂, Et₃N, DMF; (c) n-BuLi, THF, −78° C.; (d) LiBH₄, THF; (e) 2-amino-4-chloro-6-methylpyrimidine, NMP, 150° C.

Formation of (+/−)-7-chloro-4,4-dimethyl-2,3,4,5-tetrahydro-1H-azepine-1-carbaldehyde A 250 mL round-bottomed flask with magnetic stirrer under nitrogen atmosphere was charged with DMF (8.2 mL, 106 mmol) in dichloromethane (15 mL) and cooled to 0° C. in an ice bath. POCl₃ (5 mL, 53.6 mmol) in dichloromethane (10 mL) was added over 5 minutes. Reaction mixture was warmed to 40° C. and stirred at this temperature for 30 minutes. 5,5-dimethylazepan-2-one (2.5 g, 17.7 mmol) in dichloromethane (20 mL) was added over 10 minutes. The resulting reaction mixture was stirred at this temperature for 4 hours. The reaction mixture was cooled to ambient temperature, poured into crushed ice (200 mL), and then allowed warm to ambient temperature over 1 h and stirred for a further 1 h. The aqueous layer was basified with solid K₂CO₃ until pH 9-10 and stirred at room temperature over the weekend. The reaction mixture was diluted with dichloromethane (200 mL) and the organic layer separated. The aqueous layer was extracted with dichloromethane. The combined organic extracts were washed with brine, separated through a phase separator and concentrated in vacuo. The residue was purified by silica gel chromatography using a 80 g isco column (0-40% EtOAc/CH₂Cl₂ gradient) to afford 1.56 grams of the desired product: ¹H NMR (400 MHz, DMSO-d6) δ 8.53-8.04 (m, 1H), 5.92-5.77 (m, 1H), 3.56-3.38 (m, 2H), 2.05-1.82 (m, 2H), 1.63-1.39 (m, 2H), 0.97-0.83 (m, 6H).

Formation of (+/−)-7-(2-methoxy-3-pyridyl)-4,4-dimethyl-3,5-dihydro-2H-azepine-1-carbaldehyde A mixture of (2-methoxy-3-pyridyl)boronic acid (0.86 g, 5.61 mmol), 7-chloro-4,4-dimethyl-3,5-dihydro-2H-azepine-1-carbaldehyde (0.74 g, 3.74 mmol), PdCl₂(PPh₃)₂ (128 mg, 0.182 mmol), DMF (8 mL), NEt₃ (2 mL, 14.4 mmol) was heated in a 20 mL vial with pressure relief cap under nitrogen at 70° C. for 2 h. Water and EtOAc were added and the layers separated. The aqueous layer was re-extracted with EtOAc and the combined organics were washed with water then brine, dried (sodium sulfate), filtered and concentrated in vacuo. Purification by silica gel chromatography (40 g GOLD column; 0-75% EtOAc in heptane) gave 750 mg of the desired product as a brown oil: ¹H NMR (400 MHz, CD₃CN) δ 8.14 (dd, J=5.0, 1.9 Hz, 1H), 7.88 (s, 1H), 7.61 (dd, J=7.4, 1.9 Hz, 1H), 6.97 (dd, J=7.3, 5.0 Hz, 1H), 5.92 (t, J=7.1 Hz, 1H), 3.74-3.68 (m, 2H), 2.17 (m, 2H), 1.67-1.63 (m, 2H), 1.01 (s, 6H). ESI-MS m/z calc. 260.15, found 261.18 (M+1)⁺. Retention time: 0.85 minutes.

Formation of 7-(2-methoxy-3-pyridyl)-4,4-dimethyl-2,3,5,6-tetrahydroazepine

To a solution of 7-(2-methoxy-3-pyridyl)-4,4-dimethyl-3,5-dihydro-2H-azepine-1-carbaldehyde (0.75 g, 2.88 mmol) in THF (5 mL) at −78° C. was added under nitrogen n-BuLi (2.3 mL of 1.6 M solution, 3.68 mmol). After 15 minutes, added an additional 1 mL n-BuLi. After 5 minutes, the reaction was quenched with water and warmed to room temperature. Brine was added and the mixture extracted with dichloromethane. Concentration in vacuo afforded 669 mg of the desired product as a brown oil: ESI-MS m/z calc. 232.16, found 233.17 (M+1)⁺. Retention time: 0.57 minutes.

Formation of 2-(2-methoxy-3-pyridyl)-5,5-dimethyl-azepane

To a solution of 7-(2-methoxy-3-pyridyl)-4,4-dimethyl-2,3,5,6-tetrahydroazepine (300 mg, 1.29 mmol) in THF (3 mL) was added LiBH₄ (250 mg, 11.5 mmol) at RT and the mixture stirred overnight. 1M HCl (1 mL) was added and the mixture extracted with DCM twice. The layers were separated with the aid of a phase separator and the organics concentrated to give 72 mg of the desired product as a pale yellow oil: ¹H NMR (400 MHz, DMSO) δ 7.99 (dd, J=4.9, 1.9 Hz, 1H), 7.82-7.77 (m, 1H), 6.93 (dd, J=7.3, 4.9 Hz, 1H), 4.00 (dd, J=8.1, 3.5 Hz, 1H), 3.86 (s, 3H), 2.85-2.78 (m, 1H), 2.75-2.65 (m, 1H), 1.74 (ddd, J=10.4, 7.8, 3.9 Hz, 1H), 1.52-1.38 (m, 5H), 0.92 (s, 3H), 0.91 (s, 3H). ESI-MS m/z calc. 234.17, found 235.2 (M+1)⁺. Retention time: 0.57 minutes.

Formation of 4-[2-(2-methoxy-3-pyridyl)-5,5-dimethyl-azepan-1-yl]-6-methyl-pyrimidin-2-amine A mixture of 2-(2-methoxy-3-pyridyl)-5,5-dimethyl-azepane (0.21 g, 0.88 mmol) and 4-chloro-6-methyl-pyrimidin-2-amine (0.11 g, 0.77 mmol) in NMP (1.3 mL) was heated in microwave at 175° C. for 30 minutes. Purification was carried out on a reverse phase 50 g ISCO c18-aq column, running with 0.1% TFA/H₂O and 0.1% TFA/CH₃CN. The pure fractions were partially concentrated, some 1M NaOH added and extracted with dichloromethane twice. The layers were separated with the aid of a phase separator and the organics concentrated in vacuo to afford 18 mg of the desired product as a yellow solid: ¹H NMR (400 MHz, DMSO) δ 8.00 (dd, J=4.9, 1.8 Hz, 1H), 7.38-7.32 (m, 1H), 6.86 (dd, J=7.3, 4.9 Hz, 1H), 5.58 (s, 1H), 5.38 (s, 2H), 5.12 (s, 1H), 4.16 (s, 1H), 3.96 (s, 3H), 3.43-3.32 (m, 1H), 2.22-2.12 (m, 1H), 1.99 (s, 3H), 1.80 (m, 1H), 1.54-1.23 (m, 4H), 0.96 (s, 3H), 0.90 (s, 3H); ESI-MS m/z calc. 341.22, found 342.23 (M+1)⁺. Retention time: 0.67 minutes.

Example 45

Synthetic Scheme 45: (+/−)-[3-[1-(2-amino-6-methyl-pyrimidin-4-yl)azepan-2-yl]-2-pyridyl] methanol I-57

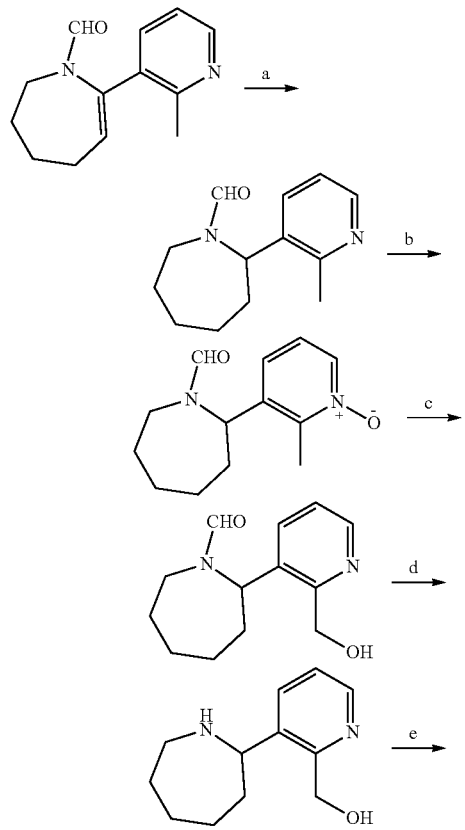

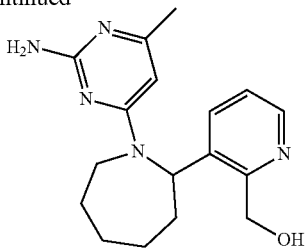

(a) H₂, 10% Pd/C, MeOH, EtOAc, AcOH; (b) mCPBA, DCM; (c) TFAA, DCM then aq. Na₂CO₃; (d) conc. HCl, 100° C.; (e) 2-amino-4-chloro-6-methylpyrimidine, NMP, 150° C.

Formation of (+/−)-2-(2-methyl-3-pyridyl)azepane-1-carbaldehyde

A mixture of 7-(2-methyl-3-pyridyl)-2,3,4,5-tetrahydroazepine-1-carbaldehyde (1.60 g, 7.40 mmol), Pd/C (10% Degussa wet type, 400 mg), MeOH (10 mL), EtOAc (10 mL) and AcOH (2 mL) was stirred under an atmosphere of hydrogen gas. After 2 hours, the reaction mixture was filtered through Celite with the aid of MeOH and then concentrated in vacuo to give 1.61 g of the desired product as a pale yellow oil: ¹H NMR (400 MHz, DMSO-d6) δ 8.27 (dd, J=4.8, 1.7 Hz, 1H), 8.15 (s, 1H), 7.95 (s, 1H), 7.15 (dd, J=7.8, 4.7 Hz, 1H), 5.01 (dd, J=12.8, 4.7 Hz, 1H), 3.87 (dd, J=15.0, 4.9 Hz, 1H), 3.59 (dd, J=14.8, 10.2 Hz, 1H), 2.89 (s, 3H), 2.12-2.02 (m, 1H), 2.00-1.92 (m, 1H), 1.82-1.61 (m, 2H), 1.37-1.28 (m, 4H). ESI-MS m/z calc. 218.14, found 219.17 (M+1)⁺. Retention time: 0.49 minutes.

Formation of (+/−)-2-(2-methyl-3-pyridyl)azepane-1-carbaldehyde

To a solution of 2-(2-methyl-3-pyridyl)azepane-1-carbaldehyde (1.61 g, 7.38 mmol) in dichloromethane (20 mL) was added mCPBA (2.54 g, 14.80 mmol) and the mixture stirred overnight at room temperature. The white solid was filtered off washing with some dichloromethane. To the filtrate was added sat. aq. sodium bicarbonate carefully. The organics were washed a second time with sat. aq. sodium bicarbonate. The layers were separated with the aid of a phase separator and the organics concentrated in vacuo to give 600 mg of the desired product as a yellow oil: ¹H NMR (400 MHz, DMSO-d6) δ 8.18 (s, 1H), 8.15 (d, J=6.0 Hz, 1H), 7.22-7.17 (m, 1H), 7.08 (d, J=7.9 Hz, 1H), 5.04-4.95 (m, 1H), 3.89 (dd, J=15.1, 5.3 Hz, 1H), 3.61-3.51 (m, 1H), 2.45 (s, 3H), 2.11-1.83 (m, 2H), 1.82-1.59 (m, 2H), 1.32 (d, J=5.8 Hz, 4H); ESI-MS m/z calc. 234.14, found 235.16 (M+1)⁺. Retention time: 0.53 minutes.

Formation of (+/−)-2-[2-(hydroxymethyl)-3-pyridyl] azepane-1-carbaldehyde

To a solution of 2-(2-methyl-1-oxido-pyridin-1-ium-3-yl) azepane-1-carbaldehyde (0.60 g, 2.56 mmol) in dichloromethane (15 mL) was added TFAA (0.36 mL, 2.59 mmol) at room temperature. After 7 hours, sat aq. Na₂CO₃ was added carefully and stirring continued overnight. Water was added and dichloromethane. The layers were separated with the aid of a phase separator. The aqueous layer was re-extracted with dichloromethane and the layers were separated through a phase separator again and the combined organics concentrated in vacuo. The crude residue was purified via silica gel chromatography with 12 g isco GOLD column using 0-12.5% MeOH/dichloromethane to afford 324 mg of the desired product as a brown solid: ¹H NMR (400 MHz, DMSO) δ 8.36 (dd, J=4.7, 1.6 Hz, 1H), 8.11 (s, 1H), 7.68 (dd, J=7.8, 1.6 Hz, 1H), 7.27 (dd, J=7.8, 4.7 Hz, 1H), 5.16 (dd, J=7.0, 4.0 Hz, 1H), 4.91 (dd, J=12.4, 7.0 Hz, 1H), 4.64 (dd, J=12.4, 3.9 Hz, 1H), 3.84 (dd, J=14.9, 4.5 Hz, 1H), 3.66 (dd, J=15.0, 10.2 Hz, 1H), 2.21-2.11 (m, 1H), 1.97-1.70 (m, 3H), 1.38-1.22 (m, 4H); ESI-MS m/z calc. 234.14, found 235.2 (M+1)⁺. Retention time: 0.48 minutes.

Formation of (+/−)-[3-(azepan-2-yl)-2-pyridyl]methanol

A mixture of 2-[2-(hydroxymethyl)-3-pyridyl]azepane-1-carbaldehyde (0.28 g, 1.20 mmol) and HCl (1.5 mL of 38% w/v, 15.6 mmol) was heated at 100° C. overnight. Purification was carried out on a reverse phase 50 g ISCO c18-aq column, running with 0.1% TFA/H₂O and 0.1% TFA/CH₃CN. The pure fractions were concentrated in vacuo and then dissolved in MeOH and passed through a SPE bicarbonate cartridge (Agilent Stratospheres 5 g/60 mL) and concentrated to give 150 mg of the desired product as an orange oil: ¹H NMR (400 MHz, DMSO) δ 8.35 (dd, J=4.7, 1.7 Hz, 1H), 7.83 (dd, J=7.8, 1.6 Hz, 1H), 7.27 (dd, J=7.8, 4.7 Hz, 1H), 4.62 (dd, J=28.7, 12.7 Hz, 2H), 4.00 (dd, J=9.4, 3.5 Hz, 1H), 2.95 (dd, J=11.6, 6.6 Hz, 1H), 2.77-2.69 (m, 1H), 1.87 (ddd, J=13.9, 6.6, 3.2 Hz, 1H), 1.80-1.72 (m, 1H), 1.72-1.45 (m, 6H); ESI-MS m/z calc. 206.14, found 207.19 (M+1)⁺. Retention time: 0.25 minutes.

Formation of (+/−)-[3-[1-(2-amino-6-methyl-pyrimidin-4-yl)azepan-2-yl]-2-pyridyl]methanol A mixture of [3-(azepan-2-yl)-2-pyridyl]methanol (0.15 g, 0.72 mmol) and 4-chloro-6-methyl-pyrimidin-2-amine (0.09 g, 0.66 mmol) was stirred in NMP (1 mL) at 170° C. in a scintillation vial for 3 h. Purification was carried out on a reverse phase 50 g ISCO c18-aq column, running with 0.1% TFA/H₂O and 0.1% TFA/CH₃CN. The pure fractions were concentrated in vacuo and then HCl (2 mL of 2 M, 4.00 mmol) and MeCN (5 mL) were added and concentrated in vacuo again to give 119 mg of the desired product as an off white solid: ¹H NMR (400 MHz, D₂O) δ 8.55 (d, J=5.8 Hz, 1H), 8.33 (d, J=8.1 Hz, 1H), 7.86-7.79 (m, 1H), 6.35 (s, 1H), 5.46-5.36 (m, 2H), 5.14-5.07 (m, 1H), 4.08 (dd, J=15.5, 4.5 Hz, 1H), 3.83 (d, J=15.7, 10.8 Hz, 1H), 2.25 (s, 3H), 2.22-2.12 (m, 1H), 2.05-1.77 (m, 4H), 1.60-1.25 (m, 3H); ESI-MS m/z calc. 313.19, found 314.23 (M+1)⁺. Retention time: 0.49 minutes.

Example 46

Synthetic Scheme 46: (+/−)-4-(3-(2-fluorophenyl)-6,6-dimethyl-1,4-oxazepan-4-yl)-6-methylpyrimidin-2-amine I-49

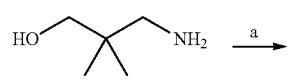

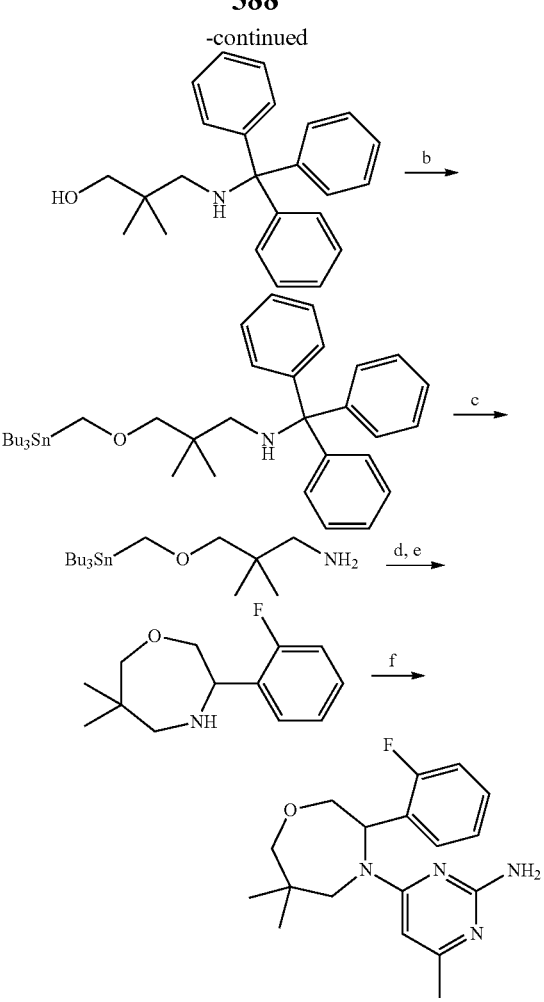

(a) trityl chloride, Et₃N, CH₂Cl₂; (b) NaH, DMF, tributyl (iodomethyl)stannane; (c) 2,2,2-trifluoroethanol, AcOH, CH₂Cl₂; (d) 2-fluorobenzaldehyde; 4 A mol sieves, CH₂Cl₂; (e) 2,6-lutidine, Cu(OTf)₂, hexafluoroisopropanol, CH₂Cl₂; (f) 2-amino-4-chloro-6-methylpyrimidine, NMP, 150° C.

Formation of 2,2-dimethyl-3-(tritylamino)propan-1-ol

To a solution of 3-amino-2,2-dimethyl-propan-1-ol (5.1 g, 49.2 mmol) and triethylamine (13.5 mL, 96.9 mmol) in CH₂Cl₂ (50 mL) at 0° C. was added dropwise a solution of trityl chloride (13.6 g, 48.8 mmol) in CH₂Cl₂ (50 mL). The reaction mixture was stirred for 48 hours with gradual warming to room temperature. The reaction mixture was washed with 50 mL water and the organic layer was extracted with 50 mL CH₂Cl₂. The combined organic phases were concentrated to dryness and purified via silica gel chromatography eluting with 0-25% EtOAc/heptanes. Pure fractions were combined and concentrated in vacuo to give 14.4 g (85%) of the desired product as a colorless oil: ¹H NMR (400 MHz, CDCl₃) δ 7.47-7.42 (m, 6H), 7.36-7.29 (m, 6H), 7.27-7.21 (m, 3H), 3.63 (s, 2H), 2.17 (s, 2H), 0.89 (s, 6H); ESI-MS m/z calc. 345.21, found 346.0 (M+1)⁺. Retention time: 0.82 minutes.

Formation of 2,2-dimethyl-3-((tributylstannyl)methoxy)-N-tritylpropan-1-amine

Sodium hydride (1.0 g, 26.0 mmol, 60% in mineral oil) was washed with heptane under nitrogen then suspended in anhydrous DMF (85 mL) and cooled to 0° C. A solution of 2,2-dimethyl-3-(tritylamino)propan-1-ol (6.0 g, 17.4 mmol) in DMF (85 mL) was added dropwise over 15 minutes and then the reaction was warmed to room temperature and stirred for 1 hour. The mixture was cooled again to 0° C. and then tributyl(iodomethyl)stannane (8.2 g, 19.0 mmol) was added dropwise. The reaction was stirred at 0° C. with gradual warming to room temperature over 4 hours. The reaction was quenched at 0° C. by slow addition of 85 mL aqueous saturated ammonium chloride solution. The layers were separated, and the organic layer was washed with water. The organic layer was concentrated, dissolved in 500 mL MTBE and washed 3×150 mL water. The organic layer was concentrated to dryness, dry loaded onto Celite, and purified via silica gel chromatography eluting with 0-35% EtOAc in heptane. Pure fractions were combined and concentrated to give 4.55 g (40%) of product as a light yellow oil: $^1$H NMR (400 MHz, CDCl$_3$) δ 7.58-7.54 (m, 7H), 7.32 (dd, J=8.4, 6.9 Hz, 7H), 7.25-7.18 (m, 3H), 3.71 (s, 2H), 3.17 (s, 2H), 2.04 (d, J=7.8 Hz, 2H), 1.85 (t, J=8.0 Hz, 1H), 1.58-1.49 (m, 5H), 1.38-1.30 (m, 10H), 0.98-0.93 (m, 18H); ESI-MS m/z calc. 649.34, found 649.0 (M+1)$^+$. Retention time: 0.95 minutes.

Formation of 2,2-dimethyl-3-((tributylstannyl) methoxy)propan-1-amine 2,2-dimethyl-3-((tributylstannyl)methoxy)-N-tritylpropan-1-amine (4.55 g, 7.02 mmol) was dissolved in dichloromethane (150 mL), 2,2,2-trifluoroethanol (43 mL), and acetic acid (22 mL) and stirred overnight at room temperature. The reaction was neutralized by portion-wise addition of saturated aqueous sodium bicarbonate solution over 90 minutes. The organic layer was removed and the aqueous layer was extracted three times with dichloromethane. The combined organic phases were dried over magnesium sulfate, filtered, and concentrated in vacuo to give 4.7 g of a light yellow oil containing a white ppt. The crude product was purified via silica gel chromatography eluting with 0-5% MeOH/dichloromethane containing 0.1% triethylamine. Pure fractions were combined and concentrated to give 1.21 g (42%) of product as a colorless oil: $^1$H NMR (400 MHz, CDCl$_3$) δ 3.68 (s, 2H), 3.08 (s, 2H), 2.52 (s, 2H), 1.60-1.45 (m, 6H), 1.36-1.28 (m, 6H), 0.95-0.87 (m, 15H), 0.86 (s, 6H); ESI-MS m/z calc. 407.22, found 408.0 (M+1)$^+$. Retention time: 0.76 minutes.

Formation of (+/−)-3-(2-fluorophenyl)-6,6-dimethyl-1,4-oxazepane

To a solution of 2,2-dimethyl-3-((tributylstannyl) methoxy)propan-1-amine (1.21 g, 2.979 mmol) in anhydrous dichloromethane (8 mL) was added 2-fluorobenzaldehyde (0.33 mL, 2.25 mmol) followed by 4 A molecular sieves (0.32 g). The hazy colorless mixture was stirred at room temperature for 2 hours then filtered over Celite. The filter pad was rinsed with 55 mL dichloromethane and the filtrate was stored under nitrogen. In a separate 250 mL round bottom flask containing hexafluoroisopropanol (15 mL) under nitrogen was added anhydrous 2,6-lutidine (0.35 mL, 3.02 mmol) followed by Cu(OTf)$_2$ (0.19 g, 2.99 mmol). The mixture was stirred at room temperature for 1 hour, then the imine solution prepared above was added. The reaction mixture was stirred overnight at room temperature and quenched with 75 mL of a 2:1 mixture of aqueous saturated sodium bicarbonate solution and 10% ammonium hydroxide. The mixture was stirred for 15 minutes and then separated. The aqueous layer was extracted 2×75 mL dichloromethane. The combined organics were washed with brine, dried over magnesium sulfate, filtered and concentrated in vacuo. The crude material was purified via silica gel chromatography eluting with 0-8% MeOH in dichloromethane. Pure fractions were combined and concentrated to give 90 mg (13%) of the desired product: $^1$H NMR (400 MHz, CDCl$_3$) δ 7.51 (td, J=7.5, 1.8 Hz, 1H), 7.30-7.20 (m, 1H), 7.14 (td, J=7.5, 1.3 Hz, 1H), 7.02 (ddd, J=10.5, 8.1, 1.3 Hz, 1H), 4.31 (dd, J=9.9, 4.4 Hz, 1H), 4.05 (ddd, J=12.0, 4.4, 0.7 Hz, 1H), 3.62 (d, J=12.1 Hz, 1H), 3.50-3.41 (m, 2H), 2.86 (d, J=13.7 Hz, 1H), 2.77 (d, J=13.7 Hz, 1H), 0.98 (s, 6H). ESI-MS m/z calc. 223.14, found 224.0 (M+1)$^+$. Retention time: 0.56 minutes.

Formation of (+/−)-4-(3-(2-fluorophenyl)-6,6-dimethyl-1,4-oxazepan-4-yl)-6-methylpyrimidin-2-amine I-49

A mixture of 3-(2-fluorophenyl)-6,6-dimethyl-1,4-oxazepane (0.09 g, 0.38 mmol) and 4-chloro-6-methyl-pyrimidin-2-amine (0.06 g, 0.38 mmol) in NMP (1.2 mL) was heated at 150° C. for 150 minutes in a sealed tube. The reaction mixture was purified via reverse phase chromatography eluting with 5-50% MeCN in water with 0.1% TFA. Pure fractions were combined, neutralized using sodium bicarbonate solution, and extracted with EtOAc. The organic layer was dried over magnesium sulfate, filtered, concentrated in vacuo, and lyophilized to give 12 mg (9%) of the desired product: $^1$H NMR (400 MHz, DMSO-d6) (heated 360K) δ 7.30-7.18 (m, 2H), 7.18-7.07 (m, 2H), 5.73 (s, 1H), 5.61 (s, 2H), 5.47-5.35 (m, 1H), 4.57 (d, J=14.9 Hz, 1H), 4.13-4.03 (m, 1H), 3.71 (dd, J=13.4, 11.0 Hz, 1H), 3.53-3.38 (m, 2H), 3.31-3.21 (m, 1H), 2.00 (s, 3H), 0.89 (d, J=8.1 Hz, 6H); ESI-MS m/z calc. 330.18, found 331.0 (M+1)$^+$. Retention time: 0.74 minutes.

Example 47

Synthetic Scheme 47: (+/−)-3-(4-(2-amino-6-methylpyrimidin-4-yl)-1,4-oxazepan-3-yl)-4-methoxy-N-methylbenzamide I-82

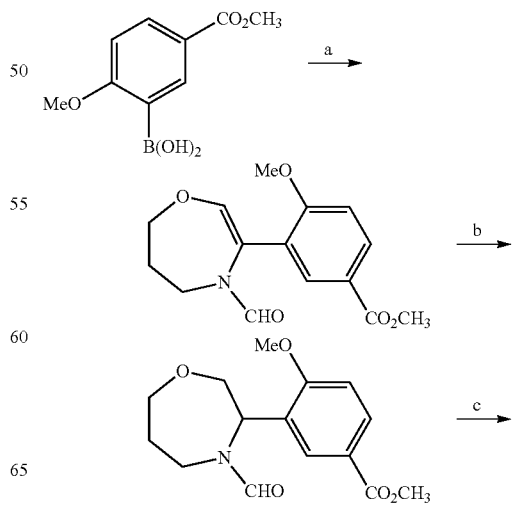

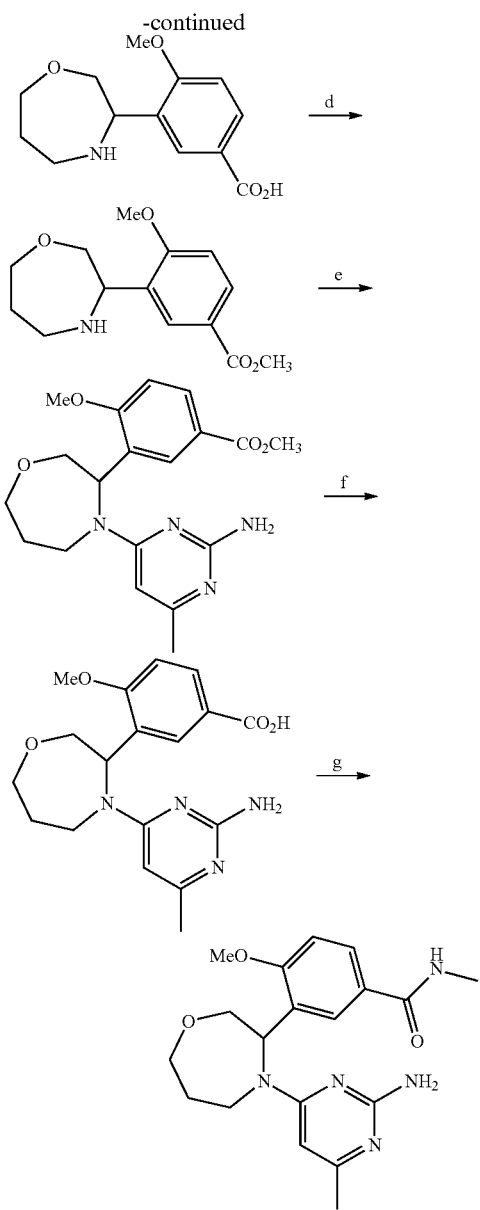

(a) 3-chloro-6,7-dihydro-5H-1,4-oxazepine-4-carbaldehyde), PdCl₂(dppf), DMF, NaHCO₃, H₂O, 80° C., microwave irradiation; (b) H₂, Pd/C, MeOH-EtOAc; (c) HCl, MeOH, 100° C.; (d) diazomethyl(trimethyl)silane, toluene, MeOH; (e) 2-amino-4-chloro-6-methylpyrimidine, NMP, 150° C.; (f) LiOH, MeOH, H₂O; (g) MeNH₂, HATU, Et₃N, DMF.

Formation of methyl 3-(4-formyl-4,5,6,7-tetrahydro-1,4-oxazepin-3-yl)-4-methoxybenzoate A mixture of 3-chloro-6,7-dihydro-5H-1,4-oxazepine-4-carbaldehyde (2.0 g, 12.4 mmol), (2-methoxy-5-methoxycarbonyl-phenyl)boronic acid (2.6 g, 12.4 mmol), and PdCl₂(dppf) (1.0 g, 1.3 mmol) in DMF (37 mL) and aqueous saturated sodium bicarbonate (12 mL) was heated in microwave reactor at 80° C. for 30 minutes. The reaction mixture was diluted with water, washed with water, and then the organic phase was concentrated to dryness. The resulting residue was purified via silica gel chromatography eluting with 40-100% EtOAc in heptanes followed by a 10% MeOH in dichloromethane flush. Fractions containing the desired product were combined and concentrated in vacuo to afford 2.4 g (63%) of the desired product as a colorless oil: $^1$H NMR (400 MHz, CDCl₃) δ 8.04 (dd, J=8.6, 2.2 Hz, 1H), 7.95 (s, 1H), 7.92 (d, J=2.2 Hz, 1H), 6.90 (d, J=8.6 Hz, 1H), 6.19 (s, 1H), 4.24 (dd, J=6.3, 5.3 Hz, 2H), 4.06 (t, J=6.6 Hz, 2H), 3.92 (s, 3H), 3.87 (s, 3H), 2.18-2.09 (m, 2H); ESI-MS m/z calc. 291.11, found 290.0 (M+1)⁺. Retention time: 0.9 minutes.

Formation of (+/−)-methyl 3-(4-formyl-1,4-oxazepan-3-yl)-4-methoxybenzoate

A mixture of methyl 3-(4-formyl-4,5,6,7-tetrahydro-1,4-oxazepin-3-yl)-4-methoxybenzoate (2.4 g, 8.2 mmol) and Pd/C (1.5 g, 0.7 mmol) in ethyl acetate (25 mL) and MeOH (25 mL) was shaken overnight under 55 psi hydrogen. The reaction mixture was filtered over Celite and the resulting filtrated was concentrated to dryness. The resulting residue was purified via silica gel chromatography eluting with 40-100% EtOAc in heptanes. Several mixed fractions containing the desired product were carried onto the next step as is: ESI-MS m/z calc. 293.13, found 294.0 (M+1)⁺. Retention time: 0.77 minutes.

Formation of (+/−)-4-methoxy-3-(1,4-oxazepan-3-yl)benzoic acid hydrochloride

A solution of methyl 3-(4-formyl-1,4-oxazepan-3-yl)-4-methoxybenzoate (2.4 g, 8.2 mmol) in MeOH (40 mL) and concentrated HCl (40 mL of 12.1 M solution, 484.0 mmol) was stirred overnight at 100° C. The mixture was concentrated to dryness. The product was taken up in MeOH and diluted into diethyl ether, then filtered and dried to give 2.2 g (84%) of a white solid: $^1$H NMR (400 MHz, DMSO-d6) δ 8.12 (d, J=2.1 Hz, 1H), 7.98 (ddd, J=8.7, 3.3, 2.1 Hz, 1H), 7.18 (d, J=8.7 Hz, 1H), 4.77-4.55 (m, 1H), 4.00 (dd, J=13.5, 8.9 Hz, 1H), 3.93 (d, J=1.9 Hz, 3H), 3.91-3.85 (m, 2H), 3.49-3.41 (m, 2H), 3.26 (ddd, J=13.4, 9.4, 3.4 Hz, 1H), 2.83 (ddt, J=47.7, 12.7, 7.3 Hz, 0.5H), 2.31-2.05 (m, 1H), 2.05-1.75 (m, 0.5H); ESI-MS m/z calc. 251.12, found 252.0 (M+1)⁺. Retention time: 0.5 minutes.

Formation of (+/−)-methyl 4-methoxy-3-(1,4-oxazepan-3-yl)benzoate

To a solution of 4-methoxy-3-(1,4-oxazepan-3-yl)benzoic acid hydrochloride (0.53 g, 1.65 mmol) in toluene (22 mL) and MeOH (2.5 mL) was added diazomethyl(trimethyl)silane (0.84 mL of 2 M solution, 1.69 mmol) in hexanes. The mixture was stirred for 15 minutes then concentrated to dryness to afford 487 mg of a colorless oil: ESI-MS m/z calc. 265.13, found 266.0 (M+1)⁺. Retention time: 0.57 minutes.

Formation of (+/−)-methyl 3-(4-(2-amino-6-methylpyrimidin-4-yl)-1,4-oxazepan-3-yl)-4-methoxybenzoate A mixture of methyl 4-methoxy-3-(1,4-oxazepan-3-yl)benzoate (0.44 g, 1.65 mmol) and 4-chloro-6-methyl-pyrimidin-2-amine (0.26 g, 1.82 mmol) in NMP (5.5 mL) was stirred for 4 hours at 150° C. in a sealed tube. The mixture was diluted with water and extracted with EtOAc. The organic layer was concentrated to dryness and the resulting residue was purified via silica gel chromatography eluting with 0-12% MeOH in dichloromethane. Pure fractions were combined and concentrated in vacuo to give 89 mg (14%) of the desired product: $^1$H NMR (400 MHz, DMSO-d6) (heated 360K) δ 7.89 (dd, J=8.6, 2.2 Hz, 1H), 7.70 (d, J=2.2 Hz, 1H), 7.16 (d, J=8.7 Hz, 1H), 6.60 (s, 2H), 5.89 (s, 1H), 5.57 (s, 1H), 4.60 (d, J=14.7 Hz, 1H), 4.19 (dd, J=13.4, 5.2 Hz, 1H), 3.95 (s, 3H), 3.90 (dt, J=12.0, 3.8 Hz, 1H), 3.79 (s, 3H), 3.77-3.68 (m, 1H), 3.63-3.54 (m, 1H), 2.14 (s, 3H), 1.80 (dt, J=7.7, 4.2 Hz, 2H). ESI-MS m/z calc. 372.18, found 373.0 (M+1)$^+$. Retention time: 0.66 minutes.

Formation of (+/−)-3-(4-(2-amino-6-methylpyrimidin-4-yl)-1,4-oxazepan-3-yl)-4-methoxybenzoic acid trifluoroacetate salt To a solution of methyl 3-(4-(2-amino-6-methylpyrimidin-4-yl)-1,4-oxazepan-3-yl)-4-methoxybenzoate (0.090 g, 0.230 mmol) in MeOH (1 mL) and water (1 mL) was added LiOH (0.025 g, 1.044 mmol). The reaction mixture was stirred at room temperature for 3 hours, acidified with 1 M HCl and the mixture was purified by reverse phase chromatography eluting with 10-90% MeCN in water with 0.1% TFA. Pure fractions were combined, concentrated, and lyophilized to give 50 mg (58%) of the desired product: $^1$H NMR (400 MHz, DMSO-d6) (heated 360K) δ 7.92 (dd, J=8.6, 2.1 Hz, 1H), 7.72 (s, 1H), 7.41 (s, 2H), 7.17 (d, J=8.6 Hz, 1H), 4.24 (s, 1H), 3.99-3.90 (m, 4H), 3.80 (t, J=7.1 Hz, 2H), 3.64 (dt, J=12.2, 7.4 Hz, 1H), 2.33-1.65 (m, 6H); ESI-MS m/z calc. 358.16, found 359.0 (M+1)$^+$. Retention time: 0.6 minutes.

Formation of (+/−)-3-(4-(2-amino-6-methylpyrimidin-4-yl)-1,4-oxazepan-3-yl)-4-methoxy-N-methylbenzamide I-82

To a solution of 3-[4-(2-amino-6-methyl-pyrimidin-4-yl)-1,4-oxazepan-3-yl]-4-chloro-benzoic acid (Trifluoroacetate salt) (0.085 g, 0.180 mmol) in DMF (1 mL) was added HATU (0.102 g, 0.268 mmol) followed by Et$_3$N (0.125 mL, 0.897 mmol). After stirring for 10 minutes, methylamine (0.700 mL of 2 M, 1.40 mmol) in THF was added and the reaction was stirred overnight. The reaction mixture was diluted with water and extracted with EtOAc. The organic layer was concentrated to dryness and purified via silica gel chromatography eluting with 0-10% MeOH in dichloromethane. Pure fractions were combined, concentrated in vacuo to afford the desired product: $^1$H NMR (400 MHz, DMSO-d6) (heated 360K) δ 7.90 (s, 1H), 7.68 (dd, J=8.5, 2.3 Hz, 1H), 7.50 (d, J=2.2 Hz, 1H), 7.04 (d, J=8.6 Hz, 1H), 5.71 (d, J=27.7 Hz, 3H), 5.25 (s, 1H), 4.43 (s, 1H), 3.92 (s, 3H), 3.45 (dd, J=14.5, 11.2 Hz, 1H), 2.74 (d, J=4.6 Hz, 3H), 2.34 (dt, J=14.0, 6.9 Hz, 1H), 2.03 (s, 3H), 1.97-1.62 (m, 2H), 1.52 (q, J=12.5 Hz, 1H), 1.43-1.21 (m, 2H); ESI-MS m/z calc. 369.22, found 370.0 (M+1)$^+$. Retention time: 0.68 minutes.

The following analogs were prepared according to Synthetic Scheme 47:

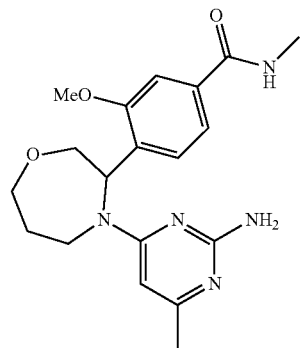 [SMILES: CNC(=O)c1ccc(C2COCCCN2c2cc(C)nc(N)n2)c(OC)c1]

(+/−)-4-(4-(2-amino-6-methylpyrimidin-4-yl)-1,4-oxazepan-3-yl)-3-methoxy-N-methylbenzamide I-83

$^1$H NMR (400 MHz, DMSO-d6) (heated 360K) δ 8.12 (s, 1H), 7.49 (d, J=1.6 Hz, 1H), 7.40 (dd, J=7.9, 1.6 Hz, 1H), 7.23 (d, J=7.9 Hz, 1H), 7.02 (s, 2H), 6.05 (s, 1H), 5.61 (s, 1H), 4.62 (s, 1H), 4.24 (dd, J=13.4, 5.2 Hz, 1H), 3.95 (s, 4H), 3.81 (dt, J=13.4, 7.9 Hz, 2H), 3.60 (ddd, J=12.1, 9.4, 5.1 Hz, 1H), 2.82 (d, J=4.5 Hz, 3H), 2.22 (s, 3H), 1.91-1.74 (m, 2H); ESI-MS m/z calc. 371.20, found 372.0 (M+1)$^+$. Retention time: 0.55 minutes.

Example 48

Synthetic Scheme 48: (+/−)-4-(4-(2-amino-6-methylpyrimidin-4-yl)-1,4-oxazepan-3-yl)indolin-2-one I-105

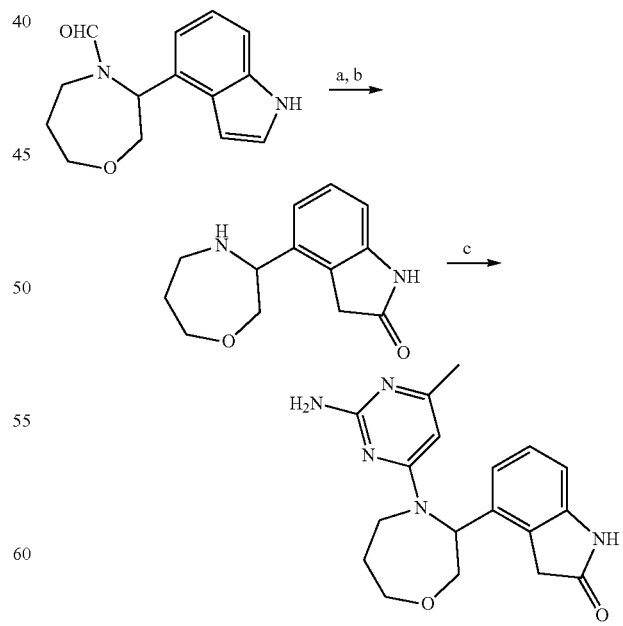

(a) NBS, t-BuOH, CH$_2$Cl$_2$; (b) aq. HCl (4M), dioxane, 110° C.; (c) 2-amino-4-chloro-6-methylpyrimidine, NMP, 150° C.

Formation of (+/−)-4-(1,4-oxazepan-3-yl)indolin-2-one

To a suspension of 3-(1H-indol-4-yl)-1,4-oxazepane-4-carbaldehyde (0.22 g, 0.91 mmol) in tBuOH (5 mL) was added NBS (0.18 g, 1.00 mmol) at room temperature. After 2 hours, dichloromethane (5 mL) was added to aid solubility. After 1 hour, additional NBS (0.08 g) was added. After another 1 hour, aqueous saturated sodium bicarbonate solution was added and the mixture extracted with twice with dichloromethane. The combined organics were washed with water and then the layers were separated with the aid of a phase separator and the organics concentrated. The brown residue was dissolved in dioxane (4 mL) and aq. HCl (4 mL, 4M) was added and the mixture was heated in microwave reactor for 10 min at 100° C. and then an additional 30 min at 110° C. The reaction was partially concentrated and then purified by column chromatography (C18 AQ 50 g column; 0.1% TFA-water/0.1% TFA-MeCN). The pure fractions were concentrated and then dissolved in MeOH and passed through a SPE bicarbonate cartridge (Agilent Stratospheres 5 g/60 mL) and concentrated to give 72 mg of the desired product. $^1$H NMR (400 MHz, DMSO) δ 10.32 (s, 1H), 7.12 (t, J=7.7 Hz, 1H), 6.96 (d, J=7.7 Hz, 1H), 6.69 (d, J=7.6 Hz, 1H), 3.89-3.65 (m, 4H), 3.51 (s, 2H), 3.35 (m, 2H), 3.08 (dt, J=13.3, 5.0 Hz, 1H), 2.80 (dt, J=13.9, 7.1 Hz, 1H), 1.91-1.78 (m, 2H); ESI-MS m/z calc. 232.12, found 233.26 (M+1)$^+$. Retention time: 0.46 minutes.

Formation of (+/−)-4-[4-(2-amino-6-methyl-pyrimidin-4-yl)-1,4-oxazepan-3-yl]indolin-2-one I-105

A mixture of 4-(1,4-oxazepan-3-yl)indolin-2-one (0.07 g, 0.30 mmol) and 4-chloro-6-methyl-pyrimidin-2-amine (0.04 g, 0.28 mmol) was heated in NMP (1.5 mL) at 150° C. overnight in a reaction vial equipped with a pressure relief cap. The mixture was cooled to room temperature and loaded directly onto a 50 g ISCO c18-aq column and purified by reverse phase running with 0.1% TFA/H$_2$O and 0.1% TFA/CH$_3$CN. The pure fractions were concentrated in vacuo and then dissolved in MeOH and passed through a SPE bicarbonate cartridge (Agilent Stratospheres 500 mg/6 mL) and concentrated to give 74.1 mg of the desired product: high temperature (360 K) $^1$H NMR (400 MHz, DMSO-d6) δ 9.97 (s, 1H), 7.03 (t, J=7.7 Hz, 1H), 6.77 (d, J=8.0 Hz, 1H), 6.62 (d, J=7.7 Hz, 1H), 5.62 (s, 1H), 5.57 (s, 1H), 5.39 (s, 2H), 5.30 (s, 1H), 4.28 (s, 1H), 3.98 (dd, J=13.4, 5.1 Hz, 1H), 3.74 (dd, J=13.5, 9.6 Hz, 2H), 3.45 (t, J=15.5 Hz, 3H), 3.24 (d, J=22.5 Hz, 1H), 1.95 (s, 3H), 1.66 (m, 2H); ESI-MS m/z calc. 339.17, found 340.25 (M+1)$^+$. Retention time: 0.51 minutes.

Example 49

Synthetic Scheme 49: (+/−)-4-(9-(2-fluorophenyl)-1,4-dioxa-8-azaspiro[4.6]undecan-8-yl)-6-methylpyrimidin-2-amine and (+/−)-1-(2-amino-6-methylpyrimidin-4-yl)-7-(2-fluorophenyl)azepan-4-one

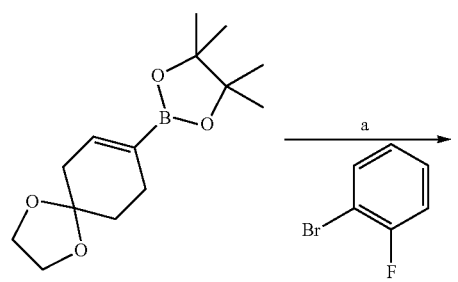

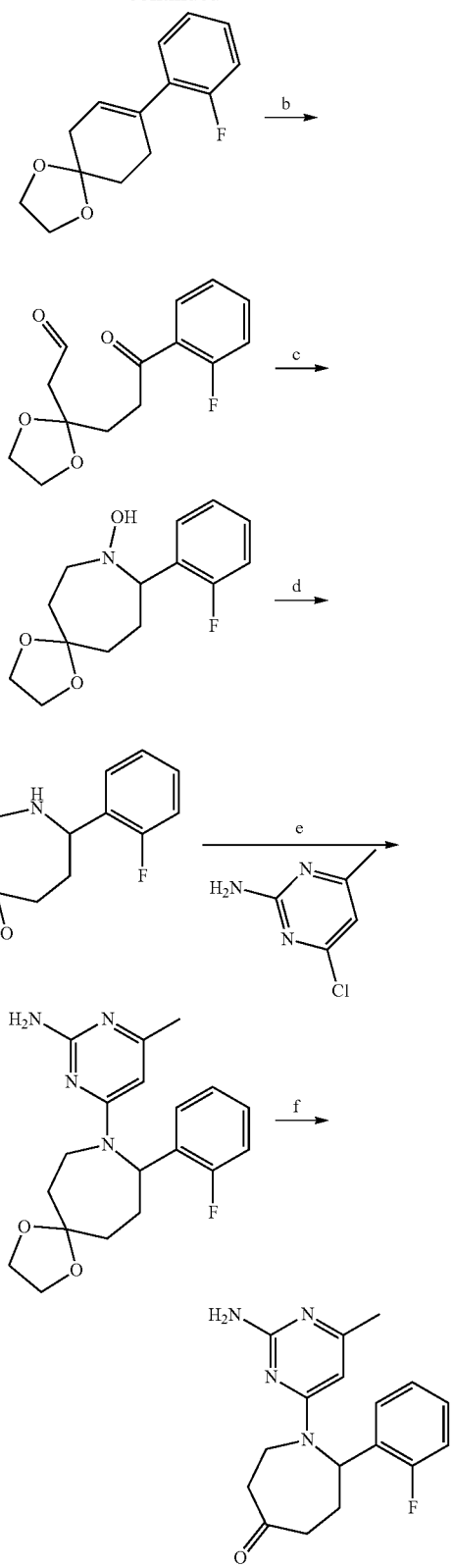

(a) PdCl$_2$(dppf), aq NaHCO$_3$, DME, 80° C.; (b) ozone, CH$_2$Cl$_2$, −78° C., then Ph$_3$P; (c) NH$_2$OH—HCl, NaCNBH$_3$, MeOH; (d) H$_2$, Pd/C, MeOH; (e) EtOH, 180° C.; (f) HCl, acetone, 50° C.

Formation of 8-(2-fluorophenyl)-1,4-dioxaspiro[4.5]dec-7-ene

To a solution of 1-bromo-2-fluoro-benzene (0.98 g, 5.64 mmol) and 2-(1,4-dioxaspiro[4.5]dec-7-en-8-yl)-4,4,5,5-tetramethyl-1,3,2-dioxaborolane (1.50 g, 5.64 mmol) in DME (20 mL) was added NaHCO₃ (9.4 mL of 1.2 M aq solution, 11.27 mmol), and PdCl₂(dppf) (0.43 g, 0.52 mmol) under a nitrogen atmosphere. The mixture was heated at 80° C. for 20 hours. The reaction mixture was filtered through a pad of celite and concentrated in vacuo. The resulting residue was purified by silica gel chromatography (40 g ISCO column) eluting with heptanes/EtOAc (0% to 40% gradient) to afford 1.0 g (76%) of the desired product: ¹H NMR (300 MHz, CDCl₃) δ 7.34-7.16 (m, 2H), 7.14-6.90 (m, 2H), 5.87 (qd, J=2.2, 0.7 Hz, 1H), 4.05 (s, 4H), 2.66 (tdd, J=5.5, 2.6, 1.5 Hz, 2H), 2.55-2.43 (m, 2H), 1.99-1.86 (m, 2H).

Formation of 2-(2-(3-(2-fluorophenyl)-3-oxopropyl)-1,3-dioxolan-2-yl)acetaldehyde To a solution of 8-(2-fluorophenyl)-1,4-dioxaspiro[4.5]dec-7-ene (1.00 g, 4.27 mmol) in dichloromethane (30 mL) was bubbled ozone at −78° C. until the solution remained blue. The ozone generator was turned off and air was bubbled through the mixture for 30 minutes. Triphenylphosphine (1.12 g, 4.27 mmol) was then added and the mixture was warmed up to room temperature and stirred for 12 hours. The crude product was purified by silica gel chromatography (40 g ISCO column) eluting with EtOAc/heptanes. The desired fractions were collected and evaporated to afford the desired product: ¹H NMR (300 MHz, CDCl₃) δ 9.77 (t, J=2.9 Hz, 1H), 7.86 (td, J=7.6, 1.9 Hz, 1H), 7.53 (dddd, J=8.3, 7.1, 5.0, 1.9 Hz, 1H), 7.32-7.21 (m, 1H), 7.15 (ddd, J=11.3, 8.3, 1.1 Hz, 1H), 4.03 (d, J=0.8 Hz, 3H), 3.10 (ddd, J=7.6, 6.8, 2.9 Hz, 2H), 2.74 (d, J=2.9 Hz, 2H), 2.23 (ddd, J=8.1, 6.9, 0.9 Hz, 2H).

Formation of 9-(2-fluorophenyl)-1,4-dioxa-8-azaspiro[4.6]undecan-8-ol

To a solution of 2-[2-[3-(2-fluorophenyl)-3-oxo-propyl]-1,3-dioxolan-2-yl]acetaldehyde (1.00 g, 3.76 mmol) in MeOH (20 mL) was added hydroxylamine hydrochloride (0.26 g, 3.76 mmol) and NaHCO₃. The mixture was stirred at room temperature for 30 minutes before sodium cyanoborohydride (1.18 g, 18.78 mmol) was added. The reaction was stirred at room temperature over night. The mixture was quenched by adding of ethylene diamine. The solvent was evaporated and the residue was purified by silica gel chromatography (40 g ISCO column) eluting with EtOAc/heptanes. The desired fractions were collected and evaporated. The desired product was used without further purification.

Formation of (+/−)-9-(2-fluorophenyl)-1,4-dioxa-8-azaspiro[4.6]undecane

To a solution of 9-(2-fluorophenyl)-1,4-dioxa-8-azaspiro[4.6]undecan-8-ol (0.20 g, 0.75 mmol) in MeOH (15 mL) was added 10% Pd/C under nitrogen atmosphere. The flask was charged with a hydrogen balloon and flushed with vacuum and hydrogen three times. The reaction was stirred at room temperature under an atmosphere of nitrogen over night. The mixture was filtered through celite and the filtrate was concentrated in vacuo. The desired product was used without further purification.

Formation of (+/−)-4-[8-(2-fluorophenyl)-1,4-dioxa-9-azaspiro[4.6]undecan-9-yl]-6-methyl-pyrimidin-2-amine I-53

To a mixture of solids 4-chloro-6-methyl-pyrimidin-2-amine (0.14 g, 0.95 mmol) and 8-(2-fluorophenyl)-1,4-dioxa-9-azaspiro[4.6]undecane (0.24 g, 0.95 mmol) in a vial was added EtOH (2 mL). The vial was placed on the hot plate and heated at 180° C. without cover for 2 hours. The crude solid was purified by silica gel chromatography (40 g ISCO column) eluting with DCM, 20% MeOH/DCM. The desired fractions were collected and evaporated to afford 260.0 mg (72%) of the desired product: ¹H NMR (300 MHz, DMSO-d6) δ 7.39-7.10 (m, 4H), 6.90 (s, 2H), 5.80 (m, 1H), 4.74-4.38 (m, 1H), 3.89 (m, 4H), 3.35 (m, 2H), 2.33-1.51 (m, 9H); ESI-MS m/z calc. 358.18, found 359.21 (M+1)⁺. Retention time: 0.66 minutes.

Formation of (+/−)-1-(2-amino-6-methyl-pyrimidin-4-yl)-7-(2-fluorophenyl)azepan-4-one I-56

To a solution of 4-[8-(2-fluorophenyl)-1,4-dioxa-9-azaspiro[4.6]undecan-9-yl]-6-methyl-pyrimidin-2-amine (0.22 g, 0.59 mmol) in acetone (10 mL) was added aq HCl (10 mL of 6 M, 59.47 mmol) at room temperature. The mixture was heated at 50° C. for 3 hours. The solvent was evaporated and the residue was purified by silica chromatography (40 g ISCO column) eluting with DCM, 10% MeOH/DCM. The desired fractions were collected and evaporated to afford 57 mg (28%) of the desired product: ¹H NMR (300 MHz, DMSO-d6) δ 7.31 (m, 1H), 7.26-7.06 (m, 3H), 5.93 (s, 2H), 5.77 (br, 1H), 4.43 (br, 1H), 3.74 (t, J=13.3 Hz, 1H), 3.35 (d, J=24.5 Hz, 2H), 2.83-2.68 (m, 1H), 2.54 (m, 2H), 2.36-2.21 (m, 2H), 2.04 (s, 3H); ESI-MS m/z calc. 314.15, found 315.26 (M+1)⁺. Retention time: 0.61 minutes.

Example 50

Synthetic Scheme 50: (+/−)-4-(3-(1H-indol-4-yl)-1,4-oxazepan-4-yl)-6-methylpyrimidin-2-amine

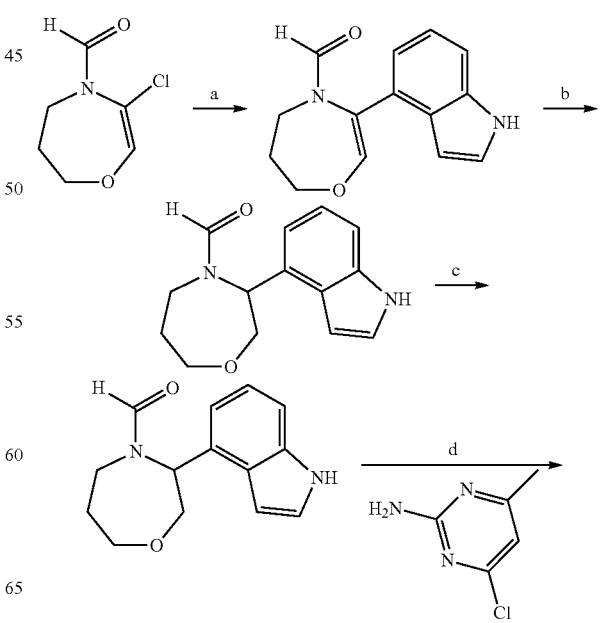

-continued

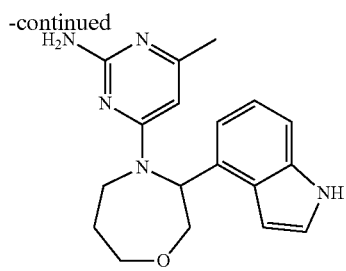

(a) 1H-indol-4-ylboronic acid, Pd(Ph₃P)₂Cl₂, Et₃N, DMF, 70° C.; (b) H2, Pd/C, MeOH; (c) nBuLi, THF; (d) 2-amino-4-chloro-6-methylpyrimidine, NMP, 140° C.

Formation of 3-(1H-indol-4-yl)-6,7-dihydro-1,4-oxazepine-4(5H)-carbaldehyde

Charged a 40 mL vial with pressure relief cap under nitrogen with 3-chloro-6,7-dihydro-5H-1,4-oxazepine-4-carbaldehyde (3.4 g, 20.0 mmol), 1H-indol-4-ylboronic acid (3.2 g, 20.0 mmol), PdCl₂(PPh₃)₂ (0.55 g, 0.78 mmol) and triethylamine (11 mL, 79 mmol) in DMF (16 mL) and bubbled nitrogen through the mixture for 10 minutes. The reaction mixture was heated at 70° C. overnight. The mixture was diluted into water and EtOAc and filtered off the dark solids. Added brine to the filtrate and then separated the layers. The aqueous layer was re-extracted with EtOAc and the combined organics were concentrated in vacuo. Purification by silica gel chromatography (120 g column; 20-100% EtOAc in heptane) gave the mostly pure desired product that was used without further purification.

Formation of (+/−)-3-(1H-indol-4-yl)-1,4-oxazepane-4-carbaldehyde

A mixture of 3-(1H-indol-4-yl)-6,7-dihydro-5H-1,4-oxazepine-4-carbaldehyde (4.8 g, 19.8 mmol) and Pd/C (10 wt % Degussa, 1.6 g) in MeOH (30 mL) was shaken under an atmosphere of hydrogen gas overnight in the Parr hydrogenator at 55 psi H₂. Filtered the reaction mixture through Florisil with the aid of MeOH and then on concentration, a white solid precipitated. 1.05 g. Discarded filtrate. Isolated solid afforded 1.05 g (22%—2 steps) of the desired product: ¹H NMR (400 MHz, DMSO-d6) δ (rotameric @ RT) 11.13 (s, 1H), 8.26 (s, 1H), 7.35-7.33 (m, 1H), 7.29 (d, J=8.1 Hz, 1H), 7.05-6.99 (m, 1H), 6.85 (d, J=7.3 Hz, 1H), 6.54-6.47 (m, 1H), 5.62 (dd, J=10.5, 5.1 Hz, 1H), 4.32 (dd, J=13.4, 5.7 Hz, 1H), 4.00-3.91 (m, 2H), 3.72 (m, 2H), 3.57-3.49 (m, 1H), 1.78-1.67 (m, 2H). ESI-MS m/z calc. 244.12, found 245.2 (M+1)⁺. Retention time: 0.62 minutes.

Formation of (+/−)-3-(1H-indol-4-yl)-1,4-oxazepane

To a solution of 3-(1H-indol-4-yl)-1,4-oxazepane-4-carbaldehyde (0.11 g, 0.44 mmol) in THF (10 mL) was added nBuLi (0.82 mL of 1.6 M solution, 1.30 mmol). The reaction was done at room temperature because of insolubility issues at colder temperatures. After 30 minutes, the mixture was diluted into water and extracted with dichloromethane. The aqueous phase was extracted again with dichloromethane. The combined organic phases were separated through a phase separator and concentrated in vacuo to afford 90 mg (95%) of the desired product as a pale yellow foam: ¹H NMR (400 MHz, DMSO-d6) δ 11.06 (s, 1H), 7.32-7.29 (m, 1H), 7.29-7.24 (m, 1H), 7.05-6.99 (m, 2H), 6.55 (ddd, J=3.0, 2.0, 0.9 Hz, 1H), 4.19 (dd, J=9.7, 3.3 Hz, 1H), 3.96-3.81 (m, 2H), 3.75 (dt, J=12.0, 6.7 Hz, 1H), 3.43 (dd, J=11.9, 9.7 Hz, 1H), 3.16 (dt, J=13.3, 5.0 Hz, 1H), 2.93-2.81 (m, 1H), 1.89 (td, J=11.8, 6.4 Hz, 2H); ESI-MS m/z calc. 216.13, found 217.19 (M+1)⁺. Retention time: 0.49 minutes.

Formation of (+/−)-4-(3-(1H-indol-4-yl)-1,4-oxazepan-4-yl)-6-methylpyrimidin-2-amine I-142

A mixture of 3-(1H-indol-4-yl)-1,4-oxazepane (0.09 g, 0.42 mmol) and 4-chloro-6-methyl-pyrimidin-2-amine (0.06 g, 0.40 mmol) was heated in NMP (1.5 mL) at 140° C. in a vial equipped with a pressure relief cap overnight. The crude reaction was loaded directly onto a C18 AQ 50 g ISCO column and purified by reverse phase chromatography eluting with 0.1% TFA/MeCN and 0.1% TFA/water. The pure fractions were partially concentrated, some 1M NaOH added and extracted with dichloromethane twice and concentrated in vacuo. Added ether and concentrated in vacuo to afford 79 mg (54%) of the desired product as a white solid: (heated 360K) ¹H NMR (400 MHz, DMSO-d6) δ 10.86 (br s, 1H), 7.34-7.24 (m, 2H), 7.06-6.97 (m, 1H), 6.90 (d, J=7.2 Hz, 1H), 6.52 (s, 1H), 5.69 (s, 1H), 5.64 (s, 1H), 5.45 (s, 2H), 4.53 (s, 1H), 4.23 (dd, J=13.3, 5.2 Hz, 1H), 3.94-3.80 (m, 2H), 3.57 (ddd, J=29.7, 18.9, 8.2 Hz, 2H), 1.94 (s, 2H), 1.87 (s, 1H), 1.73 (d, J=15.0 Hz, 1H); ESI-MS m/z calc. 323.17, found 324.27 (M+1)⁺. Retention time: 0.56 minutes.

The following analogs were prepared:

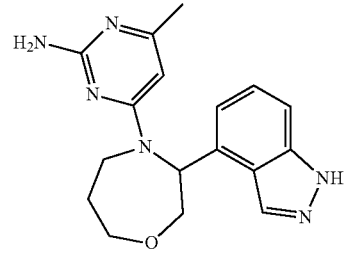 [SMILES: Cc1cc(N2CCCOCC2c2cccc3[nH]ncc23)nc(N)n1]

(+/−)-4-(3-(1H-indazol-4-yl)-1,4-oxazepan-4-yl)-6-methylpyrimidin-2-amine I-112 high temperature (360 K) ¹H NMR (400 MHz, DMSO-d6) δ 12.83 (s, 1H), 8.07 (s, 1H), 7.41 (d, J=8.4 Hz, 1H), 7.30-7.24 (m, 1H), 7.01 (d, J=7.1 Hz, 1H), 5.91 (s, 1H), 5.72 (s, 1H), 5.47 (s, 2H), 4.34 (s, 1H), 4.27 (dd, J=13.2, 5.3 Hz, 1H), 3.96 (dd, J=13.2, 8.8 Hz, 1H), 3.84 (m, 1H), 3.67-3.58 (m, 1H), 3.55-3.45 (m, 1H), 1.99 (s, 3H), 1.91 (m, 1H), 1.75 (m, 1H); ESI-MS m/z calc. 324.17, found 325.26 (M+1)⁺. Retention time: 0.52 minutes.

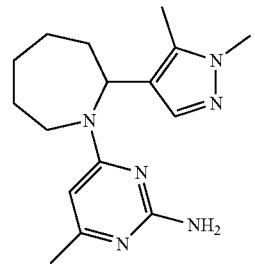 [SMILES: Cc1cc(N2CCCCCC2c2cnn(C)c2C)nc(N)n1]

(+/−)-4-[2-(1,5-dimethylpyrazol-4-yl)azepan-1-yl]-6-methyl-pyrimidin-2-amine I-48 high temperature (360 K) $^1$H NMR (400 MHz, DMSO-d6) δ 7.36 (s, 1H), 6.22 (s, 1H), 6.13 (d, J=15.9 Hz, 1H), 5.81 (dt, J=15.9, 6.8 Hz, 1H), 5.59 (s, 1H), 5.33 (s, 2H), 3.66 (s, 3H), 3.20 (dd, J=11.5, 5.8 Hz, 2H), 2.19 (s, 3H), 2.18-2.10 (m, 2H), 2.00 (s, 3H), 1.54 (dt, J=13.7, 6.9 Hz, 2H), 1.49-1.40 (m, 2H); ESI-MS m/z calc. 300.21, found 301.26 (M+1)$^+$. Retention time: 0.55 minutes.

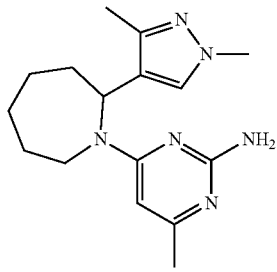 [SMILES: Cc1cc(N2CCCCCC2c2cn(C)nc2C)nc(N)n1]

(+/−)-4-[2-(1,3-dimethylpyrazol-4-yl)azepan-1-yl]-6-methyl-pyrimidin-2-amine I-39 high temperature (360 K) $^1$H NMR (400 MHz, DMSO-d6) δ 7.50 (s, 1H), 6.22 (s, 1H), 6.13 (d, J=16.0 Hz, 1H), 5.81-5.73 (m, 1H), 5.59 (s, 1H), 5.33 (s, 2H), 3.68 (s, 3H), 3.23-3.16 (m, 2H), 2.26-2.12 (m, 3H), 2.00 (s, 3H), 1.79-1.14 (m, 8H); ESI-MS m/z calc. 300.21, found 301.26 (M+1)$^+$. Retention time: 0.54 minutes.

Example 51

Synthetic Scheme 51: 4-(3-(5-amino-2-chloro-4-fluorophenyl)-1,4-oxazepan-4-yl)-6-methylpyrimidin-2-amine

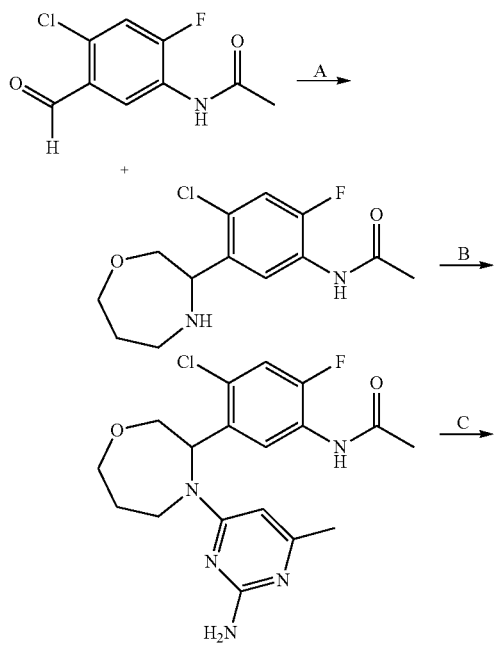

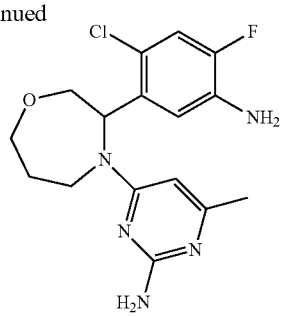

(a) 3-(tributylstannylmethoxy)propan-1-amine, Cu(OTf)$_2$, 2,6-lutidine, CH$_2$Cl$_2$; (b) nBuOH, μω 170° C., 45 mins; C. HCl, MeOH, reflux

Formation of N-[4-chloro-2-fluoro-5-(1,4-oxazepan-3-yl)phenyl]acetamide

To a solution of N-(4-chloro-2-fluoro-5-formyl-phenyl)acetamide (0.66 g, 3.06 mmol) in CH$_2$Cl$_2$ (20 mL) was added the amino tributylstannane—SnAP reagent 3-(tributyl stannylmethoxy) propan-1-amine (1.20 g, 3.17 mmol) (1.00 equiv) and Molecular sieves (0.9 g). The reaction mixture was stirred at room temperature for 2 h and filtered through a short layer of Celite (CH$_2$Cl$_2$ rinse). The filtrate was used directly Separately, to a solution of 2,6-lutidine (440 μL, 3.798 mmol) in HFIP (15 mL) (4 mL/mmol, dried over anhydrous MgSO$_4$) was added Cu(OTf)$_2$ (1.35 g, 3.73 mmol) (1.20 equiv, preheated at 110° C. for 1 h under high vacuum)) and stirred at room temperature for 1 h, during which a homogeneous suspension was formed with some white solid still existing.

A solution of the imine in CH$_2$Cl$_2$ (40 mL) (160 ml, 16 mL/mmol total) was added in one portion and the resulting mixture was stirred at room temperature for 12 h and became clear homogenous solution. The reaction was quenched at room temperature with a mixture of aqueous saturated NaHCO$_3$ solution (40 mL) and 10% aq. NH$_4$OH (20 mL), and stirred vigorously for 15 min. The layers were separated and the aqueous layer was extracted with CH$_2$Cl$_2$ (3×50 mL). The combined organic layers were washed with H$_2$O (3×5 mL) and brine (10 mL), dried over Na$_2$SO$_4$, filtered, and concentrated in vacuo. Purification by silica gel chromatography on Teledyne ISCO (MeOH/CH$_2$Cl$_2$ 0-8% in 20 mins) afforded 435 mg of desired product as a yellow liquid, then turned solid under vacuum (50%): $^1$H NMR (300 MHz, CDCl$_3$) δ 8.39 (d, J=8.6 Hz, 1H), 7.67 (s, 1H), 7.06 (d, J=10.4 Hz, 1H), 4.34 (dd, J=9.3, 3.4 Hz, 1H), 4.02-3.87 (m, 2H), 3.79 (ddd, J=12.3, 6.7, 5.9 Hz, 1H), 3.40 (dd, J=12.4, 9.3 Hz, 1H), 3.21 (dt, J=13.7, 5.0 Hz, 1H), 3.01 (ddd, J=13.6, 8.2, 5.4 Hz, 1H), 2.51 (s, 2H), 2.18 (s, 3H), 2.07-1.82 (m, 2H); ESI-MS m/z calc. 286.09, found 287.09 (M+1)$^+$. Retention time: 0.53 minutes.

Formation of N-[5-[4-(2-amino-6-methyl-pyrimidin-4-yl)-1,4-oxazepan-3-yl]-4-chloro-2-fluoro-phenyl]acetamide I-85

4-Chloro-6-methyl-pyrimidin-2-amine (0.11 g, 0.77 mmol) and N-[4-chloro-2-fluoro-5-(1,4-oxazepan-3-yl)phenyl]acetamide (0.20 g, 0.70 mmol) in nBuOH (5 mL) were irradiated in microwave at 170° C. for 45 minutes. nBuOH was removed under vacuum and the crude residue was purified by silica gel chromatography: 12 g ISCO column, eluting with 0-10% MeOH in CH$_2$Cl$_2$ to afford 186 mg of desired product as yellow solid. NMR showed two rotamers. (67%): $^1$H NMR (300 MHz, CDCl$_3$) δ 8.36 (d, J=8.2 Hz, 1H), 7.51 (s, 1H), 7.18 (dd, J=19.2, 10.3 Hz, 1H), 6.02-5.77 (m, 1H), 5.28-5.09 (m, 1H), 4.28 (dt, J=13.7, 5.1 Hz, 1H), 4.20-3.95 (m, 2H), 3.84-3.49 (m, 4H), 2.42-2.27 (m, 3H), 2.22 (d, J=0.9 Hz, 3H), 2.03-1.82 (m, 2H); ESI-MS m/z calc. 393.14, found 394.09 (M+1)$^+$. Retention time: 0.59 minutes.

Formation of 4-[3-(5-amino-2-chloro-4-fluoro-phenyl)-1,4-oxazepan-4-yl]-6-methyl-pyrimidin-2-amine I-269

To a solution of N-[5-[4-(2-amino-6-methyl-pyrimidin-4-yl)-1,4-oxazepan-3-yl]-4-chloro-2-fluoro-phenyl]acetamide (0.065 g, 0.162 mmol) in methanol (0.25 mL) was added HCl (1 mL of 2 M, 2.000 mmol). The solution was heated to 100° C. until LCMS indicated no more starting amine (2 h). Majority of solvent was removed under vacuum and remaining solution was neutralized with aqueous saturated NaHCO$_3$ solution. The aqueous phase was then extracted with CH$_2$Cl$_2$ (3×5 mL). The combined organic layers were dried (MgSO$_4$), filtered and concentrated in vacuo to afford 42 mg of desired product as a yellow solid (73%): $^1$H NMR (300 MHz, CDCl$_3$) δ 7.06 (d, J=10.4 Hz, 1H), 6.65 (d, J=9.0 Hz, 1H), 5.53 (s, 4H), 4.30 (dd, J=13.7, 5.0 Hz, 1H), 4.17-4.01 (m, 1H), 3.82 (d, J=14.4 Hz, 2H), 3.71-3.51 (m, 3H), 3.50 (s, 1H), 2.21 (s, 3H), 2.04-1.75 (m, 2H); ESI-MS m/z calc. 351.13, found 352.15 (M+1)$^+$. Retention time: 0.61 minutes.

Example 52

Synthetic Scheme 52: (+/−)-4-(3-(2-chlorothiophen-3-yl)-1,4-oxazepan-4-yl)-6-methylpyrimidin-2-amine I-163

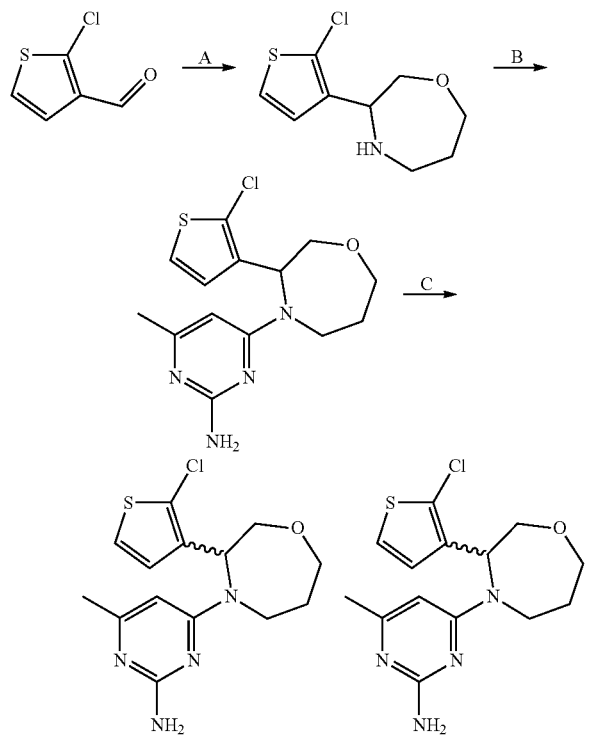

(a) 3-(tributylstannylmethoxy)propan-1-amine, Cu(OTf)$_2$, 2,6-lutidine, CH$_2$Cl$_2$, HFIP; (b) nBuOH, μω 170° C., 45 mins; (c) chiral HPLC separation Formation of 3-(2-chlorothiophen-3-yl)-1,4-oxazepane To a solution of 3-(tributylstannylmethoxy)propan-1-amine (SnAP reagent) (13.0 g, 34.4 mmol) in CH$_2$Cl$_2$ (170 mL) at room temperature was added 2-chlorothiophene-3-carbaldehyde (5.0 g, 34.1 mmol) and Molecular sieves (5.0 g). The reaction mixture was stirred at room temperature for 2 hours and filtered through a short layer of Celite (CH$_2$Cl$_2$ rinse). The filtrate was concentrated under reduced pressure to afford the imine (contain 10% aldehyde SM, δ, 9.96). $^1$H NMR (300 MHz, CDCl$_3$) δ 8.26 (s, 1H), 7.31 (t, J=6.7 Hz, 1H), 7.08-6.92 (m, 1H), 3.65 (s, 2H), 3.58 (t, J=6.9 Hz, 2H), 3.31 (t, J=6.2 Hz, 2H), 1.85 (p, J=6.5 Hz, 2H), 1.44 (qd, J=9.0, 8.0, 6.1 Hz, 6H), 1.23 (h, J=7.1 Hz, 8H), 0.82 (td, J=8.0, 7.3, 3.7 Hz, 15H).

Separately, to a solution of 2,6-lutidine (4.8 mL, 41.4 mmol) in hexafluoroisopropanol (150 mL) was added Cu(OTf)$_2$ (bis(trifluoromethylsulfonyloxy)copper) (15.0 g, 41.5 mmol) and stirred at room temperature for 1 hour, during which a mostly homogeneous suspension was formed with some white solid still existing. A solution of the imine in CH$_2$Cl$_2$ (500 mL) was added in one portion and the resulting mixture was stirred at room temperature for 12 hours. The reaction was quenched at room temperature with a mixture of aqueous saturated NaHCO$_3$ (60 mL) and 10% aq NH$_4$OH (40 mL), and stirred vigorously for 15 min. The layers were separated and the aqueous layer was extracted with CH$_2$Cl$_2$ (3×50 mL). The combined organic layers were washed with H$_2$O (3×5 mL) and brine (10 mL), dried over Na$_2$SO$_4$, filtered, and concentrated in vacuo. Purification by silica gel column chromatography (MeOH/CH$_2$Cl$_2$ 0-10% gradient) afforded 2.4 grams of the desired product as light brown liquid (32%); ESI-MS m/z calc. 217.03, found 215.13 (M+1)$^+$. Retention time: 0.36 minutes.

Formation of 4-[3-(2-chloro-3-thienyl)-1,4-oxazepan-4-yl]-6-methyl-pyrimidin-2-amine A mixture of 4-chloro-6-methyl-pyrimidin-2-amine (0.21 g, 1.46 mmol) and 3-(2-chloro-3-thienyl)-1,4-oxazepane (0.32 g, 1.41 mmol) in n-butanol (3 mL) was irradiated in a microwave for 1 hour in a sealed tube at 170° C. The mixture was concentrated to dryness and purified via silica gel chromatography eluting with 0-10% MeOH/CH$_2$Cl$_2$. Pure fractions were combined and concentrated to give 455 mg of desired product as a light yellow solid (99%): $^1$H NMR (300 MHz, Chloroform-d) δ 7.16 (d, J=5.6 Hz, 1H), 6.83 (s, 1H), 6.33 (s, 2H), 5.75 (s, 1H), 4.34-4.17 (m, 1H), 4.06 (s, 1H), 3.77 (s, 2H), 3.74-3.42 (m, 2H), 2.36 (s, 3H), 2.18-1.80 (m, 2H); ESI-MS m/z calc. 324.08, found 325.05 (M+1)$^+$. Retention time: 0.67 minutes; ESI-MS m/z calc. 324.08115, found 325.05 (M+1)+. Retention time: 0.67 minutes. The title compound was submitted for chiral HPLC separation of enantiomers.

Peak A: I-211

4-[3-(2-chloro-3-thienyl)-1,4-oxazepan-4-yl]-6-methyl-pyrimidin-2-amine (128 mg): $^1$H NMR (300 MHz, CDCl$_3$) δ 6.98 (d, J=5.8 Hz, 1H), 6.72 (d, J=5.8 Hz, 1H), 5.58 (s, 1H), 5.25 (s, 1H), 4.89 (s, 2H), 4.12 (dd, J=13.5, 5.4 Hz, 1H), 4.05-3.84 (m, 1H), 3.75-3.57 (m, 1H), 3.57-3.25 (m, 2H), 2.09 (s, 3H), 2.01-1.52 (m, 2H); ESI-MS m/z calc. 324.08, found 325.15 (M+1)$^+$. Retention time: 0.62 minutes chiral HPLC: >98% ee, Acq. Method: 20% MeOH-30% EtOH-50% HEX in 20 Mins on ChiralPAK IC column. Optical rotation: T=20.6° C., 5 mg in 1 mL of CHCl$_3$, C=1, [α]=0.92°

Peak B: I-212

4-[3-(2-chloro-3-thienyl)-1,4-oxazepan-4-yl]-6-methyl-pyrimidin-2-amine (142 mg): $^1$H NMR (300 MHz, CDCl$_3$) δ 6.98 (d, J=5.8 Hz, 1H), 6.72 (d, J=5.8 Hz, 1H), 5.58 (s, 1H), 5.25 (s, 1H), 4.89 (s, 2H), 4.12 (dd, J=13.5, 5.4 Hz, 1H), 4.05-3.84 (m, 1H), 3.75-3.57 (m, 1H), 3.57-3.25 (m, 2H), 2.09 (s, 3H), 2.01-1.52 (m, 2H); ESI-MS m/z calc. 324.08, found 325.15 (M+1)$^+$. Retention time: 0.62 minutes; Retention time: 0.62 minutes chiral HPLC: >98% ee, Acq. method: 20% MeOH, 30% EtOH, 50% HEX in 20 mins on ChiralPAK IC column Optical rotation: T=23.2° C., 5 mg in 1 mL of CHCl$_3$, C=1, [α]=2.0°.

The following analogs were prepared according to Synthetic Scheme 52: I-209 and I-210:

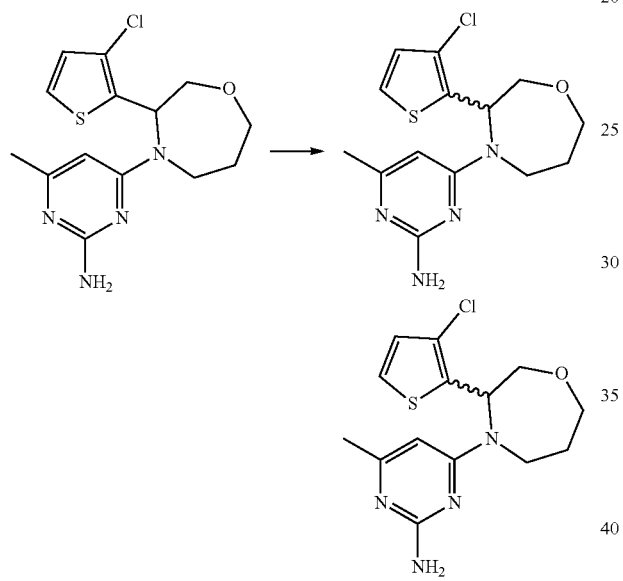

SFC separation of E29862-1390: 4-[3-(3-chloro-2-thienyl)-1,4-oxazepan-4-yl]-6-methyl-pyrimidin-2-amine (295 mg, 0.9082 mmol) Column: Cellulose-2, 20×250 mm Mobile phase: 40% MeOH (5 mM Ammonia), 60% CO$_2$ isocratic Peak A: I-210

4-[3-(3-chloro-2-thienyl)-1,4-oxazepan-4-yl]-6-methyl-pyrimidin-2-amine (122 mg, 82%) 1H NMR (300 MHz, Chloroform-d) δ 7.19 (d, J=5.3 Hz, 1H), 6.91 (d, J=5.3 Hz, 1H), 5.75 (s, 1H), 4.78 (s, 2H), 4.33 (dd, J=13.5, 5.5 Hz, 1H), 4.08 (dd, J=12.6, 5.1 Hz, 1H), 3.74 (dd, J=13.5, 10.1 Hz, 1H), 3.68-3.47 (m, 2H), 2.21 (s, 3H), 2.00 (dddd, J=14.0, 11.4, 5.4, 2.7 Hz, 1H), 1.81 (dd, J=14.3, 2.5 Hz, 1H). ESI-MS m/z calc. 324.08115, found 325.1 (M+1)+. Retention time: 0.63 minutes.

chiral HPLC: >98% ee, Acq. Method: 20% MEOH-30% ETOH-50% HEX in 20 Mins on ChiralPAK IC column Optical rotation: T=24.2° C., 5 mg in 1 mL of CHCl3, C=1, [α]=6.8°

Peak B: I-209

4-[3-(3-chloro-2-thienyl)-1,4-oxazepan-4-yl]-6-methyl-pyrimidin-2-amine (121 mg, 82%) 1H NMR (300 MHz, Chloroform-d) δ 7.19 (d, J=5.3 Hz, 1H), 6.91 (d, J=5.3 Hz, 1H), 5.75 (s, 1H), 4.78 (s, 2H), 4.33 (dd, J=13.5, 5.5 Hz, 1H), 4.08 (dd, J=12.6, 5.1 Hz, 1H), 3.74 (dd, J=13.5, 10.1 Hz, 1H), 3.68-3.47 (m, 2H), 2.21 (s, 3H), 2.00 (dddd, J=14.0, 11.4, 5.4, 2.7 Hz, 1H), 1.81 (dd, J=14.3, 2.5 Hz, 1H). ESI-MS m/z calc. 324.08115, found 325.1 (M+1)+. Retention time: 0.62 minutes. chiral HPLC: >98% ee, Acq. Method: 20% MEOH-30% ETOH-50% HEX in 20 Mins on ChiralPAK IC column Optical rotation: T=24.3° C., 5 mg in 1 mL of CHCl3, C=1, [α]=−7.4°

Example 53

Synthetic Scheme 53: 4-[4-(2-amino-6-methyl-pyrimidin-4-yl)-1,4-oxazepan-3-yl]-5-chloro-N,N-dimethyl-thiophene-2-carboxamide I-244

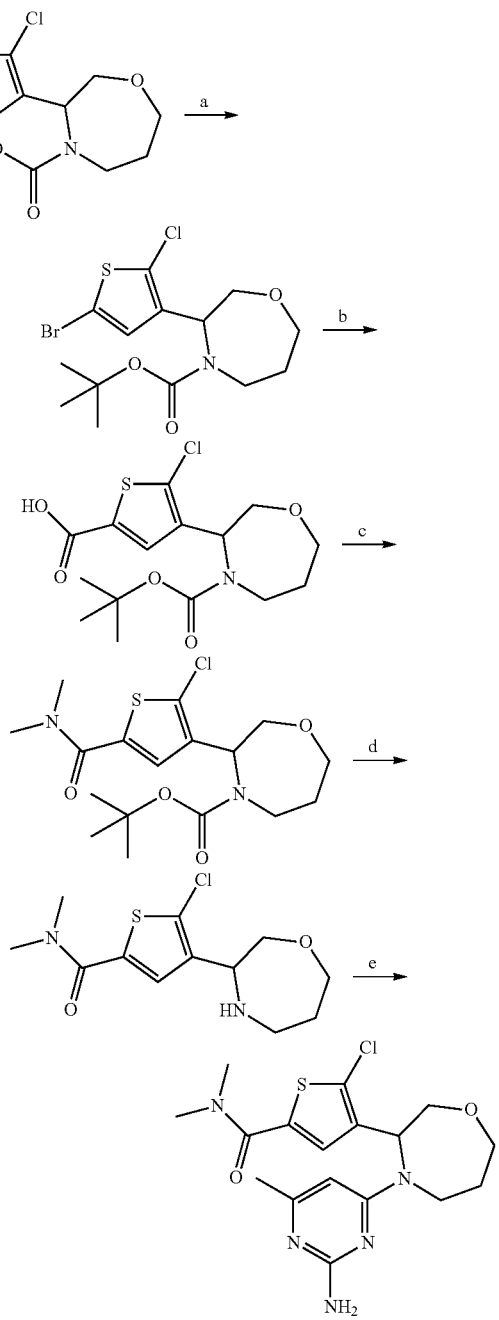

(a) NBS, CH$_3$CN; (b) nBuLi, CO$_2$, THF, −78° C.; (c) Me$_2$NH, iPr$_2$NEt, T3P, EtOAc; (d) HCl, MeOH, Reflux; (e) nBuOH, μω, 170° C., 45 mins Formation of tert-butyl 3-(5-bromo-2-chloro-3-thienyl)-1,4-oxazepane-4-carboxylate To a solution of tert-butyl 3-(2-chloro-3-thienyl)-1,4-oxazepane-4-carboxylate (0.42 g, 1.30 mmol) in CH$_3$CN (5 mL) was added NBS (0.25 g, 1.40 mmol) at room temperature. The reaction was stirred at room temperature for 1 hour. The solution was evaporated and purified by silica gel chromatography using 40 g ISCO column eluting with EtOAc/Hexane (0-30%) to afford 495 mg of product as a clear yellow oil (95%): $^1$H NMR (300 MHz, CDCl$_3$) δ 6.73 (s, 1H), 5.45-5.00 (m, 1H), 4.39-3.78 (m, 3H), 3.35 (dt, J=60.4, 12.8 Hz, 3H), 1.86 (dtdd, J=13.7, 10.9, 5.0, 2.7 Hz, 1H), 1.77-1.68 (m, 1H), 1.51-1.22 (m, 9H) Rotamers, ratio: 1:2.5; ESI-MS m/z calc. 395.00, found 395.75 (M+1)$^+$. Retention time: 1.07 minutes.

Formation of 4-(4-tert-butoxycarbonyl-1,4-oxazepan-3-yl)-5-chloro-thiophene-2-carboxylic Acid To a cold (−70° C.) solution of tert-butyl 3-(5-bromo-2-chloro-3-thienyl)-1,4-oxazepane-4-carboxylate (0.186 g, 0.468 mmol) in THF (4 mL) was added dropwise n-BuLi (0.220 mL of 2.5 M, 0.550 mmol). The color of the solution turned from light yellow to dark brown right away. After 15 minutes, dry ice CO$_2$ (0.5 g, 10 mmol) was added and the reaction was stirred for 30 minutes and then allowed to warm up to room temperature followed by workup with aqueous saturated NH$_4$Cl solution and EtOAc. The organic phase was dried (MgSO$_4$), filtered and concentrated in vacuo to afford 160 mg of crude product, (93%): $^1$H NMR (300 MHz, CDCl$_3$) δ 7.41 (s, 1H), 5.19 (d, J=40.5 Hz, 1H), 4.16 (s, 1H), 3.95 (d, J=37.3 Hz, 2H), 3.68-2.98 (m, 3H), 1.93-1.51 (m, 2H), 1.20 (qd, J=6.9, 6.2, 2.7 Hz, 9H); ESI-MS m/z calc. 361.08, found 362.1 (M+1)$^+$. Retention time: 0.87 minutes.

Formation of tert-butyl 3-[2-chloro-5-(dimethylcarbamoyl)-3-thienyl]-1,4-oxazepane-4-carboxylate To a solution of 4-(4-tert-butoxycarbonyl-1,4-oxazepan-3-yl)-5-chloro-thiophene-2-carboxylic acid (0.150 g, 0.415 mmol) in EtOAc (2 mL) was added sequentially dimethylamine (1.0 mL of 2 M, 2.0 mmol), diisopropylethyl amine (0.150 mL, 0.861 mmol) and T3P (0.50 mL of 50% w/w, 0.84 mmol) in EtOAc. The reaction was stirred overnight. LCMS indicated only product. Aqueous washes with aqueous saturated NH$_4$Cl solution and brine. The organic phase was dried over MgSO$_4$, filtered and concentrated in vacuo to afford 157 mg of crude product as yellow solid (97%): $^1$H NMR (300 MHz, CDCl$_3$) δ 7.09 (d, J=37.5 Hz, 1H), 5.26 (d, J=49.8 Hz, 1H), 4.43-3.78 (m, 4H), 3.66-3.38 (m, 2H), 3.09 (s, 6H), 1.94-1.54 (m, 2H), 1.45-1.21 (m, 9H); ESI-MS m/z calc. 388.12, found 389.27 (M+1)$^+$. Retention time: 0.85 minutes.

Formation of 5-chloro-N,N-dimethyl-4-(1,4-oxazepan-3-yl)thiophene-2-carboxamide

To a solution of tert-butyl 3-[2-chloro-5-(dimethylcarbamoyl)-3-thienyl]-1,4-oxazepane-4-carboxylate (0.16 g, 0.41 mmol) in 1,4-dioxane (3 mL) was added HCl (1.0 mL of 4 M, 4.0 mmol). After stirring for 1 hour at room temperature the volatiles were removed to afford 120 mg of desired product as a TFA salt, which was used without further purification: ESI-MS m/z calc. 288.07, found 289.16 (M+1)$^+$. Retention time: 0.53 minutes.

Formation of 4-[4-(2-amino-6-methyl-pyrimidin-4-yl)-1,4-oxazepan-3-yl]-5-chloro-N,N-dimethyl-thiophene-2-carboxamide I-244

A solution of 5-chloro-N,N-dimethyl-4-(1,4-oxazepan-3-yl)thiophene-2-carboxamide-TFA salt (0.120 g) and 4-chloro-6-methyl-pyrimidin-2-amine (0.075 g, 0.522 mmol) in n-BuOH (3 mL) was irradiated in microwave reactor at 170° C. for 45 minutes. nBuOH was removed under reduced pressure and the crude residue was purified by silica gel chromatography using 12 g ISCO column, eluting with 0-10% MeOH in CH$_2$Cl$_2$ to afford 40 mg of desired product as white solid (25%): $^1$H NMR (300 MHz, CDCl$_3$) δ 7.15 (s, 1H), 5.70 (s, 1H), 5.24 (s, 2H), 4.42 (s, 2H), 4.19 (dd, J=13.5, 5.2 Hz, 1H), 4.00 (d, J=11.7 Hz, 1H), 3.76 (dd, J=13.4, 9.5 Hz, 1H), 3.64 (d, J=10.3 Hz, 1H), 3.50 (t, J=13.1 Hz, 1H), 3.15 (s, 6H), 2.25 (s, 3H), 2.04 (s, 1H), 1.83 (d, J=14.4 Hz, 1H); ESI-MS m/z calc. 395.11, found 396.16 (M+1)$^+$. Retention time: 0.59 minutes.

The following analogs were prepared according to Synthetic Scheme 53:

4-(4-(2-amino-6-methylpyrimidin-4-yl)-1,4-oxazepan-3-yl)-5-chloro-N-methylthiophene-2-carboxamide I-182

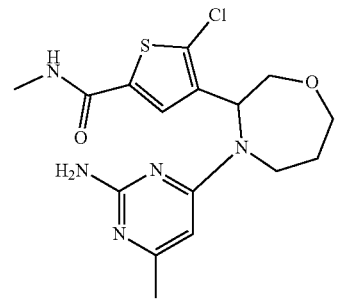 [SMILES: CNC(=O)c1cc(C2COCCCN2c2cc(C)nc(N)n2)c(Cl)s1]

$^1$H NMR (300 MHz, Methanol-d4) δ 7.53 (d, J=15.5 Hz, 1H), 6.46-5.88 (s, 1H), 6.02-5.19 (dd, J=9.3, 5.4 Hz, 1H), 4.29-3.60 (m, 6H), 2.84 (d, J=2.4 Hz, 3H), 2.30 (d, J=24.3 Hz, 3H), 1.56-1.34 (m, 3H).

Example 54

Synthetic Scheme 54: (+/−)-4-[3-(2-chloro-4-dimethylphosphoryl-phenyl)-1,4-oxazepan-4-yl]-6-methyl-pyrimidin-2-amine I-202

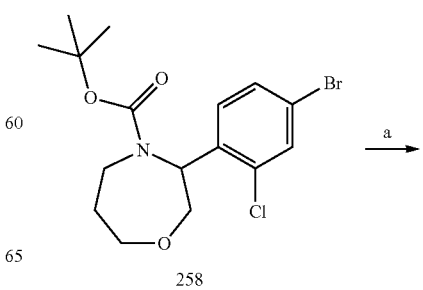

258

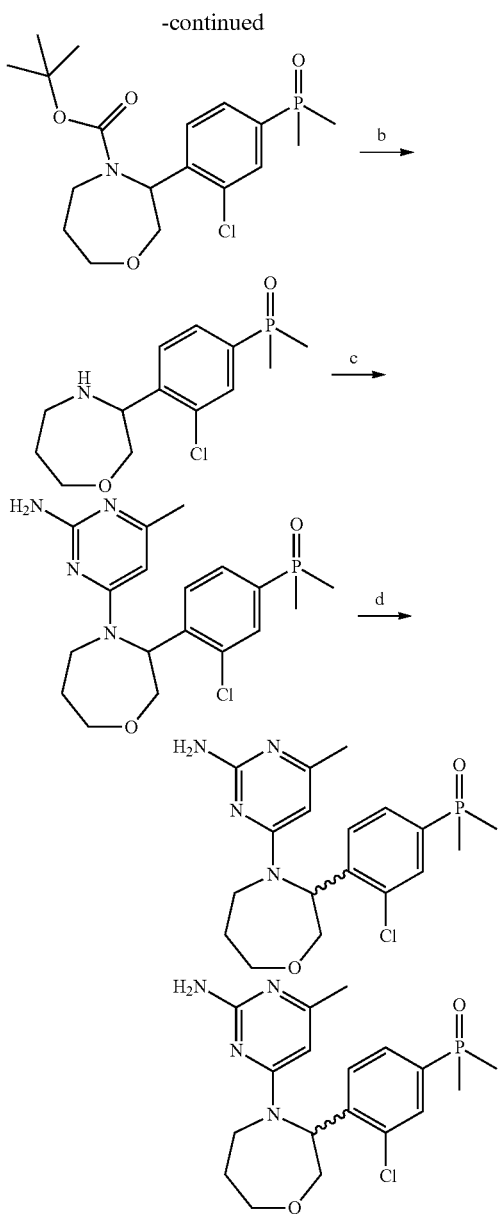

(a) methylphosphonylmethane, K₃PO₄, Pd(OAc)₂, Xantphos, DMF; (b) TFA, CH₂Cl₂; (c) 2-amino-4-chloro-6-methylpyrimidine, nBuOH, 120° C.; (d) chiral HPLC separation Formation of (+/−)-tert-butyl 3-(2-chloro-4-dimethylphosphoryl-phenyl)-1,4-oxazepane-4-carboxylate A Schlenk tube was charged with tert-butyl 3-(4-bromo-2-chloro-phenyl)-1,4-oxazepane-4-carboxylate (223 mg, 0.542 mmol), Xantphos (37 mg, 0.065 mmol), Pd(OAc)₂ (12.2 mg, 0.054 mmol), methylphosphonoylmethane (70 mg, 0.897 mmol), K₃PO₄ (230 mg, 1.08 mmol), DMF (3 mL) and vacuum/nitrogen cycled three times, then immersed in a hot bath set to 120° C. overnight. DCM and water were added to the reaction mixture and the layers separated with the aid of a phase separator. The aqueous layer was re-extracted with DCM, separated with the aid of a phase separator and the combined organics concentrated.

The resulting residue was purified via silica gel chromatography eluting with 30-100% EtOAc/heptane then 0-10% MeOH/DCM. Pure fractions were combined and concentrated in vacuo to afford 63 mg of tert-butyl 3-(2-chloro-4-dimethylphosphoryl-phenyl)-1,4-oxazepane-4-carboxylate as a straw colored oil. ¹H NMR (400 MHz, MeOH-d₄) δ 7.84 (d, J=11.7 Hz, 1H), 7.78-7.68 (m, 1H), 7.52 (dd, J=7.9, 3.0 Hz, 1H), 5.52 (dd, J=10.7, 4.2 Hz, 1H), 4.42 (d, J=15.7 Hz, 1H), 4.29 (s, 1H), 4.08-4.00 (m, 1H), 3.71-3.52 (m, 3H), 1.86 (s, 2H), 1.83 (s, 3H), 1.79 (s, 3H), 1.24 (s, 6H); ESI-MS m/z calc. 387.1, found 388.3 (M+1)⁺. Retention time 0.67 minutes.

Formation of (+/−)-3-(2-chloro-4-dimethylphosphoryl-phenyl)-1,4-oxazepane tert-Butyl 3-(2-chloro-4-dimethylphosphoryl-phenyl)-1,4-oxazepane-4-carboxylate (63 mg, 0.162 mmol) was dissolved in dichloromethane (1 mL) and trifluoroacetic acid (0.5 mL) was added. After 15 min, the volatiles were removed on a rotory evaporator. The reaction mixture was concentrated and then dissolved in MeOH and passed through a SPE bicarbonate cartridge (Agilent Stratospheres 500 mg/6 mL) and concentrated to afford 38 mg of the desired product as a straw colored oil. ¹H NMR (400 MHz, MeOH-d₄) δ 7.87-7.82 (m, 1H), 7.80-7.71 (m, 2H), 4.49 (dd, J=9.2, 3.5 Hz, 1H), 4.02-3.94 (m, 2H), 3.90-3.82 (m, 1H), 3.49 (dd, J=12.5, 9.2 Hz, 1H), 3.25 (dt, J=13.9, 5.0 Hz, 1H), 3.05-2.96 (m, 1H), 2.08-1.99 (m, 2H), 1.82 (d, J=2.9 Hz, 3H), 1.79 (d, J=2.9 Hz, 3H). ESI-MS m/z calc. 287.1, found 288.3 (M+1)⁺. Retention time: 0.46 minutes.

Formation of (+/−)-4-[3-(2-chloro-4-dimethylphosphoryl-phenyl)-1,4-oxazepan-4-yl]-6-methyl-pyrimidin-2-amine A mixture of 4-chloro-6-methyl-pyrimidin-2-amine (18.4 mg, 0.128 mmol) and 3-(2-chloro-4-dimethylphosphoryl-phenyl)-1,4-oxazepane (38 mg, 0.132 mmol) in nBuOH (1.3 mL) was heated at 125° C. overnight. The reaction mixture was concentrated and the resulting residue purified via silica gel chromatography eluting with 0-30% MeOH/DCM to afford 14 mg of a white solid. ¹H NMR (400 MHz, MeOH-d₄) δ 7.89 (d, J=11.5 Hz, 1H), 7.75-7.67 (m, 1H), 7.51 (dd, J=8.0, 3.0 Hz, 1H), 7.00-4.90 (br s, 3H), 4.35 (dd, J=13.7, 5.0 Hz, 1H), 4.06 (d, J=11.8 Hz, 1H), 3.83 (dd, J=13.7, 10.3 Hz, 2H), 3.68 (dd, J=18.9, 8.2 Hz, 1H), 2.22 (s, 3H), 2.00-1.82 (m, 2H), 1.82 (s, 3H), 1.79 (s, 3H). ESI-MS m/z calc. 394.1, found 395.4 (M+1)⁺. Retention time: 0.51 minutes.

Chiral HPLC separation: Column: AD-H, 20×250 mm; Mobile phase: 70% Hexanes, 30% EtOH/MeOH (0.2% Diethylamine); Flow: 20 mL/min; Concentrations: ~15 mg/mL (MeOH). Absolute stereochemistry of each peak unassigned.

Peak A: 4-[3-(2-chloro-4-dimethylphosphoryl-phenyl)-1,4-oxazepan-4-yl]-6-methyl-pyrimidin-2-amine; 99+% ee; ¹H NMR (400 MHz, DMSO-d₆) δ 7.77 (dd, J=11.3, 1.3 Hz, 1H), 7.67-7.60 (m, 1H), 7.43 (dd, J=7.9, 2.9 Hz, 1H), 5.64 (s, 1H), 5.54 (s, 1H), 5.44 (s, 2H), 4.55 (s, 1H), 4.14 (dd, J=13.4, 5.0 Hz, 1H), 3.90 (d, J=11.7 Hz, 1H), 3.78-3.66 (m, 2H), 3.56 (dd, J=14.6, 12.2 Hz, 1H), 2.02 (s, 3H), 1.81-1.75 (m, 2H), 1.65 (s, 3H), 1.62 (s, 3H). ESI-MS m/z calc. 394.1, found 395.2 (M+1)⁺. Retention time: 0.5 minutes. I-213.

Peak B: 4-[3-(2-chloro-4-dimethylphosphoryl-phenyl)-1,4-oxazepan-4-yl]-6-methyl-pyrimidin-2-amine; 99+% ee; ¹H NMR (400 MHz, DMSO-d₆) δ 7.77 (dd, J=11.3, 1.3 Hz, 1H), 7.67-7.60 (m, 1H), 7.43 (dd, J=7.9, 2.9 Hz, 1H), 5.64 (s, 1H), 5.54 (s, 1H), 5.44 (s, 2H), 4.55 (s, 1H), 4.14 (dd, J=13.4, 5.0 Hz, 1H), 3.90 (d, J=11.7 Hz, 1H), 3.78-3.66 (m, 2H), 3.56 (dd, J=14.6, 12.2 Hz, 1H), 2.02 (s, 3H), 1.81-1.75 (m, 2H), 1.65 (s, 3H), 1.62 (s, 3H). ESI-MS m/z calc. 394.1, found 395.1 (M+1)$^+$. Retention time: 0.5 minutes. I-214.

Example 55

Synthetic Scheme 55: 4-(3-(6-chloroimidazo[1,2-a]pyridin-7-yl)-1,4-oxazepan-4-yl)-6-methylpyrimidin-2-amine

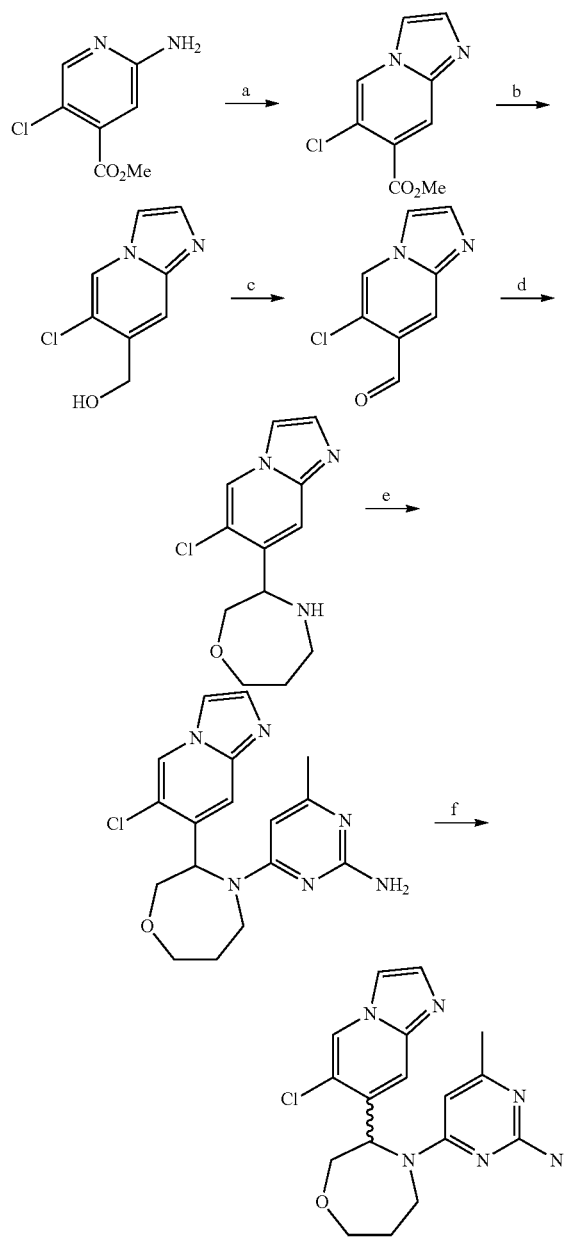

(a) 2-chloroacetaldehyde, EtOH; (b) DIBAL-H, DCM, THF; (c) MnO$_2$, DCM, 2-MeTHF, acetone; (d) 3-(tributylstannyl)methoxy)propan-1-amine 4 A mol sieves, CH$_2$Cl$_2$; then 2,6-lutidine, Cu(OTf)$_2$, hexafluoroisopropanol; (e) 2-amino-4-chloro-6-methylpyrimidine, NMP, 150° C.; (f) chiral HPLC separation Formation of methyl 6-chloroimidazo[1,2-a]pyridine-7-carboxylate A mixture of methyl 2-amino-5-chloro-pyridine-4-carboxylate (7.15 g, 38.3 mmol), 2-chloroacetaldehyde (7.3 mL, 115 mmol) and EtOH (60 mL) was heated at reflux. After 3 h, a further 3 mL chloroacetaldehyde was added and stirring continued overnight. The reaction mixture was partially concentrated. Water and 6 M NaOH were added and the mixture extracted with EtOAc twice. The combined organics were dried (Na$_2$SO$_4$), filtered and concentrated giving 8 g of methyl 6-chloroimidazo[1,2-a]pyridine-7-carboxylate as a greyish brown solid: $^1$H NMR (400 MHz, DMSO-d$_6$) δ 8.96 (d, J=0.6 Hz, 1H), 8.13 (d, J=4.2 Hz, 1H), 8.07 (d, J=0.9 Hz, 1H), 7.81 (d, J=1.1 Hz, 1H), 3.89 (s, 3H). ESI-MS m/z calc. 210.0, found 211.1 (M+1)$^+$. Retention time: 0.48 minutes.

Formation of (6-chloroimidazo[1,2-a]pyridin-7-yl)methanol

To a solution of methyl 6-chloroimidazo[1,2-a]pyridine-7-carboxylate (8 g, 37.98 mmol) in DCM (60 mL) and THF (100 mL, to aid solubility) was added at DIBAL-H (1 M, 45.6 mmol) at −78° C. over 1 h. The reaction mixture was allowed to warm to RT overnight. A further 15 mL of DIBAL-H with ice bath cooling was added. After 2 h at the same temperature, Rochelle's salt (1.5 M, 200 mL) was added and stirring continued for a further 2 h. 3.7 g of the desired product was filtered off as a white solid after washing with water: $^1$H NMR (400 MHz, DMSO-d$_6$) δ 8.82 (s, 1H), 7.88 (s, 1H), 7.58 (d, J=1.2 Hz, 2H), 5.55 (t, J=5.6 Hz, 1H), 4.57 (dd, J=5.6, 1.3 Hz, 2H). ESI-MS m/z calc. 182.0, found 183.0 (M+1)$^+$. Retention time: 0.44 minutes.

Formation of 6-chloroimidazo[1,2-a]pyridine-7-carbaldehyde

To a suspension of (6-chloroimidazo[1,2-a]pyridin-7-yl)methanol (3.7 g, 20.3 mmol) in DCM (60 mL), 2-MeTHF (50 mL) and acetone (50 mL) was added activated MnO$_2$ (10 g, 115 mmol). After three days at 50° C., the reaction mixture was filtered through Celite with the aid of EtOAc and concentrated. EtOAc was added, the mixture sonicated and 2.93 g of desired product filtered off as a yellow solid: $^1$H NMR (400 MHz, DMSO-d$_6$) δ 10.18 (s, 1H), 8.97 (d, J=0.5 Hz, 1H), 8.20 (s, 1H), 8.14 (d, J=0.8 Hz, 1H), 7.90 (d, J=1.1 Hz, 1H). ESI-MS m/z calc. 180.0, found 181.0 (M+1)$^+$. Retention time: 0.45 minutes.

Formation of 3-(6-chloroimidazo[1,2-a]pyridin-7-yl)-1,4-oxazepane and 4-(3-(6-chloroimidazo[1,2-a]pyridin-7-yl)-1,4-oxazepan-4-yl)-6-methylpyrimidin-2-amine (I-191)

Formation of the oxazepane ring system product) followed by addition into 2-amino-4-chloro-6-methylpyrimidine was carried out in same fashion as shown in Synthetic Scheme 55 to afford racemic 4-[3-(6-chloroimidazo[1,2-a]pyridin-7-yl)-1,4-oxazepan-4-yl]-6-methyl-pyrimidin-2-amine I-191.

Chiral HPLC separation: Column: AD-H, 20×250 mm; Mobile phase: 70% Hexanes, 30% EtOH/MeOH (0.2%

Diethylamine); Flow: 20 mL/min; Concentrations: ~15 mg/mL (MeOH) afforded the single enantiomer (I-221): $^1$H NMR (400 MHz, DMSO-d6) δ 8.78 (s, 1H), 7.86 (s, 1H), 7.56 (d, J=1.1 Hz, 1H), 7.40 (s, 1H), 5.71 (s, 1H), 5.45 (s, 3H), 4.51 (d, J=15.1 Hz, 1H), 4.18 (dd, J=13.5, 4.8 Hz, 1H), 3.90-3.80 (m, 2H), 3.73 (ddd, J=15.2, 9.5, 3.5 Hz, 1H), 3.60 (ddd, J=12.1, 9.7, 4.7 Hz, 1H), 2.03 (s, 3H), 1.83-1.79 (m, 2H); ESI-MS m/z calc. 358.1, found 359.1 (M+1)$^+$. Retention time: 0.45 minutes.

Example 56

Synthetic Scheme 56: 4-(3-(2-chloro-4-(cyclobutylsulfonyl)phenyl)-1,4-oxazepan-4-yl)-6-methylpyrimidin-2-amine I-222

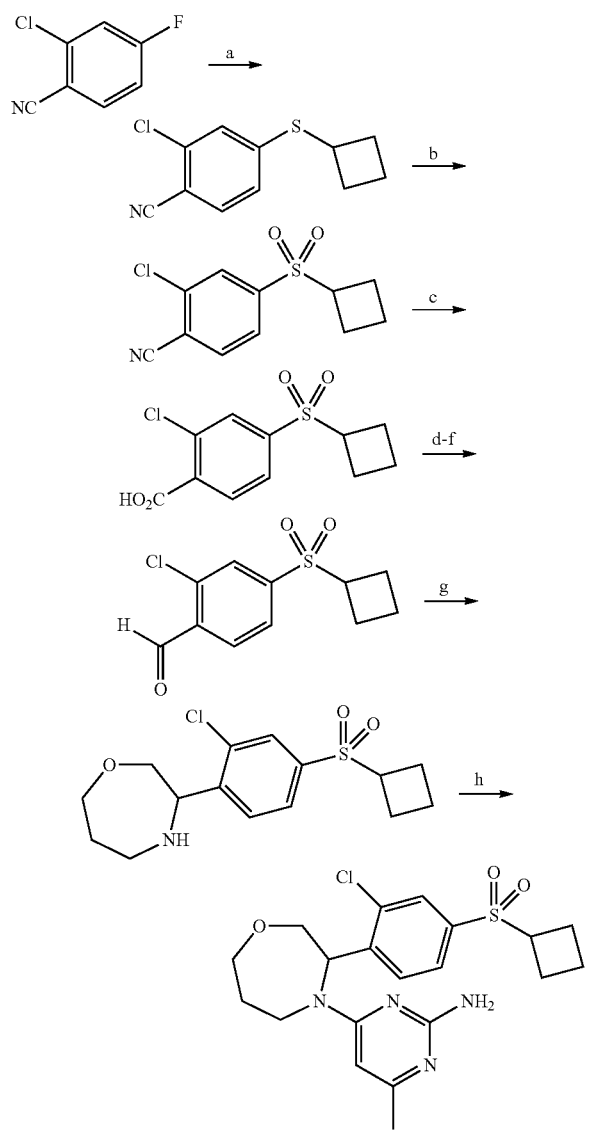

(a) cyclobutanethiol, Et$_3$N, CH$_3$CN, 60° C.; (b) Oxone, MeOH, H$_2$O; (c) NaOH, H$_2$O, then HCl; (d) TMS-diazomethane, toluene, methanol; (e) NaBH4, MeOH; (f) Dess-Martin periodinane, dichloromethane; (g) 4 A mol sieves, 3-((tributylstannyl)methoxy)propan-1-amine, CH$_2$Cl$_2$; then 2,6-lutidine, Cu(OTf)$_2$, hexafluoroisopropanol, CH$_2$Cl$_2$; (h) 2-amino-4-chloro-6-methylpyrimidine, NMP, 150° C.;

Formation of 2-chloro-4-(cyclobutylthio)benzonitrile

A mixture of 2-chloro-4-fluoro-benzonitrile (1.00 g, 6.43 mmol), cyclobutanethiol (1.15 g, 13.04 mmol), and triethylamine (1.79 mL, 12.84 mmol) in acetonitrile (8 mL) was stirred in a sealed tube at 60° C. overnight. The mixture was diluted with water and extracted with EtOAc. The organic layer was concentrated to dryness, dry loaded onto loose silica gel and purified via silica gel chromatography eluting with 0-25% EtOAc in heptane. Fractions containing the desired product were combined and concentrated to afford 1.0 g of desired product as a colorless oil: $^1$H NMR (400 MHz, Chloroform-d) δ 7.49 (d, J=8.3 Hz, 1H), 7.20 (d, J=1.8 Hz, 1H), 7.07 (dd, J=8.3, 1.8 Hz, 1H), 3.98 (dq, J=9.5, 7.1, 6.3 Hz, 1H), 2.65-2.50 (m, 2H), 2.21-2.02 (m, 4H)

Formation of 2-chloro-4-(cyclobutylsulfonyl)benzonitrile

To a solution of 2-chloro-4-(cyclobutylthio)benzonitrile (2.8 g, 11.9 mmol) in MeOH (150 mL) was added a solution of Oxone (14.6 g, 23.8 mmol) in water (75 mL). The reaction mixture was stirred for 2 days at room temperature and then concentrated to dryness. The resulting white precipitate was partitioned between water and EtOAc. The organic layer was concentrated to dryness and purified via silica gel chromatography eluting with 0-50% EtOAc in heptane. Pure fractions were combined and concentrated to give 1.07 g of desired product as a white solid: $^1$H NMR (400 MHz, Chloroform-d) δ 8.02 (t, J=1.1 Hz, 1H), 7.86 (d, J=1.1 Hz, 2H), 3.83 (pd, J=8.2, 0.7 Hz, 1H), 2.66-2.50 (m, 2H), 2.28-2.17 (m, 2H), 2.12-1.96 (m, 2H).

Formation of 2-chloro-4-(cyclobutylsulfonyl)benzoic Acid

A solution of 2-chloro-4-(cyclobutylsulfonyl)benzonitrile (1.14 g, 4.46 mmol) and NaOH (0.40 g, 10.00 mmol) pellets in water (30 mL) was refluxed for 4 hours, cooled to room temperature, and acidified to pH ~3 using HCl (10 mL of 6 M, 60 mmol). The resulting white precipitate was filtered, washed with water, and dried under vacuum overnight to afford 1.21 g of desired product as a white powder: $^1$H NMR (400 MHz, Chloroform-d) δ 7.93 (d, J=8.1 Hz, 1H), 7.81 (d, J=1.7 Hz, 1H), 7.65 (dd, J=8.2, 1.7 Hz, 1H), 3.71-3.59 (m, 1H), 2.47-2.33 (m, 2H), 2.09-1.97 (m, 2H), 1.91-1.77 (m, 2H).

Formation of 4-(3-(2-chloro-4-(cyclobutylsulfonyl)phenyl)-1,4-oxazepan-4-yl)-6-methylpyrimidin-2-amine Conversion of 2-chloro-4-(cyclobutylsulfonyl)benzoic acid to the title compound was prepared according to the procedure listed in Synthetic Scheme 8: $^1$H NMR (400 MHz, DMSO-d6) δ 7.83 (d, J=1.9 Hz, 1H), 7.76-7.68 (m, 1H), 7.56 (d, J=8.2 Hz, 1H), 5.69-5.51 (m, 2H), 5.46 (s, 2H), 4.48 (d, J=15.3 Hz, 1H), 4.12 (dq, J=12.3, 7.8, 6.8 Hz, 2H), 3.95-3.84 (m, 1H), 3.84-3.64 (m, 2H), 3.57 (q, J=10.1, 8.6 Hz, 1H), 2.34 (p, J=9.6, 9.0 Hz, 2H), 2.22-2.07 (m, 2H), 2.02 (d, J=3.7 Hz, 3H), 1.93-1.87 (m, 2H), 1.84-1.74 (m, 2H); ESI-MS m/z calc. 436.1, found 437.0 (M+1)$^+$. Retention time: 0.68 minutes. The following analogs were prepared according to Synthetic Scheme 56.

4-(3-(2-chloro-4-(ethylsulfonyl)phenyl)-1,4-oxazepan-4-yl)-6-methylpyrimidin-2-amine I-183 and I-317

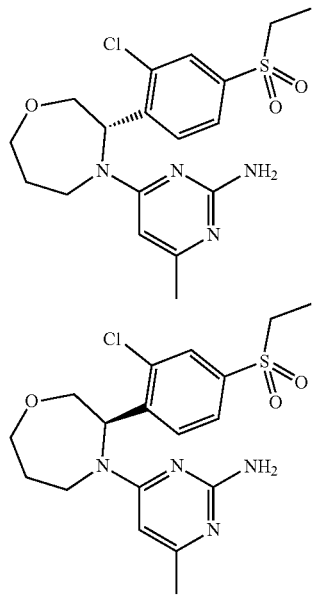

Peak A: 4-[3-(2-chloro-4-ethylsulfonyl-phenyl)-1,4-oxazepan-4-yl]-6-methyl-pyrimidin-2-amine: $^1$H NMR (400 MHz, DMSO-d6) δ 7.89 (d, J=1.9 Hz, 1H), 7.77 (dd, J=8.1, 1.9 Hz, 1H), 7.57 (d, J=8.2 Hz, 1H), 5.66 (s, 1H), 5.58 (dd, J=10.2, 4.8 Hz, 1H), 5.45 (s, 2H), 4.50 (d, J=15.3 Hz, 1H), 4.15 (dd, J=13.5, 4.9 Hz, 1H), 3.90 (dt, J=12.3, 3.9 Hz, 1H), 3.83-3.69 (m, 2H), 3.62-3.52 (m, 1H), 3.30 (q, J=7.4 Hz, 2H), 2.02 (s, 3H), 1.80 (dq, J=11.0, 6.7, 5.4 Hz, 2H), 1.12 (d, J=7.4 Hz, 3H); ESI-MS m/z calc. 410.12, found 411.0 (M+1)$^+$. Retention time: 0.64 minutes.

Peak B: 4-[3-(2-chloro-4-ethylsulfonyl-phenyl)-1,4-oxazepan-4-yl]-6-methyl-pyrimidin-2-amine $^1$H NMR (400 MHz, DMSO-d6) δ 7.88 (d, J=1.8 Hz, 1H), 7.77 (dd, J=8.2, 1.9 Hz, 1H), 7.57 (d, J=8.2 Hz, 1H), 5.66 (s, 1H), 5.58 (dd, J=10.0, 4.8 Hz, 1H), 5.44 (s, 2H), 4.50 (d, J=15.3 Hz, 1H), 4.15 (dd, J=13.5, 4.9 Hz, 1H), 3.90 (dt, J=11.9, 3.9 Hz, 1H), 3.75 (ddd, J=18.4, 14.4, 8.0 Hz, 2H), 3.57 (dt, J=12.1, 7.2 Hz, 1H), 3.30 (q, J=7.3 Hz, 2H), 2.02 (s, 3H), 1.80 (dq, J=7.2, 4.2 Hz, 2H), 1.12 (dd, J=7.4, 0.9 Hz, 3H); ESI-MS m/z calc. 410.12, found 411.0 (M+1)$^+$. Retention time: 0.64 minutes.

Example 57

$^1$H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under the following conditions:
Method: A: 0.1% TFA in H$_2$O, B: 0.1% TFA in ACN:
Runtime: 6.5 min
Flow Rate: 1.0 mL/min
Gradient: 5-95% B in 4.5 min, wavelength 254 and 215 nM.
Column: Waters Sunfire C18, 3.0×50 mm, 3.5 um, positive mode
Mass Scan: 100-900 Da Scheme 1: Synthesis of Compound C-60

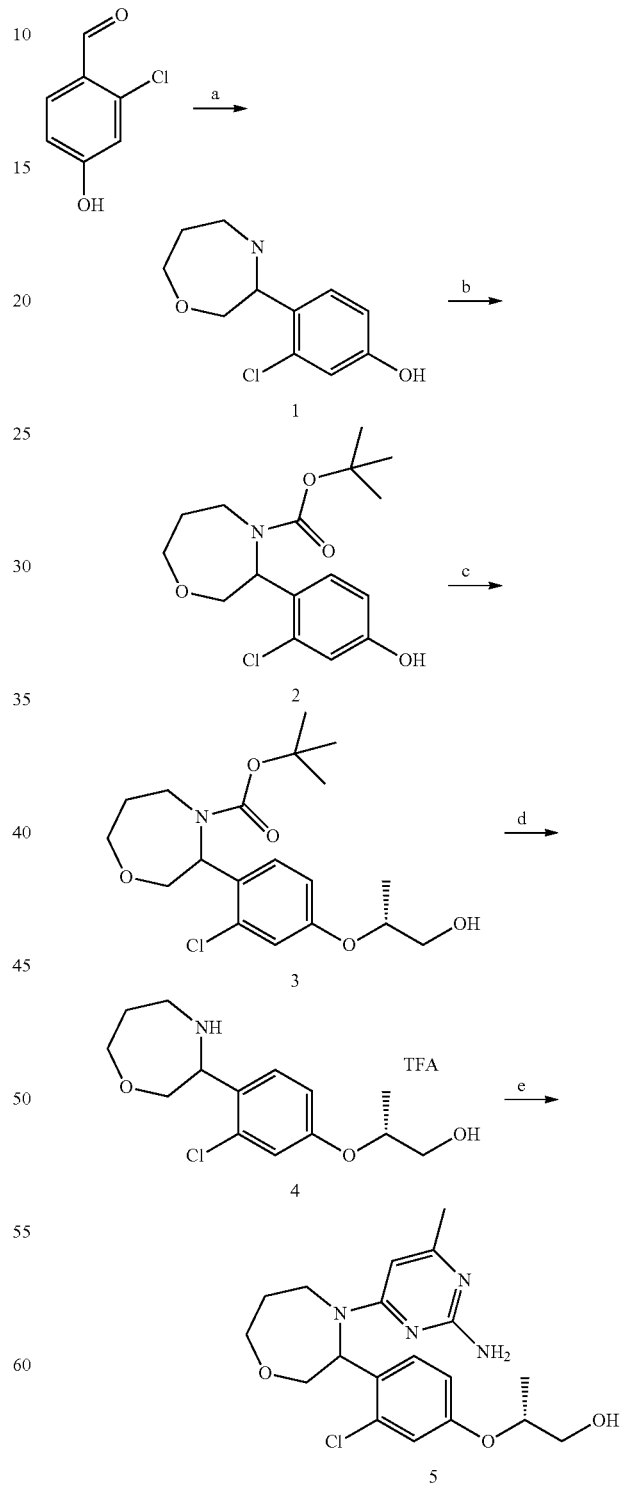

Reagents: a) i) 4 A mol sieves, 3-((tributylstannyl)methoxy)propan-1-amine, CH$_2$Cl$_2$; ii) 2,6-lutidine, Cu (OTf)₂, hexafluoroisopropanol, CH₂Cl₂; b) Di-tert-butyl decarbonate, TEA, DCM; c) (r)-(−)-2-chloropropan-1-ol, KOH, DMF; d) TFA, DCM; e) 2-amino-4-chloro-6-methylpyrimidine, nBuOH, 135° C.

Formation of 3-Chloro-4-[1,4]oxazepan-3-yl-phenol (1)

A mixture of 3-(tributylstannylmethoxy)propan-1-amine (2.42 g, 6.4 mmol), 2-chloro-4-hydroxybenzaldehyde (1.0 g, 6.4 mmol) and 4 angstrom molecular sieves in dichloromethane (10 mL) was stirred for 20 hours. The mixture was filtered. In a separate flask containing hexafluoroisopropanol (20.0 mL) was added 2,6-lutidine (0.9 mL, 7.6 mmol) followed by Cu(OTf)₂ (2.78 g, 7.6 mmol) and dichloromethane (3 mL). The mixture was stirred for 3 hours at room temperature. The filtered imine solution was added in one portion to the second flask all at once. The resulting reaction mixture was stirred overnight, filtered and then treated with 100 mL of 2:1 mixture of aqueous saturated NaHCO₃ solution and 10% ammonium hydroxide. The organic phase was separated and washed with aqueous saturated NaHCO₃ solution, dried with sodium sulfate, filtered and concentrated in vacuo. The crude mixture was purified using Biotage system, 100 g column using 2-15% MeOH:DCM to afford 1000 mg (55% yield) of product as a colorless oil. LC-MS (M+H)⁺: 228.

Formation of 3-(2-Chloro-4-hydroxy-phenyl)-[1,4]oxazepane-4-carboxylic acid tert-butyl ester (2)

To a stirred solution of 3-Chloro-4-[1,4]oxazepan-3-yl-phenol (1.6 g; 7.03 mmol; 1.00 eq.) in DCM (15.00 ml; 234.01 mmol; 33.30 eq.) was added Di-tert-butyl dicarbonate (1.68 g; 7.73 mmol; 1.10 eq.) and TEA (2.94 ml; 21.08 mmol; 3.00 eq.). The reaction was stirred at rt for 1 h. The solvent was evaporated and the crude mixture was dried to afford the title compound (2.3 g: Yield: 100%) as a off white solid. LC-MS (M-Boc): 228.

Formation of 3-[2-Chloro-4-((R)-2-hydroxy-1-methyl-ethoxy)-phenyl]-[1,4]oxazepane-4-carboxylic acid tert-butyl ester (3)

To a stirred solution of 3-(2-Chloro-4-hydroxy-phenyl)-[1,4]oxazepane-4-carboxylic acid tert-butyl ester (50.00 mg; 0.15 mmol; 1.00 eq.) in DMF (1.50 ml; 19.45 mmol; 127.54 eq.) in a microwave vial was added potassium hydroxide (34.23 mg; 0.61 mmol; 4.00 eq.) and. The reaction mixture was stirred at 100 C overnight. The reaction was quenched using water and extracted with DCM. The organic layer was concentrated under vacuum and the crude mixture was purified using Biotage system, 10 g column using 5-50% AcOEt:PS to afford 55 mg (93% yield) of title compound. LC-MS (M-Boc)⁺: 286.

Formation of (R)-2-(3-Chloro-4-[1,4]oxazepan-3-yl-phenoxy)-propan-1-ol (4)

To a stirred solution of 3-[2-Chloro-4-((R)-2-hydroxy-1-methyl-ethoxy)-phenyl]-[1,4]oxazepane-4-carboxylic acid tert-butyl ester (55.00 mg; 0.14 mmol; 1.00 eq.) in DCM (2.00 ml; 31.20 mmol; 218.91 eq.) at rt was added TFA (0.50 ml; 6.53 mmol; 45.81 eq.). The reaction continued for 30 min. The solvent was evaporated and the crude mixture was dried to afford the title compound (40 mg: Yield: 100%) as a off white solid. LC-MS (M-Boc)⁺: 286.

Formation of (R)-2-{4-[4-(2-Amino-6-methyl-pyrimidin-4-yl)-[1,4]oxazepan-3-yl]-3-chloro-phenoxy}-propan-1-ol (5) Compound C-60

To a stirred solution of (R)-2-(3-Chloro-4-[1,4]oxazepan-3-yl-phenoxy)-propan-1-ol (15.00 mg; 0.05 mmol; 1.00 eq.) in 1-butanol (1.50 ml), 2-amino-4-chloro-6-methylpyrimidine (15.07 mg; 0.10 mmol; 2.00 eq.) and TEA (0.02 ml; 0.16 mmol; 3.00 eq.) were added. The reaction was heated at 135 C overnight. Next day LCMS was recorded to confirm the completion of the reaction. The reaction mixture was loaded as is on the Intershim prep system using Basic conditions, 10-90% Acetonitrile:H2O to afford 3.7 mg (18% yield) of title product. LC-MS (M+H)⁺: 393. ¹H NMR (400 MHz, DMSO-d6) δ 8.34 (s, 1H), 7.18 (d, J=8.7 Hz, 1H), 7.03 (d, J=2.5 Hz, 1H), 6.88 (dd, J=8.7, 2.6 Hz, 1H), 5.86 (s, 3H), 4.05 (dd, J=13.6, 5.0 Hz, 1H), 3.91 (dt, J=11.6, 5.6 Hz, 2H), 3.80 (dd, J=6.0, 3.0 Hz, 1H), 3.68 (dd, J=13.4, 10.6 Hz, 2H), 3.55-3.49 (m, 2H), 3.37 (s, 5H, overlaps with H2O peak), 1.98 (s, 3H), 1.73 (s, 2H).

Compounds Prepared Similar to Compound C-60:

Compound C-42

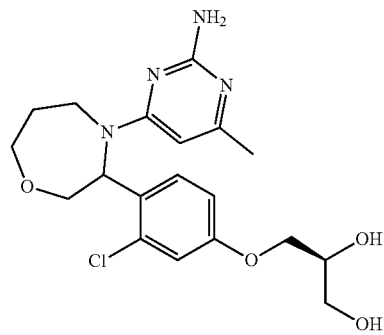

Formation of (S)-3-{4-[4-(2-Amino-6-methyl-pyrimidin-4-yl)-[1,4]oxazepan-3-yl]-3-chloro-phenoxy}-propane-1,2-diol (6) Compound C-42

(S)-3-{4-[4-(2-Amino-6-methyl-pyrimidin-4-yl)-[1,4]oxazepan-3-yl]-3-chloro-phenoxy}-propane-1,2-diol was afforded as white solid (51 mg, 63% yield). LC-MS (M+H)⁺: 409. ¹H NMR (400 MHz, DMSO-d6) δ 7.18 (d, J=8.7 Hz, 1H), 7.04 (d, J=2.5 Hz, 1H), 6.89 (dd, J=8.7, 2.6 Hz, 1H), 5.91 (s, 3H), 4.92 (dd, J=5.1, 1.6 Hz, 1H), 4.63 (dd, J=6.4, 4.9 Hz, 1H), 4.11-3.96 (m, 2H), 3.94-3.82 (m, 2H), 3.79-3.58 (m, 3H), 3.58-3.48 (m, 1H), 3.42 (t, J=5.7 Hz, 2H), 1.99 (s, 3H), 1.73 (s, 2H).

Compound C-61

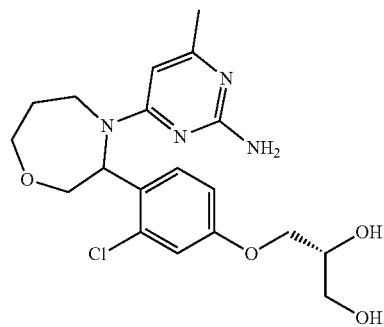

Formation of (R)-3-{4-[4-(2-Amino-6-methyl-pyrimidin-4-yl)-[1,4]oxazepan-3-yl]-3-chloro-phenoxy}-propane-1,2-diol (7) Compound C-61

(R)-3-{4-[4-(2-Amino-6-methyl-pyrimidin-4-yl)-[1,4]oxazepan-3-yl]-3-chloro-phenoxy}-propane-1,2-diol was afforded as white solid (6 mg, 11% yield). LC-MS (M+H)+: 409. ¹H NMR (400 MHz, DMSO-d6) δ 7.18 (d, J=8.7 Hz, 1H), 7.03 (d, J=2.5 Hz, 1H), 6.89 (dd, J=8.7, 2.6 Hz, 1H), 5.84 (s, 3H), 4.93 (d, J=5.1 Hz, 1H), 4.63 (d, J=6.0 Hz, 1H), 4.11-3.96 (m, 2H), 3.95-3.82 (m, 2H), 3.79-3.58 (m, 3H), 3.57-3.48 (m, 1H), 3.41 (t, J=5.1 Hz, 2H), 1.98 (s, 3H), 1.74 (d, J=9.9 Hz, 2H).

Compound C-53

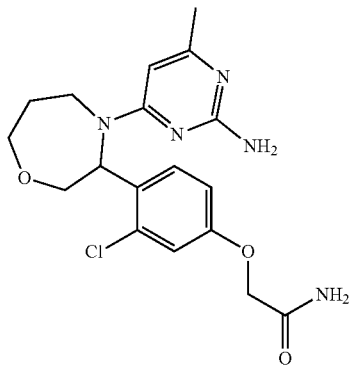

Formation of 2-{4-[4-(2-Amino-6-methyl-pyrimidin-4-yl)-[1,4]oxazepan-3-yl]-3-chloro-phenoxy}-acetamide (8) Compound C-53

2-{4-[4-(2-Amino-6-methyl-pyrimidin-4-yl)-[1,4]oxazepan-3-yl]-3-chloro-phenoxy}-acetamide was afforded as a white solid (2.8 mg, 4.8% yield). LC-MS (M+H)+: 392. ¹H NMR (400 MHz, Methanol-d₄) δ 8.49 (s, 1H), 7.28 (d, J=8.7 Hz, 1H), 7.14 (d, J=2.6 Hz, 1H), 6.97 (dd, J=8.7, 2.6 Hz, 1H), 6.22-5.19 (br s, 3H), 4.52 (s, 2H), 4.26 (dd, J=13.7, 5.1 Hz, 1H), 4.02 (d, J=12.0 Hz, 1H), 3.82 (dd, J=13.7, 10.1 Hz, 2H), 3.67 (t, J=11.1 Hz, 1H), 2.67 (s, 1H), 2.20 (s, 3H), 1.96-1.90 (m, 2H).

Compound C-105

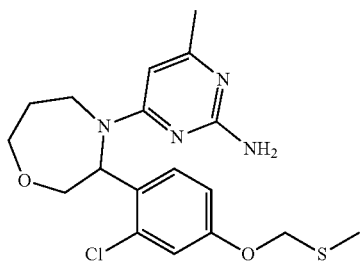

Formation of 4-[3-(2-Chloro-4-methylsulfanyl-methoxy-phenyl)-[1,4]oxazepan-4-yl]-6-methyl-pyrimidin-2-ylamine (9) Compound C-105

4-[3-(2-Chloro-4-methylsulfanylmethoxy-phenyl)-[1,4]oxazepan-4-yl]-6-methyl-pyrimidin-2-ylamine was afforded as off white solid (25 mg, 6.1% yield). LC-MS (M+H)+: 395. ¹H NMR (400 MHz, Methanol-d₄) δ 7.22 (d, J=8.7 Hz, 1H), 7.08 (d, J=2.5 Hz, 1H), 6.92 (dd, J=8.7, 2.6 Hz, 1H), 6.02-5.32 (m, 3H), 5.22 (s, 2H), 4.26 (dd, J=13.6, 5.1 Hz, 1H), 4.03 (dd, J=12.3, 4.7 Hz, 1H), 3.74 (dd, J=13.6, 10.5 Hz, 1H), 3.63 (td, J=12.2, 3.7 Hz, 2H), 2.22 (s, 3H), 2.09 (s, 3H), 1.93 (ddd, J=11.2, 5.2, 2.5 Hz, 1H), 1.88-1.75 (m, 1H).

Compound C-120

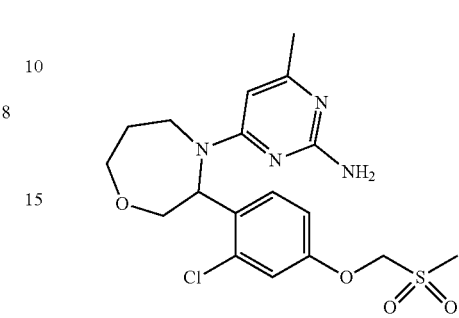

Formation of 4-[3-(2-Chloro-4-methanesulfonyl-methoxy-phenyl)-[1,4]oxazepan-4-yl]-6-methyl-pyrimidin-2-ylamine (10) Compound C-120

4-[3-(2-Chloro-4-methanesulfonylmethoxy-phenyl)-[1,4]oxazepan-4-yl]-6-methyl-pyrimidin-2-ylamine was afforded as off white solid (20 mg, 13% yield). LC-MS (M+H)+: 427. ¹H NMR (400 MHz, Methanol-d₄) δ 7.29-7.27 (m, 2H), 7.08 (d, J=8.9 Hz, 1H), 6.00-5.29 (m, 3H), 5.21 (s, 2H), 4.25 (dd, J=13.6, 5.1 Hz, 1H), 4.12-3.95 (m, 1H), 3.82-3.54 (m, 3H), 3.04 (s, 3H), 2.09 (s, 3H), 1.98-1.87 (m, 1H), 1.82 (d, J=14.9 Hz, 1H). Chiral SFC purification to obtain the individual enantiomers: Compounds C-64 and C-65

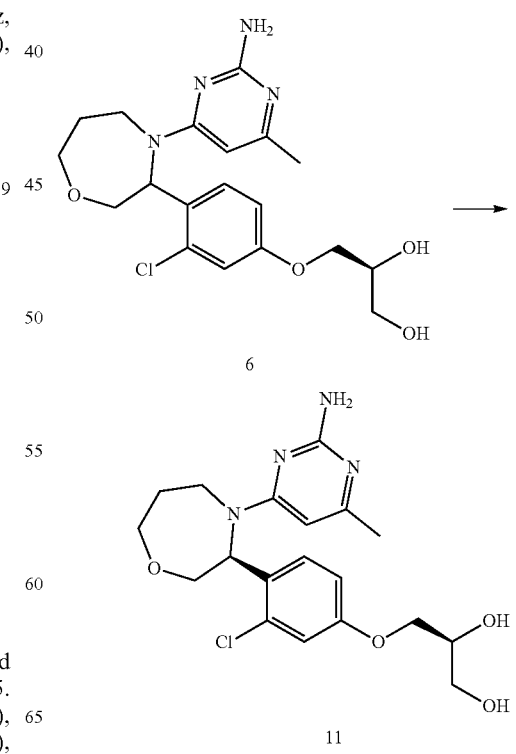

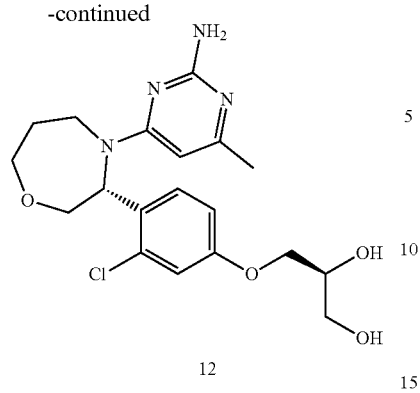

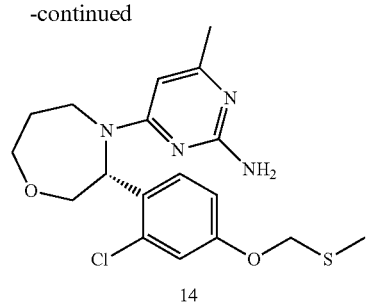

(S)-3-{4-[(S)-4-(2-Amino-6-methyl-pyrimidin-4-yl)-[1,4]oxazepan-3-yl]-3-chloro-phenoxy}-propane-1,2-diol (11) Compound C-64

The racemic mixture (6) was submitted for SFC purification: AD-H 10×250 mm column using 5-60% MeOH (0.5% DMEA) gradient method over 5 min. LC-MS (M+H)⁺: 409. ¹H NMR (400 MHz, DMSO-d6) δ 7.18 (d, J=8.7 Hz, 1H), 7.03 (d, J=2.5 Hz, 1H), 6.89 (dd, J=8.7, 2.6 Hz, 1H), 5.83 (s, 3H), 4.93 (d, J=5.1 Hz, 1H), 4.64 (t, J=5.6 Hz, 1H), 4.09-3.95 (m, 2H), 3.93-3.82 (m, 2H), 3.81-3.61 (m, 3H), 3.57-3.48 (m, 1H), 3.41 (t, J=5.6 Hz, 2H), 1.98 (s, 3H), 1.73 (s, 2H). Retention time: 3.58 minutes.

(S)-3-{4-[(R)-4-(2-Amino-6-methyl-pyrimidin-4-yl))-[1,4]oxazepan-3-yl]-3-chloro-phenoxy}-propane-1,2-diol (12) Compound C-65

The racemic mixture (6) was submitted for SFC purification: AD-H 10×250 mm column using 5-60% MeOH (0.5% DMEA) gradient method over 5 min. LC-MS (M+H)⁺: 409. ¹H NMR (400 MHz, DMSO-d6) δ 7.18 (d, J=8.7 Hz, 1H), 7.03 (d, J=2.5 Hz, 1H), 6.89 (dd, J=8.7, 2.6 Hz, 1H), 5.84 (s, 3H), 4.97 (s, 1H), 4.69 (s, 1H), 4.05 (d, J=13.5, 5.0 Hz, 1H), 3.99 (dt, J=10.0, 4.1 Hz, 1H), 3.94-3.82 (m, 2H), 3.80-3.58 (m, 3H), 3.57-3.48 (m, 1H), 3.42 (d, J=5.7 Hz, 2H), 1.98 (s, 3H), 1.73 (s, 2H). Retention time: 4.16 minutes.

4-[(S)-3-(2-Chloro-4-methylsulfanylmethoxy-phenyl)-[1,4]oxazepan-4-yl]-6-methyl-pyrimidin-2-ylamine (13) Compound C-121

The racemic mixture (9) was submitted for SFC purification: IA-H 4.6×100 mm column using 5-50% MeOH (0.5% DMEA) gradient method for 5 min followed by 50% MeOH (0.5% DMEA) isocratic method for 3 min. LC-MS (M+H)⁺: 395. ¹H NMR (400 MHz, Methanol-d₄) δ 7.22 (d, J=8.6 Hz, 1H), 7.07 (d, J=2.1 Hz, 1H), 6.92 (d, J=8.4 Hz, 1H), 6.07-5.43 (m, 3H), 5.21 (s, 2H), 4.25 (dd, J=13.6, 5.1 Hz, 1H), 4.12-3.98 (m, 1H), 3.80-3.69 (m, 1H), 3.63 (dd, J=13.9, 10.5 Hz, 2H), 2.22 (s, 3H), 2.09 (s, 3H), 2.02-1.87 (m, 1H), 1.82 (d, J=13.0 Hz, 1H). Retention time: 3.20 minutes.

4-[(R)-3-(2-Chloro-4-methylsulfanylmethoxy-phenyl)-[1,4]oxazepan-4-yl]-6-methyl-pyrimidin-2-ylamine (14) Compound C-122

The racemic mixture (9) was submitted for SFC purification: IA-H 4.6×100 mm column using 5-50% MeOH (0.5% DMEA) gradient method for 5 min followed by 50% MeOH (0.5% DMEA) isocratic method for 3 min. LC-MS (M+H)⁺: 395. ¹H NMR (400 MHz, Methanol-d₄) δ 7.21 (d, J=8.6 Hz, 1H), 7.07 (d, J=2.4 Hz, 1H), 7.00-6.84 (m, 1H), 6.09-5.22 (m, 3H), 5.21 (s, 2H), 4.25 (dd, J=13.6, 5.1 Hz, 1H), 4.03 (dd, J=12.9, 4.4 Hz, 1H), 3.78-3.69 (m, 1H), 3.70-3.57 (m, 2H), 2.22 (d, J=1.6 Hz, 3H), 2.09 (s, 3H), 1.93 (dd, J=12.3, 4.1 Hz, 1H), 1.87-1.74 (m, 1H). Retention time: 3.34 minutes.

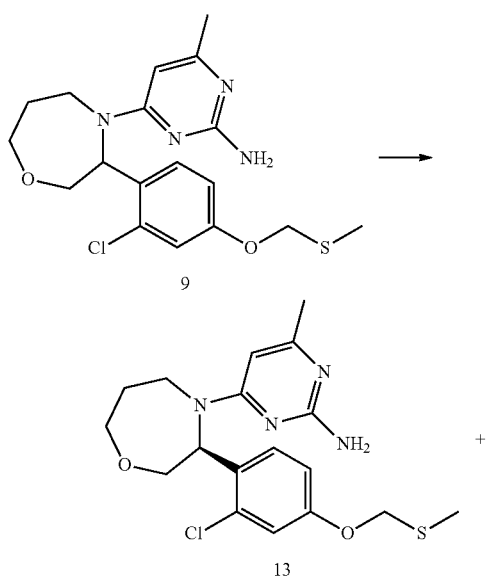

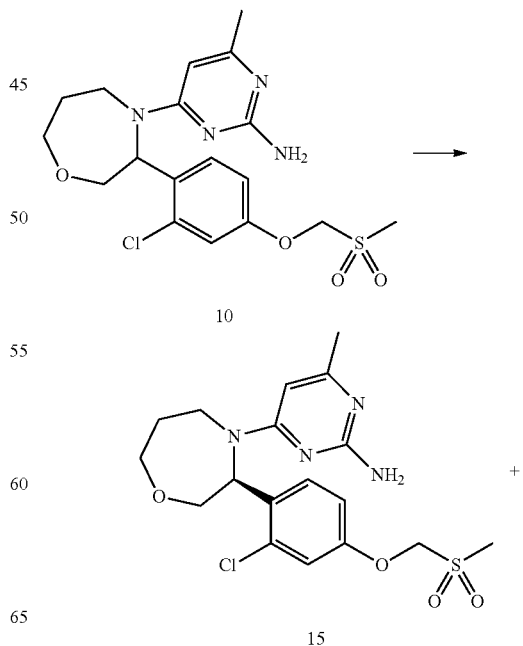

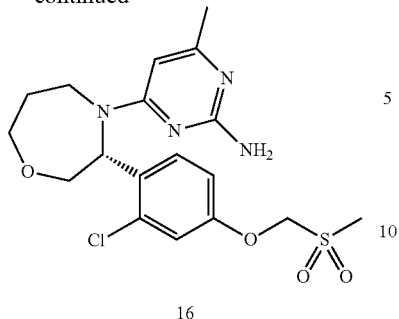

16

4-[(S)-3-(2-Chloro-4-methanesulfonylmethoxy-phenyl)-[1,4]oxazepan-4-yl]-6-methyl-pyrimidin-2-ylamine (15) Compound C-153

The racemic mixture (10) was submitted for SFC purification: IA-H 4.6×250 mm column using 5-60% MeOH (0.5% DMEA) gradient method for 5 min followed by 50% MeOH (0.5% DMEA) isocratic method for 3 min. LC-MS (M+H)$^+$: 427. $^1$H NMR (400 MHz, DMSO-$d_6$) δ 7.32 (s, 1H), 7.24 (d, J=8.8 Hz, 1H), 7.09 (d, J=8.7 Hz, 1H), 5.83 (br s, 3H), 5.34 (s, 2H), 4.07 (d, J=12.6 Hz, 1H), 3.91 (d, J=13.3 Hz, 1H), 3.77-3.60 (m, 2H), 3.52 (d, J=14.3 Hz, 1H), 3.05 (s, 3H), 1.99 (s, 3H), 1.74 (br s, 2H). Retention time: 4.72 minutes.

4-[(R)-3-(2-Chloro-4-methanesulfonylmethoxy-phenyl)-[1,4]oxazepan-4-yl]-6-methyl-pyrimidin-2-ylamine (16) Compound C-154

The racemic mixture (10) was submitted for SFC purification: IA-H 4.6×250 mm column using 5-60% MeOH (0.5% DMEA) gradient method for 5 min followed by 50% MeOH (0.5% DMEA) isocratic method for 3 min. LC-MS (M+H)$^+$: 427. $^1$H NMR (400 MHz, DMSO-$d_6$) δ 7.32 (s, 1H), 7.24 (d, J=8.6 Hz, 1H), 7.17-7.03 (m, 1H), 6.06-5.64 (m, 3H), 5.34 (s, 2H), 4.07 (d, J=11.8 Hz, 1H), 3.91 (d, J=12.7 Hz, 1H), 3.77-3.43 (m, 3H), 3.05 (s, 3H), 1.99 (s, 3H), 1.74 (br s, 2H). Retention time: 5.38 minutes.

Scheme: Synthesis of Compound C-63

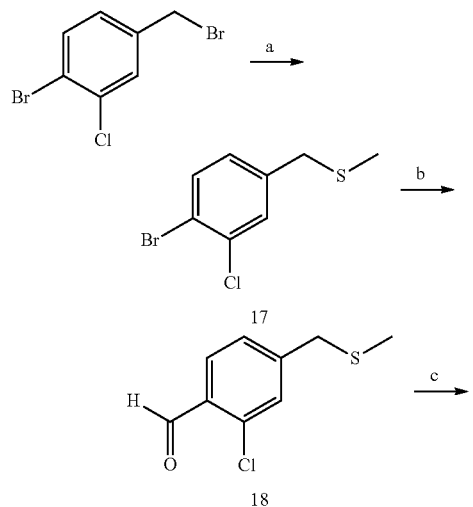

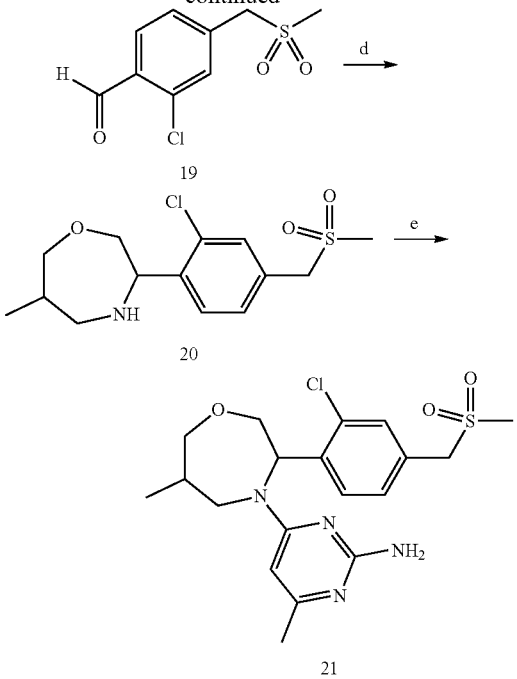

Reagents: (a) NaSMe, MeOH, 0° C. to RT; (b) nBuLi, THF, −78° C., then DMF; (c) mCPBA, CH$_2$Cl$_2$; (d) i) 4 A mol sieves, 2-Methyl-3-tributylstannanylmethoxy-propylamine, CH$_2$Cl$_2$; ii) 2,6-lutidine, Cu(OTf)$_2$, hexafluoroisopropanol, CH$_2$Cl$_2$; (e) 2-amino-4-chloro-6-methylpyrimidine, nBuOH, 135° C.

Formation of (4-bromo-3-chlorobenzyl)(methyl)sulfane (17)

The 1-bromo-4-(bromomethyl)-2-chloro-benzene (3.5 g, 12.3 mmol) was dissolved in MeOH (40 ml) in a 250 ml round-bottomed flask equipped with an overhead stirrer, temperature probe, and a 25 mL addition funnel. The solution was cooled to 0° C. in a brine bath. The NaSMe (2.1 g, 29.5 mmol in 5 ml MeOH) solution was added dropwise at a rate to keep the temperature below 10° C. A white solid precipitated. The solution was run for 24 h at rt. The reaction was poured into 1N NaOH and extracted three times with dichloromethane. The extracts were combined, dried (MgSO$_4$), filtered and evaporated in vacuo to afford 1-bromo-2-chloro-4-(methylsulfanylmethyl)benzene (2.8 g, 86% yield) as a clear oil. $^1$H NMR (300 MHz, CDCl$_3$) 7.54 (d, J=8.2 Hz, 1H), 7.40 (s, 1H), 7.07 (dd, J=8.2, 1.6 Hz, 1H), 3.59 (s, 1H), 1.99 (s, 2H) ppm.

Formation of 2-Chloro-4-methylsulfanylmethyl-benzaldehyde (18)

To a stirred solution of 1-Bromo-2-chloro-4-methylsulfanylmethyl-benzene (4800.00 mg; 19.08 mmol; 1.00 eq.) in THF (130.00 ml) at −78 C was added n-butyllithium (8.40 ml; 20.99 mmol; 1.10 eq.). The reaction was stirred for 30 min followed by addition of DMF (2.00 ml). Stirring continued for addition 15 min at −78 C followed by stirring at rt for 3 h. The reaction mixture was poured into 1N HCl and extracted with MTBE. The extract was dried (MgSO$_4$), filtered and evaporated in vacuo to afford crude product as a yellow oil. The product was purified using Biotage system, 100 g column using 10-50% dichloromethane/hexane. Obtained 3000 mg (76% yield) of desired compound. LC-MS (M+H)+: 201.

Formation of 2-Chloro-4-methanesulfonylmethyl-benzaldehyde (19)

To a stirred solution of 2-Chloro-4-methylsulfanylmethyl-benzaldehyde (2000.00 mg; 9.97 mmol; 1.00 eq.) in DCM (80.00 ml) was added 3-chloroperoxybenzoic acid (3783.47 mg; 21.92 mmol; 2.20 eq.) at rt. After 15 min a white solid precipitated. After stirring for 1 hour, the reaction mixture was poured into saturated aqueous $NaHCO_3$ solution and extracted with dichloromethane. The crude mixture was purified using Biotage system, 100 g column using 5-40% AcOEt:DCM. Obtained 2000 mg (78% yield) of product. LC-MS (M+H)+: 233.

Formation of 3-(2-Chloro-4-methanesulfonylmethyl-phenyl)-6-methyl-[1,4]oxazepane (20)

This is a 2 step reaction. Step 1: A mixture of 2-Chloro-4-methanesulfonylmethyl-benzaldehyde (75 mg; 0.32 mmol; 1.00 eq.), 2-Methyl-3-tributylstannanylmethoxy-propylamine (126 mg; 0.32 mmol; 1.00 eq.) and 4 angstrom molecular sieves in DCM (1 ml) was stirred for 20 hours. The mixture was filtered and carried forward for next reaction. Step 2: To a stirred solution of copper(ii) trifluoromethanesulfonate (139.50 mg; 0.39 mmol; 1.50 eq.) in 1,1,1,3,3,3-hexafluoro-2-propanol (4 ml) at rt was added 2,6-dimethylpyridine (0.04 ml; 0.39 mmol; 1.50 eq.). The reaction mixture was stirred for 1.5 hours followed by addition of [1-(2-Chloro-4-methanesulfonylmethyl-phenyl)-meth-(E)-ylidene]-(3-tributylstannanylmethoxy-propyl)-amine (195 mg; 0.32 mmol; 1.00 eq.). The resulting reaction mixture was stirred at rt overnight. The reaction mixture is diluted with CH2Cl2, treated with a solution of 12% aq $NH_4OH$ and brine (1:1), and stirred vigorously for 15 min at rt. The layers are separated and the aqueous layer is extracted with CH2Cl2. The combined organic layers are washed with H2O and brine, dried over anhydrous Na2SO4, filtered, and concentrated. Purification by Biotage system, 330 g column using 10-40% AcOEt:DCM followed by 5-20% MeOH:DCM. Isolated 75 mg (51% yield) of title compound. LC-MS (M+H)+: 318.

Formation of 4-[3-(2-Chloro-4-methanesulfonylmethyl-phenyl)-6-methyl-[1,4]oxazepan-4-yl]-6-methyl-pyrimidin-2-ylamine (21) Compound C-63

To a mixture of 3-(2-Chloro-4-methanesulfonylmethyl-phenyl)-6-methyl-[1,4]oxazepane (75.00 mg; 0.24 mmol; 1.00 eq.) and 2-amino-4-chloro-6-methylpyrimidine (67.76 mg; 0.47 mmol; 2.00 eq.) was added 1-butanol (2.00 ml). The reaction mixture was heated at 135 C for 16 hours.

Next day LCMS was recorded to confirm the completion of the reaction. The reaction mixture was loaded as is on the Intershim prep system using Basic conditions, 10-90% Acetonitrile:H2O to afford 44 mg (44% yield) of pure product. LC-MS (M+H)+: 425. $^1$H NMR (400 MHz, DMSO-d6) δ 7.50 (d, J=8.2 Hz, 1H), 7.33 (d, J=2.1 Hz, 1H), 7.30 (dd, J=8.2, 2.1 Hz, 1H), 5.79 (s, 2H), 5.43 (s, 1H), 5.22 (s, 1H), 4.51-4.38 (m, 2H), 4.03 (dd, J=13.6, 4.4 Hz, 1H), 3.82 (d, J=15.0 Hz, 1H), 3.72-3.51 (m, 3H), 2.76 (s, 3H), 2.07 (s, 2H), 1.93 (s, 3H), 0.87 (d, J=7.0 Hz, 3H).

Compounds Prepared Similar to (21):

Compound C-62

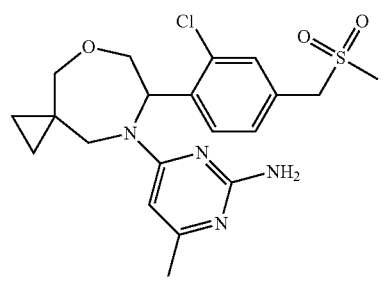

(22)

Formation of 4-[7-(2-Chloro-4-methanesulfonylmethyl-phenyl)-5-oxa-8-aza-spiro[2.6]non-8-yl]-6-methyl-pyrimidin-2-ylamine (22) Compound C-62

4-[7-(2-Chloro-4-methanesulfonylmethyl-phenyl)-5-oxa-8-aza-spiro[2.6]non-8-yl]-6-methyl-pyrimidin-2-ylamine was afforded as a white solid (30 mg, 30% yield). LC-MS (M+H)+: 437. $^1$H NMR (400 MHz, DMSO-d6) δ 7.52 (d, J=8.2 Hz, 1H), 7.38 (d, J=2.2 Hz, 1H), 7.32 (dd, J=8.2, 2.1 Hz, 1H), 5.81 (s, 2H), 5.33 (s, 2H), 4.56-4.38 (m, 3H), 4.10 (dd, J=13.7, 4.6 Hz, 1H), 4.01 (d, J=15.0 Hz, 1H), 3.85 (dd, J=13.4, 10.3 Hz, 2H), 3.09 (d, J=12.1 Hz, 1H), 2.78 (s, 3H), 1.94 (s, 3H), 0.89 (d, J=22.3 Hz, 1H), 0.57 (dt, J=9.3, 4.7 Hz, 1H), 0.39 (ddt, J=33.0, 9.5, 4.8 Hz, 2H).

Compound C-73

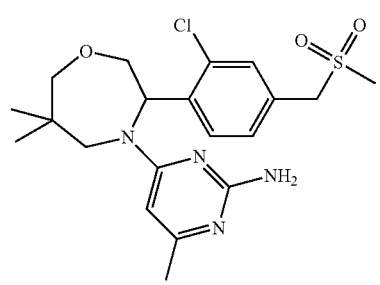

(23)

Formation of 4-[3-(2-Chloro-4-methanesulfonylmethyl-phenyl)-6,6-dimethyl-[1,4]oxazepan-4-yl]-6-methyl-pyrimidin-2-ylamine (23) Compound C-73

4-[3-(2-Chloro-4-methanesulfonylmethyl-phenyl)-6,6-dimethyl-[1,4]oxazepan-4-yl]-6-methyl-pyrimidin-2-ylamine was afforded as a white solid (50 mg, 50% yield). LC-MS (M+H)+: 439. $^1$H NMR (400 MHz, DMSO-d6) δ 7.50 (d, J=8.6 Hz, 1H), 7.30 (d, J=2.0 Hz, 2H), 5.85 (s, 1H), 5.14 (s, 2H), 4.44 (s, 2H), 4.04 (dd, J=13.6, 4.9 Hz, 1H), 3.60 (dd, J=13.5, 11.1 Hz, 1H), 3.48-3.38 (m, 1H), 3.32-3.22 (m, 4H, overlaps with H2O peak), 2.75 (s, 3H), 1.93 (s, 3H), 0.88 (d J=43 Hz 6H)

Compound C-74

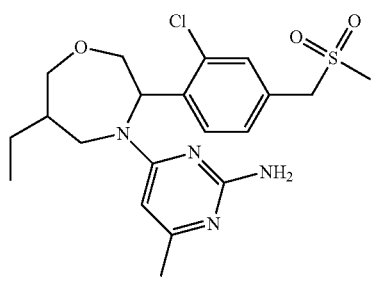

24

Formation of 4-[3-(2-Chloro-4-methanesulfonylm-ethyl-phenyl)-6-ethyl-[1,4]oxazepan-4-yl]-6-methyl-pyrimidin-2-ylamine (24) Compound C-74

4-[3-(2-Chloro-4-methanesulfonylmethyl-phenyl)-6-ethyl-[1,4]oxazepan-4-yl]-6-methyl-pyrimidin-2-ylamine was afforded as white solid (40 mg, 40% yield). LC-MS (M+H)$^+$: 439. 1H NMR (400 MHz, DMSO-d6) δ 7.50 (d, J=8.2 Hz, 1H), 7.33 (d, J=2.2 Hz, 1H), 7.30 (dd, J=8.2, 2.2 Hz, 1H), 5.81 (s, 2H), 5.18 (s, 1H), 4.50-4.38 (m, 2H), 4.00 (dd, J=13.6, 4.4 Hz, 1H), 3.83-3.75 (m, 2H), 3.69 (dd, J=13.6, 10.0 Hz, 1H), 3.54 (dd, J=12.1, 2.8 Hz, 1H), 3.33 (d, J=2.7 Hz, 3H, overlaps with H2O peak), 2.75 (s, 3H), 1.92 (s, 3H), 1.40 (tq, J=12.7, 7.4, 6.5 Hz, 1H), 1.29-1.14 (m, 1H), 0.88 (t, J=7.4 Hz, 3H).

Compound C-11

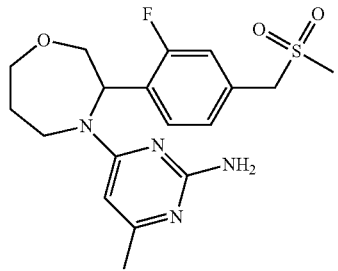

25

Formation of 4-[3-(2-Fluoro-4-methanesulfonylm-ethyl-phenyl)-[1,4]oxazepan-4-yl]-6-methyl-pyrimi-din-2-ylamine (25) Compound C-11

4-[3-(2-Fluoro-4-methanesulfonylmethyl-phenyl)-[1,4]oxazepan-4-yl]-6-methyl-pyrimidin-2-ylamine was afforded as white solid (15 mg, 44% yield). LC-MS (M+H)$^+$: 395. $^1$H NMR (400 MHz, DMSO-d$_6$) δ 7.31-7.18 (m, 3H), 5.97 (s, 3H), 4.49 (s, 2H), 4.25-4.14 (m, 1H), 3.96-3.90 (m, 1H), 3.74 (t, J=12.0 Hz, 1H), 3.63 (d, J=11.9 Hz, 1H), 3.52 (td, J=11.7, 3.9 Hz, 1H), 3.32 (s, 2H, overlaps with H2O peak), 2.92 (s, 3H), 2.04 (s, 3H), 1.77-1.69 (m, 2H).

Compound C-12

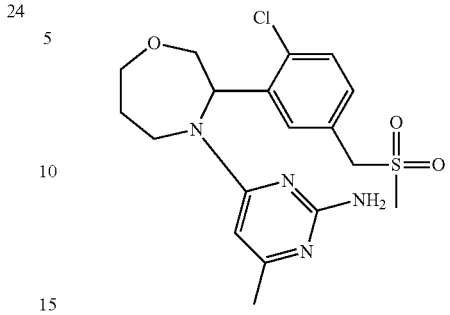

26

Formation of 4-[3-(2-Chloro-5-methanesulfonylm-ethyl-phenyl)-[1,4]oxazepan-4-yl]-6-methyl-pyrimi-din-2-ylamine (26) Compound C-12

4-[3-(2-Chloro-5-methanesulfonylmethyl-phenyl)-[1,4]oxazepan-4-yl]-6-methyl-pyrimidin-2-ylamine was afforded as white solid (55 mg, 54% yield). LC-MS (M+H)$^+$: 411. $^1$H NMR (400 MHz, DMSO-d6) δ 7.51 (d, J=8.1 Hz, 1H), 7.36 (d, J=2.1 Hz, 1H), 7.32 (dd, J=8.2, 2.1 Hz, 1H), 5.66 (d, J=144.9 Hz, 3H), 4.55-4.39 (m, 2H), 4.15 (dd, J=13.4, 5.0 Hz, 1H), 3.92 (dt, J=12.2, 3.8 Hz, 1H), 3.72-3.48 (m, 3H), 3.33 (s, 2H, overlap with H2O peak), 2.83 (s, 3H), 1.99 (s, 3H), 1.77 (q, J=3.7 Hz, 2H). Chiral SFC purification to obtain the individual enantiomers: Compounds C-49 and C-50

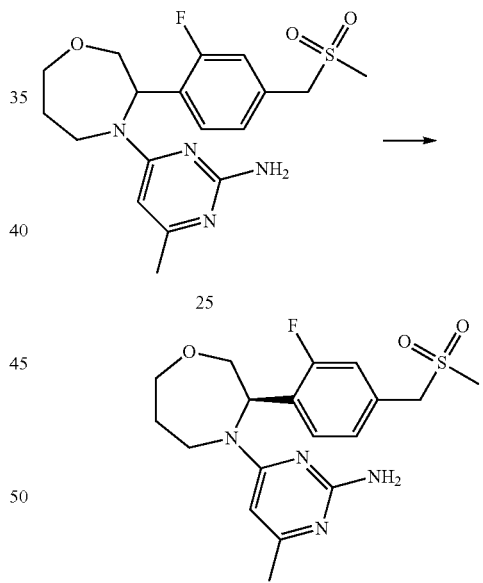

25

27

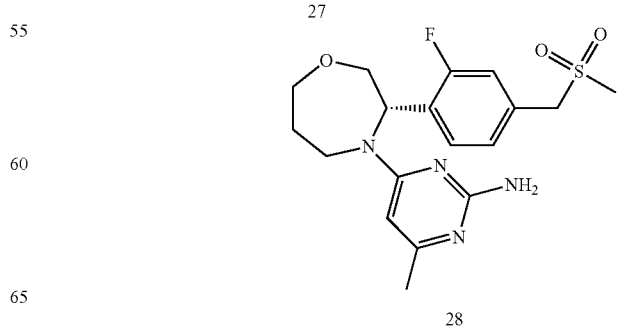

28

Formation of 4-[(R)-3-(2-Fluoro-4-methanesulfonyl-methyl-phenyl)-[1,4]oxazepan-4-yl]-6-methyl-pyrimidin-2-ylamine (27) Compound C-49

The racemic mixture (25) was submitted for SFC purification: IC 4.6×100 mm column using 5-60% MeOH (0.5% DMEA) gradient method for 5 min followed by 50% MeOH (0.5% DMEA) isocratic method for 3 min. LC-MS (M+H)$^+$: 395. $^1$H NMR (400 MHz, DMSO-d$_6$) δ 7.31-7.18 (m, 3H), 5.97 (s, 3H), 4.49 (s, 2H), 4.25-4.14 (m, 1H), 3.96-3.90 (m, 1H), 3.74 (t, J=12.0 Hz, 1H), 3.63 (d, J=11.9 Hz, 1H), 3.52 (td, J=11.7, 3.9 Hz, 1H), 3.32 (s, 2H, overlaps with H2O peak), 2.92 (s, 3H), 2.04 (s, 3H), 1.77-1.69 (m, 2H). Retention time: 5.06 minutes.

Formation of 4-[(S)-3-(2-Fluoro-4-methanesulfonyl-methyl-phenyl)-[1,4]oxazepan-4-yl]-6-methyl-pyrimidin-2-ylamine (27) Compound C-50

The racemic mixture (25) was submitted for SFC purification: IC 4.6×100 mm column using 5-60% MeOH (0.5% DMEA) gradient method for 5 min followed by 50% MeOH (0.5% DMEA) isocratic method for 3 min. LC-MS (M+H)$^+$: 395. $^1$H NMR (400 MHz, DMSO-d$_6$) δ 7.31-7.18 (m, 3H), 5.97 (s, 3H), 4.49 (s, 2H), 4.25-4.14 (m, 1H), 3.96-3.90 (m, 1H), 3.74 (t, J=12.0 Hz, 1H), 3.63 (d, J=11.9 Hz, 1H), 3.52 (td, J=11.7, 3.9 Hz, 1H), 3.32 (s, 2H, overlaps with H2O peak), 2.92 (s, 3H), 2.04 (s, 3H), 1.77-1.69 (m, 2H). Retention time: 5.50 minutes.

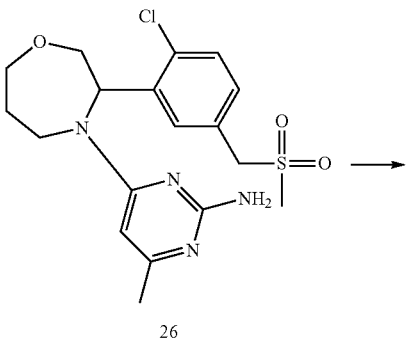

26

4-[(R)-3-(2-Chloro-5-methanesulfonylmethyl-phenyl)-[1,4]oxazepan-4-yl]-6-methyl-pyrimidin-2-ylamine (29) Compound C-51

The racemic mixture (26) was submitted for SFC purification: OD-H 4.6×100 mm column using 5-60% MeOH (0.5% DMEA) gradient method for 5 min followed by 50% MeOH (0.5% DMEA) isocratic method for 3 min. LC-MS (M+H)$^+$: 411. $^1$H NMR (400 MHz, DMSO-d6) δ 7.51 (d, J=8.1 Hz, 1H), 7.36 (d, J=2.1 Hz, 1H), 7.32 (dd, J=8.2, 2.1 Hz, 1H), 5.66 (d, J=144.9 Hz, 3H), 4.55-4.39 (m, 2H), 4.15 (dd, J=13.4, 5.0 Hz, 1H), 3.92 (dt, J=12.2, 3.8 Hz, 1H), 3.72-3.48 (m, 3H), 3.33 (s, 2H, overlap with H2O peak), 2.83 (s, 3H), 1.99 (s, 3H), 1.77 (q, J=3.7 Hz, 2H). Retention time: 2.37 minutes.

4-[(R)-3-(2-Chloro-5-methanesulfonylmethyl-phenyl)-[1,4]oxazepan-4-yl]-6-methyl-pyrimidin-2-ylamine (30) Compound C-52

The racemic mixture (26) was submitted for SFC purification: OD-H 4.6×100 mm column using 5-60% MeOH (0.5% DMEA) gradient method for 5 min followed by 50% MeOH (0.5% DMEA) isocratic method for 3 min. LC-MS (M+H)$^+$: 411. $^1$H NMR (400 MHz, DMSO-d6) δ 7.51 (d, J=8.1 Hz, 1H), 7.36 (d, J=2.1 Hz, 1H), 7.32 (dd, J=8.2, 2.1 Hz, 1H), 5.66 (d, J=144.9 Hz, 3H), 4.55-4.39 (m, 2H), 4.15 (dd, J=13.4, 5.0 Hz, 1H), 3.92 (dt, J=12.2, 3.8 Hz, 1H), 3.72-3.48 (m, 3H), 3.33 (s, 2H, overlap with H2O peak), 2.83 (s, 3H), 1.99 (s, 3H), 1.77 (q, J=3.7 Hz, 2H). Retention time: 2.77 minutes.

Example 58

Colo 205 Reporter Assay

The compounds of the invention described herein were screened using the assay procedure for β-catenin-TCF-mediated reporter transcription activity described below.

In cells with activated WNT signaling, we have found that induction of ER Stress by the mechanism of these compounds results in a rapid reduction in the activity of this reporter gene and that the activity in the assay correlates with the activity of these compounds as inducers of ER Stress and the UPR, and all other measures of specific activity of these compounds, including calcium release, viability, and displacement of radiolabeled version of these compounds from their specific binding site in cells.

Reporter cell lines were generated by stably transfecting cells of cancer cell lines (e.g., colon cancer) with a plasmid reporter construct (From SABiosciences, a QIAGEN company) that includes TCF/LEF promoter driving expression of the firefly luciferase gene. TCF/LEF reporter constructs were made in which TCF/LEF promoter, a promoter with optimal number of TCF/LEF binding sites designed by SABiosceinces, was linked upstream of the firefly luciferase gene. This construct could also include a puromycin resistance gene as a selectable marker. This construct could also be used to stably transfect Colo 205 cells, a colon cancer cell line having a mutated APC gene that causes a constitutively active β-catenin. A control cell line was generated using another plasmid construct containing the luciferase gene under the control of a CMV basal promoter which is not activated by β-catenin.

Colo 205 Cultured cells with a stably transfected reporter construct were plated at approximately 10,000 cells per well into 384 well multi-well plates for twenty four hours. The testing compounds were then added to the wells in 2-fold

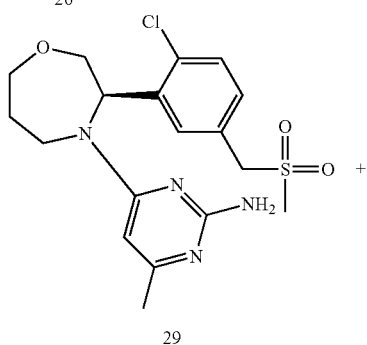

29

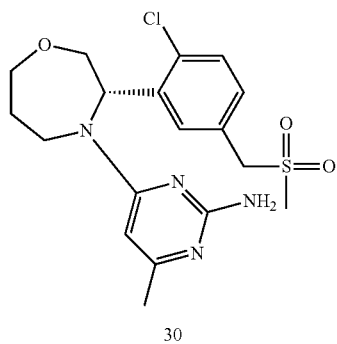

30 serial dilutions using a twenty micromolar top concentration. A series of control wells for each cell type received only compound solvent. Five hours after the addition of compound, reporter activity for luciferase was assayed, by addition of the SteadyGlo luminescence reagent (Promega). The reporter luminescence activity was measured using Pherastar plate reader (BMG Labtech). Readings were normalized to DMSO only treated cells, and normalized activities were then used in the IC50 calculations. The Colo 205 reporter assay data are summarized in Table 3: A<0.3 µM; 0.3 µM≤B<1.0 µM; 1.0 µM≤C<5.0 µM; D≥5.0 µM.

HepG2 XBP1 Reporter Assay

HepG2 hepatoma cells were transduced with a retrovirus encoding the cDNA for unspliced (u) XBP1, which contains a non-processed intron, fused to the cDNA for firefly luciferase. Upon induction of ER stress, the non-processed intron of XBP1(u) is spliced out by active IRE1alpha endonuclease. The resulting spliced (s) XBP1 is now in frame with luciferase which causes the production of active luciferase protein, resulting in bioluminescence HepG2 XBP1(u)-Luc cells were plated Colo 205 Cultured cells with a stably transfected reporter construct were plated at approximately 30,000 cells per well into 96 well multi-well plates for twenty four hours. The testing compounds were then added to the wells in 3-fold serial dilutions using a twenty seven micromolar top concentration. A series of control wells for each cell type received only compound solvent. Six hours after the addition of compound, reporter activity for luciferase was assayed, by addition of the SteadyGlo luminescence reagent (Promega). The reporter luminescence activity was measured using Pherastar plate reader (BMG Labtech). Readings was normalized to DMSO only treated cells, and normalized activities were then used in the IC50 calculations. The HepG2 XBP1 reporter assay data are summarized in Tables 3-5: A<0.6 µM; 0.6 µM≤B<2.0 µM; 2.0 µM≤C<5.0 µM; D≥5.0 µM.

Calcium Flux Assay

Compounds described herein induced ER stress by causing intracellular calcium flux. Calcium flux was measured in Colo-205 cells using the FLIPR® Calcium 5 Assay Kit according to manufacter's protocol (Molecular Devices, Cat. # R8186) on a FLIPR3 system (Molecular Devices). Calcium flux is measured over 36 minutes. The Colo-205 calcium flux assay data are summarized in Table 3: A<0.6 µM; 0.6 µM≤B<2.0 µM; 2.0 µM≤C<10.0 µM; D≥10.0 µM.

Cell Culture Methods

Cells were removed from liquid nitrogen storage, thawed and expanded in appropriate growth media. Once expanded, cells were seeded in 384-well tissue culture treated plates at 500 cells per well. After 24 hours, cells were treated for either 0 hours or treated for 96 hours with a testing compound (at the concentrations of 100 nM and 2 uM). At the end of either 0 hours or 96 hours, cell status was analyzed using ATPLite (Perkin Elmer) to assess the biological response of cells to the testing compound. The IC50 data in NCI-H929 (Multiple myeloma cells) and DU4475 (breast cancer cells) are summarized in Tables 4 and 5: A<1 µM; 1 µM≤B<10.0 µM; 10.0 µM≤C<25.0 µM; D≥25.0 µM.

TABLE 3

| Compound # | Colo205 IC50 | Colo 205 Calcium Flux assay 384w Boston Ca assay FLIPR3 Colo EC50 | XBP1-luc HepG2 1 EC50 |
|---|---|---|---|
| I-3 | A | | A |
| I-4 | B | | C |
| I-5 | B | | |
| I-243 | A | | A |
| I-6 | B | | C |
| I-11 | A | | C |
| I-14 | A | | A |
| I-16 | B | B | C |
| I-17 | B | B | A |
| I-19 | A | | |
| I-20 | B | B | B |
| I-21 | B | B | C |
| I-22 | B | A | B |
| I-23 | B | | D |
| I-25 | A | | B |
| I-27 | A | A | |
| I-31 | A | | |
| I-32 | A | | |
| I-36 | B | | |
| I-37 | B | A | |
| I-40 | A | A | A |
| I-45 | B | | B |
| I-47 | B | B | |
| I-50 | B | | B |
| I-51 | B | A | A |
| I-55 | B | A | |
| I-59 | B | A | |
| I-62 | B | A | |
| I-63 | B | | |
| I-66 | C | | |
| I-68 | B | A | A |
| I-69 | B | | A |
| I-70 | B | A | |
| I-71 | A | A | |
| I-72 | B | | |
| I-74 | A | A | |
| I-79 | A | A | |
| I-82 | B | B | |
| I-84 | A | | |
| I-85 | B | | B |
| I-87 | A | | |
| I-88 | B | | |
| I-90 | B | | |
| I-92 | A | A | A |
| I-93 | B | | |
| I-97 | B | | |
| I-98 | B | | A |
| I-99 | A | | |
| I-101 | A | | |
| I-106 | A | | |
| I-107 | A | | |
| I-108 | A | | |
| I-110 | B | | |
| I-111 | B | | |
| I-113 | B | | |
| I-114 | B | | |
| I-115 | B | | |
| I-117 | B | | |
| I-118 | B | | |
| I-119 | B | | |
| I-122 | B | | |
| I-123 | B | | |
| I-124 | A | | B |
| I-126 | B | | |
| I-127 | A | | |
| I-129 | B | | |
| I-132 | B | | |
| I-133 | B | | |
| I-134 | B | | |
| I-135 | B | | |
| I-138 | A | | |
| I-139 | B | | |
| I-140 | A | | |
| I-141 | A | | |
| I-144 | B | | |
| I-146 | B | | |
| I-147 | A | | |
| I-148 | A | | |

TABLE 3-continued

| Compound # | Colo205 IC50 | Colo 205 Calcium Flux assay 384w Boston Ca assay FLIPR3 Colo EC50 | XBP1-luc HepG2 1 EC50 |
|---|---|---|---|
| I-150 | B | A | C |
| I-151 | B | | |
| I-153 | B | | |
| I-157 | B | | |
| I-158 | B | | |
| I-159 | A | | |
| I-161 | A | | A |
| I-162 | A | A | A |
| I-168 | B | | |
| I-170 | A | A | |
| I-171 | C | A | B |
| I-172 | B | A | C |
| I-173 | B | A | B |
| I-174 | B | | B |
| I-175 | A | A | A |
| I-176 | B | A | B |
| I-177 | A | A | A |
| I-178 | A | A | A |
| I-179 | A | A | A |
| I-181 | A | A | A |
| I-183 | B | A | A |
| I-184 | B | A | C |
| I-185 | B | A | C |
| I-186 | A | A | A |
| I-188 | A | A | B |
| I-190 | A | A | A |
| I-191 | B | A | B |
| I-192 | B | A | A |
| I-193 | A | A | A |
| I-195 | A | A | A |
| I-197 | B | A | A |
| I-199 | B | A | B |
| I-201 | B | A | A |
| I-202 | B | B | D |
| I-204 | A | A | A |
| I-205 | B | A | A |
| I-207 | A | A | A |
| I-208 | A | A | A |
| I-214 | B | A | C |
| I-215 | A | A | A |
| I-216 | A | A | A |
| I-217 | A | A | A |
| I-218 | A | A | A |
| I-219 | B | A | A |
| I-220 | A | A | A |
| I-221 | A | A | A |
| I-222 | B | A | B |
| I-224 | A | A | A |
| I-225 | B | | B |
| I-226 | B | A | A |
| I-227 | B | | B |
| I-228 | B | | A |
| I-229 | B | | A |
| I-230 | B | | A |
| I-231 | A | | A |
| I-232 | A | | A |
| I-233 | A | | B |
| I-234 | B | | A |
| I-235 | A | | A |
| I-236 | A | | A |
| I-237 | A | | A |
| I-238 | A | | A |
| I-239 | B | | A |
| I-240 | A | | A |
| I-241 | A | | A |
| I-242 | A | | A |
| I-245 | B | | A |
| I-246 | A | | A |
| I-247 | A | | A |
| I-248 | A | | A |
| I-249 | A | | A |
| I-250 | A | | A |
| I-251 | A | | B |
| I-253 | A | | A |
| I-254 | A | | A |
| I-255 | A | | B |
| I-256 | A | | A |
| I-257 | B | | A |
| I-258 | A | | A |
| I-259 | A | | A |
| I-260 | A | | A |
| I-261 | A | | A |
| I-262 | A | | A |
| I-263 | A | | A |
| I-265 | A | | A |
| I-266 | A | | A |
| I-267 | A | | A |
| I-268 | A | | A |
| I-271 | B | | A |
| I-272 | B | | B |
| I-273 | A | | A |
| I-274 | B | | D |
| I-275 | B | | A |
| I-277 | A | | A |
| I-278 | A | | A |
| I-279 | A | | A |
| I-280 | B | | A |
| I-281 | B | | B |
| I-282 | B | | B |
| I-284 | B | | |
| I-285 | B | | C |
| I-286 | B | | |
| I-287 | B | | D |
| I-288 | A | A | C |
| I-289 | B | A | |
| I-290 | B | | |
| I-291 | B | | |
| I-292 | B | | |
| I-293 | B | | |
| I-294 | B | | |
| I-295 | B | A | B |
| I-297 | B | A | A |
| I-298 | A | A | C |
| I-299 | B | A | B |
| I-300 | B | A | B |
| I-301 | A | | |
| I-302 | A | | A |
| I-303 | B | A | A |
| I-304 | B | A | B |
| I-305 | B | A | A |
| I-306 | B | A | A |
| I-307 | A | | A |
| I-308 | A | | A |
| I-309 | A | A | A |

TABLE 4

| Compound # | XBP1 (IC50) | H929 (IC50) | DU4475 (IC50) |
|---|---|---|---|
| C-1 | A | A | A |
| C-2 | B | B | B |
| C-3 | B | B | B |
| C-4 | B | B | B |
| C-5 | A | A | A |
| C-6 | B | B | A |
| C-7 | B | B | B |
| C-8 | B | | |
| C-9 | B | | |
| C-10 | C | | |
| C-11 | B | A | A |
| C-12 | B | B | A |
| C-13 | A | B | A |
| C-14 | B | B | A |
| C-15 | B | A | A |
| C-16 | A | A | A |
| C-17 | | D | D |
| C-18 | C | B | B |
| C-19 | B | B | A |
| C-20 | A | A | A |

TABLE 4-continued

| Compound # | XBP1 (IC50) | H929 (IC50) | DU4475 (IC50) |
|---|---|---|---|
| C-21 | A | A | A |
| C-22 |   | D | D |
| C-23 | A | A | A |
| C-24 | A | B | A |
| C-25 | A |   |   |
| C-26 | B |   |   |
| C-27 | B |   |   |
| C-28 | B |   |   |
| C-29 | A |   |   |
| C-30 | B | B | B |
| C-31 | A | B | A |
| C-32 | A | A | A |
| C-33 |   | B | B |
| C-34 | D | B | B |
| C-35 | A | A | A |
| C-36 | A | A | A |
| C-37 |   | A | A |
| C-38 | C | B | B |
| C-39 | B | B | A |
| C-40 | A | B | A |
| C-41 | A | C | A |
| C-42 | B | A | A |
| C-43 | A |   |   |
| C-44 | B |   |   |
| C-45 | B |   |   |
| C-46 | C |   |   |
| C-47 | B |   |   |
| C-48 | B |   |   |
| C-49 |   |   |   |
| C-50 | A |   |   |
| C-51 |   |   |   |
| C-52 | B |   |   |
| C-53 | A |   |   |
| C-54 | A |   |   |
| C-55 | B |   |   |
| C-56 | C |   |   |
| C-57 | B |   |   |
| C-58 |   |   |   |
| C-59 | A |   |   |
| C-60 | B |   |   |
| C-61 | A |   |   |
| C-62 | D |   |   |
| C-63 | D |   |   |
| C-64 | C |   |   |
| C-65 |   |   |   |
| C-66 |   |   |   |
| C-67 | D |   |   |
| C-68 | A |   |   |
| C-69 |   |   |   |
| C-70 | A |   |   |
| C-71 | D |   |   |
| C-72 | A |   |   |
| C-73 |   |   |   |
| C-74 |   |   |   |
| C-75 | A |   |   |
| C-76 | A |   |   |
| C-77 | B |   |   |
| C-78 | A |   |   |
| C-79 | D |   |   |
| C-80 | A |   |   |
| C-81 | D |   |   |
| C-82 | B |   |   |
| C-83 |   |   |   |
| C-84 |   |   |   |
| C-85 | A |   |   |
| C-86 | D |   |   |
| C-87 | B |   |   |
| C-88 | C |   |   |
| C-89 | B |   |   |
| C-90 | A |   |   |
| C-91 | B |   |   |
| C-92 |   |   |   |
| C-93 | A |   |   |
| C-94 | A |   |   |
| C-95 | A |   |   |
| C-96 | B |   |   |
| C-97 | B |   |   |
| C-98 | A |   |   |
| C-99 | B |   |   |
| C-100 | C |   |   |
| C-101 | B |   |   |
| C-102 | B |   |   |
| C-103 | A |   |   |
| C-104 | D |   |   |
| C-105 | A |   |   |
| C-106 |   |   |   |
| C-107 |   |   |   |
| C-108 |   |   |   |
| C-109 |   |   |   |
| C-110 | D |   |   |
| C-111 |   |   |   |
| C-112 | B |   |   |
| C-113 | A |   |   |
| C-114 | D |   |   |
| C-115 | A |   |   |
| C-116 |   |   |   |
| C-117 | A |   |   |
| C-118 |   |   |   |
| C-119 | A |   |   |
| C-120 | A |   |   |
| C-121 | D |   |   |
| C-122 | A |   |   |
| C-123 | B |   |   |
| C-124 | A |   |   |
| C-125 | B |   |   |
| C-126 | B |   |   |
| C-127 | C |   |   |
| C-128 | B |   |   |
| C-129 | D |   |   |
| C-130 | B |   |   |
| C-131 | B |   |   |
| C-132 |   |   |   |
| C-133 |   |   |   |
| C-134 | A |   |   |
| C-135 |   |   |   |
| C-136 | D |   |   |
| C-137 |   |   |   |
| C-138 |   |   |   |
| C-139 | D |   |   |
| C-140 |   |   |   |
| C-141 | A |   |   |
| C-142 |   |   |   |
| C-143 | B |   |   |
| C-144 | B |   |   |
| C-145 |   |   |   |
| C-146 | A |   |   |
| C-147 |   |   |   |
| C-148 |   |   |   |
| C-149 | C |   |   |
| C-150 | B |   |   |
| C-151 | A | A | A |
| C-152 | A | A | A |
| C-153 | A | A | A |
| C-154 | A | A | A |
| C-155 |   | D | D |

TABLE 5

| Compound # | XBP1 (IC50) | H929 (IC50) |
|---|---|---|
| D-1 | B | D |
| D-2 | A | A |
| D-3 | B | D |
| D-4 | A | D |
| D-5 | B | B |
| D-6 | B | B |
| D-7 | B | A |
| D-8 | B | D |
| D-9 | A | A |
| D-10 | A | A |
| D-11 | C | C |
| D-12 | B | B |
| D-13 | B | D |

TABLE 5-continued

| Compound # | XBP1 (IC50) | H929 (IC50) |
|---|---|---|
| D-14 | A | A |
| D-15 | | |
| D-16 | B | |
| D-17 | B | B |
| D-18 | B | B |
| D-19 | B | B |
| D-20 | A | A |
| D-21 | A | B |
| D-22 | A | A |
| D-23 | A | D |
| D-24 | A | D |
| D-25 | A | D |
| D-26 | A | A |
| D-27 | A | C |
| D-28 | A | A |
| D-29 | A | D |
| D-30 | A | A |
| D-31 | A | A |
| D-32 | B | |
| D-33 | C | D |
| D-34 | A | A |
| D-35 | C | C |
| D-36 | A | A |
| D-37 | B | D |
| D-38 | A | A |
| D-39 | B | B |
| D-40 | A | A |
| D-41 | A | A |
| D-42 | B | B |
| D-43 | B | B |
| D-44 | B | |
| D-45 | A | A |
| D-46 | A | A |
| D-47 | B | |
| D-48 | B | |
| D-49 | A | A |
| D-50 | A | A |
| D-51 | A | A |
| D-52 | A | A |
| D-53 | C | |
| D-54 | A | B |
| D-55 | A | A |
| D-56 | D | C |
| D-57 | A | A |
| D-58 | A | A |
| D-59 | A | A |
| D-60 | A | B |
| D-61 | A | B |
| D-62 | C | |
| D-63 | A | A |
| D-64 | B | B |
| D-65 | A | A |
| D-66 | C | |
| D-67 | B | |
| D-68 | A | A |
| D-69 | B | |
| D-70 | C | |
| D-71 | A | A |
| D-72 | B | |
| D-73 | B | |
| D-74 | A | |
| D-75 | A | |
| D-76 | A | |
| D-77 | B | |
| D-78 | A | A |
| D-79 | B | |
| D-80 | A | A |
| D-81 | A | A |
| D-82 | B | |
| D-83 | A | |
| D-84 | B | |
| D-85 | B | |
| D-86 | A | A |
| D-87 | D | |
| D-88 | C | |
| D-89 | C | |
| D-90 | A | |
| D-91 | A | |
| D-92 | B | |
| D-93 | A | |
| D-94 | C | |
| D-95 | B | |
| D-96 | B | |
| D-97 | A | |
| D-98 | A | |
| D-99 | A | |
| D-100 | B | |
| D-101 | A | |
| D-102 | D | |
| D-103 | C | |
| D-104 | A | A |
| D-105 | A | |
| D-106 | A | |
| D-107 | B | |
| D-108 | C | |
| D-109 | A | |
| D-110 | A | A |
| D-111 | A | A |
| D-112 | A | |
| D-113 | B | |
| D-114 | D | |
| D-115 | B | |
| D-116 | A | A |
| D-117 | A | A |
| D-118 | B | |
| D-119 | A | A |
| D-120 | A | |
| D-121 | D | |
| D-122 | A | |
| D-123 | C | |
| D-124 | A | |
| D-125 | A | |
| D-126 | A | |
| D-127 | A | |
| D-128 | B | |
| D-129 | D | |
| D-130 | D | |
| D-131 | D | |
| D-132 | A | |
| D-133 | A | |
| D-134 | D | |
| D-135 | D | |
| D-136 | A | |
| D-137 | A | |
| D-138 | D | |
| D-139 | B | |
| D-140 | D | |
| D-141 | D | B |
| D-142 | D | A |
| D-143 | D | D |
| D-144 | D | D |
| D-145 | D | D |
| D-146 | D | D |
| D-147 | | |
| D-148 | | |
| D-149 | | |
| D-150 | | |
| D-151 | | |
| D-152 | D | D |
| D-153 | D | D |
| D-154 | D | D |
| D-155 | D | D |
| D-156 | D | |
| D-157 | D | D |
| D-158 | D | D |
| D-159 | D | D |
| D-160 | D | |
| D-161 | D | |
| D-162 | D | |
| D-163 | D | |
| D-164 | D | |
| D-165 | D | |
| D-166 | D | |
| D-167 | D | |
| D-168 | D | |
| D-169 | D | |

TABLE 5-continued

| Compound # | XBP1 (IC50) | H929 (IC50) |
|---|---|---|
| D-170 | D | |
| D-171 | D | |
| D-172 | D | |
| D-173 | D | |
| D-174 | D | |
| D-175 | D | |
| D-176 | D | |
| D-177 | D | |
| D-178 | D | |
| D-179 | D | |
| D-180 | D | |
| D-181 | D | |
| D-182 | D | |
| D-183 | D | |
| D-184 | D | |
| D-185 | D | |
| D-186 | D | |
| D-187 | D | |
| D-188 | D | |
| D-189 | D | |
| D-190 | D | |
| D-191 | D | |
| D-192 | | |
| D-193 | | |

Example 59

Synthetic of (+/−)-4-(3-(2-chloro-4-(methylsulfonyl)phenyl)-1,4-oxazepan-4-yl)-6-methylpyrimidin-2-amine (I-66), and (R)-4-(3-(2-chloro-4-(methylsulfonyl)phenyl)-1,4-oxazepan-4-yl)-6-methylpyrimidin-2-amine (I-67) and (S)-4-(3-(2-chloro-4-(methylsulfonyl)phenyl)-1,4-oxazepan-4-yl)-6-methylpyrimidin-2-amine (I-68)

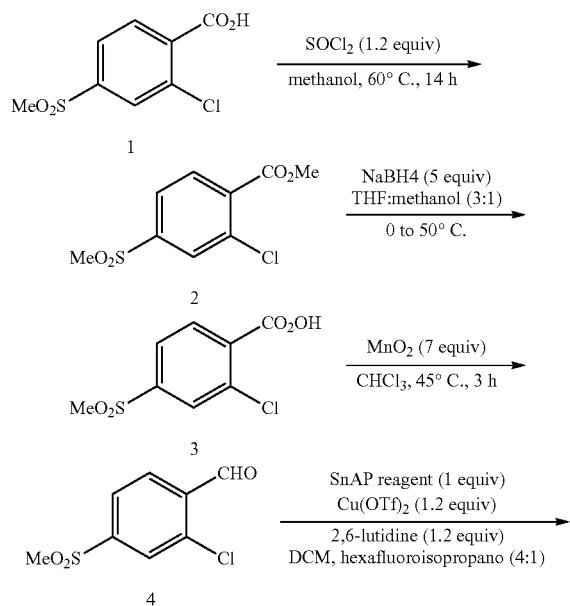

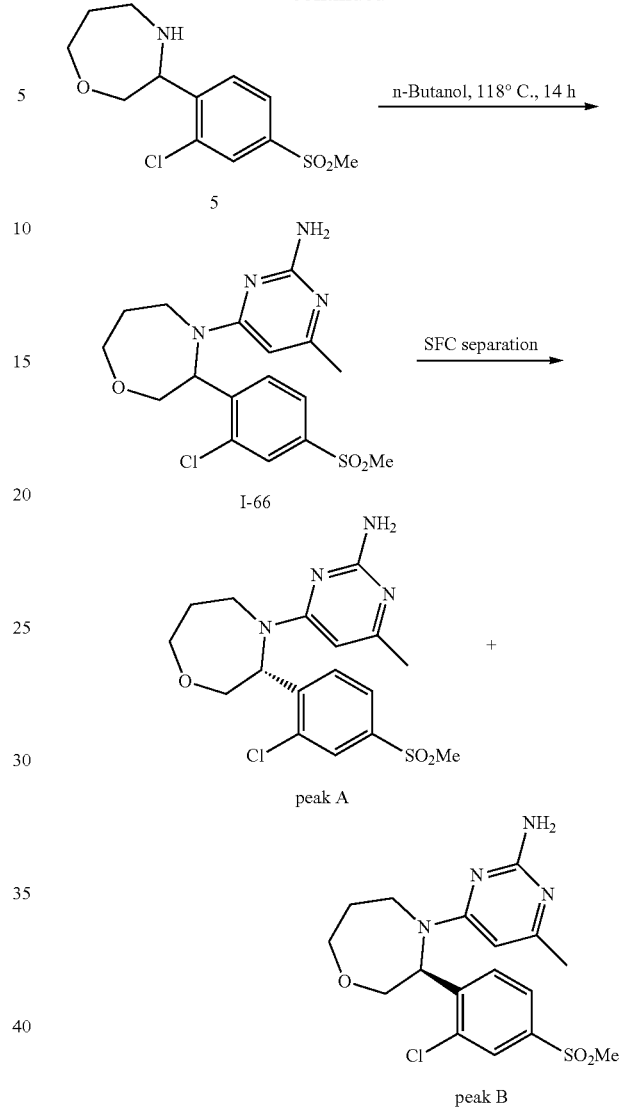

peak A peak B

Formation of methyl 2-chloro-4-methylsulfonyl-benzoate

A 5 L 3-neck RB flask with overhead stirrer, temperature probe, reflux condenser and additional funnel was charged 2-chloro-4-methylsulfonylbenzoic acid (100 g, 426.2 mmol) in methanol (1.5 L), stirred for 10 minutes and then cooled to 0° C. with an ice bath. Thionyl chloride (40 mL, 548.4 mmol) was added over 20 minutes, allowed to ambient temperature over 1 h and then warmed to 60° C., stirred at this temperature for 12 h (overnight) at which time LCMS and HPLC-analysis revealed consumption of the starting material.

HPLC shows starting material 1 peak retention time at 1.23 minutes, desired product 2 peak retention time at 2.37 minutes.

Reaction mixture was cooled to ambient temperature, concentrated under reduced pressure, the crude material was partitioned between ethyl acetate (1 L) and aqueous sat. NaHCO₃ solution (500 mL), stirred for 20 minutes and then organic phase was separated. Aqueous layer was extracted with ethyl acetate (500 mL), combined organic phase were washed with water, (100 mL), brine (100 mL), dried over $Na_2SO_4$, filtered and concentrated under reduced pressure to afford methyl 2-chloro-4-methylsulfonyl-benzoate (106 g, 99%) as a white solid. 1H-NMR conform to structure.

1H NMR (400 MHz, CDCl3) δ 8.04 (d, J=1.6 Hz, 1H), 8.00-7.93 (m, 1H), 7.88 (dd, J=8.1, 1.8 Hz, 1H), 3.98 (s, 3H), 3.08 (s, 3H).

Formation of
(2-chloro-4-methylsulfonyl-phenyl)methanol

A 5 L 3-neck RB flask with overhead stirrer, temperature probe and reflux condenser was charged methyl 2-chloro-4-methylsulfonyl-benzoate (110 g, 437.9 mmol) in a mixture of THF (1.3 L) and methanol (450 mL), stirred for 10 minutes and then cooled to 0° C. with an ice bath. $NaBH_4$ (85 g, 2.247 mol) was added in four portion over 30 minutes. After the addition cooling bath was removed and allowed to ambient temperature (observed exotherm, T max 50° C.), stirred at this temperature (40 to 50° C.) for 4 h at which time TLC, and HPLC-analysis revealed consumption of the starting material.

HPLC shows starting material 1 peak retention time at 2.47 minutes, desired product 3 peak retention time at 1.48 minutes. TLC (50% ethyl acetate in Heptane) shows starting material Rf=0.5 and product Rf=0.4.

The reaction mixture was cooled to ambient temperature, quenched with slow addition of methanol (100 mL), followed by aqueous 1 N HCl solution (~1 L) until pH ~7 to 8. The reaction mixture was extracted with ethyl acetate (2×500 mL). The combined organic phase was washed with brine (~300 mL), dried over $Na_2SO_4$, filtered and concentrated under reduced pressure to afford (2-chloro-4-methylsulfonyl-phenyl)methanol (90 g, 92%) as a white solid. 1H-NMR conform to structure.

1H NMR (400 MHz, CDCl3) δ 7.92 (d, J=1.8 Hz, 1H), 7.85 (dd, J=8.1, 1.8 Hz, 1H), 7.78 (d, J=8.1 Hz, 1H), 4.87 (d, J=5.9 Hz, 2H), 3.06 (s, 3H).

This material was taken into the next step without further purification.

Formation of
2-chloro-4-methylsulfonyl-benzaldehyde

A 5 L 3-neck RB flask with overhead stirrer, temperature probe and reflux condenser was charged (2-chloro-4-methylsulfonyl-phenyl)methanol (96 g, 435.0 mmol) in $CHCl_3$ (2.5 L), stirred for 15 minutes and then added Manganese dioxide (250 g, 2.876 mol). The resulting reaction mixture was warmed to 45° C. (exotherm T max 50° C.), stirred at this temperature for 3 h at which time TLC-analysis revealed consumption of the starting material. TLC (50% EtOAc/heptane) shows no more starting material (Rf=0.2).

The reaction mixture was filtered through celite bed, bed was washed with DCM (3×100 mL), combined filtrates were concentrated under reduced pressure to afford 2-chloro-4-methylsulfonyl-benzaldehyde (82.5 g, 86%) as a white solid. 1H-NMR conform to structure.

1H NMR (400 MHz, CDCl3) δ 10.54 (d, J=0.8 Hz, 1H), 8.13-8.09 (m, 1H), 8.07 (d, J=1.7 Hz, 1H), 7.95 (ddd, J=8.1, 1.7, 0.8 Hz, 1H), 3.11 (s, 3H).

Formation of 2-chloro-methylsulfonylphenyl
oxazepane

To a solution of 3-(tributylstannylmethoxy)propan-1-amine (70 g, 185.1 mmol) in anhydrous dichloromethane (1.4 L) was added 2-chloro-4-methylsulfonyl-benzaldehyde (40 g, 182.9 mmol) followed by 4 angstrom molecular sieves (130 g). The mixture was stirred for 12 h at which time 1H-NMR of the aliquot revealed consumption of the starting materials.

1H NMR (300 MHz, CDCl3) δ 8.72 (d, J=0.5 Hz, 1H), 8.23 (d, J=8.2 Hz, 1H), 7.97 (d, J=1.6 Hz, 1H), 7.83 (ddd, J=8.2, 1.8, 0.7 Hz, 1H), 3.89-3.63 (m, 4H), 3.40 (t, J=6.1 Hz, 2H), 3.07 (s, 3H), 1.96 (p, J=6.7 Hz, 2H), 1.70-1.39 (m, 8H), 1.40-1.19 (m, 6H), 0.98-0.77 (m, 15H).

The reaction mixture was filtered through celite bed, bed was washed with dichloromethane (1.5 L). In a separate flask containing hexafluoroisopropanol (700 mL) was added 2,6-lutidine (25 mL, 215.8 mmol) followed by $Cu(OTf)_2$ (70 g, 193.5 mmol) [$Cu(OTf)_2$ was dried under reduced pressure for 8 h at 100° C.]. The blue suspension was stirred for 1 h, then the imine solution (product 3) prepared above was added in one portion. The green reaction mixture was stirred overnight at room temperature.

LCMS shows small peak corresponding to desired product —RT=0.48 minutes (M+H) 289.95. The mixture was diluted with 1.7 L of 2:1 aqueous saturated $NaHCO_3$ solution and 10% ammonium hydroxide. After stirring for 30 minutes, the organic phase was separated, washed twice with aqueous saturated $NaHCO_3$ solution (2×200 mL), brine (~200 mL), dried over $Na_2SO_4$, filtered and concentrated under reduced pressure.

The residue was diluted with acetonitrile (600 mL), washed with heptane (4×100 mL) to remove stannane impurities. Acetonitrile phase (bottom layer) was evaporated under reduced pressure to afford yellow solid which was triturated with MTBE (400 mL), filtered through medium fritted funnel, rinsed with MTBE (100 mL) to afford desired product 4 (28 g, 52% yield) as a yellow solid. 1H-NMR and LCMS conform to structure. 1H NMR (400 MHz, DMSO) δ 7.96-7.92 (m, 1H), 7.92-7.83 (m, 2H), 4.31 (dd, J=8.7, 3.3 Hz, 1H), 3.94-3.78 (m, 2H), 3.78-3.62 (m, 1H), 3.36-3.28 (m, 2H), 3.26 (s, 3H), 3.18-3.04 (m, 1H), 3.00-2.82 (m, 2H), 1.98-1.71 (m, 2H). ESI-MS m/z calc. 289.05396, found 290.1 (M+1)+. Retention time: 0.49 minutes.

Filtrate was concentrated under reduced pressure to afford light brown oil which was purified by silica gel chromatography (330 g isco column linear gradient, 20 CV, 0%→100% ethyl acetate which contain 1% $Et_3N/CH_2Cl_2$), fractions which contained desired product were collected, concentrated under reduced pressure, followed by trituration with MTBE (~100 mL) to afford desired product 4 (5.8 g) as a yellow solid. 1H-NMR conform to structure.

Formation of I-66

A 2 L 3-neck RB flask with overhead stirrer, temperature probe, reflux condenser and nitrogen inlet was charged 3-(2-chloro-4-methylsulfonyl-phenyl)-1,4-oxazepane (28 g, 92.76 mmol) in n-BuOH (550 mL), stirred for 15 minutes and then added 4-chloro-6-methyl-pyrimidin-2-amine (17 g, 118.4 mmol). The resulting reaction mixture was warmed to 118° C., stirred at this temperature for 14 h (overnight), at which time HPLC and LCMS analysis revealed consumption of the starting material. The reaction mixture was cooled to ambient temperature (observed precipitation), diluted with MTBE (500 mL). stirred for 30 minutes white precipitate was formed which was filtered through medium fritted funnel, rinsed with MTBE (2×100 mL).

The precipitate (HCl salt of product 3) was partitioned between ethyl acetate (500 mL) and aqueous sat. $NaHCO_3$ solution (~700 mL), stirred for 30 minutes (pH ~8), organic phase was separated. Aqueous phase was extracted with ethyl acetate (2×100 mL), combined organic phase was washed with brine (~100 mL), dried over Na₂SO₄, filtered and concentrated under reduced pressure.

The residue was purified by trituration with 10% ethyl acetate in MTBE (500 mL) to afford 4-[3-(2-chloro-4-methylsulfonyl-phenyl)-1,4-oxazepan4-yl]-6-methyl-pyrimidin-2-amine (32 g, 86%) as a white solid. 1H-NMR and LCMS conform to structure. 1H NMR (400 MHz, DMSO) δ 7.96 (d, J=1.7 Hz, 1H), 7.82 (dd, J=8.2, 1.8 Hz, 1H), 7.58 (d, J=8.2 Hz, 1H), 5.69 (d, J=8.6 Hz, 1H), 5.61 (dd, J=9.7, 4.6 Hz, 1H), 5.46 (s, 2H), 4.52 (d, J=15.6 Hz, 1H), 4.16 (dd, J=13.5, 4.9 Hz, 1H), 3.92 (dt, J=12.0, 3.8 Hz, 1H), 3.85-3.69 (m, 2H), 3.66-3.53 (m, 1H), 3.23 (s, 3H), 2.05 (s, 3H), 1.88-1.76 (m, 2H). ESI-MS m/z calc. 396.1023, found 397.1 (M+1)+. Retention time: 0.55 minutes.

Formation of I-67 and I-68

I-66 (66 g, 166.3 mmol) was separated via SFC using AD-H column with 30% MeOH and 0.2% ammonia.

Peak B obtained by SFC is desired enantiomer (S-conformer) which was dissolved in CH2Cl2 (1 L), washed with aqueous sat. NaHCO₃ solution (2×200 mL), water (50 mL), brine (100 mL), dried over Na2SO4, filtered through silicagel bed (~80 g), bed was washed with DCM (60 mL). Combined filtrates were concentrated under reduced pressure to afford desired product as an amorphous material ~32 g, which was dissolved in ethyl acetate (200 mL), concentrated under reduced pressure. This material was triturated with MTBE (2×200 mL) to afford white solid, followed by azeotropped with ethyl acetate (200 mL), and 1:1 mixture of ethyl acetate and heptane (2×200 mL), dried in vacuum oven at 50° C. for 14 h to afford desired product which contained residual solvent ethyl acetate ~4.6% by moles, which was further dried in vacuum oven at 70° C. for 14 h to afford 4-[(3S)-3-(2-chloro-4-methylsulfonyl-phenyl)-1,4-oxazepan-4-yl]-6-methyl-pyrimidin-2-amine (28.7 g, 85%) ~2.6% by moles of residual ethyl acetate. 1H NMR (400 MHz, DMSO) δ 7.96 (s, 1H), 7.83 (dd, J=8.2, 1.4 Hz, 1H), 7.58 (d, J=8.2 Hz, 1H), 5.70 (s, 1H), 5.66-5.55 (m, 1H), 5.46 (s, 2H), 4.52 (d, J=14.9 Hz, 1H), 4.16 (dd, J=13.5, 4.9 Hz, 1H), 4.00-3.88 (m, 1H), 3.85-3.70 (m, 2H), 3.65-3.52 (m, 1H), 3.23 (s, 3H), 2.05 (s, 3H), 1.88-1.72 (m, 2H).

ESI-MS m/z calc. 396.1023, found 397.15 (M+1)+. Retention time: 0.55 minutes.

XRPD confirms material is crystalline.
DSC shows melting point 194° C.
Small molecule X-ray crystal structure for the peak B confirms this is S-conformer.
[α]$_D^{23}$=29.47 (c=1.1, MeOH) for 99.4% ee (peak B)
Peak A (R-conformer)
4-[(3R)-3-(2-chloro-4-methylsulfonyl-phenyl)-1,4-oxazepan-4-yl]-6-methyl-pyrimidin-2-amine (25 g, 74%) as an off-white solid.
ESI-MS m/z calc. 396.1023, found 397.1 (M+1)+. Retention time: 0.55 minutes.
[α]$_D^{23}$=−23.33 (c=1.0, MeOH) for 99% ee (peak A)

Example 60

Synthethis of 3-chloro-6,7-dihydro-1,4-oxazepine-4 (5H)-carbaldehyde

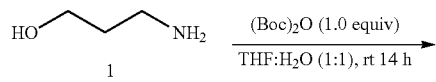

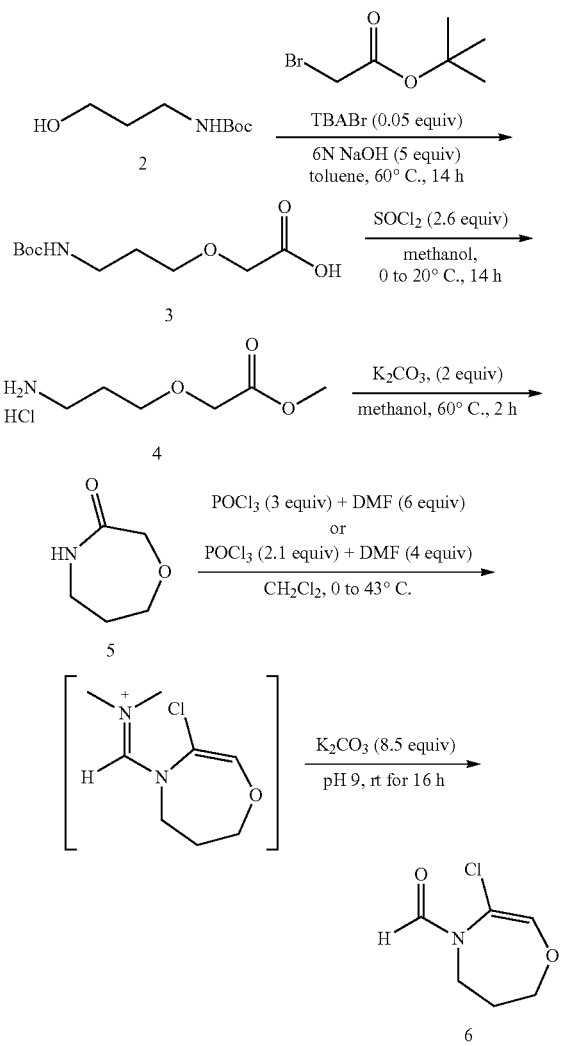

Formation of tert-butyl N-(3-hydroxypropyl)carbamate

A 3-neck 2 L RB flask with magnetic stirrer, temperature probe was charged 3-aminopropan-1-ol (43 g, 572.5 mmol) in a mixture of THF (450 mL) and water (450 mL), stirred for 10 minutes and then cooled to 0° C. with an ice-bath. tert-butoxycarbonyl tert-butyl carbonate (131 g, 600.2 mmol) was added portion wise over 10 minutes and then the resulting reaction mixture was slowly allowed to ambient temperature over 12 h (overnight) at which time TLC (50% ethyl acetate in heptane)-analysis revealed consumption of the starting material. Reaction mixture was concentrated to ~50% of the volume (to remove THF) and then extracted with DCM (2×500 mL). Combined organic extracts were washed with water (100 mL), brine (100 ml), dried over Na2SO4, filtered and concentrated under reduced pressure to afford tert-butyl N-(3-hydroxypropyl)carbamate (98 g, 98%) as a clear, colorless oil. 1H-NMR conform to structure. 1H NMR (300 MHz, Chloroform-d) δ 4.73 (s, 1H), 3.66 (t, J=5.7 Hz, 2H), 3.28 (t, J=6.2 Hz, 2H), 2.55 (s, 1H), 1.77-1.58 (m, 2H), 1.44 (s, 9H).

Formation of 2-[3-(tert-butoxycarbonylamino) propoxy]acetic Acid

A 3-neck 2 L RB flask with overhead stirrer, temperature probe and reflux condenser was charged tert-butyl N-(3-hydroxypropyl)carbamate (42 g, 239.7 mmol) and tetrabutylammonium (Bromide Ion (1)) (4 g, 12.41 mmol) in toluene (300 mL), stirred for 5 minutes and then cooled to 0° C. with an ice bath. NaOH (200 mL of 6 M, 1.200 mol) was added while maintaining internal temperature below 10° C. and stirred further 20 minutes. tert-butyl 2-bromoacetate (55 g, 282.0 mmol) in toluene (50 mL) was added over 5 minutes. The resulting reaction mixture was warmed to 60° C. (T max 65° C.), stirred at this temperature for 14 h. Reaction mixture was cooled to ambient temperature and layers were separated, aqueous layer was extracted with toluene (60 mL). Aqueous phase was cooled to 0° C. with an ice bath and acidified with 12 N HCl until pH is 3. Ethyl acetate (150 mL) was added and the layers were separated, aqueous layer was extracted with ethyl acetate (50 mL). Combined organic layer was dried over Na2SO4, filtered and concentrated under reduced pressure to afford 2-[3-(tert-butoxycarbonylamino)propoxy]acetic acid (36 g, 61%) as a clear, colorless oil which contained small amounts of ethyl acetate. 1H NMR (300 MHz, MeOD) δ 4.07 (s, 2H), 3.60-3.54 (m, 2H), 3.32-3.30 (m, 2H), 1.79-1.70 (m, 2H), 1.47 (s, 9H)

This material was taken into the next step without further purification.

Formation of methyl 2-(3-aminopropoxy)acetate

A 3-neck 1 L RB flask with magnetic stirrer, temperature probe, was charged 2-[3-(tert-butoxycarbonylamino) propoxy]acetic acid (12 g, 51.44 mmol) in methanol (120.0 mL), stirred for 5 minutes and then cooled to 0° C. with an ice bath. thionyl chloride (10 mL, 137.1 mmol) was added over 10 minutes and then slowly allowed to ambient temperature for 12 h (overnight). Reaction mixture was concentrated under reduced pressure. The residue was azeotropped with DCM (2×60 mL) to afford methyl 2-(3-aminopropoxy)acetate (Hydrochloride salt) (10 g, 95%), ~90% purity as a clear, colorless viscous oil. 1H-NMR conform to structure. 1H NMR (300 MHz, DMSO-d6) δ 8.05 (s, 3H), 4.12 (s, 2H), 3.66 (s, 3H), 3.54 (t, J=6.0 Hz, 2H), 2.84 (t, J=7.4 Hz, 2H), 1.95-1.75 (m, 2H).

This material was taken into the next step without further purification.

Formation of 1,4-oxazepan-3-one

A 3-neck 1 L RB flask with magnetic stirrer, temperature probe and reflux condenser was charged methyl 2-(3-aminopropoxy)acetate (Hydrochloride salt) (10 g, 49.01 mmol) in methanol (100 mL), stirred for 5 minutes and then added K2CO3 (14 g, 101.3 mmol). The resulting reaction mixture was warmed to 60° C., stirred at this temperature for 2 h, observed desired product 2 spot (TLC 10% methanol in DCM) and baseline spot could be starting material). Reaction mixture was cooled to ambient temperature, filtered through celite bed, bed was washed with methanol (2×25 mL). Combined filtrates were concentrated under reduced pressure. The residue was partitioned between DCM (150 mL) and water (50 mL), organic phase was separated, washed with brine (50 mL), dried over Na2SO4, filtered and concentrated under reduced pressure. The residue was purified by silica gel chromatography (40 g isco column linear gradient, 20 CV, 0%→20% methanol/DC), fractions which contained desired product were collected, concentrated under reduced pressure to afford 1,4-oxazepan-3-one (1.8 g, 32%) as a white solid. 1H-NMR conform to structure. 1H NMR (300 MHz, DMSO-d6) δ 7.65 (s, 1H), 3.99 (s, 2H), 3.83-3.61 (m, 2H), 3.25-3.06 (m, 2H), 1.87-1.62 (m, 2H).

Formation of 3-chloro-6,7-dihydro-5H-1,4-oxazepine-4-carbaldehyde

A 3-neck 2 L RB flask with overhead stirrer, temperature probe, additional funnel, nitrogen inlet and reflux condenser was charged DMF (141.6 g, 150.0 mL, 1.937 mol) in DCM (300.0 mL), stirred for 5 minutes and then cooled to 0° C. with an ice bath. POCl3 (90 mL, 965.6 mmol) in DCM (100.0 mL) was added over 30 minutes while maintaining the internal temperature below 6° C. Reaction mixture was warmed to 40° C. (Note: reaction mixture turned into clear, red color solution and observed exotherm, maintained internal temperature ~40° C.) stirred at this temperature for 45 minutes. 1,4-oxazepan-3-one (50 g, 434.3 mmol) in DCM (300 mL) was added over 40 minutes, observed exotherm, maintained internal temperature ~40° C. The resulting reaction mixture was stirred at this temperature for 90 minutes at which time TLC (10% methanol in DCM) and LCMS-analysis revealed consumption of the starting material 1, major peak RT=0.51 minutes (M+H)+ 189/191 which corresponds to the amidine intermediate. Reaction mixture was cooled to ambient temperature, poured into crushed ice (1.2 L), and then allowed to ambient temperature over 1 h and stirred further 1 h. Separated the aqueous layer, basified with solid K2CO3 until pH 9, allowed to ambient temperature, stirred at this temperature for 12 h (overnight) at which time LCMS-analysis revealed major peak at 0.69 minutes (M+1)+162.04 which corresponds to desired product 2. Reaction mixture was diluted with DCM (300 mL), organic layer was separated. Aqueous layer was extracted with DCM (100 mL), combined organic extracts were dried over Na2SO4, filtered and concentrated under reduced pressure. The residue was purified by silica gel chromatography (330 g isco column linear gradient, 20 CV, 0%→50% ethyl acetate/heptane-which contained 1% Et3N), fractions which contained desired product were collected, concentrated under reduced pressure to afford 3-chloro-6,7-dihydro-5H-1,4-oxazepine-4-carbaldehyde (41 g, 58%) as a clear, colorless oil. 1H NMR (400 MHz, DMSO-d6) δ 8.32 (rotamer; d, J=157.3 Hz, 1H), 6.59 (d, J=4.2 Hz, 1H), 4.19-3.87 (m, 2H), 3.85-3.51 (m, 2H), 2.02-1.71 (m, 2H).

1H-NMR shows mixture of rotamers.

Compounds in Table 2A are prepared by synthesis methods similar to those as described above. Analytical data of some of the compounds are listed below.

| D# | NMR | LC/MS | HPLC Purity | enantiomeric purity | melting point (° C.) |
|---|---|---|---|---|---|
| 1 | 1H NMR (400 MHz, DMSO-d6) δ 7.32 (s, 1H), 7.24 (d, J = 8.6 Hz, 1H), 7.09 (d, J = 8.8 Hz, 1H), 5.83 (s, 3H), 5.34 (s, 2H), 5.04 (s, 1H), 4.06 (d, J = 11.9 Hz, 2H), 3.91 (d, J = 12.9 Hz, 1H), 3.76-3.61 (m, 2H), 3.54 (s, 1H), 3.05 (s, 3H), 1.99 (s, 3H), 1.74 (s, 2H). | [M + H]+ Cac. 427.9; found 427.2 | 100 | first eluting isomer (SFC ADH-100 column) ee = >99% | |
| 2 | 1H NMR (400 MHz, DMSO-d6) δ 7.32 (s, 1H), 7.24 (d, J = 8.7 Hz, 1H), 7.09 (dd, J = 8.7, 2.6 Hz, 1H), 5.83 (s, 3H), 5.34 (s, 2H), 5.03 (s, 1H), 4.07 (d, J = 13.2 Hz, 2H), 3.91 (d, J = 12.5 Hz, 1H), 3.77-3.58 (m, 2H), 3.55 (d, J = 13.8 Hz, 1H), 3.05 (s, 3H), 1.99 (s, 3H), 1.74 (s, 2H). | [M + H]+ Cac. 427.9; found 427.2 | 100 | second eluting isomer (SFC ADH column) ee = >99% | |
| 3 | 1H NMR (400 MHz, Methanol-d4) δ 7.93 (d, J = 1.8 Hz, 1H), 7.77 (dd, J = 8.2, 1.9 Hz, 1H), 7.56 (d, J = 8.2 Hz, 1H), 5.75 (s, 3H), 4.32 (dd, J = 13.6, 5.0 Hz, 1H), 4.09-3.99 (m, 2H), 3.86-3.72 (m, 2H), 3.64 (td, J = 11.8, 3.5 Hz, 1H), 2.57-2.42 (m, 2H), 2.26-2.16 (m, 2H), 2.13 (s, 3H), 2.08-1.93 (m, 3H), 1.91-1.83 (m, 1H). | [M + H]+ Cac. 437.0; found 437.1 | 100 | first eluting isomer (SFC IA-100 column) ee = >99% | |
| 4 | 1H NMR (400 MHz, DMSO-d6) δ 7.20 (dd, J = 12.7, 6.7 Hz, 1H), 7.06 (dd, J = 11.3, 9.1 Hz, 1H), 5.84 (s, 3H), 5.53-4.77 (m, 2H), 4.13 (s, 1H), 3.97-3.81 (m, 4H), 3.62 (t, J = 12.1 Hz, 2H), 3.53-3.40 (m, 1H), 2.00 (s, 3H), 1.80-1.63 (m, 2H). | [M + H]+ Cac. 351.4; found 351.1 | 100 | first eluting isomer (SFC IC-100 column) ee = >99% | |
| 5 | 1H NMR (400 MHz, DMSO-d6) δ 7.20 (dd, J = 12.7, 6.7 Hz, 1H), 7.13-6.97 (m, 1H), 5.84 (s, 3H), 5.55-4.86 (m, 2H), 4.13 (s, 1H), 3.88 (s, 4H), 3.60 (d, J = 13.1 Hz, 2H), 3.53-3.40 (m, 1H), 2.17-1.88 (m, 3H), 1.71 (s, 2H). | [M + H]+ Cac. 351.4; found 351.1 | 99 | second eluting isomer (SFC IC-100 column) ee = >99% | |
| 6 | 1H NMR (400 MHz, DMSO-d6) δ 10.00 (s, 1H), 7.72-7.54 (m, 2H), 7.37 (d, J = 8.5 Hz, 1H), 5.90 (s, 3H), 5.13 (d, J = 83.3 Hz, 3H), 4.63 (s, 1H), 4.14 (d, J = 13.6 Hz, 1H), 3.93 (d, J = 12.2 Hz, 1H), 3.73-3.61 (m, 3H), 3.54 (td, J = 11.6, 4.4 Hz, 1H), 2.41 (t, J = 6.3 Hz, 2H), 1.98 (s, 3H), 1.77 (s, 2H). | [M + H]+ Cac. 406.9; found 406.1 | 97 | first eluting isomer (SFC IC-100 column) ee = >99% | |
| 7 | 1H NMR (400 MHz, DMSO-d6) δ 10.00 (s, 1H), 7.68-7.54 (m, 2H), 7.37 (d, J = 8.5 Hz, 1H), 5.90 (s, 3H), 5.43-4.86 (m, 3H), 4.63 (s, 1H), 4.14 (d, J = 13.3 Hz, 1H), 3.93 (d, J = 10.5 Hz, 1H), 3.75-3.62 (m, 3H), 3.54 (td, J = 11.5, 4.5 Hz, 1H), 2.41 (t, J = 6.3 Hz, 2H), 1.98 (s, 3H), 1.77 (s, 2H). | [M + H]+ Cac. 406.9; found 406.1 | 100 | second eluting isomer (SFC IC-100 column) ee = >99% | |
| 8 | 1H NMR (400 MHz, DMSO-d6) δ 10.88 (s, 1H), 7.86 (s, 1H), 7.49 (d, J = 8.5 Hz, 1H), 7.29 (d, J = 8.5 Hz, 1H), 6.35 (t, J = 53.7 Hz, 1H), 5.83 (s, 3H), 5.03 (s, 2H), 4.16-4.05 (m, 1H), 3.92 (d, J = 10.6 Hz, 1H), 3.76-3.60 (m, 2H), 3.52 (d, J = 13.7 Hz, 1H), 1.99 (s, 3H), 1.75 (s, 2H). | [M + H]+ Cac. 412.8; found 412.1 | 100 | first eluting isomer (SFC IC-100 column) ee = >99% | |
| 9 | (300 MHz, DMSO-d6): 6.75 (s, 1H), 6.49 (s, 1H), 5.68 (s, 1H), 5.57 (s, 1H), 5.46 (s, 2H), 5.16 (s, 1H), 4.00 (dd, J = 13.5, 5.1 Hz, 1H), 3.89 (d, J = 12.4 Hz, 1H), 3.74-3.41 (m, 3H), 3.15 (s, 2H), 2.65-2.54 (m, 2H), 2.01 (s, 3H), 1.74 (s, 4H). | [M + H]+ Cac. 374.1; found 374.1 | 97.7 | second eluting enantiomer (chiral PAK IG) | 117-119 |
| 10 | 1H NMR (300 MHz, DMSO-d6 mixed with one drop of DCl in deuterium oxide solution, ppm) (contains two rotamers) δ = 7.44 (s, 0.45 H), 7.35 (s, 0.55 H), 6.89-6.87 (m, 1 H), 6.67 (s, 0.55 H), 5.84-5.81 (m, 0.55 H), 5.56 (s, 0.45 H), 5.10-5.06 (m, 0.45 H), 4.98-4.94 (m, 0.45 H), 4.29-4.17 (m, 1.55 H), 3.93-3.81 (m, 2 H), 3.78-3.71 (m, 1 H), 3.63-3.57 (m, 1 H), 2.30 (s, 1.65 H), 2.20 (s, 1.35 H), 1.90-1.72 (m, 2 H). | [M + H]+ Cac. 402.1; found 402.0 | 99.9 | chiral PAK IG | 190-192 |
| 11 | 1H NMR (300 MHz): 7.73-7.71 (m, 1H), 7.19 (d, J = 13.6 Hz, 2H), 5.70-5.67 (m, 1H), 4.47 (d, J = 15.2 Hz, 1H), 4.13-4.03 (m, 1H), 3.88-3.64 (m, 4H), 2.07-2.03 (m, 3H), 1.78 (d, J = 5.6 Hz, 2H). | [M + H]+ Cac. 419.1; found 419.1 | 99.2 | | 148-152 |
| 12 | 1HNMR (300 MHz, DMSO, ppm) 8.93 (s, 1H), 7.60 (s, 1H), 7.09 (s, 1H), 5.57 (s, 1H), 5.46 (s, 2H), 5.33 (s, 1H), 4.66 (d, J = 15.3 Hz, 1H), 4.07 (dd, J = 13.4, 5.0 Hz, 1H), 3.90 (d, J = 11.3 Hz, 1H), 3.78-3.43 (m, 3H), 2.34 (q, J = 7.5 Hz, 2H), 2.14 (s, 3H), 2.00 (s, 3H), 1.76 (s, 2H), 1.10 (t, J = 7.5 Hz, 3H). | [M + H]+ Cac. 404.2; found 404.0 | 99.9 | | 131 |
| 13 | 1H NMR (300 MHz, DMSO-d6) 7.04 (s, 1H), 6.99 (s, 1H), 5.57 (s, 1H), 5.46 (s, 2H), 5.31 (s, 1H), 4.66 (d, J = 14.7 Hz, 1H), 4.05 (dd, J = 13.4, 5.2 Hz, 1H), 3.97-3.81 (m, 1H), 3.77-3.43 (m, 3H), 2.98-2.83 (m, 2H), 2.83-2.67 (m, 2H), 2.16 (s, 3H), 2.00 (s, 3H), 1.75 (s, 2H), 1.60 (t, J = 5.6 Hz, 4H), 1.18 (s, 3H). | [M + H]+ Cac. 446.1; found 446.1 | 98.5 | | 220 |

-continued

| D# | NMR | LC/MS | HPLC Purity | enantiomeric purity | melting point (° C.) |
|---|---|---|---|---|---|
| 14 | (300 MHz, DMSO-d6): 6.92 (s, 1H), 6.45 (s, 1H), 5.56 (s, 1H), 5.47 (s, 2H), 5.22 (s, 1H), 4.74 (d, J = 15.5 Hz, 1H), 4.01 (dd, J = 13.4, 5.1 Hz, 1H), 3.90 (d, J = 11.9 Hz, 1H), 3.74-3.45 (m, 3H), 3.30 (t, J = 8.3 Hz, 2H), 2.83 (t, J = 8.3 Hz, 2H), 2.71 (s, 3H), 2.00 (s, 3H), 1.76 (s, 2H). | [M + H]+ Cac. 374.1; found 374.0 | 99.9 | second eluting enantiomer (chiral PAK IG) | 102-104 |
| 15 | 1HNMR (300 MHz, DMSO, D2O) 6.63 (s, 1H), 6.54 (s, 1H), 5.85 (s, 2H), 5.40 (s, 1H), 5.00 (s, 3H), 4.03-3.80 (m, 2H), 3.68 (s, 5H), 3.50 (t, J = 13.5 Hz, 1H), 1.96 (s, 3H), 1.70 (s, 2H). | [M + H]+ Cac. 363.8; found 363.9 | 99.2 | Chiral ART cellulose SB | 190 |
| 16 | 1H NMR (300 MHz, DMSO-d6) 7.02 (s, 1H), 6.85 (s, 1H), 5.59 (d, J = 11.2 Hz, 3H), 5.33 (s, 1H), 4.60 (s, 1H), 4.07 (dd, J = 13.4, 5.0 Hz, 1H), 3.88 (d, J = 11.6 Hz, 5H), 3.80-3.64 (m, 1H), 3.54 (d, J = 20.5 Hz, 2H), 2.03 (s, 3H), 1.75 (s, 2H), 0.61 (d, J = 3.1 Hz, 4H). | [M + H]+ Cac. 417.0; found 417.0 | 99.7 |  | 105 |
| 17 | 1H NMR (300 MHz, DMSO-d6, ppm, 353 K) δ = 6.71 (s, 1 H), 6.57 (s, 1 H), 5.58 (s, 1H), 5.47 (br s, 2 H), 5.24-5.20 (m, 1 H), 4.72-4.68 (m, 1 H), 4.02 (dd, J = 13.5, 5.1 Hz, 1 H), 3.90-3.86 (m, 1H), 3.76-3.52 (m, 6 H), 3.25-3.22 (m, 4 H), 2.00 (s, 3 H), 1.83-1.80 (m, 4 H), 1.76 (br s, 2 H). | [M + H]+ Cac. 418.2; found 418.0 | 98.5 |  | 180 |
| 18 | 1HNMR (300 MHz, DMSO-d6, ppm) 7.07 (s, 1H), 6.73 (s, 1H), 5.89 (s, 2H), 5.17 (d, J = 120.5 Hz, 3H), 4.13-3.83 (m, 4H), 3.70 (s, 5H), 3.51 (m, J = 11.9, 7.5 Hz, 1H), 2.60 (t, J = 7.2 Hz, 2H), 2.12-1.84 (m, 5H), 1.72 (s, 2H). | [M + H]+ Cac. 431.9; found 432.0 | 98.5 |  | 130 |
| 19 | (300 MHz, DMSO-d6) 6.84 (s, 1H), 6.78 (s, 1H), 5.59 (s, 2H), 5.31 (s, 1H), 4.66 (d, J = 15.1 Hz, 1H), 4.05 (dd, J = 13.4, 5.0 Hz, 1H), 3.91 (s, 1H), 3.88-3.16 (m, 11H), 2.99-2.95 (m, 3H), 2.01 (s, 3H), 1.76 (s, 2H). | [M + H]+ Cac. 434.2; found 434.4 | 99.1 |  | 118 |
| 20 | HTEM- NMR (300 MHz, DMSO-d6) 9.14 (s, 1H), 7.09 (s, 1H), 6.73 (s, 1H), 5.50 (d, J = 5.4 Hz, 3H), 5.21 (d, J = 5.1 Hz, 3H), 4.72 (d, J = 14.1 Hz, 1H), 3.99 (dd, J = 5.1, 53.4 Hz, 1H), 3.78 (d, J = 56.7 Hz, 1H), 3.69-3.49 (m, 3H), 2.07 (s, 3H), 1.98 (s, 3H), 1.89-1.75 (m, 2H), | [M + H]+ Cac. 348.9; found 348.9 | 99.4 |  | 230 |
| 21 | 1H NMR (300 MHz, DMSO, ppm) 9.03 (s, 1H), 6.83 (s, 1H), 6.74 (s, 1H), 5.55 (s, 1H), 5.48 (s, 2H), 5.24 (s, 1H), 4.67 (d, J = 14.0 Hz, 1H), 3.96 (qt, J = 16.3, 7.9 Hz, 3H), 3.79-3.64 (m, 1H), 3.00 (s, 6H), 2.00 (s, 3H), 1.80-1.72 (m, 2H), 1.26 (t, J = 7.0 Hz, 4H). | [M + H]+ Cac. 379.0; found 379.0 | 98.9 |  | 110-112 |
| 22 | (300 MHz, DMSO-d6): 7.47-6.93 (m, 4H), 5.70 (s, 1H), 5.52 (d, J = 23.6 Hz, 3H), 4.44 (s, 3H), 4.14 (dd, J = 13.4, 5.2 Hz, 1H), 3.91 (d, J = 12.7 Hz, 1H), 3.79-3.45 (m, 3H), 2.88 (s, 3H), 2.02 (s, 3H), 1.76 (s, 2H). | [M + H]+ Cac. 443.15; found 443.1 | 99.6 | second eluting enatiomer (Chiral ART cellulose SB) | 102-104 |
| 23 | 1H NMR (300 MHz, DMSO-d6)7.65 (s, 1H), 6.52 (s, 1H), 6.01 (s, 1.5H), 5.67 (s, 1H), 5.33-5.31 (m, 1H), 4.67-4.66 (m, 1H), 4.13 (dd, J = 13.5, 5.1 Hz, 1H), 3.89 (d, J = 11.1 Hz, 1H), 3.85-3.44 (m, 3.5H), 2.06 (s, 3H), 1.77 (s, 2H). | [M + H]+ Cac. 379.0; found 379.0 | 95.3 |  | 300 |
| 24 | 1HNMR (300 MHz, DMSO, ppm) 6.98 (s, 1H), 6.81 (s, 1H), 5.58 (s, 1H), 5.47 (s, 2H), 5.31 (s, 1H), 4.75 (s, 2H), 4.63 (s, 1H), 4.04 (dd, J = 13.4, 5.0 Hz, 1H), 3.89 (d, J = 11.3 Hz, 1H), 3.74 (s, 7H), 3.45-3.37 (m, 4H), 2.01 (s, 3H), 1.77 (s, 2H), 1.58 (d, J = 5.1 Hz, 2H), 1.49 (s, 4H). | [M + H]+ Cac. 490.2; found 490.1 | 99.6 |  | 115 |
| 25 | 1H NMR (300 MHz, DMSO-d6) 6.90 (s, 1H), 6.80 (s, 2H), 6.46 (s, 1H), 5.86 (s, 1H), 5.35 (s, 1H), 5.10 (s, 1H), 4.65 (s, 1H), 4.09-3.94 (m, 1H), 3.91-3.80 (m, 1H), 3.80-3.65 (m, 2H), 3.66-3.51 (m, 1H), 2.73 (s, 3H), 2.15 (s, 3H), 2.01 (s, 3H), 1.81 (d, J = 7.4 Hz, 2H). | [M + H]+ Cac. 362.2; found 362.3 | 99.5 | chiral ART cellulose SB | 163-165 |
| 26 | 1H NMR (300 MHz, DMSO-d6) 6.85 (s, 1H), 6.44 (s, 1H), 5.53 (d, J = 15.2 Hz, 3H), 5.18 (d, J = 7.9 Hz, 1H), 5.00 (d, J = 5.3 Hz, 1H), 4.73 (d, J = 15.3 Hz, 1H), 4.00 (m, J = 13.4, 5.1 Hz, 1H), 3.88 (d, J = 11.9 Hz, 1H), 3.74-3.41 (m, 3H), 2.72 (d, J = 4.8 Hz, 3H), 1.99 (d, J = 1.6 Hz, 6H), 1.73 (d, J = 5.8 Hz, 2H). | [M + H]+ Cac. 362.3; found 362.3 | 99.5 | chiral ART cellulose SB | 108-110 |

-continued

| D# | NMR | LC/MS | HPLC Purity | enantiomeric purity | melting point (° C.) |
|---|---|---|---|---|---|
| 27 | 1H NMR (300 MHz, DMSO-d6, ppm, 353 K) δ = 6.91 (s, 1 H), 6.43 (s, 1 H), 5.55 (s, 1 H), 5.49 (br s, 2 H), 5.22-5.19 (m, 1 H), 4.75-4.68 (m, 1 H), 3.99 (dd, J = 13.2, 5.1 Hz, 1 H), 3.90-3.86 (m, 1 H), 3.69-3.49 (m, 3 H), 3.28 (t, J = 8.4 Hz, 2 H), 2.81 (t, J = 8.4 Hz, 2 H), 2.69 (s, 3 H), 1.99 (s, 3 H), 1.73 (br s, 2 H). | [M + H]+ Cac. 374.9; found 374.2 | 98.1 | first eluting enantiomer (chiral pak AG) | |
| 28 | 1H NMR (300 MHz, DMSO-d6, ppm, 353 K) δ = 6.91 (s, 1 H), 6.43 (s, 1 H), 5.55 (s, 1 H), 5.49 (br s, 2 H), 5.22-5.19 (m, 1 H), 4.75-4.68 (m, 1 H), 3.99 (dd, J = 13.2, 5.1 Hz, 1 H), 3.90-3.86 (m, 1 H), 3.69-3.49 (m, 3 H), 3.28 (t, J = 8.4 Hz, 2 H), 2.81 (t, J = 8.4 Hz, 2 H), 2.69 (s, 3 H), 1.99 (s, 3 H), 1.73 (br s, 2 H). | [M + H]+ Cac. 374.9; found 374.2 | 96.2 | second eluting enantiomer (chiral pak AG) | |
| 29 | 1H NMR (300 MHz, CD3OD, ppm) δ = 6.96 (d, J = 8.4, 1 H), 6.72 (d, J = 2.1, 1 H), 6.56 (dd, J = 8.4, 2.4 Hz, 1 H), 5.56 (br s, 1 H), 5.30-4.92 (br, 2 H), 4.18 (dd, J = 13.5, 5.1 Hz, 1 H), 4.03-3.98 (m, 1 H), 3.72-3.54 (m, 3 H), 2.07 (s, 3 H), 1.93-1.75 (m, 2 H). | [M + H]+ Cac. 334.0; found 334.0 | 99.6 | First eluting enantiomer (chiral pak IA) | |
| 30 | 1H NMR (300 MHz, CD3OD, ppm) δ = 6.96 (d, J = 8.4, 1 H), 6.72 (d, J = 2.1, 1 H), 6.56 (dd, J = 8.4, 2.4 Hz, 1 H), 5.56 (br s, 1 H), 5.30-4.92 (br, 2 H), 4.18 (dd, J = 13.5, 5.1 Hz, 1 H), 4.03-3.98 (m, 1 H), 3.72-3.54 (m, 3 H), 2.07 (s, 3 H), 1.93-1.75 (m, 2 H). | [M + H]+ Cac. 334.0; found 334.0 | 99.4 | second eluting enantiomer (chiral pak AI) | 85 |
| 31 | 1H NMR (300 MHz, DMSO-d6, ppm, 353 K) δ = 6.99 (s, 1 H), 6.81 (s, 1 H), 5.61 (s, 1 H), 5.49 (br s, 2 H), 5.34-5.30 (m, 1 H), 4.60-4.55 (m, 1 H), 4.05 (dd, J = 13.5, 5.1 Hz, 1 H), 3.88-3.51 (m, 8 H), 2.01 (s, 3 H), 1.74 (br s, 2 H), 0.95 (s, 6 H). | [M + H]+ Cac. 419.0; found 419.0 | 98.9 | second eluting enantiomer (Chiral PAK AG3) | |
| 32 | 1HNMR (300 MHz, DMSO, ppm) 7.45 (s, 1H), 6.98 (s, 1H), 6.75 (s, 1H), 5.86 (s, 2H), 5.37 (s, 1H), 4.98 (s, 1H), 4.41 (s, 2H), 3.94 (dd, J = 26.6, 12.4 Hz, 2H), 3.73 (s, 5H), 3.51 (dd, J = 18.2, 8.9 Hz, 1H), 1.97 (s, 3H), 1.72 (s, 2H), 1.26 (s, 10H). | [M + H]+ Cac477.9; found 478.0 | 99.9 | | 192 |
| 33 | (300 MHz, DMSO-d6): 7.94-7.75 (m, 1H), 7.40 (dd, J = 7.6, 2.1 Hz, 1H), 5.80 (s, 1H), 5.56 (d, J = 29.6 Hz, 3H), 4.54 (s, 2H), 4.33-4.07 (m, 2H), 3.97-3.76 (m, 2H), 3.72-3.45 (m, 2H), 3.06 (s, 3H), 2.05 (s, 3H), 1.91-1.62 (m, 2H). | [M + H]+ Cac. 396.4; found 396.1 | 97.3 | | 100-102 |
| 34 | | | 95.9 | | |
| 35 | 1H NMR (300 MHz, DMSO-d6, ppm, 353 K) δ = 7.93 (s, 1 H), 7.46 (s, 1 H), 5.66 (s, 1 H), 5.56-5.51 (m, 1 H), 5.45 (br s, 2 H), 4.50-4.46 (m, 1 H), 4.12-4.05 (m, 3 H), 3.90-3.87 (m, 3 H), 3.77-3.65 (m, 2 H), 3.60-3.52 (m, 1 H), 2.02 (s, 3 H), 1.79 (br s, 2 H), 1.12 (t, J = 9.6 Hz, 3 H). | [M + H]+ Cac. 430.2; found 430.2 | 94.7 | | |
| 36 | 1H NMR (300 MHz, DMSO-d6, ppm, 353 K) δ = 6.62 (s, 2 H), 5.95 (s, 1 H), 5.88 (br s, 2 H), 5.66 (s, 1 H), 5.25-5.21 (m, 1 H), 4.67-4.63 (m, 1 H), 4.12-4.02 (m, 3 H), 3.89-3.83 (m, 1 H), 3.75-3.68 (m, 1 H), 3.63-3.51 (m, 3 H), 3.02-2.98 (m, 1 H), 2.02 (s, 3 H), 1.74 (br s, 2 H) 1.42 (s, 3 H), 1.12 (t, J = 9.6 Hz, 3 H). | [M + H]+ Cac. 462.9; found 462.1 | 95.1 | third eluting isomer (Chiral PAK ADH) | |
| 37 | 1H NMR (300 MHz, DMSO-d6, ppm, 353 K) δ = 6.62 (s, 2 H), 5.95 (s, 1 H), 5.78 (br s, 2 H), 5.63 (s, 1 H), 5.22-5.19 (m, 1 H), 4.70-4.65 (m, 1 H), 4.05-3.95 (m, 3 H), 3.89-3.82 (m, 1 H), 3.71-3.65 (m, 1H), 3.62-3.50 (m, 3 H), 3.02-2.98 (m, 1 H), 2.02 (s, 3 H), 1.74 (br s, 2 H) 1.42 (s, 3 H), 0.98 (t, J = 9.6 Hz, 3 H). | [M + H]+ Cac. 462.9; found 462.2 | 98.2 | fourth eluting isomer (Chiral PAK ADH) | |
| 38 | 1H NMR (300 MHz, DMSO-d6, ppm, 353 K) δ = 7.19 (s, 1 H), 6.89 (s, 1 H), 5.79 (br s, 2 H), 5.69 (s, 1 H), 5.42-5.38 (m, 1 H), 5.09 (s, 2 H), 4.63-4.58 (m, 1 H), 4.06 (dd, J = 13.5, 5.1 Hz, 1 H), 3.91-3.69 (m, 6 H), 3.60-3.53 (m, 1 H), 2.05 (s, 3 H), 1.79 (br s, 2 H). | [M + H]+ Cac. 405.0; found 404.1 | 99.5 | second eluting enantiomer (chiral ART cellulose-SB) | 83-85 |
| 39 | 1HNMR (300 MHz, DMSO, ppm) 10.06 (s, 1H), 7.68-7.54 (m, 2H), 7.31 (t, J = 7.9 Hz, 2H), 7.15-6.98 (m, 2H), 6.77 (s, 1H), 5.86 (s, 2H), 5.45 (s, 1H), 4.94 (s, 1H), 4.72 (s, 2H), 3.95 (dd, J = 30.9, 11.3 Hz, 2H), 3.75 (s, 5H), 3.65-3.39 (m, 1H), 1.97 (s, 3H), 1.72 (s, 2H), 1.22 (s, 1H). | [M + H]+ Cac. 497.9; found 498.0 | 97 | | 213 |
| 40 | 1H NMR (300 MHz, DMSO-d6) 8.46 (d, J = 1.9 Hz, 1H), 7.89 (d, J = 1.9 Hz, 1H), 5.77 (d, J = 20.9 Hz, 2H), 5.35 (s, 2H), 4.51 (s, 2H), 4.27 (s, 1H), 4.17 (dd, J = 13.2, 5.5 Hz, 1H), 3.98 (d, J = 11.3 Hz, 2H), 3.85-3.78 (m, 1H), 3.56 (d, J = 14.1 Hz, 1H), 2.94 (s, 3H), 2.03 (s, 3H), 1.78 (s, 2H). | [M + H]+ Cac. 411.9; found 412.05 | 96.6 | | 115-117 |

-continued

| D# | NMR | LC/MS | HPLC Purity | enantiomeric purity | melting point (° C.) |
|---|---|---|---|---|---|
| 41 | 1H NMR (300 MHz, DMSO-d6, ppm, 353 K) δ = 7.42-7.36 (m, 3 H), 5.67 (s, 1 H), 5.54-5.49 (m, 1 H), 5.41 (br s, 2 H), 4.50 (s, 2 H), 4.49-4.42 (m, 1 H), 4.12-4.05 (m, 1 H), 3.90-3.75 (m, 2 H), 3.64-3.52 (m, 2 H), 2.88 (s, 3 H), 2.01 (s, 3 H), 1.85-1.72 (m, 2 H). | [M + H]+ Cac. 461.4; found 461.1 | 99 | second eluting enantiomer (chiral pak IE) | 98-100 |
| 42 | 1H NMR (300 MHz): 7.00-6.98 (m, 1H), 6.84 (s, 1H), 5.60-5.56 (m, 1H), 5.50-5.46 (m, 2H), 5.36-5.27 (m, 1H), 4.76-4.72 (m, 2H), 4.66 (d, J = 15.4 Hz, 1H), 4.23-4.16 (m, 2H), 4.08-3.99 (m, 3H), 3.90 (d, J = 12.2 Hz, 1H), 3.79-3.59 (m, 3H), 2.05-2.00 (m, 3H), 1.80-1.72 (m, 2H), 1.29-1.20 (m, 6H). | [M + H]+ Cac. 465.2; found 465.0 | 96.3 | | 135-138 |
| 43 | (300 MHz, DMSO-d6): 8.39 (d, J = 1.7 Hz, 1H), 7.67 (dd, J = 10.8, 1.8 Hz, 1H), 5.79 (s, 2H), 5.40 (s, 2H), 4.54 (s, 2H), 4.36-4.09 (m, 2H), 4.06-3.77 (m, 3H), 3.63-3.47 (m, 1H), 3.00 (s, 3 H), 2.04 (s, 3H), 1.92-1.68 (m, 2H). | [M + H]+ Cac. 396.4; found 395.9 | 99.1 | | 110-112 |
| 44 | 1H NMR (300 MHz, DMSO, ppm) 6.99 (s, 1H), 6.82 (s, 1H), 5.57 (s, 1H), 5.47 (s, 2H), 5.21-5.38 (m, 1H), 4.75 (s, 2H), 4.60-4.66 (m, 1H), 3.55-4.08 (m, 10H), 2.01 (s, 1H), 1.66-1.86 (m, 2H), 1.20-1.31 (m, 3H). | [M + H]+ Cac. 451.9; found 451.3 | 97.9 | | 199-201 |
| 45 | 1HNMR (300 MHz, DMSO, ppm) 7.17 (d, J = 1.6 Hz, 1H), 6.84 (s, 1H), 5.60 (s, 1H), 5.29 (s, 3H), 4.67 (s, J = 15.0 Hz, 1 H), 4.15 (dd, J = 13.5, 5.0 Hz, 1H), 3.93 (d, J = 12.1 Hz, 1H), 3.66 (ddd, J = 22.6, 14.0, 9.3 Hz, 3H), 2.06 (s, 3H), 1.81 (s, 2H). | [M + H]+ Cac. 418.1; found 417.9 | 99.4 | Second eluting enantiomer (chiral pack IG) | 210 |
| 46 | (300 MHz, DMSO-d6) 7.24 (d, J = 42.0 Hz, 2H), 5.46 (t, J = 32.6 Hz, 4H), 4.69 (d, J = 15.0 Hz, 1H), 4.18-3.83 (m, 2H), 3.81-3.39 (m, 5H), 2.22 (s, 3H), 2.01 (d, J = 9.6 Hz, 3H), 1.87-1.71 (m, 2H), 1.54 (s, 2H). | [M + H]+ Cac. 362.2; found 362.4 | 99.5 | | 228-230 |
| 47 | 1H NMR (300 MHz, DMSO, ppm) 7.15 (s, 1H), 7.02 (s, 1H), 6.79 (s, 1H), 5.56 (d, J = 19.2 Hz, 3H), 5.25 (s, 1H), 4.69 (s, 1H), 4.39 (s, 2H), 4.12-3.83 (m, 4H), 3.80-3.50 (m, 2H), 1.99 (s, 3H), 1.74 (s, 3H), 1.28 (d, J = 13.9 Hz, 2H), 1.28 (s, 12H). | [M + H]+ Cac. 492.0; found 492.1 | 96.3 | | 105-107 |
| 48 | 1H NMR (300 MHz, DMSO-d6 mixed with one drop of DCl in deuterium oxide solution, ppm) (contains two rotamers) δ = 7.11 (s, 0.5 H), 7.03 (s, 0.5 H), 6.80 (s, 0.5 H), 6.78 (s, 0.5 H), 6.57 (s, 0.5 H), 6.10-5.89 (m, 2 H), 5.64 (s, 0.5 H), 5.42-5.35 (m, 1 H), 5.27-5.25 (m, 1 H), 5.13-5.10 (m, 0.5 H), 4.61-4.57 (m, 2 H), 4.21-3.80 (m, 6.5 H), 3.69-3.58 (m, 1 H), 2.30 (s, 1.5 H), 2.18 (s, 1.5 H), 1.87-1.70 (m, 2 H), 1.31-1.26 (m, 3 H). | [M + H]+ Cac. 419.2; found 419.2 | 98 | | 132-135 |
| 49 | 1HNMR (300 MHz, DMSO, ppm) 8.48 (s, 1H), 7.61 (s, 1H), 5.72 (s, 1H), 5.60 (dd, J = 9.9, 4.9 Hz, 1H), 5.45 (s, 2H), 4.58 (s, 2H), 4.41 (d, J = 15.2 Hz, 1H), 4.12 (dd, J = 13.5, 5.1 Hz, 1 H), 3.94-3.84 (m, 2H), 3.85-3.71 (m, 1H), 3.66-3.49 (m, 1H), 2.48 (m, J = 1.9 Hz, 3H), 2.04 (s, 3H). | [M + H]+ Cac. 412.1; found 411.9 | 97.7 | | 150 |
| 50 | 1H NMR (300 MHz, DMSO-d6, ppm, 353 K) δ = 7.12 (s, 1 H), 7.03 (t, J = 75 Hz, 1 H), 6.87 (s, 1 H), 5.55 (s, 1 H), 5.49 (br s, 2 H), 5.29-5.25 (m, 1 H), 4.65-4.61 (m, 1 H), 4.10 (dd, J = 13.5, 5.1 Hz, 1H), 3.90-3.86 (m, 3 H), 3.71-3.50 (m, 3 H), 2.01 (s, 3 H), 1.77 (br s, 2 H). | [M + H]+ Cac. 401.8; found 400.9 | 98.3 | | 130-132 |
| 51 | (300 MHz, DMSO-d6) 7.22 (d, J = 8.9 Hz, 1H), 7.00 (d, J = 3.0 Hz, 1H), 6.86 (d, J = 8.4 Hz, 1H), 5.66-5.18 (m, 4H), 4.70-4.54 (m, 1H), 4.05 (s, 1H), 3.87 (s, 1H), 3.70 (s, 3H), 3.56 (s, 3H), 2.48 (s, 3H), 1.76 (s, 2H). | [M + H]+ Cac. 349.1; found 349.3 | 98.3 | | 161-163 |
| 52 | (300 MHz, DMSO-d6) 7.50 (s, 1H), 7.33 (d, J = 1.0 Hz, 2H), 5.70-5.31 (m, 4H), 4.45 (s, 3H), 4.12 (dd, J = 13.4, 5.0 Hz, 1H), 3.91 (d, J = 12.3 Hz, 1H), 3.80-3.61 (m, 2H), 3.59-3.46 (m, 1H), 2.88 (s, 3H), 2.35-2.18 (m, 2H), 1.77 (s, 2H), 1.10-0.94 (m, 3H). | [M + H]+ Cac. 425.1; found 425.3 | 97.9 | | 108-110 |
| 53 | 1H NMR (300 MHz, DMSO-d6, ppm, 353 K) δ = 7.93 (s, 1 H), 7.47 (s, 1 H), 5.67 (s, 1 H), 5.56-5.51 (m, 1 H), 5.44 (br s, 2 H), 4.50-4.43 (m, 1 H), 4.11 (dd, J = 13.5, 5.1 Hz, 1 H), 3.92-3.88 (m, 3 H), 3.78-3.53 (m, 6 H), 2.02 (s, 3 H), 1.79 (br s, 2 H). | [M + H]+ Cac. 416.8; found 416.0 | 94.1 | | |
| 54 | 1HNMR (300 MHz, DMSO, ppm) 8.00-7.42 (m, 2H), 7.32 (d, J = 7.7 Hz, 1H), 5.65 (d, J = 38.2 Hz, 4H), 4.53 (s, 2H), 4.38 (s, 1H), 4.17 (dd, J = 13.4, 5.2 Hz, 1H), 3.92 (d, J = 12.3 Hz, 1H), 3.83-3.58 (m, 2H), 3.52 (td, J = 11.6, 4.7 Hz, 1H), 3.01 (s, 3H), 2.02 (s, 3H), 1.76 (s, 2H). | [M + H]+ Cac. 444.1; found 444.0 | 97.5 | | 95 |

| D# | NMR | LC/MS | HPLC Purity | enantiomeric purity | melting point (° C.) |
|---|---|---|---|---|---|
| 55 | 1H NMR (300 MHz, DMSO-d6, ppm, 353 K) δ = 7.50 (s, 1 H), 7.34 (s, 2 H), 5.60 (s, 1 H), 5.45 (br s, 3 H), 4.62-4.57 (m, 1 H), 4.45 (s, 2 H), 4.14 (dd, J = 13.5, 5.1 Hz, 1 H), 3.91-3.87 (m, 1 H), 3.78-3.51 (m, 3 H), 2.89 (s, 3 H), 2.01 (s, 3 H), 1.78 (br s, 2 H). | [M + H]+ Cac. 412.0; found 410.9 | 99.1 | | 188-190 |
| 56 | 1H NMR (300 MHz, DMSO-d6, ppm, 353 K) δ = 9.84 (br s, 1 H), 7.17 (s, 1 H), 7.00 (t, J = 75.0 Hz, 1 H), 6.91 (s, 1 H), 5.56 (s, 1 H), 5.50 (br s, 2 H), 5.32-5.28 (m, 1 H), 4.65-4.60 (m, 1 H), 4.15-4.09 (m, 1 H), 3.91-3.86 (m, 1 H), 3.73-3.56 (m, 3 H), 2.01 (s, 3 H), 1.77 (br s, 2 H). | [M + H]+ Cac. 401.8; found 401.0 | 99.3 | first eluting enantiomer ((R,R)WELK chromasil) | 118-120 |
| 57 | 1H NMR (300 MHz, DMSO-d6, ppm, 353 K) δ = 9.84 (br s, 1 H), 7.17 (s, 1 H), 7.00 (t, J = 75.0 Hz, 1 H), 6.91 (s, 1 H), 5.56 (s, 1 H), 5.50 (br s, 2 H), 5.32-5.28 (m, 1 H), 4.65-4.60 (m, 1 H), 4.15-4.09 (m, 1 H), 3.91-3.86 (m, 1 H), 3.73-3.56 (m, 3 H), 2.01 (s, 3 H), 1.77 (br s, 2H). | [M + H]+ Cac. 401.8; found 401.0 | 98.8 | Second eluting enantiomer ((R,R)WELK chromasil) | 118-120 |
| 58 | 1H NMR (400 MHz, Methanol-d4) δ 7.89 (d, J = 2.1 Hz, 1H), 7.53 (dd, J = 8.5, 2.2 Hz, 1H), 7.27 (d, J = 8.5 Hz, 1H), 5.88-5.33 (m, 3H), 4.28 (dd, J = 13.6, 5.1 Hz, 1H), 4.14 (s, 1H), 4.11-3.98 (m, 4H), 3.76 (dd, J = 13.6, 10.5 Hz, 1H), 3.72-3.58 (m, 2H), 2.69-2.54 (m, 1H), 2.44-2.30 (m, 1H), 2.09 (s, 3H), 1.99-1.88 (m, 1H), 1.83 (d, J = 14.5 Hz, 1H). | [M + H]+ Cac. 450.9; found 450.2 | 100 | first eluting isomer (SFC whelk-01 column) ee = 98.4% | |
| 59 | (300 MHz, DMSO-d6) 7.50 (s, 1H), 7.34 (d, J = 1.1 Hz, 2H), 5.56 (s, 1H), 5.47 (s, 3H), 4.65 (d, J = 15.1 Hz, 1H), 4.43 (s, 2H), 4.12 (dd, J = 13.5, 5.0 Hz, 1H), 3.91 (d, J = 12.0 Hz, 1H), 3.80-3.67 (m, 2H), 3.61-3.50 (m, 1H), 2.87 (s, 3H), 2.37-2.20 (m, 2H), 1.78 (s, 2H), 1.12-0.91 (m, 3H). | [M + H]+ Cac. 425.3; found 425.3 | 99.7 | Second eluting enantiomer (chiral pak IA) | 115-117 |
| 60 | 1H NMR (300 MHz, DMSO, ppm): 7.13-7.08 (m, 1 H), 6.88-6.82 (m, 1 H), 5.66-5.60 (m, 1 H), 5.48 (s, 2 H), 5.36 (d, J = 7.9 Hz, 1 H), 4.80 (d, J = 2.4 Hz, 2 H), 4.75-4.60 (m, 1 H), 4.11-4.02 (m, 1 H), 3.92 (d, J = 12.0 Hz, 1 H), 3.82 (d, J = 2.9 Hz, 1 H), 3.77 (d, J = 8.1 Hz, 3 H), 3.71-3.53 (m, 2 H), 3.43-3.38 (m, 1 H), 2.04 (s, 3 H), 1.84-1.76 (m, 2 H). | [M + H]+ Cac. 403.8; found 403.0 | 98.5 | | 174-176 |
| 61 | (300 MHz, DMSO-d6) 7.27-7.19 (m, 2H), 7.16-7.07 (m, 1H), 5.58 (s, 1H), 5.46 (s, 3H), 4.62 (d, J = 15.1 Hz, 1H), 4.11 (dd, J = 13.4, 5.1 Hz, 1H), 3.89 (d, J = 11.7 Hz, 1H), 3.76-3.42 (m, 3H), 3.06-2.85 (m, 3H), 2.67-2.52 (m, 3H), 2.00 (s, 3H), 1.86-1.60 (m, 4H), 1.53-1.38 (m, 2H). | [M + H]+ Cac. 402.1; found 402.1 | 96 | | 95-97 |
| 62 | 1H NMR (400 MHz, Methanol-d4) δ 7.89 (d, J = 2.1 Hz, 1H), 7.53 (dd, J = 8.5, 2.2 Hz, 1H), 7.27 (d, J = 8.5 Hz, 1H), 5.86-5.26 (m, 3H), 4.28 (dd, J = 13.6, 5.0 Hz, 1H), 4.14 (s, 1H), 4.12-3.99 (m, 4H), 3.76 (dd, J = 13.6, 10.5 Hz, 1H), 3.72-3.56 (m, 2H), 2.61 (ddt, J = 30.5, 13.9, 8.3 Hz, 1H), 2.44-2.28 (m, 1H), 2.09 (s, 3H), 1.92 (dddd, J = 11.4, 8.1, 5.0, 2.6 Hz, 1H), 1.88-1.79 (m, 1H). | [M + H]+ Cac. 450.9; found 450.2 | 100 | second eluting isomer (SFC whelk-01 column) ee = 97.7% | |
| 63 | 1H NMR (400 MHz, Methanol-d4) δ 7.20 (d, J = 8.8 Hz, 1H), 6.49 (dd, J = 8.8, 2.9 Hz, 1H), 6.37 (d, J = 2.9 Hz, 1H), 5.77-5.37 (m, 2H), 5.17 (s, 2H), 4.49 (dq, J = 4.8, 2.5 Hz, 1H), 4.31 (dd, J = 13.5, 5.0 Hz, 1H), 4.11-4.01 (m, 1H), 3.89-3.48 (m, 4H), 3.46-3.33 (m, 2H), 3.32-3.23 (m, 1H), 3.15 (dt, J = 10.3, 1.6 Hz, 1H), 2.12 (dd, J = 8.7, 4.5 Hz, 1H), 2.08 (d, J = 5.5 Hz, 3H), 1.97 (dddd, J = 25.8, 13.0, 5.5, 2.4 Hz, 2H), 1.89-1.77 (m, 2H). | [M + H]+ Cac. 404.9; found 404.9 | 92 | second eluting isomer (SFC ODH column) ee = 99.7% | |
| 64 | 1H NMR (400 MHz, Methanol-d4) δ 7.20 (d, J = 8.7 Hz, 1H), 6.49 (dd, J = 8.8, 2.9 Hz, 1H), 6.37 (d, J = 2.9 Hz, 1H), 5.54 (s, 2H), 5.18 (s, 2H), 4.49 (dt, J = 4.9, 2.4 Hz, 1H), 4.34-4.27 (m, 1H), 4.08-4.02 (m, 1H), 3.79-3.71 (m, 1H), 3.70 (d, J = 6.7 Hz, 1H), 3.67-3.57 (m, 2H), 3.48-3.42 (m, 1H), 3.42-3.35 (m, 1H), 3.27-3.20 (m, 1H), 3.10 (dt, J = 10.4, 1.6 Hz, 1H), 2.15-2.02 (m, 4H), 2.02-1.91 (m, 2H), 1.87-1.75 (m, 2H). | [M + H]+ Cac. 404.9; found 404.9 | 82 | first eluting isomer (SFC ODH column) ee = 100% | |
| 65 | 1HNMR (300 MHz, DMSO, ppm) 9.83 (s, 1H), 7.33 (s, 1H), 6.87 (s, 1H), 5.56 (s, 1H), 5.48 (s, 2H), 5.32 (d, J = 6.0 Hz, 1H), 4.65 (d, J = 15.1 Hz, 1H), 4.46-4.24 (m, 2H), 4.16 (dd, J = 13.5, 5.0 Hz, 1H), 3.90 (d, J = 11.9 Hz, 1H), 3.76-3.46 (m, 3H), 2.85 (s, 3H), 2.01 (s, 3H), 1.77 (d, J = 6.2 Hz, 2H), 1.25 (s, 1H). | [M + H]+ Cac. 427.1; found 427.0 | 96.4 | | |

-continued

| D# | NMR | LC/MS | HPLC Purity | enantiomeric purity | melting point (° C.) |
|---|---|---|---|---|---|
| 66 | (300 MHz, DMSO-d6) 7.33-7.20 (m, 2H), 7.14 (dd, J = 8.1, 1.8 Hz, 1H), 5.59 (s, 1H), 5.45 (m, 3H), 4.63 (d, J = 15.2 Hz, 1H), 4.11 (dd, J = 13.5, 5.0 Hz, 1H), 3.90 (d, J = 11.8 Hz, 1H), 3.76-3.42 (m, 3H), 3.02 (d, J = 12.5 Hz, 3H), 2.68-2.51 (m, 3H), 2.00 (s, 3H), 1.83-1.60 (m, 4H), 1.53-1.34 (m, 2H). | [M + H]+ Cac. 402.2; found 402.1 | 95.2 | Second eluting enantiomer (chiral pack IG) | 105-107 |
| 67 | 1H NMR (300 MHz, DMSOδ ppm) 7.86 (d, J = 1.8 Hz, 1H), 7.17 (s, 1H), 6.88 (d, J = 73.1 Hz, 1H), 5.33 (s, 1H), 5.23 (s, 3H), 4.00 (s, 2H), 3.80 (d, J = 15.7 Hz, 1H), 3.71-3.57 (m, 1H), 3.48-3.26 (m, 2H), 3.05-2.90 (m, 1H), 1.98-1.93 (m, 4H), 1.53 (s, 3H). | [M + H]+ Cac. 444.4; found 444.0 | 97.3 | | 120-123 |
| 68 | (300 MHz, DMSO-d6) 7.23 (d, J = 8.3 Hz, 2H), 7.14 (d, J = 7.1 Hz, 1H), 5.58 (s, 1H), 5.44 (s, 3H), 4.60 (s, 1H), 4.11 (dd, J = 13.3, 5.1 Hz, 1H), 3.89 (d, J = 12.1 Hz, 1H), 3.69 (dd, J = 13.5, 10.2 Hz, 3H), 2.98 (s, 3H), 2.67-2.50 (m, 3H), 2.00 (s, 3H), 1.86-1.60 (m, 4H), 1.47 (dd, J = 12.4, 8.4 Hz, 2H). | [M + H]+ Cac. 402.2; found 402.2 | 99.5 | First eluting enantiomer (chiral pack IG) | 120-122 |
| 69 | (300 MHz, DMSO-d6) 7.38-7.10 (m, 3H), 5.58 (s, 1H), 5.44 (s, 3H), 4.62 (d, J = 15.6 Hz, 1H), 4.56-4.48 (m, 2H), 4.48-4.37 (m, 2H), 4.11 (dd, J = 13.4, 5.1 Hz, 1H), 3.89 (d, J = 12.2 Hz, 1H), 3.77-3.38 (m, 4H), 2.80 (d, J = 11.0 Hz, 2H), 1.95 (d, J = 25.7 Hz, 5H), 1.80-1.47 (m, 7H). | [M + H]+ Cac. 458.2; found 458.1 | 99.2 | Second eluting enantiomer (chiral pack IG) | 95-98 |
| 70 | (300 MHz, DMSO-d6) 7.34-7.08 (m, 3H), 5.58 (s, 1H), 5.44 (s, 3H), 4.68-3.90 (m, 7H), 3.79-3.41 (m, 4H), 2.80 (d, J = 11.4 Hz, 2H), 2.09-1.86 (m, 5H), 1.76 (d, J = 9.9 Hz, 4H), 1.67-1.44 (m, 3H). | [M + H]+ Cac. 458.1; found 458.0 | 94 | | 118-120 |
| 71 | 1HNMR (300 MHz, DMSO, ppm) 8.84 (s, 1H), 6.94 (d, J = 4.2 Hz, 1H), 6.72 (s, 1H), 5.49 (d, J = 21.6 Hz, 3H), 5.21 (d, J = 8.6 Hz, 1H), 4.74 (d, J = 14.8 Hz, 1H), 4.06 (dd, J = 13.4, 5.0 Hz, 1H), 3.96-3.83 (m, 1H), 3.76 (d, J = 4.9 Hz, 3H), 3.68-3.45 (m, 3H), 2.39-2.18 (m, 2H), 1.76 (s, 2H), 1.05 (dd, J = 8.7, 6.4 Hz, 3H). | [M + H]+ Cac. 379.1; found 379.0 | 98.5 | | 120 |
| 72 | 1H NMR (300 MHz, DMSO, ppm) 7.03 (s, 1H), 6.82 (s, 1H), 5.58 (s, 1H), 5.47 (s, 2H), 5.31 (s, 1H), 4.63 (d, J = 16.1 Hz, 1H), 4.43 (s, 2H), 4.11-3.91 (m, 3H), 3.88 (m = 12.5 Hz, 1H), 3.74 (m = 13.4, 10.1 Hz, 1H), 2.99 (s, 1H), 2.01 (s, 3H), 1.76 (s, 2H), 1.28 (m = 7.0 Hz, 3H). | [M + H]+ Cac. 435.9; found 436.1 | 99.5 | | 138-140 |
| 73 | 1H NMR (300 MHz, DMSO-d6) 7.40 (s, 1H), 7.16 (s, 1H), 5.65 (s, 1H), 5.43 (s, 3H), 4.42 (d, J = 15.5 Hz, 1H), 3.93 (dd, J = 13.6, 5.0 Hz, 1H), 3.88-3.74 (m, 2H), 3.71 (s, 2H), 3.68-3.53 (m, 2H), 2.37 (s, 3H), 2.02 (s, 3H), 1.77 (d, J = 5.5 Hz, 2H), 1.58 (s, 2H). | [M + H]+ Cac. 362.2; found 362.2 | 99.8 | | 210-212 |
| 74 | 1H NMR (300 MHz, DMSO, ppm) 7.32-7.29 (s, 1 H), 7.00-6.95 (s, 1 H), 5.60-5.57 (s, 1 H), 5.50-5.46 (m, 2H), 5.39-5.30 (m, 1 H), 4.60 (d, J = 14.8 Hz, 1 H), 4.18-4.11 (s, 1 H), 3.93-3.85 (s, 1 H), 3.74-3.56 (m, 3 H), 1.84-1.73 (m, 3 H), 1.27-1.25 (m, 2 H). | [M + H]+ Cac. 419.9; found 418.95 | 95.7 | | 120.00-122.00 |
| 75 | (300 MHz, DMSO-d6) 7.31 (s, 1H), 7.17 (s, 1H), 5.57 (s, 1H), 5.44 (s, 2H), 5.35 (s, 1H), 4.69 (d, J = 15.1 Hz, 1H), 4.06 (dd, J = 13.4, 5.1 Hz, 1H), 3.91 (d, J = 11.9 Hz, 1H), 3.72 (s, 1H), 3.68-3.61 (m, 2H), 3.59-3.35 (m, 2H), 2.22 (s, 3H), 1.99 (s, 3H), 1.86-1.73 (m, 2H), 1.65 (s, 2H). | [M + H]+ Cac. 362.2; found 362.2 | 98.2 | Second eluting enantiomer (chiral pack IG) | 87-90 |
| 76 | 1HNMR (300 MHz, DMSO, ppm) 8.48 (s, 1H), 7.61 (s, 1H), 5.73 (s, 1H), 5.60 (dd, J = 9.8, 4.9 Hz, 1H), 5.45 (s, 2H), 4.58 (s, 1H), 4.41 (d, J = 15.4 Hz, 1H), 4.12 (dd, J = 13.5, 5.0 Hz, 2H), 3.97-3.83 (m, 1H), 3.77 (m, J = 15.3, 10.4, 5.6 Hz, 1H), 3.68-3.52 (m, 3H), 2.99 (s, 6H), 2.04 (s, 3H), 1.79 (d, J = 6.9 Hz, 2H). | [M + H]+ Cac. 412.1; found 412.1 | 98.9 | First eluting enantiomer (chiral pack IG) | 140 |
| 77 | (300 MHz, DMSO-d6, ppm): 8.11 (s, 1H), 7.92 (s, 1H), 5.73 (s, 1H), 5.60 (d, J = 5.9 Hz, 1H), 5.46 (s, 2H), 4.42 (d, J = 15.2 Hz, 1H), 4.21-3.99 (m, 1H), 3.99-3.68 (m, 6H), 3.58 (d, J = 16.4 Hz, 1H), 2.04 (s, 3H), 1.81 (s, 2H). | [M + H]+ Cac. 403.0; found 402.1 | 93.9 | | 103-105 |
| 78 | (300 MHz, DMSO-d6, ppm): 9.13 (s, 1 H), 7.09 (s, 1 H), 6.73 (s, 1 H), 5.50 (d, J = 8.3 Hz, 3 H), 5.22 (s, 1 H), 4.75 (s, 1 H), 4.19-4.06 (m, 1 H), 3.92 (s, 1 H), 3.71-3.47 (m, 3 H), 2.07 (s, 3 H), 1.99 (s, 3 H), 1.77 (s, 2 H). | [M + H]+ Cac. 350.0; found 349.1 | 99.8 | First eluting enantiomer (chiral pack IG) | 264-267 |

| D# | NMR | LC/MS | HPLC Purity | enantiomeric purity | melting point (° C.) |
|----|-----|-------|-------------|---------------------|----------------------|
| 79 | 1H NMR (300 MHz, DMSO, ppm) 7.64 (s, 1H), 6.94 (s, 1H), 5.64 (s, 1H), 5.53 (s, 2H), 4.59 (m = 15.0 Hz, 1H), 4.19 (m = 13.5, 5.0 Hz, 1H), 3.93 (m = 12.1 Hz, 1H), 3.72 (m = 13.5, 10.0 Hz, 1H), 3.59 (s, 2H), 2.06 (s, 3H), 1.81 (s, 2H). | [M + H]+ Cac. 412.9; found 413.10 | 96.3 | | 190-192 |
| 80 | (300 MHz, DMSO-d6) 7.21 (d, J = 8.7 Hz, 1H), 6.99 (d, J = 2.6 Hz, 1H), 6.86 (dd, J = 8.6, 2.6 Hz, 1H), 5.56 (s, 1H), 5.45 (s, 2H), 5.34 (dd, J = 10.1, 5.0 Hz, 1H), 4.64 (d, J = 15.6 Hz, 1H), 4.06 (dd, J = 13.4, 5.0 Hz, 1H), 3.88 (d, J = 12.0 Hz, 1H), 3.74 (s, 3H), 3.71-3.47 (m, 3H), 2.00 (s, 3H), 1.75 (dd, J = 8.2, 4.0 Hz, 2H). | [M + H]+ Cac. 349.1; found 349.1 | 99.3 | second eluting enantiomer (CHIRALPAK IG) | 88.00-90.00 |
| 81 | (300 MHz, DMSO-d6) 8.50 (d, J = 1.9 Hz, 1H), 7.92 (d, J = 1.9 Hz, 1H), 5.83 (s, 1H), 5.76 (s, 1H), 5.37 (s, 2H), 4.54 (s, 2H), 4.31 (s, 1H), 4.20 (dd, J = 13.2, 5.4 Hz, 1H), 4.09-3.93 (m, 2H), 3.83 (dd, J = 13.3, 10.7 Hz, 1H), 3.57 (dd, J = 15.2, 12.0 Hz, 1H), 3.06 (s, 3H), 2.06 (s, 3H), 1.89-1.72 (m, 2H). | [M + H]+ Cac. 412.1; found 412.1 | 99 | second eluting enantiomer chiral pack IG | 119-121 |
| 82 | 1H NMR (400 MHz, Methanol-d4) δ 7.15 (d, J = 8.6 Hz, 1H), 7.02 (s, 1H), 6.91 (d, J = 8.7 Hz, 1H), 5.58 (d, J = 22.1 Hz, 2H), 4.24 (dd, J = 13.6, 5.1 Hz, 2H), 4.10-3.96 (m, 2H), 3.78-3.60 (m, 4H), 3.56 (s, 3H), 3.16 (s, 3H), 2.08 (s, 3H), 1.94-1.77 (m, 3H), 1.49 (d, J = 1.6 Hz, 8H), 1.36-1.29 (m, 1H). | [M + H]+ Cac. 504.04; found 504.30 | 98 | | |
| 83 | 1H NMR (400 MHz, Methanol-d4) δ 7.00 (d, J = 8.6 Hz, 1H), 6.66 (d, J = 2.4 Hz, 1H), 6.54 (dd, J = 8.6, 2.4 Hz, 1H), 5.76-5.30 (m, 2H), 5.13 (s, 1H), 4.21 (dd, J = 13.5, 5.1 Hz, 1H), 4.03 (d, J = 11.5 Hz, 1H), 3.93-3.82 (m, 2H), 3.80-3.73 (m, 1H), 3.73-3.66 (m, 1H), 3.66-3.51 (m, 3H), 3.06 (dd, J = 7.4, 1.0 Hz, 2H), 2.56 (dt, J = 13.3, 6.3 Hz, 1H), 2.13 (dd, J = 7.8, 5.3 Hz, 1H), 2.12-2.02 (m, 3H), 2.02-1.86 (m, 1H), 1.82 (s, 1H), 1.69 (dd, J = 13.0, 6.4 Hz, 1H). | [M + H]+ Cac. 417.9; found 418.2 | 100 | | |
| 84 | 1H NMR (400 MHz, Methanol-d4) δ 7.14 (d, J = 8.7 Hz, 1H), 6.98 (d, J = 2.4 Hz, 1H), 6.88 (d, J = 8.8 Hz, 1H), 5.68-5.46 (m, 2H), 4.24 (dd, J = 13.6, 5.1 Hz, 1H), 4.03 (d, J = 11.1 Hz, 1H), 3.83-3.57 (m, 5H), 3.53 (d, J = 11.8 Hz, 2H), 2.34 (t, J = 11.2 Hz, 2H), 2.08 (s, 3H), 1.98-1.75 (m, 3H), 1.23 (d, J = 6.2 Hz, 6H). (2H were overlap with solvent/water peaks) | [M + H]+ Cac. 432.0; found 432.3 | 100 | | |
| 85 | 1HNMR (300 MHz, DMSO, ppm) 8.38 (s, 1H), 7.66-7.01 (m, 2H), 5.68 (s, 1H), 5.49 (d, J = 5.5 Hz, 1H), 5.38 (s, 2H), 4.50 (s, 2H), 4.31 (d, J = 15.1 Hz, 1H), 4.11-3.97 (m, J = 13.4, 5.1 Hz, 1H), 3.89-3.56 (m, 3H), 3.56-3.41 (m, 1H), 2.91 (s, 3H), 1.97 (s, 3H), 1.71 (s, 2H). | [M + H]+ Cac. 444.1; found 444.2 | 97.4 | | 100 |
| 86 | 1HNMR (300 MHz, DMSO, ppm) 9.81 (s, 1H), 7.34 (s, 1H), 6.87 (s, 1H), 5.54 (d, J = 14.3 Hz, 3H), 5.32 (s, 1H), 4.65 (d, J = 15.4 Hz, 1H), 4.46-4.03 (m, 3H), 3.90 (d, J = 12.0 Hz, 1H), 3.78-3.38 (m, 3H), 2.85 (s, 3H), 2.01 (s, 3H), 1.78 (s, 2H). | [M + H]+ Cac. 427.1; found 426.9 | 98.7 | (R,R)-Welk-01 | 300 |
| 87 | 1H NMR (300 MHz, DMSO, ppm) 7.61 (s, 1H), 6.93 (s, 1H), 5.59 (s, 1H), 5.41-5.32 (m, 1H), 4.59 (m = 15.1 Hz, 1H), 4.14 (m = 13.5, 4.9 Hz, 1H), 3.95-3.85 (m, 1H), 3.77-3.48 (m, 3H), 3.19 (s, 3H), 2.42 (s, 1H), 2.31 (m = 7.6 Hz, 2H), 1.79 (m = 4.0 Hz, 1H), 1.77 (s, 2H), 1.06 (m = 7.6 Hz, 3H). | [M + H]+ Cac. 426.9; found 427.0 | 97.9 | | 176-178 |
| 88 | 1H NMR (300 MHz, DMSO-d6) 7.47-7.34 (m, 1H), 7.30-7.15 (m, 2H), 5.56 (s, 1H), 5.42 (d, J = 22.6 Hz, 3H), 4.64 (d, J = 15.2 Hz, 1H), 4.17-3.99 (m, 2H), 3.90 (d, J = 11.7 Hz, 1H), 3.78-3.46 (m, 3H), 3.10-2.79 (m, 3H), 2.21-2.04 (m, 1H), 1.99 (s, 3H), 1.85-1.62 (m, 4H), 1.59-1.36 (m, 1H). | [M + H]+ Cac. 388.9; found 388.2 | 98.1 | Chiral Pak IG | 107-109 |
| 89 | 1H NMR (300 MHz, DMSO-d6) 7.40 (d, J = 1.6 Hz, 1H), 7.33-7.13 (m, 2H), 5.57 (s, 1H), 5.42 (d, J = 23.4 Hz, 3H), 4.64 (d, J = 15.1 Hz, 1H), 4.18-3.99 (m, 2H), 3.89 (d, J = 12.0 Hz, 1H), 3.78-3.45 (m, 3H), 3.05-2.84 (m, 3H), 2.17-2.05 (m, 1H), 1.99 (s, 3H), 1.85-1.62 (m, 4H), 1.56-1.42 (m, 1H). | [M + H]+ Cac. 388.9; found 388.2 | 99.2 | Chiral Pak IG | 106-108 |
| 90 | 1H NMR (300 MHz, DMSO-d6) 7.40 (s, 1H), 7.30-7.12 (m, 2H), 5.57 (s, 1H), 5.43 (d, J = 14.4 Hz, 3H), 4.64 (d, J = 15.2 Hz, 1H), 4.16-3.99 (m, 2H), 3.89 (d, J = 12.2 Hz, 1H), 3.79-3.35 (m, 3H), 3.16-2.77 (m, 3H), 2.23-2.03 (m, 1H), 1.99 (s, 3H), 1.88-1.64 (m, 4H), 1.56-1.36 (m, 1H). | [M + H]+ Cac. 388.1; found 388.1 | 97.6 | Chiral Pak IG | 96-98 |

| D# | NMR | LC/MS | HPLC Purity | enantiomeric purity | melting point (° C.) |
|---|---|---|---|---|---|
| 91 | 1H NMR (300 MHz, DMSO-d6) 7.41 (d, J = 1.4 Hz, 1H), 7.22 (d, J = 2.2 Hz, 2H), 5.56 (s, 1H), 5.46 (s, 2H), 5.43-5.33 (m, 1H), 4.64 (d, J = 14.8 Hz, 1H), 4.18-3.99 (m, 2H), 3.95-3.83 (m, 1H), 3.79-3.37 (m, 4H), 2.99-2.78 (m, 2H), 2.10 (dtd, J = 12.5, 7.6, 5.4 Hz, 1H), 1.99 (s, 3H), 1.88-1.61 (m, 4H), 1.53-1.36 (m, 1H). | [M + H]+ Cac. 388.9; found 388.2 | 96 | Chiral Pak IG | 95-98 |
| 92 | 1H NMR (300 MHz, DMSO, ppm) 9.72 (s, 1H), 7.81 (m = 2.1 Hz, 1H), 7.37 (m = 8.5, 2.2 Hz, 1H), 7.21 (m = 8.5 Hz, 1H), 5.56 (s, 1H), 5.46 (s, 2H), 4.64 (m = 15.0 Hz, 1H), 4.08 (m = 13.5, 5.0 Hz, 1H), 3.89 (m = 11.8 Hz, 1H), 3.76-3.51 (m, 2H), 3.00 (s, 2H), 2.17 (d, J = 6.4 Hz, 2H), 2.16-2.03 (m, 1H), 2.00 (s, 3H), 1.76 (s, 2H), 0.93 (m = 6.5 Hz, 6H). | [M + H]+ Cac. 418.9; found 418.0 | 99.6 | | 134-136 |
| 93 | 1HNMR (300 MHz, DMSO, ppm) 7.98-7.39 (m, 2H), 7.32 (d, J = 7.7 Hz, 1H), 5.73 (s, 1H), 5.45 (s, 3H), 4.51 (s, 2H), 4.38 (d, J = 15.3 Hz, 1H), 4.21-4.08 (m, J = 13.3, 5.1 Hz, 1H), 3.91 (d, J = 12.1 Hz, 1H), 3.84-3.74 (m, J = 13.3, 10.2 Hz, 1H), 3.68 (t, J = 12.4 Hz, 1H), 3.54 (s, 1H), 2.99 (s, 3H), 2.03 (s, 3H), 1.77 (s, 2H). | [M + H]+ Cac. 444.1; found 444.0 | 99.9 | Chiral Pak IG | 100 |
| 94 | 1H NMR (300 MHz, DMSO-d6, ppm, 353 K) δ = 9.68 (s, 1 H), 7.82 (s, 1 H), 7.39 (d, J = 8.4 Hz, 1 H), 7.23 (d, J = 8.4 Hz, 1 H), 5.57 (s, 1 H), 5.47 (br s, 2 H), 5.36-5.32 (m, 1 H), 4.69-4.63 (m, 1 H), 4.09 (dd, J = 13.5, 4.8 Hz, 1 H), 3.92-3.87 (m, 1 H), 3.75-3.53 (m, 3 H), 2.22 (d, J = 6.9 Hz, 1 H), 2.01 (s, 3 H), 1.77 (br s, 2 H), 1.09-1.01 (m, 1 H), 0.51-0.46 (m, 2 H), 0.21-0.17 (m, 2 H). | [M + H]+ Cac. 415.9; found 416.1 | 98.3 | | |
| 95 | 1H NMR (300 MHz, DMSO-d6, ppm, 353 K) δ = 9.72 (s, 1 H), 7.80 (d, J = 2.1 Hz, 1 H), 7.37 (dd, J = 8.7, 2.1 Hz, 1 H), 7.21 (d, J = 8.7 Hz, 1 H), 5.55 (s, 1 H), 5.46 (br s, 2 H), 5.35-5.31 (m, 1 H), 4.67-4.62 (m, 1 H), 4.07 (dd, J = 13.5, 4.8 Hz, 1 H), 3.91-3.87 (m, 1 H), 3.73-3.50 (m, 3 H), 2.26 (t, J = 7.5 Hz, 2 H), 1.99 (s, 3 H), 1.74 (br s, 2 H), 1.63-1.56 (m, 2 H), 2.26 (t, J = 7.5 Hz, 3 H). | [M + H]+ Cac. 403.9; found 404.1 | 99.6 | | |
| 96 | 1H NMR (300 MHz, DMSO, ppm) 9.66 (s, 1H), 7.81 (m = 2.1 Hz, 1H), 7.37 (m = 8.5, 2.2 Hz, 1H), 7.21 (m = 8.5 Hz, 1H), 5.56 (s, 1H), 5.45 (s, 2H), 4.64 (m = 15.2 Hz, 1H), 4.08 (m = 13.5, 5.0 Hz, 1H), 3.89 (m = 12.0 Hz, 1H), 3.69 (m = 13.5, 10.2 Hz, 1H), 3.62 (s, 1H), 2.99 (s, 1H), 2.44 (s, 1H), 2.18 (s, 2H), 2.00 (s, 3H), 1.02 (s, 9H), 0.90 (s, 2H). | [M + H]+ Cac. 433.0; found 432.0 | 99.7 | | 140-142 |
| 97 | 1H NMR (300 MHz, DMSO-d6) 9.72 (s, 1H), 8.87 (s, 1H), 7.89 (s, 1H), 6.79 (s, 1H), 5.50 (d, J = 13.8 Hz, 3H), 5.23 (s, 1H), 4.70 (d, J = 14.9 Hz, 1H), 4.11 (dd, J = 13.5, 5.0 Hz, 1H), 3.96-3.80 (m, 1H), 3.68 (dd, J = 13.5, 10.1 Hz, 1H), 3.58 (dd, J = 14.5, 7.6 Hz, 2H), 2.44-2.27 (m, 2H), 2.00 (s, 3H), 1.76 (d, J = 5.9 Hz, 2H), 1.08 (d, 3H). | [M + H]+ Cac. 406.8; found 406.1 | 97.4 | | 155-158 |
| 98 | 1HNMR (300 MHz, DMSO, ppm) 9.86 (s, 1H), 7.34 (s, 1H), 6.86 (s, 1H), 5.51 (d, J = 12.5 Hz, 3H), 5.30 (d, J = 8.2 Hz, 1 H), 4.70 (d, J = 15.0 Hz, 1H), 4.43-4.22 (m, 2H), 4.20-4.11 (m, J = 13.4, 4.9 Hz, 1H), 3.90 (d, J = 12.1 Hz, 1H), 3.78-3.44 (m, 3H), 2.84 (s, 2H), 2.28 (q, J = 7.5 Hz, 3H), 1.79 (s, 2H), 1.03 (t, J = 7.6 Hz, 3H). | [M + H]+ Cac. 441.1; found 441.0 | 99.1 | | |
| 99 | 1H NMR (300 MHz, DMSO-d6) 7.40 (s, 1H), 7.17 (s, 1H), 5.66 (s, 1H), 5.40 (d, J = 17.3 Hz, 3H), 4.42 (d, J = 16.2 Hz, 1H), 4.00-3.46 (m, 7H), 2.37 (s, 3H), 2.02 (s, 3H), 1.91-1.65 (m, 2H). | [M + H]+ Cac. 362.1; found 362.1 | 99.3 | Chiral Pak IG | 110-112 |
| 100 | 1H NMR (300 MHz, DMSO-d6) 9.32 (s, 1H), 8.11 (s, 1H), 6.82 (s, 1H), 5.53 (d, J = 16.3 Hz, 3H), 5.26 (s, 1H), 4.73 (d, J = 14.5 Hz, 1H), 4.14 (dd, J = 13.4, 5.0 Hz, 1H), 4.01-3.82 (m, 1H), 3.70 (dd, J = 13.4, 10.0 Hz, 1H), 3.60 (d, J = 9.4 Hz, 2H), 2.44-2.27 (m, 2H), 2.03 (s, 3H), 1.78 (d, J = 7.1 Hz, 2H), 1.24 (s, 6H). | [M + H]+ Cac. 450.9; found 450.2 | 97 | | 160-162 |
| 101 | 1H NMR (300 MHz, DMSO, ppm) 7.08 (m = 9.6 Hz, 4H), 6.85 (s, 1H), 5.61 (s, 1H), 5.49 (s, 2H), 5.39-5.30 (m, 1H), 4.66 (m = 15.2 Hz, 1H), 4.46 (s, 2H), 4.04 (m = 13.4, 6.0, 2.7 Hz, 3H), 3.90 (m = 12.3 Hz, 1H), 3.76 (m = 13.4, 10.1 Hz, 1H), 3.68 (s, 1H), 3.58 (s, 1H), 2.03 (s, 3H), 1.79 (m = 4.4 Hz, 2H), 1.31 (m = 6.9 Hz, 3H). | [M + H]+ Cac. 436.9; found 436.0 | 99.9 | Chiral Pak AG | 112-114 |

-continued

| D# | NMR | LC/MS | HPLC Purity | enantiomeric purity | melting point (° C.) |
|---|---|---|---|---|---|
| 102 | 1H NMR (300 MHz, DMSO, ppm) 7.81-7.73 (m, 2H), 7.44 (m = 8.3 Hz, 2H), 7.02 (s, 2H), 5.75 (s, 1H), 4.32 (m = 14.7 Hz, 1H), 4.19 (m = 13.3, 5.4 Hz, 1H), 3.93-3.76 (m, 1H), 3.63-3.50 (m, 1H), 3.49 (m = 14.3 Hz, 1H), 2.98 (s, 2H), 2.40 (s, 1H), 2.03 (s, 3H), 1.90-1.79 (m, 1H), 1.71 (m = 8.4 Hz, 1H). | [M + H]+ Cac. 364.4; found 364.0 | 99.1 | | 140-142 |
| 103 | 1H NMR (300 MHz, DMSO, ppm) 5.92-5.76 (m, 4H), 5.60 (m = 6.0 Hz, 4H), 4.16-4.03 (m, 2H), 4.01-3.87 (m, 1H), 3.79 (s, 2H), 3.67 (s, 2H), 3.59-3.51 (m, 3H), 3.00 (m = 7.0 Hz, 3H), 2.49 (s, 3H), 2.34 (s, 1H), 2.14-2.05 (m, 6H), 1.80 (s, 5H). | [M + H]+ Cac. 361.3; found 360.0 | 99 | | 185-187 |
| 104 | 1HNMR (300 MHz, DMSO, ppm) 8.86 (s, 1H), 6.94 (s, 1H), 6.72 (s, 1H), 5.49 (d, J = 16.8 Hz, 1H), 5.21 (d, J = 8.0 Hz, 1H), 4.74 (d, J = 14.6 Hz, 1H), 4.12-4.01 (m, 1H), 3.89 (d, J = 11.8 Hz, 1H), 3.76 (s, 3H), 3.73-3.66 (m, 1H), 3.66-3.48 (m, 2H), 2.32-2.21 (m, 2H), 1.75 (s, 2H), 1.04 (t, J = 7.5 Hz, 3H). | [M + H]+ Cac. 379.1; found 378.9 | 99.7 | Chiral Pak AG-03 | 128 |
| 105 | 1H NMR (300 MHz): 7.13-7.10 (m, 1H), 6.84 (s, 1H), 5.61 (s, 1H), 5.49 (s, 2H), 5.34 (s, 1H), 4.81-4.77 (m, 2H), 4.66 (d, J = 15.9 Hz, 1H), 4.07 (m, J = 13.5, 5.0 Hz, 1H), 3.91 (d, J = 12.1 Hz, 1H), 3.74 (s, 5H), 3.41 (t, J = 2.6 Hz, 1H), 3.01 (s, 1H), 2.03 (s, 3H), 1.78 (s, 2H). | [M + H]+ Cac. 403.0; found 403.0 | 99.5 | Chiral Pak AD-03 | 78-80 |
| 106 | 1H NMR (300 MHz, DMSO-d6) 7.34-7.24 (m, 1H), 7.23-7.02 (m, 3H), 5.66 (s, 1H), 5.48 (dd, J = 8.8, 5.0 Hz, 1H), 5.4-5.32 (m, 2H), 4.42 (d, J = 15.1 Hz, 1H), 3.95 (dd, J = 13.6, 5.0 Hz, 1H), 3.89-3.71 (m, 2H), 3.68-3.47 (m, 2H), 2.87-2.63 (m, 2H), 2.00 (s, 3H), 1.89-1.66 (m, 2H), 1.34-1.14 (m, 3H). | [M + H]+ Cac. 313.4; found 313.2 | 99.3 | | 200-202 |
| 107 | 1H NMR (300 MHz, DMSO-d6, ppm, 353 K) δ = 7.93 (s, 1 H), 7.70 (d, J = 8.1 Hz, 1 H), 7.47 (d, J = 8.1 Hz, 1 H), 5.67 (s, 1 H), 5.57-5.52 (m, 1 H), 5.47 (br s, 2 H), 4.50-4.43 (m, 1 H), 4.11 (dd, J = 13.5, 4.8 Hz, 1 H), 3.91-3.87 (m, 1 H), 3.80-3.67 (m, 2 H), 3.60-3.52 (m, 1 H), 1.99 (s, 3 H), 1.79 (br s, 2 H). | [M + H]+ Cac. 343.8; found 344.05 | 97.8 | | |
| 108 | 1H NMR (300 MHz, DMSO-d6, ppm) 12.86 (s, 1H), 8.07 (s, 1H), 7.41 (d, J = 8.3 Hz, 1H), 7.30-7.15 (m, 1H), 7.01 (d, J = 7.2 Hz, 1H), 5.91 (s, 1H), 5.72 (s, 1H), 5.50 (s, 2H), 4.27 (m, J = 13.3, 5.3 Hz, 2H), 4.10-3.80 (m, 2H), 3.70-3.34 (m, 2H), 1.99 (s, 4H), 1.75 (s, 1H). | [M + H]+ Cac. 325.4; found 325.0 | 99.3 | | 156-158 |
| 109 | 1H NMR (300 MHz, DMSO-d6, ppm) 7.88 (s, 1H), 6.73 (s, 1H), 5.52 (s, 1H), 5.42 (s, 2H), 5.21 (d, J = 8.2 Hz, 1H), 4.68 (d, J = 15.3 Hz, 1H), 4.10 (m, J = 13.5, 5.0 Hz, 1H), 3.89 (d, J = 11.7 Hz, 1H), 3.74-3.62 (m, 1H), 3.59-3.42 (m, 2H), 2.06 (s, 3H), 1.99 (s, 3H), 1.75 (s, 2H). | [M + H]+ Cac. 392.9; found 392.1 | 99.6 | | 189-191 |
| 110 | 1H NMR (300 MHz, DMSO-d6, ppm) 9.02 (s, 1H), 7.88 (s, 1H), 6.77 (s, 1H), 5.49 (d, J = 16.7 Hz, 3H), 5.25-5.19 (m, 1H), 4.72 (d, J = 15.2 Hz, 1H), 4.09 (dd, J = 13.5, 5.0 Hz, 1H), 3.89 (d, J = 11.5 Hz, 1H), 3.74-3.48 (m, 3H), 2.28 (q, J = 7.5 Hz, 3H), 2.07 (s, 3H), 1.76 (s, 2H), 1.04 (t, J = 7.6 Hz, 3H). | [M + H]+ Cac. 406.8; found 406.1 | 99.7 | | 170-173 |
| 111 | 1H NMR (300 MHz, DMSO-d6, ppm): 9.70 (s, 1 H), 7.29 (d, J = 8.6 Hz, 1 H), 7.07 (d, J = 2.6 Hz, 1 H), 7.03-6.88 (m, 1 H), 5.65 (s, 1 H), 5.47-5.21 (m, 3 H), 4.68 (d, J = 15.0 Hz, 1 H), 4.05-3.94 (m, 1H), 3.88 (d, J = 11.7 Hz, 1 H), 3.78-3.60 (m, 2 H), 3.60-3.46 (m, 1 H), 1.98 (s, 3 H), 1.82-1.70 (m, 2 H). | [M + H]+ Cac. 369.3; found 369.1 | 98.8 | | 158-160 |
| 112 | 1H NMR (300 MHz, DMSO-d6, ppm) 7.88 (s, 1H), 6.79 (s, 1H), 5.53 (s, 1H), 5.48 (s, 2H), 5.27-5.19 (m, 1H), 4.69 (d, J = 15.1 Hz, 1H), 4.11 (dd, J = 13.4, 5.0 Hz, 1H), 3.94-3.84 (m, 1H), 3.76-3.64 (m, 1H), 3.64-3.47 (m, 3H), 2.00 (s, 4H), 1.80-1.73 (m, 2H), 0.88-0.70 (m, 4H). | [M + H]+ Cac. 418.8; found 418.1 | 98.7 | | |
| 113 | 1H NMR (300 MHz, DMSO-d6, ppm) 7.50 (d, J = 7.7 Hz, 1 H), 7.35 (d, J = 7.8 Hz, 1 H), 7.28 (brs, 2 H), 5.58 (s, 1 H), 5.47 (s, 2 H), 4.76-4.76 (m, 1 H), 4.36 (s, 1 H), 4.20-4.16 (m, 1 H), 3.94-3.90 (m, 1 H), 3.73-3.65 (m, 2 H), 3.55 (brs, 1 H), 1.97 (s, 3 H), 1.76 (brs, 2 H). | [M + H]+ Cac. 309.2; found 309.1 | 99.9 | | 205-208 |

| D# | NMR | LC/MS | HPLC Purity | enantiomeric purity | melting point (° C.) |
|---|---|---|---|---|---|
| 114 | 1H NMR (400 MHz, CD3OD, ppm) 6.66 (d, J = 11.8 Hz, 2 H), 6.01-6.04 (m, 0.2 H), 5.72 (s, 1 H), 5.19 (m, 0.8 H), 5.14-5.19 (s, 0.6 H), 4.28-4.22 (m, 1 H), 4.22-4.14 (m, 0.4 H), 4.07-3.77 (m, 3 H), 3.72-3.59 (m, 2 H), 3.08 (m, 1 H), 2.35 (s, 1 H), 2.23 (s, 2 H), 1.92 (m, 2 H), 1.52 (s, 3 H). | [M + H]+ Cac. 434.0; found 434.0 | 99.7 | | 218-222 |
| 115 | 1H NMR (300 MHz, DMSO-d6, ppm): 7.94-7.88 (m, 2H), 6.77 (s, 1H), 5.60 (s, 1H), 5.49 (s, 2H), 5.38 (s, 1H), 4.58-4.57 (m, 1H), 4.17-4.10 (m, 1H), 3.91-3.87 (m, 1H), 3.80-3.48 (m, 4H), 2.10-1.93 (m, 3H), 1.77 (s, 2H). | [M + H]+ Cac. 378.1; found 348.1 | 94.4 | ee = 98.2% | 220 |
| 116 | 1H NMR (300 MHz, DMSO, ppm) 7.46 (s, 1 H), 6.74 (s, 1 H), 6.64 (s, 1 H), 5.92 (s, 1 H), 5.57 (s, 1 H), 5.50 (s, 2 H), 5.21 (s, 1 H), 4.71 (s, 1 H), 4.05 (s, 1 H), 3.90 (s, 1 H), 3.61 (m, 4 H), 3.37 (d, J = 11.7 Hz, 2 H), 2.62 (s, 3 H), 2.02 (m, 3 H), 1.83-1.73 (m, 2H), 1.33 (s, 3H). | [M + H]+ Cac. 447.0; found 447.0 | 98.9 | | 148-150 |
| 117 | 1H NMR (300 MHz, DMSO-d6, ppm) 7.14 (s, 1 H), 6.83 (s, 1 H), 5.54-5.36 (m, 3 H), 5.30-5.22 (m, 1 H), 4.67-4.63 (m, 1 H), 4.22-4.09 (m, 1 H), 3.99-3.92 (m, 1 H), 3.78-3.50 (m, 3 H), 2.89 (s, 6 H), 2.03 (s, 3 H), 1.80-1.67 (m, 2 H). | [M + H]+ Cac. 406.2; found 406.2 | 99.4 | ee = 97.8% | 179 |
| 118 | 1H NMR (300 MHz, DMSO-d6, ppm) 8.70 (s, 1 H), 7.88 (s, 1 H), 6.78 (s, 1 H), 5.60 (s, 1 H), 5.49 (s, 2 H), 5.44-5.32 (m, 1 H), 4.62 (d, J = 14.7 Hz, 1 H), 4.20-4.10 (m, 1 H), 3.97-3.87 (m, 1 H), 3.81-3.49 (m, 3 H), 2.82 (s, 3 H), 2.03 (s, 3 H), 1.79-1.76 (m, 2 H). | [M + H]+ Cac. 392.1; found 392.1 | 92.4 | ee = 96.9% | 190 |
| 119 | 1H NMR (300 MHz, DMSO, ppm) 7.41-7.25 (s, 1 H), 7.01 (s, 1 H), 5.62 (s, 1 H), 5.53 (s, 2 H), 5.42-5.30 (m, 1 H), 4.61 (d, J = 15.0 Hz, 1 H), 4.16 (dd, J = 13.5, 5.0 Hz, 1 H), 4.0-3.85 (m, 1 H), 3.85-3.72 (m, 1 H), 3.72-3.39 (m, 3 H), 2.05 (s, 3 H), 1.91-1.72 (m, 2 H). | [M + H]+ Cac. 419.8; found 419.1 | 98.2 | (R,R) Welk-O | 141-143 |
| 120 | 1H NMR (300 MHz, DMSO, ppm) 6.94 (s, 2 H), 6.74 (s, 1 H), 6.64 (s, 1 H), 5.91 (s, 1 H), 5.57 (s, 1 H), 5.49 (s, 2 H), 5.20 (s, 1 H), 4.70 (s, 1 H), 4.13-4.00 (m, 1 H), 3.91 (s, 1 H), 3.75-3.40 (m, 4H), 2.02 (s, 3 H), 1.76 (m, 2 H), 1.35 (s, 3 H). | [M + H]+ Cac. 433.0; found 433.0 | 98.5 | ee = 100% | 208-210 |
| 121 | 1H NMR (300 MHz, DMSO, ppm) 12.35 (s, 1 H), 8.42 (s, 1 H), 7.98 (s, 1 H), 6.79 (s, 1 H), 5.77-5.05 (m, 4 H), 4.73-4.49 (m, 1 H), 4.24-4.00 (m, 2 H), 4.00-3.45 (m, 3 H), 2.03 (s, 3 H), 1.79 (s, 2 H), 1.34-0.93 (m, 6 H). | [M + H]+ Cac. 420.2; found 420.1 | 96.4 | ee = 98.7% | 192 |
| 122 | 1H NMR (300 MHz, DMSO, ppm) 7.36 (s, 1 H), 6.73 (s, 1 H), 6.61 (s, 1 H), 5.92 (s, 1 H), 5.55 (s, 1 H), 5.47 (s, 2 H), 5.25-5.18 (m, 1 H), 4.72-4.68 (m, 1 H), 4.06-4.00 (m, 1 H), 3.91-3.87 (m, 1 H), 3.67-3.52 (m, 3 H), 3.47-3.39 (m, 1 H), 3.10-3.00 (m, 1 H), 2.70-2.60 (m, 1 H), 2.00 (s, 3 H), 1.80-1.72 (m, 2 H), 1.31 (s, 3 H), 0.62-0.50 (m, 2 H), 0.48-0.34 (m, 2 H). | [M + H]+ Cac. 474.0; found 474.0 | 93.6 | ee = 95.6% | 156-160 |
| 123 | 1H NMR (300 MHz, DMSO, ppm) 12.83 (s, 1 H), 8.44 (s, 1 H), 7.97 (s, 1 H), 6.79 (s, 1 H), 5.73-5.28 (m, 4 H), 4.62-4.58 (m, 1 H), 4.20-4.14 (m, 2 H), 3.95-3.91 (m, 1 H), 3.85-3.51 (m, 3 H), 2.03 (s, 3 H), 1.88-1.79 (m, 2 H), 1.33-1.07 (m, 6 H). | [M + H]+ Cac. 420.2; found 420.2 | 96.5 | ee = 98.3% | 192 |
| 124 | 1H NMR (300 MHz, DMSO, ppm) 7.04 (s, 1 H), 6.78 (s, 1 H), 6.64 (s, 1 H), 5.95 (s, 1 H), 5.58 (s, 1 H), 5.48 (s, 2 H), 5.20 (s, 1 H), 4.73 (s, 1 H), 4.04 (m, 1 H), 3.96-3.77 (m, 2 H), 3.77-3.47 (m, 4 H), 3.41 (m, 1 H), 2.02 (s, 3 H), 1.77 (s, 2 H), 1.34 (s, 3 H), 1.10 (d, J = 6.6 Hz, 3 H), 0.97 (d, J = 6.6 Hz, 3 H). | [M + H]+ Cac. 474.9; found 475.0 | 96.5 | ee = 95.7% | 180-182 |
| 125 | 1H NMR (300 MHz, DMSO, ppm) 7.23 (s, 2 H), 6.67 (d, J = 7.2 Hz, 2 H), 6.10 (s, 2 H), 4.80 (s, 1 H), 4.67 (s, 1H), 4.16-4.01 (m, 1 H), 3.99-3.47 (m, 7 H), 2.23 (s, 3 H), 1.84 (s, 2 H), 1.52-1.37 (m, 3 H), 1.17-1.01 (m, 3 H), 1.00-0.86 (m, 3 H). | [M + H]+ Cac. 476.0; found 476.0 | 97.8 | | 175-180 |
| 126 | 1H NMR (300 MHz, DMSO, ppm) 6.65 (s, 1 H), 6.63 (s, 1 H), 5.97 (s, 1 H), 5.57 (s, 1 H), 5.49 (s, 2 H), 5.21 (s, 1 H), 4.69 (d, J = 15.0 Hz, 1 H), 4.07 (m, 1 H), 3.90 (d, 1 H), 3.80-3.38 (m, 12 H), 2.99-2.90 (m, 2 H), 2.02 (s, 3 H), 1.77 (s, 2 H), 1.47 (s, 3 H). | [M + H]+ Cac. 503.0; found 503.0 | 95 | ee = 95.6% | 160-162 |

-continued

| D# | NMR | LC/MS | HPLC Purity | enantiomeric purity | melting point (° C.) |
|---|---|---|---|---|---|
| 127 | 1H NMR (300 MHz, DMSO-d6, ppm) 8.47-8.03 (brs, 1 H), 6.65 (s, 1 H), 6.54 (s, 1 H), 5.55 (s, 1 H), 5.44 (s, 2 H), 5.30-5.08 (m, 1 H), 4.81-4.60 (m, 1 H), 4.23-4.04 (m, 1 H), 4.00-3.85 (m, 1H), 3.86-3.79 (m, 3 H), 3.77 (s, 3 H), 3.51 (s, 3 H), 1.98 (s, 3 H), 1.84-1.60 (m, 2 H). | [M + H]+ Cac. 361.4; found 361.1 | 98.3 | | 198-200 |
| 128 | 1H NMR (300 MHz, DMSO, ppm) 7.23 (s, 2 H), 6.67 (d, J = 7.2 Hz, 2 H), 6.10 (s, 2 H), 4.80 (s, 1 H), 4.67 (s, 1 H), 4.16-4.01 (m, 1 H), 3.99-3.47 (m, 7 H), 2.23 (s, 3 H), 1.84 (s, 2 H), 1.52-1.37 (m, 3 H), 1.17-1.01 (m, 3 H), 1.00-0.86 (m, 3 H). | [M + H]+ Cac. 477.0; found 477.0 | 96.5 | | 156-160 |
| 129 | 1H NMR (300 MHz, DMSO-d6, ppm) 8.14 (s, 1 H), 7.95 (s, 1 H), 6.64 (s, 2 H), 6.10 (s, 1 H), 5.90-5.50 (m, 1 H), 4.56-4.28 (m, 3 H), 4.28-4.05 (m, 1 H), 4.05-3.76 (m, 3 H), 3.76-3.55 (m, 1 H), 2.21 (s, 3 H), 2.04-1.72 (m, 2 H), 1.59-1.13 (m, 3 H). | [M + H]+ Cac. 416.8; found 416.1 | 95.5 | | 210-212 |
| 130 | 1H NMR (300 MHz, DMSO-d6, ppm) 8.82-8.78 (m, 1 H), 7.90 (s, 1 H), 6.76 (s, 1 H), 5.58 (s, 1 H), 5.48 (s, 2 H), 5.34 (s, 1 H), 4.63-4.48 (m, 1H), 4.14 (dd, J = 13.5, 5.0 Hz, 1 H), 3.90 (d, J = 11.7 Hz, 1 H), 3.81-3.45 (m, 5 H), 3.38-3.35 (m, 2 H), 2.03 (s, 3 H), 1.78-1.76 (m, 2 H). | [M + H]+ Cac. 422.2; found 422.2 | 90.6 | ee = 98.0% | 170 |
| 131 | 1H NMR (300 MHz, DMSO-d6, ppm) 12.61-12.19 (m, 1 H), 8.58 (s, 1 H), 8.00 (s, 1 H), 6.82 (s, 1 H), 6.61 (s, 2 H), 5.90-5.87 (m, 1 H), 5.54-5.52 (m, 1 H), 4.60-4.57 (m, 1 H), 4.16-4.14 (m, 1 H), 3.96-3.72 (m, 3 H), 3.63-3.54 (m, 1 H), 2.90-2.87 (m, 1H), 2.17 (s, 3 H), 1.84-1.82 (m, 2 H), 0.72-0.61 (m, 4 H). | [M + H]+ Cac. 418.2; found 418.1 | 98.2 | ee = 97.6% | 180 |
| 132 | 1H NMR (300 MHz, DMSO, ppm) 6.70 (s, 1 H), 6.65 (s, 1 H), 6.50 (s, 2 H), 6.02 (s, 1 H), 5.85 (s, 1 H), 5.35 (s, 1 H), 4.61 (d, J = 15.1 Hz, 1 H), 4.06 (m, 1 H), 3.94-3.52 (m, 6 H), 2.93 (s, 6 H), 2.15 (s, 3 H), 1.81 (s, 2 H), 1.45 (s, 3 H). | [M + H]+ Cac. 460.9; found 461.0 | 93.8 | ee = 94.9% | 215-218 |
| 133 | 1H NMR (300 MHz, DMSO, ppm) 7.36 (s, 1 H), 6.74 (s, 1 H), 6.65 (s, 1 H), 5.95 (s, 1 H), 5.58 (s, 1 H), 5.48 (s, 2 H), 5.22 (s, 1 H), 4.72 (s, 1 H), 4.33 (s, 1 H), 4.16-4.02 (m, 1 H), 3.90 (d, J = 11.9 Hz, 1 H), 3.75-3.48 (m, 3 H), 3.48-3.31 (m, 3H), 3.17 (d, J = 7.7 Hz, 3 H), 2.02 (s, 3 H), 1.77 (s, 2 H), 1.35 (s, 3 H). | [M + H]+ Cac. 476.9; found 477.2 | 97.3 | ee = 100% | 158-160 |
| 134 | 1H NMR (300 MHz, DMSO, ppm) 8.08 (s, 1 H), 7.79 (s, 1 H), 5.77 (s, 1 H), 5.68-5.57 (m, 1 H), 5.43 (s, 2 H), 4.49-4.34 (m, 3 H), 4.10 (dd, J = 13.6, 4.7 Hz, 1 H), 3.97-3.78 (m, 3 H), 3.62 (d, J = 12.9 Hz, 1 H), 2.07 (d, J = 1.4 Hz, 3 H), 1.82 (s, 2 H), 1.43-1.32 (m, 3 H). | [M + H]+ Cac. 416.1; found 416.0 | 98.1 | | 210-212 |
| 135 | 1H NMR (300 MHz, DMSO, ppm) 8.09 (s, 1 H), 7.80 (s, 1 H), 5.77 (s, 1 H), 5.68-5.57 (m, 1 H), 5.43 (s, 2 H), 4.41 (d, J = 15.5 Hz, 1 H), 4.10 (dd, J = 13.5, 4.7 Hz, 1 H), 3.98-3.78 (m, 6 H), 3.67-3.54 (m, 1 H), 2.07 (s, 3 H), 1.84 (d, J = 10.6 Hz, 2 H). | [M + H]+ Cac. 402.1; found 402.1 | 95.8 | | 219-221 |
| 136 | 1H NMR (300 MHz, DMSO, ppm) 7.63 (d, J = 2.1 Hz, 1 H), 7.54 (d, J = 8.3, 2.1 Hz, 1 H), 7.36 (d, J = 8.3 Hz, 1 H), 5.63 (s, 1 H), 5.47 (s, 3 H), 4.59 (d, J = 14.5 Hz, 1 H), 4.23-4.10 (m, 1 H), 3.91 (d, J = 11.7 Hz, 1 H), 3.83-3.47 (m, 3 H), 2.68 (d, J = 1.1 Hz, 3 H), 2.02 (s, 3 H), 1.75 (d, J = 1.5 Hz, 8 H). | [M + H]+ Cac. 439.1; found 439.1 | 98.1 | | 142-144 |
| 137 | 1H NMR (300 MHz, DMSO, ppm) 10.18 (s, 1 H), 7.22 (s, 1 H), 6.79 (s, 1 H), 5.94 (s, 2 H), 5.12 (d, J = 79.4 Hz, 2 H), 4.23-4.07 (m, 1 H), 3.92 (d, J = 11.7 Hz, 1 H), 3.71 (d, J = 11.7 Hz, 9 H), 3.16 (s, 2 H), 2.00 (s, 3 H), 1.75 (s, 2 H). | [M + H]+ Cac. 448.2; found 448.2 | 99.2 | second eluting isomer (Chiracel ODH column- SFC) ee = 100% | 184.0-186.0 |
| 138 | 1H NMR (300 MHz, DMSO-d6, ppm, 353 K) δ = 7.95 (s, 1 H), 7.83-7.72 (m, 2 H), 7.56 (d, J = 5.4 Hz, 1 H), 5.98 (br s, 2 H), 5.87 (d, J = 5.4 Hz, 1 H), 5.59 (br s, 1 H), 4.55-4.49 (m, 1 H), 4.16-4.12 (m, 1 H), 3.90-3.75 (m, 3 H), 3.60-3.56 (m, 1 H), 3.20 (s, 3 H), 1.79 (br s, 2 H). | [M + H]+ Cac 382.8; found 383.05 | 99.8 | | |
| 139 | 1H NMR (300 MHz, DMSO-d6, ppm) 7.51 (s, 1 H), 7.37-7.32 (m, 2 H), 5.62 (s, 1 H), 5.55-5.39 (m, 3 H), 4.70-4.44 (m, 2 H), 4.17-4.10 (m, 1 H), 4.00-3.82 (m, 1 H), 3.84-3.48 (m, 3 H), 2.80 (s, 3 H), 2.03 (s, 3 H), 1.88-1.68 (m, 2 H), 1.61 (d, J = 6.9 Hz, 3 H). | [M + H]+ Cac. 425.1; found 424.95 | 99.7 | fourth eluting isomer (column Chiral pak ID) ee = 99.1 | 140.0-142.0 |

-continued

| D# | NMR | LC/MS | HPLC Purity | enantiomeric purity | melting point (° C.) |
|---|---|---|---|---|---|
| 140 | 1H NMR (400 MHz, DMSO-d6) δ 7.61 (d, J = 17.9 Hz, 2H), 7.44 (d, J = 8.3 Hz, 1H), 6.57 (s, 1H), 5.96 (s, 1H), 5.76 (d, J = 10.5 Hz, 1H), 5.47 (s, 1H), 5.23 (s, 1H), 4.06 (s, 1H), 4.01 (d, J = 9.5 Hz, 1H), 3.82 (s, 1H), 3.69 (s, 2H), 2.02 (d, J = 0.8 Hz, 3H), 1.83 (s, 2H). | [M + H]+ Cac. 448.25; found 448.20 | 89 | | |
| 141 | 1H NMR (400 MHz, Methanol-d4) δ 7.93 (d, J = 1.8 Hz, 1H), 7.77 (dd, J = 8.1, 1.9 Hz, 1H), 7.56 (d, J = 8.2 Hz, 1H), 6.12-5.41 (m, 3H), 4.32 (dd, J = 13.6, 5.0 Hz, 1H), 4.11-3.97 (m, 2H), 3.88-3.72 (m, 2H), 3.65 (td, J = 11.8, 3.6 Hz, 1H), 2.60-2.42 (m, 2H), 2.25-2.16 (m, 2H), 2.13 (s, 3H), 2.09-1.91 (m, 3H), 1.89 (s, 1H). | [M + H]+ Cac. 437.0; found 437.1 | 100 | second eluting isomer (SFC IA-100 column) ee = 98% | |
| 142 | 1H NMR (400 MHz, DMSO-d6) δ 10.89 (s, 1H), 7.86 (s, 1H), 7.50 (d, J = 8.5 Hz, 1H), 7.29 (d, J = 8.5 Hz, 1H), 6.36 (t, J = 53.7 Hz, 1H), 5.84 (s, 3H), 5.03 (s, 2H), 4.10 (d, J = 12.5 Hz, 1H), 3.92 (d, J = 12.3 Hz, 1H), 3.70 (t, J = 12.0 Hz, 2H), 3.54 (s, 1H), 1.99 (s, 3H), 1.75 (s, 2H). | [M + H]+ Cac. 412.8; found 412.1 | 100 | second eluting isomer (SFC IC-100 column) ee = 99% | |
| 143 | (300 MHz, DMSO-d6): 6.75 (s, 1H), 6.48 (s, 1H), 5.67 (s, 1H), 5.56 (s, 1H), 5.46 (s, 2H), 5.14 (d, J = 9.8 Hz, 1H), 4.72 (d, J = 13.8 Hz, 1H), 4.00 (dd, J = 13.4, 5.1 Hz, 1H), 3.88 (d, J = 12.2 Hz, 1H), 3.73-3.43 (m, 3H), 3.22-3.08 (m, 2H), 2.58 (t, J = 6.4 Hz, 2H), 2.01 (s, 3H), 1.84-1.58 (m, 4H). | [M + H]+ Cac. 374.1; found 374.1 | 97.4 | first eluting enantiomer (chiral PAK IG) | 115-117 |
| 144 | (300 MHz, DMSO-d6): 6.93 (s, 1H), 6.46 (s, 1H), 5.55 (d, J = 16.2 Hz, 3H), 5.23 (s, 1H), 4.75 (d, J = 15.1 Hz, 1H), 4.12-3.82 (m, 2H), 3.75-3.44 (m, 3H), 3.31 (t, J = 8.3 Hz, 2H), 2.84 (t, J = 8.2 Hz, 2H), 2.76-2.60 (m, 3H), 2.02 (s, 3H), 1.76 (s, 2H). | [M + H]+ Cac. 374.1; found 373.9 | 99.9 | first eluting enantiomer (chiral PAK IG) | 103-105 |
| 145 | 1HNMR (300 MHz, DMSO, ppm) 7.34 (s, 1H), 6.77 (s, 1H), 5.76 (s, 2H), 4.95 (s, 3H), 4.12 (s, 2H), 3.91 (d, J = 11.5 Hz, 1H), 3.65 (d, J = 12.2 Hz, 1H), 3.62-3.48 (m, 3H), 1.99 (s, 3H), 1.73 (s, 2H). | [M + H]+ Cac. 402.1; found 402.0 | 99.7 | chiral PAK IG | 195-197 |
| 146 | (300 MHz, DMSO-d6): 11.37 (b, 1H), 7.25 (d, J = 7.1 Hz, 1H), 6.29 (d, J = 7.0 Hz, 1H), 5.63 (s, 1H), 5.49 (s, 2H), 5.24 (s, 1H), 4.55-4.24 (m, 4H), 3.89 (d, J = 13.6 Hz, 1H), 3.70-3.40 (m, 3H), 3.00 (s, 3H), 2.02 (s, 3H), 1.89-1.64 (m, 2H). | [M + H]+ Cac. 394.1; found 394.1 | 98.1 | | 148-150 |
| 147 | 1HNMR (300 MHz, DMSO, ppm) 7.01 (s, 1H), 6.82 (s, 1H), 5.58 (s, 1H), 5.47 (s, 2H), 5.31 (s, 1H), 4.78 (s, 2H), 4.65 (d, J = 14.6 Hz, 1H), 4.04 (dd, J = 13.4, 5.0 Hz, 1H), 3.89 (d, J = 11.2 Hz, 1H), 3.74 (s, 5H), 3.57 (dd, J = 5.7, 3.9 Hz, 5H), 3.46 (dd, J = 5.7, 3.9 Hz, 4H), 2.01 (s, 3H), 1.76 (d, J = 6.1 Hz, 2H). | [M + H]+ Cac. 492.2; found 492.1 | 99.4 | | 115 |
| 148 | 1H NMR (300 MHz, DMSO-d6, ppm, 353 K) δ = 6.90 (s, 1 H), 6.23 (s, 1 H), 5.54 (s, 1 H), 5.46 (br s, 3 H), 5.22-5.18 (m, 1 H), 4.86-4.82 (m, 2 H), 4.72-4.67 (m, 1 H), 4.54-4.48 (m, 1 H), 4.00 (dd, J = 13.5, 5.1 Hz, 1 H), 3.90-3.86 (m, 1 H), 3.69-3.48 (m, 3 H), 2.07 (s, 3 H), 1.99 (s, 3 H), 1.73 (br s, 2 H). | n.a | 95 | | |
| 149 | 1H NMR (300 MHz, DMSO-d6) 7.02 (s, 1H), 6.85 (s, 1H), 5.58 (s, 1H), 5.47 (s, 2H), 5.33 (s, 1H), 4.59 (d, J = 15.4 Hz, 1H), 4.07 (dd, J = 13.4, 5.0 Hz, 1H), 3.88 (d, J = 11.7 Hz, 5H), 3.80-3.41 (m, 3H), 2.01 (s, 3H), 1.74 (d, J = 5.0 Hz, 2H), 0.60 (d, J = 3.1 Hz, 4H). | [M + H]+ Cac. 417.0; found 417.0 | 99.8 | chiral pak IG | 105 |
| 150 | 1H NMR (300 MHz, DMSO, ppm) 12.90 (s, 2H), 7.90 (s, 2H), 7.58 (s, 2H), 7.10 (s, 1H), 7.03 (s, 1H), 6.79 (d, J = 8.1 Hz, 2H), 6.56 (s, 1H), 5.96 (dd, J = 9.6, 5.3 Hz, 1H), 5.66 (s, 1H), 5.12 (dd, J = 9.6, 5.2 Hz, 1H), 4.96 (d, J = 14.5 Hz, 1H), 4.67-4.47 (m, 2H), 4.18-4.00 (m, 1H), 4.06-3.95 (m, 2H), 4.01-3.86 (m, 3H), 3.92-3.78 (m, 1H), 2.29 (s, 3H), 2.18 (s, 3H), 1.83 (s, 5H), 1.27 (ddd, J = 15.5, 6.4, 2.7 Hz, 18H). | [M + H]+ Cac. 421.0; found 421.15 | 98.8 | | 139-141 |
| 151 | 1HNMR (300 MHz, DMSO, D2O) 6.63 (s, 1H), 6.54 (s, 1H), 5.86 (s, 2H), 5.40 (s, 1H), 5.00 (s, 3H), 3.93 (m, J = 17.1, 8.5 Hz, 2H), 3.68 (s, 5H), 3.50 (s, 1H), 1.96 (s, 3H), 1.70 (s, 2H). | n.a | 97.5 | Chiral ART cellulose SB | 150 |

-continued

| D# | NMR | LC/MS | HPLC Purity | enantiomeric purity | melting point (° C.) |
|---|---|---|---|---|---|
| 152 | (300 MHz, DMSO-d6): 7.51-6.86 (m, 4H) 5.67 (s, 1H), 5.46 (s, 3H), 4.52 (d, J = 15.7 Hz, 3H), 4.14 (dd, J = 13.3, 5.2 Hz, 1H), 3.91 (d, J = 12.0 Hz, 1H), 3.77-3.45 (m, 3H), 2.86 (s, 3H), 2.01 (s, 3H), 1.76 (s, 2H). | [M + H]+ Cac. 443.15; found 443.1 | 99.8 | first eluting enantiomer (Chiral ART cellulose SB) | 101-103 |
| 153 | | | 99.7 | | |
| 154 | 1H NMR (300 MHz, DMSO-d6, ppm, 353 K) δ = 6.99 (s, 1 H), 6.81 (s, 1 H), 5.61 (s, 1 H), 5.58 (br s, 2 H), 5.34-5.30 (m, 1 H), 4.60-4.55 (m, 1 H), 4.05 (dd, J = 13.5, 5.1 Hz, 1 H), 3.88-3.51 (m, 8 H), 2.01 (s, 3 H), 1.74 (br s, 2 H), 0.95 (s, 6 H). | [M + H]+ Cac. 419.0; found 419.0 | 97 | first eluting enatiomer (chiral pak IG-3) | 110 |
| 155 | 1H NMR (300 MHz, DMSO-d6, ppm, 353 K) δ = 6.61 (s, 1 H), 6.60 (s, 1 H), 5.92 (s, 1 H), 5.54 (s, 1 H), 5.46 (br s, 2 H), 5.20-5.17 (m, 1 H), 4.72-4.65 (m, 1 H), 4.12-4.01 (m, 3 H), 3.89-3.85 (m, 1 H), 3.71-3.63 (m, 1 H), 3.58-3.51 (m, 3 H), 3.01-2.98 (m, 1 H), 1.99 (s, 3 H), 1.74 (br s, 2 H) 1.40 (s, 3 H), 1.12 (t, J = 9.6, 3 H). | [M + H]+ Cac. 462.9; found 462.2 | 99.9 | first eluting isomer (Chiral ART cellulose SB) | |
| 156 | 1H NMR (300 MHz, D2O mixed with one drop of DCl in deuterium oxide solution, ppm) (contains two rotamers) δ = 7.86 (s, 0.3 H), 7.80 (s, 0.7 H), 7.27 (s, 0.3 H), 7.24 (s, 0.7 H), 6.39 (s, 0.7 H), 5.90-5.86 (m, 0.7 H), 5.50 (s, 0.3 H), 5.38-5.34 (m, 0.3 H), 5.01-4.94 (m, 3 H), 4.36-4.20 (m, 1.7 H), 4.07-3.93 (m, 1.7 H), 3.84-3.73 (m, 3.3 H), 3.63-3.58 (m, 1 H), 2.21 (s, 2.1 H), 2.09 (s, 0.9 H), 1.96-1.80 (m, 2 H). | [M + H]+ Cac. 402.8; found 402.1 | 97.7 | | |
| 157 | 1H NMR (300 MHz, DMSO-d6, ppm, 353 K) δ = 6.61 (s, 1 H), 6.60 (s, 1 H), 5.92 (s, 1 H), 5.54 (s, 1 H), 5.46 (br s, 2 H), 5.20-5.17 (m, 1 H), 4.72-4.65 (m, 1 H), 4.04-3.84 (m, 4 H), 3.69-3.50 (m, 4 H), 3.01-2.98 (m, 1 H), 1.99 (s, 3 H), 1.74 (br s, 2 H) 1.40 (s, 3 H), 0.97 (t, J = 9.6, 3 H). | [M + H]+ Cac. 462.9; found 462.1 | 99.7 | second eluting isomer (Chiral ART cellulose SB) | |
| 158 | 1H NMR (300 MHz, DMSO-d6, ppm, 353 K) δ = 7.42-7.36 (m, 3 H), 5.67 (s, 1 H), 5.54-5.49 (m, 1 H), 5.41 (br s, 2 H), 4.50 (s, 3 H), 4.49-4.42 (m, 1 H), 4.08 (dd, J = 13.5, 5.1 Hz, 1 H), 3.90-3.75 (m, 2 H), 3.64-3.52 (m, 2 H), 2.88 (s, 3 H), 2.01 (s, 3 H), 1.85-1.72 (m, 2 H). | [M + H]+ Cac. 461.4; found 461.1 | 99.5 | first eluting enantiomer (chiral pak IE) | 95-97 |
| 159 | (300 MHz, DMSO-d6): 7.20 (s, 1H), 6.90 (s, 1H), 5.63 (s, 1H), 5.54 (s, 1H), 5.10 (s, 2H), 4.63 (d, J = 14.3 Hz, 1H), 4.07 (dd, J = 13.4, 5.0 Hz, 1H), 3.90 (d, J = 11.7 Hz, 1H), 3.72 (s, 5H), 3.58 (t, J = 13.4 Hz, 1H), 2.03 (s, 3H), 1.79 (s, 2H). | [M + H]+ Cac. 405.0; found 404.1 | 98.3 | first eluting enantiomer (chiral ART cellulose-SB) | 82-84 |
| 160 | 1H NMR (300 MHz, DMSO, ppm) 6.94 (s, 1H), 6.82 (s, 1H), 5.65 (d, J = 15.1 Hz, 3H), 5.33 (s, 1H), 4.67 (d, J = 15.5 Hz, 1H), 4.55 (s, 2H), 4.14-3.86 (m, 3H), 3.77 (dd, J = 13.6, 10.1 Hz, 1H), 3.67-3.53 (m, 0H), 2.05 (s, 3H), 1.79 (s, 2H), 1.38-1.21 (m, 4H), 0.89 (s, 0H). | [M + H]+ Cac. 436.9; found 437.0 | 97.5 | | 155-157 |
| 161 | 1HNMR (300 MHz, DMSO, ppm) 7.14 (d, J = 16 Hz, 1H), 6.81 (s, 1H), 5.55 (d, J = 7.0 Hz, 3H), 5.26 (s, 3H), 4.67 (s, 1H), 4.12 (dd, J = 13.5, 5.0 Hz, 1H), 3.90 (d, J = 11.9 Hz, 1H), 3.74-3.48 (m, 3H), 2.02 (s, 3H), 1.77 (s, 2H). | [M + H]+ Cac. 418.1; found 417.9 | 99.4 | first eluting enantiomer (chiral pack IG) | 215 |
| 162 | (300 MHz, DMSO-d6) 7.50 (s, 1H), 7.34 (d, J = 1.1 Hz, 2H), 5.58 (s, 1H), 5.50 (s, 3H), 4.64 (d, J = 15.3 Hz, 1H), 4.43 (s, 2H), 4.12 (dd, J = 13.5, 4.9 Hz, 1H), 3.91 (d, J = 12.2 Hz, 1H), 3.79-3.65 (m, 2H), 3.54 (d, J = 11.5 Hz, 1H), 2.87 (s, 3H), 2.29 (q, J = 7.6 Hz, 2H), 1.79 (s, 2H), 1.04 (t, J = 7.6 Hz, 3H). | [M + H]+ Cac. 425.3; found 425.0 | 98.7 | First eluting enantiomer (chiral pak IA) | 108-110 |
| 163 | (300 MHz, DMSO-d6) 7.39-7.07 (m, 3H), 5.58 (s, 1H), 5.44 (s, 3H), 4.62 (d, J = 16.5 Hz, 1H), 4.56-4.49 (m, 2H), 4.48-4.41 (m, 2H), 4.11 (dd, J = 13.4, 5.0 Hz, 1H), 3.89 (d, J = 11.6 Hz, 1H), 3.72-3.43 (m, 4H), 2.80 (d, J = 11.1 Hz, 2H), 2.00 (s, 3H), 1.97-1.86 (m, 2H), 1.76 (d, J = 8.3 Hz, 4H), 1.70-1.52 (m, 3H). | [M + H]+ Cac. 458.2; found 458.1 | 98.9 | First eluting enantiomer (chiral pack IG) | 100-102 |
| 164 | (300 MHz, DMSO-d6) 7.31 (s, 1H), 7.17 (s, 1H), 5.57 (s, 1H), 5.45 (s, 2H), 5.38-5.29 (m, 1H), 4.69 (d, J = 15.0 Hz, 1H), 4.06 (dd, J = 13.5, 5.1 Hz, 1H), 3.92 (d, J = 11.8 Hz, 1H), 3.78-3.61 (m, 4H), 3.56-3.46 (m, 3H), 2.22 (s, 3H), 1.99 (s, 3H), 1.76 (d, J = 6.6 Hz, 2H), 1.67 (s, 2H). | [M + H]+ Cac. 362.2; found 362.2 | 99.1 | First eluting enantiomer (chiral pack IG) | 93-95 |

| D# | NMR | LC/MS | HPLC Purity | enantiomeric purity | melting point (° C.) |
|---|---|---|---|---|---|
| 165 | (300 MHz, DMSO-d6, ppm): 9.12 (s, 1 H), 7.09 (s, 1 H), 6.73 (s, 1 H), 5.49 (d, J = 10.8 Hz, 3 H), 5.22 (s, 1 H), 4.72 (d, J = 15.4 Hz, 1 H), 4.11 (d, J = 11.7 Hz, 1 H), 3.90 (d, J = 11.8 Hz, 1 H), 3.73-3.45 (m, 3 H), 2.07 (s, 3 H), 1.99 (s, 3 H), 1.76 (s, 2 H). | [M + H]+ Cac. 350.0; found 349.1 | 99.7 | Second eluting enantiomer (chiral pack IG) | 263-265 |
| 166 | 1HNMR (300 MHz, DMSO, ppm) 8.51 (s, 1H), 7.63 (s, 1H), 6.39 (s, 2H), 6.02 (s, 1H), 5.82-5.62 (m, 1H), 4.60 (s, 2H), 4.41 (d, J = 15.0 Hz, 1H), 4.25-4.05 (m, J = 13.5, 5.0 Hz, 1H), 4.04-3.75 (m, 3H), 3.72-3.55 (m, J = 12.2, 11.5, 4.8 Hz, 1H), 3.00 (s, 3H), 2.16 (s, 3H), 1.83 (d, J = 4.6 Hz, 2H). | [M + H]+ Cac. 412.1; found 412.1 | 99.5 | Second eluting enantiomer (chiral pack IG) | 160 |
| 167 | 1H NMR (300 MHz, DMSO-d6) 8.46 (d, J = 1.9 Hz, 1H), 7.89 (d, J = 1.9 Hz, 1H), 5.73 (s, 1H), 5.62 (s, 1H), 5.35 (s, 2H), 4.51 (s, 2H), 4.27 (s, 1H), 4.17 (dd, J = 13.3, 5.5 Hz, 1H), 3.97 (d, J = 11.6 Hz, 2H), 3.80 (dd, J = 13.3, 10.7 Hz, 1H), 3.53 (s, 1H), 2.94 (s, 3H), 2.03 (s, 3H), 1.77 (d, J = 3.7 Hz, 2H). | [M + H]+ Cac. 412.1; found 412.1 | 99.5 | first eluting enantiomer chiral pack IG | 120-122 |
| 168 | (300 MHz, DMSO-d6) 7.21 (d, J = 8.7 Hz, 1H), 6.99 (d, J = 2.6 Hz, 1H), 6.86 (dd, J = 8.6, 2.6 Hz, 1H), 5.56 (s, 1H), 5.46 (s, 2H), 5.39-5.29 (m, 1H), 4.64 (d, J = 14.8 Hz, 1H), 4.07 (dd, J = 13.4, 5.0 Hz, 1H), 3.94-3.81 (m, 1H), 3.70 (dd, J = 13.5, 10.2 Hz, 4H), 3.64-3.49 (m, 2H), 2.00 (s, 3H), 1.75 (dd, J = 8.4, 4.2 Hz, 2H). | [M + H]+ Cac. 349.1; found 349.1 | 98.4 | first eluting enantiomer (CHIRALPAK IG) | 89-91 |
| 169 | 1H NMR (300 MHz, DMSO-d6, ppm): 7.58 (s, 1 H), 6.46 (s, 3 H), 5.74 (s, 1 H), 5.31 (s, 1 H), 4.59 (d, J = 15.0 Hz, 1 H), 4.18-3.98 (m, 1 H), 3.87-3.77 (m, 1 H), 3.77-3.59 (m, 2 H), 3.57-3.44 (m, 2 H), 2.06 (s, 3 H), 1.73 (s, 2 H). | [M + H]+ Cac. 379.8; found 379.1 | 98.9 | Chiral-pak-IG | 278.00-280.00 |
| 170 | (300 MHz, DMSO-d6, ppm): 7.58 (s, 1H), 6.50 (s, 3H), 5.76 (s, 1H), 5.32 (s, 1H), 4.59 (d, J = 14.5 Hz, 1H), 4.18-4.01 (m, 1H), 3.89-3.60 (m, 3H), 3.60-3.39 (m, 2H), 2.07 (s, 3H), 1.74 (s, 2H). | [M + H]+ Cac. 379.8; found 379.1 | 98.2 | Chiral-pak-IG | 278.00-280.00 |
| 171 | 1HNMR (300 MHz, DMSO, ppm) 9.83 (s, 1H), 7.34 (s, 1H), 6.87 (s, 1H), 5.53 (d, J = 16.0 Hz, 3H), 5.32 (s, 1H), 4.65 (d, J = 15.1 Hz, 1H), 4.43-4.06 (m, 3H), 3.90 (d, J = 11.7 Hz, 1H), 3.79-3.37 (m, 3H), 2.85 (s, 3H), 2.01 (s, 3H), 1.77 (d, J = 6.0 Hz, 2H). | [M + H]+ Cac. 427.1; found 427.0 | 99.3 | (R,R)-Welk-01 | 300 |
| 172 | 1HNMR (300 MHz, Methanol, ppm) 8.03 (s, 0.5H), 7.95 (s, 0.5H), 6.43 (s, 0.5H), 6.00 (s, 0.5H), 5.77 (s, 0.5H), 5.18 (s, 0.5H), 4.78-3.57 (m, 2H), 4.48-3.96 (m, 4H), 3.95-3.50 (m, 2H), 3.16-3.00 (m, 3H), 2.30 (d, J = 19.6 Hz, 3H), 1.88 (s, 2H). | [M + H]+ Cac. 395.1; found 395.0 | 98.8 | | 150 |
| 173 | 1HNMR (300 MHz, DMSO, ppm) 8.01-7.41 (m, 2H), 7.32 (d, J = 7.7 Hz, 1H), 5.73 (s, 1H), 5.45 (s, 3H), 4.51 (s, 2H), 4.38 (d, J = 15.3 Hz, 1H), 4.25-4.08 (m, J = 13.3, 5.1 Hz, 1H), 3.91 (d, J = 12.4 Hz, 1H), 3.83-3.76 (m, J = 13.4, 10.2 Hz, 1H), 3.74-3.60 (m, 1H), 3.60-3.42 (m, 1H), 2.99 (s, 3H), 2.03 (s, 3H), 1.77 (s, 2H). | [M + H]+ Cac. 444.1; found 444.0 | 99.3 | Chiral Pak IG | 80 |
| 174 | 1H NMR (300 MHz, DMSO-d6) 7.43 (s, 1H), 7.19 (s, 1H), 5.69 (s, 1H), 5.45 (s, 3H), 4.45 (d, J = 16.2 Hz, 1H), 4.13-3.39 (m, 7H), 2.40 (s, 3H), 2.05 (s, 3H), 1.87-1.64 (m, 2H). | [M + H]+ Cac. 362.1; found 362.1 | 99.6 | Chiral Pak AG | 106-108 |
| 175 | 1H NMR (300 MHz, DMSO, ppm) 8.79 (s, 1H), 8.40 (s, 1H), 7.77 (m = 9.1 Hz, 1H), 7.65 (m = 9.2, 1.8 Hz, 1H), 5.88 (s, 1H), 5.72 (s, 1H), 5.60 (s, 2H), 4.25 (m = 13.2, 5.2 Hz, 2H), 4.03 (m = 13.4, 9.4 Hz, 1H), 3.92 (m = 10.6 Hz, 1H), 3.64 (m = 12.8 Hz, 2H), 2.08 (s, 3H), 1.87 (s, 1H), 1.79 (s, 3H). | [M + H]+ Cac. 326.4; found 326.0 | 95.3 | | 95-97 |
| 176 | 1H NMR (300 MHz, DMSO, ppm) 7.08 (m = 13.1 Hz, 3H), 6.85 (s, 1H), 5.61 (s, 1H), 5.51 (s, 2H), 5.39-5.30 (m, 1H), 4.66 (m = 14.9 Hz, 1H), 4.46 (s, 2H), 4.05 (s, 1H), 4.15-3.95 (m, 2H), 3.91 (m = 12.1 Hz, 1H), 3.83-3.51 (m, 3H), 2.03 (s, 3H), 1.78 (m = 7.8, 3.8 Hz, 2H), 1.31 (m = 6.9 Hz, 3H). | [M + H]+ Cac. 436.9; found 436.0 | 99.7 | Chiral Pak AG | 110-112 |
| 177 | 1H NMR (300 MHz): 7.94-7.89 (m, 1H), 7.82 (d, J = 8.2 Hz, 1H), 7.43 (d, J = 8.0 Hz, 1H), 5.69-5.62 (m, 1H), 4.59 (d, J = 15.5 Hz, 1H), 4.21-4.11 (m, 1H), 3.92 (d, J = 11.8 Hz, 1H), 3.75 (d, J = 11.8 Hz, 2H), 3.57 (t, J = 10.0 Hz, 1H), 2.08-1.98 (m, 3H), 1.80 (s, 2H). | [M + H]+ Cac. 363.8; found 363.8 | 99 | | 260-262 |

-continued

| D# | NMR | LC/MS | HPLC Purity | enantiomeric purity | melting point (° C.) |
|---|---|---|---|---|---|
| 178 | 1H NMR (300 MHz): 7.13-7.10 (m, 1H), 6.84 (s, 1H), 5.61 (s, 1H), 5.49 (s, 2H), 5.34 (s, 1H), 4.81-4.77 (m, 2H), 4.66 (d, J = 15.9 Hz, 1H), 4.07 (m, J = 13.5, 5.0 Hz, 1H), 3.91 (d, J = 12.1 Hz, 1H), 3.74 (s, 5H), 3.41 (t, J = 2.6 Hz, 1H), 3.01 (s, 1H), 2.03 (s, 3H), 1.78 (s, 2H). | [M + H]+ Cac. 403.8; found 403.8 | 98.8 | Chiral Pak AD-03 | 78-80 |
| 179 | 1HNMR (300 MHz, DMSO, ppm) 8.86 (s, 1H), 6.94 (s, 1H), 6.71 (s, 1H), 5.52 (s, 1H), 5.47 (s, 2H), 5.26-5.13 (m, 1H), 4.74 (d, J = 14.9 Hz, 1H), 4.14-3.98 (m, 1H), 3.89 (d, J = 11.9 Hz, 1H), 3.76 (d, J = 0.9 Hz, 3H), 3.72-3.66 (m, 1H), 3.60-3.45 (m, 1H), 2.54-2.19 (m, 2H), 1.84-1.66 (m, 2H), 1.10-0.95 (m, 3H). | [M + H]+ Cac. 379.1; found 378.9 | 99.6 | Chiral Pak AG-3 | 135 |
| 180 | 1H NMR (300 MHz, DMSO-d6, ppm) 7.92 (s, 2 H), 6.75 (s, 1 H), 5.60 (s, 1 H), 5.49 (s, 2 H), 5.36 (brs, 1 H), 4.63 (d, J = 14.8 Hz, 1 H), 4.21-4.10 (m, 1 H), 3.91 (d, J = 11.8 Hz, 1 H), 3.81-3.47 (m, 4 H), 2.03 (s, 3H), 1.78 (brs, 2 H). | [M + H]+ Cac. 378.1; found 378.1 | 95 | ee = 96.3% | 220 |
| 181 | 1H NMR (300 MHz, DMSO, ppm) 6.70-6.59 (m, 2 H), 5.90 (m, 0.6 H), 5.70 (s, 1 H), 5.19 (m, 0.4 H), 4.87-5.19 (s, 0.6 H), 4.21-4.11 (m, 0.4 H), 4.03 (m, 1 H), 3.95-3.73 (m, 3 H), 3.52 (m, 2 H), 2.97 (m, 1 H), 2.28 (s, 1 H), 2.19 (s, 2 H), 1.79 (m, 2 H), 1.43 (s, 3 H). | [M + H]+ Cac. 434.0; found 434.0 | 97.6 | | |
| 182 | 1H NMR (300 MHz, DMSO-d6, ppm) 8.67 (s, 1 H), 7.88 (s, 1 H), 6.79 (s, 1 H), 5.60 (s, 1 H), 5.48 (s, 2 H), 5.43-5.33 (m, 1 H), 4.61 (d, J = 15.4 Hz, 1 H), 4.18-4.08 (m, 1 H), 3.95-3.86 (m, 1 H), 3.79-3.52 (m, 3 H), 2.82 (s, 3 H), 2.02 (s, 3 H), 1.78 (s, 2 H). | [M + H]+ Cac. 392.1; found 392.1 | 95 | ee = 96.6% | 190 |
| 183 | 1H NMR (300 MHz, DMSO-d6, ppm) 7.14 (s, 1 H), 6.84 (s, 1 H), 5.57 (s, 1 H), 5.51 (s, 2 H), 5.40-5.26 (m, 1 H), 4.67 (d, J = 15.0 Hz, 1 H), 4.17 (s, 1 H), 3.96-3.87 (m, 1 H), 3.78-3.52 (m, 3 H), 2.88 (s, 6 H), 2.03 (s, 3H), 1.80 (s, 2 H). | [M + H]+ Cac. 406.2; found 406.2 | 99.5 | ee = 98.6% | 179 |
| 184 | 1H NMR (300 MHz, DMSO, ppm) 7.34 (s, 1 H), 7.01 (s, 1 H), 5.64 (s, 3 H), 5.31-5.45 (m, 1 H), 4.61 (d, J = 14.6 Hz, 1 H), 4.16 (dd, J = 13.5, 4.9 Hz, 1 H), 3.97-3.86 (m, 1 H), 3.83-3.51 (m, 4 H), 2.06 (s, 3 H), 1.91-1.70 (m, 2 H). | [M + H]+ Cac. 419.8; found 419.1 | 95.9 | (R,R) Welk-O | 140-142 |
| 185 | 1H NMR (300 MHz, DMSO-d6, ppm) 8.72-8.69 (m, 1 H), 7.92 (s, 1 H), 6.77 (s, 1 H), 5.60 (s, 1 H), 5.48 (s, 2 H), 5.43-5.30 (m, 1 H), 4.63 (d, J = 14.8 Hz, 1 H), 4.15 (dd, J = 13.4, 4.8 Hz, 1 H), 3.98-3.85 (m, 1 H), 3.81-3.48 (m, 5 H), 3.39 (t, J = 6.0 Hz, 2 H), 2.01 (s, 3 H), 1.79-1.76 (m, 2 H). | [M + H]+ Cac. 422.2; found 422.1 | 93.6 | First eluting isomer (Lux Cellulose-4) - ee = 97.6% | 170 |
| 186 | 1H NMR (300 MHz, DMSO, ppm) 12.14 (s, 1 H), 8.60 (s, 1 H), 7.90 (s, 1 H), 6.78 (s, 1 H), 5.60 (s, 1 H), 5.48 (s, 2 H), 5.37 (s, 1 H), 4.62 (d, J = 14.9 Hz, 1 H), 4.20-4.09 (m, 1 H), 3.90 (d, J = 11.8 Hz, 1 H), 3.83-3.48 (m, 3 H), 2.88 (s, 1 H), 2.03 (s, 3 H), 1.79 (s, 2 H), 0.74 (d, J = 6.8 Hz, 2 H), 0.62 (s, 2 H). | [M + H]+ Cac. 418.2; found 418.1 | 97 | ee = 98.8% | 180 |
| 187 | 1H NMR (300 MHz, DMSO, ppm) 7.99-7.77 (m, 2 H), 7.52-7.36 (m, 1 H), 6.62 (s, 0.5 H), 5.98-5.85 (m, 0.5 H), 5.55 (s, 0.5 H), 4.94 (d, J = 14.4 Hz, 0.5 H), 4.32-4.09 (m, 2 H), 4.08-3.74 (m, 3 H), 3.56 (d, J = 13.3 Hz, 1 H), 2.21 (d, J = 35.9 Hz, 3 H), 1.97-1.64 (m, 2 H). | [M + H]+ Cac. 363.1; found 363.1 | 97.3 | | |
| 188 | 1H NMR (300 MHz, DMSO-d6, ppm) 7.96 (d, J = 1.9 Hz, 1H), 7.82 (dd, J = 8.2, 1.9 Hz, 1H), 7.61 (d, J = 8.2 Hz, 1H), 6.17 (s, 3H), 5.65 (s, 1H), 4.55 (s, 1H), 4.15 (dd, J = 13.6, 4.8 Hz, 1H), 4.04-3.78 (m, 3H), 3.69-3.53 (m, 1H), 3.21 (s, 3H), 1.84 (s, 2H). | [M + H]+ Cac. 450.9; found 451.1 | 93.8 | | 248-250 |
| 189 | 1H NMR (300 MHz, DMSO, ppm) 10.12 (s, 1 H), 7.22 (s, 1 H), 6.80 (s, 1 H), 5.94 (s, 2 H), 5.14 (d, J = 82.2 Hz, 2 H), 4.16 (d, J = 12.7 Hz, 1 H), 3.92 (d, J = 11.7 Hz, 1 H), 3.82-3.44 (m, 10 H), 3.16 (s, 2 H), 2.11-1.86 (m, 3 H), 1.75 (d, J = 5.9 Hz, 2 H). | [M + H]+ Cac. 448.2; found 448.2 | 97.7 | first eluting isomer (Chiracel ODH column-SFC) ee = 100% | 184.0-186.0 |
| 190 | 1H NMR (300 MHz, DMSO-d6, ppm) 8.30 (d, J = 1.9 Hz, 1H), 8.11 (m, J = 8.3, 2.0 Hz, 1H), 7.75 (d, J = 8.4 Hz, 1H), 5.85 (s, 1H), 5.66 (m, J = 10.2, 4.9 Hz, 1H), 5.43 (s, 2H), 4.27 (d, J = 16.1 Hz, 1H), 4.14 (m, J = 13.6, 5.0 Hz, 1H), 3.93 (m, J = 10.4, 3.3 Hz, 2H), 3.88-3.75 (m, 1H), 3.66-3.53 (m, 1H), 3.21-3.29 (s, 3H), 2.06 (s, 3H), 1.81 (m, J = 8.2, 4.4 Hz, 2H). | [M + H]+ Cac. 388.5; found 388.0 | 98.2 | | 140.0-142.0 |

| D# | NMR | LC/MS | HPLC Purity | enantiomeric purity | melting point (° C.) |
|---|---|---|---|---|---|
| 191 | 1H NMR (300 MHz, DMSO-d6, ppm) 7.53 (s, 1 H), 7.36-7.29 (m, 2 H), 5.62 (s, 1 H), 5.55-5.39 (m, 3 H), 4.60-4.46 (m, 2 H), 4.16-4.11 (m, 1 H), 3.92-3.82 (m, 1 H), 3.84-3.47 (m, 3 H), 3.00 (s, 3 H), 2.00 (s, 3 H), 1.88-1.68 (m, 2 H), 1.62 (d, J = 6.0 Hz, 3 H). | [M + H]+ Cac. 425.1; found 424.95 | 99.8 | third eluting isomer (column Chiral pak ID) ee = 100% | 140.0-142.0 |
| 192 | 1H NMR (300 MHz, DMSO-d6, ppm) 7.53 (s, 1 H), 7.48-7.24 (m, 2 H), 5.62 (s, 1 H), 5.55-5.31 (m, 3 H), 4.65-4.40 (m, 2 H), 4.21-4.02 (m, 1 H), 4.00-3.80 (m, 1 H), 3.80-3.46 (m, 3 H), 2.79 (s, 3 H), 2.01 (s, 3 H), 1.85-1.68 (m, 2 H), 1.64 (d, J = 7.2 Hz, 3 H). | [M + H]+ Cac. 425.1; found 424.95 | 98.3 | second eluting isomer (column Chiral pak ID) ee = 99.5 | 135.0-137.0 |
| 193 | 1H NMR (300 MHz, DMSO-d6, ppm) 7.53 (s, 1 H), 7.45-7.28 (m, 2 H), 5.62 (s, 1 H), 5.55-5.31 (m, 3 H), 4.69-4.43 (m, 2 H), 4.17-4.11 (m, 1 H), 4.00-3.82 (m, 1 H), 3.83-3.45 (m, 3 H), 2.80 (s, 3 H), 2.03 (s, 3 H), 1.91-1.70 (m, 2 H), 1.61 (d, J = 6.0 Hz, 3 H). | [M + H]+ Cac. 425.1; found 424.95 | 99.4 | first eluting isomer (column Chiral pak ID) ee = 99.5 | 135.0-137.0 |
| | 1H NMR (400 MHz, DMSO-d6) δ 7.61 (d, J = 17.9 Hz, 2H), 7.44 (d, J = 8.3 Hz, 1H), 6.57 (s, 1H), 5.96 (s, 1H), 5.76 (d, J = 10.5 Hz, 1H), 5.47 (s, 1H), 5.23 (s, 1H), 4.06 (s, 1H), 4.01 (d, J = 9.5 Hz, 1H), 3.82 (s, 1H), 3.69 (s, 2H), 2.02 (d, J = 0.8 Hz, 3H), 1.83 (s, 2H). | [M + H]+ Cac. 448.25; found 448.20 | 89 | | |

The invention claimed is:

1. A compound of formula I':

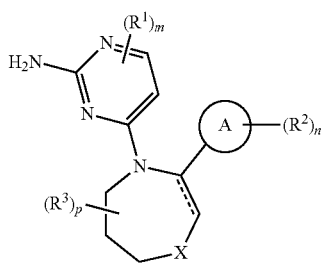

or a pharmaceutically acceptable salt thereof, wherein:

Ring A is ring selected from phenyl, a 5-7 membered saturated or partially unsaturated carbocyclic ring, a 8-12 membered saturated or partially unsaturated bicyclic heterocyclic ring having 1-2 heteroatoms independently selected from nitrogen, oxygen, or sulfur, a 5-6 membered heteroaromatic ring having 1-4 heteroatoms independently selected from nitrogen, oxygen, or sulfur; or an 8-10 membered bicyclic heteroaromatic ring having 1-5 heteroatoms independently selected from nitrogen, oxygen, or sulfur;

each $R^1$ is independently hydrogen, or $C_{1-3}$ aliphatic optionally substituted by 1-6 halogen; or two $R^1$ groups are optionally taken together with their intervening atoms to form a 5-8 membered partially unsaturated fused carbocyclic ring;

each of $R^2$ is independently hydrogen, halogen, —CN, —$NO_2$, —C(O)OR, —C(O)$NR_2$, —$NR_2$, —NRC(O)R, —NRC(O)OR, —NRS(O)$_2$R, —OR, —P(O)$R_2$, —SR, —S(O)R, —S(O)$_2$R, —S(O)(NH)R, —S(O)$_2$$NR_2$, or R; or two $R^2$ groups are optionally taken together to form =O; or two $R^2$ groups are optionally taken together with their intervening atoms to form a 3-8 membered saturated spirocyclic ring having 0-2 heteroatoms independently selected from nitrogen, oxygen or sulfur;

each $R^3$ is independently hydrogen, —OH, or $C_{1-3}$ aliphatic; or two $R^3$ groups are optionally taken together to form =O; or two $R^3$ groups are optionally taken together to form =$CH_2$; or two $R^3$ groups are optionally taken together with their intervening atoms to form a 3-8 membered saturated spirocyclic ring having 0-2 heteroatoms independently selected from nitrogen, oxygen or sulfur; or two $R^3$ groups are optionally taken together with their intervening atoms to form a 5-8 membered saturated bridged bicyclic ring having 0-2 heteroatoms independently selected from nitrogen, oxygen or sulfur;

each R is independently hydrogen or an optionally substituted group selected from $C_{1-6}$ aliphatic, a 3-8 membered saturated or partially unsaturated monocyclic carbocyclic ring, phenyl, a 7-10 membered saturated spirobicyclic heterocyclic ring having 1-2 heteroatoms independently selected from nitrogen, oxygen, or sulfur, a 7-10 membered saturated or partially unsaturated fused bicyclic heterocyclic ring having 1-2 heteroatoms independently selected from nitrogen, oxygen, or sulfur, a 4-8 membered saturated or partially unsaturated monocyclic heterocyclic ring having 1-2 heteroatoms independently selected from nitrogen, oxygen, or sulfur, or a 5-6 membered monocyclic heteroaromatic ring having 1-4 heteroatoms independently selected from nitrogen, oxygen, or sulfur; or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen and sulfur, optionally substituted with 1-2 oxo groups;

===== is a single bond or a double bond;

X is —O—;

m is 0, 1, or 2;

n is 0, 1, 2, 3, 4 or 5; and p is 0, 1, or 2.

2. The compound of claim 1, or a pharmaceutically acceptable salt thereof, wherein Ring A is phenyl.

3. The compound of claim 1, or a pharmaceutically acceptable salt thereof, wherein at least one of $R^1$ is $C_{1-3}$ aliphatic.

4. The compound of claim 1, or a pharmaceutically acceptable salt thereof, wherein at least one of $R^1$ is —$CH_3$.

5. The compound of claim 1, or a pharmaceutically acceptable salt thereof, wherein at least one of $R^1$ is attached to position 6 of the pyrimidine.

6. The compound of claim 1, or a pharmaceutically acceptable salt thereof, wherein at least one of $R^2$ is $C_{1-6}$ aliphatic, optionally substituted 1-4 times by halogen, —OH, $NH_2$, —$OCH_3$, —NHC(O)$CH_3$, —S(O)$_2CH_3$, —COOH, —$CO_2CH_3$, —$CO_2C_2H_5$, or —N($CH_3$)C(O)$CH_3$.

7. The compound of claim 1, or a pharmaceutically acceptable salt thereof, wherein at least one of $R^2$ is a 3-6 membered saturated monocyclic carbocyclic ring.

8. The compound of claim 1, or a pharmaceutically acceptable salt thereof, wherein at least one of $R^2$ is a 7-10 membered saturated spirobicyclic heterocyclic ring having 1-2 heteroatoms independently selected from nitrogen or oxygen.

9. The compound of claim 1, or a pharmaceutically acceptable salt thereof, wherein at least one of $R^2$ is a 7-10 membered saturated fused bicyclic heterocyclic ring having 1-2 heteroatoms independently selected from nitrogen or oxygen.

10. The compound of claim 1, or a pharmaceutically acceptable salt thereof, wherein at least one of $R^2$ is a 4-6 membered saturated monocyclic heterocyclic ring having 1-2 heteroatoms independently selected from nitrogen, oxygen, or sulfur, optionally substituted 1-4 times by halogen, —OH, —$CH_3$, —$OCH_3$, =O, 0, or

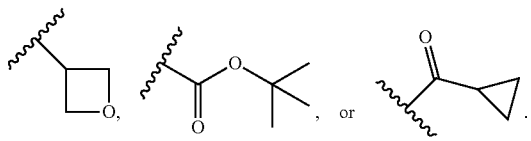

11. The compound of claim 1, or a pharmaceutically acceptable salt thereof, wherein at least one of $R^2$ is a 5-6 membered monocyclic heteroaromatic ring having 1-2 heteroatoms independently selected from nitrogen, oxygen, or sulfur.

12. The compound of claim 1, or a pharmaceutically acceptable salt thereof, wherein at least one of $R^2$ is —C(O)OR, wherein R is hydrogen or $C_{1-6}$ aliphatic.

13. The compound of claim 1, or a pharmaceutically acceptable salt thereof, wherein at least one of $R^2$ is —C(O)$NR_2$, wherein each of R is independently hydrogen, $C_{1-6}$ aliphatic which is optionally substituted by a —N($CH_3$)$_2$, unsubstituted 3-6 membered saturated monocyclic carbocyclic ring, or unsubstituted 4-6 membered saturated monocyclic heterocyclic ring having 1-2 heteroatoms independently selected from nitrogen or oxygen, or two R taken together with their intervening atoms to form a 4-7 membered saturated and unsubstituted ring having 0-3 heteroatoms, in addition to the nitrogen, independently selected from nitrogen, oxygen and sulfur.

14. The compound of claim 1, or a pharmaceutically acceptable salt thereof, wherein at least one of $R^2$ is —$NR_2$, wherein each of R is independently:

hydrogen;

$C_{1-6}$ aliphatic which is optionally substituted 1-2 times by —OH,

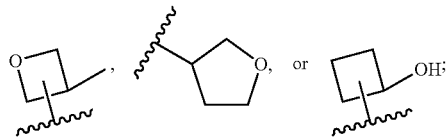

unsubstituted 3-6 membered saturated monocyclic carbocyclic ring;

4-6 membered saturated monocyclic heterocyclic ring having 1-2 heteroatoms independently selected from nitrogen or oxygen, which is optionally substituted 1-2 times by $CH_3$, —OH, —C(O)OC($CH_3$)$_3$, or —C(O)$CH_3$; or 6 membered monocyclic heteroaromatic ring having 1-2 heteroatoms independently selected from nitrogen, oxygen, or sulfur which is optionally substituted 1-2 times by —$CH_3$ or —$NH_2$.

15. The compound of claim 1, or a pharmaceutically acceptable salt thereof, wherein at least one of $R^2$ is —NHC(O)R, wherein R is $C_{1-6}$ aliphatic optionally substituted 1-3 times by halogen, —$OCH_3$, —N($CH_3$)$_2$, or —OH, 3-6 membered saturated monocyclic carbocyclic ring optionally substituted 1-2 times by halogen or —OH, or 4-6 membered saturated monocyclic heterocyclic ring having 1-2 heteroatoms independently selected from nitrogen, oxygen or sulfur optionally substituted 1-2 times by halogen, —OH, or —$CH_3$.

16. The compound of claim 1, or a pharmaceutically acceptable salt thereof, wherein at least one of $R^2$ is —NHC(O)OR, wherein R is unsubstituted $C_{1-6}$ aliphatic.

17. The compound of claim 1, or a pharmaceutically acceptable salt thereof, wherein at least one of $R^2$ is —NHS(O)$_2$R, wherein R is unsubstituted $C_{1-6}$ aliphatic.

18. The compound of claim 1, or a pharmaceutically acceptable salt thereof, wherein at least one of $R^2$ is —OR, wherein R is:

hydrogen;

$C_{1-6}$ aliphatic optionally substituted by a halogen, —OH,

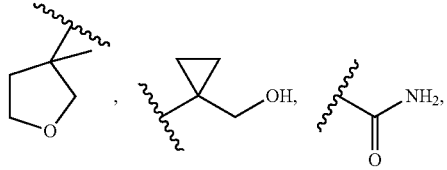

—C(O)NHC$_{1-4}$aliphatic, —COOH, —C(O)OC$_{1-4}$ aliphatic, —CN, —SO$_2$C$_{1-4}$aliphatic, or

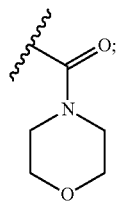 [SMILES: *C(=O)N1CCOCC1]

or 4-6 membered saturated monocyclic heterocyclic ring having 1-2 heteroatoms independently selected from nitrogen or oxygen.

19. The compound of claim 1, or a pharmaceutically acceptable salt thereof, wherein at least one of $R^2$ is —P(O)$R_2$, wherein each of R is independently unsubstituted $C_{1-6}$ aliphatic.

20. The compound of claim 1, or a pharmaceutically acceptable salt thereof, wherein at least one of $R^2$ is —SR, wherein R is unsubstituted $C_{1-6}$ aliphatic.

21. The compound of claim 1, or a pharmaceutically acceptable salt thereof, wherein at least one of $R^2$ is —S(O)R, wherein R is unsubstituted $C_{1-6}$ aliphatic.

22. The compound of claim 1, or a pharmaceutically acceptable salt thereof, wherein at least one of $R^2$ is —S(O)$_2$R, where R is unsubstituted $C_{1-6}$ aliphatic or 3-6 membered saturated monocyclic carbocyclic ring.

23. The compound of claim 1, or a pharmaceutically acceptable salt thereof, wherein at least one of $R^2$ is —S(O)(NH)R, wherein R is unsubstituted $C_{1-6}$ aliphatic.

24. The compound of claim 1, or a pharmaceutically acceptable salt thereof, wherein at least one of $R^2$ is —S(O)$_2$NR$_2$.

25. The compound of claim 1, or a pharmaceutically acceptable salt thereof, wherein at least one of $R^2$ is selected from the group consisting of: —CH$_3$, —CF$_3$, —CH$_2$CH$_3$, —C≡CH,

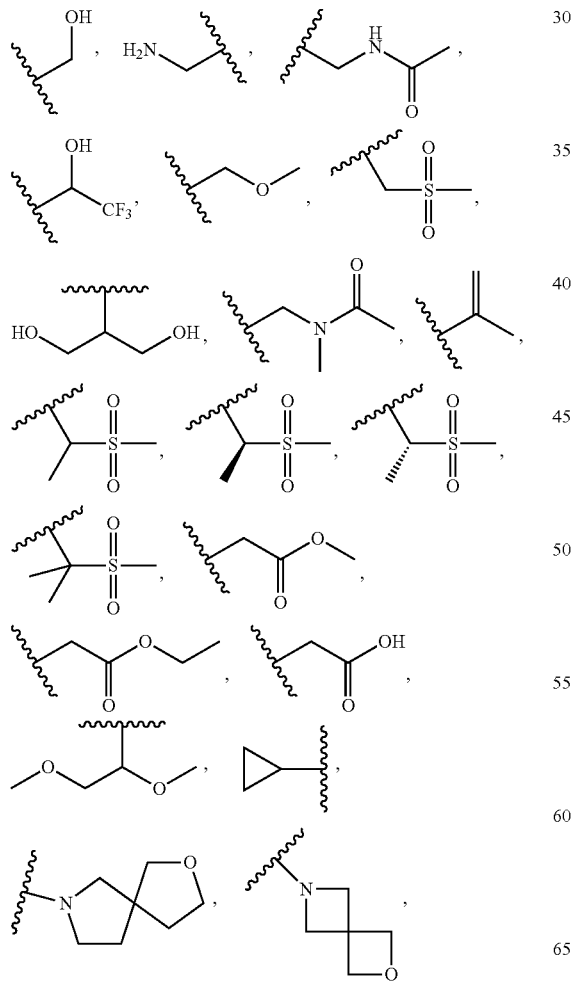

-continued

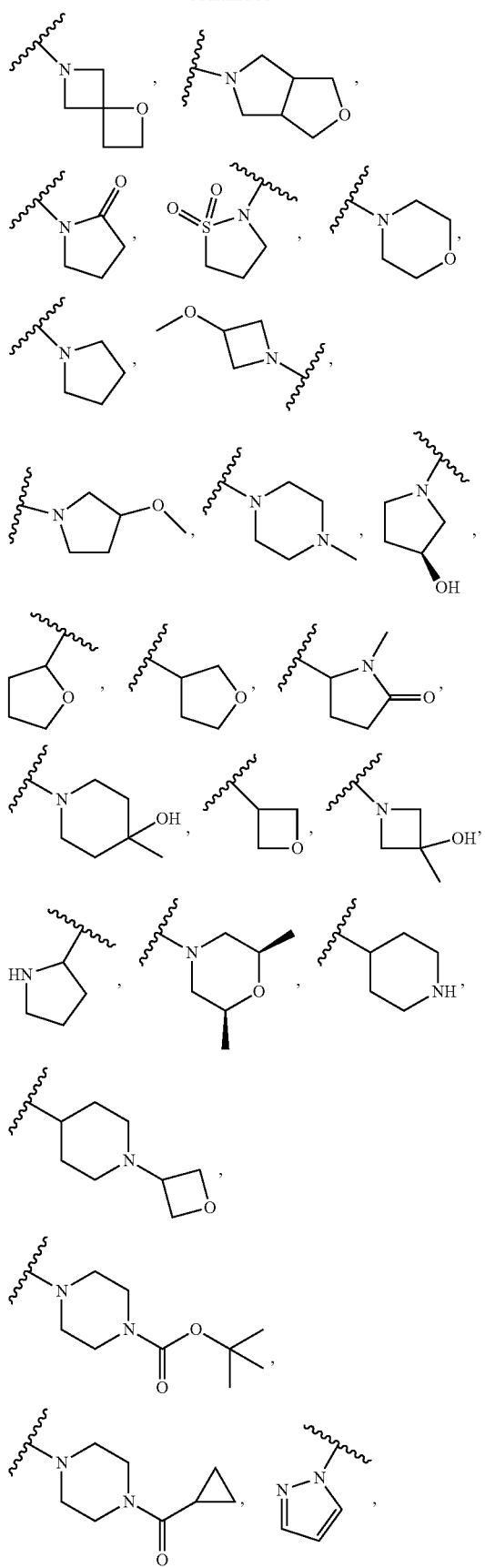

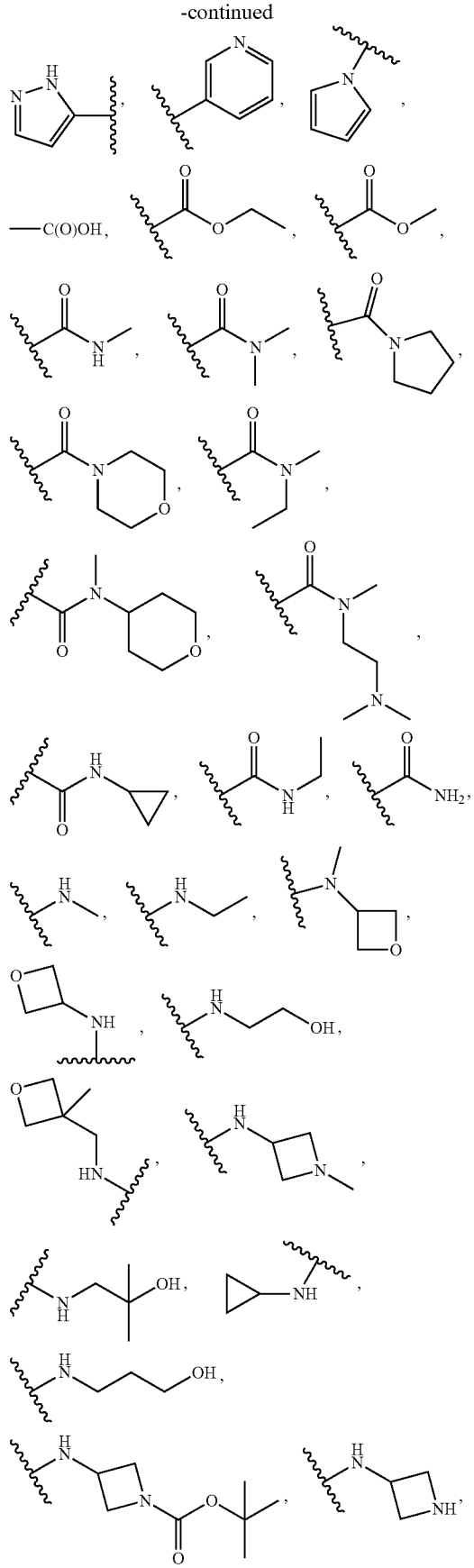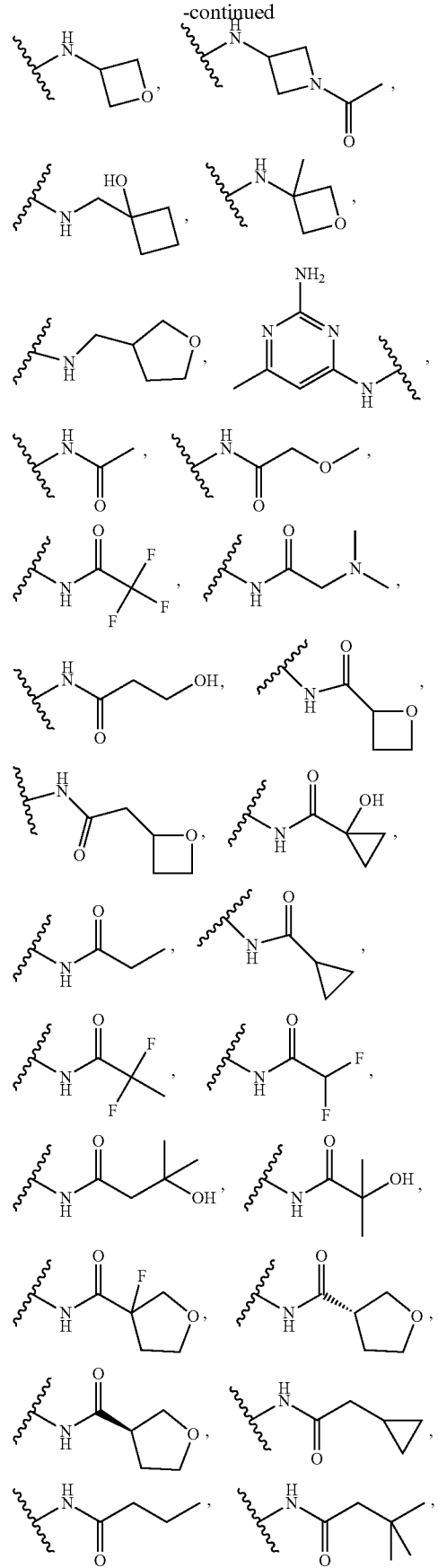

485

-continued

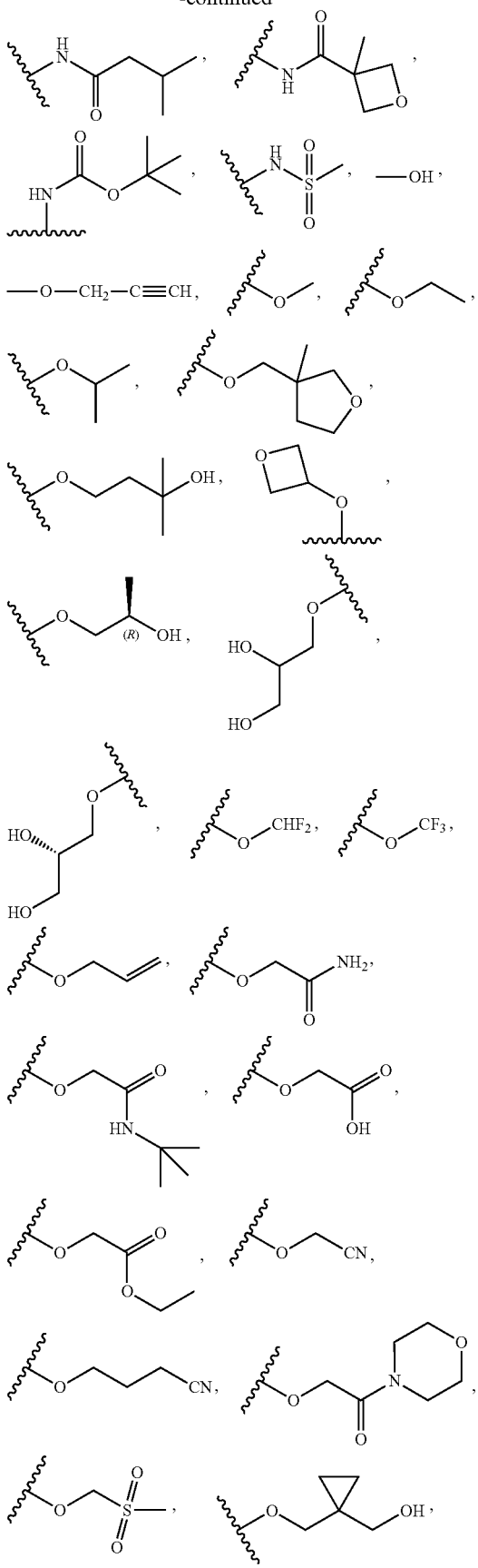

486

-continued

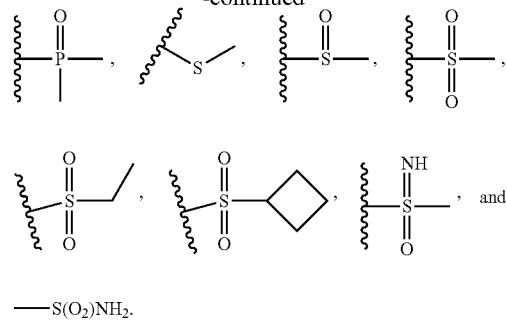

—S(O₂)NH₂.

26. The compound of claim 1, or a pharmaceutically acceptable salt thereof, wherein at least one of $R^3$ is $C_{1-3}$ aliphatic.

27. The compound of claim 1, or a pharmaceutically acceptable salt thereof, wherein m is 1.

28. The compound of claim 1, or a pharmaceutically acceptable salt thereof, wherein p is 0.

29. The compound of claim 1, or a pharmaceutically acceptable salt thereof, wherein n is 1, 2, 3, 4, or 5.

30. The compound of claim 1, or a pharmaceutically acceptable salt thereof, wherein ====== is a single bond.

31. The compound of claim 1, wherein the compound is of Formula VII

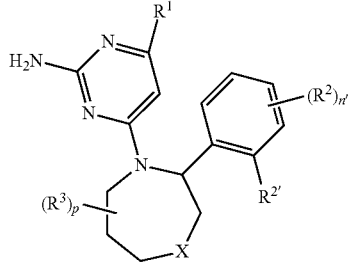

VII or a pharmaceutically acceptable salt thereof, wherein:

n' is 1 or 2; and $R^{2'}$ is halogen or —$OC_{1-3}$ aliphatic.

32. The compound of claim 31, or a pharmaceutically acceptable salt thereof, wherein $R^{2'}$ is halogen or —$OC_{1-3}$ alkyl.

33. The compound of claim 31, or a pharmaceutically acceptable salt thereof, wherein $R^{2'}$ is Cl.

34. The compound of claim 31, or a pharmaceutically acceptable salt thereof, wherein $R^{2'}$ is —$OCH_3$.

35. A pharmaceutical composition comprising a compound according to claim 1, or a pharmaceutically acceptable salt thereof, and a pharmaceutically acceptable carrier, adjuvant, or vehicle.

36. The compound of claim 31, wherein the compound is of Formulae:

IX

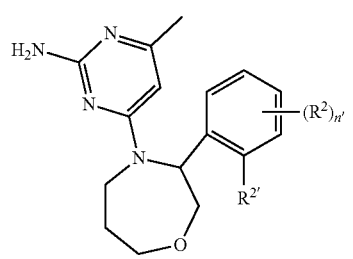

X

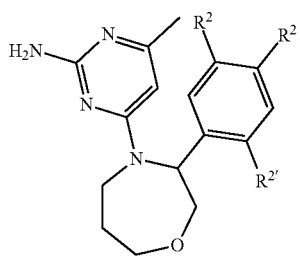

XI

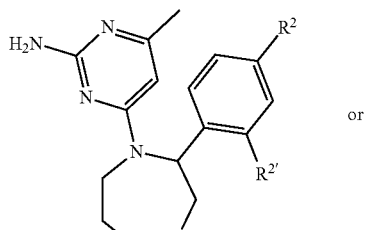

or

XII

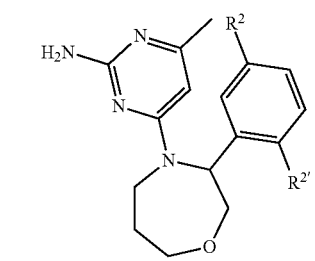

or a pharmaceutically acceptable salt thereof.

37. The compound of claim 31, wherein the compound is of Formulae:

IX-a

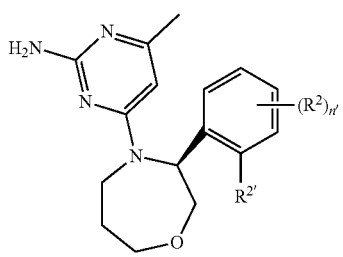

X-a

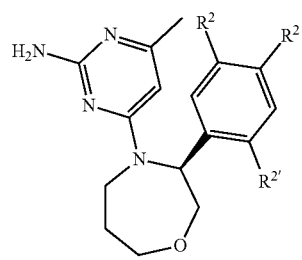

-continued

XI-a

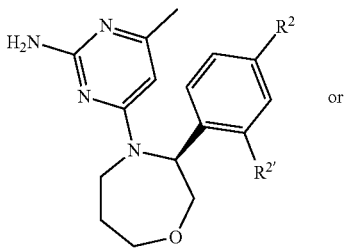

or

XII-a

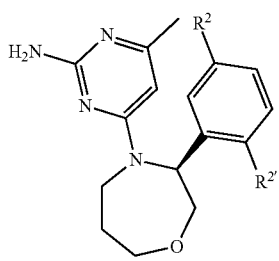

or a pharmaceutically acceptable salt thereof.

38. A compound of Formula XI-a

XI-a

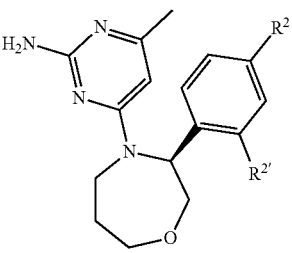

or a pharmaceutically acceptable salt thereof, wherein:

$R^2$ is —S(O)$_2$R, wherein R is unsubstituted $C_{1-6}$ aliphatic; and $R^{2'}$ is halogen or —OC$_{1-3}$ aliphatic.

39. The compound of claim 38, or a pharmaceutically acceptable salt thereof, wherein $R^2$ is —S(O)$_2$R, wherein R is unsubstituted $C_{1-6}$ alkyl.

40. The compound of claim 38, or a pharmaceutically acceptable salt thereof, wherein $R^{2'}$ is halogen.

41. A pharmaceutical composition comprising a compound according to claim 38, or a pharmaceutically acceptable salt thereof, and a pharmaceutically acceptable carrier, adjuvant, or vehicle.

42. A compound selected from:

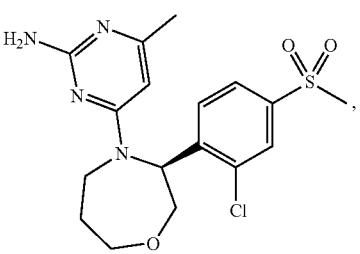

489
-continued
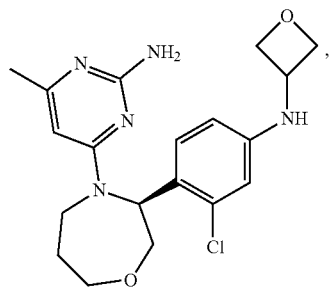
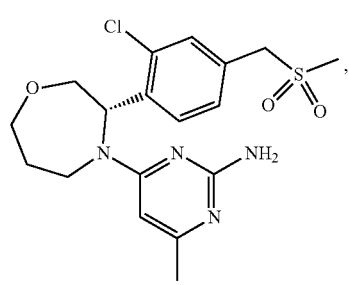
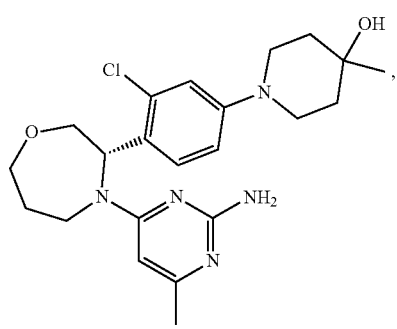
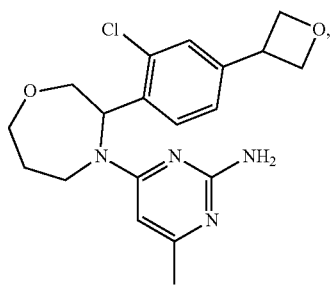
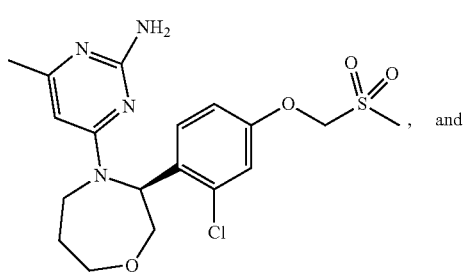, and
490
-continued
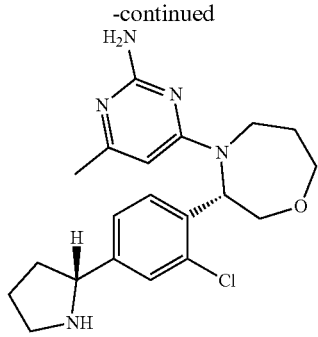
or a pharmaceutically acceptable salt thereof.
43. The compound of claim 42, which is
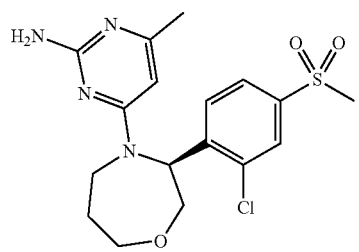 [SMILES: Cc1cc(N2CCCOC[C@@H]2c2ccc(S(C)(=O)=O)cc2Cl)nc(N)n1]
or a pharmaceutically acceptable salt thereof.
44. The compound of claim 42, which is
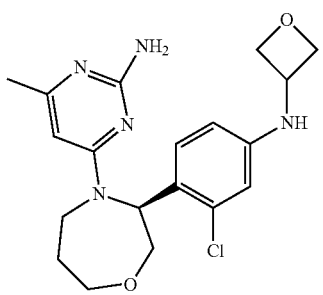 [SMILES: Cc1cc(N2CCCOC[C@@H]2c2ccc(NC3COC3)cc2Cl)nc(N)n1]
or a pharmaceutically acceptable salt thereof.
45. The compound of claim 42, which is
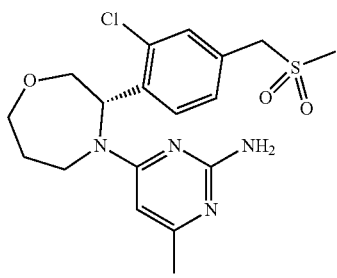 [SMILES: Cc1cc(N2CCCOC[C@@H]2c2ccc(CS(C)(=O)=O)cc2Cl)nc(N)n1]
or a pharmaceutically acceptable salt thereof.

46. The compound of claim 42, which is

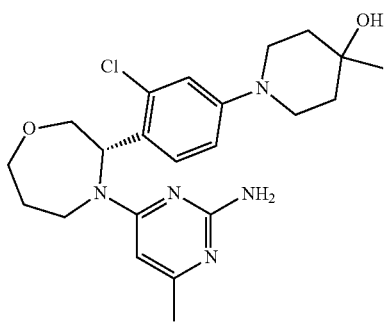 [SMILES: Cc1cc(N2CCCOC[C@@H]2c2ccc(N3CCC(C)(O)CC3)cc2Cl)nc(N)n1]

or a pharmaceutically acceptable salt thereof.

47. The compound of claim 42, which is

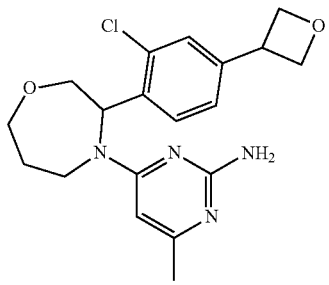 [SMILES: Cc1cc(N2CCCOCC2c2ccc(C3COC3)cc2Cl)nc(N)n1]

or a pharmaceutically acceptable salt thereof.

48. The compound of claim 42, which is

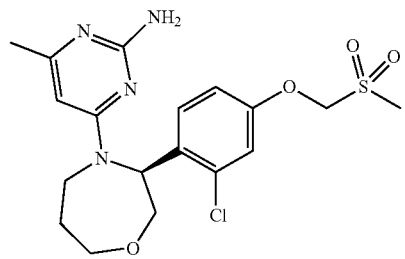

or a pharmaceutically acceptable salt thereof.

49. The compound of claim 42, which is

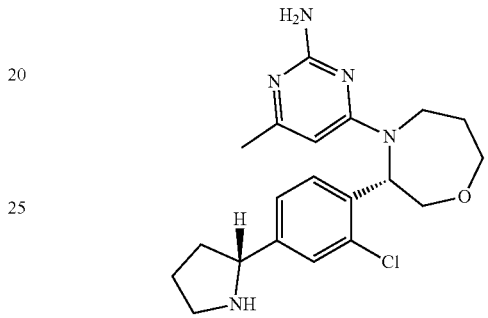

or a pharmaceutically acceptable salt thereof.

50. A pharmaceutical composition comprising a compound according to claim 42, or a pharmaceutically acceptable salt thereof, and a pharmaceutically acceptable carrier, adjuvant, or vehicle.

* * * * *